US012129246B1

United States Patent
Angst et al.

(10) Patent No.: US 12,129,246 B1
(45) Date of Patent: Oct. 29, 2024

(54) HYDROQUINAZOLINE DERIVATIVES FOR THE TREATMENT OF A DISEASE OR DISORDER

(71) Applicant: Novartis AG, Basel (CH)

(72) Inventors: Daniela Angst, Basel (CH); Philippe Bolduc, Weymouth, MA (US); Matthew William Carson, Harvard, MA (US); Atwood Kim Cheung, Arlington, MA (US); Véronique Darsigny, Somerville, MA (US); Xiang Gao, Cambridge, MA (US); Viktor Hornak, Arlington, MA (US); Keith Jendza, Cambridge, MA (US); Rajesh Karki, Weymouth, MA (US); Ajay Kumar Lal, Boston, MA (US); Gang Liu, Waltham, MA (US); Justin Yik Ching Mao, North Reading, MA (US); Jeffrey M. McKenna, Basel (CH); Erik Meredith, Hudson, MA (US); Muneto Mogi, Waltham, MA (US); Vivek Rauniyar, Cambridge, MA (US); Liansheng Su, Winchester, MA (US); Ritesh Tichkule, Cambridge, MA (US); Shuangxi Wang, Auburndale, MA (US); Chun Zhang, Sudbury, MA (US); Liang Zhao, Lexington, MA (US); Rui Zheng, Needham, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/589,841

(22) Filed: Feb. 28, 2024

Related U.S. Application Data

(60) Provisional application No. 63/550,180, filed on Feb. 6, 2024, provisional application No. 63/487,756, filed on Mar. 1, 2023.

(51) Int. Cl.
| | |
|---|---|
| *C07D 403/14* | (2006.01) |
| *A61K 31/517* | (2006.01) |
| *A61K 31/55* | (2006.01) |
| *A61K 45/06* | (2006.01) |
| *C07D 239/95* | (2006.01) |
| *C07D 401/12* | (2006.01) |
| *C07D 401/14* | (2006.01) |

(52) U.S. Cl.
CPC .......... *C07D 403/14* (2013.01); *A61K 31/517* (2013.01); *A61K 31/55* (2013.01); *A61K 45/06* (2013.01); *C07D 239/95* (2013.01); *C07D 401/12* (2013.01); *C07D 401/14* (2013.01)

(58) Field of Classification Search
CPC .. C07D 403/14; C07D 239/95; C07D 401/12; C07D 401/14; A61K 31/517; A61K 31/55; A61K 45/06
See application file for complete search history.

(56) References Cited

U.S. PATENT DOCUMENTS

| | | |
|---|---|---|
| 3,299,068 A | 1/1967 | Chinn |
| 2004/0063690 A1 | 4/2004 | Schindler |
| 2010/0016344 A1 | 1/2010 | Wakefield |
| 2018/0065938 A1 | 3/2018 | Chin |

FOREIGN PATENT DOCUMENTS

| | | | |
|---|---|---|---|
| WO | 2006050843 A1 | 5/2006 | |
| WO | 2009047255 A1 | 4/2009 | |
| WO | 2016048861 A2 | 3/2016 | |
| WO | WO-2018045144 A1 * | 3/2018 | .......... A61K 31/517 |
| WO | 2020150113 A1 | 7/2020 | |

OTHER PUBLICATIONS

Iwaki et al., Discovery and in vivo effects of novel human natriuretic peptide receptor A (NPR-A) agonists with improved activity for rat NPR-A, Bioorganic & Medicinal Chemistry, 25, 6680-6694, Nov. 6, 2017.
Iwaki et al., Discovery and SAR of a novel series of Natriuretic Peptide Receptor-A (NPR-A) agonists, Bioorganic & Medicinal Chemistry Letters, 27, 4904-4907, Sep. 18, 2017.
International Search Report and Written Opinion for PCT Application No. PCT/IB2024/051925, mailed Jun. 11, 2024 (12 pages).

\* cited by examiner

*Primary Examiner* — Matthew P Coughlin
*Assistant Examiner* — Meghan C Heasley
(74) *Attorney, Agent, or Firm* — Timothy P. O'Dea

(57) ABSTRACT

The disclosure relates to a compound of Formula (I):

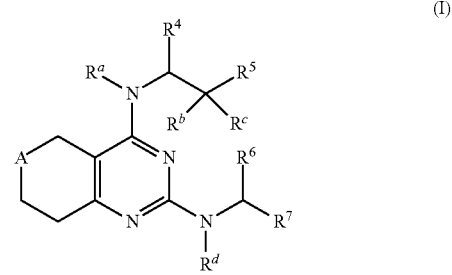

or a pharmaceutically acceptable salt thereof wherein A, $R^a$ to $R^d$, and $R^4$ to $R^7$, are as described herein, as well as compositions and methods of using such compounds.

30 Claims, No Drawings

HYDROQUINAZOLINE DERIVATIVES FOR THE TREATMENT OF A DISEASE OR DISORDER

RELATED APPLICATIONS

This application claims the benefit of and priority to U.S. Provisional Application No. 63/487,756, filed Mar. 1, 2023, and U.S. Provisional Application No. 63/550,180, filed Feb. 6, 2024, the entire contents of each of which are hereby incorporated by reference in their entireties.

BACKGROUND

Heart failure is a major public health problem concerning more than 20 million patients around the world and is associated with high morbidity. Natriuretic Peptide Receptor 1 (NPR1; also known as NPRA) is a receptor guanylate cyclase, which is activated by Atrial Natriuretic Peptide (ANP) resulting in lowering of blood pressure and blood volume. ANP binding induces dimerization and twisting of the receptor that induces activation of the guanylate cyclase domain and conversion of GTP into cGMP. ANP is cleared by NPR3, a natriuretic peptide receptor that lacks the guanylate cyclase domain, and degraded by Neutral Endopeptidase (NEP).

It has been shown that an increase in ANP via infusions may be beneficial for patients with chronic heart failure with reduced ejection fraction (outbound pumping of blood by heart). However, there is a need for oral agents that are able to supplement or replace existing therapies.

SUMMARY

In a first aspect, the disclosure relates to a compound of Formula (I):

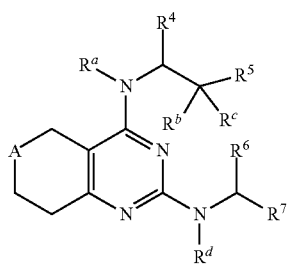

(I)

or a pharmaceutically acceptable salt thereof wherein:

A is $NR^1$ or $CR^2R^3$;

$R^1$ and $R^2$ are each, independently H, $(C_3-C_6)$cycloalkyl, or $(C_6-C_{10})$aryl, wherein the $(C_6-C_{10})$aryl is optionally substituted with one or more (e.g., 1, 2, 3, 4, or 5) substituents independently selected from halo, —CN, —OH, —CO$_2$H, $(C_1-C_6)$alkyl and $(C_3-C_6)$cycloalkyl;

$R^3$ is H or $(C_1-C_6)$alkyl;

$R^4$ is $(C_6-C_{10})$aryl or a 5- or 6-membered heteroaryl comprising 1, 2, 3, or 4 heteroatoms selected from N, O, and S, wherein the $(C_6-C_{10})$aryl or the 5- or 6-membered heteroaryl are each optionally substituted with one or more (e.g., 1, 2, 3, 4, or 5) substituents independently selected from halo, —CN, —OH, —CO$_2$H, oxo, $(C_1-C_6)$alkyl, $(C_1-C_6)$haloalkyl, $(C_3-C_6)$cycloalkyl, $(C_3-C_6)$cycloalkyl-$(C_1-C_6)$alkyl, and $(C_1-C_6)$alkyl $(C_3-C_6)$cycloalkyl;

$R^5$ is $NR^8R^9$;

$R^6$ is selected from H, $(C_1-C_6)$alkyl, $(C_3-C_6)$cycloalkyl, and $(C_3-C_6)$cycloalkyl-$(C_1-C_6)$alkyl;

$R^7$ is $(C_3-C_6)$cycloalkyl or $(C_6-C_{10})$aryl, wherein the $(C_3-C_6)$cycloalkyl and $(C_6-C_{10})$aryl are each optionally substituted with one or more (e.g., 1, 2, 3, 4, or 5) substituents independently selected from halo, —CN, —OH, —CO$_2$H, and HO$_2$C—$(C_1-C_6)$alkyl;

$R^8$ and $R^9$ are each, independently H, $(C_1-C_6)$alkyl or a 3- to 6-membered heterocycle comprising 1 to 3 heteroatoms selected from N, O, and S; or $R^8$ and $R^9$ together with the N to which there are bound form a 3- to 10-membered heterocycle optionally comprising 1 or 2 additional heteroatoms selected from N, O, and S, wherein the 3- to 10-membered heterocycle is optionally substituted with one or more (e.g., 1, 2, 3, 4, or 5) substituents independently selected from halo, —CN, —OH, —CO$_2$H, $(C_1-C_6)$alkyl, $(C_1-C_6)$haloalkyl, $(C_3-C_6)$cycloalkyl-$(C_1-C_6)$alkyl, $(C_3-C_6)$cycloalkyl, $(C_1-C_6)$alkyl-O—$(C_1-C_6)$alkyl, $(C_1-C_6)$hydroxyalkyl, $(C_1-C_6)$alkoxy, and a 3- to 7-membered heterocycle comprising 1 to 2 heteroatoms selected from N, O, and S; and $R^a$, $R^b$, $R^c$, and $R^d$ are each, independently H or $(C_1-C_6)$alkyl.

In another aspect, the present disclosure relates to a pharmaceutical composition comprising a compound of Formula I or a pharmaceutically acceptable salt thereof and one or more pharmaceutically acceptable carriers.

In another aspect, the present disclosure relates to a combination comprising a compound of Formula I or a pharmaceutically acceptable salt thereof and one or more pharmaceutical agents.

In another aspect, the present disclosure relates to a method for treating a disease or disorder comprising administering to a patient in need thereof a therapeutically effective amount of a compound of Formula I or a pharmaceutically acceptable salt thereof. In some embodiments, the disease or disorder is a cardiovascular disease or disorder. In some embodiments, the cardiovascular disease or disorder is selected from hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI). In some embodiments, the disease or disorder is disorder is a disorder or disease associated with natriuretic peptide receptor activity In another aspect, the present disclosure relates to a compound of Formula I or a pharmaceutically acceptable salt thereof for use as a medicament.

In another aspect, the present disclosure relates to a compound of Formula I or a pharmaceutically acceptable salt thereof for use in the treatment of a disease or disorder.

In yet another aspect, the present disclosure relates to a compound of Formula I for use in the manufacture of a medicament for treating a disease or disorder.

In still another aspect, the present disclosure relates to use of a compound of Formula I or a pharmaceutically acceptable salt thereof in the treatment of a disease or disorder.

Other features and advantages of the disclosure will be apparent from the following detailed description and claims.

DETAILED DESCRIPTION

In certain aspects, the disclosure provides substituted hydroquinazoline derivatives compounds, and pharmaceutical compositions thereof. In particular, such substituted compounds are useful as activators of NPR1 and thus can be used to treat or prevent a disease or condition.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Compounds

In one aspect, the disclosure therefore provides a compound of Formula (I):

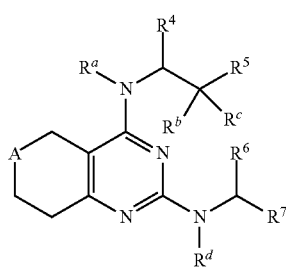

(I)

or a pharmaceutically acceptable salt thereof wherein:

A is $NR^1$ or $CR^2R^3$;

$R^1$ and $R^2$ are each, independently H, $(C_3-C_6)$cycloalkyl, or $(C_6-C_{10})$aryl, wherein the $(C_6-C_{10})$aryl is optionally substituted with one or more (e.g., 1, 2, 3, 4, or 5) substituents independently selected from halo, —CN, —OH, —CO$_2$H, $(C_1-C_6)$alkyl and $(C_3-C_6)$cycloalkyl;

$R^3$ is H or $(C_1-C_6)$alkyl;

$R^4$ is $(C_6-C_{10})$aryl or a 5- or 6-membered heteroaryl comprising 1, 2, 3, or 4 heteroatoms selected from N, O, and S, wherein the $(C_6-C_{10})$aryl or the 5- or 6-membered heteroaryl are each optionally substituted with one or more (e.g., 1, 2, 3, 4, or 5) substituents independently selected from halo, —CN, —OH, —CO$_2$H, oxo, $(C_1-C_6)$alkyl, $(C_1-C_6)$haloalkyl, $(C_3-C_6)$cycloalkyl, $(C_3-C_6)$cycloalkyl-$(C_1-C_6)$alkyl, and $(C_1-C_6)$alkyl $(C_3-C_6)$cycloalkyl;

$R^5$ is $NR^8R^9$;

$R^6$ is selected from H, $(C_1-C_6)$alkyl, $(C_3-C_6)$cycloalkyl, and $(C_3-C_6)$cycloalkyl-$(C_1-C_6)$alkyl;

$R^7$ is $(C_3-C_6)$cycloalkyl or $(C_6-C_{10})$aryl, wherein the $(C_3-C_6)$cycloalkyl and $(C_6-C_{10})$aryl are each optionally substituted with one or more (e.g., 1, 2, 3, 4, or 5) substituents independently selected from halo, —CN, —OH, —CO$_2$H, and HO$_2$C—$(C_1-C_6)$alkyl;

$R^8$ and $R^9$ are each, independently H, $(C_1-C_6)$alkyl or a 3- to 6-membered heterocycle comprising 1 to 3 heteroatoms selected from N, O, and S; or $R^8$ and $R^9$ together with the N to which there are bound form a 3- to 10-membered heterocycle optionally comprising 1 or 2 additional heteroatoms selected from N, O, and S, wherein the 3- to 10-membered heterocycle is optionally substituted with one or more (e.g., 1, 2, 3, 4, or 5) substituents independently selected from halo, —CN, —OH, —CO$_2$H, $(C_1-C_6)$alkyl, $(C_1-C_6)$haloalkyl, $(C_3-C_6)$cycloalkyl-$(C_1-C_6)$alkyl, $(C_3-C_6)$cycloalkyl, $(C_1-C_6)$alkyl-O—$(C_1-C_6)$alkyl, $(C_1-C_6)$hydroxyalkyl, $(C_1-C_6)$alkoxy, and a 3- to 7-membered heterocycle comprising 1 to 2 heteroatoms selected from N, O, and S; and $R^a$, $R^b$, $R^c$, and $R^d$ are each, independently H or $(C_1-C_6)$alkyl.

Unless specified otherwise, the term "compounds of the present disclosure" or "compound of the present disclosure" refers to compounds of Formula (I) thereof, and exemplified compounds, and salts thereof, as well as all stereoisomers (including diastereoisomers and enantiomers), rotamers, tautomers and isotopically labeled compounds (including deuterium substitutions), as well as inherently formed moieties.

Various embodiments of the disclosure are described herein. It will be recognized that features specified in each embodiment may be combined with other specified features of other embodiments to provide further embodiments.

In some embodiments, A is $NR^1$ and $R^1$ is $(C_3-C_6)$cycloalkyl or $(C_6-C_{10})$aryl, wherein the $(C_6-C_{10})$aryl is optionally substituted with one or more (e.g., 1, 2, 3, 4, or 5) substituents independently selected from halo, —CN, —OH, —CO$_2$H, $(C_1-C_6)$alkyl and $(C_3-C_6)$ cycloalkyl. In some embodiments, A is $NR^1$ and $R^1$ is $(C_6-C_{10})$aryl which is optionally substituted with one or more (e.g., 1, 2, 3, 4, or 5) substituents independently selected from halo, —CN, —OH, —CO$_2$H, $(C_1-C_6)$alkyl and $(C_3-C_6)$cycloalkyl. In some embodiments, A is $NR^1$ and $R^1$ is $(C_6-C_{10})$aryl which is optionally substituted with one or more (e.g., 1, 2, 3, 4, or 5) substituents independently selected from halo and —CN. In some embodiments, A is $NR^1$ and $R^1$ is phenyl which is optionally substituted with 1 or 2 substituents independently selected from halo and —CN. In some embodiments, A is $NR^1$ and $R^1$ is phenyl which is optionally substituted with 1 substituent independently selected from halo and —CN. In some embodiments, A is $NR^1$ and $R^1$ is phenyl which is optionally substituted with 1 substituent independently selected from fluoro and —CN.

In some embodiments, A is $NR^1$ and $R^1$ is selected from

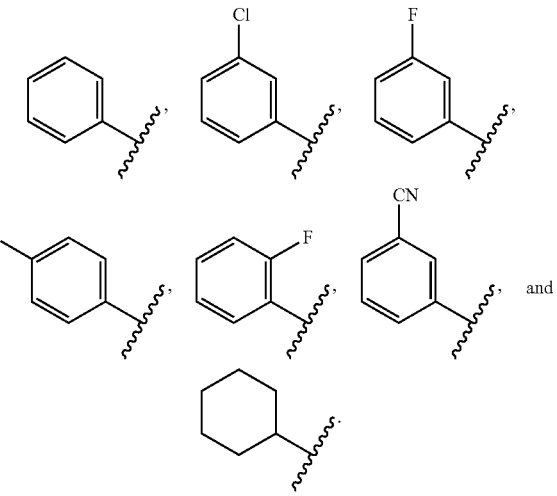

In some embodiments, A is NR$^1$ and R$^1$ is selected from

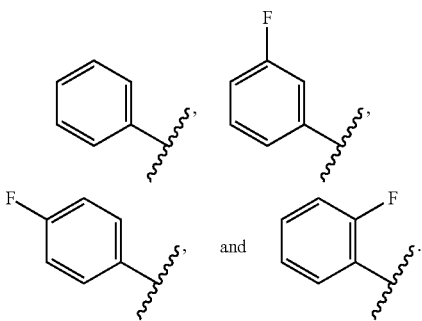

In some embodiments, A is CR$^2$R$^3$ and R$^2$ is (C$_6$-C$_{10}$)aryl, which is optionally substituted with one or more (e.g., 1, 2, 3, 4, or 5) substituents independently selected from halo, —CN, —OH, —CO$_2$H, (C$_1$-C$_6$)alkyl and (C$_3$-C$_6$)cycloalkyl. In some embodiments, A is CR$^2$R$^3$ and R$^2$ is (C$_6$-C$_{10}$) aryl, which is optionally substituted with one or more (e.g., 1, 2, 3, 4, or 5) substituents independently selected from halo. In some embodiments, A is CR$^2$R$^3$ and R$^2$ is phenyl which is optionally substituted with 1 or 2 substituents independently selected from halo. In some embodiments, A is CR$^2$R$^3$ and R$^2$ is phenyl which is optionally substituted with 1 substituents selected from halo. In some embodiments, A is CR$^2$R$^3$ and R$^2$ is phenyl which is optionally substituted with 1 substituents selected from fluoro.

In some embodiments, A is CR$^2$R$^3$ and R$^2$ is selected from

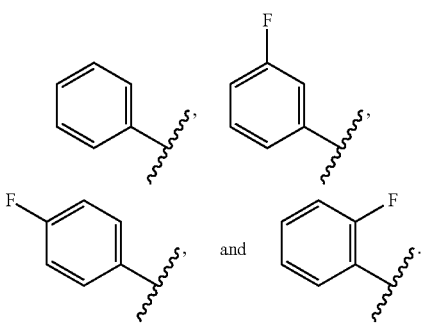

In some embodiments, A is CR$^2$R$^3$ and R$^3$ is selected from H and —CH$_3$.

In some embodiments, R$^4$ is (C$_6$-C$_{10}$)aryl or a 5- or 6-membered heteroaryl comprising 1, 2, 3, or 4 heteroatoms selected from N, O, and S, wherein the (C$_6$-C$_{10}$)aryl is optionally substituted with one or more (e.g., 1, 2, 3, 4, or 5) substituents independently selected from halo, —CN, —OH, —CO$_2$H, and (C$_1$-C$_6$)alkyl and the 5- or 6-membered heteroaryl is optionally substituted with one or more (e.g., 1, 2, 3, 4, or 5) substituents independently selected from halo, —CN, —OH, —CO$_2$H, oxo, (C$_1$-C$_6$)alkyl, (C$_1$-C$_6$)haloalkyl, (C$_3$-C$_6$)cycloalkyl, (C$_3$-C$_6$)cycloalkyl-(C$_1$-C$_6$)alkyl, and (C$_1$-C$_6$)alkyl(C$_3$-C$_6$)cycloalkyl. In certain embodiments, R$^4$ is (C$_6$-C$_{10}$)aryl or a 5- or 6-membered heteroaryl comprising 1 to 2 heteroatoms selected from N and S, wherein the (C$_6$-C$_{10}$)aryl is optionally substituted with one or more (e.g., 1, 2, 3, 4, or 5) substituents independently selected from halo and (C$_1$-C$_6$)alkyl and the 5- or 6-membered heteroaryl is optionally substituted with one or more (e.g., 1, 2, 3, 4, or 5) substituents independently selected from oxo, (C$_1$-C$_6$)alkyl, (C$_1$-C$_6$)haloalkyl, (C$_3$-C$_6$)cycloalkyl, and (C$_3$-C$_6$)cycloalkyl-(C$_1$-C$_6$)alkyl.

In some embodiments, R$^4$ is a 5- or 6-membered heteroaryl comprising 1 to 2 heteroatoms selected from N and S, which is optionally substituted with one or more (e.g., 1, 2, 3, 4, or 5) substituents independently selected from oxo, (C$_1$-C$_6$)alkyl, (C$_1$-C$_6$)haloalkyl, (C$_3$-C$_6$)cycloalkyl, and (C$_3$-C$_6$)cycloalkyl-(C$_1$-C$_6$)alkyl. In some embodiments, R$^4$ is a 5-membered heteroaryl comprising 1 to 2 heteroatoms selected from N and S, which is optionally substituted with one or more (e.g., 1, 2, 3, 4, or 5) substituents independently selected from oxo, (C$_1$-C$_6$)alkyl, (C$_1$-C$_6$)fluoroalkyl, (C$_3$-C$_6$)cycloalkyl, and (C$_3$-C$_6$)cycloalkyl-(C$_1$-C$_6$)alkyl. In some embodiments, R$^4$ is a 5-membered heteroaryl comprising 1 to 2 heteroatoms selected from N and S, which is optionally substituted with 1 or 2 substituents independently selected from (C$_1$-C$_6$)alkyl, (C$_1$-C$_6$)fluoroalkyl, (C$_3$-C$_6$)cycloalkyl, and (C$_3$-C$_6$)cycloalkyl-(C$_1$-C$_6$)alkyl. In some embodiments, R$^4$ is a 5-membered heteroaryl comprising 2 heteroatoms selected from N and S, which is optionally substituted with 1 or 2 substituents independently selected from (C$_1$-C$_6$) alkyl, (C$_1$-C$_6$)fluoroalkyl, (C$_3$-C$_6$)cycloalkyl, and (C$_3$-C$_6$) cycloalkyl-(C$_1$-C$_6$)alkyl.

In certain embodiments, R$^4$ is (C$_6$-C$_{10}$)aryl, which is optionally substituted with one or more (e.g., 1, 2, 3, 4, or 5) substituents independently selected from halo, oxo, and (C$_1$-C$_6$)alkyl. In certain embodiments, R$^4$ is phenyl, which is optionally substituted with 1 or 2 substituents independently selected from halo, oxo, and (C$_1$-C$_6$)alkyl. In certain embodiments, R$^4$ is (C$_6$-C$_{10}$)aryl, which is optionally substituted with one or more (e.g., 1, 2, 3, 4, or 5) substituents independently selected from halo.

In some embodiments, R$^4$ is selected from

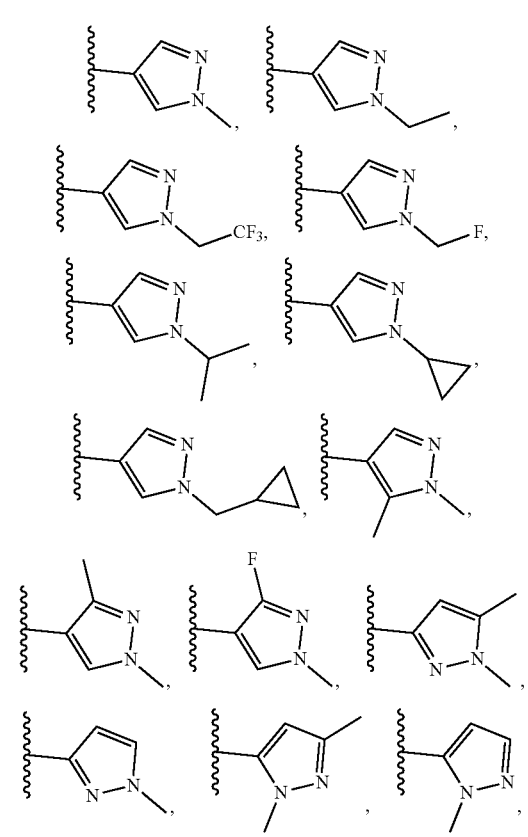

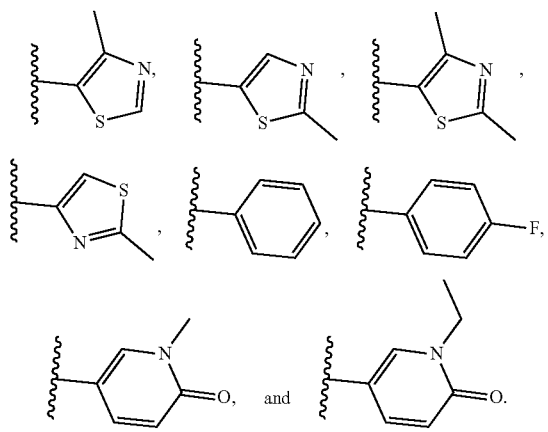
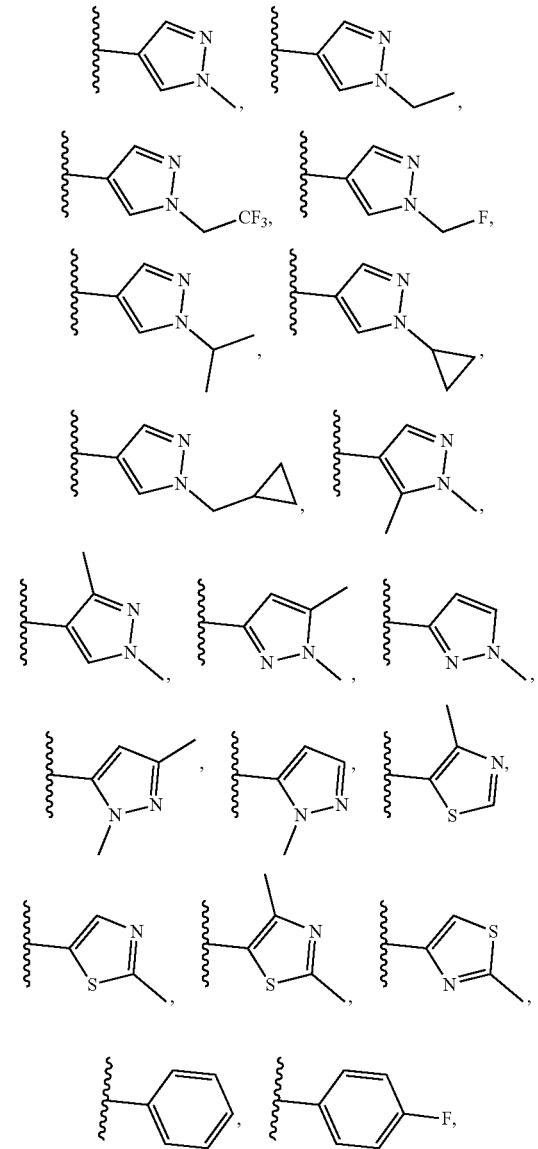
In certain embodiments, R⁴ is selected from
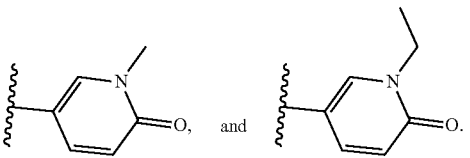
In certain embodiments, R⁴ is selected from
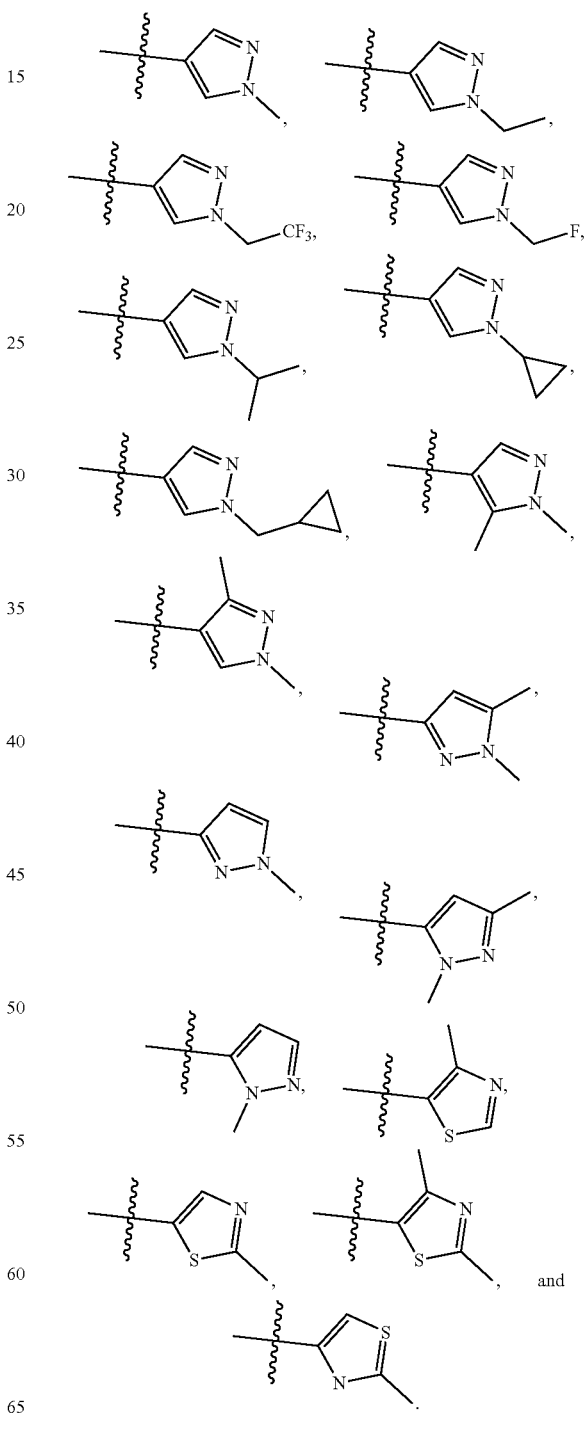

In some embodiments, $R^5$ is $NR^8R^9$ and $R^8$ and $R^9$ together with the N to which there are bound form a 3- to 10-membered heterocycle optionally comprising 1 or 2 additional heteroatoms selected from N, O, and S, wherein the 3- to 10-membered heterocycle is optionally substituted with one or more (e.g., 1, 2, 3, 4, or 5) substituents independently selected from halo, —CN, —OH, —CO$_2$H, ($C_1$-$C_6$)alkyl, ($C_1$-$C_6$)haloalkyl, ($C_3$-$C_6$)cycloalkyl-($C_1$-$C_6$)alkyl, ($C_3$-$C_6$)cycloalkyl, ($C_1$-$C_6$)alkyl-O—($C_1$-$C_6$)alkyl, ($C_1$-$C_6$)hydroxyalkyl, ($C_1$-$C_6$)alkoxy, and a 3- to 7-membered heterocycle comprising 1 to 2 heteroatoms selected from N, O, and S.

In some embodiments, $R^5$ is $NR^8R^9$ and $R^8$ and $R^9$ together with the N which there are bound form a 3- to 10-membered heterocycle optionally comprising 1 to 2 additional O heteroatoms, wherein the 3- to 10-membered heterocycle is optionally substituted with one or more (e.g., 1, 2, 3, 4, or 5) substituents independently selected from halo, —CN, —OH, —CO$_2$H, ($C_1$-$C_6$)alkyl, ($C_1$-$C_6$)haloalkyl, ($C_3$-$C_6$)cycloalkyl-($C_1$-$C_6$)alkyl, ($C_3$-$C_6$)cycloalkyl, ($C_1$-$C_6$)alkyl-O—($C_1$-$C_6$)alkyl, ($C_1$-$C_6$)hydroxyalkyl, ($C_1$-$C_6$)alkoxy, and a 3- to 7-membered heterocycle comprising 1 to 2 heteroatoms selected from N, O, and S.

In some embodiments, $R^5$ is $NR^8R^9$ and $R^8$ and $R^9$ together with the N which there are bound form a 3- to 10-membered heterocycle optionally comprising 1 to 2 additional O heteroatoms, wherein the 3- to 10-membered heterocycle is optionally substituted with one or more (e.g., 1, 2, 3, 4, or 5) substituents independently selected from halo, —OH, ($C_1$-$C_6$)alkyl, ($C_1$-$C_6$)haloalkyl, ($C_3$-$C_6$)cycloalkyl, ($C_1$-$C_6$)alkyl-O—($C_1$-$C_6$)alkyl, ($C_1$-$C_6$)hydroxyalkyl, ($C_1$-$C_6$)alkoxy, and a 3- to 7-membered heterocycle comprising a heteroatom selected from N, O, and S.

In some embodiments, $R^5$ is $NR^8R^9$ and $R^8$ and $R^9$ together with the N which there are bound form a 5- to 10-membered heterocycle optionally comprising 1 to 2 additional O heteroatoms, wherein the 5- to 10-membered heterocycle is optionally substituted with one or more (e.g., 1, 2, 3, 4, or 5) substituents independently selected from halo, —OH, ($C_1$-$C_6$)alkyl, ($C_1$-$C_6$)haloalkyl, ($C_3$-$C_6$)cycloalkyl, ($C_1$-$C_6$)alkyl-O—($C_1$-$C_6$)alkyl, ($C_1$-$C_6$)hydroxyalkyl, ($C_1$-$C_6$)alkoxy, and a 3- to 7-membered heterocycle comprising a heteroatom selected from N and O. In some embodiments, the 5- to 10-membered heterocycle is optionally substituted with one or more (e.g., 1, 2, 3, 4, or 5) substituents independently selected from fluoro, —OH, ($C_1$-$C_6$)alkyl, ($C_1$-$C_6$)fluoroalkyl, $CH_3O$—($C_1$-$C_6$)alkyl, ($C_1$-$C_6$)hydroxyalkyl, and a 5-membered heterocycle comprising a heteroatom selected from 0. In some embodiments, the 5- to 10-membered heterocycle is optionally substituted with one or more (e.g., 1, 2, 3, 4, or 5) substituents independently selected from fluoro, —OH, —CH$_3$, —CH$_2$F, —CF$_2$H, —CH$_2$CH$_3$, —CH$_2$OH, —OCH$_3$, and —CH$_2$OCH$_3$. In some embodiments, the 5- to 10-membered heterocycle is optionally substituted with 1 or 2 substituents independently selected from fluoro, —OH, —CH$_3$, —CH$_2$F, —CF$_2$H, —CH$_2$CH$_3$, —CH$_2$OH, —OCH$_3$, and —CH$_2$OCH$_3$. In some embodiments, the 5- to 10-membered heterocycle is optionally substituted with 1 substituents independently selected from ($C_3$-$C_6$)cycloalkyl and a 5-membered heterocycle comprising a heteroatom selected from N and O.

In some embodiments, $R^5$ is selected from

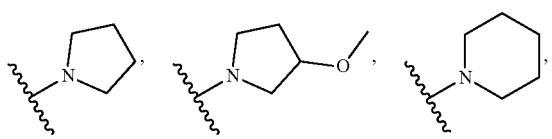

-continued

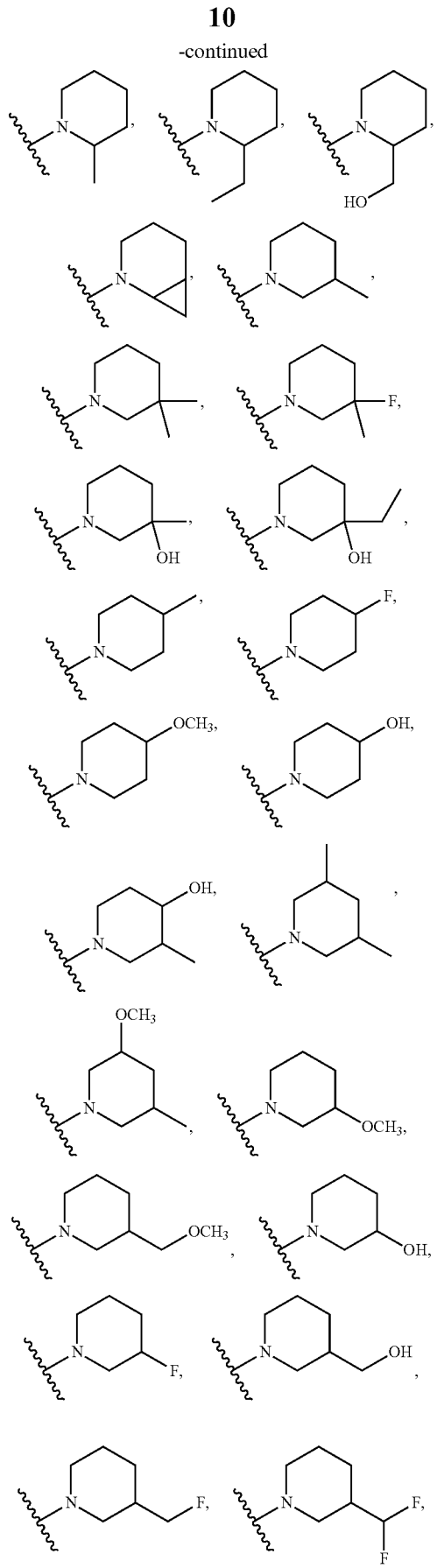

-continued
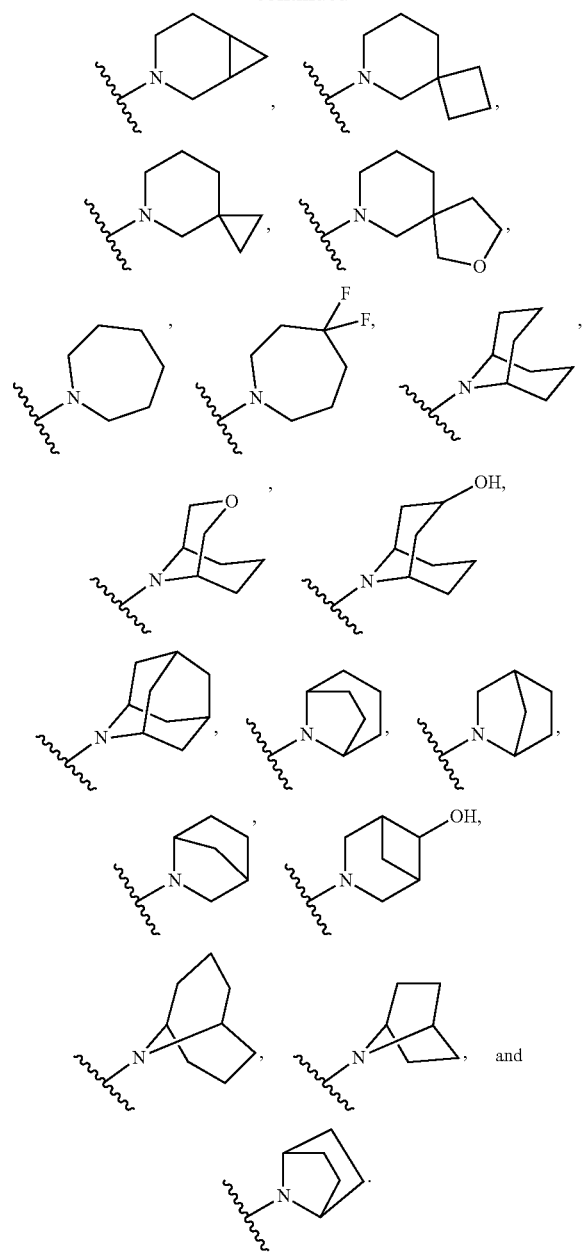
In certain embodiments, R⁵ is selected from
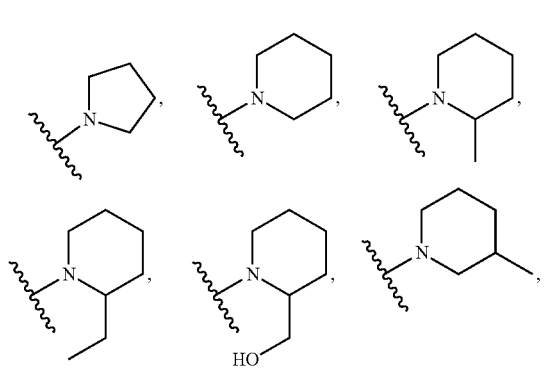
-continued
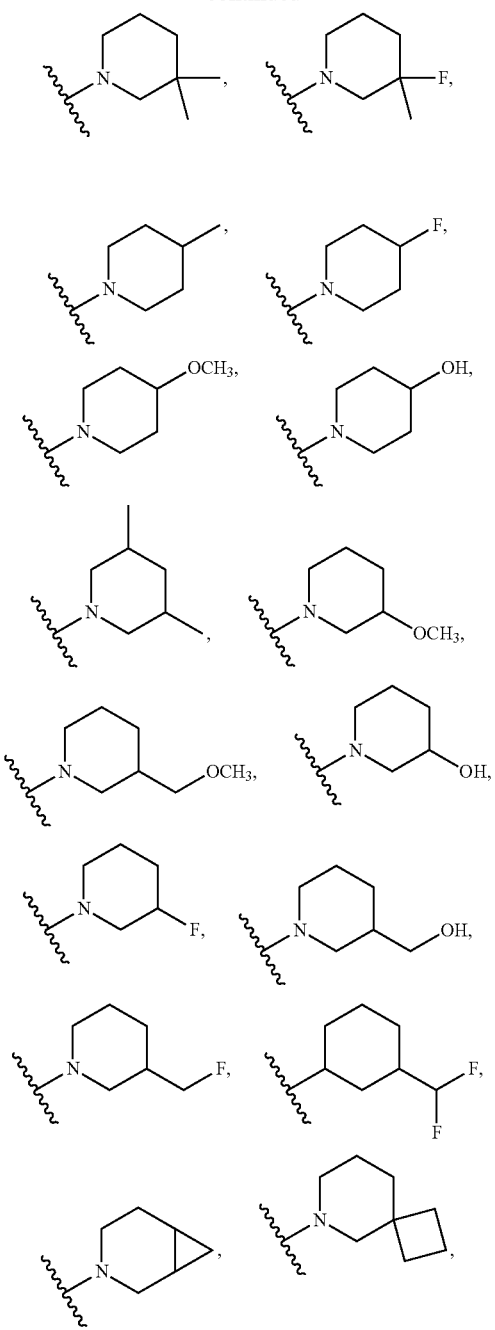
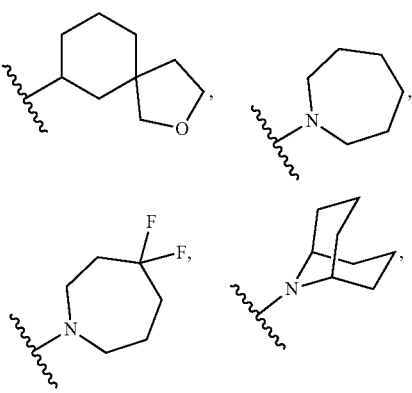

-continued

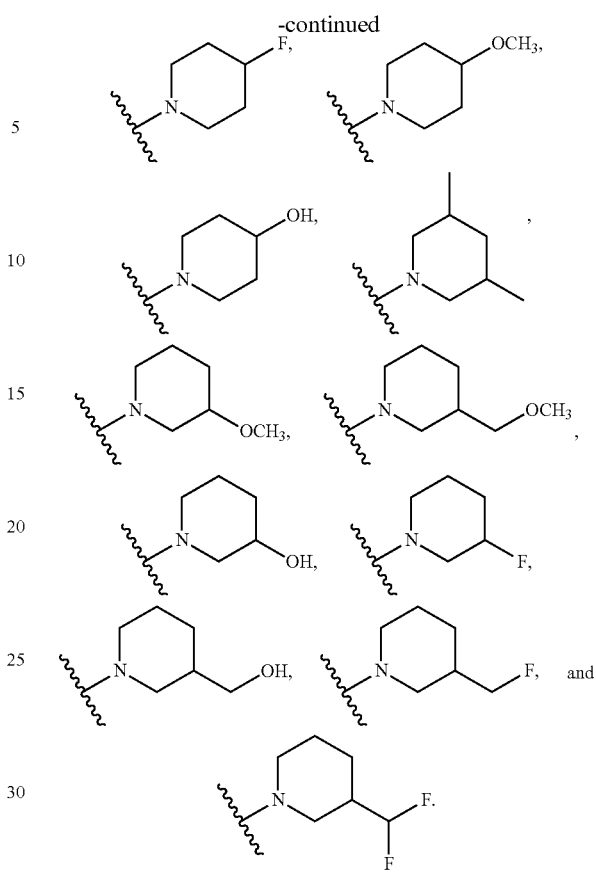

In some embodiments, $R^5$ is $NR^8R^9$ and $R^8$ is selected from H and $(C_1-C_6)$alkyl. In some embodiments, $R^5$ is $NR^8R^9$ and $R^9$ is selected from H, $(C_1-C_6)$alkyl, and a 3- to 6-membered heterocycle comprising an O heteroatom.

In some embodiments, $R^6$ is selected from selected from $(C_1-C_4)$alkyl, $(C_3-C_5)$cycloalkyl, and $(C_3-C_5)$cycloalkyl-$(C_1-C_4)$alkyl. In certain embodiments, $R^6$ is selected from, —$CH_3$, —$CH_2CH_3$,

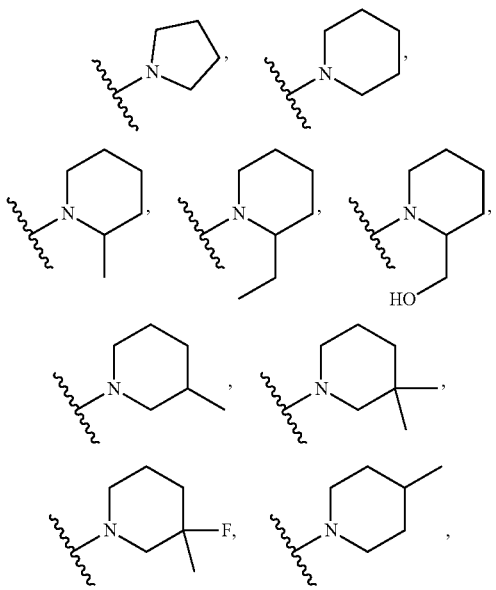

In some embodiments, $R^5$ is selected from

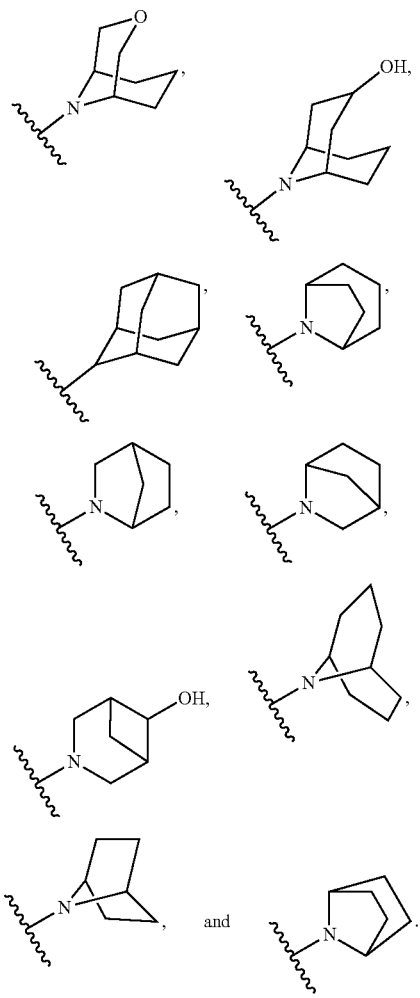

and

In some embodiments, $R^7$ is selected from $(C_3-C_6)$cycloalkyl or $(C_6-C_{10})$aryl, wherein the $(C_3-C_6)$cycloalkyl and $(C_6-C_{10})$aryl are each optionally substituted with one or more (e.g., 1, 2, 3, 4, or 5) substituents independently selected from halo, —$CO_2H$, and —$CH_2CO_2H$. In some embodiments, $R^7$ is selected from $(C_5-C_6)$cycloalkyl or $(C_6-C_{10})$aryl, wherein the $(C_5-C_6)$cycloalkyl and $(C_6-C_{10})$aryl are each optionally substituted with one or more (e.g., 1, 2, 3, 4, or 5) substituents independently selected from halo, —CO$_2$H, and —CH$_2$CO$_2$H. In some embodiments, R$^7$ is selected from (C$_5$-C$_6$)cycloalkyl or (C$_6$-C$_{10}$)aryl, wherein the (C$_5$-C$_6$)cycloalkyl and (C$_6$-C$_{10}$)aryl are each optionally substituted with 1 or 2 substituents independently selected from fluoro, —CO$_2$H, and —CH$_2$CO$_2$H.

In certain embodiments, R$^7$ is selected from

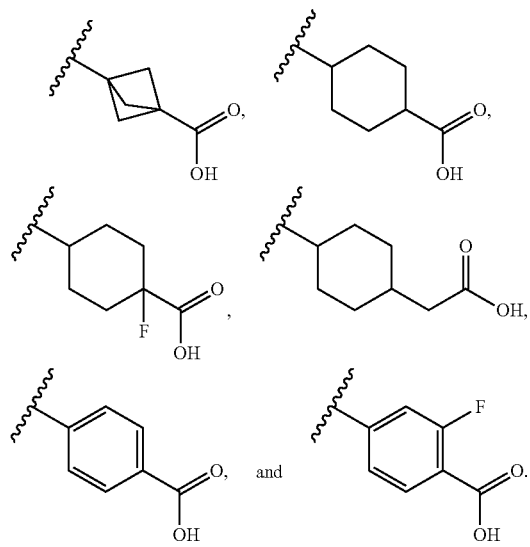

In some embodiments, R$^a$, R$^b$, R$^c$, and R$^d$ are each, independently H or —CH$_3$. In some embodiments, R$^a$, R$^b$, R$^c$, and R$^d$ are each H. In some embodiments, R$^a$, R$^b$, and R$^c$ are each H. In some embodiments, R$^a$ is H. In some embodiments, R$^b$ and R$^c$ are each H. In some embodiments, R$^a$, R$^b$, R$^c$, and R$^d$ are each —CH$_3$. In some preferred embodiments, R$^d$ is —CH$_3$.

In some embodiments, the disclosure relates to a compound of Formula (I):

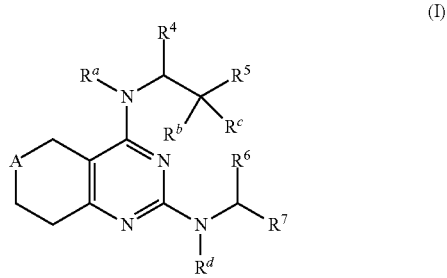

I or a pharmaceutically acceptable salt thereof wherein:
A is CR$^2$R$^3$;
R$^2$ is (C$_6$-C$_{10}$)aryl, wherein the (C$_6$-C$_{10}$)aryl is optionally substituted with one or more (e.g., 1, 2, 3, 4, or 5) substituents independently selected from halo, —CN, —OH, —CO$_2$H, (C$_1$-C$_6$)alkyl and (C$_3$-C$_6$)cycloalkyl;
R$^3$ is H or (C$_1$-C$_6$)alkyl;
R$^4$ is a 5- or 6-membered heteroaryl comprising 1, 2, 3, or 4 heteroatoms selected from N, O, and S, wherein the 5- or 6-membered heteroaryl is optionally substituted with one or more (e.g., 1, 2, 3, 4, or 5) substituents independently selected from halo, —CN, —OH, —CO$_2$H, oxo, (C$_1$-C$_6$)alkyl, (C$_1$-C$_6$)haloalkyl, (C$_3$-C$_6$)cycloalkyl, (C$_3$-C$_6$)cycloalkyl-(C$_1$-C$_6$)alkyl, and (C$_1$-C$_6$)alkyl(C$_3$-C$_6$)cycloalkyl;
R$^5$ is NR$^8$R$^9$;
R$^6$ is selected from H, (C$_1$-C$_6$)alkyl, (C$_3$-C$_6$)cycloalkyl, and (C$_3$-C$_6$)cycloalkyl-(C$_1$-C$_6$)alkyl;
R$^7$ is (C$_3$-C$_6$)cycloalkyl or (C$_6$-C$_{10}$)aryl, wherein the (C$_3$-C$_6$)cycloalkyl and (C$_6$-C$_{10}$)aryl are each optionally substituted with one or more (e.g., 1, 2, 3, 4, or 5) substituents independently selected from halo, —CN, —OH, —CO$_2$H, and HO$_2$C—(C$_1$-C$_6$)alkyl;
R$^8$ and R$^9$ are each, independently H, (C$_1$-C$_6$)alkyl or a 3- to 6-membered heterocycle comprising 1 to 3 heteroatoms selected from N, O, and S; or
R$^8$ and R$^9$ together with the N to which there are bound form a 3- to 10-membered heterocycle optionally comprising 1 or 2 additional heteroatoms selected from N, O, and S, wherein the 3- to 10-membered heterocycle is optionally substituted with one or more (e.g., 1, 2, 3, 4, or 5) substituents independently selected from halo, —CN, —OH, —CO$_2$H, (C$_1$-C$_6$)alkyl, (C$_1$-C$_6$)haloalkyl, (C$_3$-C$_6$)cycloalkyl-(C$_1$-C$_6$)alkyl, (C$_3$-C$_6$)cycloalkyl, (C$_1$-C$_6$)alkyl-O—(C$_1$-C$_6$)alkyl, (C$_1$-C$_6$)hydroxyalkyl, (C$_1$-C$_6$)alkoxy, and a 3- to 7-membered heterocycle comprising 1 to 2 heteroatoms selected from N, O, and S; and
R$^a$, R$^b$, R$^c$, and R$^d$ are each, independently H or (C$_1$-C$_6$)alkyl.

In some embodiments, the disclosure relates to a compound of Formula (I):

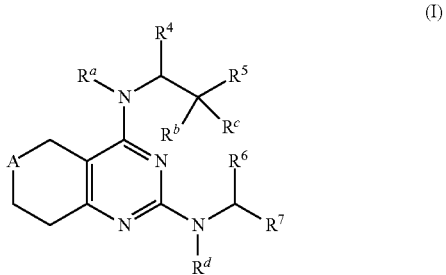

or a pharmaceutically acceptable salt thereof wherein:
A is CR$^2$R$^3$;
R$^2$ is phenyl, wherein the phenyl is optionally substituted with one or more (e.g., 1, 2, 3, 4, or 5) substituents independently selected from halo, —CN, —OH, —CO$_2$H, (C$_1$-C$_6$)alkyl and (C$_3$-C$_6$)cycloalkyl;
R$^3$ is H or (C$_1$-C$_6$)alkyl;
R$^4$ is (C$_6$-C$_{10}$)aryl or a 5- or 6-membered heteroaryl comprising 1, 2, 3, or 4 heteroatoms selected from N, O, and S, wherein the (C$_6$-C$_{10}$)aryl or the 5- or 6-membered heteroaryl are each optionally substituted with one or more (e.g., 1, 2, 3, 4, or 5) substituents independently selected from halo, —CN, —OH, —CO$_2$H, oxo, (C$_1$-C$_6$)alkyl, (C$_1$-C$_6$)haloalkyl, (C$_3$-C$_6$)cycloalkyl, (C$_3$-C$_6$)cycloalkyl-(C$_1$-C$_6$)alkyl, and (C$_1$-C$_6$)alkyl(C$_3$-C$_6$)cycloalkyl;
R$^5$ is NR$^8$R$^9$;
R$^6$ is selected from H, (C$_1$-C$_6$)alkyl, (C$_3$-C$_6$)cycloalkyl, and (C$_3$-C$_6$)cycloalkyl-(C$_1$-C$_6$)alkyl;
R$^7$ is (C$_3$-C$_6$)cycloalkyl or (C$_6$-C$_{10}$)aryl, wherein the (C$_3$-C$_6$)cycloalkyl and (C$_6$-C$_{10}$)aryl are each optionally substituted with one or more (e.g., 1, 2, 3, 4, or 5)

substituents independently selected from halo, —CN, —OH, —CO$_2$H, and HO$_2$C—(C$_1$-C$_6$)alkyl;

R$^8$ and R$^9$ are each, independently H, (C$_1$-C$_6$)alkyl or a 3- to 6-membered heterocycle comprising 1 to 3 heteroatoms selected from N, O, and S; or R$^8$ and R$^9$ together with the N to which there are bound form a 3- to 10-membered heterocycle optionally comprising 1 or 2 additional heteroatoms selected from N, O, and S, wherein the 3- to 10-membered heterocycle is optionally substituted with one or more (e.g., 1, 2, 3, 4, or 5) substituents independently selected from halo, —CN, —OH, —CO$_2$H, (C$_1$-C$_6$)alkyl, (C$_1$-C$_6$)haloalkyl, (C$_3$-C$_6$)cycloalkyl-(C$_1$-C$_6$)alkyl, (C$_3$-C$_6$)cycloalkyl, (C$_1$-C$_6$)alkyl-O—(C$_1$-C$_6$)alkyl, (C$_1$-C$_6$)hydroxyalkyl, (C$_1$-C$_6$)alkoxy, and a 3- to 7-membered heterocycle comprising 1 to 2 heteroatoms selected from N, O, and S; and R$^a$, R$^b$, R$^c$, and R$^d$ are each, independently H or (C$_1$-C$_6$)alkyl.

In some embodiments, the disclosure relates to a compound of Formula (I):

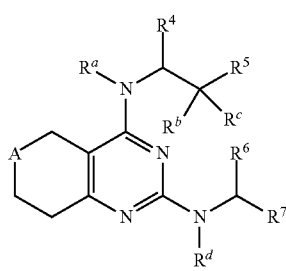

(I)

or a pharmaceutically acceptable salt thereof wherein:

A is CR$^2$R$^3$;

R$^2$ is phenyl, wherein the phenyl is optionally substituted with one or more (e.g., 1, 2, 3, 4, or 5) substituents independently selected from halo, —CN, —OH, —CO$_2$H, (C$_1$-C$_6$)alkyl and (C$_3$-C$_6$)cycloalkyl;

R$^3$ is H or (C$_1$-C$_6$)alkyl;

R$^4$ is (C$_6$-C$_{10}$)aryl or a 5- or 6-membered heteroaryl comprising 1, 2, 3, or 4 heteroatoms selected from N, O, and S, wherein the (C$_6$-C$_{10}$)aryl or the 5- or 6-membered heteroaryl are each optionally substituted with one or more (e.g., 1, 2, 3, 4, or 5) substituents independently selected from halo, —CN, —OH, —CO$_2$H, oxo, (C$_1$-C$_6$)alkyl, (C$_1$-C$_6$)haloalkyl, (C$_3$-C$_6$)cycloalkyl, (C$_3$-C$_6$)cycloalkyl-(C$_1$-C$_6$)alkyl, and (C$_1$-C$_6$)alkyl (C$_3$-C$_6$)cycloalkyl;

R$^5$ is NR$^8$R$^9$;

R$^6$ is selected from H, (C$_1$-C$_6$)alkyl, (C$_3$-C$_6$)cycloalkyl, and (C$_3$-C$_6$)cycloalkyl-(C$_1$-C$_6$)alkyl;

R$^7$ is (C$_3$-C$_6$)cycloalkyl or (C$_6$-C$_{10}$)aryl, wherein the (C$_3$-C$_6$)cycloalkyl and (C$_6$-C$_{10}$)aryl are each optionally substituted with one or more (e.g., 1, 2, 3, 4, or 5) substituents independently selected from halo, —CN, —OH, —CO$_2$H, and HO$_2$C—(C$_1$-C$_6$)alkyl;

R$^8$ and R$^9$ are each, independently H, (C$_1$-C$_6$)alkyl or a 3- to 6-membered heterocycle comprising 1 to 3 heteroatoms selected from N, O, and S; or R$^8$ and R$^9$ together with the N to which there are bound form a 3- to 10-membered heterocycle optionally comprising 1 or 2 additional heteroatoms selected from N, O, and S, wherein the 3- to 10-membered heterocycle is optionally substituted with one or more (e.g., 1, 2, 3, 4, or 5) substituents independently selected from halo, —CN, —OH, —CO$_2$H, (C$_1$-C$_6$)alkyl, (C$_1$-C$_6$)haloalkyl, (C$_3$-C$_6$)cycloalkyl-(C$_1$-C$_6$)alkyl, (C$_3$-C$_6$)cycloalkyl, (C$_1$-C$_6$)alkyl-O—(C$_1$-C$_6$)alkyl, (C$_1$-C$_6$)hydroxyalkyl, (C$_1$-C$_6$)alkoxy, and a 3- to 7-membered heterocycle comprising 1 to 2 heteroatoms selected from N, O, and S; and R$^a$, R$^b$, R$^c$, and R$^d$ are each, independently H or (C$_1$-C$_6$)alkyl.

In some embodiments, the disclosure relates to a compound of Formula (I):

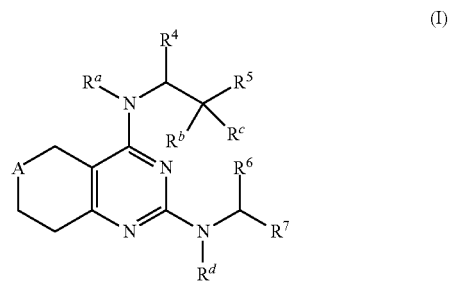

(I)

or a pharmaceutically acceptable salt thereof wherein:

A is NR$^1$;

R$^1$ is (C$_6$-C$_{10}$)aryl, wherein the (C$_6$-C$_{10}$)aryl is optionally substituted with one or more (e.g., 1, 2, 3, 4, or 5) substituents independently selected from halo, —CN, —OH, —CO$_2$H, (C$_1$-C$_6$)alkyl and (C$_3$-C$_6$)cycloalkyl;

R$^3$ is H or (C$_1$-C$_6$)alkyl;

R$^4$ is (C$_6$-C$_{10}$)aryl or a 5- or 6-membered heteroaryl comprising 1, 2, 3, or 4 heteroatoms selected from N, O, and S, wherein the (C$_6$-C$_{10}$)aryl is optionally substituted with one or more (e.g., 1, 2, 3, 4, or 5) substituents independently selected from halo, —CN, —OH, —CO$_2$H, and (C$_1$-C$_6$)alkyl and the 5- or 6-membered heteroaryl is optionally substituted with one or more (e.g., 1, 2, 3, 4, or 5) substituents independently selected from halo, —CN, —OH, —CO$_2$H, oxo, (C$_1$-C$_6$)alkyl, (C$_1$-C$_6$)haloalkyl, (C$_3$-C$_6$)cycloalkyl, (C$_3$-C$_6$)cycloalkyl-(C$_1$-C$_6$)alkyl, and (C$_1$-C$_6$)alkyl (C$_3$-C$_6$)cycloalkyl;

R$^5$ is NR$^8$R$^9$;

R$^6$ is selected from (C$_1$-C$_6$)alkyl, (C$_3$-C$_6$)cycloalkyl, and (C$_3$-C$_6$)cycloalkyl-(C$_1$-C$_6$)alkyl;

R$^7$ is (C$_3$-C$_6$)cycloalkyl or (C$_6$-C$_{10}$)aryl, wherein the (C$_3$-C$_6$)cycloalkyl and (C$_6$-C$_{10}$)aryl are each optionally substituted with one or more (e.g., 1, 2, 3, 4, or 5) substituents independently selected from halo, —CO$_2$H, and HO$_2$C—(C$_1$-C$_6$)alkyl;

R$^8$ and R$^9$ together with the N to which there are bound form a 3- to 10-membered heterocycle optionally comprising 1 or 2 additional heteroatoms selected from N, O, and S, wherein the 3- to 10-membered heterocycle is optionally substituted with one or more (e.g., 1, 2, 3, 4, or 5) substituents independently selected from halo, —CN, —OH, —CO$_2$H, (C$_1$-C$_6$)alkyl, (C$_1$-C$_6$)haloalkyl, (C$_3$-C$_6$)cycloalkyl-(C$_1$-C$_6$)alkyl, (C$_3$-C$_6$)cycloalkyl, (C$_1$-C$_6$)alkyl-O—(C$_1$-C$_6$)alkyl, (C$_1$-C$_6$)hydroxyalkyl, (C$_1$-C$_6$)alkoxy, and a 3- to 7-membered heterocycle comprising 1 to 2 heteroatoms selected from N, O, and S; and R$^a$, R$^b$, R$^c$, and R$^d$ are each, independently H or (C$_1$-C$_6$)alkyl.

In certain embodiments, the compound is a compound or a pharmaceutically acceptable salt thereof selected from:

| Cmp # | Structure | Name |
|---|---|---|
| 1 | 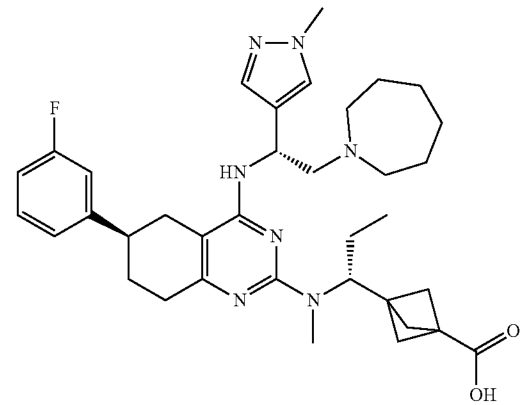 [SMILES: CC[C@@H](N(C)c1nc2c(c(N[C@@H](CN3CCCCCC3)c3cnn(C)c3)n1)C[C@H](c1cccc(F)c1)CC2)C12CC(C(=O)O)(C1)C2] | 3-((R)-1-(((R)-4-(((R)-2-(azepan-1-yl)-1-(1-methyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |
| 2 | 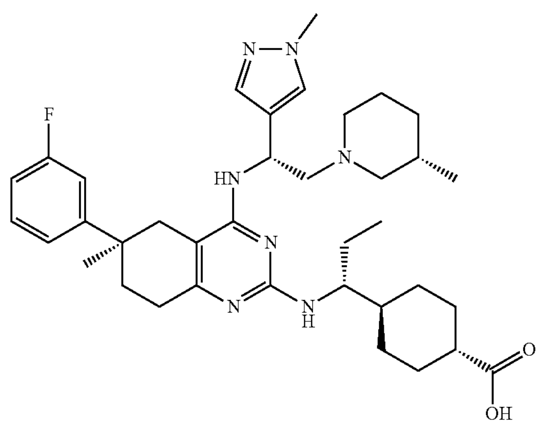 [SMILES: CC[C@@H](Nc1nc2c(c(N[C@@H](CN3CCC[C@H](C)C3)c3cnn(C)c3)n1)C[C@](C)(c1cccc(F)c1)CC2)[C@H]1CC[C@H](C(=O)O)CC1] | (1R,4r)-4-((R)-1-(((R)-6-(3-fluorophenyl)-6-methyl-4-(((R)-1-(1-methyl-1H-pyrazol-4-yl)-2-((S)-3-methylpiperidin-1-yl)ethyl)amino)-5,6,7,8-tetrahydroquinazolin-2-yl)amino)propyl)cyclohexane-1-carboxylic acid |
| 3 | 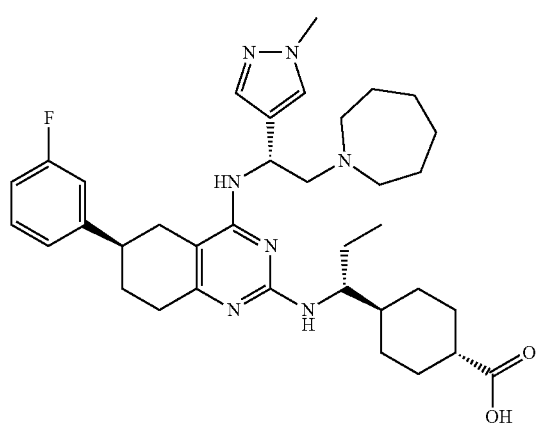 [SMILES: CC[C@@H](Nc1nc2c(c(N[C@@H](CN3CCCCCC3)c3cnn(C)c3)n1)C[C@H](c1cccc(F)c1)CC2)[C@H]1CC[C@H](C(=O)O)CC1] | (1R,4r)-4-((R)-1-(((R)-4-(((R)-2-(azepan-1-yl)-1-(1-methyl-1H-pyrazol-4-yl)ethyl)amino)-6-(3-fluorophenyl)-5,6,7,8-tetrahydroquinazolin-2-yl)amino)propyl)cyclohexane-1-carboxylic acid |

| Cmp # | Structure | Name |
|---|---|---|
| 4 | 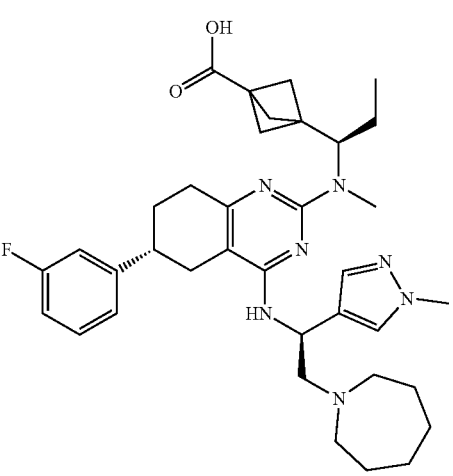 [SMILES: CC[C@@H](N(C)c1nc2c(c(N[C@H](CN3CCCCCC3)c3cnn(C)c3)n1)C[C@H](c1cccc(F)c1)CC2)C12CC(C(=O)O)(C1)C2] | 3-((R)-1-(((R)-4-(((S)-2-(azepan-1-yl)-1-(1-methyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |
| 5 | 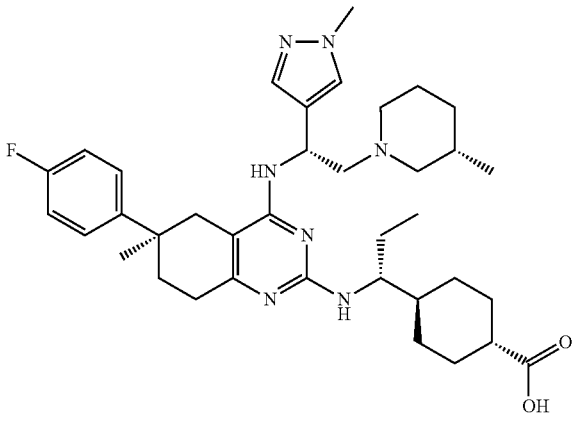 [SMILES: CC[C@@H](Nc1nc2c(c(N[C@@H](CN3CCC[C@H](C)C3)c3cnn(C)c3)n1)C[C@](C)(c1ccc(F)cc1)CC2)[C@H]1CC[C@H](C(=O)O)CC1] | (1R,4r)-4-((R)-1-(((R)-6-(4-fluorophenyl)-6-methyl-4-(((R)-1-(1-methyl-1H-pyrazol-4-yl)-2-((S)-3-methylpiperidin-1-yl)ethyl)amino)-5,6,7,8-tetrahydroquinazolin-2-yl)amino)propyl)cyclohexane-1-carboxylic acid |
| 6 | 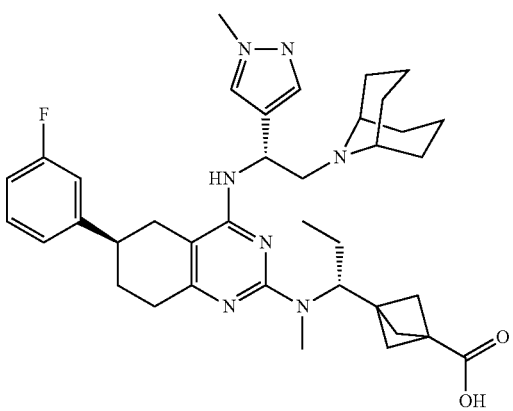 | 3-((R)-1-(((R)-4-(((R)-2-((1S,5S)-9-azabicyclo[3.3.1]nonan-9-yl)-1-(1-methyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |

-continued

| Cmp # | Structure | Name |
|---|---|---|
| 7 | 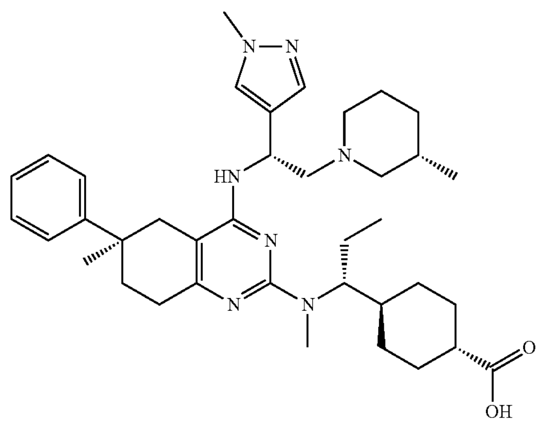 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@](C)(c1ccccc1)CC2] | (1R,4r)-4-((R)-1-(methyl((R)-6-methyl-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid |
| 8 | 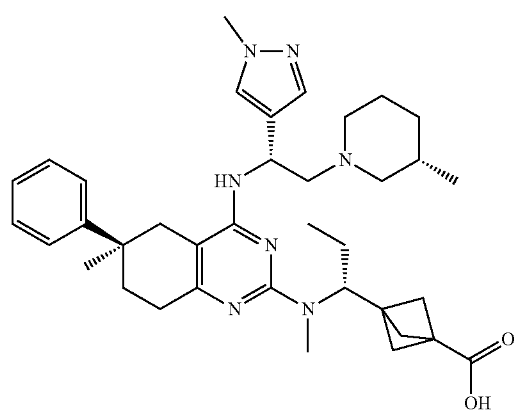 [SMILES: CC[C@@H](N(C)c1nc2c(c(N[C@@H](CN3CCC[C@H](C)C3)c3cnn(C)c3)n1)C[C@](C)(c1ccccc1)CC2)C12CC(C(=O)O)(C1)C2] | 3-((R)-1-(methyl((R)-6-methyl-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)bicyclo[1.1.1]pentane-1-carboxylic acid |
| 9 | 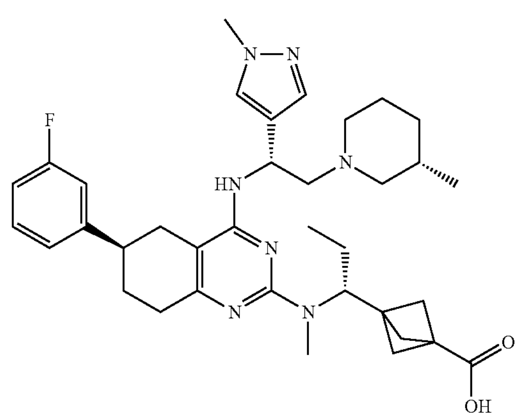 [SMILES: CC[C@@H](N(C)c1nc2c(c(N[C@@H](CN3CCC[C@H](C)C3)c3cnn(C)c3)n1)C[C@H](c1cccc(F)c1)CC2)C12CC(C(=O)O)(C1)C2] | 3-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)bicyclo[1.1.1]pentane-1-carboxylic acid |

-continued

| Cmp # | Structure | Name |
|---|---|---|
| 10 | 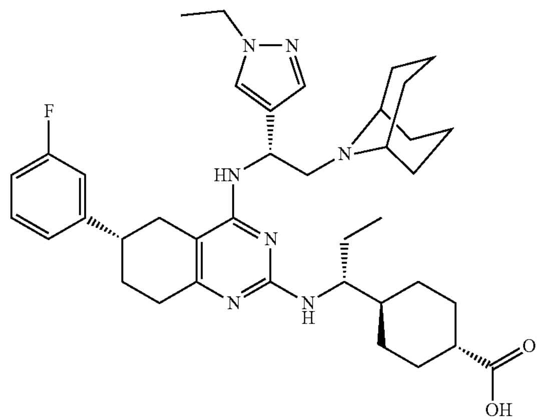 [SMILES: CC[C@@H](Nc1nc2c(c(N[C@@H](CN3C4CCCC3CCC4)c3cnn(CC)c3)n1)C[C@@H](c1cccc(F)c1)CC2)[C@H]1CC[C@H](C(=O)O)CC1] | (1R,4r)-4-((R)-1-(((S)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)amino)propyl)cyclohexane-1-carboxylic acid |
| 11 | 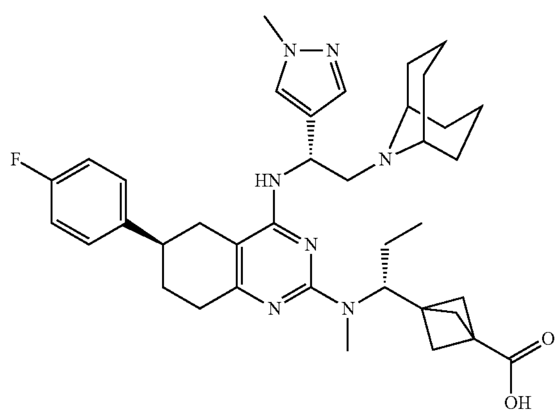 [SMILES: CC[C@@H](N(C)c1nc2c(c(N[C@@H](CN3C4CCCC3CCC4)c3cnn(C)c3)n1)C[C@H](c1ccc(F)cc1)CC2)C12CC(C(=O)O)(C1)C2] | 3-((R)-1-(((R)-4-(((R)-2-((1S,5S)-9-azabicyclo[3.3.1]nonan-9-yl)-1-(1-methyl-1H-pyrazol-4-yl)ethyl)amino)-6-(4-fluorophenyl)-5,6,7,8-tetrahydroquinazolin-2-yl)(methyl)amino)propyl)bicyclo[1.1.1]pentane-1-carboxylic acid |
| 12 | 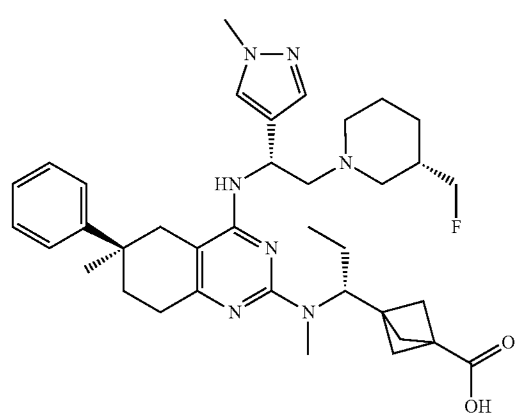 [SMILES: CC[C@@H](N(C)c1nc2c(c(N[C@@H](CN3CCC[C@H](CF)C3)c3cnn(C)c3)n1)C[C@](C)(c1ccccc1)CC2)C12CC(C(=O)O)(C1)C2] | 3-((R)-1-(((R)-4-(((R)-2-((S)-3-(fluoromethyl)piperidin-1-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid |

| Cmp # | Structure | Name |
|---|---|---|
| 13 | 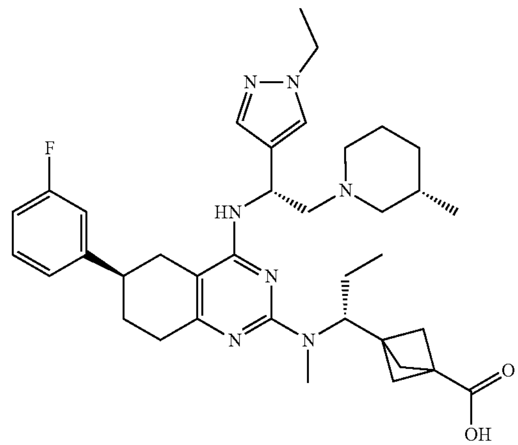 [SMILES: CC[C@@H](N(C)c1nc2c(c(N[C@@H](CN3CCC[C@H](C)C3)c3cnn(CC)c3)n1)C[C@H](c1cccc(F)c1)CC2)C12CC(C(=O)O)(C1)C2] | 3-((R)-1-(((R)-4-(((R)-1-(1-ethyl-1H-pyrazol-4-yl)-2-((S)-3-methylpiperidin-1-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |
| 14 | 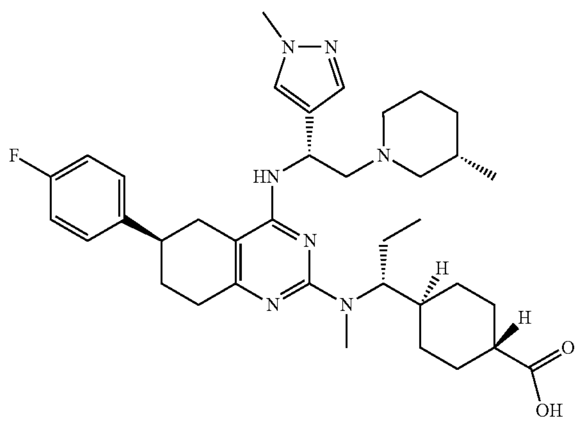 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@H](c1ccc(F)cc1)CC2] | (1R,4r)-4-((R)-1-(((R)-6-(4-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid |
| 15 | 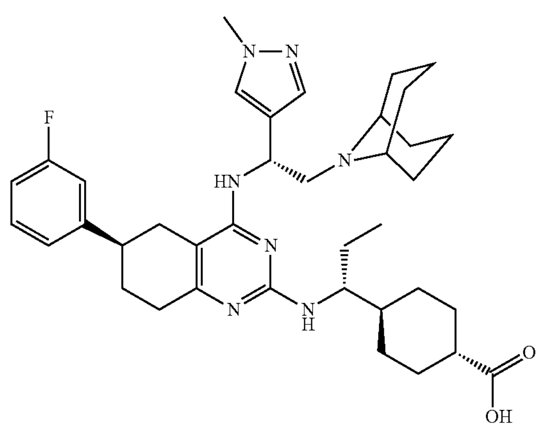 [SMILES: CC[C@@H](Nc1nc2c(c(N[C@@H](CN3C4CCCC3CCC4)c3cnn(C)c3)n1)C[C@H](c1cccc(F)c1)CC2)[C@H]1CC[C@H](C(=O)O)CC1] | (1R,4r)-4-((R)-1-(((R)-4-(((R)-2-((1S,5S)-9-azabicyclo[3.3.1]nonan-9-yl)-1-(1-methyl-1H-pyrazol-4-yl)ethyl)amino)-6-(3-fluorophenyl)-5,6,7,8-tetrahydroquinazolin-2-yl)amino)propyl)cyclohexane-1-carboxylic acid |

-continued

| Cmp # | Structure | Name |
|---|---|---|
| 16 | 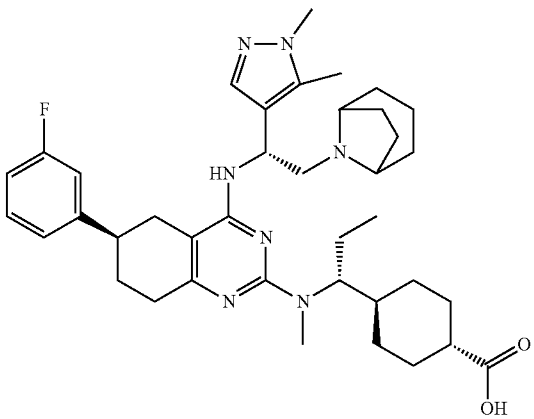 [SMILES: CC[C@H]([C@H]1CC[C@H](C(=O)O)CC1)N(C)c1nc2c(c(N[C@@H](CN3C4CCCC3CC4)c3cnn(C)c3C)n1)C[C@H](c1cccc(F)c1)CC2] | (1R,4r)-4-((1R)-1-(((6R)-4-(((1R)-2-(8-azabicyclo[3.2.1]octan-8-yl)-1-(1,5-dimethyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |
| 17 | 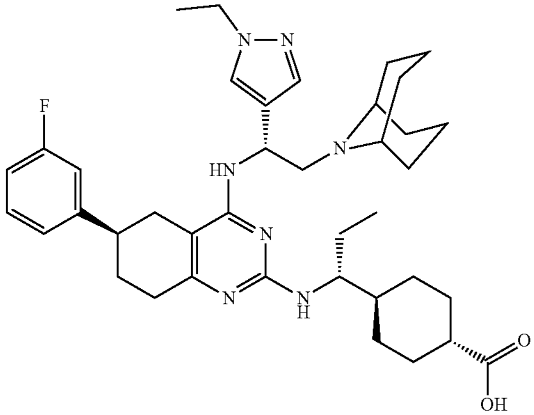 [SMILES: CC[C@@H](Nc1nc2c(c(N[C@@H](CN3C4CCCC3CCC4)c3cnn(CC)c3)n1)C[C@H](c1cccc(F)c1)CC2)[C@H]1CC[C@H](C(=O)O)CC1] | (1R,4r)-4-((R)-1-(((R)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)amino)propyl)cyclohexane-1-carboxylic acid |
| 18 | 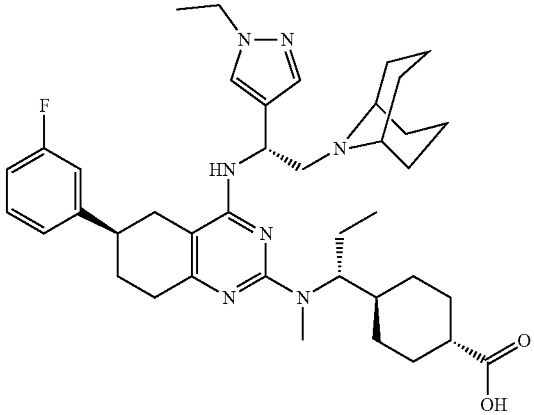 [SMILES: CC[C@H]([C@H]1CC[C@H](C(=O)O)CC1)N(C)c1nc2c(c(N[C@@H](CN3C4CCCC3CCC4)c3cnn(CC)c3)n1)C[C@H](c1cccc(F)c1)CC2] | (1R,4r)-4-((R)-1-(((R)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |

| Cmp # | Structure | Name |
|---|---|---|
| 19 | 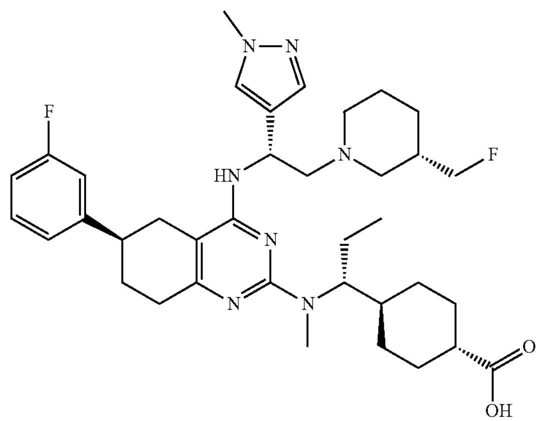 [SMILES: CC[C@H]([C@H]1CC[C@H](C(=O)O)CC1)N(C)c1nc2c(c(N[C@@H](CN3CCC[C@H](CF)C3)c3cnn(C)c3)n1)C[C@H](c1cccc(F)c1)CC2] | (1R,4r)-4-((R)-1-(((R)-4-(((R)-2-((S)-3-(fluoromethyl)piperidin-1-yl)-1-(1-methyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |
| 20 | 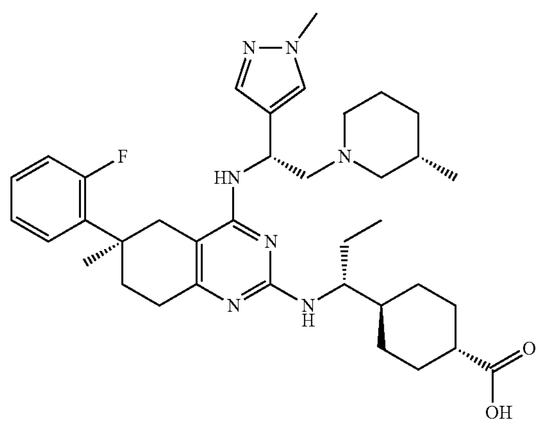 [SMILES: CC[C@@H](Nc1nc2c(c(N[C@@H](CN3CCC[C@H](C)C3)c3cnn(C)c3)n1)C[C@](C)(c1ccccc1F)CC2)[C@H]1CC[C@H](C(=O)O)CC1] | (1R,4r)-4-((R)-1-(((R)-6-(2-fluorophenyl)-6-methyl-4-(((R)-1-(1-methyl-1H-pyrazol-4-yl)-2-((S)-3-methylpiperidin-1-yl)ethyl)amino)-5,6,7,8-tetrahydroquinazolin-2-yl)amino)propyl)cyclohexane-1-carboxylic acid |
| 21 | 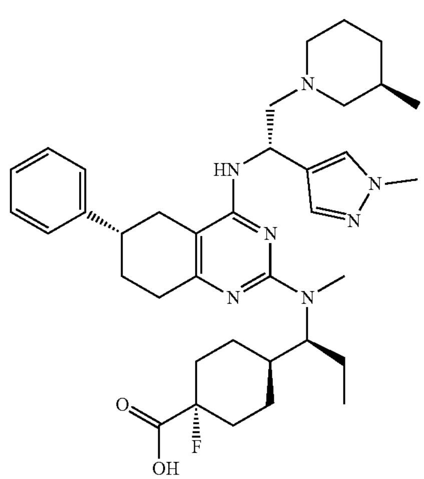 [SMILES: CC[C@@H]([C@H]1CC[C@@](F)(C(=O)O)CC1)N(C)c1nc2c(c(N[C@H](CN3CCC[C@@H](C)C3)c3cnn(C)c3)n1)C[C@@H](c1ccccc1)CC2] | (1S,4r)-1-fluoro-4-((S)-1-(methyl((S)-4-(((S)-1-(1-methyl-1H-pyrazol-4-yl)-2-((R)-3-methylpiperidin-1-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 22 | 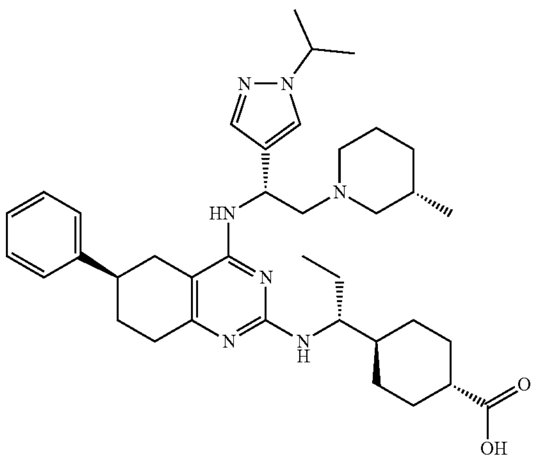 [SMILES: CC[C@@H](Nc1nc2c(c(N[C@@H](CN3CCC[C@H](C)C3)c3cnn(C(C)C)c3)n1)C[C@H](c1ccccc1)CC2)[C@H]1CC[C@H](C(=O)O)CC1] | (1R,4r)-4-((R)-1-(((R)-4-(((R)-1-(1-isopropyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid |
| 23 | 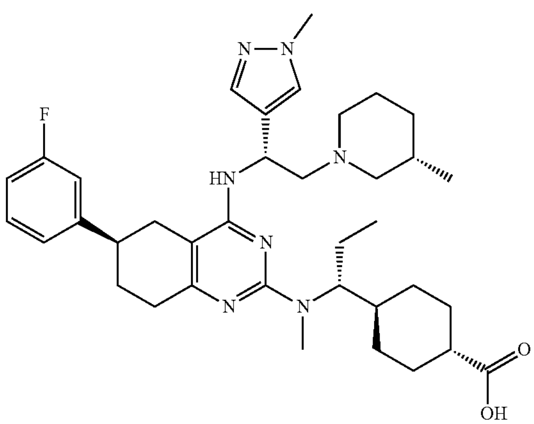 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@H](c1cccc(F)c1)CC2] | (1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid |
| 24 | 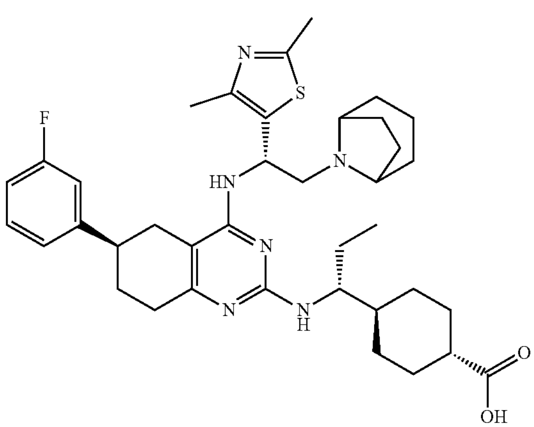 [SMILES: CC[C@@H](Nc1nc2c(c(N[C@@H](CN3C4CCCC3CC4)c3sc(C)nc3C)n1)C[C@H](c1cccc(F)c1)CC2)[C@H]1CC[C@H](C(=O)O)CC1] | (1R,4r)-4-((1R)-1-(((6R)-4-(((1S)-2-(8-azabicyclo[3.2.1]octan-8-yl)-1-(2,4-dimethylthiazol-5-yl)ethyl)amino)-6-(3-fluorophenyl)-5,6,7,8-tetrahydroquinazolin-2-yl)amino)propyl)cyclohexane-1-carboxylic acid |

-continued

| Cmp # | Structure | Name |
|---|---|---|
| 25 | 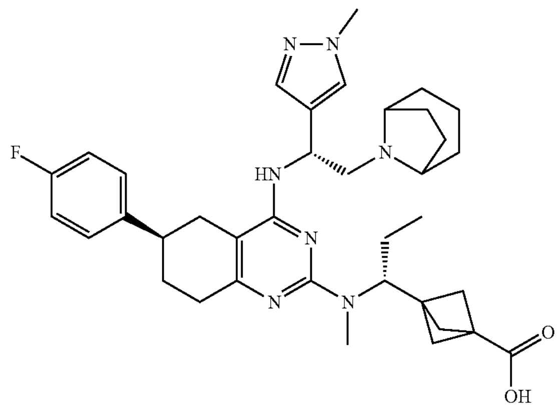 [SMILES: CC[C@@H](N(C)c1nc2c(c(N[C@@H](CN3C4CCCC3CC4)c3cnn(C)c3)n1)C[C@H](c1ccc(F)cc1)CC2)C12CC(C(=O)O)(C1)C2] | 3-(((1R)-1-(((6R)-4-(((1R)-2-(8-azabicyclo[3.2.1]octan-8-yl)-1-(1-methyl-1H-pyrazol-4-yl)ethyl)amino)-6-(4-fluorophenyl)-5,6,7,8-tetrahydroquinazolin-2-yl)(methyl)amino)propyl)bicyclo[1.1.1]pentane-1-carboxylic acid |
| 26 | 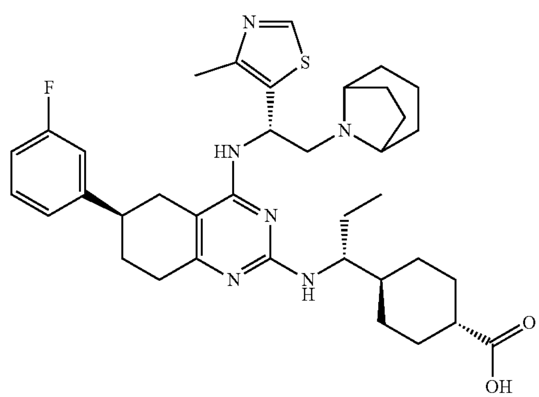 [SMILES: CC[C@@H](Nc1nc2c(c(N[C@@H](CN3C4CCCC3CC4)c3scnc3C)n1)C[C@H](c1cccc(F)c1)CC2)[C@H]1CC[C@H](C(=O)O)CC1] | (1R,4r)-4-(((1R)-1-(((6R)-4-(((1S)-2-(8-azabicyclo[3.2.1]octan-8-yl)-1-(4-methylthiazol-5-yl)ethyl)amino)-6-(3-fluorophenyl)-5,6,7,8-tetrahydroquinazolin-2-yl)amino)propyl)cyclohexane-1-carboxylic acid |
| 27 | 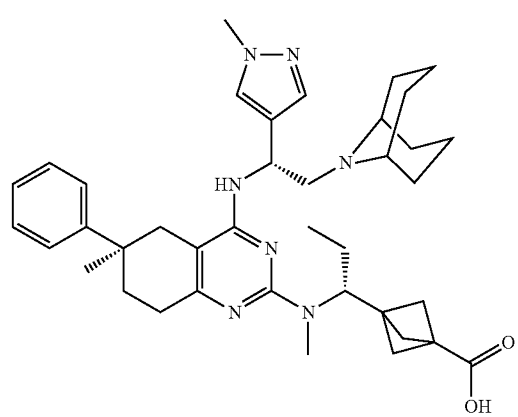 [SMILES: CC[C@@H](N(C)c1nc2c(c(N[C@@H](CN3C4CCCC3CCC4)c3cnn(C)c3)n1)C[C@](C)(c1ccccc1)CC2)C12CC(C(=O)O)(C1)C2] | 3-(((R)-1-(((R)-4-(((R)-2-((1S,5S)-9-azabicyclo[3.3.1]nonan-9-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid |

| Cmp # | Structure | Name |
|---|---|---|
| 28 | 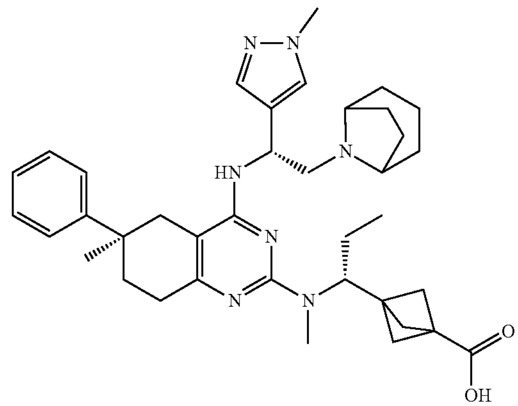 [SMILES: CC[C@@H](N(C)c1nc2c(c(N[C@@H](CN3C4CCCC3CC4)c3cnn(C)c3)n1)C[C@](C)(c1ccccc1)CC2)C12CC(C(=O)O)(C1)C2] | 3-((1R)-1-(((6R)-4-(((1R)-2-(8-azabicyclo[3.2.1]octan-8-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid |
| 29 | 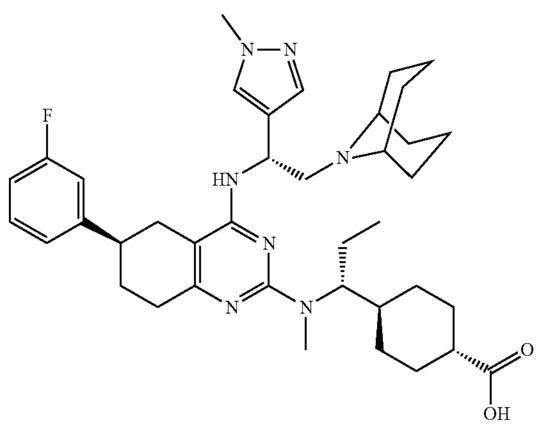 [SMILES: CC[C@H]([C@H]1CC[C@H](C(=O)O)CC1)N(C)c1nc2c(c(N[C@@H](CN3C4CCCC3CCC4)c3cnn(C)c3)n1)C[C@H](c1cccc(F)c1)CC2] | (1R,4r)-4-((R)-1-(((R)-4-(((R)-2-((1S,5S)-9-azabicyclo[3.3.1]nonan-9-yl)-1-(1-methyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |
| 30 | 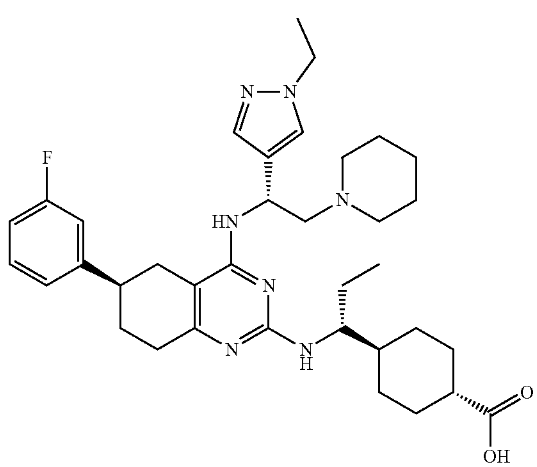 [SMILES: CC[C@@H](Nc1nc2c(c(N[C@@H](CN3CCCCC3)c3cnn(CC)c3)n1)C[C@H](c1cccc(F)c1)CC2)[C@H]1CC[C@H](C(=O)O)CC1] | (1R,4r)-4-((R)-1-(((R)-4-(((R)-1-(1-ethyl-1H-pyrazol-4-yl)-2-(piperidin-1-yl)ethyl)amino)-6-(3-fluorophenyl)-5,6,7,8-tetrahydroquinazolin-2-yl)amino)propyl)cyclohexane-1-carboxylic acid |

-continued

| Cmp # | Structure | Name |
|---|---|---|
| 31 | 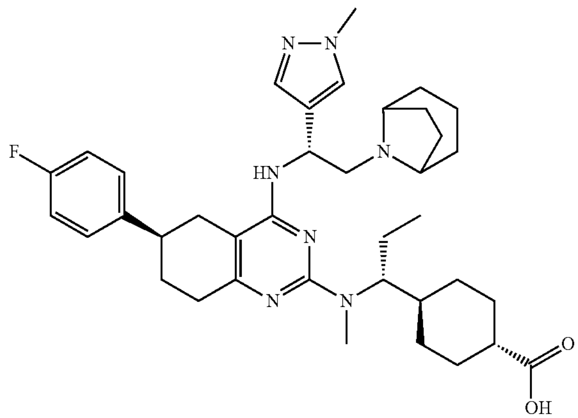 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@H](c1ccc(F)cc1)CC2] | (1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-(4-fluorophenyl)-5,6,7,8-tetrahydroquinazolin-2-yl)(methyl)amino)propyl)cyclohexane-1-carboxylic acid |
| 32 | 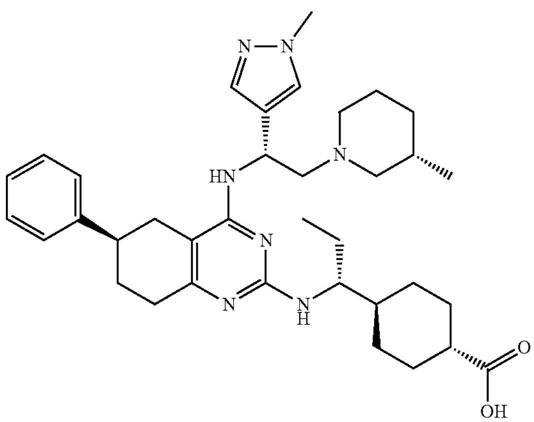 [SMILES: CC[C@@H](Nc1nc2c(c(N[C@@H](CN3CCC[C@H](C)C3)c3cnn(C)c3)n1)C[C@H](c1ccccc1)CC2)[C@H]1CC[C@H](C(=O)O)CC1] | (1R,4r)-4-((R)-1-(((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid |
| 33 | 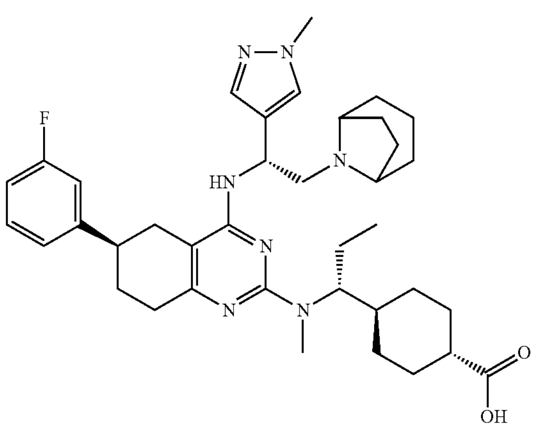 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@H](c1cccc(F)c1)CC2] | (1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |

-continued

| Cmp # | Structure | Name |
|---|---|---|
| 34 | 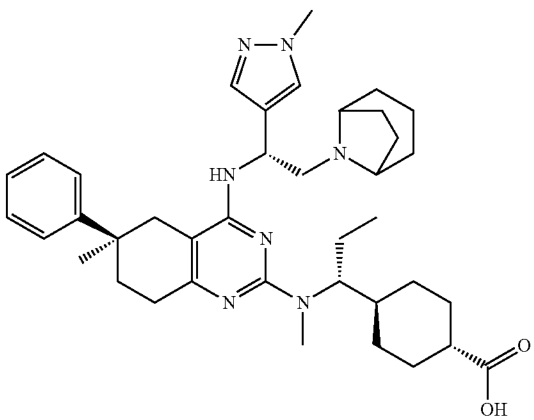 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@](C)(c1ccccc1)CC2] | (1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-methyl-6-phenyl-5,6,7,8-tetrahydroquinazolin-2-yl)(methyl)amino)propyl)cyclohexane-1-carboxylic acid |
| 35 | 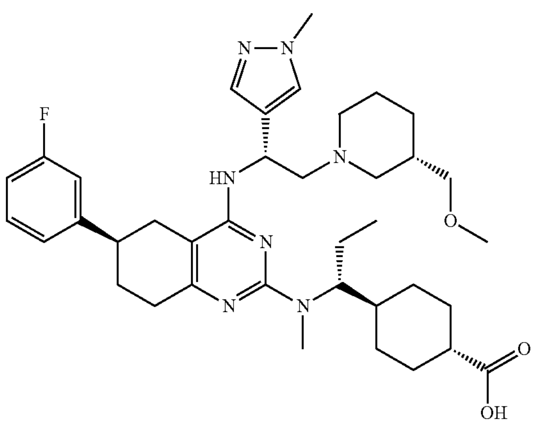 [SMILES: CC[C@H]([C@H]1CC[C@H](C(=O)O)CC1)N(C)c1nc2c(c(N[C@@H](CN3CCC[C@H](COC)C3)c3cnn(C)c3)n1)C[C@H](c1cccc(F)c1)CC2] | (1R,4r)-4-((R)-1-(((R)-6-(3-fluorophenyl)-4-(((R)-2-((S)-3-(methoxymethyl)piperidin-1-yl)-1-(1-methyl-1H-pyrazol-4-yl)ethyl)amino)-5,6,7,8-tetrahydroquinazolin-2-yl)(methyl)amino)propyl)cyclohexane-1-carboxylic acid |
| 36 | 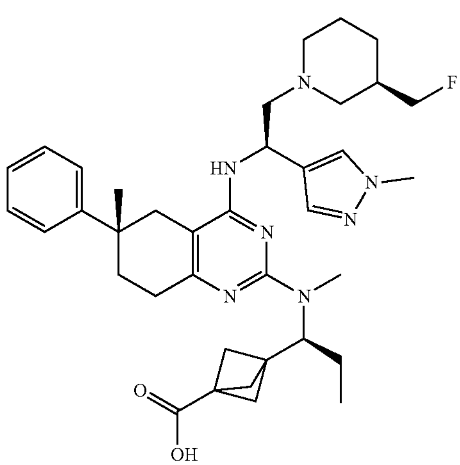 [SMILES: CC[C@H](N(C)c1nc2c(c(N[C@@H](CN3CCC[C@@H](CF)C3)c3cnn(C)c3)n1)C[C@@](C)(c1ccccc1)CC2)C12CC(C(=O)O)(C1)C2] | 3-((S)-1-(((S)-4-(((R)-2-((R)-3-(fluoromethyl)piperidin-1-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid |

| Cmp # | Structure | Name |
|---|---|---|
| 37 | 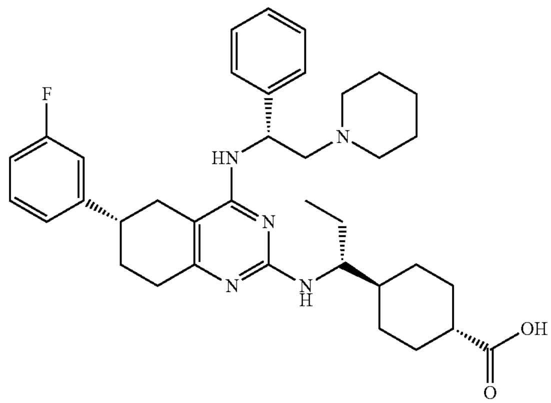 [SMILES: CC[C@@H](Nc1nc2c(c(N[C@@H](CN3CCCCC3)c3ccccc3)n1)C[C@@H](c1cccc(F)c1)CC2)[C@H]1CC[C@H](C(=O)O)CC1] | (1R,4r)-4-((R)-1-(((S)-6-(3-fluorophenyl)-4-(((R)-1-phenyl-2-(piperidin-1-yl)ethyl)amino)-5,6,7,8-tetrahydroquinazolin-2-yl)amino)propyl)cyclohexane-1-carboxylic acid |
| 38 | 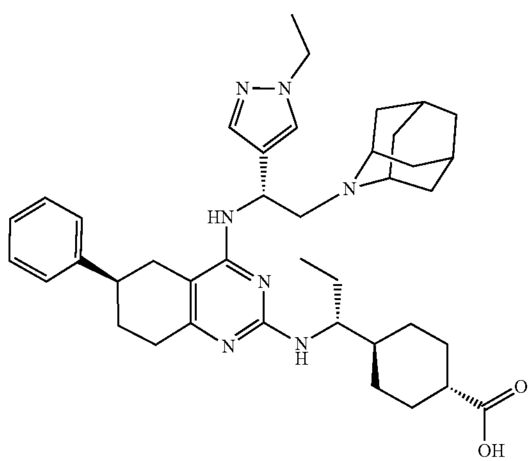 [SMILES: CC[C@@H](Nc1nc2c(c(N[C@@H](CN3C4CC5CC(C4)CC3C5)c3cnn(CC)c3)n1)C[C@H](c1ccccc1)CC2)[C@H]1CC[C@H](C(=O)O)CC1] | (1R,4r)-4-((R)-1-(((R)-4-(((R)-2-((1R,3R,5R,7R)-2-azaadamantan-2-yl)-1-(1-ethyl-1H-pyrazol-4-yl)ethyl)amino)-6-phenyl-5,6,7,8-tetrahydroquinazolin-2-yl)amino)propyl)cyclohexane-1-carboxylic acid |
| 39 | 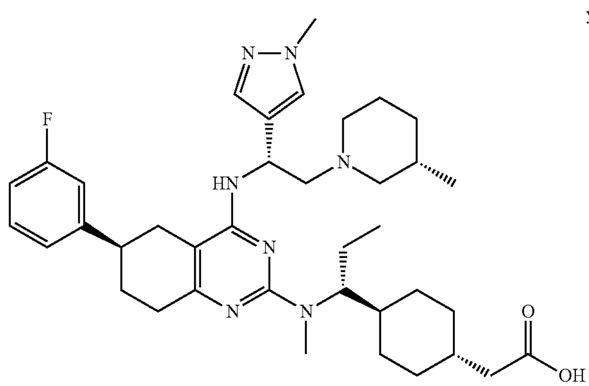 | 2-((1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexyl)acetic acid |

| Cmp # | Structure | Name |
|---|---|---|
| 40 | 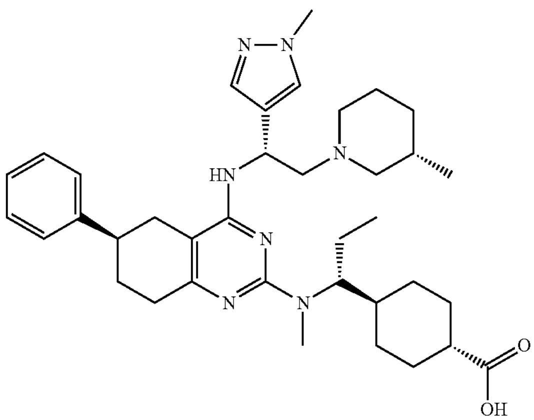 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@H](c1ccccc1)CC2] | (1R,4r)-4-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid |
| 41 | 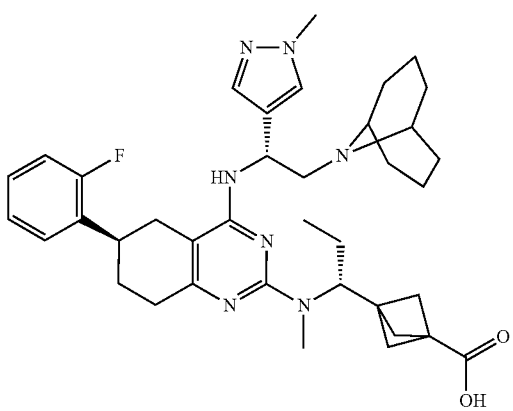 | 3-((R)-1-(((R)-4-(((R)-2-(9-azabicyclo[3.3.1]nonan-9-yl)-1-(1-methyl-1H-pyrazol-4-yl)ethyl)amino)-6-(2-fluorophenyl)-5,6,7,8-tetrahydroquinazolin-2-yl)(methyl)amino)propyl)bicyclo[1.1.1]pentane-1-carboxylic acid |
| 42 | 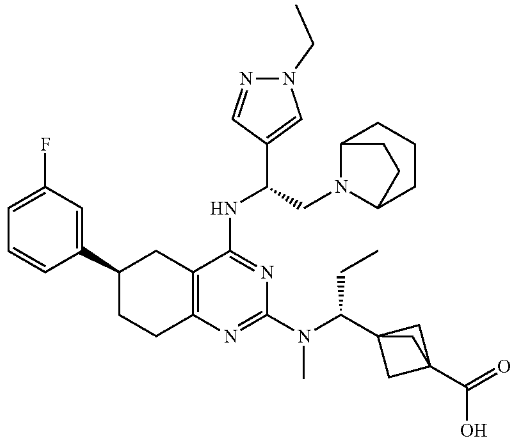 [SMILES: CC[C@@H](N(C)c1nc2c(c(N[C@@H](CN3C4CCCC3CC4)c3cnn(CC)c3)n1)C[C@H](c1cccc(F)c1)CC2)C12CC(C(=O)O)(C1)C2] | 3-((1R)-1-(((6R)-4-(((1R)-2-(8-azabicyclo[3.2.1]octan-8-yl)-1-(1-ethyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |

-continued

| Cmp # | Structure | Name |
|---|---|---|
| 43 | 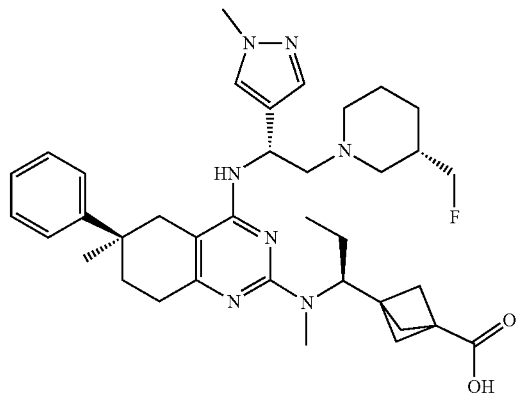 [SMILES: CC[C@H](N(C)c1nc2c(c(N[C@@H](CN3CCC[C@H](CF)C3)c3cnn(C)c3)n1)C[C@](C)(c1ccccc1)CC2)C12CC(C(=O)O)(C1)C2] | 3-((S)-1-(((R)-4-(((R)-2-((S)-3-(fluoromethyl)piperidin-1-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid |
| 44 | 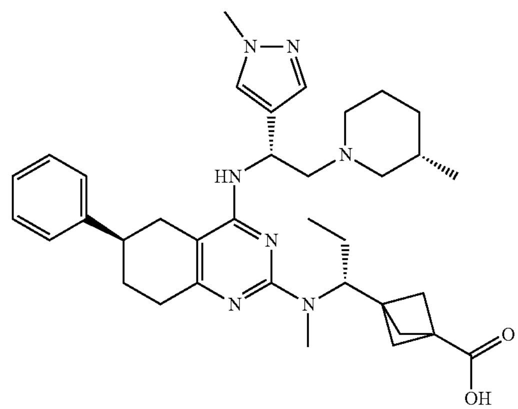 [SMILES: CC[C@@H](N(C)c1nc2c(c(N[C@@H](CN3CCC[C@H](C)C3)c3cnn(C)c3)n1)C[C@H](c1ccccc1)CC2)C12CC(C(=O)O)(C1)C2] | 3-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)bicyclo[1.1.1]pentane-1-carboxylic acid |
| 45 | 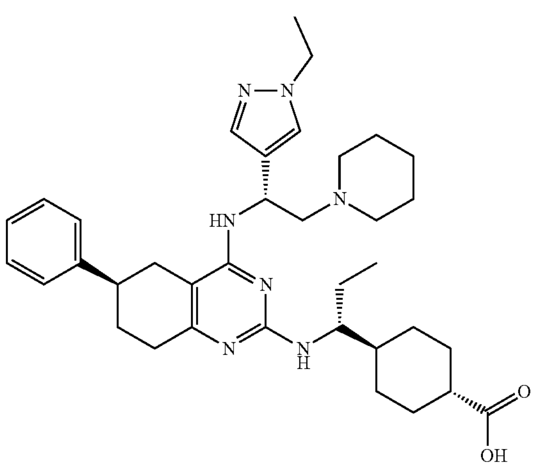 [SMILES: CC[C@@H](Nc1nc2c(c(N[C@@H](CN3CCCCC3)c3cnn(CC)c3)n1)C[C@H](c1ccccc1)CC2)[C@H]1CC[C@H](C(=O)O)CC1] | (1R,4r)-4-((R)-1-(((R)-4-(((R)-1-(1-ethyl-1H-pyrazol-4-yl)-2-(piperidin-1-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 46 | 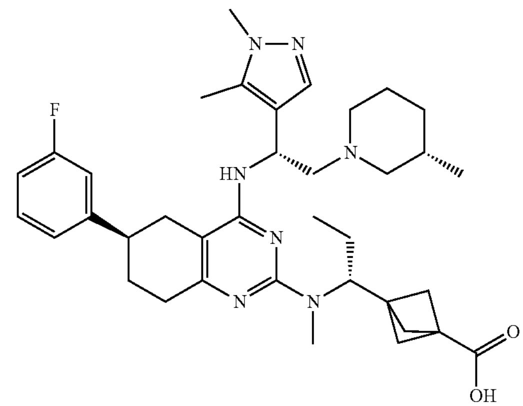 [SMILES: CC[C@@H](N(C)c1nc2c(c(N[C@@H](CN3CCC[C@H](C)C3)c3cnn(C)c3C)n1)C[C@H](c1cccc(F)c1)CC2)C12CC(C(=O)O)(C1)C2] | 3-(R)-1-(R)-4-(R)-1-(1,5-dimethyl-1H-pyrazol-4-yl)-2-((S)-3-methylpiperidin-1-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |
| 47 | 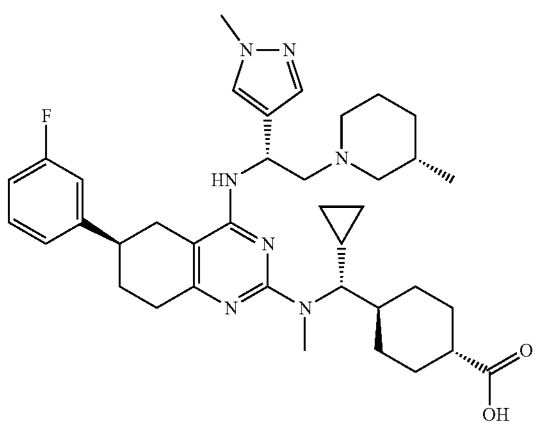 [SMILES: C[C@H]1CCCN(C[C@H](Nc2nc(N(C)[C@H](C3CC3)[C@H]3CC[C@H](C(=O)O)CC3)nc3c2C[C@H](c2cccc(F)c2)CC3)c2cnn(C)c2)C1] | (1R,4r)-4-((R)-cyclopropyl(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)methyl)cyclohexane-1-carboxylic acid |
| 48 | 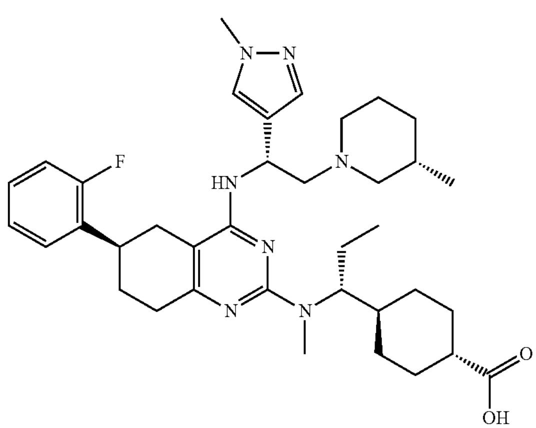 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@H](c1ccccc1F)CC2] | (1R,4r)-4-((R)-1-(((R)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid |

| Cmp # | Structure | Name |
|---|---|---|
| 49 | 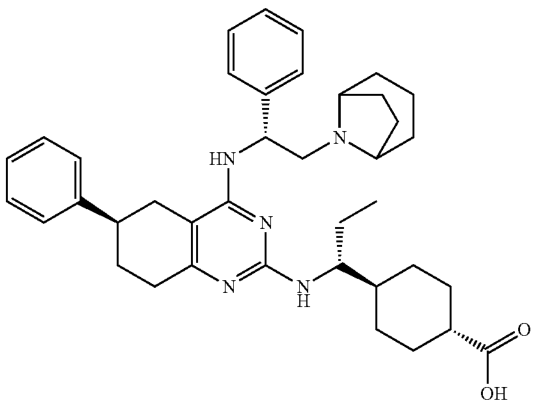 [SMILES: CC[C@@H](Nc1nc2c(c(N[C@@H](CN3C4CCCC3CC4)c3ccccc3)n1)C[C@H](c1ccccc1)CC2)[C@H]1CC[C@H](C(=O)O)CC1] | (1R,4r)-4-((1R)-1-(((6R)-4-(((1R)-2-(8-azabicyclo[3.2.1]octan-8-yl)-1-phenylethyl)amino)-6-phenyl-5,6,7,8-tetrahydroquinazolin-2-yl)amino)propyl)cyclohexane-1-carboxylic acid |
| 50 | 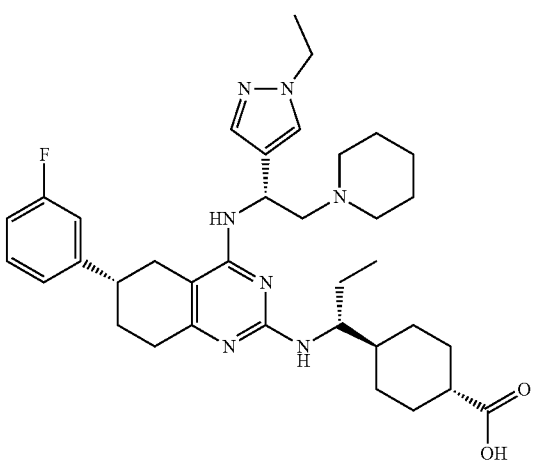 [SMILES: CC[C@@H](Nc1nc2c(c(N[C@@H](CN3CCCCC3)c3cnn(CC)c3)n1)C[C@@H](c1cccc(F)c1)CC2)[C@H]1CC[C@H](C(=O)O)CC1] | (1R,4r)-4-((R)-1-(((S)-4-(((R)-1-(1-ethyl-1H-pyrazol-4-yl)-2-(piperidin-1-yl)ethyl)amino)-6-(3-fluorophenyl)-5,6,7,8-tetrahydroquinazolin-2-yl)amino)propyl)cyclohexane-1-carboxylic acid |
| 51 | 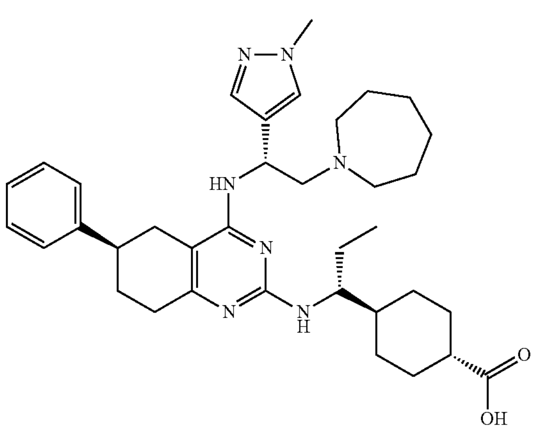 [SMILES: CC[C@@H](Nc1nc2c(c(N[C@@H](CN3CCCCCC3)c3cnn(C)c3)n1)C[C@H](c1ccccc1)CC2)[C@H]1CC[C@H](C(=O)O)CC1] | (1R,4r)-4-((R)-1-(((R)-4-(((R)-2-(azepan-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |

-continued

| Cmp # | Structure | Name |
|---|---|---|
| 52 | 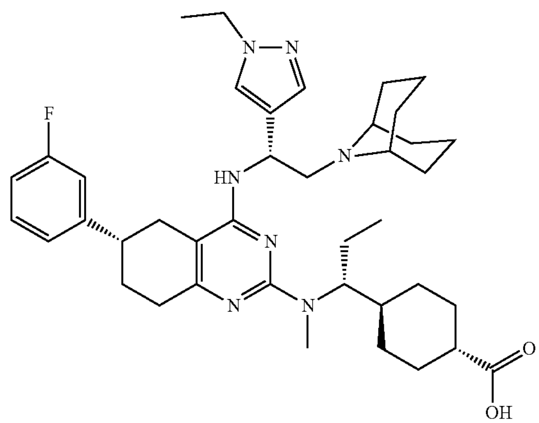 [SMILES: CC[C@H]([C@H]1CC[C@H](C(=O)O)CC1)N(C)c1nc2c(c(N[C@@H](CN3C4CCCC3CCC4)c3cnn(CC)c3)n1)C[C@@H](c1cccc(F)c1)CC2] | (1R,4r)-4-((R)-1-(((S)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |
| 53 | 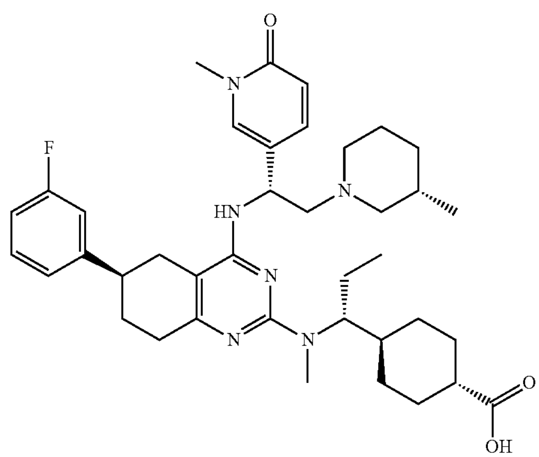 [SMILES: CC[C@H]([C@H]1CC[C@H](C(=O)O)CC1)N(C)c1nc2c(c(N[C@@H](CN3CCC[C@H](C)C3)c3ccc(=O)n(C)c3)n1)C[C@H](c1cccc(F)c1)CC2] | (1R,4r)-4-((R)-1-(((R)-6-(3-fluorophenyl)-4-(((R)-1-(1-methyl-6-oxo-1,6-dihydropyridin-3-yl)-2-((S)-3-methylpiperidin-1-yl)ethyl)amino)-5,6,7,8-tetrahydroquinazolin-2-yl)(methyl)amino)propyl)cyclohexane-1-carboxylic acid |
| 54 | 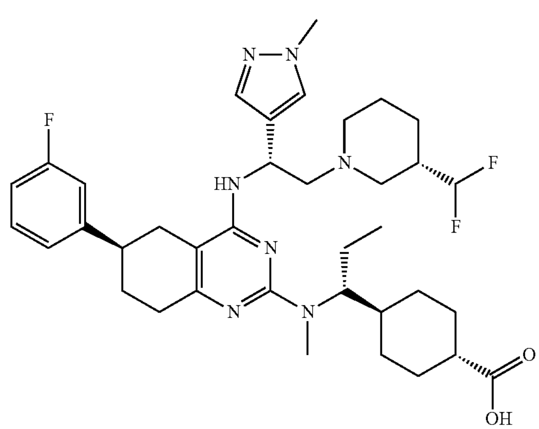 [SMILES: CC[C@H]([C@H]1CC[C@H](C(=O)O)CC1)N(C)c1nc2c(c(N[C@@H](CN3CCC[C@H](C(F)F)C3)c3cnn(C)c3)n1)C[C@H](c1cccc(F)c1)CC2] | (1R,4r)-4-((R)-1-(((R)-4-(((R)-2-((S)-3-(difluoromethyl)piperidin-1-yl)-1-(1-methyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |

| Cmp # | Structure | Name |
|---|---|---|
| 55 | 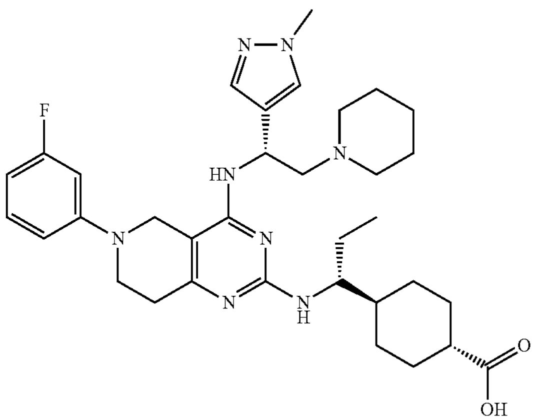 [SMILES: CC[C@@H](Nc1nc2c(c(N[C@@H](CN3CCCCC3)c3cnn(C)c3)n1)CN(c1cccc(F)c1)CC2)[C@H]1CC[C@H](C(=O)O)CC1] | (1R,4r)-4-((R)-1-((6-(3-fluorophenyl)-4-(((R)-1-(1-methyl-1H-pyrazol-4-yl)-2-(piperidin-1-yl)ethyl)amino)-5,6,7,8-tetrahydropyrido[4,3-d]pyrimidin-2-yl)amino)propyl)cyclohexane-1-carboxylic acid |
| 56 | 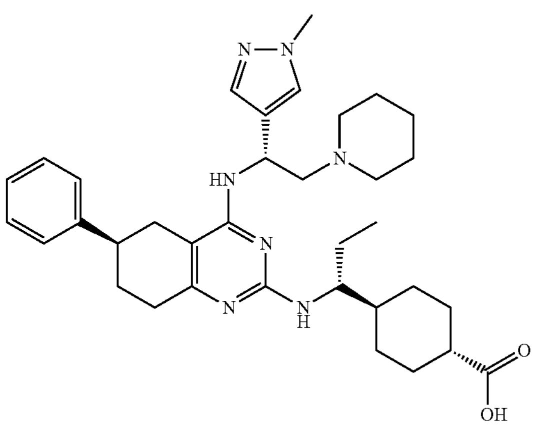 | (1R,4r)-4-((R)-1-(((R)-4-(((R)-1-(1-methyl-1H-pyrazol-4-yl)-2-(piperidin-1-yl)ethyl)amino)-6-phenyl-5,6,7,8-tetrahydroquinazolin-2-yl)amino)propyl)cyclohexane-1-carboxylic acid |
| 57 | 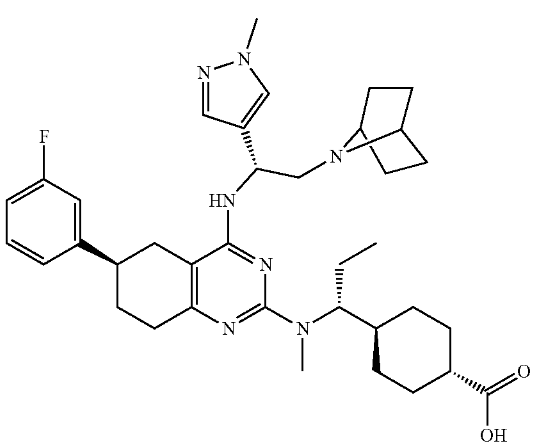 [SMILES: CC[C@H]([C@H]1CC[C@H](C(=O)O)CC1)N(C)c1nc2c(c(N[C@@H](CN3C4CCC3CC4)c3cnn(C)c3)n1)C[C@H](c1cccc(F)c1)CC2] | (1R,4r)-4-((R)-1-(((R)-4-(((R)-2-(7-azabicyclo[2.2.1]heptan-7-yl)-1-(1-methyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |

| Cmp # | Structure | Name |
|---|---|---|
| 58 | 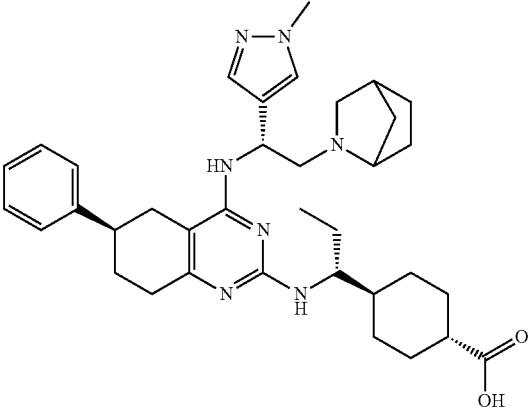 [SMILES: CC[C@@H](Nc1nc2c(c(N[C@@H](CN3CC4CCC3C4)c3cnn(C)c3)n1)C[C@H](c1ccccc1)CC2)[C@H]1CC[C@H](C(=O)O)CC1] | (1R,4r)-4-((1R)-1-(((6R)-4-(((1R)-2-(2-azabicyclo[2.2.1]heptan-2-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |
| 59 | 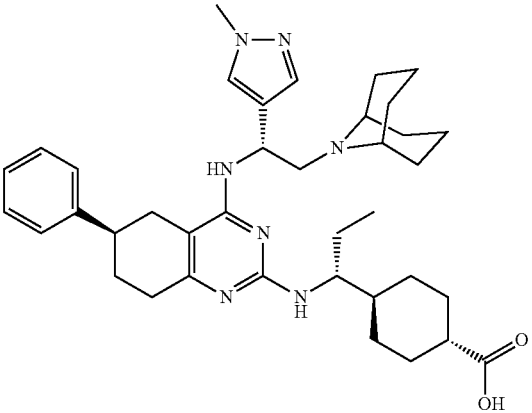 [SMILES: CC[C@@H](Nc1nc2c(c(N[C@@H](CN3C4CCCC3CCC4)c3cnn(C)c3)n1)C[C@H](c1ccccc1)CC2)[C@H]1CC[C@H](C(=O)O)CC1] | (1R,4r)-4-((R)-1-(((R)-4-(((R)-2-((1S,5S)-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |
| 60 | 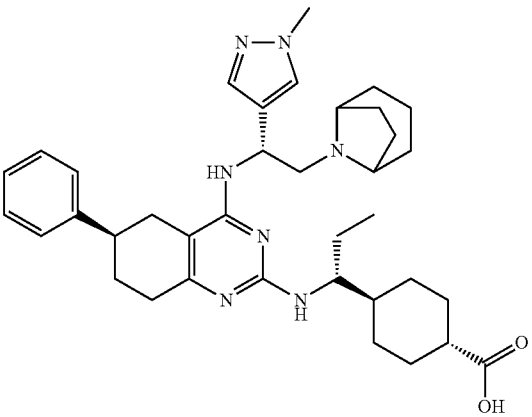 [SMILES: CC[C@@H](Nc1nc2c(c(N[C@@H](CN3C4CCCC3CC4)c3cnn(C)c3)n1)C[C@H](c1ccccc1)CC2)[C@H]1CC[C@H](C(=O)O)CC1] | (1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 61 | 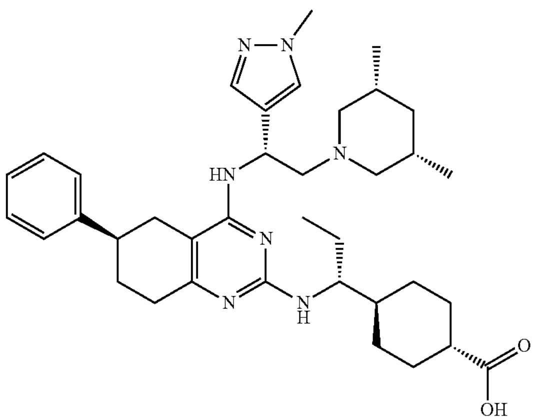 [SMILES: CC[C@@H](Nc1nc2c(c(N[C@@H](CN3C[C@H](C)C[C@H](C)C3)c3cnn(C)c3)n1)C[C@H](c1ccccc1)CC2)[C@H]1CC[C@H](C(=O)O)CC1] | (1R,4r)-4-((R)-1-(((R)-4-(((R)-2-((3S,5R)-3,5-dimethylpiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |
| 62 | 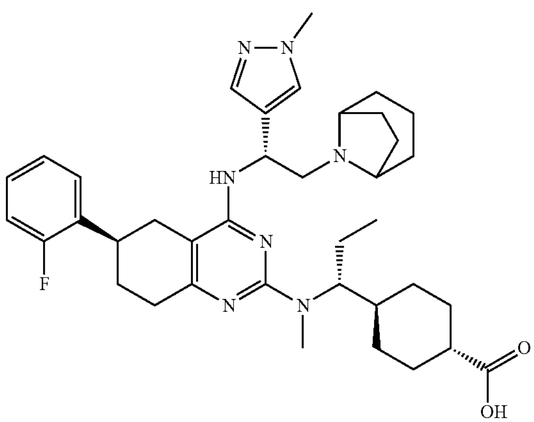 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@H](c1ccccc1F)CC2] | (1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-(2-fluorophenyl)-5,6,7,8-tetrahydroquinazolin-2-yl)(methyl)amino)propyl)cyclohexane-1-carboxylic acid |
| 63 | 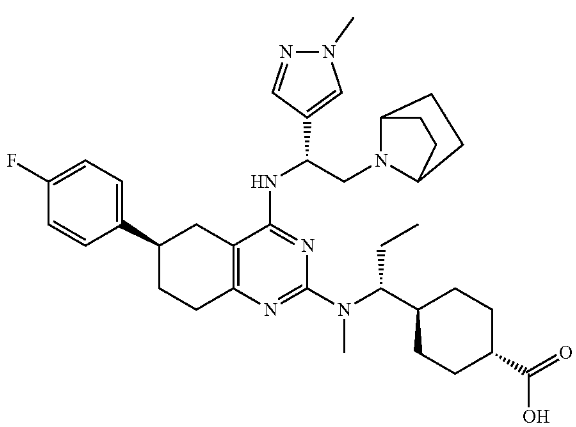 [SMILES: CC[C@H]([C@H]1CC[C@H](C(=O)O)CC1)N(C)c1nc2c(c(N[C@@H](CN3C4CCC3CC4)c3cnn(C)c3)n1)C[C@H](c1ccc(F)cc1)CC2] | (1R,4r)-4-((R)-1-(((R)-4-(((R)-2-(7-azabicyclo[2.2.1]heptan-7-yl)-1-(1-methyl-1H-pyrazol-4-yl)ethyl)amino)-6-(4-fluorophenyl)-5,6,7,8-tetrahydroquinazolin-2-yl)(methyl)amino)propyl)cyclohexane-1-carboxylic acid |

-continued

| Cmp # | Structure | Name |
|---|---|---|
| 64 | 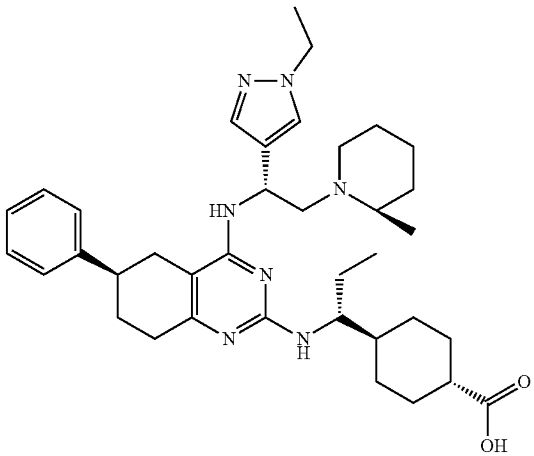 [SMILES: CC[C@@H](Nc1nc2c(c(N[C@@H](CN3CCCC[C@H]3C)c3cnn(CC)c3)n1)C[C@H](c1ccccc1)CC2)[C@H]1CC[C@H](C(=O)O)CC1] | (1R,4r)-4-((R)-1-(((R)-4-(((R)-1-(1-ethyl-1H-pyrazol-4-yl)-2-((R)-2-methylpiperidin-1-yl)ethyl)amino)-6-phenyl-5,6,7,8-tetrahydroquinazolin-2-yl)amino)propyl)cyclohexane-1-carboxylic acid |
| 65 | 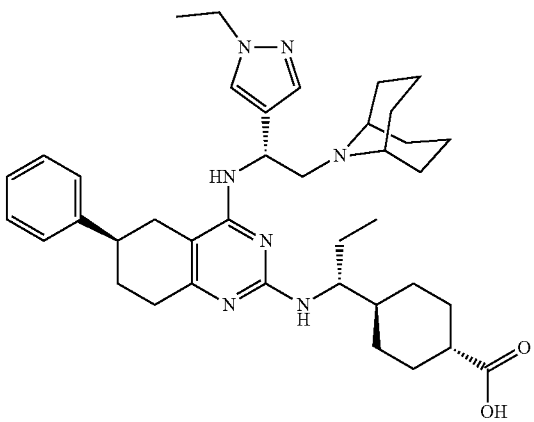 [SMILES: CC[C@@H](Nc1nc2c(c(N[C@@H](CN3C4CCCC3CCC4)c3cnn(CC)c3)n1)C[C@H](c1ccccc1)CC2)[C@H]1CC[C@H](C(=O)O)CC1] | (1R,4r)-4-((R)-1-(((R)-4-(((R)-2-((1S,5S)-9-azabicyclo[3.3.1]nonan-9-yl)-1-(1-ethyl-1H-pyrazol-4-yl)ethyl)amino)-6-phenyl-5,6,7,8-tetrahydroquinazolin-2-yl)amino)propyl)cyclohexane-1-carboxylic acid |
| 66 | 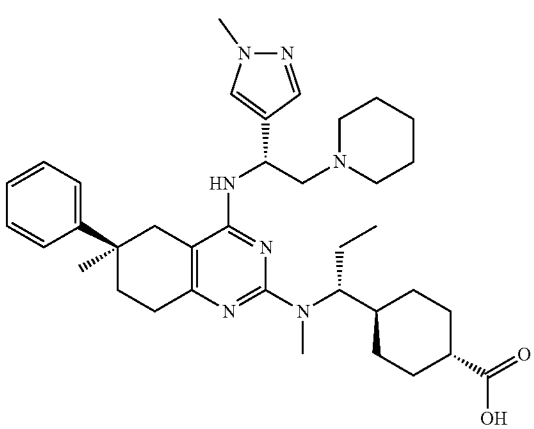 [SMILES: CC[C@H]([C@H]1CC[C@H](C(=O)O)CC1)N(C)c1nc2c(c(N[C@@H](CN3CCCCC3)c3cnn(C)c3)n1)C[C@](C)(c1ccccc1)CC2] | (1R,4r)-4-((R)-1-(methyl((R)-6-methyl-4-(((R)-1-(1-methyl-1H-pyrazol-4-yl)-2-(piperidin-1-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 67 | 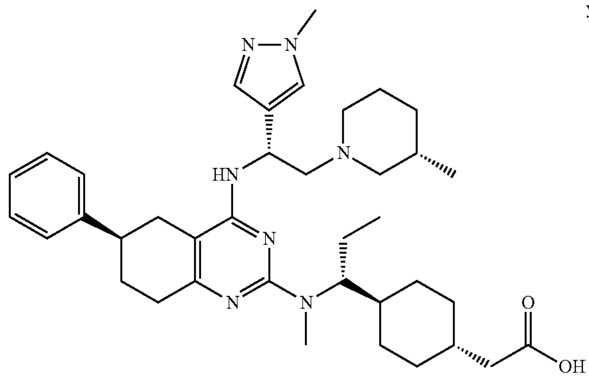 | 2-((1R,4r)-4-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexyl)acetic acid |
| 68 | 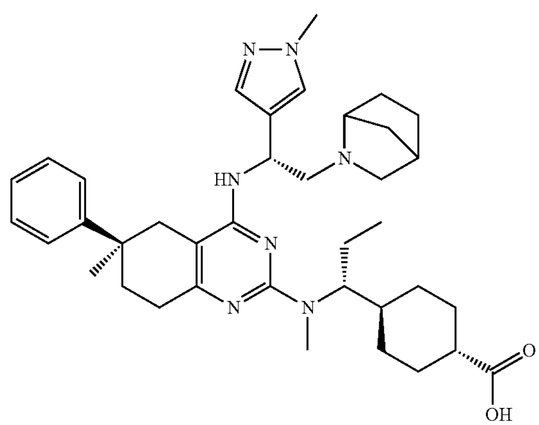 [SMILES: CC[C@H]([C@H]1CC[C@H](C(=O)O)CC1)N(C)c1nc2c(c(N[C@@H](CN3CC4CCC3C4)c3cnn(C)c3)n1)C[C@](C)(c1ccccc1)CC2] | (1R,4r)-4-((1R)-1-(((6R)-4-(((1R)-2-(2-azabicyclo[2.2.1]heptan-2-yl)-1-(1-methyl-1H-pyrazol-4-yl)ethyl)amino)-6-methyl-6-phenyl-5,6,7,8-tetrahydroquinazolin-2-yl)(methyl)amino)propyl)cyclohexane-1-carboxylic acid |
| 69 | 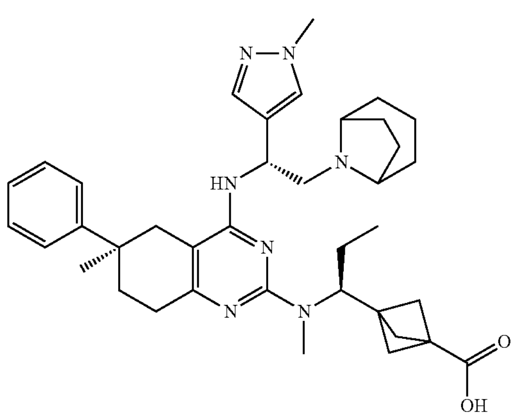 [SMILES: CC[C@H](N(C)c1nc2c(c(N[C@@H](CN3C4CCCC3CC4)c3cnn(C)c3)n1)C[C@](C)(c1ccccc1)CC2)C12CC(C(=O)O)(C1)C2] | 3-((1S)-1-(((6R)-4-(((1R)-2-(8-azabicyclo[3.2.1]octan-8-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid |

| Cmp # | Structure | Name |
|---|---|---|
| 70 | 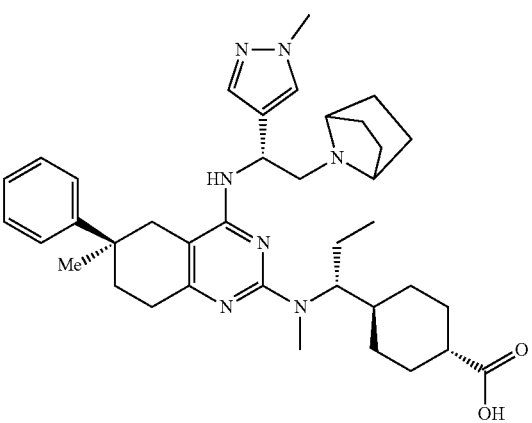 [SMILES: CC[C@H]([C@H]1CC[C@H](C(=O)O)CC1)N(C)c1nc2c(c(N[C@@H](CN3C4CCC3CC4)c3cnn(C)c3)n1)C[C@](C)(c1ccccc1)CC2] | (1R,4r)-4-((R)-1-(((R)-4-(((R)-2-(7-azabicyclo[2.2.1]heptan-7-yl)-1-(1-methyl-1H-pyrazol-4-yl)ethyl)amino)-6-methyl-6-phenyl-5,6,7,8-tetrahydroquinazolin-2-yl)(methyl)amino)propyl)cyclohexane-1-carboxylic acid |
| 71 | 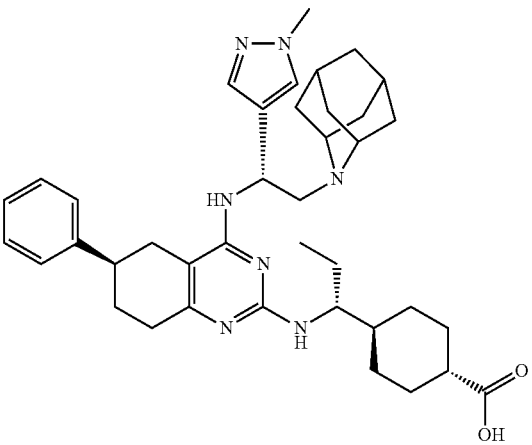 [SMILES: CC[C@@H](Nc1nc2c(c(N[C@@H](CN3C4CC5CC(C4)CC3C5)c3cnn(C)c3)n1)C[C@H](c1ccccc1)CC2)[C@H]1CC[C@H](C(=O)O)CC1] | (1R,4r)-4-((R)-1-(((R)-4-(((R)-2-((5R,7R)-2-azaadamantan-2-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |
| 72 | 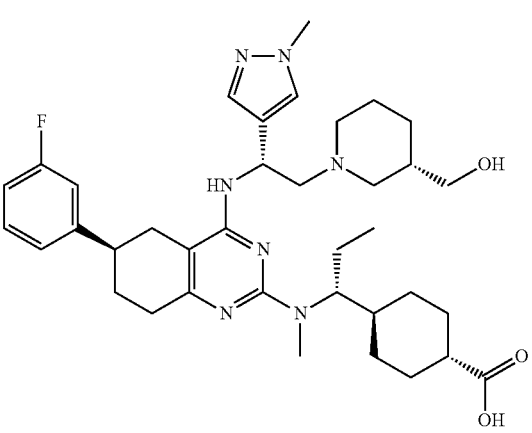 [SMILES: CC[C@H]([C@H]1CC[C@H](C(=O)O)CC1)N(C)c1nc2c(c(N[C@@H](CN3CCC[C@H](CO)C3)c3cnn(C)c3)n1)C[C@H](c1cccc(F)c1)CC2] | (1R,4r)-4-((R)-1-(((R)-6-(3-fluorophenyl)-4-(((R)-2-((S)-3-(hydroxymethyl)piperidin-1-yl)-1-(1-methyl-1H-pyrazol-4-yl)ethyl)amino)-5,6,7,8-tetrahydroquinazolin-2-yl)(methyl)amino)propyl)cyclohexane-1-carboxylic acid |

| Cmp # | Structure | Name |
|---|---|---|
| 73 | 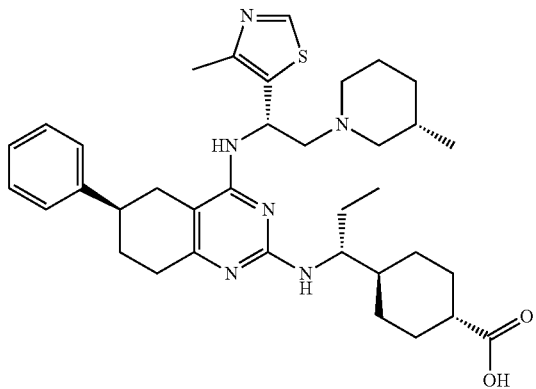 [SMILES: CC[C@@H](Nc1nc2c(c(N[C@@H](CN3CCC[C@H](C)C3)c3scnc3C)n1)C[C@H](c1ccccc1)CC2)[C@H]1CC[C@H](C(=O)O)CC1] | (1R,4r)-4-((R)-1-(((R)-4-(((S)-2-((S)-3-methylpiperidin-1-yl)-1-(4-methylthiazol-5-yl)ethyl)amino)-6-phenyl-5,6,7,8-tetrahydroquinazolin-2-yl)amino)propyl)cyclohexane-1-carboxylic acid |
| 74 | 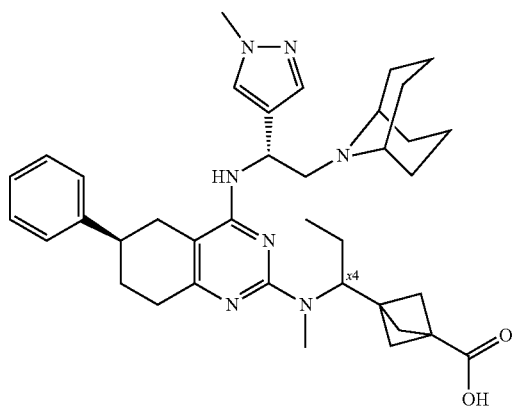 [SMILES: CCC(N(C)c1nc2c(c(N[C@@H](CN3C4CCCC3CCC4)c3cnn(C)c3)n1)C[C@H](c1ccccc1)CC2)C12CC(C(=O)O)(C1)C2] | 3-(1-(((R)-4-(((R)-2-((1S,5S)-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)(methyl)amino)-1l3-propyl)bicyclo[1.1.1]pentane-1-carboxylic acid |
| 75 | 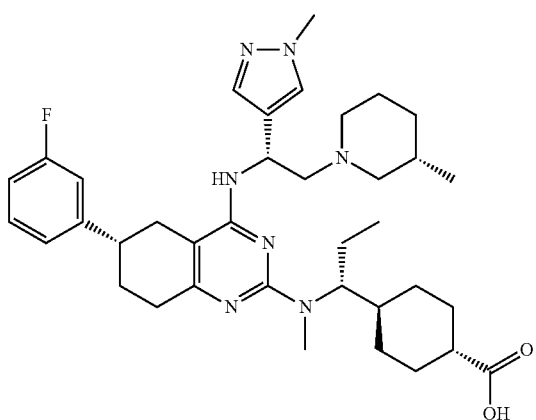 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@@H](c1cccc(F)c1)CC2] | (1R,4r)-4-((R)-1-(((S)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid |

| Cmp # | Structure | Name |
|---|---|---|
| 76 | 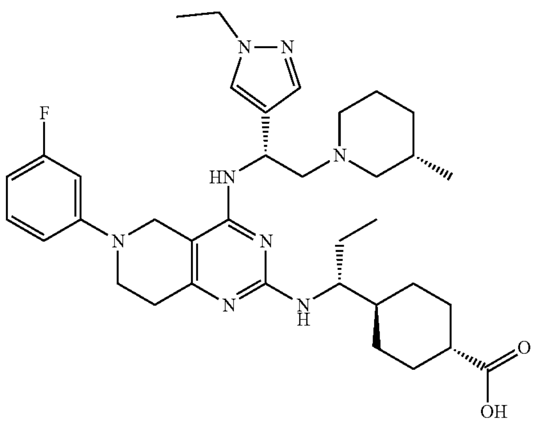 [SMILES: CC[C@@H](Nc1nc2c(c(N[C@@H](CN3CCC[C@H](C)C3)c3cnn(CC)c3)n1)CN(c1cccc(F)c1)CC2)[C@H]1CC[C@H](C(=O)O)CC1] | (1R,4r)-4-((R)-1-((4-(((R)-1-(1-ethyl-1H-pyrazol-4-yl)-2-((S)-3-methylpiperidin-1-yl)ethyl)amino)-6-(3-fluorophenyl)-5,6,7,8-tetrahydropyrido[4,3-d]pyrimidin-2-yl)amino)propyl)cyclohexane-1-carboxylic acid |
| 77 | 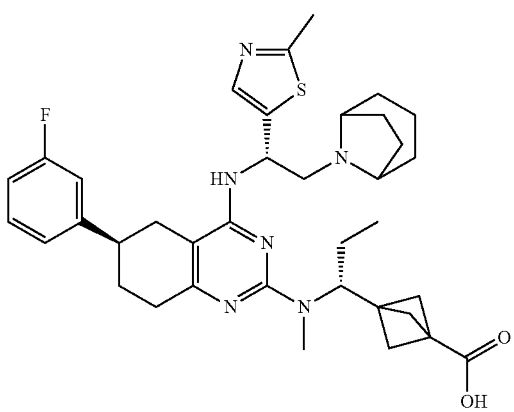 [SMILES: CC[C@@H](N(C)c1nc2c(c(N[C@@H](CN3C4CCCC3CC4)c3cnc(C)s3)n1)C[C@H](c1cccc(F)c1)CC2)C12CC(C(=O)O)(C1)C2] | 3-((1R)-1-(((6R)-4-(((1S)-2-(8-azabicyclo[3.2.1]octan-8-yl)-1-(2-methylthiazol-5-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |
| 78 | 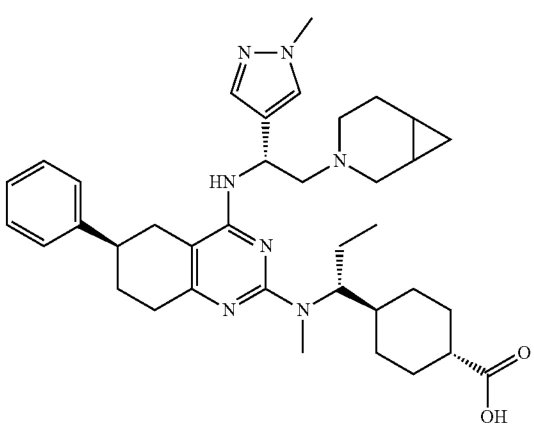 [SMILES: CC[C@H]([C@H]1CC[C@H](C(=O)O)CC1)N(C)c1nc2c(c(N[C@@H](CN3CCC4CC4C3)c3cnn(C)c3)n1)C[C@H](c1ccccc1)CC2] | (1R,4r)-4-((1R)-1-(((6R)-4-(((1R)-2-(3-azabicyclo[4.1.0]heptan-3-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |

| Cmp # | Structure | Name |
|---|---|---|
| 79 | 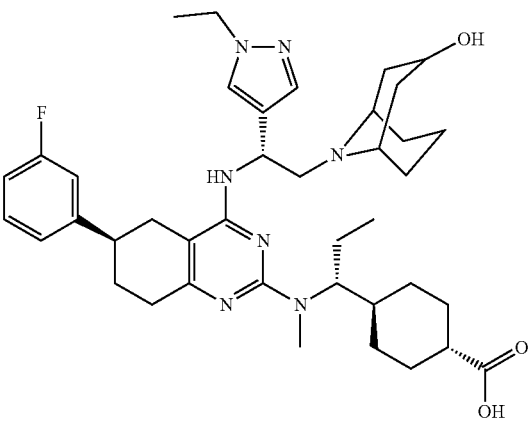 [SMILES: CC[C@H]([C@H]1CC[C@H](C(=O)O)CC1)N(C)c1nc2c(c(N[C@@H](CN3C4CCCC3CC(O)C4)c3cnn(CC)c3)n1)C[C@H](c1cccc(F)c1)CC2] | (1R,4r)-4-((1R)-1-(((6R)-4-(((1R)-1-(1-ethyl-1H-pyrazol-4-yl)-2-((1R,5S)-3-hydroxy-9-azabicyclo[3.3.1]nonan-9-yl)ethyl)amino)-6-(3-fluorophenyl)-5,6,7,8-tetrahydroquinazolin-2-yl)(methyl)amino)propyl)cyclohexane-1-carboxylic acid |
| 80 | 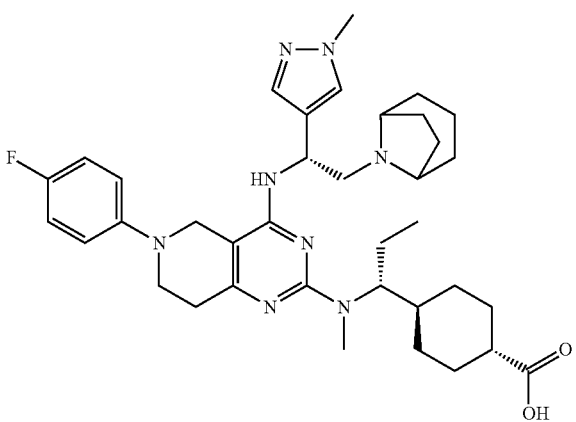 [SMILES: CC[C@H]([C@H]1CC[C@H](C(=O)O)CC1)N(C)c1nc2c(c(N[C@@H](CN3C4CCCC3CC4)c3cnn(C)c3)n1)CN(c1ccc(F)cc1)CC2] | (1R,4r)-4-((1R)-1-((4-(((1R)-2-(8-azabicyclo[3.2.1]octan-8-yl)-1-(1-methyl-1H-pyrazol-4-yl)ethyl)amino)-6-(4-fluorophenyl)-5,6,7,8-tetrahydropyrido[4,3-d]pyrimidin-2-yl)(methyl)amino)propyl)cyclohexane-1-carboxylic acid |
| 81 | 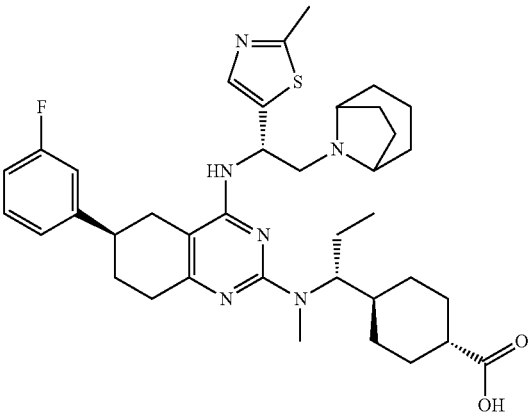 [SMILES: CC[C@H]([C@H]1CC[C@H](C(=O)O)CC1)N(C)c1nc2c(c(N[C@@H](CN3C4CCCC3CC4)c3cnc(C)s3)n1)C[C@H](c1cccc(F)c1)CC2] | (1R,4r)-4-((1R)-1-(((6R)-4-(((1S)-2-(8-azabicyclo[3.2.1]octan-8-yl)-1-(2-methylthiazol-5-yl)ethyl)amino)-6-(3-fluorophenyl)-5,6,7,8-tetrahydroquinazolin-2-yl)(methyl)amino)propyl)cyclohexane-1-carboxylic acid |

| Cmp # | Structure | Name |
|---|---|---|
| 82 | 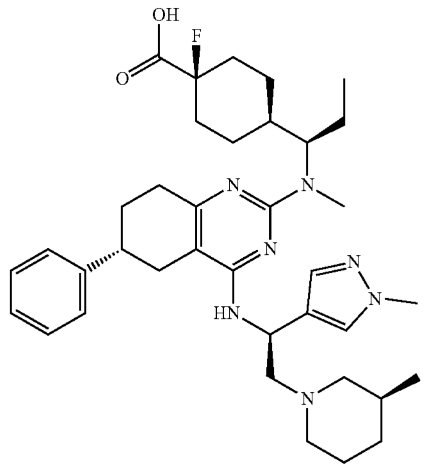 [SMILES: CC[C@H]([C@H]1CC[C@](F)(C(=O)O)CC1)N(C)c1nc2c(c(N[C@H](CN3CCC[C@H](C)C3)c3cnn(C)c3)n1)C[C@H](c1ccccc1)CC2] | (1S,4s)-1-fluoro-4-((R)-1-(methyl((R)-4-(((S)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid |
| 83 | 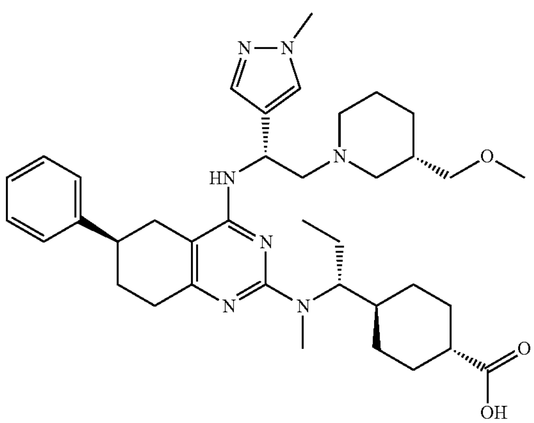 [SMILES: CC[C@H]([C@H]1CC[C@H](C(=O)O)CC1)N(C)c1nc2c(c(N[C@@H](CN3CCC[C@H](COC)C3)c3cnn(C)c3)n1)C[C@H](c1ccccc1)CC2] | (1R,4r)-4-((R)-1-(((R)-4-(((R)-2-((S)-3-(methoxymethyl)piperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 84 | 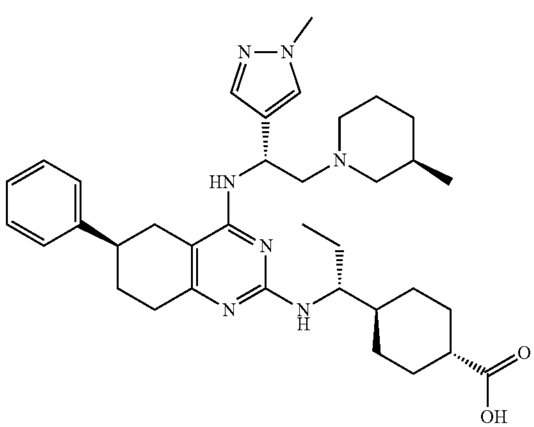 [SMILES: CC[C@@H](Nc1nc2c(c(N[C@@H](CN3CCC[C@@H](C)C3)c3cnn(C)c3)n1)C[C@H](c1ccccc1)CC2)[C@H]1CC[C@H](C(=O)O)CC1] | (1R,4r)-4-((R)-1-(((R)-4-(((R)-1-(1-methyl-1H-pyrazol-4-yl)-2-((R)-3-methylpiperidin-1-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 85 | 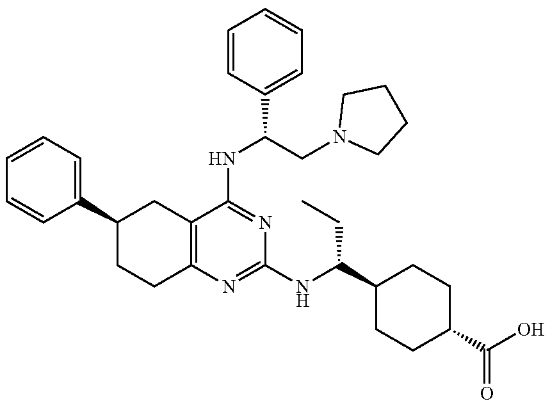 [SMILES: CC[C@@H](Nc1nc2c(c(N[C@@H](CN3CCCC3)c3ccccc3)n1)C[C@H](c1ccccc1)CC2)[C@H]1CC[C@H](C(=O)O)CC1] | (1R,4r)-4-((R)-1-(((R)-6-phenyl-4-(((R)-1-phenyl-2-(pyrrolidin-1-yl)ethyl)amino)-5,6,7,8-tetrahydroquinazolin-2-yl)amino)propyl)cyclohexane-1-carboxylic acid |
| 86 | 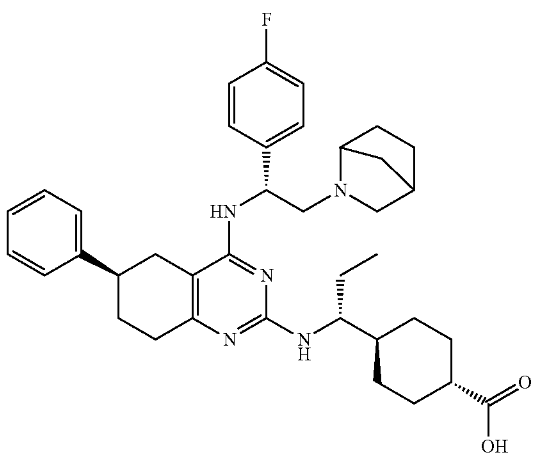 [SMILES: CC[C@@H](Nc1nc2c(c(N[C@@H](CN3CC4CCC3C4)c3ccc(F)cc3)n1)C[C@H](c1ccccc1)CC2)[C@H]1CC[C@H](C(=O)O)CC1] | (1R,4r)-4-((1R)-1-(((6R)-4-(((1R)-2-(2-azabicyclo[2.2.1]heptan-2-yl)-1-(4-fluorophenyl)ethyl)amino)-6-phenyl-5,6,7,8-tetrahydroquinazolin-2-yl)amino)propyl)cyclohexane-1-carboxylic acid |
| 87 | 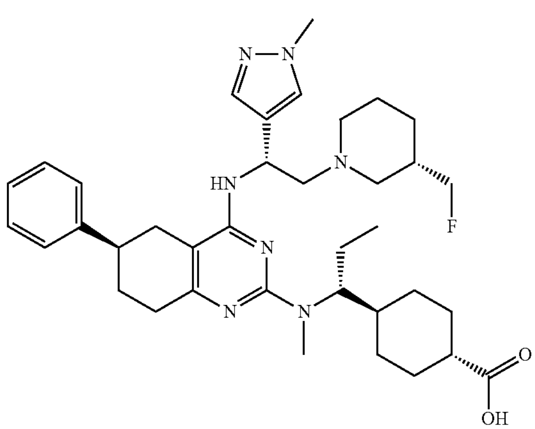 [SMILES: CC[C@H]([C@H]1CC[C@H](C(=O)O)CC1)N(C)c1nc2c(c(N[C@@H](CN3CCC[C@H](CF)C3)c3cnn(C)c3)n1)C[C@H](c1ccccc1)CC2] | (1R,4r)-4-((R)-1-(((R)-4-(((R)-2-((S)-3-(fluoromethyl)piperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |

-continued

| Cmp # | Structure | Name |
|---|---|---|
| 88 | 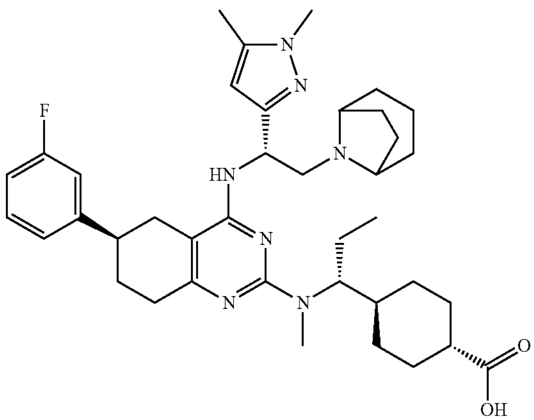 [SMILES: CC[C@H]([C@H]1CC[C@H](C(=O)O)CC1)N(C)c1nc2c(c(N[C@@H](CN3C4CCCC3CC4)c3cc(C)n(C)n3)n1)C[C@H](c1cccc(F)c1)CC2] | (1R,4r)-4-((1R)-1-(((6R)-4-(((1S)-2-(8-azabicyclo[3.2.1]octan-8-yl)-1-(1,5-dimethyl-1H-pyrazol-3-yl)ethyl)amino)-6-(3-fluorophenyl)-5,6,7,8-tetrahydroquinazolin-2-yl)(methyl)amino)propyl)cyclohexane-1-carboxylic acid |
| 89 | 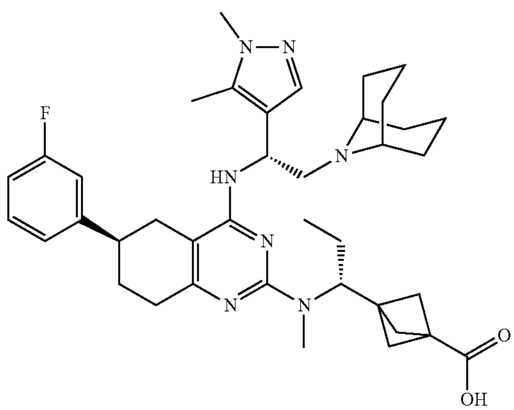 [SMILES: CC[C@@H](N(C)c1nc2c(c(N[C@@H](CN3C4CCCC3CCC4)c3cnn(C)c3C)n1)C[C@H](c1cccc(F)c1)CC2)C12CC(C(=O)O)(C1)C2] | 3-((R)-1-(((R)-4-(((R)-2-((1S,5S)-9-azabicyclo[3.3.1]nonan-9-yl)-1-(1,5-dimethyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |
| 90 | 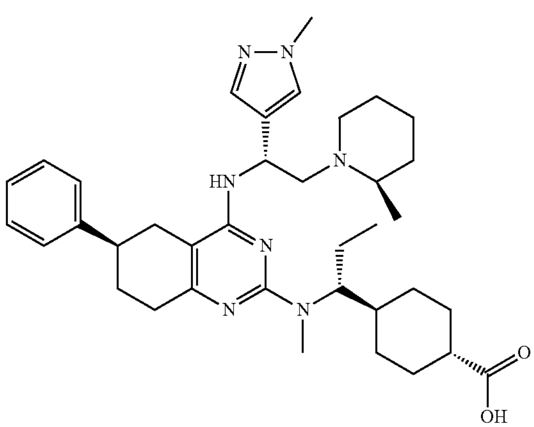 [SMILES: CC[C@H]([C@H]1CC[C@H](C(=O)O)CC1)N(C)c1nc2c(c(N[C@@H](CN3CCCC[C@H]3C)c3cnn(C)c3)n1)C[C@H](c1ccccc1)CC2] | (1R,4r)-4-((R)-1-(((R)-4-(((R)-1-(1-methyl-1H-pyrazol-4-yl)-2-((R)-2-methylpiperidin-1-yl)ethyl)amino)-6-phenyl-5,6,7,8-tetrahydroquinazolin-2-yl)amino)propyl)cyclohexane-1-carboxylic acid |

-continued

| Cmp # | Structure | Name |
|---|---|---|
| 91 | 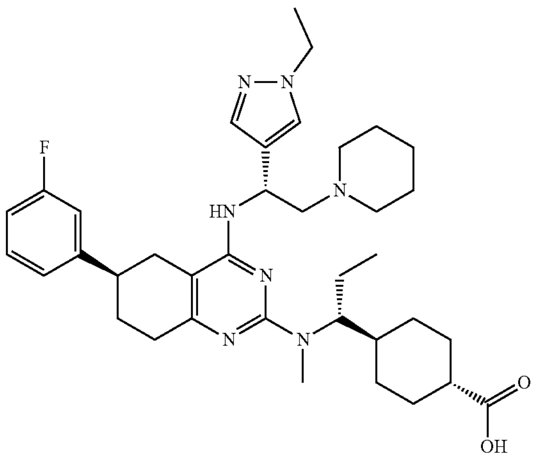 [SMILES: CC[C@H]([C@H]1CC[C@H](C(=O)O)CC1)N(C)c1nc2c(c(N[C@@H](CN3CCCCC3)c3cnn(CC)c3)n1)C[C@H](c1cccc(F)c1)CC2] | (1R,4r)-4-((R)-1-(((R)-4-(((R)-1-(1-ethyl-1H-pyrazol-4-yl)-2-(piperidin-1-yl)ethyl)amino)-6-(3-fluorophenyl)-5,6,7,8-tetrahydroquinazolin-2-yl)(methyl)amino)propyl)cyclohexane-1-carboxylic acid |
| 92 | 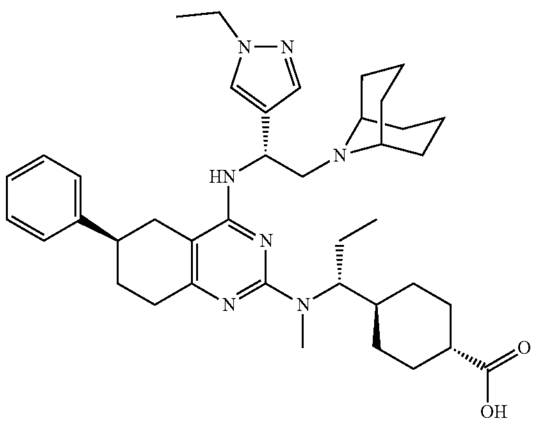 [SMILES: CC[C@H]([C@H]1CC[C@H](C(=O)O)CC1)N(C)c1nc2c(c(N[C@@H](CN3C4CCCC3CCC4)c3cnn(CC)c3)n1)C[C@H](c1ccccc1)CC2] | (1R,4r)-4-((R)-1-(((R)-4-(((R)-2-((1S,5S)-9-azabicyclo[3.3.1]nonan-9-yl)-1-(1-ethyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 93 | 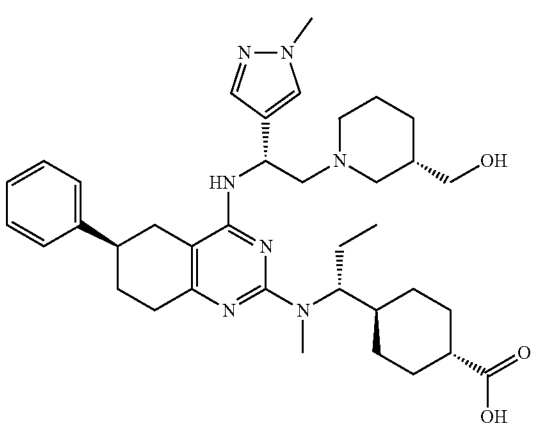 [SMILES: CC[C@H]([C@H]1CC[C@H](C(=O)O)CC1)N(C)c1nc2c(c(N[C@@H](CN3CCC[C@H](CO)C3)c3cnn(C)c3)n1)C[C@H](c1ccccc1)CC2] | (1R,4r)-4-((R)-1-(((R)-4-(((R)-2-((S)-3-(hydroxymethyl)piperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |

| Cmp # | Structure | Name |
|---|---|---|
| 94 | 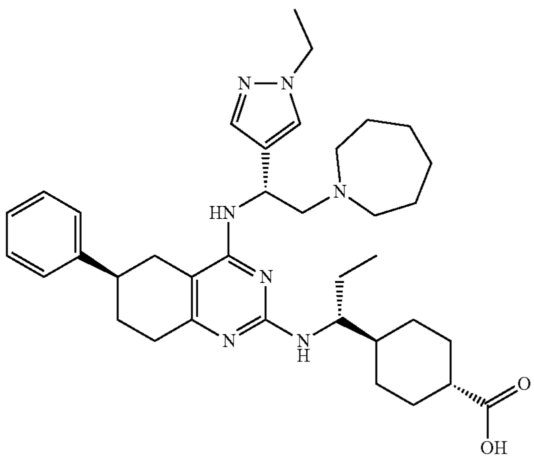 [SMILES: CC[C@@H](Nc1nc2c(c(N[C@@H](CN3CCCCCC3)c3cnn(CC)c3)n1)C[C@H](c1ccccc1)CC2)[C@H]1CC[C@H](C(=O)O)CC1] | (1R,4r)-4-((R)-1-(((R)-4-(((R)-2-(azepan-1-yl)-1-(1-ethyl-1H-pyrazol-4-yl)ethyl)amino)-6-phenyl-5,6,7,8-tetrahydroquinazolin-2-yl)amino)propyl)cyclohexane-1-carboxylic acid |
| 95 | 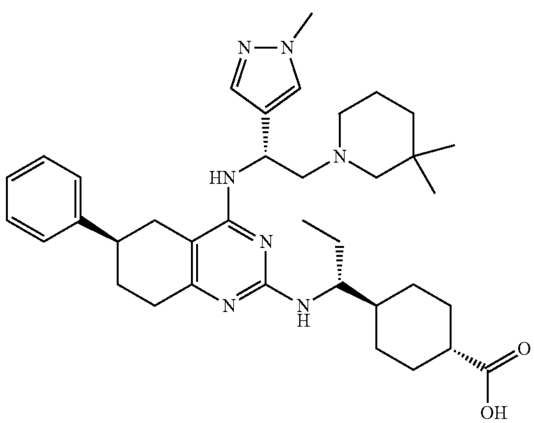 [SMILES: CC[C@@H](Nc1nc2c(c(N[C@@H](CN3CCCC(C)(C)C3)c3cnn(C)c3)n1)C[C@H](c1ccccc1)CC2)[C@H]1CC[C@H](C(=O)O)CC1] | (1R,4r)-4-((R)-1-(((R)-4-(((R)-2-(3,3-dimethylpiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |
| 96 | 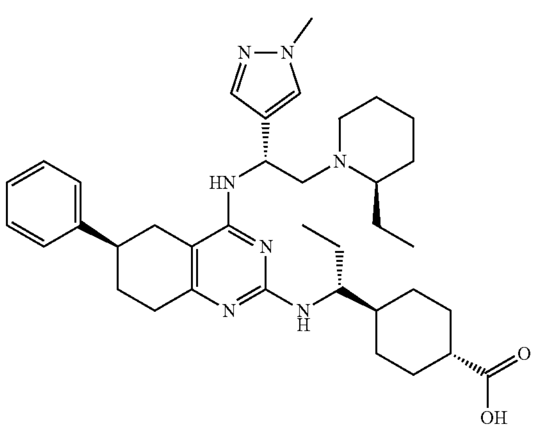 [SMILES: CC[C@@H]1CCCCN1C[C@H](Nc1nc(N[C@H](CC)[C@H]2CC[C@H](C(=O)O)CC2)nc2c1C[C@H](c1ccccc1)CC2)c1cnn(C)c1] | (1R,4r)-4-((R)-1-(((R)-4-(((R)-2-((R)-2-ethylpiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 97 | 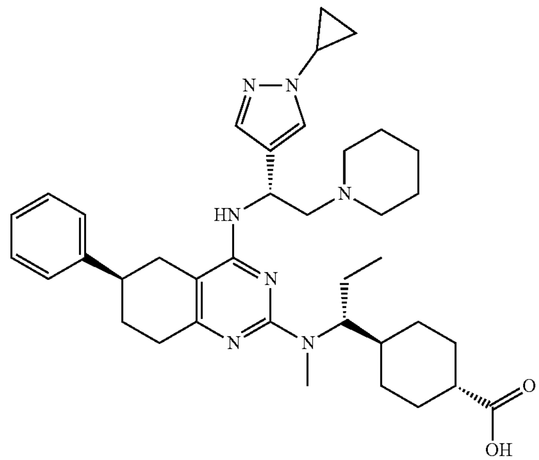 [SMILES: CC[C@H]([C@H]1CC[C@H](C(=O)O)CC1)N(C)c1nc2c(c(N[C@@H](CN3CCCCC3)c3cnn(C4CC4)c3)n1)C[C@H](c1ccccc1)CC2] | (1R,4r)-4-((R)-1-(((R)-4-(((R)-1-(1-cyclopropyl-1H-pyrazol-4-yl)-2-(piperidin-1-yl)ethyl)amino)-6-phenyl-5,6,7,8-tetrahydroquinazolin-2-yl)(methyl)amino)propyl)cyclohexane-1-carboxylic acid |
| 98 | 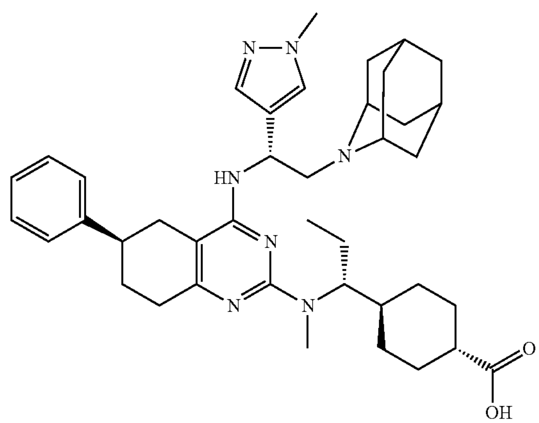 [SMILES: CC[C@H]([C@H]1CC[C@H](C(=O)O)CC1)N(C)c1nc2c(c(N[C@@H](CN3C4CC5CC(C4)CC3C5)c3cnn(C)c3)n1)C[C@H](c1ccccc1)CC2] | (1R,4r)-4-((R)-1-(((R)-4-(((R)-2-((1R,3R,5R,7R)-2-azaadamantan-2-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 99 | 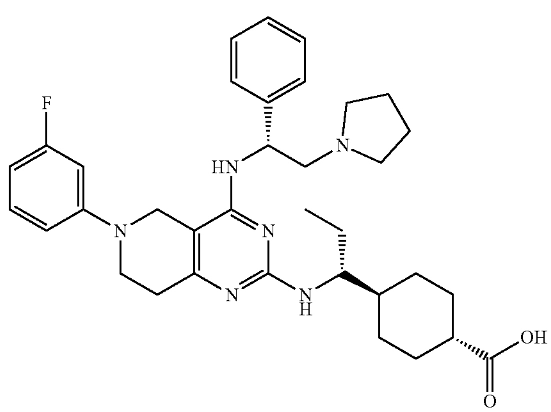 [SMILES: CC[C@@H](Nc1nc2c(c(N[C@@H](CN3CCCC3)c3ccccc3)n1)CN(c1cccc(F)c1)CC2)[C@H]1CC[C@H](C(=O)O)CC1] | (1R,4r)-4-((R)-1-((6-(3-fluorophenyl)-4-(((R)-1-phenyl-2-(pyrrolidin-1-yl)ethyl)amino)-5,6,7,8-tetrahydropyrido[4,3-d]pyrimidin-2-yl)amino)propyl)cyclohexane-1-carboxylic acid |

-continued

| Cmp # | Structure | Name |
|---|---|---|
| 100 | 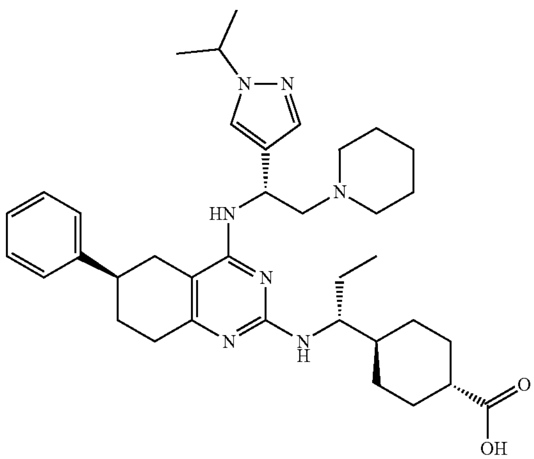 [SMILES: CC[C@@H](Nc1nc2c(c(N[C@@H](CN3CCCCC3)c3cnn(C(C)C)c3)n1)C[C@H](c1ccccc1)CC2)[C@H]1CC[C@H](C(=O)O)CC1] | (1R,4r)-4-((R)-1-(((R)-4-(((R)-1-(1-isopropyl-1H-pyrazol-4-yl)-2-(piperidin-1-yl)ethyl)amino)-6-phenyl-5,6,7,8-tetrahydroquinazolin-2-yl)amino)propyl)cyclohexane-1-carboxylic acid |
| 101 | 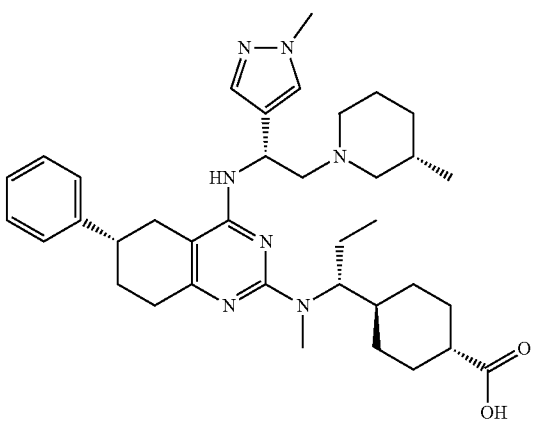 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@@H](c1ccccc1)CC2] | (1R,4r)-4-((R)-1-(methyl((S)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid |
| 102 | 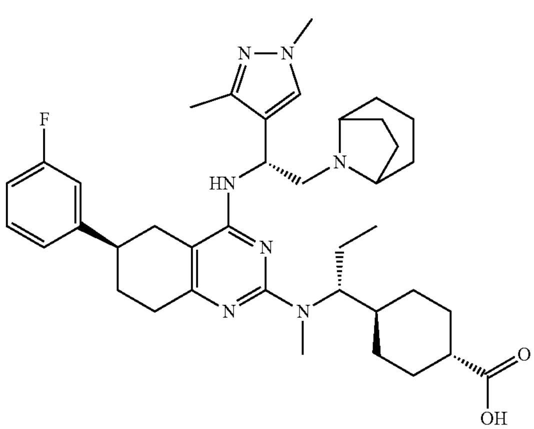 [SMILES: CC[C@H]([C@H]1CC[C@H](C(=O)O)CC1)N(C)c1nc2c(c(N[C@@H](CN3C4CCCC3CC4)c3cn(C)nc3C)n1)C[C@H](c1cccc(F)c1)CC2] | (1R,4r)-4-((1R)-1-(((6R)-4-(((1R)-2-(8-azabicyclo[3.2.1]octan-8-yl)-1-(1,3-dimethyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid |

| Cmp # | Structure | Name |
|---|---|---|
| 103 | 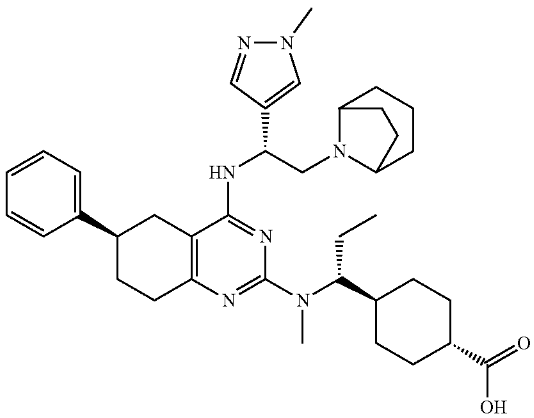 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@H](c1ccccc1)CC2] | (1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 104 | 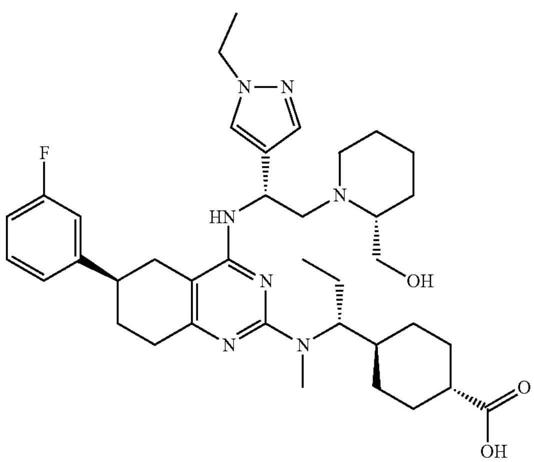 [SMILES: CC[C@H]([C@H]1CC[C@H](C(=O)O)CC1)N(C)c1nc2c(c(N[C@@H](CN3CCCC[C@@H]3CO)c3cnn(CC)c3)n1)C[C@H](c1cccc(F)c1)CC2] | (1R,4r)-4-((R)-1-(((R)-4-(((R)-1-(1-ethyl-1H-pyrazol-4-yl)-2-((R)-2-(hydroxymethyl)piperidin-1-yl)ethyl)amino)-6-(3-fluorophenyl)-5,6,7,8-tetrahydroquinazolin-2-yl)(methyl)amino)propyl)cyclohexane-1-carboxylic acid |
| 105 | 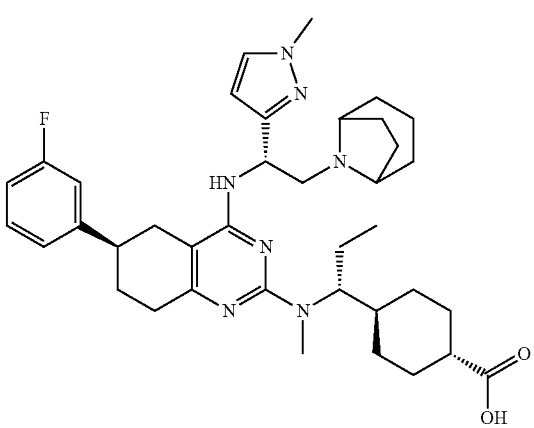 [SMILES: CC[C@H]([C@H]1CC[C@H](C(=O)O)CC1)N(C)c1nc2c(c(N[C@@H](CN3C4CCCC3CC4)c3ccn(C)n3)n1)C[C@H](c1cccc(F)c1)CC2] | (1R,4r)-4-((1R)-1-(((6R)-4-(((1S)-2-(8-azabicyclo[3.2.1]octan-8-yl)-1-(1-methyl-1H-pyrazol-3-yl)ethyl)amino)-6-(3-fluorophenyl)-5,6,7,8-tetrahydroquinazolin-2-yl)(methyl)amino)propyl)cyclohexane-1-carboxylic acid |

-continued

| Cmp # | Structure | Name |
|---|---|---|
| 106 | 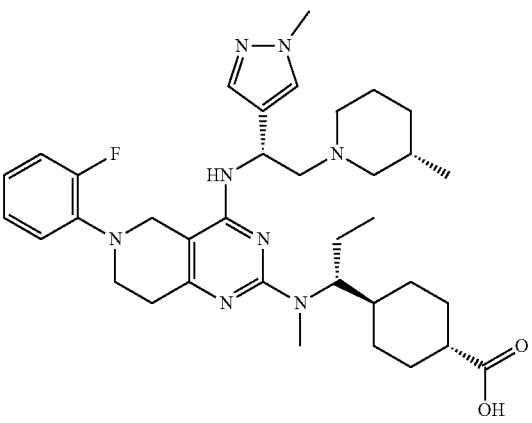 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(c1ccccc1F)CC2] | (1R,4r)-4-((R)-1-(((6-(2-fluorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid |
| 107 | 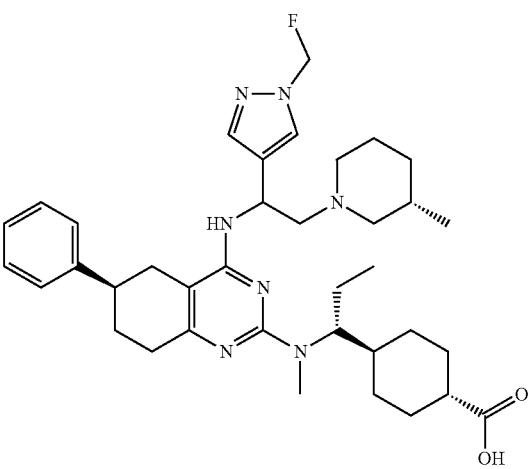 [SMILES: CC[C@H]([C@H]1CC[C@H](C(=O)O)CC1)N(C)c1nc2c(c(NC(CN3CCC[C@H](C)C3)c3cnn(CF)c3)n1)C[C@H](c1ccccc1)CC2] | (1R,4r)-4-((1R)-1-(((6R)-4-((1-(1-(fluoromethyl)-1H-pyrazol-4-yl)-2-((S)-3-methylpiperidin-1-yl)ethyl)amino)-6-phenyl-5,6,7,8-tetrahydroquinazolin-2-yl)(methyl)amino)propyl)cyclohexane-1-carboxylic acid |
| 108 | 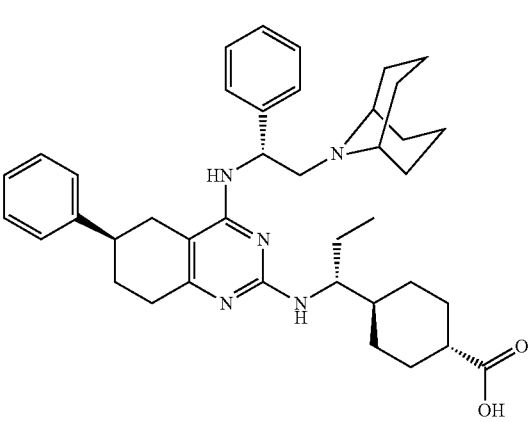 [SMILES: CC[C@@H](Nc1nc2c(c(N[C@@H](CN3C4CCCC3CCC4)c3ccccc3)n1)C[C@H](c1ccccc1)CC2)[C@H]1CC[C@H](C(=O)O)CC1] | (1R,4r)-4-((R)-1-(((R)-4-(((R)-2-((1S,5S)-9-azabicyclo[3.3.1]nonan-9-yl)-1-phenylethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 109 | 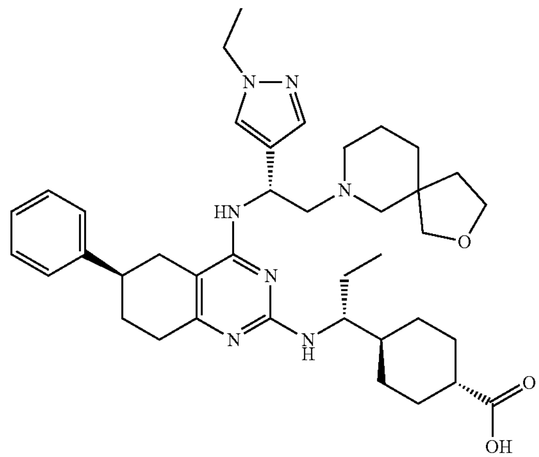 [SMILES: CC[C@@H](Nc1nc2c(c(N[C@@H](CN3CCCC4(CCOC4)C3)c3cnn(CC)c3)n1)C[C@H](c1ccccc1)CC2)[C@H]1CC[C@H](C(=O)O)CC1] | (1R,4r)-4-((1R)-1-(((6R)-4-(((1R)-1-(1-ethyl-1H-pyrazol-4-yl)-2-(2-oxa-7-azaspiro[4.5]decan-7-yl)ethyl)amino)-6-phenyl-5,6,7,8-tetrahydroquinazolin-2-yl)amino)propyl)cyclohexane-1-carboxylic acid |
| 110 | 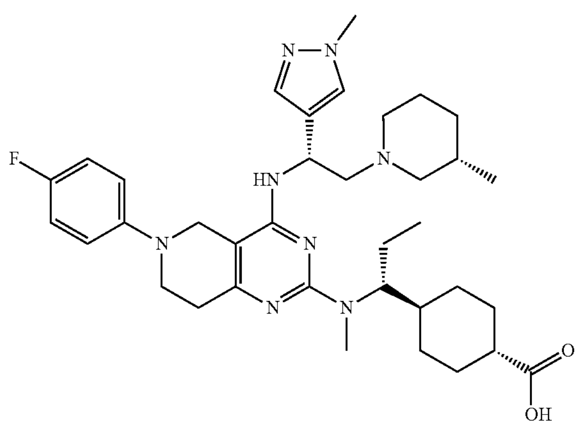 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(c1ccc(F)cc1)CC2] | (1R,4r)-4-((R)-1-((6-(4-fluorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid |
| 111 | 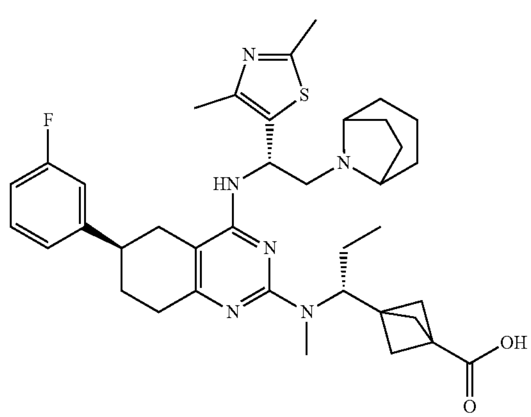 [SMILES: CC[C@@H](N(C)c1nc2c(c(N[C@@H](CN3C4CCCC3CC4)c3sc(C)nc3C)n1)C[C@H](c1cccc(F)c1)CC2)C12CC(C(=O)O)(C1)C2] | 3-((1R)-1-(((6R)-4-(((1S)-2-(8-azabicyclo[3.2.1]octan-8-yl)-1-(2,4-dimethylthiazol-5-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |

| Cmp # | Structure | Name |
|---|---|---|
| 112 | 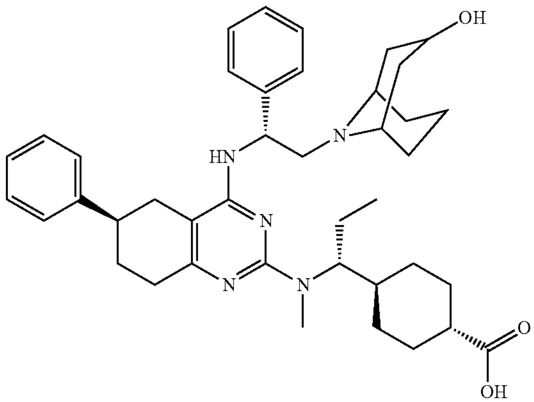 [SMILES: CC[C@H]([C@H]1CC[C@H](C(=O)O)CC1)N(C)c1nc2c(c(N[C@@H](CN3C4CCCC3CC(O)C4)c3ccccc3)n1)C[C@H](c1ccccc1)CC2] | (1R,4r)-4-((1R)-1-(((6R)-4-(((1R)-2-((1R,5S)-3-hydroxy-9-azabicyclo[3.3.1]nonan-9-yl)-1-phenylethyl)amino)-6-phenyl-5,6,7,8-tetrahydroquinazolin-2-yl)(methyl)amino)propyl)cyclohexane-1-carboxylic acid |
| 113 | 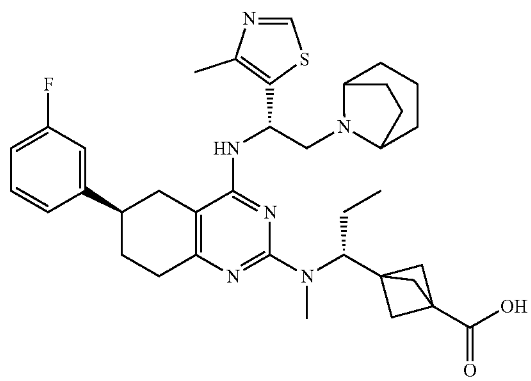 [SMILES: CC[C@@H](N(C)c1nc2c(c(N[C@@H](CN3C4CCCC3CC4)c3scnc3C)n1)C[C@H](c1cccc(F)c1)CC2)C12CC(C(=O)O)(C1)C2] | 3-((1R)-1-(((6R)-4-(((1S)-2-(8-azabicyclo[3.2.1]octan-8-yl)-1-(4-methylthiazol-5-yl)ethyl)amino)-6-(3-fluorophenyl)-5,6,7,8-tetrahydroquinazolin-2-yl)(methyl)amino)propyl)bicyclo[1.1.1]pentane-1-carboxylic acid |
| 114 | 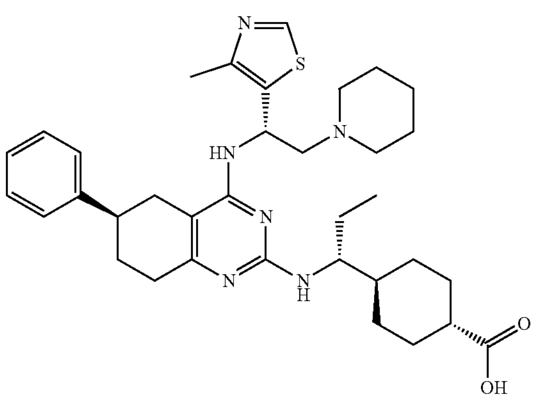 [SMILES: CC[C@@H](Nc1nc2c(c(N[C@@H](CN3CCCCC3)c3scnc3C)n1)C[C@H](c1ccccc1)CC2)[C@H]1CC[C@H](C(=O)O)CC1] | (1R,4r)-4-((R)-1-(((R)-4-(((S)-1-(4-methylthiazol-5-yl)-2-(piperidin-1-yl)ethyl)amino)-6-phenyl-5,6,7,8-tetrahydroquinazolin-2-yl)amino)propyl)cyclohexane-1-carboxylic acid |
| 115 | 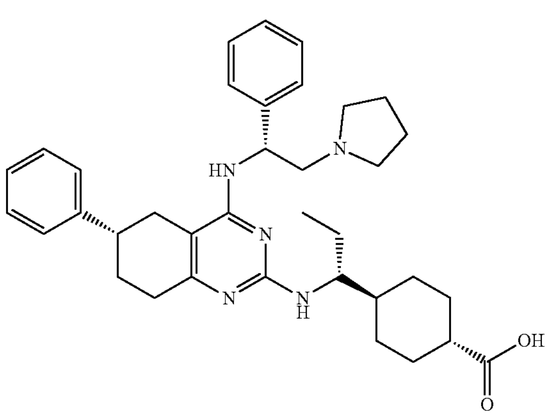 [SMILES: CC[C@@H](Nc1nc2c(c(N[C@@H](CN3CCCC3)c3ccccc3)n1)C[C@@H](c1ccccc1)CC2)[C@H]1CC[C@H](C(=O)O)CC1] | (1R,4r)-4-((R)-1-(((S)-6-phenyl-4-(((R)-1-phenyl-2-(pyrrolidin-1-yl)ethyl)amino)-5,6,7,8-tetrahydroquinazolin-2-yl)amino)propyl)cyclohexane-1-carboxylic acid |

| Cmp # | Structure | Name |
|---|---|---|
| 116 | 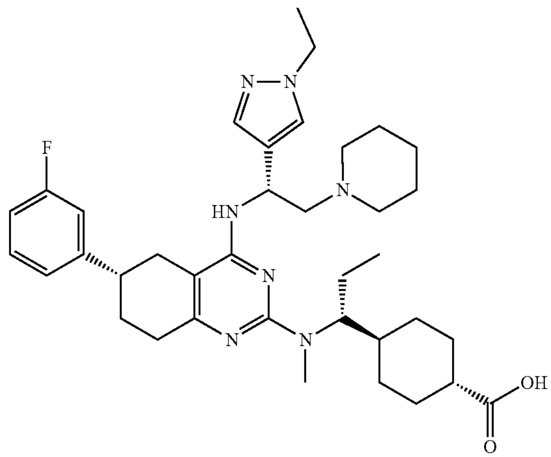 [SMILES: CC[C@H]([C@H]1CC[C@H](C(=O)O)CC1)N(C)c1nc2c(c(N[C@@H](CN3CCCCC3)c3cnn(CC)c3)n1)C[C@@H](c1cccc(F)c1)CC2] | (1R,4r)-4-((R)-1-(((S)-4-(((R)-1-(1-ethyl-1H-pyrazol-4-yl)-2-(piperidin-1-yl)ethyl)amino)-6-(3-fluorophenyl)-5,6,7,8-tetrahydroquinazolin-2-yl)(methyl)amino)propyl)cyclohexane-1-carboxylic acid |
| 117 | 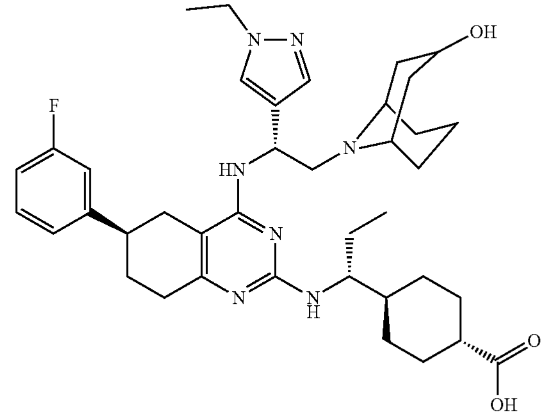 [SMILES: CC[C@@H](Nc1nc2c(c(N[C@@H](CN3C4CCCC3CC(O)C4)c3cnn(CC)c3)n1)C[C@H](c1cccc(F)c1)CC2)[C@H]1CC[C@H](C(=O)O)CC1] | (1R,4r)-4-((1R)-1-(((6R)-4-(((1R)-1-(1-ethyl-1H-pyrazol-4-yl)-2-((1R,5S)-3-hydroxy-9-azabicyclo[3.3.1]nonan-9-yl)ethyl)amino)-6-(3-fluorophenyl)-5,6,7,8-tetrahydroquinazolin-2-yl)amino)propyl)cyclohexane-1-carboxylic acid |
| 118 | 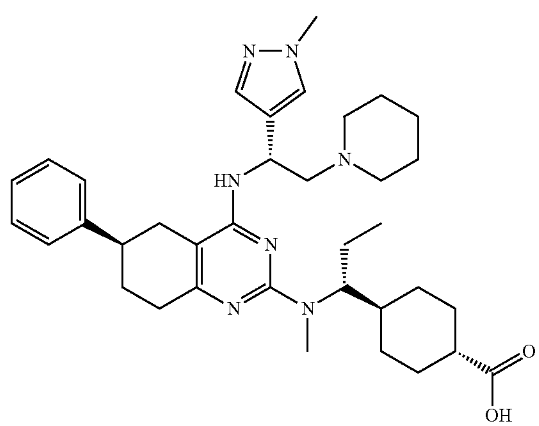 [SMILES: CC[C@H]([C@H]1CC[C@H](C(=O)O)CC1)N(C)c1nc2c(c(N[C@@H](CN3CCCCC3)c3cnn(C)c3)n1)C[C@H](c1ccccc1)CC2] | (1R,4r)-4-((R)-1-(methyl((R)-4-(((R)-1-(1-methyl-1H-pyrazol-4-yl)-2-(piperidin-1-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 119 | 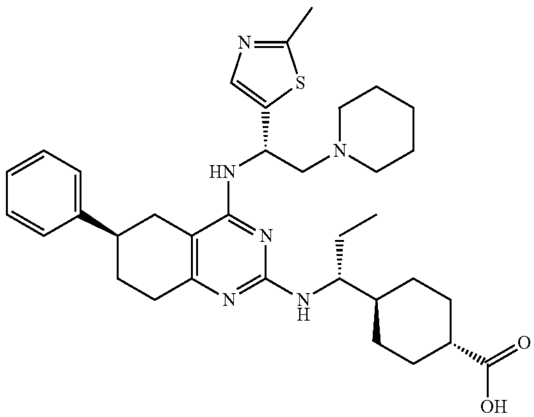 [SMILES: CC[C@@H](Nc1nc2c(c(N[C@@H](CN3CCCCC3)c3cnc(C)s3)n1)C[C@H](c1ccccc1)CC2)[C@H]1CC[C@H](C(=O)O)CC1] | (1R,4r)-4-((R)-1-(((R)-4-(((S)-1-(2-methylthiazol-5-yl)-2-(piperidin-1-yl)ethyl)amino)-6-phenyl-5,6,7,8-tetrahydroquinazolin-2-yl)amino)propyl)cyclohexane-1-carboxylic acid |
| 120 | 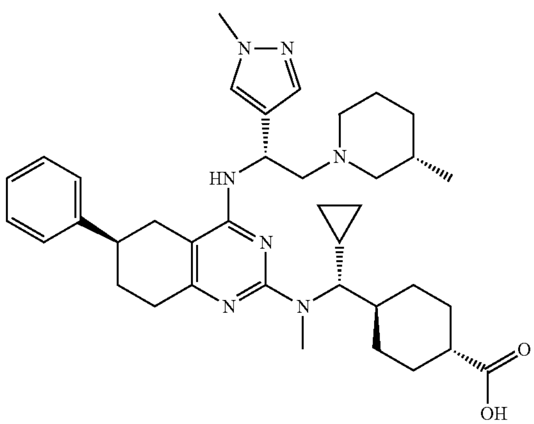 [SMILES: C[C@H]1CCCN(C[C@H](Nc2nc(N(C)[C@H](C3CC3)[C@H]3CC[C@H](C(=O)O)CC3)nc3c2C[C@H](c2ccccc2)CC3)c2cnn(C)c2)C1] | (1R,4r)-4-((R)-cyclopropyl(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)methyl)cyclohexane-1-carboxylic acid |
| 121 | 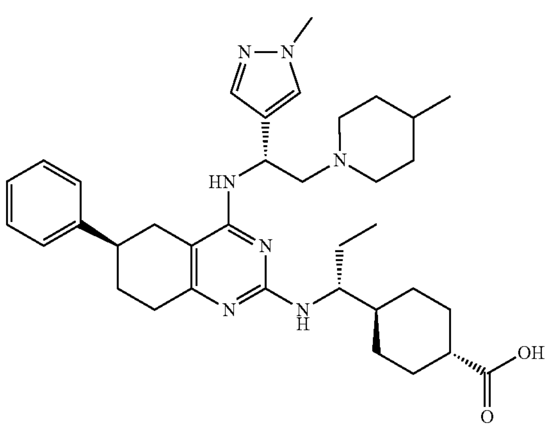 [SMILES: CC[C@@H](Nc1nc2c(c(N[C@@H](CN3CCC(C)CC3)c3cnn(C)c3)n1)C[C@H](c1ccccc1)CC2)[C@H]1CC[C@H](C(=O)O)CC1] | (1R,4r)-4-((R)-1-(((R)-4-(((R)-1-(1-methyl-1H-pyrazol-4-yl)-2-(4-methylpiperidin-1-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 122 | 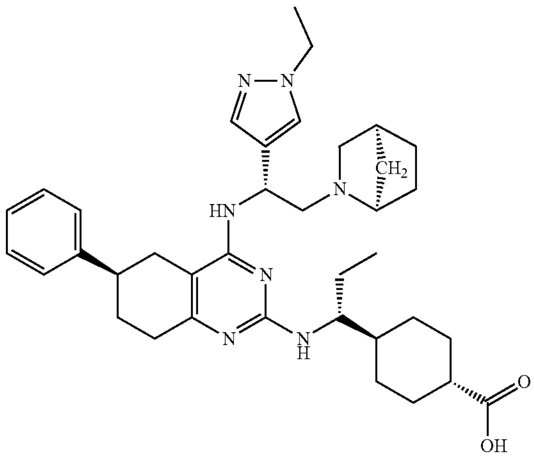 [SMILES: CC[C@@H](Nc1nc2c(c(N[C@@H](CN3C[C@H]4CC[C@@H]3C4)c3cnn(CC)c3)n1)C[C@H](c1ccccc1)CC2)[C@H]1CC[C@H](C(=O)O)CC1] | (1R,4r)-4-((R)-1-(((R)-4-(((R)-2-((1R,4S)-2-azabicyclo[2.2.1]heptan-2-yl)-1-(1-ethyl-1H-pyrazol-4-yl)ethyl)amino)-6-phenyl-5,6,7,8-tetrahydroquinazolin-2-yl)amino)propyl)cyclohexane-1-carboxylic acid |
| 123 | 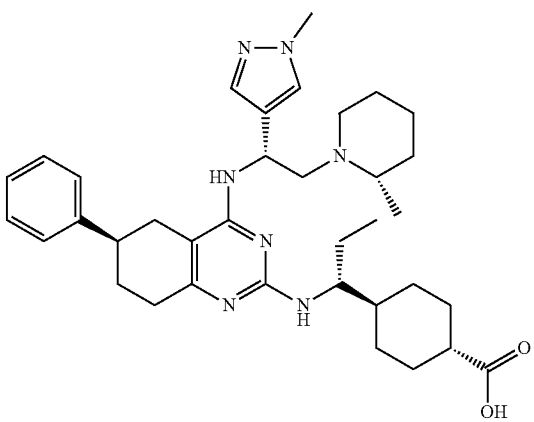 [SMILES: CC[C@@H](Nc1nc2c(c(N[C@@H](CN3CCCC[C@@H]3C)c3cnn(C)c3)n1)C[C@H](c1ccccc1)CC2)[C@H]1CC[C@H](C(=O)O)CC1] | (1R,4r)-4-((R)-1-(((R)-4-(((R)-1-(1-methyl-1H-pyrazol-4-yl)-2-((S)-2-methylpiperidin-1-yl)ethyl)amino)-6-phenyl-5,6,7,8-tetrahydroquinazolin-2-yl)amino)propyl)cyclohexane-1-carboxylic acid |
| 124 | 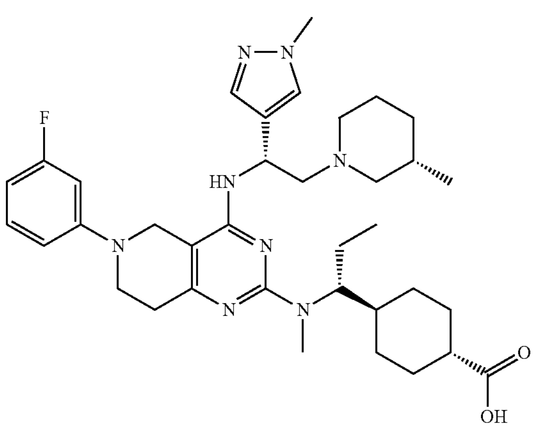 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(c1cccc(F)c1)CC2] | (1R,4r)-4-((R)-1-((6-(3-fluorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid |

| Cmp # | Structure | Name |
|---|---|---|
| 125 | 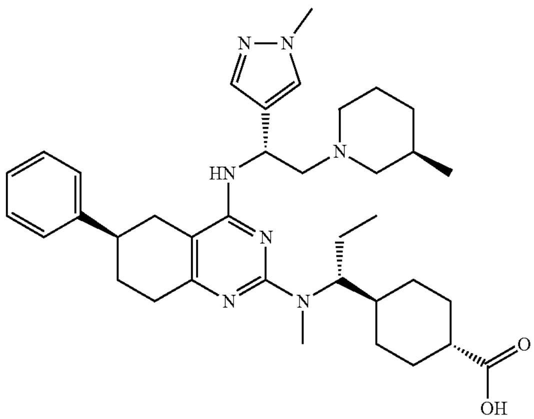 [SMILES: CC[C@H]([C@H]1CC[C@H](C(=O)O)CC1)N(C)c1nc2c(c(N[C@@H](CN3CCC[C@@H](C)C3)c3cnn(C)c3)n1)C[C@H](c1ccccc1)CC2] | (1R,4r)-4-((R)-1-(methyl((R)-4-(((R)-1-(1-methyl-1H-pyrazol-4-yl)-2-((R)-3-methylpiperidin-1-yl)ethyl)amino)-6-phenyl-5,6,7,8-tetrahydroquinazolin-2-yl)amino)propyl)cyclohexane-1-carboxylic acid |
| 126 | 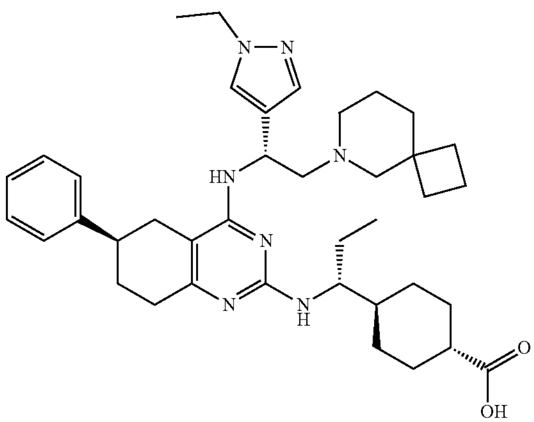 [SMILES: CC[C@@H](Nc1nc2c(c(N[C@@H](CN3CCCC4(CCC4)C3)c3cnn(CC)c3)n1)C[C@H](c1ccccc1)CC2)[C@H]1CC[C@H](C(=O)O)CC1] | (1R,4r)-4-((R)-1-(((R)-4-(((R)-1-(1-ethyl-1H-pyrazol-4-yl)-2-(6-azaspiro[3.5]nonan-6-yl)ethyl)amino)-6-phenyl-5,6,7,8-tetrahydroquinazolin-2-yl)amino)propyl)cyclohexane-1-carboxylic acid |
| 127 | 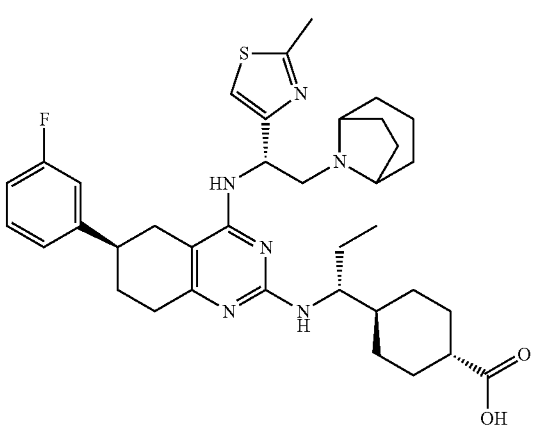 [SMILES: CC[C@@H](Nc1nc2c(c(N[C@@H](CN3C4CCCC3CC4)c3csc(C)n3)n1)C[C@H](c1cccc(F)c1)CC2)[C@H]1CC[C@H](C(=O)O)CC1] | (1R,4r)-4-((1R)-1-(((6R)-4-(((1S)-2-(8-azabicyclo[3.2.1]octan-8-yl)-1-(2-methylthiazol-4-yl)ethyl)amino)-6-(3-fluorophenyl)-5,6,7,8-tetrahydroquinazolin-2-yl)amino)propyl)cyclohexane-1-carboxylic acid |

-continued

| Cmp # | Structure | Name |
|---|---|---|
| 128 | 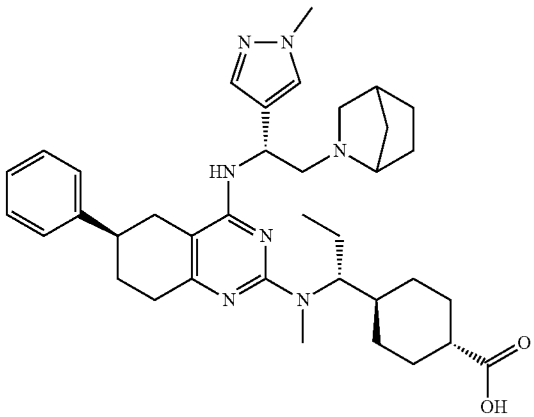 [SMILES: CC[C@H]([C@H]1CC[C@H](C(=O)O)CC1)N(C)c1nc2c(c(N[C@@H](CN3CC4CCC3C4)c3cnn(C)c3)n1)C[C@H](c1ccccc1)CC2] | (1R,4r)-4-((1R)-1-(((6R)-4-(((1R)-2-(2-azabicyclo[2.2.1]heptan-2-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 129 | 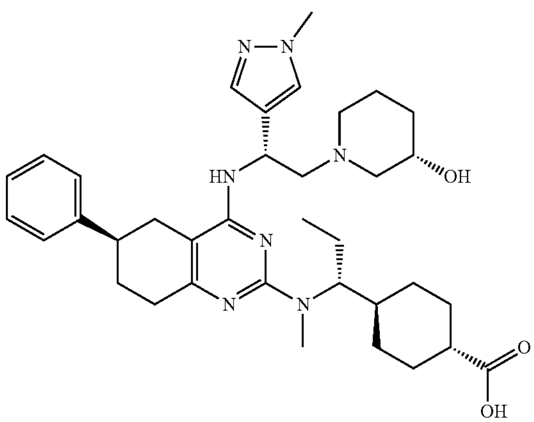 [SMILES: CC[C@H]([C@H]1CC[C@H](C(=O)O)CC1)N(C)c1nc2c(c(N[C@@H](CN3CCC[C@H](O)C3)c3cnn(C)c3)n1)C[C@H](c1ccccc1)CC2] | (1R,4r)-4-((R)-1-(((R)-4-(((R)-2-((S)-3-hydroxypiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 130 | 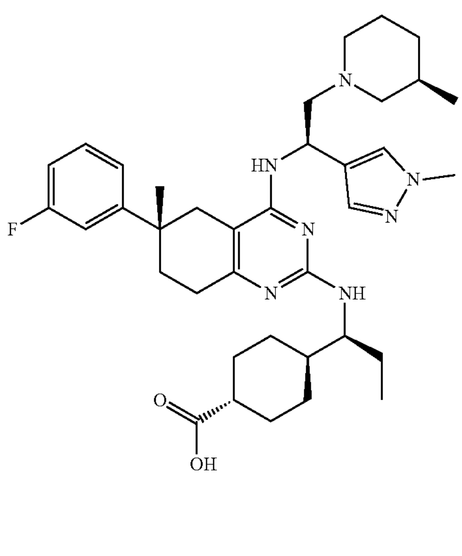 [SMILES: CC[C@H](Nc1nc2c(c(N[C@@H](CN3CCC[C@@H](C)C3)c3cnn(C)c3)n1)C[C@@](C)(c1cccc(F)c1)CC2)[C@H]1CC[C@H](C(=O)O)CC1] | (1S,4r)-4-((S)-1-(((S)-6-(3-fluorophenyl)-6-methyl-4-(((R)-1-(1-methyl-1H-pyrazol-4-yl)-2-((R)-3-methylpiperidin-1-yl)ethyl)amino)-5,6,7,8-tetrahydroquinazolin-2-yl)amino)propyl)cyclohexane-1-carboxylic acid |

| Cmp # | Structure | Name |
|---|---|---|
| 131 | 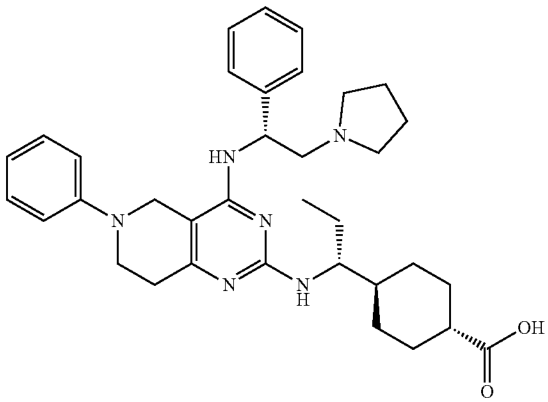 [SMILES: CC[C@@H](Nc1nc2c(c(N[C@@H](CN3CCCC3)c3ccccc3)n1)CN(c1ccccc1)CC2)[C@H]1CC[C@H](C(=O)O)CC1] | (1R,4r)-4-((R)-1-((6-phenyl-4-(((R)-1-phenyl-2-(pyrrolidin-1-yl)ethyl)amino)-5,6,7,8-tetrahydropyrido[4,3-d]pyrimidin-2-yl)amino)propyl)cyclohexane-1-carboxylic acid |
| 132 | 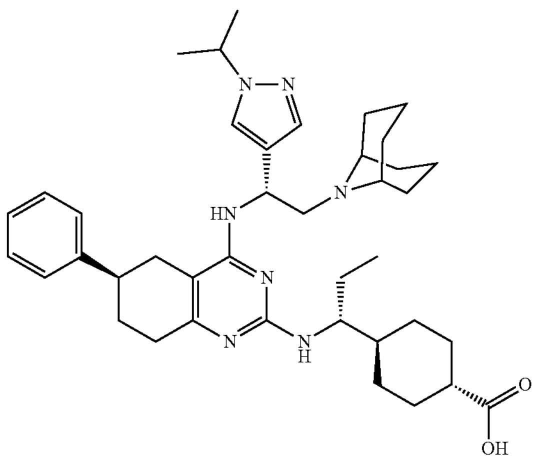 [SMILES: CC[C@@H](Nc1nc2c(c(N[C@@H](CN3C4CCCC3CCC4)c3cnn(C(C)C)c3)n1)C[C@H](c1ccccc1)CC2)[C@H]1CC[C@H](C(=O)O)CC1] | (1R,4r)-4-((R)-1-(((R)-4-(((R)-2-((1S,5S)-9-azabicyclo[3.3.1]nonan-9-yl)-1-(1-isopropyl-1H-pyrazol-4-yl)ethyl)amino)-6-phenyl-5,6,7,8-tetrahydroquinazolin-2-yl)amino)propyl)cyclohexane-1-carboxylic acid |
| 133 | 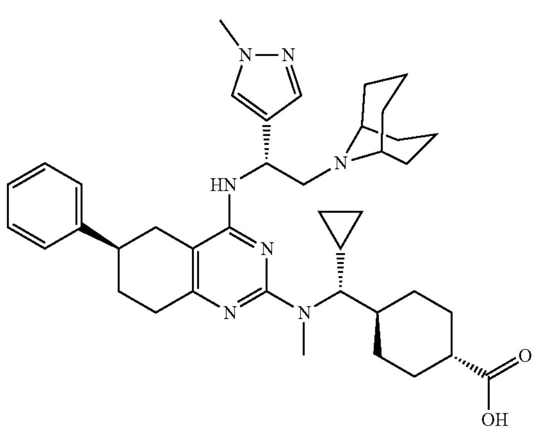 [SMILES: CN(c1nc2c(c(N[C@@H](CN3C4CCCC3CCC4)c3cnn(C)c3)n1)C[C@H](c1ccccc1)CC2)[C@H](C1CC1)[C@H]1CC[C@H](C(=O)O)CC1] | (1R,4r)-4-((R)-(((R)-4-(((R)-2-((1S,5S)-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)(methyl)amino)(cyclopropyl)methyl)cyclohexane-1-carboxylic acid |

| Cmp # | Structure | Name |
|---|---|---|
| 134 | 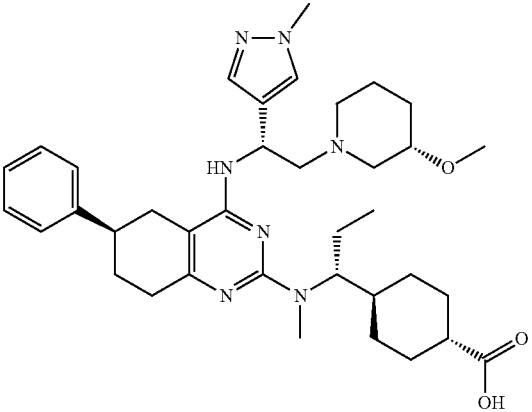 [SMILES: CC[C@H]([C@H]1CC[C@H](C(=O)O)CC1)N(C)c1nc2c(c(N[C@@H](CN3CCC[C@H](OC)C3)c3cnn(C)c3)n1)C[C@H](c1ccccc1)CC2] | (1R,4r)-4-((R)-1-(((R)-4-(((R)-2-((S)-3-methoxypiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 135 | 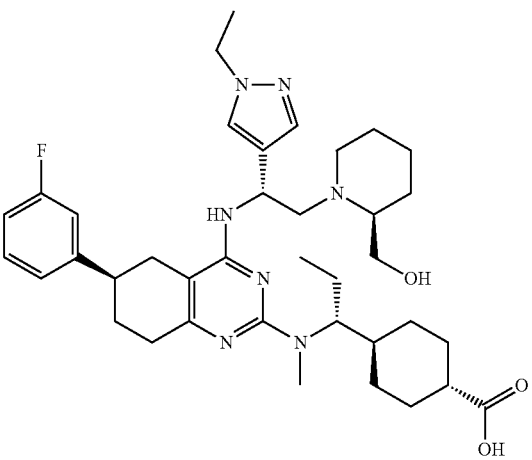 [SMILES: CC[C@H]([C@H]1CC[C@H](C(=O)O)CC1)N(C)c1nc2c(c(N[C@@H](CN3CCCC[C@H]3CO)c3cnn(CC)c3)n1)C[C@H](c1cccc(F)c1)CC2] | (1R,4r)-4-((R)-1-(((R)-4-(((R)-1-(1-ethyl-1H-pyrazol-4-yl)-2-((S)-2-(hydroxymethyl)piperidin-1-yl)ethyl)amino)-6-(3-fluorophenyl)-5,6,7,8-tetrahydroquinazolin-2-yl)(methyl)amino)propyl)cyclohexane-1-carboxylic acid |
| 136 | 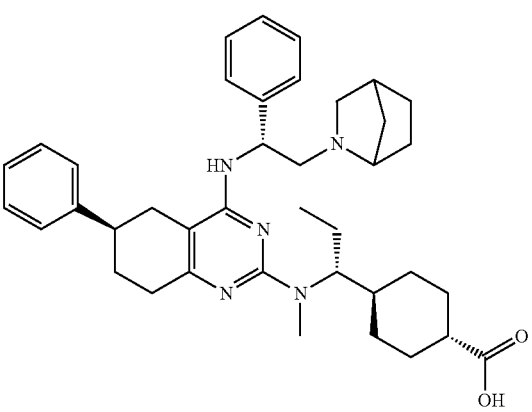 [SMILES: CC[C@H]([C@H]1CC[C@H](C(=O)O)CC1)N(C)c1nc2c(c(N[C@@H](CN3CC4CCC3C4)c3ccccc3)n1)C[C@H](c1ccccc1)CC2] | (1R,4r)-4-((1R)-1-(((6R)-4-(((1R)-2-(2-azabicyclo[2.2.1]heptan-2-yl)-1-phenylethyl)amino)-6-phenyl-5,6,7,8-tetrahydroquinazolin-2-yl)(methyl)amino)propyl)cyclohexane-1-carboxylic acid |

-continued

| Cmp # | Structure | Name |
|---|---|---|
| 137 | 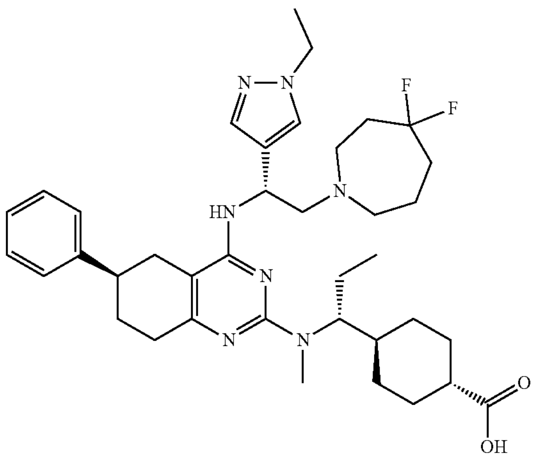 [SMILES: CC[C@H]([C@H]1CC[C@H](C(=O)O)CC1)N(C)c1nc2c(c(N[C@@H](CN3CCCC(F)(F)CC3)c3cnn(CC)c3)n1)C[C@H](c1ccccc1)CC2] | (1R,4r)-4-((R)-1-(((R)-4-(((R)-2-(4,4-difluoroazepan-1-yl)-1-(1-ethyl-1H-pyrazol-4-yl)ethyl)amino)-6-phenyl-5,6,7,8-tetrahydroquinazolin-2-yl)amino)propyl)cyclohexane-1-carboxylic acid |
| 138 | 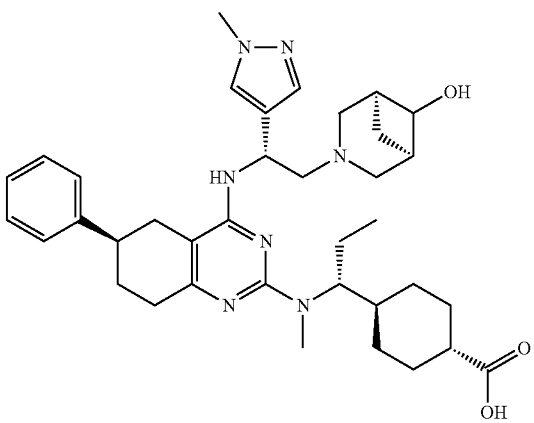 [SMILES: CC[C@H]([C@H]1CC[C@H](C(=O)O)CC1)N(C)c1nc2c(c(N[C@@H](CN3C[C@H]4C[C@@H](C3)C4O)c3cnn(C)c3)n1)C[C@H](c1ccccc1)CC2] | (1R,4r)-4-((1R)-1-(((6R)-4-(((1R)-2-((1R,5S)-6-hydroxy-3-azabicyclo[3.1.1]heptan-3-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 139 | 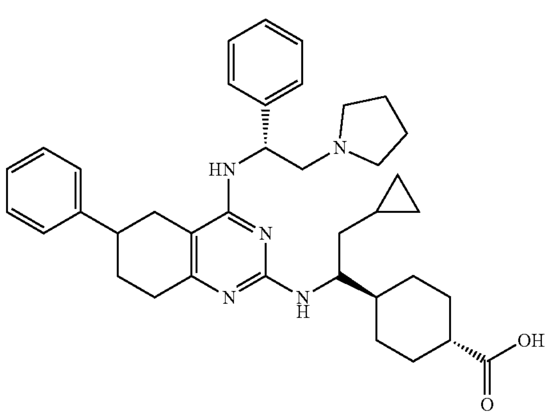 [SMILES: O=C(O)[C@H]1CC[C@H](C(CC2CC2)Nc2nc3c(c(N[C@@H](CN4CCCC4)c4ccccc4)n2)CC(c2ccccc2)CC3)CC1] | (1R,4r)-4-((1R)-2-cyclopropyl-1-((6-phenyl-4-(((R)-1-phenyl-2-(pyrrolidin-1-yl)ethyl)amino)-5,6,7,8-tetrahydroquinazolin-2-yl)amino)ethyl)cyclohexane-1-carboxylic acid |

| Cmp # | Structure | Name |
|---|---|---|
| 140 | 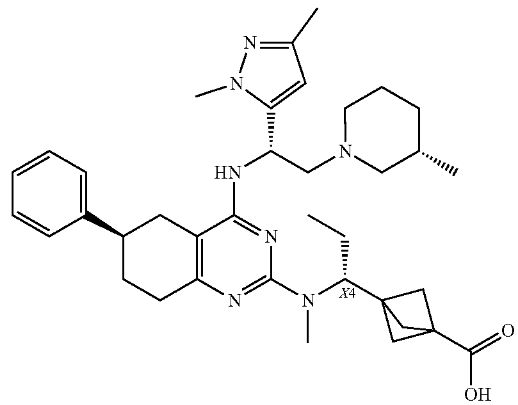 | 3-(1-(((R)-4-(((S)-1-(1,3-dimethyl-1H-pyrazol-5-yl)-2-((S)-3-methylpiperidin-1-yl)ethyl)amino)-6-phenyl-5,6,7,8-tetrahydroquinazolin-2-yl)(methyl)amino)-1l3-propyl)bicyclo[1.1.1]pentane-1-carboxylic acid |
| 141 | 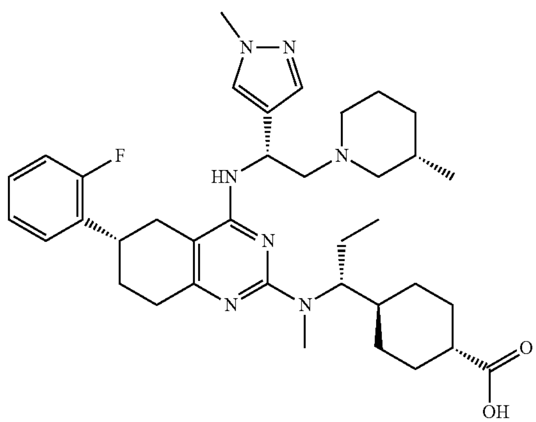 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@@H](c1ccccc1F)CC2] | (1R,4r)-4-((R)-1-(((S)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid |
| 142 | 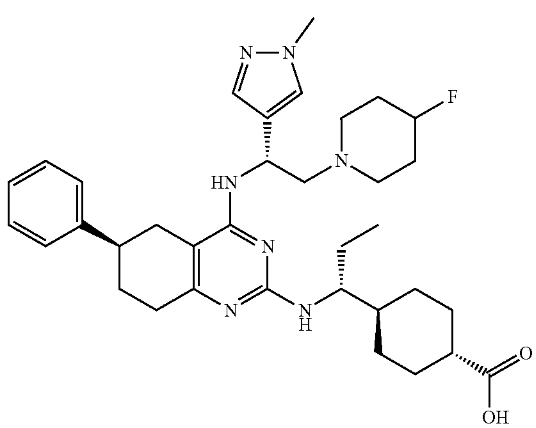 [SMILES: CC[C@@H](Nc1nc2c(c(N[C@@H](CN3CCC(F)CC3)c3cnn(C)c3)n1)C[C@H](c1ccccc1)CC2)[C@H]1CC[C@H](C(=O)O)CC1] | (1R,4r)-4-((R)-1-(((R)-4-(((R)-2-(4-fluoropiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 143 | 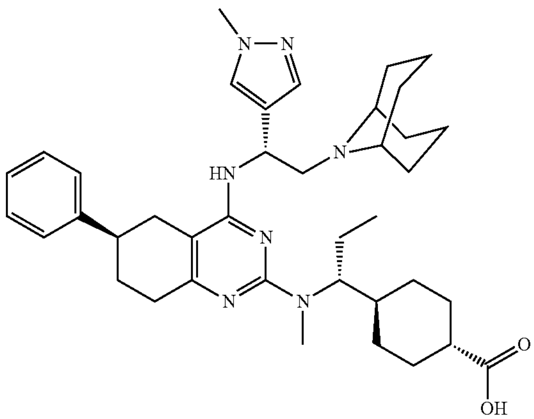 [SMILES: CC[C@H]([C@H]1CC[C@H](C(=O)O)CC1)N(C)c1nc2c(c(N[C@@H](CN3C4CCCC3CCC4)c3cnn(C)c3)n1)C[C@H](c1ccccc1)CC2] | (1R,4r)-4-((R)-1-(((R)-4-(((R)-2-((1S,5S)-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 144 | 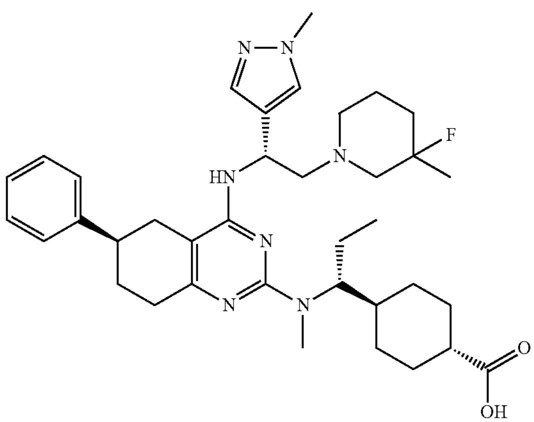 [SMILES: CC[C@H]([C@H]1CC[C@H](C(=O)O)CC1)N(C)c1nc2c(c(N[C@@H](CN3CCCC(C)(F)C3)c3cnn(C)c3)n1)C[C@H](c1ccccc1)CC2] | (1R,4r)-4-((1R)-1-(((6R)-4-(((1R)-2-(3-fluoro-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 145 | 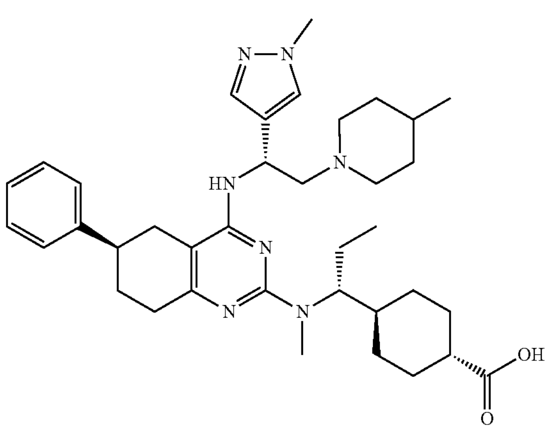 [SMILES: CC[C@H]([C@H]1CC[C@H](C(=O)O)CC1)N(C)c1nc2c(c(N[C@@H](CN3CCC(C)CC3)c3cnn(C)c3)n1)C[C@H](c1ccccc1)CC2] | (1R,4r)-4-((R)-1-(methyl((R)-4-(((R)-1-(1-methyl-1H-pyrazol-4-yl)-2-(4-methylpiperidin-1-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 146 | 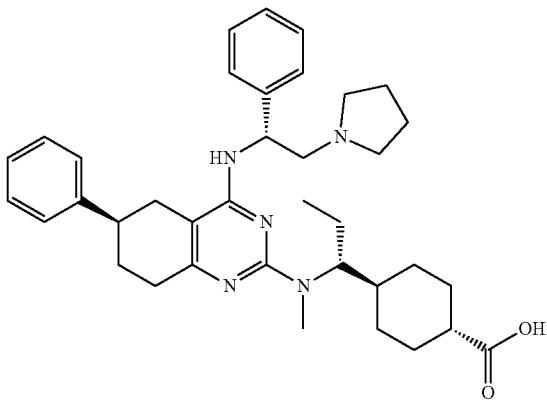 | (1R,4r)-4-((R)-1-(methyl((R)-6-phenyl-4-(((R)-1-phenyl-2-(pyrrolidin-1-yl)ethyl)amino)-5,6,7,8-tetrahydroquinazolin-2-yl)amino)propyl)cyclohexane-1-carboxylic acid |
| 147 | 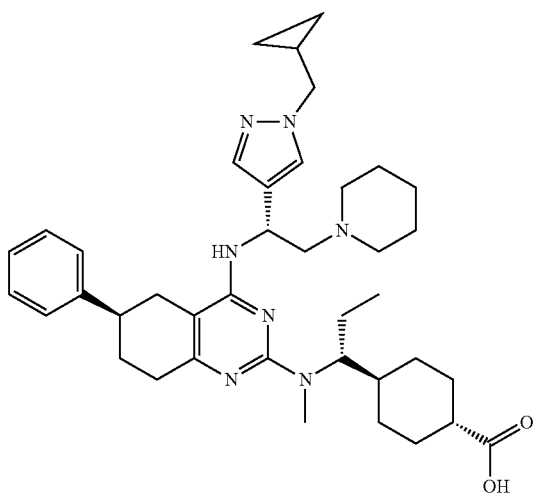 [SMILES: CC[C@H]([C@H]1CC[C@H](C(=O)O)CC1)N(C)c1nc2c(c(N[C@@H](CN3CCCCC3)c3cnn(CC4CC4)c3)n1)C[C@H](c1ccccc1)CC2] | (1R,4r)-4-((R)-1-(((R)-4-(((R)-1-(1-(cyclopropylmethyl)-1H-pyrazol-4-yl)-2-(piperidin-1-yl)ethyl)amino)-6-phenyl-5,6,7,8-tetrahydroquinazolin-2-yl)(methyl)amino)propyl)cyclohexane-1-carboxylic acid |
| 148 | 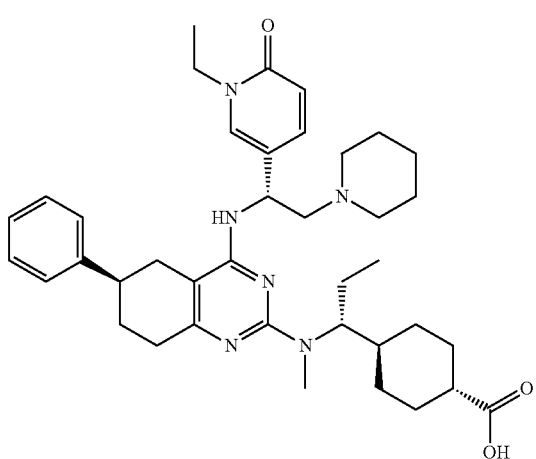 [SMILES: CC[C@H]([C@H]1CC[C@H](C(=O)O)CC1)N(C)c1nc2c(c(N[C@@H](CN3CCCCC3)c3ccc(=O)n(CC)c3)n1)C[C@H](c1ccccc1)CC2] | (1R,4r)-4-((R)-1-(((R)-4-(((R)-1-(1-ethyl-6-oxo-1,6-dihydropyridin-3-yl)-2-(piperidin-1-yl)ethyl)amino)-6-phenyl-5,6,7,8-tetrahydroquinazolin-2-yl)(methyl)amino)propyl)cyclohexane-1-carboxylic acid |

-continued

| Cmp # | Structure | Name |
|---|---|---|
| 149 | 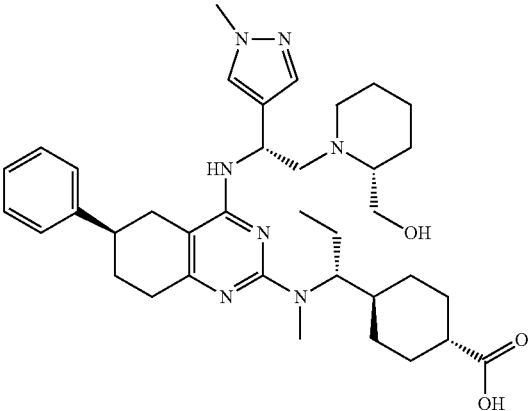 [SMILES: CC[C@H]([C@H]1CC[C@H](C(=O)O)CC1)N(C)c1nc2c(c(N[C@@H](CN3CCCC[C@@H]3CO)c3cnn(C)c3)n1)C[C@H](c1ccccc1)CC2] | (1R,4r)-4-((R)-1-(((R)-4-(((R)-2-((R)-2-(hydroxymethyl)piperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 150 | 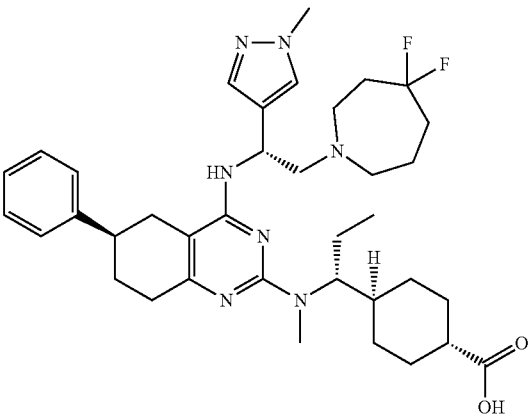 [SMILES: CC[C@H]([C@H]1CC[C@H](C(=O)O)CC1)N(C)c1nc2c(c(N[C@@H](CN3CCCC(F)(F)CC3)c3cnn(C)c3)n1)C[C@H](c1ccccc1)CC2] | (1R,4r)-4-((R)-1-(((R)-4-(((R)-2-(4,4-difluoroazepan-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 151 | 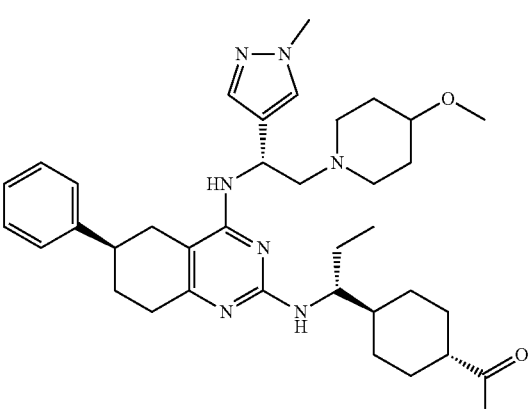 | (1R,4r)-4-((R)-1-(((R)-4-(((R)-2-(4-methoxypiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 152 | 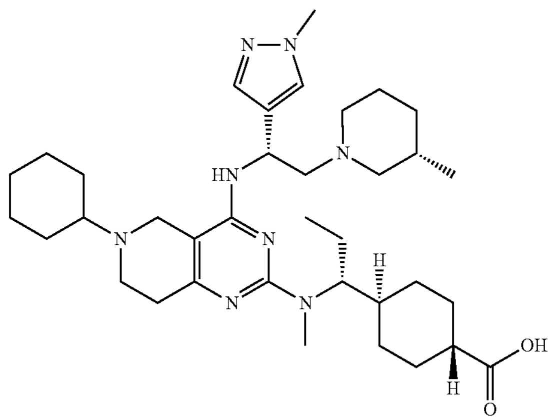 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(C1CCCCC1)CC2] | (1R,4r)-4-((R)-1-((6-cyclohexyl-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid |
| 153 | 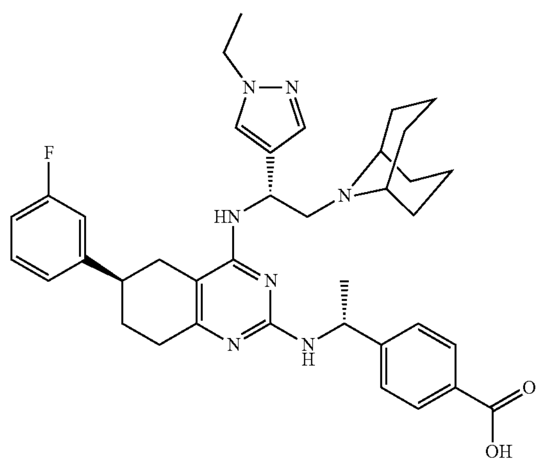 [SMILES: CCn1cc([C@H](CN2C3CCCC2CCC3)Nc2nc(N[C@H](C)c3ccc(C(=O)O)cc3)nc3c2C[C@H](c2cccc(F)c2)CC3)cn1] | 4-((R)-1-(((R)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)amino)ethyl)benzoic acid |
| 154 | 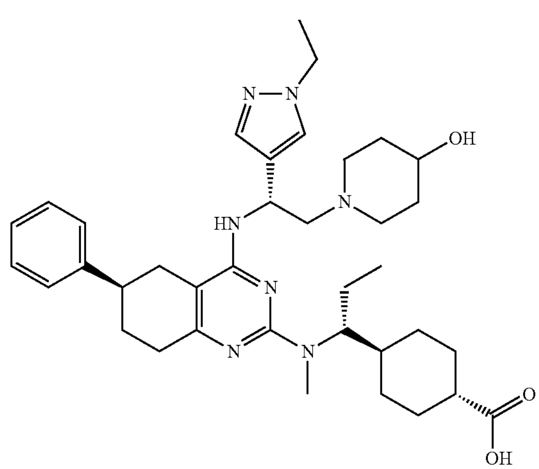 [SMILES: CC[C@H]([C@H]1CC[C@H](C(=O)O)CC1)N(C)c1nc2c(c(N[C@@H](CN3CCC(O)CC3)c3cnn(CC)c3)n1)C[C@H](c1ccccc1)CC2] | (1R,4r)-4-((R)-1-(((R)-4-(((R)-1-(1-ethyl-1H-pyrazol-4-yl)-2-(4-hydroxypiperidin-1-yl)ethyl)amino)-6-phenyl-5,6,7,8-tetrahydroquinazolin-2-yl)(methyl)amino)propyl)cyclohexane-1-carboxylic acid |

| Cmp # | Structure | Name |
|---|---|---|
| 155 | 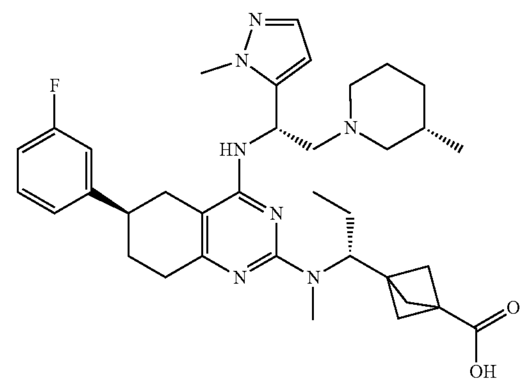 [SMILES: CC[C@@H](N(C)c1nc2c(c(N[C@@H](CN3CCC[C@H](C)C3)c3ccnn3C)n1)C[C@H](c1cccc(F)c1)CC2)C12CC(C(=O)O)(C1)C2] | 3-((R)-1-(((R)-6-(3-fluorophenyl)-4-(((S)-1-(1-methyl-1H-pyrazol-5-yl)-2-((S)-3-methylpiperidin-1-yl)ethyl)amino)-5,6,7,8-tetrahydroquinazolin-2-yl)(methyl)amino)propyl)bicyclo[1.1.1]pentane-1-carboxylic acid |
| 156 | 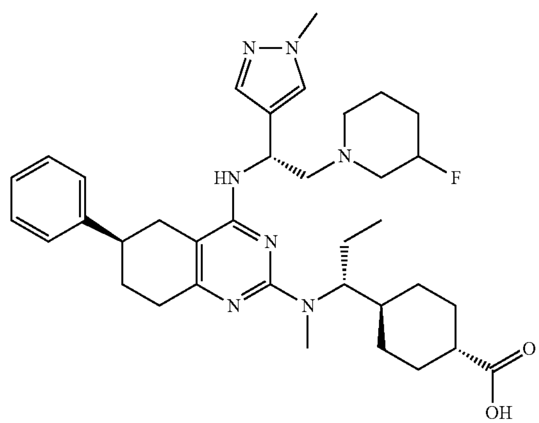 [SMILES: CC[C@H]([C@H]1CC[C@H](C(=O)O)CC1)N(C)c1nc2c(c(N[C@@H](CN3CCCC(F)C3)c3cnn(C)c3)n1)C[C@H](c1ccccc1)CC2] | (1R,4r)-4-((1R)-1-(((6R)-4-(((1R)-2-(3-fluoropiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 157 | 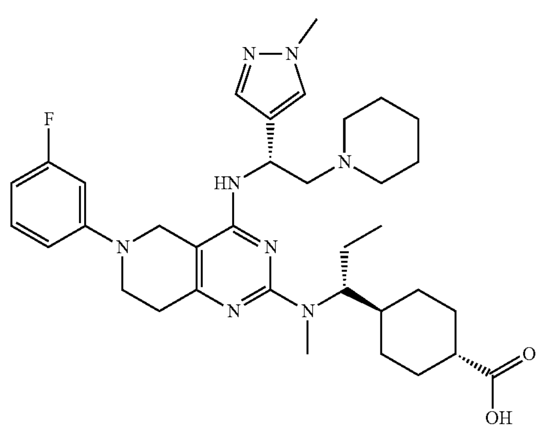 [SMILES: CC[C@H]([C@H]1CC[C@H](C(=O)O)CC1)N(C)c1nc2c(c(N[C@@H](CN3CCCCC3)c3cnn(C)c3)n1)CN(c1cccc(F)c1)CC2] | (1R,4r)-4-((R)-1-((6-(3-fluorophenyl)-4-(((R)-1-(1-methyl-1H-pyrazol-4-yl)-2-(piperidin-1-yl)ethyl)amino)-5,6,7,8-tetrahydropyrido[4,3-d]pyrimidin-2-yl)(methyl)amino)propyl)cyclohexane-1-carboxylic acid |

-continued

| Cmp # | Structure | Name |
|---|---|---|
| 158 | 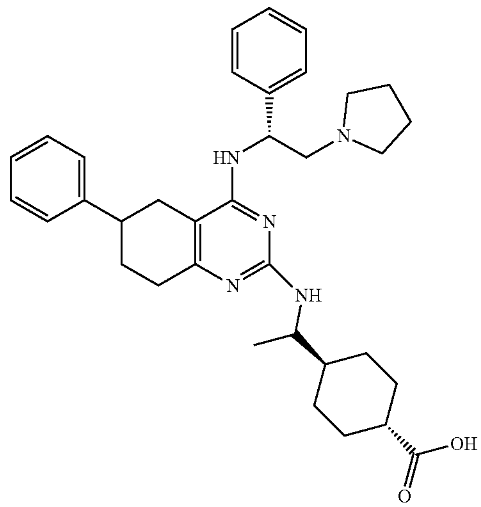 [SMILES: CC(Nc1nc2c(c(N[C@@H](CN3CCCC3)c3ccccc3)n1)CC(c1ccccc1)CC2)[C@H]1CC[C@H](C(=O)O)CC1] | (1S,4r)-4-((1S)-1-((6-phenyl-4-(((R)-1-phenyl-2-(pyrrolidin-1-yl)ethyl)amino)-5,6,7,8-tetrahydroquinazolin-2-yl)amino)ethyl)cyclohexane-1-carboxylic acid |
| 159 | 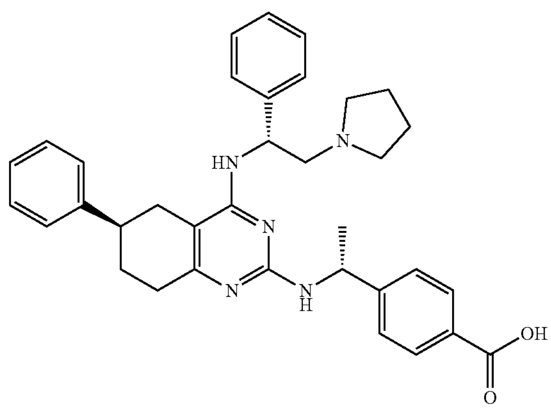 [SMILES: C[C@@H](Nc1nc2c(c(N[C@@H](CN3CCCC3)c3ccccc3)n1)C[C@H](c1ccccc1)CC2)c1ccc(C(=O)O)cc1] | 4-((R)-1-(((R)-6-phenyl-4-(((R)-1-phenyl-2-(pyrrolidin-1-yl)ethyl)amino)-5,6,7,8-tetrahydroquinazolin-2-yl)amino)ethyl)benzoic acid |
| 160 | 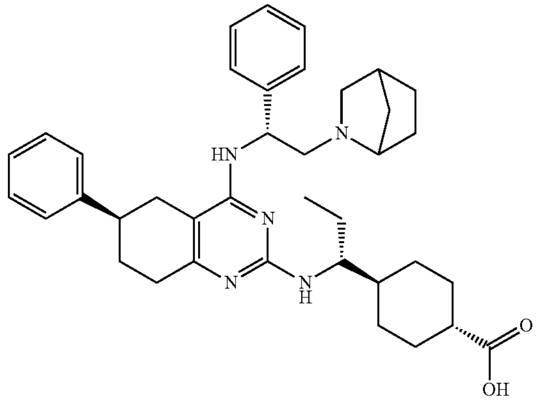 [SMILES: CC[C@@H](Nc1nc2c(c(N[C@@H](CN3CC4CCC3C4)c3ccccc3)n1)C[C@H](c1ccccc1)CC2)[C@H]1CC[C@H](C(=O)O)CC1] | (1R,4r)-4-((1R)-1-(((6R)-4-(((1R)-2-(2-azabicyclo[2.2.1]heptan-2-yl)-1-phenylethyl)amino)-6-phenyl-5,6,7,8-tetrahydroquinazolin-2-yl)amino)propyl)cyclohexane-1-carboxylic acid |

| Cmp # | Structure | Name |
|---|---|---|
| 161 | 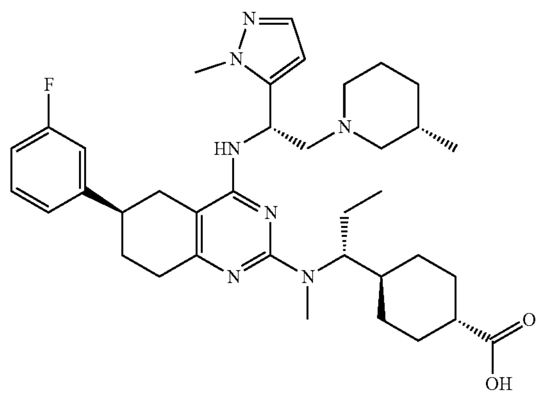 [SMILES: CC[C@H]([C@H]1CC[C@H](C(=O)O)CC1)N(C)c1nc2c(c(N[C@@H](CN3CCC[C@H](C)C3)c3ccnn3C)n1)C[C@H](c1cccc(F)c1)CC2] | (1R,4r)-4-((R)-1-(((R)-6-(3-fluorophenyl)-4-(((S)-1-(1-methyl-1H-pyrazol-5-yl)-2-((S)-3-methylpiperidin-1-yl)ethyl)amino)-5,6,7,8-tetrahydroquinazolin-2-yl)(methyl)amino)propyl)cyclohexane-1-carboxylic acid |
| 162 | 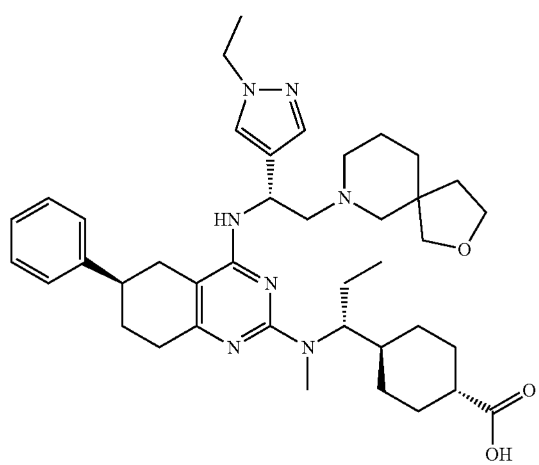 | (1R,4r)-4-((1R)-1-(((6R)-4-(((1R)-1-(1-ethyl-1H-pyrazol-4-yl)-2-(2-oxa-7-azaspiro[4.5]decan-7-yl)ethyl)amino)-6-phenyl-5,6,7,8-tetrahydroquinazolin-2-yl)(methyl)amino)propyl)cyclohexane-1-carboxylic acid |
| 163 | 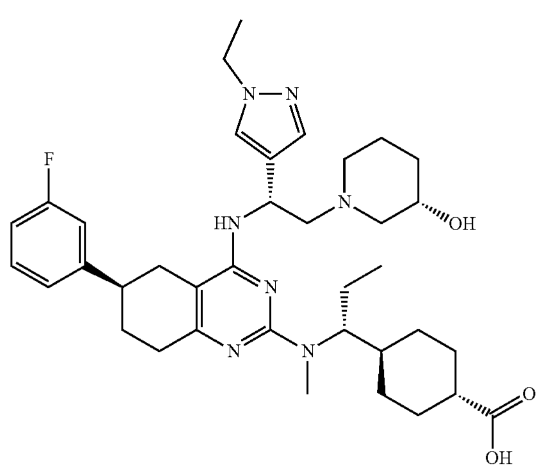 [SMILES: CC[C@H]([C@H]1CC[C@H](C(=O)O)CC1)N(C)c1nc2c(c(N[C@@H](CN3CCC[C@H](O)C3)c3cnn(CC)c3)n1)C[C@H](c1cccc(F)c1)CC2] | (1R,4r)-4-((R)-1-(((R)-4-(((R)-1-(1-ethyl-1H-pyrazol-4-yl)-2-((S)-3-hydroxypiperidin-1-yl)ethyl)amino)-6-(3-fluorophenyl)-5,6,7,8-tetrahydroquinazolin-2-yl)(methyl)amino)propyl)cyclohexane-1-carboxylic acid |

| Cmp # | Structure | Name |
|---|---|---|
| 164 | 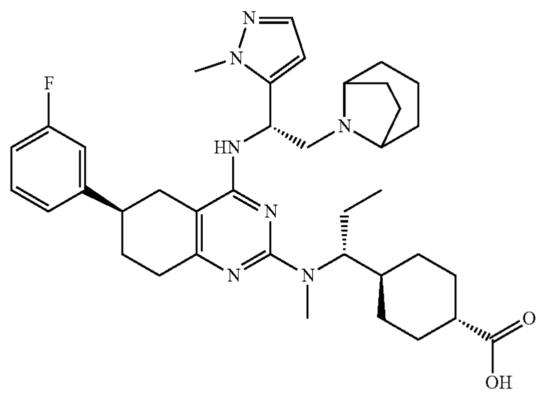 [SMILES: CC[C@H]([C@H]1CC[C@H](C(=O)O)CC1)N(C)c1nc2c(c(N[C@@H](CN3C4CCCC3CC4)c3ccnn3C)n1)C[C@H](c1cccc(F)c1)CC2] | (1R,4r)-4-((1R)-1-(((6R)-4-(((1S)-2-(8-azabicyclo[3.2.1]octan-8-yl)-1-(1-methyl-1H-pyrazol-5-yl)ethyl)amino)-6-(3-fluorophenyl)-5,6,7,8-tetrahydroquinazolin-2-yl)(methyl)amino)propyl)cyclohexane-1-carboxylic acid |
| 165 | 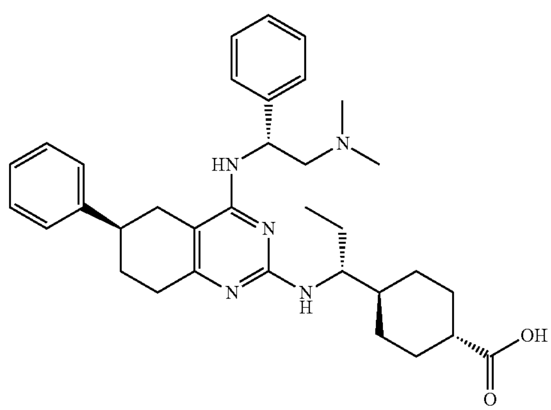 [SMILES: CC[C@@H](Nc1nc2c(c(N[C@@H](CN(C)C)c3ccccc3)n1)C[C@H](c1ccccc1)CC2)[C@H]1CC[C@H](C(=O)O)CC1] | (1R,4r)-4-((R)-1-(((R)-4-(((R)-2-(dimethylamino)-1-phenylethyl)amino)-6-phenyl-5,6,7,8-tetrahydroquinazolin-2-yl)amino)propyl)cyclohexane-1-carboxylic acid |
| 166 | 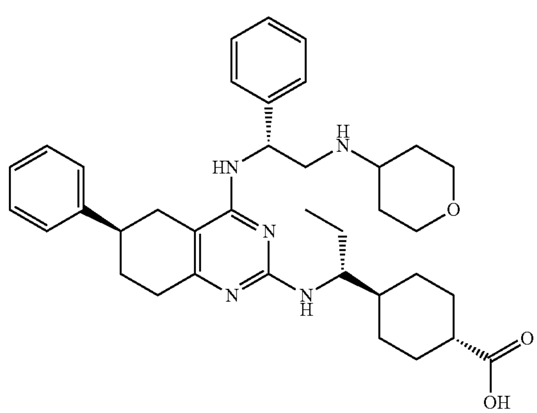 [SMILES: CC[C@@H](Nc1nc2c(c(N[C@@H](CNC3CCOCC3)c3ccccc3)n1)C[C@H](c1ccccc1)CC2)[C@H]1CC[C@H](C(=O)O)CC1] | (1R,4r)-4-((R)-1-(((R)-6-phenyl-4-(((R)-1-phenyl-2-((tetrahydro-2H-pyran-4-yl)amino)ethyl)amino)-5,6,7,8-tetrahydroquinazolin-2-yl)amino)propyl)cyclohexane-1-carboxylic acid |

| Cmp # | Structure | Name |
|---|---|---|
| 167 | 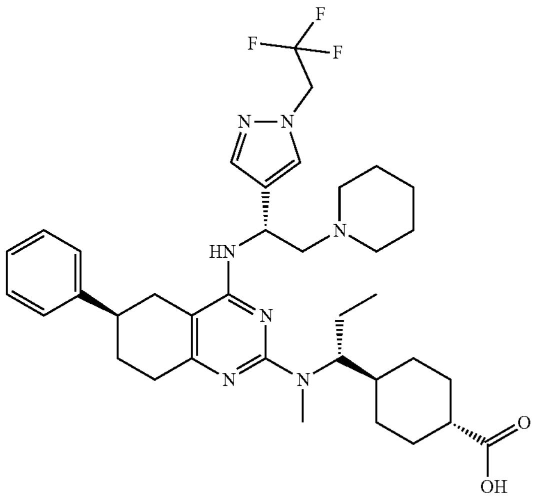 [SMILES: CC[C@H]([C@H]1CC[C@H](C(=O)O)CC1)N(C)c1nc2c(c(N[C@@H](CN3CCCCC3)c3cnn(CC(F)(F)F)c3)n1)C[C@H](c1ccccc1)CC2] | (1R,4r)-4-((R)-1-(methyl((R)-6-phenyl-4-(((R)-2-(piperidin-1-yl)-1-(1-(2,2,2-trifluoroethyl)-1H-pyrazol-4-yl)ethyl)amino)-5,6,7,8-tetrahydroquinazolin-2-yl)amino)propyl)cyclohexane-1-carboxylic acid |
| 168 | 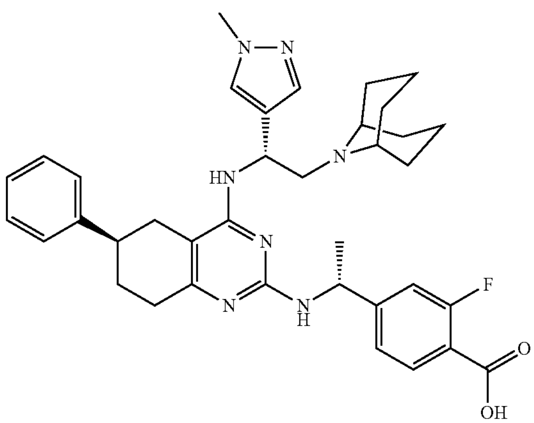 [SMILES: C[C@@H](Nc1nc2c(c(N[C@@H](CN3C4CCCC3CCC4)c3cnn(C)c3)n1)C[C@H](c1ccccc1)CC2)c1ccc(C(=O)O)c(F)c1] | 4-((R)-1-(((R)-4-(((R)-2-((1S,5S)-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)amino)ethyl)-2-fluorobenzoic acid |
| 169 | 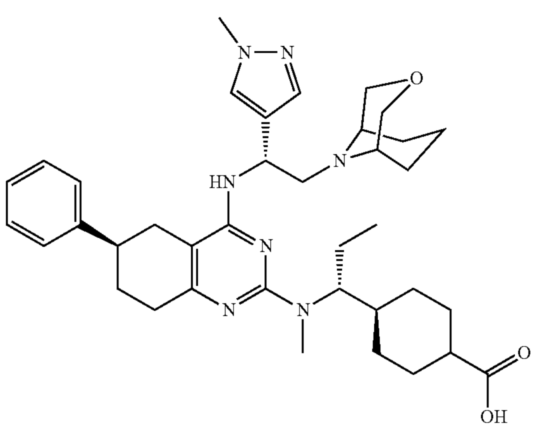 | (1R,4r)-4-((R)-1-(((R)-4-(((R)-2-((1R,5S)-3-oxa-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |

-continued

| Cmp # | Structure | Name |
|---|---|---|
| 170 | 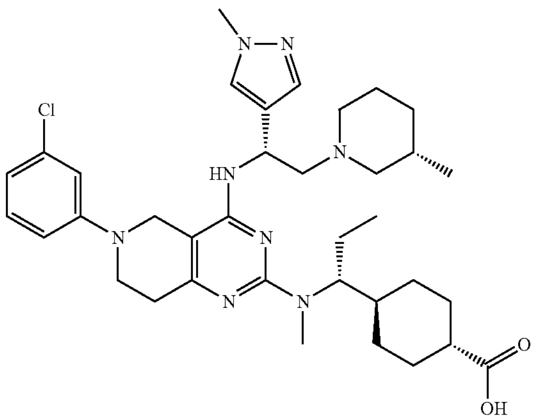 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(c1cccc(Cl)c1)CC2] | (1R,4r)-4-((R)-1-(((6-(3-chlorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid |
| 171 | 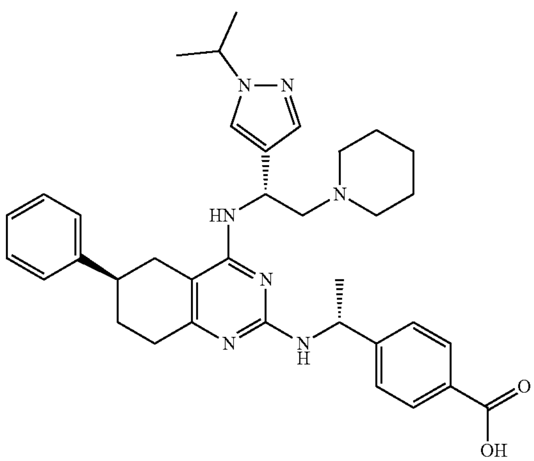 [SMILES: CC(C)n1cc([C@H](CN2CCCCC2)Nc2nc(N[C@H](C)c3ccc(C(=O)O)cc3)nc3c2C[C@H](c2ccccc2)CC3)cn1] | 4-((R)-1-(((R)-4-(((R)-1-(1-isopropyl-1H-pyrazol-4-yl)-2-(piperidin-1-yl)ethyl)amino)-6-phenyl-5,6,7,8-tetrahydroquinazolin-2-yl)amino)ethyl)benzoic acid |
| 172 | 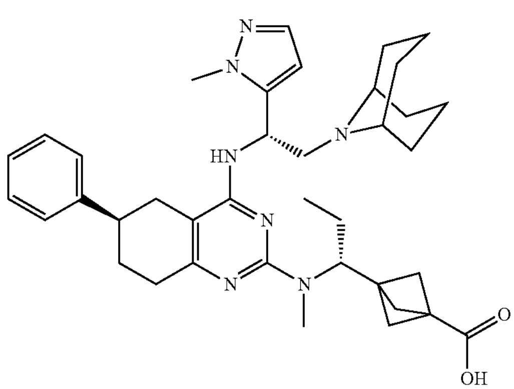 [SMILES: CC[C@@H](N(C)c1nc2c(c(N[C@@H](CN3C4CCCC3CCC4)c3ccnn3C)n1)C[C@H](c1ccccc1)CC2)C12CC(C(=O)O)(C1)C2] | 3-((R)-1-(((R)-4-(((S)-2-((1R,5R)-9-azabicyclo[3.3.1]nonan-9-yl)-1-(1-methyl-1H-pyrazol-5-yl)ethyl)amino)-6-phenyl-5,6,7,8-tetrahydroquinazolin-2-yl)(methyl)amino)propyl)bicyclo[1.1.1]pentane-1-carboxylic acid |

-continued

| Cmp # | Structure | Name |
|---|---|---|
| 173 | 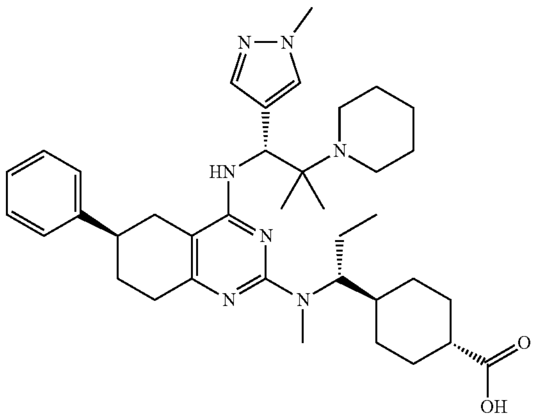 [SMILES: CC[C@H]([C@H]1CC[C@H](C(=O)O)CC1)N(C)c1nc2c(c(N[C@H](c3cnn(C)c3)C(C)(C)N3CCCCC3)n1)C[C@H](c1ccccc1)CC2] | (1R,4r)-4-((R)-1-(methyl((R)-4-(((R)-2-methyl-1-(1-methyl-1H-pyrazol-4-yl)-2-(piperidin-1-yl)propyl)amino)-6-phenyl-5,6,7,8-tetrahydroquinazolin-2-yl)amino)propyl)cyclohexane-1-carboxylic acid |
| 174 | 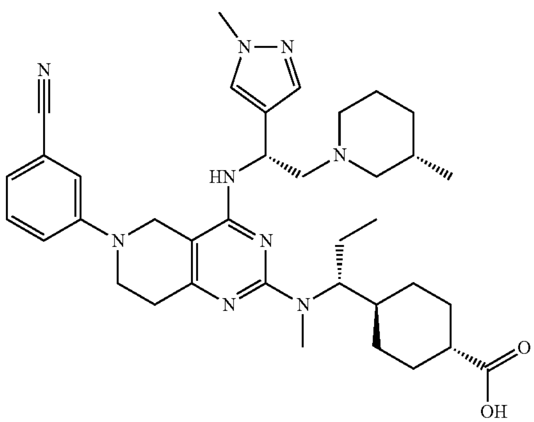 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(c1cccc(C#N)c1)CC2] | (1R,4r)-4-((R)-1-((6-(3-cyanophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid |
| 175 | 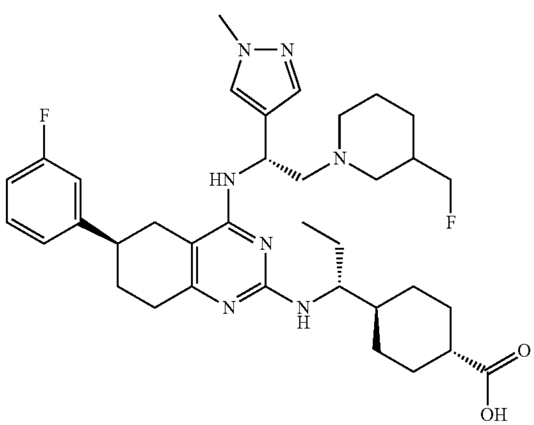 [SMILES: CC[C@@H](Nc1nc2c(c(N[C@@H](CN3CCCC(CF)C3)c3cnn(C)c3)n1)C[C@H](c1cccc(F)c1)CC2)[C@H]1CC[C@H](C(=O)O)CC1] | (1R,4r)-4-((1R)-1-(((6R)-4-(((1R)-2-(3-(fluoromethyl)piperidin-1-yl)-1-(1-methyl-1H-pyrazol-4-yl)ethyl)amino)-6-(3-fluorophenyl)-5,6,7,8-tetrahydroquinazolin-2-yl)amino)propyl)cyclohexane-1-carboxylic acid |

| Cmp # | Structure | Name |
|---|---|---|
| 176 | 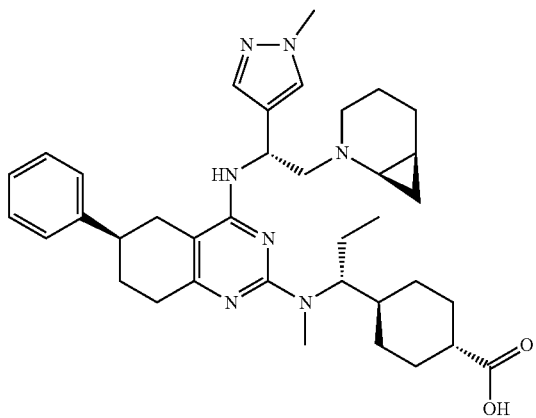 [SMILES: CC[C@H]([C@H]1CC[C@H](C(=O)O)CC1)N(C)c1nc2c(c(N[C@@H](CN3CCC[C@H]4C[C@H]43)c3cnn(C)c3)n1)C[C@H](c1ccccc1)CC2] | (1R,4r)-4-((R)-1-(((R)-4-(((R)-2-((1R,6S)-2-azabicyclo[4.1.0]heptan-2-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 177 | 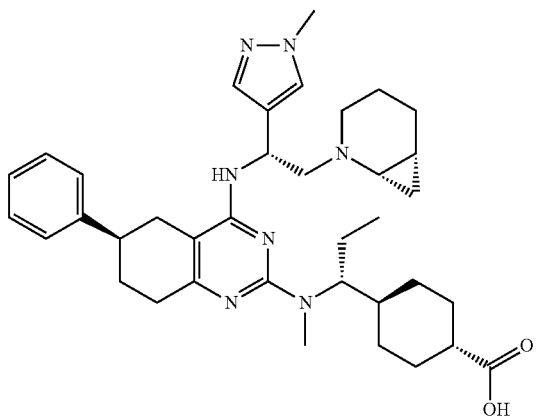 [SMILES: CC[C@H]([C@H]1CC[C@H](C(=O)O)CC1)N(C)c1nc2c(c(N[C@@H](CN3CCC[C@@H]4C[C@@H]43)c3cnn(C)c3)n1)C[C@H](c1ccccc1)CC2] | (1R,4r)-4-((R)-1-(((R)-4-(((R)-2-((1S,6R)-2-azabicyclo[4.1.0]heptan-2-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 178 | 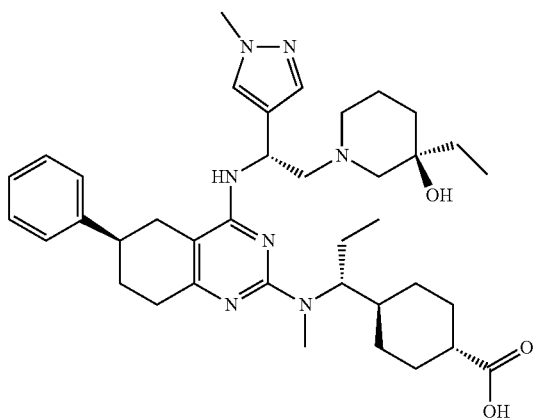 [SMILES: CC[C@H]([C@H]1CC[C@H](C(=O)O)CC1)N(C)c1nc2c(c(N[C@@H](CN3CCC[C@](O)(CC)C3)c3cnn(C)c3)n1)C[C@H](c1ccccc1)CC2] | (1R,4r)-4-((R)-1-(((R)-4-(((R)-2-((R)-3-ethyl-3-hydroxypiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |

| Cmp # | Structure | Name |
|---|---|---|
| 179 | 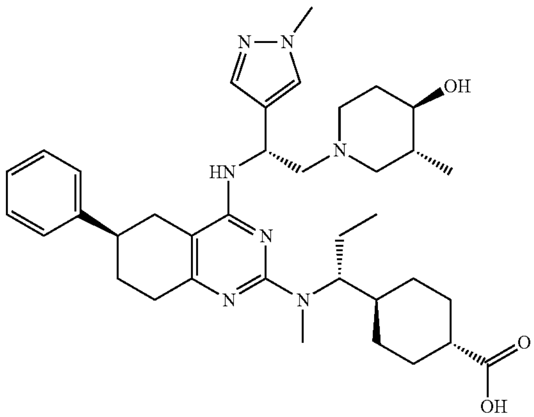 [SMILES: CC[C@H]([C@H]1CC[C@H](C(=O)O)CC1)N(C)c1nc2c(c(N[C@@H](CN3CC[C@@H](O)[C@H](C)C3)c3cnn(C)c3)n1)C[C@H](c1ccccc1)CC2] | (1R,4r)-4-((R)-1-(((R)-4-(((R)-2-((3R,4R)-4-hydroxy-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 180 | 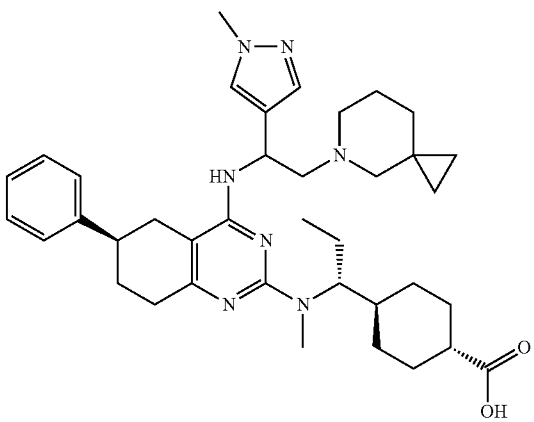 [SMILES: CC[C@H]([C@H]1CC[C@H](C(=O)O)CC1)N(C)c1nc2c(c(NC(CN3CCCC4(CC4)C3)c3cnn(C)c3)n1)C[C@H](c1ccccc1)CC2] | (1R,4r)-4-((R)-1-(methyl((R)-4-(((R)-1-(1-methyl-1H-pyrazol-4-yl)-2-(5-azaspiro[2.5]octan-5-yl)ethyl)amino)-6-phenyl-5,6,7,8-tetrahydroquinazolin-2-yl)amino)propyl)cyclohexane-1-carboxylic acid |
| 181 | 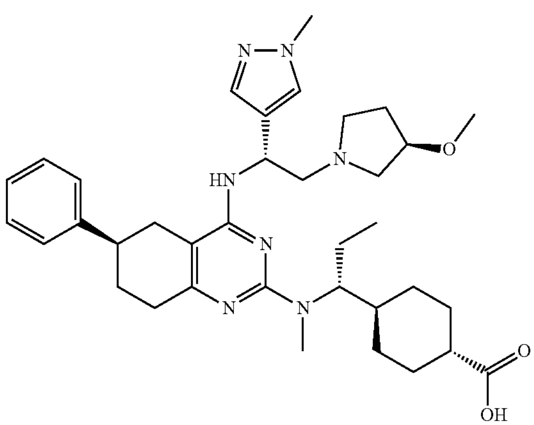 [SMILES: CC[C@H]([C@H]1CC[C@H](C(=O)O)CC1)N(C)c1nc2c(c(N[C@@H](CN3CC[C@@H](OC)C3)c3cnn(C)c3)n1)C[C@H](c1ccccc1)CC2] | (1R,4r)-4-((R)-1-(((R)-4-(((R)-2-((R)-3-methoxypyrrolidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |

| Cmp # | Structure | Name |
|---|---|---|
| 182 | 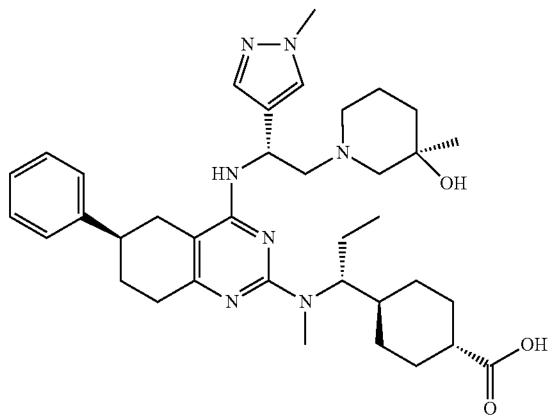 [SMILES: CC[C@H]([C@H]1CC[C@H](C(=O)O)CC1)N(C)c1nc2c(c(N[C@@H](CN3CCC[C@@](C)(O)C3)c3cnn(C)c3)n1)C[C@H](c1ccccc1)CC2] | (1R,4r)-4-((R)-1-(((R)-4-(((R)-2-((R)-3-hydroxy-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 183 | 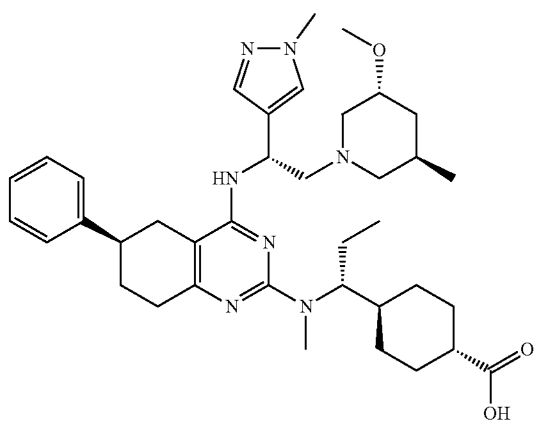 [SMILES: CC[C@H]([C@H]1CC[C@H](C(=O)O)CC1)N(C)c1nc2c(c(N[C@@H](CN3C[C@H](C)C[C@@H](OC)C3)c3cnn(C)c3)n1)C[C@H](c1ccccc1)CC2] | (1R,4r)-4-((R)-1-(((R)-4-(((R)-2-((3R,5R)-3-methoxy-5-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |
| 184 | 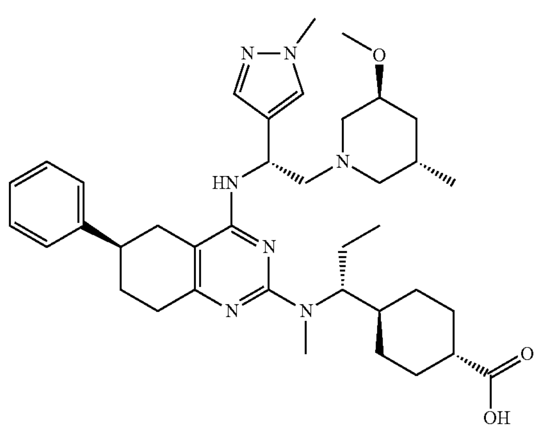 [SMILES: CC[C@H]([C@H]1CC[C@H](C(=O)O)CC1)N(C)c1nc2c(c(N[C@@H](CN3C[C@@H](C)C[C@H](OC)C3)c3cnn(C)c3)n1)C[C@H](c1ccccc1)CC2] | (1R,4r)-4-((R)-1-(((R)-4-(((R)-2-((3S,5S)-3-methoxy-5-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |

| Cmp # | Structure | Name |
|---|---|---|
| 185 | 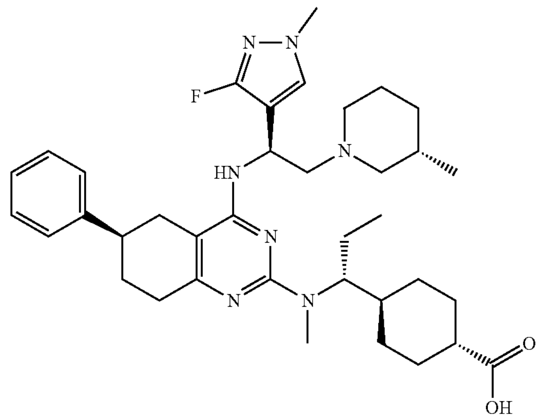 [SMILES: CC[C@H]([C@H]1CC[C@H](C(=O)O)CC1)N(C)c1nc2c(c(N[C@H](CN3CCC[C@H](C)C3)c3cn(C)nc3F)n1)C[C@H](c1ccccc1)CC2] | (1R,4r)-4-((R)-1-(((R)-4-(((S)-1-(3-fluoro-1-methyl-1H-pyrazol-4-yl)-2-((S)-3-methylpiperidin-1-yl)ethyl)amino)-6-phenyl-5,6,7,8-tetrahydroquinazolin-2-yl)(methyl)amino)propyl)cyclohexane-1-carboxylic acid |
| 186 | 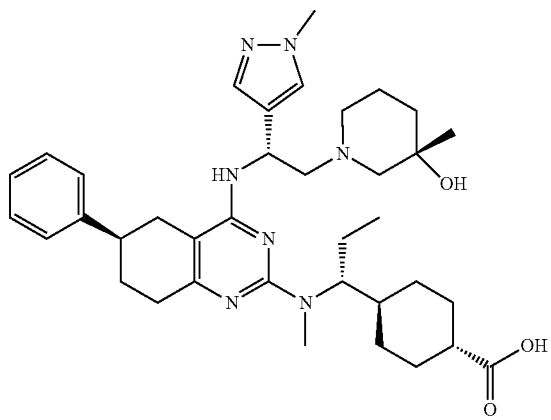 [SMILES: CC[C@H]([C@H]1CC[C@H](C(=O)O)CC1)N(C)c1nc2c(c(N[C@@H](CN3CCC[C@](C)(O)C3)c3cnn(C)c3)n1)C[C@H](c1ccccc1)CC2] | (1R,4r)-4-((R)-1-(((R)-4-(((R)-2-((S)-3-hydroxy-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid |

As used herein, the terms "salt" or "salts" refers to an acid addition or base addition salt of a compound of the present disclosure. "Salts" include in particular "pharmaceutical acceptable salts". The term "pharmaceutically acceptable salts" refers to salts that retain the biological effectiveness and properties of the compounds of this disclosure and, which typically are not biologically or otherwise undesirable. In many cases, the compounds of the present disclosure are capable of forming acid and/or base salts by virtue of the presence of amino and/or carboxyl groups or groups similar thereto. When both a basic group and an acid group are present in the same molecule, the compounds of the present disclosure may also form internal salts, e.g., zwitterionic molecules.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present disclosure provides compounds of the present disclosure in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present disclosure. The concentration of deuterium, may be defined by the isotopic enrichment factor. The term "isotopic enrichment factor" as used herein means the ratio between the isotopic abundance and the natural abundance of a specified isotope. If a substituent in a compound of this disclosure is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the disclosure include isotopes of hydrogen, carbon, nitrogen, oxygen, phosphorous, fluorine, and chlorine, such as $^3$H, $^{11}$C, $^{13}$C $^{14}$C, $^{15}$N, $^{18}$F $^{31}$P, $^{32}$P, $^{35}$S, $^{36}$Cl, $^{123}$I, $^{124}$I, $^{125}$I respectively. Accordingly it should be understood that the disclosure includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of the present disclosure can generally be prepared by conventional techniques known to those skilled in the art or by processes analogous to those described in the accompanying Examples and Preparations using an appropriate isotopically-labeled reagents in place of the non-labeled reagent previously employed.

Any asymmetric atom (e.g., carbon or the like) of the compound(s) of the present disclosure can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)—configuration. Substituents at atoms with unsaturated double bonds may, if possible, be present in cis- (Z)- or trans- (E)- form.

Accordingly, as used herein a compound of the present disclosure can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-0,0'-p-toluoyl tartaric acid, mandelic acid, malic acid or camphor-10-sulfonic acid. Racemic compounds of the present disclosure or racemic intermediates can also be resolved by chiral chromatography, e.g., high pressure liquid chromatography (HPLC) using a chiral adsorbent.

Pharmaceutical Compositions

In another aspect, the present disclosure provides a pharmaceutical composition comprising a compound of the present disclosure, or a pharmaceutically acceptable salt thereof, and one or more pharmaceutically acceptable carriers. In a further embodiment, the composition comprises at least two pharmaceutically acceptable carriers, such as those described herein.

In some embodiments, a pharmaceutical composition further comprises at least one additional pharmaceutically active agent. In some embodiments, the additional pharmaceutically active agent is selected from an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), or combinations thereof.

The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present disclosure can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The pharmaceutical composition or combination of the present disclosure may, for example, be in unit dosage of about 1-1000 mg of active ingredient(s) for a subject of about 50-70 kg. In one embodiment, the compositions are in the form of a tablet that can be scored. The therapeutically effective dosage of a compound, the pharmaceutical composition, or the combinations thereof, is dependent on the species of the subject, the body weight, age and individual condition, the disorder or disease or the severity thereof being treated.

Methods of Use

In yet another aspect, the present disclosure is directed to a method of treating or preventing a disease or disorder comprising administering to a patient in need thereof an effective amount of a compound of Formula (I), or a pharmaceutically acceptable salt thereof or a pharmaceutical composition comprising a compound of Formula (I), or a pharmaceutically acceptable salt thereof, and a pharmaceutically acceptable carrier.

In another aspect, the present disclosure relates to a method for treating a disease or disorder comprising administering to a patient in need thereof an effective amount of a compound of Formula (I), or a pharmaceutically acceptable salt thereof, or a pharmaceutical composition comprising a compound of Formula (I), or a pharmaceutically acceptable salt thereof, and a pharmaceutically acceptable carrier, wherein the disease or disorder is a cardiovascular disease or disorder.

In certain embodiments, the cardiovascular disease or disorder is selected from hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI). In some embodiments, the heart failure is selected from a heart failure with reduced ejection fraction (HFrEF), heart failure with preserved ejection fraction (HFpEF), heart failure after acute myocardial infarction, or acute decompensated heart failure. In some embodiments, the hypertrophic cardiomyopathy is ventricular hypertrophy. In some embodiments, the hypertension is selected from resistant hypertension, hypertensive heart disease, pulmonary hypertension, pulmonary arterial hypertension, isolated systolic hypertension, resistant hypertension, and pulmonary arterial hypertension. In some embodiments, the hypertension is selected from resistant hypertension and hypertensive heart disease.

In some embodiments, the disease or disorder is preeclampsia, asthma, glaucoma, a kidney disorder, and/or cytokine release syndrome in a subject in need of such treatment. In some embodiments, the kidney disorder is selected from: diabetic renal insufficiency, non-diabetic renal insufficiency, renal failure, diabetic nephropathy, non-diabetic nephropathy, acute renal injury, contrast induced nephropathy, nephrotic syndrome, glomerulonephritis, scleroderma, glomerular sclerosis, proteinuria of primary renal disease, renal vascular hypertension, diabetic retinopathy and end-stage renal disease (ESRD), endothelial dysfunction, diastolic dysfunction, renal fibrosis, and polycystic kidney disease (PKD).

In some embodiments, the disease or disorder is a disorder or disease associated with natriuretic peptide receptor activity.

In another aspect of the present disclosure relates to the use of a compound of Formula (I), or a pharmaceutically acceptable salt thereof, or a pharmaceutical composition described herein for the manufacture of a medicament for use to treat a disease or disorder disclosed herein.

In another aspect, the present disclosure relates to a compound of Formula (I), or a pharmaceutically acceptable salt thereof or a pharmaceutical composition described herein for use as a medicament.

Another aspect of the present disclosure relates to a compound of Formula (I), or a pharmaceutically acceptable salt thereof, or a pharmaceutical composition described herein for use in the in the treatment of a disease or disorder disclosed herein. In some embodiments, the disease or disorder is a cardiovascular disease or disorder (e.g., a cardiovascular disease or disorder as disclosed herein).

In another aspect, the present disclosure relates to the use of a compound of Formula (I), or a pharmaceutically acceptable salt thereof, or a pharmaceutical composition described herein in the treatment of a disease or disorder disclosed herein.

The disclosed compounds of the disclosure can be administered in effective amounts to treat or prevent a disorder and/or prevent the development thereof in subjects.

Combination Therapy

The compounds of the disclosure can be administered in therapeutically effective amounts in a combinational therapy with one or more pharmaceutically active agents (pharmaceutical combinations) or modalities, e.g., non-drug therapies. The compounds of the present disclosure may be administered either simultaneously with, or before or after, one or more other pharmaceutically active agent. The compound of the present disclosure may be administered separately, by the same or different route of administration, or together in the same pharmaceutical composition as the other agents. A pharmaceutically active agent is, for example, a chemical compound, peptide, antibody, antibody fragment or nucleic acid, which is therapeutically active or enhances the therapeutic activity when administered to a patient in combination with a compound of the present disclosure.

In one embodiment, the disclosure provides a product comprising a compound of the present disclosure and at least one other pharmaceutically active agent as a combined preparation for simultaneous, separate or sequential use as disclosed herein. Products provided as a combined preparation include a composition comprising the compound of the present disclosure and the other pharmaceutically active agent(s) together in the same pharmaceutical composition as described herein, or the compound of the present disclosure and the other pharmaceutically active agent (s) in separate form, e.g. in the form of a kit.

In another aspect, the disclosure includes a compound of Formula (I) or a pharmaceutically acceptable salt thereof, for use in a combination therapy.

Another aspect of the disclosure is directed to pharmaceutical compositions comprising a compound of Formula (I), or a pharmaceutically acceptable salt thereof, a pharmaceutically acceptable carrier, and one or more pharmaceutically active agent. The pharmaceutical acceptable carrier may further include an excipient, diluent, or surfactant.

Combination therapy includes the administration of the subject compounds in further combination with other biologically active ingredients. For instance, the compounds of the application can be used in combination with other pharmaceutically active agents, preferably compounds that are able to enhance the effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

Exemplary additional pharmaceutically active agents that may be used in combination with the compounds of the disclosure, include, but are not limited to an ACE (angiotensin-converting-enzyme) inhibitor, an angiotensin receptor blocker (ARB), a neprilysin inhibitor, a beta blocker, a diuretic, a calcium channel blocker, a cardiac glycoside, a sodium-glucose co-transporter 2 inhibitor (SGLT2i), or combinations thereof. As a non-limiting set of examples, a compound or a pharmaceutically acceptable salt thereof described herein may be combined with an additional pharmaceutically active agent selected from enalapril, benazepril, captopril, fosinopril, lisinopril, moexipril, perindopril, quinapril, ramipril, trandolapril, valsartan, azilsartan, candesartan, eprosartan, irbesartan, losartan, olmesartan, telmisartan, sacubitril, bisoprolol, carvedilol, propanolol, metoprolol, metoprolol tartrate, metoprolol succinate, thiazide diuretics, loop diuretics, potassium-sparing diuretics, amlodipine, clevidipine, diltiazem, felodipine, isradipine, nicardipine, nifedipine, nisoldipine, verapamil, a *digitalis* glycoside, canagliflozin, dapagliflozin, empagliflozin, ertugliflozin, and combinations thereof. Exemplary diuretics and *digitalis* glycosides include, but are not limited to, chlorothiazide, chlorthalidone, hydrochlorothiazide, indapamide, metolazone, bumetanide, ethacrynic acid, furosemide, torsemide, amiloride, eplerenone, spironolactonem, triamterene, digoxin, and combinations thereof. In some embodiments, a compound or a pharmaceutically acceptable salt thereof described herein may be combined with an angiotensin receptor-neprilysin inhibitor (ARNi) such as a combination of sacubitril and valsartan (e.g., Entresto®). In some embodiments, a compound or a pharmaceutically acceptable salt thereof described herein can be combined with one or more of a corticosteroid (e.g., an inhaled corticosteroid such as fluticasone, budesonide, mometasone, beclomethasone, ciclesonide, or fluticasone furoate; or an oral or intravenous corticosteroid such as prednisone or methylprednisolone), a leukotriene modifier (e.g., montelukast, zafirlukast, or zileuton), a bronchodilator (e.g., a long-acting beta agonist (e.g., salmeterol or formoterol), a short-acting beta agonist (e.g., albuterol or levalbuterol), theophylline or ipratropium), or combinations thereof (e.g., a combination of fluticasone and salmeterol, a combination of budesonide and formoterol, or a combination of formoterol and mometasone). In some embodiments, a compound or a pharmaceutically acceptable salt thereof described herein can be combined with one or more of a beta-adrenoceptor antagonist (e.g., timolol, levobunolol, metipranolol, carteolol, or betaxolol), a carbonic anhydrase inhibitor (e.g., acetazolamide, dorzolamide, brinzolamide, or methazolamide), an alpha 2-adrenoceptor agonist (e.g., brimonidine or apraclonidine), a parasympathomimetic (e.g., cholinomimetics like pilocarpine), a prostaglandin analog (e.g., latanoprost, latanoprostene bunod, travoprost, bimatoprost, or tafluprost), a rho kinase inhibitor (e.g., netarsudil or ripasudil), or combinations thereof (e.g., a combination of rho kinase inhibitor and latanoprost).

"Combination therapy" is intended to embrace administration of these therapeutic agents in a sequential manner, wherein each therapeutic agent is administered at a different time and in any order, or in alternation and in any order, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

Method of Synthesizing the Compounds

The compounds of the present disclosure may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M.

Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

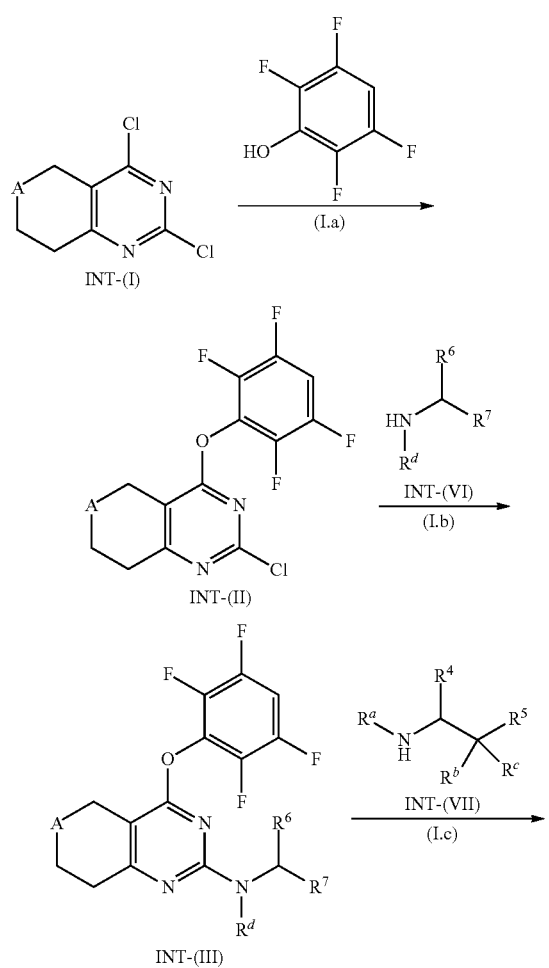

General Reaction Scheme 1

INT-(I)

INT-(II)

INT-(III)

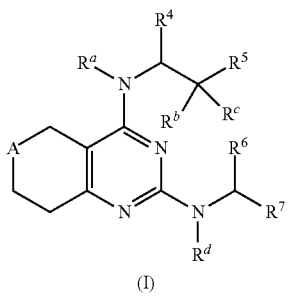

(I)

wherein A, $R^a$ to $R^d$, and $R^4$ to $R^7$ are defined herein for Formula (I).

A general scheme for preparing compounds of Formula (I) is described in General Reaction Scheme I. I.a: C—O cross coupling step, for example: DIPEA, MeCN, 80° C., 40 h; I.b, C—N cross coupling step, for example: DIPEA, MeCN, 100° C., 72 h; I.c, C—N cross coupling step followed by hydrolysis, for example: DIPEA, i-PrOH, 110° C., 48 h, purification then treated with 4N NaOH aq solution in THF/MeOH. Step I.a: A compound of formula INT-(II) may be prepared by reaction of a compound of formula INT-(I) with 2,3,5,6-tetrafluorophenol and base such as DIPEA, in a suitable solvent such as MeCN at a temperature of 80° C. for 40 hours followed by flash column chromatography. A compound of formula INT-(I) may be prepared by any suitable method known including for example by the methods shown to prepare Intermediates 1 to 5 in Examples 1 to 5 below. Step I.b: A compound of formula INT-(III) may be prepared by reaction of compounds of formula INT-(II) and INT-(VI) (see e.g., Intermediates 6 to 8 for exemplary prepartions) with base such as DIPEA, in a suitable solvent such as MeCN at a temperature of 100° C. for 72 hours followed by flash column chromatography. Step I.c: A compound of formula (I) may be prepared by following sequence: a reaction of compounds of formula INT-(III) and INT-(VII) (see e.g., Intermediate 9 for an exemplary prepartion) with base such as DIPEA, in a suitable solvent such as i-PrOH was performed at a temperature of 110° C. for 40 hours followed by flash column chromatography or used as crude material after concentration; the above material may then be treated with base such as NaOH in THF/MeOH/water followed by reverse phase purification to give a compound of formula (I).

General Reaction Scheme II

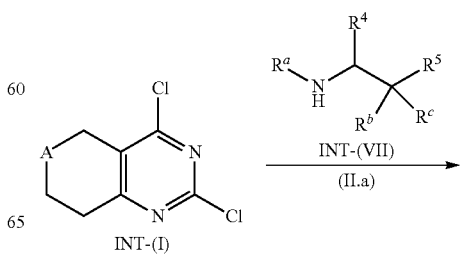

INT-(I)

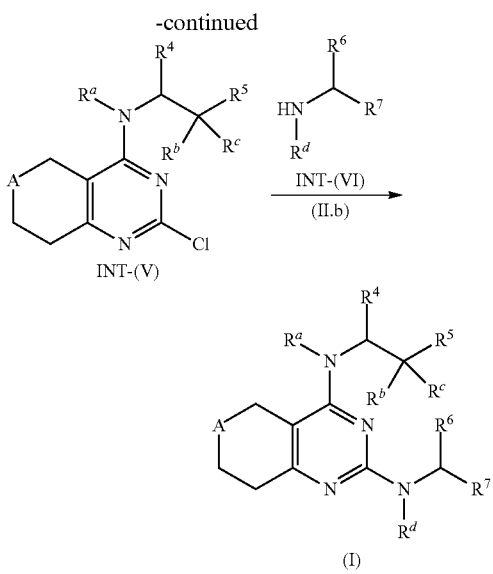

wherein A, $R^a$ to $R^d$, and $R^4$ to $R^7$ are defined herein for Formula (I).

A general scheme for preparing compounds of Formula (I) is described in General Reaction Scheme II. II.a: C—N cross coupling step, for example: DIPEA, MeCN, 70° C., 3 h; II.b, C—N cross coupling step followed by hydrolysis, for example: DIPEA, MeCN, 160° C., 48 h in microwave reactor, purification then treated with 4N NaOH aq solution in THF/MeOH. Step II.a: A compound of formula INT-(V) may be prepared by reaction of compounds of formula INT-(I) with INT-(VII) (see e.g., Intermediate 9 for an exemplary prepartion) and base such as DIPEA, in a suitable solvent such as MeCN at a temperature of 70° C. for 3 hours followed by flash column chromatography. A compound of formula INT-(I) may be prepared by any suitable method known including for example by the methods shown to prepare Intermediates 1 to 5 in Examples 1 to 5 below. Step II.b: A compound of formula (I) may be prepared by following sequence: a reaction of compounds of formula INT-(V) and INT-(VI) (see e.g., Intermediates 6 to 8 for exemplary prepartions) with base such as DIPEA, in a suitable solvent such as i-PrOH was performed at a temperature of 160° C. for 480 hours followed by flash column chromatography or used as crude material after concentration; the above material may then be treated with base such as NaOH in THF/MeOH/water followed by reverse phase purification to give a compound of Formula (I)

Definitions

Terms not specifically defined herein should be given the meanings that would be given to them by one of skill in the art in light of the disclosure and the context. For purposes of interpreting this specification, the following definitions will apply unless specified otherwise and whenever appropriate, terms used in the singular will also include the plural and vice versa.

It must be noted that as used herein and in the appended claims, the singular forms "a", "an" and "the" include plural referents unless the context clearly dictates otherwise. Thus, for example, reference to "the pharmaceutical formulation" includes reference to one or more pharmaceutical formulations; and so forth.

The term "alkoxy", as used herein, refers to an alkyl group, preferably a lower alkyl group, having an oxygen attached thereto, e.g., —O(alkyl). Representative alkoxy groups include, but are not limited to, methoxy, ethoxy, propoxy, tert-butoxy and the like. Representative substituted alkoxy groups include, but are not limited to, —OCF$_3$ and the like.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, ter-butyl, pentyl, hexyl, pentyl and octyl. A $C_1$-$C_6$ straight chained or branched alkyl group is also referred to as a "lower alkyl" group.

The term "aryl", as used herein, include single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

The term "$C_x$-$C_y$" when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$alkyl" refers to substituted or unsubstituted saturated hydrocarbon groups, including straight-chain alkyl and branched-chain alkyl groups that contain from x to y carbons in the chain. $C_0$ alkyl indicates a hydrogen where the group is in a terminal position, a bond if internal. The terms "$C_2$-$C_y$alkenyl" and "$C_2$-Cyalkynyl" refer to substituted or unsubstituted unsaturated aliphatic groups analogous in length and possible substitution to the alkyls described above, but that contain at least one double or triple bond respectively.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings.

The term "cycloalkyl-alkyl", as used herein, refers to an alkyl group substituted with a cycloalkyl group.

The term "alkyl-cycloalkyl", as used herein, refers to an cycloalkyl group substituted with an alkyl group.

The terms "halo" and "halogen", as used herein, means halogen and includes chloro, fluoro, bromo, and iodo.

"Haloalkyl", as used herein, refers to an alkyl group substituted with one or more (e.g., 1, 2, 3, 4, 5, or 6) halogens. Examples of haloalkyl groups include, but are not limited to, trifluoromethyl, difluoromethyl, pentafluoroethyl, trichloromethyl, etc. "Fluoroalkyl", as used herein, refers to an alkyl group substituted with one or more (e.g., 1, 2, 3, 4, 5, or 6) fluoro groups.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, but are not limited to, furyl, thienyl, pyrrolyl, pyridyl, pyridyl N-oxide, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1Δ2-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4 d]thiazolyl, imidazo[2,1-b][1,3,4]thiadiazolyl, thieno[2,3-b]pyrrolyl, 3H-indolyl, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl", "heterocycle", and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. The polycyclic ring systems may be fused or bridged. Heterocyclyl groups include, for example, piperidine, piperazine, pyrrolidine, morpholine, lactones, lactams, azaadamantane and the like. Heterocyclyl groups can also be substituted by oxo groups. For example, "heterocyclyl" encompasses both pyrrolidine and pyrrolidinone.

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The term "optionally substituted" means that a given chemical moiety (e.g., an alky 1 group) can (but is not required to) be bonded to other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen, wherein the substituents are as defined herein. "Optionally substituted" as used herein also refers to substituted or unsubstituted whose meaning is described below.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

The term "unsubstituted" means that the specified group bears no substituents.

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

The terms "pharmaceutically effective amount" or "therapeutically effective amount" or "effective amount" means an amount of a compound according to the disclosure which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound according to the disclosure which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the disclosure, and the age, body weight, general health, sex, and diet of the patient. Such a therapeutically effective amount can be determined routinely by one of ordinary skill in the art having regard to their own knowledge, the prior art, and this disclosure.

As used herein, the term "pharmaceutical composition" refers to a compound of the disclosure, or a pharmaceutically acceptable salt, hydrate, solvate, stereoisomer, or tautomer thereof, together with at least one pharmaceutically acceptable carrier, in a form suitable for oral or parenteral administration.

"Carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

A subject is "in need of" a treatment if such subject would benefit biologically, medically, or in quality of life from such treatment (preferably, a human).

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

"Compounds of the present disclosure", "Compounds of Formula (I)", "compounds of the disclosure", and equivalent expressions (unless specifically identified otherwise) refer to compounds of Formula (I) as herein described including the salts particularly the pharmaceutically acceptable salts thereof, where the context so permits thereof, as well as all stereoisomers (including diastereoisomers and enantiomers), rotamers, tautomers, and isotopically labelled compounds (including deuterium ("D") substitutions).

In a specific embodiment, the term "about" or "approximately" means within 20%, preferably within 10%, and more preferably within 5% of a given value or range.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art.

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. NMR spectra are given in ppm ($\delta$) and coupling constants, J, are reported in Hertz. Tetramethylsilane (TMS) was used as an internal standard. Chemical shifts are reported in ppm relative to dimethyl sulfoxide ($\delta$ 2.50), methanol ($\delta$ 3.31), chloroform ($\delta$ 7.26) or other solvent as indicated in NMR spectral data. A small amount of dry sample (2-5 mg) is dissolved in an appropriate deuterated solvent (1 mL). Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The chemical names were generated using ChemBioDraw Ultra v14 from CambridgeSoft.

Temperatures are given in degrees Celsius. As used herein, unless specified otherwise, the term "room temperature" or "ambient temperature" means a temperature of from 15 degrees centigrade to 30 degrees centigrade, such as of from 20 degrees centigrade to 30 degrees centigrade, such as of from 20 degrees centigrade to 25 degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present disclosure are either commercially available or can be produced by organic synthesis methods known to one of ordinary skill in the art.

Example 1—Intermediate 1: 2,4-dichloro-6-phenyl-5,6,7,8-tetrahydroquinazoline

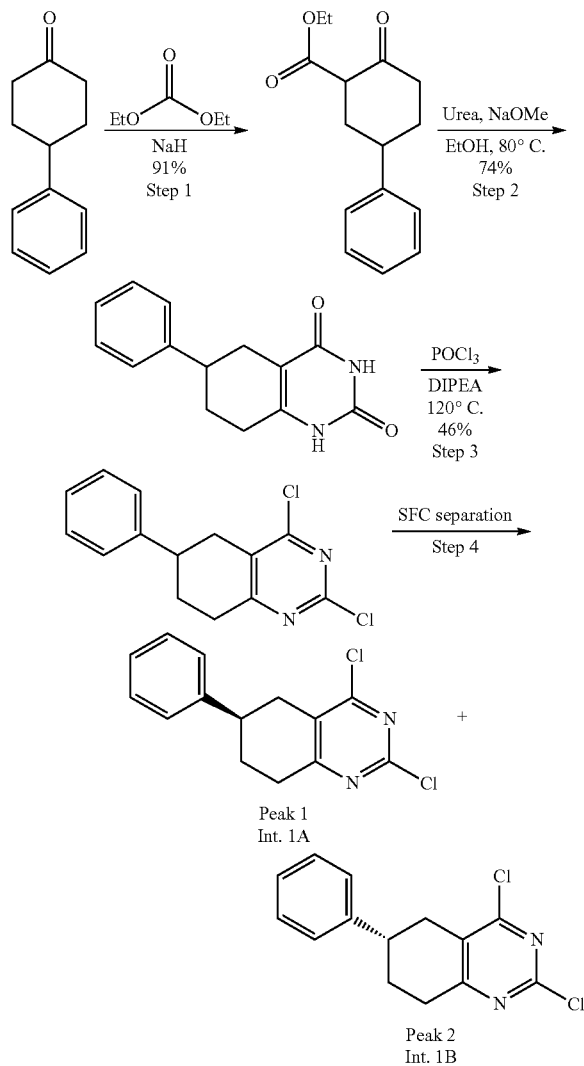

Step 1: To a stirred solution of diethyl carbonate (2110.0 mL, 17.0 mol, 5.0 eq) in tetrahydrofuran (2.4 L) at room temperature, NaH (165 g, 4.1 mol, 1.2 eq, 60% dispersion in mineral oil) was added portions wise. The resulting mixture was heated to 80° C. and then the solution of 4-phenylcyclohexanone (600.0 g, 3.4 mol) in tetrahydrofuran (2.4 L) was added dropwise over 1 h. The reaction mixture was then stirred at 80° C. for 1 h and quenched with saturated aqueous NH$_4$Cl (1.2 L) solution at 0° C. and then extracted with EtOAc (3×5.0 L). The combined organic layer was dried over anhydrous sodium sulfate, filtered and then concentrated to get crude residue, which was purified by silica gel column with Heptane/EtOAc=100/1 to afford desired compound ethyl 2-oxo-5-phenylcyclohexane-1-carboxylate (771.8 g, purity: 64.5%, 86.4% crude yield) as colorless liquid. $^1$H NMR (400 MHz, DMSO) δ 7.42-7.05 (m, 5H), 4.19-4.10 (m, 2H), 2.84-2.66 (m, 1H), 2.52-2.43 (m, 2H), 2.41-2.27 (m, 1H), 2.17 (ddd, J=33.6, 21.5, 2.3 Hz, 2H), 1.93-1.75 (m, 2H), 1.26-1.12 (m, 3H).

Step 2: To a solution of ethyl 2-oxo-5-phenylcyclohexane-1-carboxylate (700.0 g, 2.8 mol, 1.0 eq) and urea (341 g, 5.7 mol, 2.0 eq) in ethanol (12.5 L) at room temperature, sodium methoxide (1570.0 mL, 20% in methanol, 5.7 mol, 2.0 eq) was added. The resulting reaction mixture was stirred at 80° C. for 16 h. The reaction was monitored by HPLC. The reaction mixture was cooled to room temperature. The precipitated solid was filtered, washed with methyl tertbutylether (1 L×3) and dried to get 6-phenyl-5,6,7,8-tetrahydroquinazoline-2,4(1H,3H)-dione as an off-white solid (510 g, purity: 98.6%, 74% yield). H NMR (400 MHz, DMSO) δ 7.47-7.01 (m, 5H), 5.43 (s, 1H), 2.81-2.64 (m, 1H), 2.57 (d, J=4.6 Hz, 1H), 2.43-2.22 (m, 2H), 2.11 (dd, J=15.5, 10.6 Hz, 1H), 1.88 (d, J=10.3 Hz, 1H), 1.77 (dt, J=11.7, 6.2 Hz, 1H).

Step 3: To a mixture of 6-phenyl-5,6,7,8-tetrahydroquinazoline-2,4(1H,3H)-dione (500.0 g, 2.1 mol, 1.0 eq) in POCl$_3$ (2.0 L, 4.0 V) was added N, N-Diisopropylethylamine (266 g, 2.1 mol, 1.0 eq) dropwise over 30 min at room temperature under nitrogen atmosphere. After addition, the resulting mixture was heated to 120° C. and stirred for 16 h. The reaction was monitored by HPLC. The reaction mixture was cooled down to 25° C. in the air and diluted with dichloromethane (2.0 L). The diluted suspension was concentrated under vacuum to remove the most POCl$_3$. The residue was dissolved in dichloromethane (6.0 L) and then residual POCl$_3$ was quenched by adding ice water (10.0 L) at 0° C. The aqueous phase was extracted with dichloromethane (3.0 L) again, dried over anhydrous Na$_2$SO$_4$ and the filtrate was concentrated to get crude residue, which was purified by silica gel column with Heptane/EtOAc=20/1 to afford desired product 2,4-dichloro-6-phenyl-5,6,7,8-tetrahydroquinazoline (266.0 g, purity: 99.2%, 46% yield) as a yellow solid. LCMS: m/z=257.00 [M+H]+; $^1$H NMR (400 MHz, DMSO) δ 7.46-7.02 (m, 5H), 3.17-2.88 (m, 4H), 2.75 (dd, J=16.9, 11.0 Hz, 1H), 2.14-1.90 (m, 2H).

Step 4: Racemic 2,4-dichloro-6-phenyl-5,6,7,8-tetrahydroquinazoline (266.0 g) was purified by chiral SFC (Chiralcel OJ-H, Flowrate: 4 ml/min, Co-Solvent: 40%, Co-Solvent: Methanol, Injected Volume: 2 μl, Outlet Pressure: 100 bar, Temperature: 35° C.) to afford 105.0 g, 99.7% ee of (R)-2,4-dichloro-6-phenyl-5,6,7,8-tetrahydroquinazoline and 105.0 g, 98.6% ee of (S)-2,4-dichloro-6-phenyl-5,6,7,8-tetrahydroquinazoline. Absolute stereochemistry was determined by small molecule X-ray crystallography.

Example 2—Intermediate 2: 2,4-dichloro-6-methyl-6-phenyl-5,6,7,8-tetrahydroquinazoline

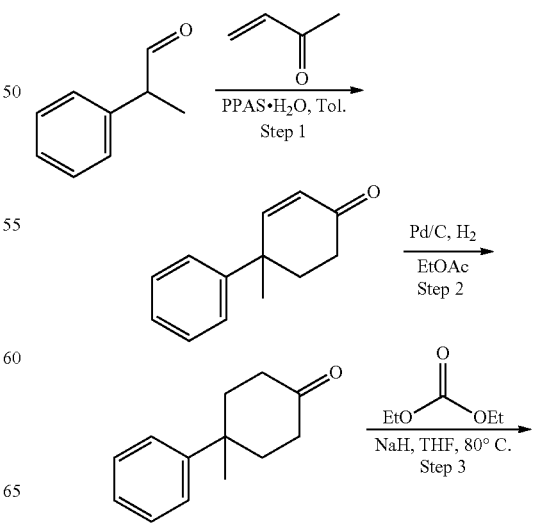

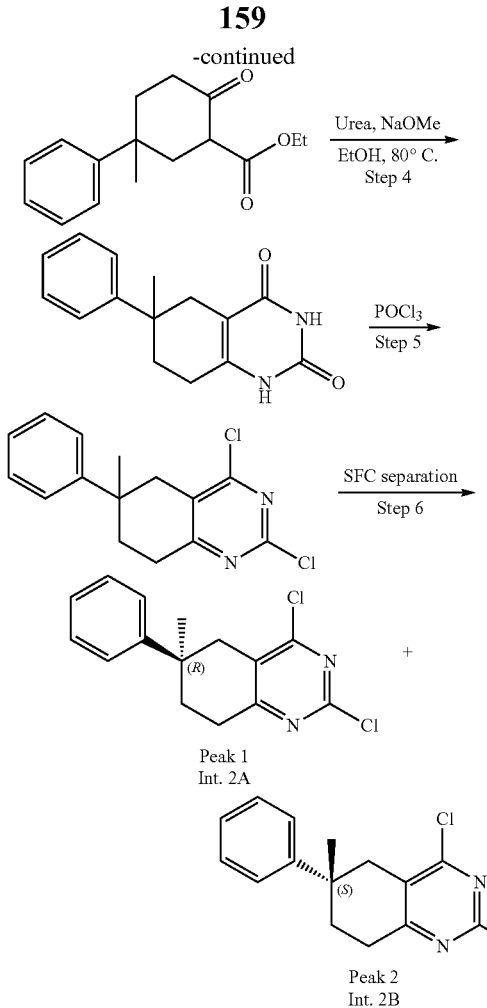

Peak 1
Int. 2A

Peak 2
Int. 2B

Step 1: To a solution of 2-phenylpropanal (430 g, 3.20 mol, 430 mL, 1 eq) in toluene (1.50 L) was added PPAS·H₂O (121 g, 640 mmol, 0.2 eq) and but-3-en-2-one (336 g, 4.81 mol, 400 mL, 1.5 eq) at 25° C. The mixture was stirred at 80° C. for 16 h. TLC (Petroleum ether/Ethyl acetate=10/1, Rf/reactant=0.45, Rf/product=0.45) indicated that starting material was disappeared and the new spots were formed. The reaction mixture (totally 860 g) was combined and cooled to room temperature and added into water (5.00 L) slowly. The mixture was extracted with EtOAc (5.00 L). The organic layer was washed with sat. K₂CO₃ solution (3.00 L), brine (3.00 L), dried over Na₂SO₄, filtered and concentrated. The product was used to next step directly. 1-methyl-2,3-dihydro-[1,1'-biphenyl]-4(1H)-one (1.20 kg, crude) was obtained as yellow oil.

Step 2: To a solution of 1-methyl-2,3-dihydro-[1,1'-biphenyl]-4(1H)-one (200 g, 1.07 mol, 1 eq, crude) in EtOAc (1.00 L) was added Pd/C (20.0 g, 107 mmol,10% purity, 0.1 eq) under N₂ atmosphere. The mixture was degassed and purged with H₂ (50 Psi) for 3 times. The mixture was stirred at 40° C. for 12 h. TLC (Petroleum ether/Ethyl acetate=10/1, Rf/reactant=0.45, Rf/product=0.65) indicated that starting materail was disappeared and the new spots were formed. The reaction mixture was filtered and the cake was washed with EtOAc (600 mL×3). The filtrate was concentrated. The product was purified by silica gel column chromatography (SiO₂, Petroleum ether/Ethyl acetate=10/1). 4-methyl-4-phenylcyclohexan-1-one (438 g, 2.33 mol, 54.1% yield) was obtained as a yellow oil. ¹H NMR (400 MHz CDCl₃) δ 7.50-7.45 (m, 2H), 7.44-7.37 (m, 2H), 7.30-7.24 (m, 1H), 2.59-2.47 (m, 2H), 2.44-2.28 (m, 4H), 2.03-1.91 (m, 2H), 1.35 (s, 3H).

Step 3: To a solution of 4-methyl-4-phenylcyclohexan-1-one (608 g, 5.15 mol, 624 mL, 5 eq) in THF (1.16 L) was added NaH (49.4 g, 1.24 mol, 60% purity, 1.2 eq) at 20° C. slowly. A solution of diethylcarbonate (194 g, 1.03 mol, 1 eq) in THF (388 mL) was added drop wise at 80° C., over 0.5 h. The mixture was stirred at 80° C. for 1 h. TLC (Petroleum ether/Ethyl acetate=10/1, Rf/reactant=0.40, Rf/product=0.55) indicated that starting material was disappeared and the new spot was formed. The reaction mixture was quenched with sat. NH₄Cl (2 L) and extracted with EtOAc (400 mL). The organic layer was separated, washed with brine (700 mL×2), dried over Na₂SO₄, filtered and concentrated. The product was purified by silica gel column chromatography (SiO₂, Petroleum ether). Ethyl 5-methyl-2-oxo-5-phenylcyclohexane-1-carboxylate (325 g, 1.25 mol, 60.5% yield) was obtained as yellow oil. ¹H NMR, (400 MHz CDCl₃) δ 7.32-7.22 (m, 4H), 7.19-7.10 (m, 1H), 4.22 (q, J=7.2 Hz, 2H), 4.07 (q, J=7.2 Hz, 1H), 2.82-2.70 (m, 1H), 2.29 (br d, J=16.4 Hz, 1H), 2.25-2.17 (m, 1H), 2.06-2.00 (m, 2H), 1.82-1.73 (m, 1H), 1.33-1.23 (m, 6H).

Step 4: To a mixture of ethyl 5-methyl-2-oxo-5-phenyl-cyclohexane-1-carboxylate (295 g, 1.13 mol, 1 eq) in EtOH (2.95 L) was added urea (136 g, 2.27 mol,121 mL, 2 eq) and NaOMe (122 g, 2.27 mol, 2 eq) slowly. The mixture was stirred at 80° C. for 12 h. HPLC indicated that the ~7.2% of the starting material was remained and ~77.5% of the desired peak was detected on 220 nm. The reaction mixture was concentrated to remove most of the ethanol. The product was triturated with MTBE (1.50 L) at 20° C. for 0.5 h. 6-methyl-6-phenyl-5,6,7,8-tetrahydroquinazoline-2,4(1H, 3H)-dione (210 g, crude) was obtained as white solid and used to next step directly.

Step 5: To a mixture of 6-methyl-6-phenyl-5,6,7,8-tetrahydroquinazoline-2,4(1H,3H)-dione (200 g, 780 mmol, 1 eq) in dioxane (2.00 L) was added Et₃N (236 g, 2.34 mol, 325 mL, 3 eq) and followed by POCl₃ (1.20 kg, 7.80 mol, 725 mL, 10 eq) dropwise at 0-5° C. over 0.5 h. The mixture was stirred at 125° C. for 5 h. LCMS indicated that the reactant was disappeared and the new peak with desired mass was detected. The reaction mixture was concentrated under reduced pressure and diluted with CH₂C₂ (3.00 L). The mixture was added into sat. NaHCO₃ solution (5.00 L) and stirred at 20-40° C. for 0.5 h. The mixture was filtered with celite. The organic layer was separated, washed with brine (1.00 L), dried over Na₂SO₄, filtered and concentrated. The product was purified by silica gel column chromatography (SiO₂, Petroleum ether/Ethyl acetate=10/1 to 5/1). 2,4-dichloro-6-methyl-6-phenyl-5,6,7,8-tetrahydroquinazoline (65.0 g, 220 mmol, 28.3% yield, 99.6% purity) was obtained as yellow solid. LCMS: RT=0.862 min, MS (ESI) m/z=292.9 [M+H]+; ¹H NMR (400 MHz CDCl₃) δ 7.35-7.20 (m, 5H), 3.38-3.34 (m, 1H), 2.93-2.86 (m, 1H), 2.87-2.80 (m, 1H), 2.60 (dd, J=2.8, 5.2 Hz, 1H), 2.34-2.31 (m, 1H), 2.01-1.97 (m, 1H), 1.43 (s, 3H).

Step 6: Chiral separation of 2,4-dichloro-6-methyl-6-phenyl-5,6,7,8-tetrahydroquinazoline (65.0 g, 221 mmol, 1 eq) was separated by SFC (column: DAICEL CHIRALPAK AY (250 mm×50 mm, 10 μm); mobile phase: [0.1% NH₃·H₂O EtOH]; B %: 15%-15%, 2.2; 2105 min). The product was concentrated. (R)-2,4-dichloro-6-methyl-6-phenyl-5,6,7,8-tetrahydroquinazoline (27.0 g) eluted as Peak 1 and (S)-2,4-dichloro-6-methyl-6-phenyl-5,6,7,8-tetrahydroquinazoline (24.0 g) eluted as Peak 2 and obtained as yellow oil.

Example 3—Intermediate 3: 2,4-dichloro-6-(3-fluorophenyl)-6-methyl-5,6,7,8-tetrahydroquinazoline

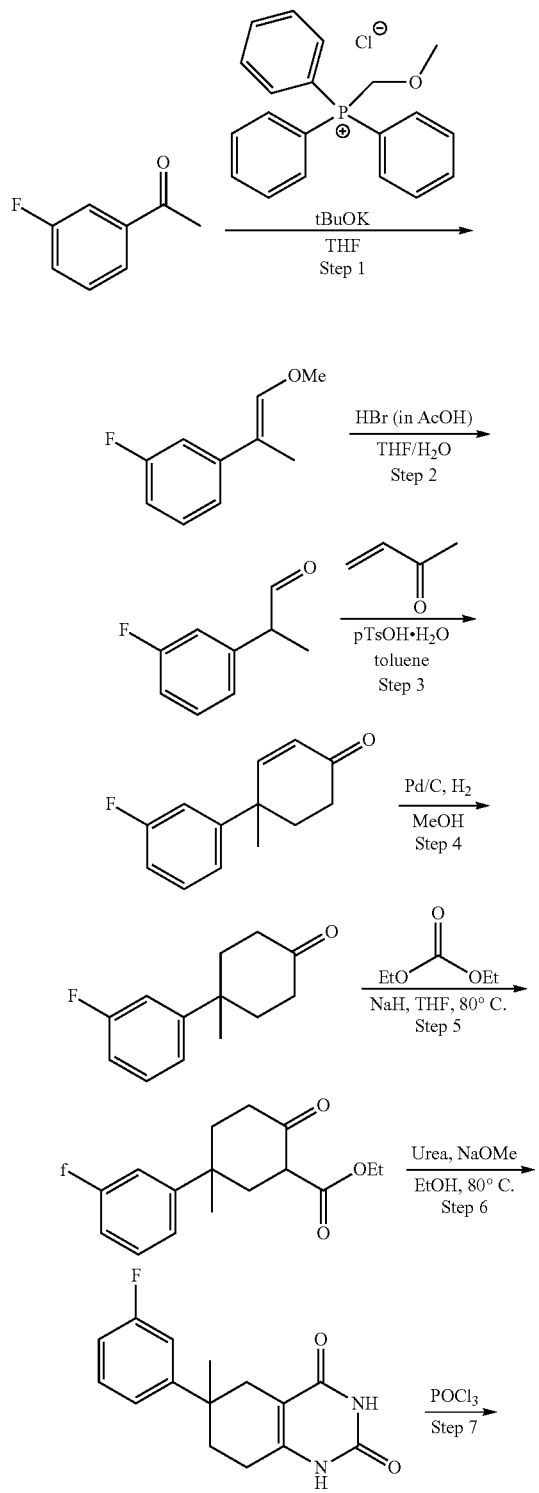

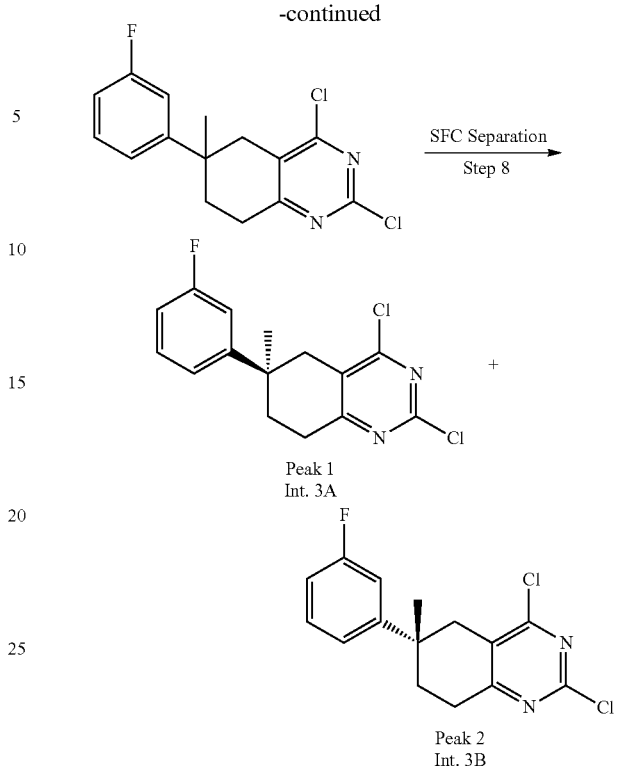

Step 1: To a solution of 1-(3-fluorophenyl)ethan-1-one (100 g, 723.91 mmol) in THF (1 L) was added t-BuOK (130 g, 1160 mmol) at 20° C. The reaction mixture was stirred at 20° C. for 1 h. Then a solution of (methoxymethyl)triphenylphosphonium chloride (372 g, 1090 mmol) in THF (1 L) was added dropwise at 0° C. The reaction was allowed to warm to 20° C. and stirred for 16 h. TLC (Petroleum ether/Ethyl acetate=10/1) showed starting material was consumed and one major new spot was formed. The reaction mixture was poured into petroleum ether (2 L) and then filtered. The filter was filtered through silica pad and concentrated under vacuum to afford desired product (E)-1-fluoro-3-(1-methoxyprop-1-en-2-yl)benzene (100 g, 602 mmol, 83.26% yield) as yellow oil which was used to next step directly.

Step 2: To a solution of (E)-1-fluoro-3-(1-methoxyprop-1-en-2-yl)benzene (150 g, 902.57 mmol) in THF (1.5 L) was added a solution of HBr (663 g, 2170.71 mmol, in AcOH) in $H_2O$ (300 mL) drop wise at 0° C. The reaction was allowed to warm to 40° C. after the addition was completed and stirred for 3 h. TLC (Petroleum ether/Ethyl acetate=10/1, Rf=0.3) showed starting material was consumed and new spot was formed. The reaction mixture was separated and the water phase was extracted by EtOAc (100 mL×2). The combined organic layer was washed with brine, dried over anhydrous $Na_2SO_4$, filtered and concentrated under vacuum to give 2-(3-fluorophenyl)propanal (150 g, crude) which was used to next step directly.

Step 3: To a solution of 2-(3-fluorophenyl)propanal (140 g, crude) in toluene (1200 mL) was added but-3-en-2-one (96 g, 1380.25 mmol) and pTsOH·$H_2O$ (35 g, 184.01 mmol) at 25° C. The mixture was stirred at 80° C. for 16 h. TLC (Petroleum ether/Ethyl acetate=10/1) showed starting material was consumed completely and major spot was formed. The reaction mixture was concentrated to remove toluene. The residue was purified by silica gel column chromatography (SiO$_2$ (1000 g, 1000 mesh), from Petroleum ether to Petroleum ether/Ethyl acetate=2/1) and then the desired fraction was concentrated to afford 3-fluoro-1-methyl-2,3-dihydro-[1,1'-biphenyl]-4(1H)-one (120 g, 579.61 mmol, 98.65% purity, 48.09% yield over two step). LCMS: m/z=205.2 [M+H]$^+$, RT=0.883 min; $^1$H NMR (400 MHz, DMSO-d6) δ=7.41 (dt, J=6.7, 8.0 Hz, 1H), 7.28-7.20 (m, 2H), 7.15-7.07 (m, 2H), 6.03 (d, J=10.1 Hz, 1H), 2.43-2.33 (m, 1H), 2.29-2.19 (m, 1H), 2.16-2.08 (m, 2H), 1.53-1.49 (m, 3H).

Step 4: To a solution of 3'-fluoro-1-methyl-2,3-dihydro-[1,1'-biphenyl]-4(1H)-one (60 g, 293.76 mmol) in MeOH (600 mL) was added Pd/C (62 g, 58.75 mmol, 10% on carbon). The mixture was purge and degassed by H$_2$ three times. The mixture was stirred at 25° C. for 16 h. The reaction mixture was filtered to remove Pd/C and the filterate was concentrated under vacuum. The residue was purified by silica gel column chromatography (From PE to PE/EA=2/1) and concentrated to afford 4-(3-fluorophenyl)-4-methylcyclohexan-1-one (37.5 g, 62% yield, 88% purity). LCMS: RT=0.909 min, m/z=207.2 [M+H]$^+$; $^1$H NMR (400 MHz, DMSO-d6) δ 7.45-7.37 (m, 1H), 7.36-7.29 (m, 2H), 7.09-7.01 (m, 1H), 2.40-2.29 (m, 4H), 2.19-2.11 (m, 2H), 1.98-1.89 (m, 2H), 1.30 (s, 3H).

Step 5: To a solution of 4-(3-fluorophenyl)-4-methylcyclohexan-1-one (100 g, 848.46 mmol) and NaH (8.14 g, 87.27 mmol, 60%) in THF (200 mL) was added a solution of diethylcarbonate (35 g, 169.69 mmol) in THF (100 mL) drop wise at 80° C. under N$_2$ atmosphere. The mixture was stirred at 80° C. for 3 h. The reaction mixture was poured into HCl (200 mL, 1N) and extracted with EtOAc (50 mL×3). The combined organic layer was washed with brine (30 mL×3), dried over anhydrous Na$_2$SO$_4$, filtered and concentrated under vacuum to afford desired product ethyl 5-(3-fluorophenyl)-5-methyl-2-oxocyclohexane-1-carboxylate (30 g, 56% yield, 88.11% purity) as yellow oil. LCMS: RT=1.063 min, m/z=279.2 [M+H]+; $^1$H NMR (400 MHz, DMSO-d6) δ ppm 7.32-7.41 (m, 1H), 7.11-7.20 (m, 2H), 7.02 (td, J=8.28, 2.26 Hz, 1H), 4.23 (q, J=7.03 Hz, 2H), 2.69 (br d, J=15.94 Hz, 1H), 2.47-2.56 (m, 1H), 2.20-2.36 (m, 2H), 2.03-2.16 (m, 1H), 1.84-1.98 (m, 1H); 1.73-1.84 (m, 1H), 1.12-1.31 (m, 6H).

Step 6: To a solution of 5-(3-fluorophenyl)-5-methyl-2-oxocyclohexane-1-carboxylate (30 g, 107.79 mmol) in EtOH (300 mL) was added urea (13 g, 215.58 mmol) and NaOMe (12 g, 215.58 mmol). The mixture was stirred at 80° C. for 16 h and the mixture was filtered to give 6-(3-fluorophenyl)-6-methyl-5,6,7,8-tetrahydroquinazoline-2,4 (1H,3H)-dione (35 g crude) as yellow solid which was used to next step directly. LCMS: RT=0.806 min, m/z=275.2 [M+H]$^+$.

Step 7: To a solution of 6-(3-fluorophenyl)-6-methyl-5,6,7,8-tetrahydroquinazoline-2,4(1H,3H)-dione (30 g, 109.49 mmol) and TEA (2.2 g, 16.41 mmol, 2.2 mL) in dioxane (200 mL) was added POCl$_3$ (84 g, 546.87 mmol. 50.8 mL) drop wise at 0° C. The mixture was warmed to 125° C. and stirred for 3 h and the reaction mixture was concentrated under vacuum. The residue was purified by flash chromatography (Column: 300 g SiO$_2$, PE and EA condition) and the product fractions were concentrated under vacuum to give 2,4-dichloro-6-(3-fluorophenyl)-6-methyl-5,6,7,8-tetrahydroquinazoline (27 g, 80.7% yield) as yellow oil. LCMS: RT=1.028 min, m/z=311.2 [M+H]+.

Step 8: Racemate 2,4-dichloro-6-(3-fluorophenyl)-6-methyl-5,6,7,8-tetrahydroquinazoline (64 g, 205.78 mmol) was separated by SFC (Column: DAICEL CHIRALPAK AY-H(250 mm*30 mm, 10 um), Condition: 0.1% NH$_3$·H$_2$O EtOH, Begin B %: 20% to End B %: 20%). The solution was concentrated under vacuum to yield:

(R)-2,4-dichloro-6-(3-fluorophenyl)-6-methyl-5,6,7,8-tetrahydroquinazoline (14.6 g, 45.65 mmol, 22.20% yield, 94.7% purity). LCMS: RT=1.034 min, m/z=312.2 [M+H]$^+$, SFC: RT=0.905 min; $^1$H NMR (400 MHz, DMSO-d6) δ=7.41-7.30 (m, 1H), 7.20 (br d, J=11.4 Hz, 1H), 7.13 (br d, J=7.8 Hz, 1H), 7.09-6.98 (m, 1H), 3.21 (br d, J=17.5 Hz, 1H), 3.00-2.78 (m, 2H), 2.59-2.52 (m, 1H), 2.40-2.16 (m, 1H), 2.11-1.89 (m, 1H), 1.34 (s, 3H)

(S)-2,4-dichloro-6-(3-fluorophenyl)-6-methyl-5,6,7,8-tetrahydroquinazoline (11.2 g, 36.01 mmol, 17.50% yield, 99.3% purity). LCMS: RT=1.034 min, m/z=312.2 [M+H]$^+$, SFC: RT=0.905 min; $^1$H NMR (400 MHz, DMSO-d6) δ=7.35 (dt, J=6.6, 8.0 Hz, 1H), 7.20 (td, J=2.2, 11.4 Hz,1H), 7.13 (dd, J=0.9, 8.0 Hz, 1H), 7.08-7.00 (m, 1H), 3.21 (d, J=17.7 Hz, 1H), 3.05-2.81 (m, 2H), 2.58-2.53 (m, 1H), 2.37-2.19 (m, 1H), 2.00 (ddd, J=6.1, 8.2, 13.9 Hz, 1H), 1.36-1.27 (m, 3H).

Example 4—Preparation of Intermediate 4: 2,4-dichloro-6-(3-fluorophenyl)-5,6,7,8-tetrahydroquinazoline

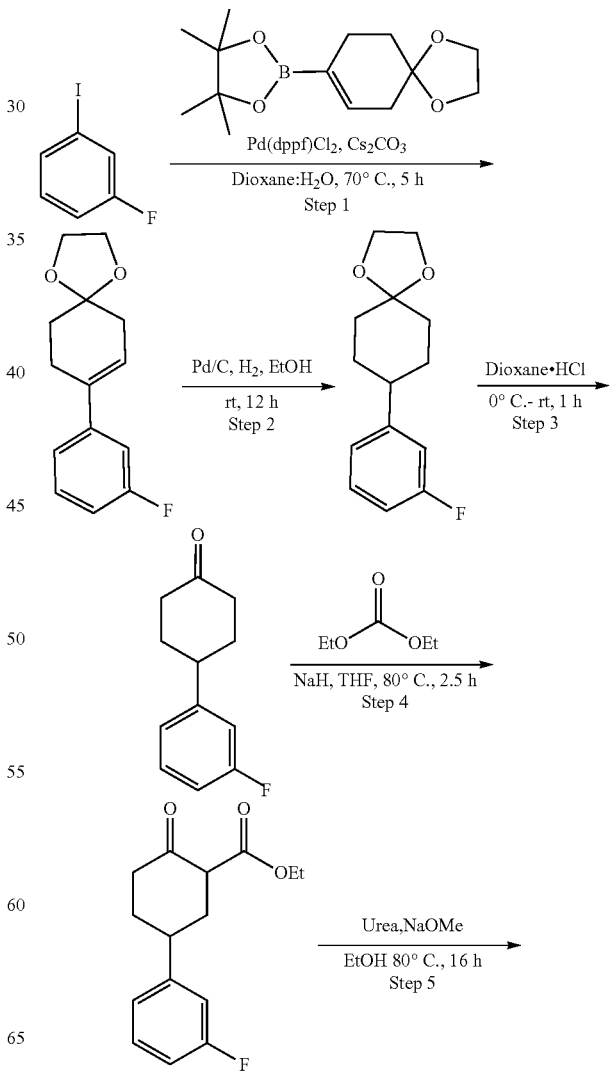

-continued

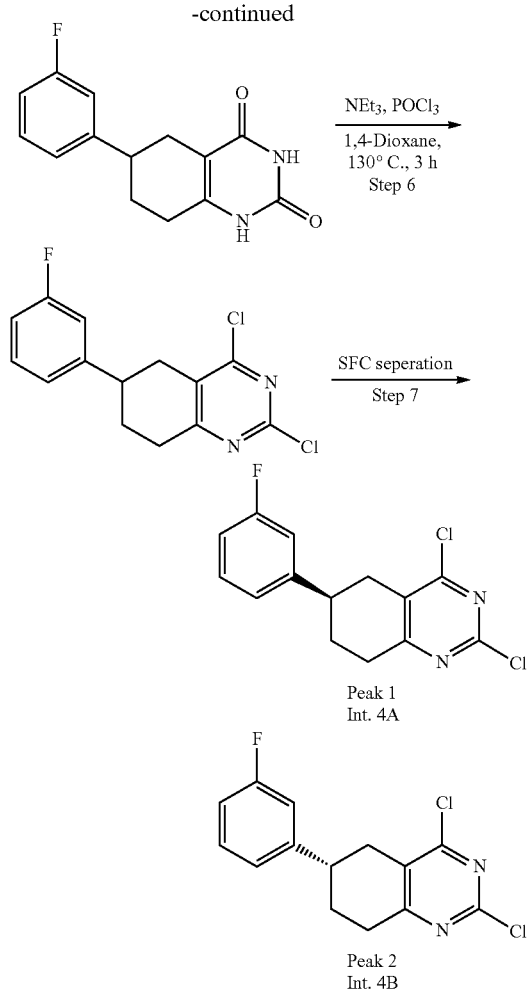

Step 1: The stirred suspension of 1-fluoro-3-iodobenzene (140 g, 630 mmol, 74.0 mL, 1.00 eq), 4,4,5,5-tetramethyl-2-(1,4-dioxaspiro[4.5]dec-7-en-8-yl)-1,3,2-dioxaborolane (149 g, 561 mmol, 0.89 eq) and $Cs_2CO_3$ (308 g, 945 mmol, 1.50 eq) in dioxane (1200 mL)/$H_2O$ (300 mL) (8/2) was degassed with argon for 15 min. Then Pd(dppf)$Cl_2 \cdot CH_2Cl_2$ (29.8 g, 36.5 mmol, 0.058 eq) was added and again degassed for 5 min. Then the reaction mixture was heated to 70° C. for 16 h. TLC (Petroleum ether/Ethyl acetate=10/1, reactant Rf=0.50, new spot Rf=0.34) showed starting material was consumed completely and a new spot was detected. The reaction mixture was concentrated under reduced pressure to remove dioxane. The residue was diluted with $H_2O$ (1.5 L) and extracted with EtOAc (1.5 L×2). The combined organic layers were washed with brine (2 L×2), dried over $Na_2SO_4$, filtered and concentrated under reduced pressure to give a residue. The residue was purified by column chromatography (SiO$_2$, Petroleum ether/Ethyl acetate=I/O to 5/1) to give 8-(3-fluorophenyl)-1,4-dioxaspiro[4.5]dec-7-ene (137 g, 584 mmol, 92.7% yield) as brown oil. LCMS: MS (ESI) m/z=235.2 [M+H]+; $^1$H NMR: (400 MHz, DMSO-d6) δ 7.52-7.45 (m, 1H), 7.40-7.31 (m, 2H), 7.23-7.15 (m, 1H), 6.26-6.21 (m, 1H), 4.06-4.02 (m, 4H), 2.76-2.55 (m, 3H), 1.97-1.89 (m, 2H), 1.33-1.27 (m, 1H), 1.23-1.19 (m, 1H).

Step 2: To a solution of 8-(3-fluorophenyl)-1,4-dioxaspiro[4.5]dec-7-ene (80.0 g, 341 mmol, 1.00 eq) in EtOH (880 mL) was added Pd/C (8.00 g, 10% purity) under $N_2$ atmosphere. The suspension was degassed and purged with $H_2$ for 3 times. The mixture was stirred under $H_2$ (15 psi) at 20° C. for 12 h. TLC (Petroleum ether/Ethyl acetate=10/1, reactant Rf=0.35, new spot Rf=0.42) showed that starting material was consumed and a new spot was detected. The reaction mixture was filtered through celite pad and washed with excess of EtOH (1 L) and EtOAc (1 L), the filtrate was concentrated to get desired compound. The residue was purified by column chromatography (SiO$_2$, Petroleum ether/ Ethyl acetate=5/1) to give 8-(3-fluorophenyl)-1,4-dioxaspiro[4.5]decane (74.4 g, 314 mmol, 92.2% yield) as colorless oil. LCMS: MS (ESI) m/z=237.1 [M+H], $^1$H NMR: δ 7.36-7.27 (m, 1H), 7.11-6.92 (m, 3H), 3.92-3.85 (m, 4H), 2.68-2.57 (m, 1H), 1.82-1.70 (m, 4H), 1.69 (s, 4H).

Step 3: To a solution of 8-(3-fluorophenyl)-1,4-dioxaspiro [4.5]decane (74.4 g, 314 mmol, 1.00 eq) in dioxane (620 mL)/$H_2O$ (310 mL) (2/1) was added HCl (12 M, 309 mL, 11.7 eq). The mixture was stirred at 20° C. for 3 h. LCMS show that starting material was consumed and desired compound was detected. The reaction mixture was concentrated under reduced pressure to remove dioxane. The residue was extracted with EtOAc (500 mL×2) and the combined organic layers were washed with sat. NaHCO$_3$ 500 mL and brine 500 mL, dried over anhydrous Na$_2$SO$_4$, filtered and concentrated under reduced pressure to give a residue. The crude product 4-(3-fluorophenyl)cyclohexan-1-one (64.5 g, crude) was used into the next step without further purification as colorless oil. LCMS: product RT=0.836 min, MS (ESI) m/z=193.2 [M+H]+; $^1$H NMR: (400 MHz, DMSO-d6) δ 7.38-7.30 (m, 1H), 7.17-7.10 (m, 2H), 7.06-6.98 (m, 1H), 3.15-3.04 (m, 1H), 2.63-2.52 (m, 2H), 2.31-2.21 (m, 2H), 2.12-2.02 (m, 2H), 1.96-1.80 (m, 2H).

Step 4: To a stirred solution of diethyl carbonate (245 g, 2.08 mol, 251 mL, 5.00 eq) in THF (400 mL) at 25° C., NaH (19.9 g, 498 mmol, 60.0% purity, 1.20 eq) was added portionwise. The resulting mixture was heated to 80° C. and then a solution of 4-(3-fluorophenyl)cyclohexan-1-one (79.9 g, 415 mmol, 1.00 eq) in THF (400 mL) was added dropwise over~20 min. The reaction mixture was then stirred at 80° C. for 30 min. LCMS showed the starting material was consumed and desired compound was detected. The reaction mixture was quenched with sat. NH$_4$Cl solution (1 L) and extracted with EtOAc (1 L X 2). The combined organic layer was washed with sat. NaHCO$_3$ solution (800 mL) and brine (600 mL), dried over anhydrous Na$_2$SO$_4$ and concentrated under reduced pressure. The residue was purified by column chromatography (SiO$_2$, Petroleum ether/Ethyl acetate=I/O to 10/1, desired spot Rf=0.33) to give ethyl 5-(3-fluorophenyl)-2-oxocyclohexane-1-carboxylate (65.3 g, 247 mmol, 59.4% yield) as light yellow oil. LCMS product RT=1.005 min, MS (ESI) m/z=265.2 [M+H]+; $^1$H NMR: (400 MHz, DMSO-d6) δ 7.40-7.29 (m, 1H), 7.19-7.09 (m, 2H), 7.08-6.97 (m, 1H), 4.21 (br s, 3H), 2.88-2.69 (m, 1H), 2.49-2.41 (m, 1H), 2.35-2.04 (m, 2H), 2.01-1.92 (m, 1H), 1.90-1.80 (m, 1H), 1.77-1.41 (m, 1H), 1.22-1.17 (m, 3H).

Step 5: To a stirred solution of ethyl 5-(3-fluorophenyl)-2-oxocyclohexane-1-carboxylate (75.0 g, 283 mmol, 1.00 eq) in EtOH (1680 mL) was added urea (34.0 g, 567 mmol, 30.4 mL, 2.00 eq) and followed by NaOMe (30.6 g, 567 mmol, 2.00 eq) and the reaction mixture was heated to 80° C. for 16 h. LCMS showed the starting material was consumed and desired compound was detected. The reaction mixture was filtered, the solid was washed with MBTE (900 mL) and water (500 mL), and concentrated under reduced pressure to give a residue. The crude product 6-(3-fluorophenyl)-5,6,7,8-tetrahydroquinazoline-2,4(1H,3H)-dione (48.5 g, crude) was used into the next step without further purification as a white solid.

LCMS: product RT=0.777 min, MS (ESI) m/z=261.0 [M+H]+; ¹H NMR: (400 MHz, DMSO-d6) δ 7.39-7.28 (m, 1H), 7.15-7.06 (m, 2H), 7.04-6.96 (m, 1H), 2.84-2.70 (m, 1H), 2.60-2.52 (m, 1H), 2.44-2.37 (m, 1H), 2.34-2.25 (m, 1H), 2.18-2.05 (m, 1H), 1.94-1.84 (m, 1H), 1.82-1.71 (m, 1H).

Step 6: To a stirred suspension of 6-(3-fluorophenyl)-5,6,7,8-tetrahydroquinazoline-2,4(1H,3H)-dione (44.0 g, 169 mmol, 1.00 eq) in dioxane (1760 mL) were added TEA (5.65 g, 55.7 mmol, 7.77 mL, 0.33 eq) and followed by POCl₃ (259 g, 1.69 mol, 157 mL, 10.0 eq) (dropwise) at 0° C. and the reaction mixture was heated to 130° C. for 3 h. LCMS showed the starting material was consumed and desired compound was detected. The reaction mixture was concentrated under reduced pressure to remove solvent. The residue was slowly diluted with H₂O (300 mL) and was adjusted to pH 7 with sat. NaHCO₃ (700 mL), then extracted with EtOAc (1 L×3), dried over anhydrous Na₂SO₄, filtered and concentrated under reduced pressure to give a residue. The crude product was triturated with MTBE (20 mL 3 times) at 25° C. for 2 h to give 2,4-dichloro-6-(3-fluorophenyl)-5,6,7,8-tetrahydroquinazoline (24.5 g, 82.4 mmol, 48.7% yield) as a yellow solid. LCMS: product RT=1.020 min, MS (ESI) m/z=296.7 [M+H]+; ¹H NMR: (400 MHz, CHLOROFORM-d) δ 7.38-7.30 (m, 1H), 7.09-7.03 (m, 1H), 7.01-6.93 (m, 2H), 3.22-2.96 (m, 4H), 2.79-2.67 (m, 1H), 2.30-2.19 (m, 1H), 2.08-1.92 (m, 1H).

Step 7: Racemic 2,4-dichloro-6-(3-fluorophenyl)-5,6,7,8-tetrahydroquinazoline was purified by SFC (column: DAICEL CHIRALCEL OJ (250 mm*30 mm, 10 um); mobile phase: [0.1% NH₃·H₂O MeOH]; B %: 30%-30%, 2.8 min; 1100 min) to give:

(R)-2,4-dichloro-6-(3-fluorophenyl)-5,6,7,8-tetrahydroquinazoline (10.6 g, >99% ee): LCMS: product RT=1.047 min, MS (ESI) m/z=297.2 [M+H]⁺; ¹H NMR: (400 MHz, CHLOROFORM-d) δ 7.37-7.30 (m, 1H), 7.08-7.03 (m, 1H), 7.03-6.93 (m, 2H), 5.32-5.30 (m, 1H), 3.20-2.98 (m, 4H), 2.80-2.69 (m, 1H), 2.29-2.20 (m, 1H), 2.06-1.94 (m, 1H) as a yellow solid.

(S)-2,4-dichloro-6-(3-fluorophenyl)-5,6,7,8-tetrahydroquinazoline (12.0 g, >99% ee): LCMS: RT=1.005 min, MS (ESI) m/z=296.7 [M+H]⁺; ¹H NMR: (400 MHz, CHLOROFORM-d) δ 7.39-7.31 (m, 1H), 7.08-7.03 (m, 1H), 7.03-6.94 (m, 2H), 3.20-2.97 (m, 4H), 2.79-2.69 (m, 1H), 2.29-2.20 (m, 1H), 2.07-1.94 (m, 1H) as a yellow solid.

Example 5—Preparation of Intermediate 5: (R)-2,4-dichloro-6-(4-fluorophenyl)-5,6,7,8-tetrahydroquinazoline

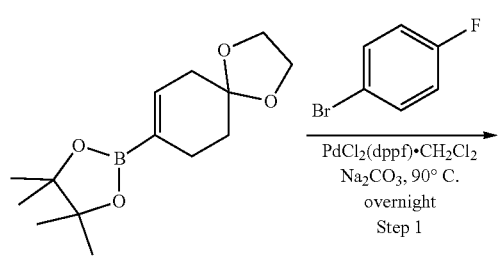

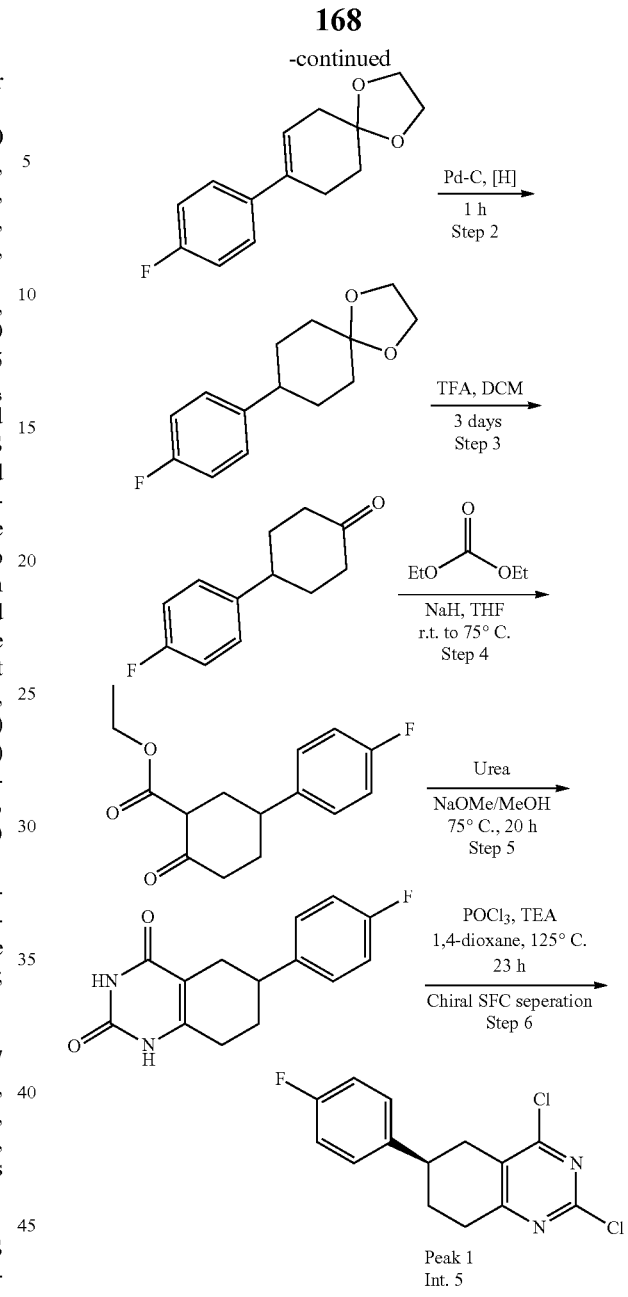

Step 1: 4,5,5-tetramethyl-2-(1,4-dioxaspiro[4.5]dec-7-en-8-yl)-1,3,2-dioxaborolane (10 g, 37.6 mmol), 1-bromo-4-fluorobenzene (7.89 g, 45.1 mmol), Na₂CO₃ (15.93 g, 150 mmol) were mixed in 1,4-dioxane (150 mL) and water (37.5 mL). The mixture was degassed with nitrogen for 5 min. PdCl₂(dppf)·CH₂Cl₂ adduct (1.534 g, 1.879 mmol) was added and the rxn was heated at 90° C. overnight. LCMS showed that the reaction was complete. The crude was cooled to rt, diluted with EtOAc, and filtered through celite (flushed the celite with EtOAc). The filtrate was concentrated and purified on 2×120 g silica column 0-20% EtOAc in heptane to afford 8-(4-fluorophenyl)-1,4-dioxaspiro[4.5]dec-7-ene (7.33 g, 31.3 mmol, 83% yield) as a white solid. LCMS (basic): RT=1.03 min; MS m/z=387.2 [M+H]⁺.

Step 2: A solution of 8-(4-fluorophenyl)-1,4-dioxaspiro[4.5]dec-7-ene (3.67 g, 15.67 mmol) in EtOH (50 mL) was vacuumed and filled with nitrogen for three times. Pd—C wet 50% (1.667 g, 1.567 mmol) was added. 1 atm hydrogen balloon was connected via an adapter. The reaction flask was vacuumed and filled with hydrogen for three times. The rxn was stirred at rt under hydrogen for 1 h. LCMS showed that the reaction was complete. The flask was vacuumed to remove hydrogen, filtered through celite (flushed with DCM), and concentrated to afford 8-(4-fluorophenyl)-1,4-dioxaspiro[4.5]decane (3.3 g, 13.97 mmol, 89% yield) as white solid. The material was used as is in next step. LCMS (basic): Rt=1.08 min; MS not observed. TLC: Rf=0.6, 1:1 EtOAc/heptane.

Step 3: To a solution of 8-(4-fluorophenyl)-1,4-dioxaspiro[4.5]decane (4.63 g, 19.59 mmol) in DCM (15 mL) was added TFA (30.2 mL, 392 mmol). The resulting mixture was stirred at rt for 2 days. LCMS showed rxn was incomplete. More TFA (12 mL) was added. The rxn was continued for another day. The mixture was concentrated, diluted with EtOAc, and washed with sat. NaHCO$_3$, water, and brine. It was then dried over Na$_2$SO$_4$ and concentrated via rotovap. The residue was purified by chromatography (120 g silica gel column, 0-50% EtOAc/heptane; product came out of column at ~30% EtOAc/heptane) to afford 4-(4-fluorophenyl)cyclohexan-1-one (3.1 g, 16.13 mmol, 82% yield) as colorless oil. LCMS (basic): Rt=0.93 min; MS m/z=192.5 [M+H]+.

Step 4: To a stirred solution of diethyl carbonate (19.60 mL, 162 mmol) in anhydrous THF (20 mL) was added NaH in mineral oil (0.776 g, 19.41 mmol). A solution of 4-(4-fluorophenyl)cyclohexan-1-one (3.11 g, 16.18 mmol) in anhydrous THF (10 mL) was added. The reaction was stirred at rt for 30 min before heated to 75° C. and stirred under nitrogen for 1.5 h. TLC showed no SM left, instead a new major spot. LCMS showed a major new peak and nearly no SM left. The reaction was cooled to 0° C., quenched with 30 mL of sat. NH$_4$C$_1$ and extracted with 150 mL of EtOAc. The organic phase was washed with brine and dried over sodium sulfate. It was then concentrated via rotovap and purified by ISCO (120 g silica gel column, 0-20% EtOAc in heptane), affording Ethyl 5-(4-fluorophenyl)-2-oxocyclohexane-1-carboxylate (2.5 g, 9.46 mmol, 58.5% yield). LCMS (basic): Rt=1.28 min, MS m/z=265.2 [M+H]$^+$. TLC: Rf=0.80, 1:1 EtOAc/heptane. The product contained minor impurities. It was used 'as is' in next step.

Step 5: To a solution of Ethyl 5-(4-fluorophenyl)-2-oxocyclohexane-1-carboxylate 4.25 g, 16.08 mmol) in MeOH (40 mL) was added urea (1.931 g, 32.2 mmol) and NaOMe (1.737 g, 32.2 mmol). The mixture was heated at 75° C. under the presence of nitrogen for 20 h; LCMS showed that the reaction was complete (LCMS: RT=0.74 min, MS m/z=261.1 [M+H]$^+$). White precipitates were observed. The reaction was cooled down to rt, and the precipitate was filtered and washed with Et$_{2O}$, and dried to afford desired product 6-(4-fluorophenyl)-5,6,7,8-tetrahydroquinazoline-2,4(1H,3H)-dione (2.5 g, 59.4% yield). LCMS (basic): RT=0.74 min, MS m/z=261.1 [M+H]+; $^1$H NMR (400 MHz, DMSO-d6) δ 7.36-7.21 (m, 2H), 7.11 (t, J=8.8 Hz, 2H), 2.75 (dtd, J=14.3, 7.7, 3.5 Hz, 1H), 2.55 (dd, J=15.8, 5.0 Hz, 1H), 2.45-2.21 (m, 2H), 2.09 (dd, J=16.0, 10.9 Hz, 1H), 1.95-1.82 (m, 1H), 1.73 (td, J=11.9, 5.4 Hz, 1H).

Step 6: To a stirred suspension of 6-(4-fluorophenyl)-5, 6,7,8-tetrahydroquinazoline-2,4(1H,3H)-dione (2.5 g, 9.61 mmol) and TEA (3.21 mL, 23.05 mmol) in 1,4-dioxane (10 mL), at 0° C. was added POCl$_3$ (8.95 mL, 96 mmol) dropwise over 10 min. The resulting reaction mixture was stirred at 125° C. for 23 h (dark precipitates were observed). LCMS showed the reaction was complete. The crude was cooled and concentrated under reduced pressure to remove 1,4-dioxane and excessive POCl$_3$. The obtained residue was poured into ice water and stirred for ~30 min. The mixture was extracted with EtOAc and DCM. The separated organic layers were washed with half saturated NaHCO$_3$, brine, concentrated and purified by ISCO (120 g silica gel column, 0-50% EtOAc in heptane) to afford the racemic product (1.51 g, 4.83 mmol, 50.3% yield) as beige color solid. This material was separated by chiral SFC (column: DAICEL CHIRALCEL OJ (250 mm*30 mm, 10 um); mobile phase: [0.1% NH$_3$·H$_2$O MeOH]; B %: 30%-30%, 2.8 min; 1100 min) to afford the enantiomeric product (R)-2,4-dichloro-6-(4-fluorophenyl)-5,6,7,8-tetrahydroquinazoline (peak 1, 630 mg, 42% yield). LCMS (basic):

RT=1.20 min, MS=299.3 [M+H]+; $^1$H NMR (400 MHz, Methylene Chloride-d2) δ 7.37-7.23 (m, 2H), 7.17-7.05 (m, 2H), 3.23-2.97 (m, 4H), 2.82-2.68 (m, 1H), 2.23 (ddq, J=13.7, 5.8, 2.9 Hz, 1H), 2.11-1.91 (m, 1H).

Example 6—Preparation of Intermediate 6: (R)-3-(1-(methylamino)propyl)bicyclo[1.1.1]pentane-1-carboxylate hydrochloride

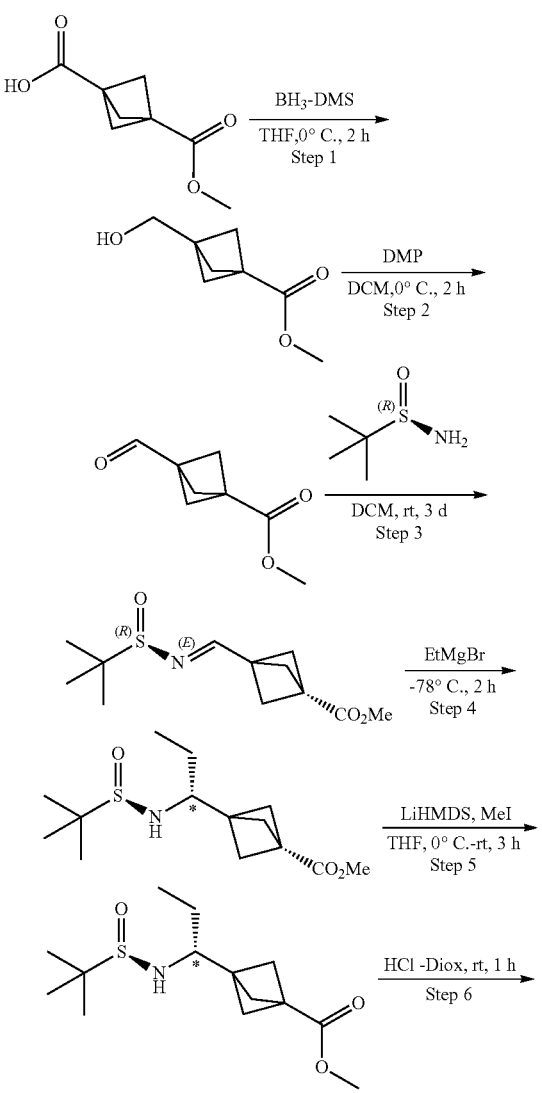

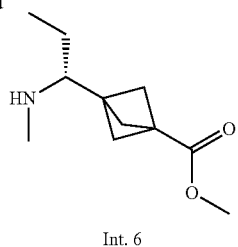

Int. 6

Step 1: To a solution of 3-(methoxycarbonyl)bicyclo[1.1.1]pentane-1-carboxylic acid (253.0 g, 1.5 mol, 1.0 eq) in anhydrous THF (2500.0 mL) and was added dropwise boranemethyl sulfide complex (2232.0 mL, 2.0 mol/L, 4.5 mol, 3.0 eq) at 0° C., and the reaction mixture was stirred at 0° C. for 2 h. The reaction was monitored by GC. The reaction mixture was quenched with MeOH (750.0 mL) until no bubbles were generated at 25° C. The mixture was concentrated under reduced pressure at 45° C. The residue was dissolved in MTBE (5060.0 mL, 20 V), washed with saturated NaCl aqueous (759.0 mL×2), and dried over anhydrous $Na_2SO_4$, filter and concentrated under reduced pressure to afford methyl 3-(hydroxymethyl)bicyclo[1.1.1]pentane-1-carboxylate (255.0 g, GC purity: 98.8%, crude yield: 100%) as a light-yellow solid. $^1$H NMR (300 MHz, $CDCl_3$) δ 3.75 (s, 2H), 3.67 (s, 3H), 1.96 (dd, J=9.2, 5.7 Hz, 6H).

Step 2: To a solution of methyl 3-(hydroxymethyl)bicyclo[1.1.1]pentane-1-carboxylate (255.0 g crude, 1.5 mol, 1.0 eq) in dry DCM (2500.0 mL) was added $NaHCO_3$ (250.0 g, 3.0 mol, 2 eq) and DMP (753.3 g, 1.8 mol, 1.2 eq) at 0° C., and the mixture was warmed to 25° C. and stirred for 2 h. The reaction was monitored by GC. The reaction mixture was filtered through a pad of celite, and the filter cake was washed with DCM (1000.0 mL×3). The combined organic layers were concentrated under reduced pressure. The residue was diluted with EtOAc (5100.0 mL), and washed with saturated sodium thiosulfate aqueous (500.0 mL×2) and saturated $NaHCO_3$ aqueous (500.0 mL), dried over anhydrous $Na_2SO_4$, filtered and concentrated. The residue was purified by column with heptane/EA=10/1 to afford methyl 3-formylbicyclo[1.1.1]pentane-1-carboxylate (187.0 g, purity: 83.4%, crude yield: 70.2%) as a white solid. $^1$H NMR (300 MHz, $CDCl_3$) δ 9.60 (s, 1H), 3.71 (s, 3H), 2.32 (s, 6H).

Step 3: To a mixture of methyl 3-formylbicyclo[1.1.1]pentane-1-carboxylate (180.0 g, 1.3 mol, 1.0 eq) in DCM (1800.0 mL, 10 V) was added (R)-(+)-2-Methyl-2-propanesulfinamide (156.8 g, 1.3 mol, 1.0 eq) at 25° C., and the mixture was stirred for 72 h. The reaction was monitored by GC. The reaction mixture was diluted with $H_2O$ (900.0 mL), and separated. The aqueous phase was extracted with DCM (2700.0 mL, 15 V), and the combined organic phases were washed with saturated NaCl aqueous (500.0 mL), dried over anhydrous $Na_2SO_4$, filtered and concentrated under reduced pressure. The mixture was purified by column with heptane/EA=5/1 to afford methyl (R,E)-3-(((tert-butylsulfinyl)imino)methyl)bicyclo[1.1.1]pentane-1-carboxylate (210.0 g, purity: 59.2%, containing 40.8% of (R)-2-methylpropane-2-sulfinamide (crude yield of 63.0%) as an off-white solid which was used to the next step directly without further purification. $^1$H NMR (300 MHz, $CDCl_3$) δ 7.97 (s, 1H), 3.68 (s, 3H), 2.28 (s, 6H), 1.16 (s, 9H).

Step 4: To a solution of methyl (R,E)-3-(((tert-butylsulfinyl)imino)methyl)bicyclo[1.1.1]pentane-1-carboxylate (200.0 g, 0.77 mol, 1.0 eq) in dry THF (1600.0 mL) was added dropwise ethyl magnesium bromide (777.0 mL, 1.5 mol, 2 mol/L, 2.0 eq) at −78° C., and the mixture was stirred for 2 h. The reaction was monitored by HPLC. The reaction mixture was quenched with saturated $NH_4Cl$ aqueous (1200.0 mL) at −78° C. The reaction mixture was warmed up to 25° C. The mixture was extracted with EtOAc (3000.0 mL×2), and the combined organic layers were dried over anhydrous $Na_2SO_4$, filtered and concentrated under reduced pressure. The residue was purified by column with heptane/EA=3/1 to crude product as a yellow oil. The crude product was purified by preparatory-HPLC to afford 27.0 g of methyl (S)-3-(1-((tert-butylsulfinyl)amino)-113-propyl)bicyclo[1.1.1]pentane-1-carboxylate with 93.9% purity and 81.0 g of methyl (R)-3-(1-((tert-butylsulfinyl)amino)-113-propyl)bicyclo[1.1.1]pentane-1-carboxylate with 97.2% purity. $^1$H NMR (300 MHz, $CDCl_3$) δ 3.65 (d, J=8.7 Hz, 3H), 3.11 (td, J=8.3, 4.5 Hz, 1H), 2.87 (d, J=7.7 Hz, 1H), 1.99 (qd, J=9.6, 1.8 Hz, 6H), 1.55 (ddd, J=14.1, 7.4, 4.5 Hz, 1H), 1.41-1.25 (m, 1H), 1.25-1.11 (m, 9H), 0.93 (t, J=7.4 Hz, 3H).

Step 5: To a solution of methyl (R)-3-(1-((tert-butylsulfinyl)amino)-113-propyl)bicyclo[1.1.1]pentane-1-carboxylate (63.0 g, 0.21 mol, 1.0 eq) in dry THF (0.7 L) was added LiHMDS (2 M, 210.0 mL, 0.42 mol, 2.0 eq) at 0° C. under $N_2$, and the reaction mixture was stirred for 0.5 h at 0° C. Then MeI (59.6 g, 0.42 mol, 2.0 eq) was added dropwise at 0° C., and the mixture was warmed to 25° C. and stirred for 2 h. The reaction was monitored by HPLC. The reaction mixture was quenched with ice-water (1200.0 mL). The mixture was extracted with EtOAc (1000.0 mL×3), and the combined organic phases were washed with saturated NaCl aqueous (500.0 mL), dried over anhydrous $Na_2SO_4$, filtered and concentrated under reduced pressure to afford methyl (R)-3-(1-((tert-butylsulfinyl)(methyl)amino)-113-propyl)bicyclo[1.1.1]pentane-1-carboxylate (55.0 g, purity: 82.1%, crude yield: 83.2%). $^1$H NMR (300 MHz, $CDCl_3$) δ 3.66 (s, 3H), 3.11 (dd, J=8.7, 6.6 Hz, 1H), 2.49 (s, 3H), 2.13 (dd, J=9.5, 1.8 Hz, 3H), 2.00 (dd, J=9.5, 1.8 Hz, 3H), 1.62-1.46 (m, 2H), 1.23 (dd, J=9.0, 5.2 Hz, 2H), 1.23-1.11 (m, 9H), 0.98 (t, J=7.4 Hz, 3H).

Step 6: Methyl (R)-3-(1-((tert-butylsulfinyl)(methyl)amino)-113-propyl)bicyclo[1.1.1]pentane-1-carboxylate (55.0 g, 182.5 mmol, 1.0 eq) was added into 4M HCl in 1,4-dioxane (467.0 mL, 1.8 mol, 10.0 eq) at 0° C., and the mixture was warmed to 25° C. and stirred for 2 h. The reaction was monitored by HPLC. The reaction mixture was concentrated under reduced pressure, and swapped with MTBE (110.0 mL×2). The residue was triturated with MTBE/EtOAc (50/1, 165.0 mL) at 25° C. for 2 h. The mixture was filtered, and the filter cake was triturated with MTBE (275.0 mL, 5 V) at 25° C. for 2 h. The mixture was filtered, and the filter cake was dried to afford methyl (R)-3-(1-(methylamino)propyl)bicyclo[1.1.1]pentane-1-carboxylate hydrochloride (25.5 g, yield: 59.8%) as a white solid. $^1$H NMR (300 MHz, MeOD) δ 3.70 (s, 2H), 3.20-3.07 (m, 1H), 2.73 (s, 3H), 2.19 (dd, J=4.4, 1.3 Hz, 6H), 1.75 (t, J=7.6 Hz, 2H), 1.07 (t, J=7.5 Hz, 3H).

Example 7—Preparation of Intermediate 7: methyl (1R,4r)-4-((R)-1-(methylamino)propyl)cyclohexane-1-carboxylate hydrochloride

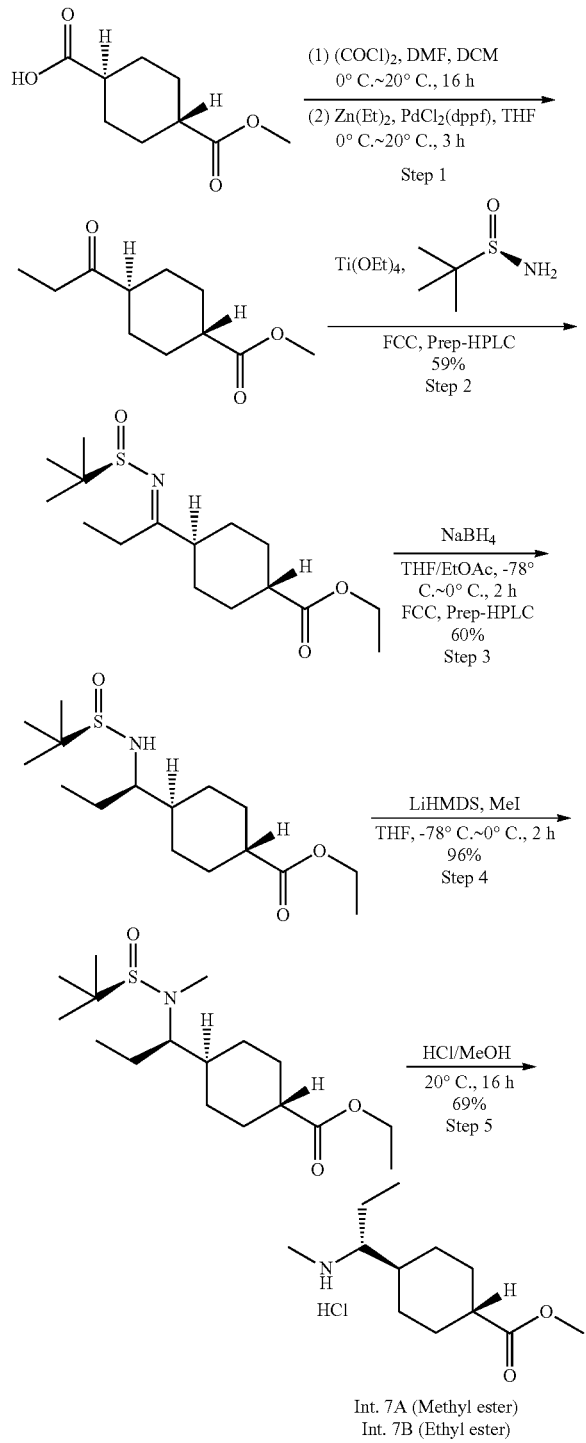

Int. 7A (Methyl ester)
Int. 7B (Ethyl ester)

Step 1: To a solution (1r,4r)-4-(methoxycarbonyl)cyclohexane-1-carboxylic acid g, mmol, 1 eq) in $CH_2Cl_2$ (700 mL) was added DMF (549 mg, 7.52 mmol, 578 uL, 0.01 eq) under an atmosphere of nitrogen. The reaction was cooled to 0° C. and then $(COCl)_2$ (101 g, 796 mmol, 69.7 mL, 1.06 eq) was added dropwise. The reaction was stirred at 25° C. for 10 h. $Pd(dppf)Cl_2$ (16.5 g, 22.5 mmol, 0.03 eq) was added to the reaction, followed by THF (700 mL), the mixture was then cooled to 0° C. and a solution of $ZnEt_2$ (1 M, 902 mL, 1.2 eq) was added slowly at 0° C. After addition, the mixture stirred at 25° C. for 10 h. TLC (Petroleum ether/Ethyl acetate=5/1, Rf/reactant=0.20, Rf/new spot=0.55) showed that the material was consumed and desired new spot was formed. The reaction mixture was quenched by addition ice sat. $NH_4C_1$ (1000 mL) and extracted with $CH_2C_2$ (600 mL×3), the combined organic layers were washed with brine (1000 mL), dried over, filtered and concentrated under reduced pressure to give a residue. The residue was purified by column chromatography ($SiO_2$, Petroleum ether/Ethyl acetate=4/1 to ¼) to get a product methyl (1r,4r)-4-propionylcyclohexane-1-carboxylate (170 g, 514 mmol, 68.4% yield, 60.0% purity) was obtained as a light yellow oil. $^1H$ NMR (400 MHz, $CDCl_3$) δ 3.60 (s, 3H), 2.44-2.36 (m, 1H), 2.30-2.14 (m, 2H), 2.04-1.93 (m, 4H), 1.92-1.84 (m, 1H), 1.82-1.69 (m, 3H), 1.68-1.61 (m, 1H), 1.45-1.35 (m, 1H), 1.33 (br d, J=10.4 Hz, 1H), 1.45-1.30 (m, 1H), 1.33-1.24 (m, 1H), 1.23-1.15 (m, 1H), 1.00-0.92 (m, 1H).

Step 2: To a solution of methyl (1R,4r)-4-propionylcyclohexane-1-carboxylate (340 g, 1.71 mol, 1 eq) was added $Ti(OEt)_4$ (782 g, 3.43 mol, 711 mL, 2 eq) and (R)-2-methylpropane-2-sulfinamide (228 g, 1.89 mol, 1.1 eq). The mixture was stirred at 75° C. for 5 h. TLC (Petroleum ether/Ethyl acetate=5/1, Rf/reactant=0.45, Rf/new spot=0.20) showed that the material was consumed and desired spot was formed. The reaction was cooled to 25° C. and diluted with 800 mL of EtOAc and quenched with $H_2O$ (229 g), the resulting suspension was stirred intensely and filtered through a short plug of celite, the cake solid was washed with EtOAc (1500 mL×2), the filtrate was concentrated in vacuum to get a residue. The residue was purified by column chromatography ($SiO_2$, Petroleum ether/Ethyl acetate=I/O to 0/1) to get a product (230 g crude). The product was then purified by Prep-HPLC (Phenomenex luna c18 250 mm*100 mm*10 um; mobile phase: [water (10 mM $NH_4HCO_3$)–ACN], B %: 45.0%-65.0%, 20 minutes) to give desired product ethyl (1R,4r)-4-((E)-1-(((R)-tert-butylsulfinyl)imino)propyl)cyclohexane-1-carboxylate (98.0 g, 304 mmol, 17.7% yield, 98.0% purity) as a light yellow oil. LCMS: RT=0.938 min, m/z=316.3 [M+H]$^+$; $^1H$ NMR (400 MHz, $CDCl_3$) δ 4.08 (q, J=7.2 Hz, 2H), 2.78-2.57 (m, 1H), 2.32-2.14 (m, 2H), 2.08-1.97 (m, 2H), 1.95-1.78 (m, 2H), 1.85-1.77 (m, 1H), 1.53-1.28 (m, 4H), 1.24-1.11 (m, 13H).

Step 3: To a solution of ethyl (1R,4r)-4-((E)-1-(((R)-tert-butylsulfinyl)imino)propyl)cyclohexane-1-carboxylate (96.0 g, 304 mmol, 1 eq) and $Ti(OEt)_4$ (208 g, 912 mmol, 189 mL, 3 eq) in THF (960 mL) and EtOAc (240 mL) was added $NaBH_4$ (34.5 g, 912 mmol, 3 eq) at −78° C., The resulting mixture was continued and stirred at −78-0° C. for 2 h (removed −78° C. bath and put into ice bath). Then the mixture was stirred at 0° C. for 2 h. The reaction was re-cooled to −78° C. and quenched with $NH_4C_1$ (137 mL). The mixture was allowed to warm to 25° C. and filtrated, the cake was washed with EtOAc (1000 mL×2). The combined organic layers were concentrated in vacuum to get a residue. The residue was purified by Prep-HPLC (Phenomenex luna C18 (250*70 mm, 10 um), mobile phase: [water (10 mM $NH_4HCO_3$)-ACN], B %: 45%-70%, 20 minutes) to give desired product ethyl (1R,4r)-4-((R)-1-(((R)-tert-butylsulfinyl)amino)propyl)cyclohexane-1-carboxylate (58.0 g, 178 mmol, 58.7% yield, 97.8% purity) as a light yellow oil. LCMS: RT=0.886 min, m/z=318.2 [M+H]$^+$; $^1H$ NMR (400 MHz, $CDCl_3$) δ 4.03 (q, J=7.2 Hz, 2H), 3.02 (d, J=7.6 Hz, 1H), 2.95-2.86 (m, 1H), 2.22-2.09 (m, 1H), 2.02-1.90 (m, 2H), 1.84-1.74 (m, 1H), 1.70 (br d, J=12.8 Hz, 1H), 1.56-1.43 (m, 2H), 1.43-1.28 (m, 3H), 1.22-1.10 (m, 12H), 1.06-0.93 (m, 1H), 0.85 (t, J=7.2 Hz, 3H).

Step 4: To a solution of ethyl (1R,4r)-4-((R)-1-(((R)-tert-butylsulfinyl)amino)propyl)cyclohexane-1-carboxylate (55.0 g, 173 mmol, 1 eq) in THF (1100 mL) at −70° C. was added LiHMDS (1M, 207 mL, 1.2 eq) and then the mixture was stirred at 0° C. for 30 min, at 0° C., CH$_3$I (122 g, 866 mmol, 53.9 mL, 5 eq) was added and the reaction mixture was slowly warm to 25° C. for 2 h. LCMS showed that the material was consumed and desired spot was formed. The reaction mixture was quenched by addition ice sat. NH$_4$C$_1$ (300 mL), extracted with EtOAc (300 mL×3). The combined organic layers were washed with brine (300 mL), dried over Na$_2$SO$_4$, filtered and concentrated under reduced pressure to give a residue. The residue was purified by column chromatography (SiO$_2$, Petroleum ether/Ethyl acetate=1/0 to 0/1) to give desired product ethyl (1R,4r)-4-((R)-1-(((R)-tert-butylsulfinyl)(methyl)amino)propyl)cyclohexane-1-carboxylate (32.0 g, 90.7 mmol, 52.3% yield, 94.0% purity) as a yellow oil. LCMS: RT=0.978 min, m/z=332.3 [M+H]+; $^1$H NMR (400 MHz, CDCl$_3$) δ 4.12-4.00 (m, 2H), 2.74 (td, J=8.8, 4.0 Hz, 1H), 2.48-2.40 (m, 3H), 2.23-2.08 (m, 1H), 2.06-1.92 (m, 3H), 1.80 (br d, J=12.8 Hz, 1H), 1.72-1.62 (m, 1H), 1.58-1.46 (m, 1H), 1.44-1.27 (m, 3H), 1.24-1.10 (m, 11H), 1.07-0.88 (m, 5H).

Step 5: To a solution of ethyl (1R,4r)-4-((R)-1-(((R)-tert-butylsulfinyl)(methyl)amino)propyl)cyclohexane-1-carboxylate (64.0 g, 193 mmol, 1 eq) in MeOH (448 mL) were added HCl/MeOH (4 M, 448 mL, 9.28 eq) at 0° C., the resulting mixture was continued and stirred at 25° C. for 5 h. LCMS showed that the material was consumed and desired product was formed. The reaction mixture was concentrated to get a product as a yellow oil. Then the product was dissolved into EtOAc/MTBE (1/10, 220 mL) and concentrated to get a product as a white solid. The product was triturated with MTBE (100 mL) at 25° C. for 10 minutes to get methyl (1R,4r)-4-((R)-1-(methylamino)propyl)cyclohexane-1-carboxylate hydrochloride (36.2 g, 144 mmol, 75.0% yield).

LCMS: RT=0.341 min, m/z=213.9 [M+H]+; $^1$H NMR (400 MHz, CDCl$_3$) δ 9.49-8.92 (m, 2H), 3.63 (s, 3H), 2.68 (t, J=5.2 Hz, 4H), 2.38-2.21 (m, 1H), 2.13-2.02 (m, 2H), 1.97-1.84 (m, 2H), 1.83-1.72 (m, 3H), 1.53-1.38 (m, 3H), 1.37-1.24 (m, 1H), 1.12-1.04 (m, 3H).

Example 8—Preparation of Intermediate 8: methyl (1R,4r)-4-((R)-1-aminopropyl)cyclohexane-1-carboxylate

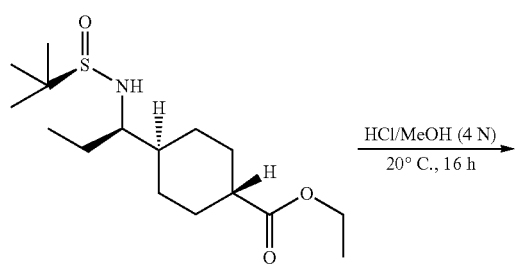

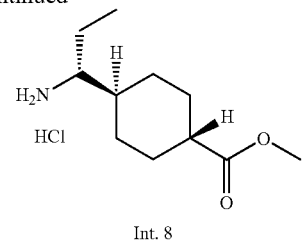

Int. 8

Ethyl (1R,4r)-4-((R)-1-(((R)-tert-butylsulfinyl)amino)propyl)cyclohexane-1-carboxylate (75 g, 236 mmol) was dissolved in MeOH (400 mL). HCl in MeOH (295 mL, 4 mol/L in MeOH) was added at 0° C. The resulting mixture was continued and stirred at 0° C. for 2 h. The reaction was concentrated in vacuum. The residue was triturated with MTBE (800 mL) to give methyl (1R,4r)-4-((R)-1-aminopropyl)cyclohexane-1-carboxylate (40.6 g, 203 mmol, yield: 93.7%) as white solid. LCMS: RT=0.215 min, m/z=200.2 [M+H]+; $^1$H NMR (400 MHz, DMSO-d6) δ 8.18-7.83 (m, 3H), 3.59 (s, 3H), 2.91-2.76 (m, 1H), 2.30-2.17 (m, 1H), 1.93 (br s, 2H), 1.72 (br s, 2H), 1.65-1.44 (m, 3H), 1.29 (br s, 2H), 1.11 (s, 2H), 0.91 (t, J=7.4 Hz, 3H).

Example 9—General Method for Amine Intermediates Synthesis—Preparation of Intermediate 9

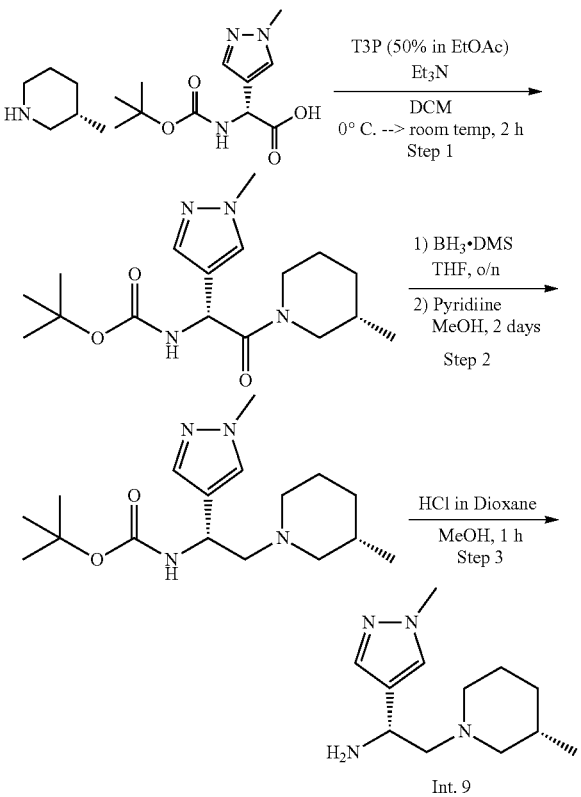

Int. 9

Step 1: (S)-3-methylpiperidine hydrochloride (3.19 g, 23.50 mmol), (R)-2-((tert-butoxycarbonyl)amino)-2-(1-methyl-1H-pyrazol-4-yl)acetic acid (5 g, 19.59 mmol) and Et$_3$N (10.92 ml, 78 mmol) were dissolved in DCM (75 ml).

The solution was cooled down to 0° C. and T3P (50% in EtOAc) (23.56 ml, 39.2 mmol) was added slowly. The solution became unclear and mixture was stirred at room temperature for 2 h. LC-MS indicated complete reaction. The reaction mixture was partitioned between EtOAc and water, the organic phase was washed with water, saturated NaHCO₃ solution, brine and dried over MgSO₄. The solid was filtered off and concentrated under reduced pressure. The crude material was purified by ISCO combi-flash chromatography (ELSD detection), eluting with a gradient of 20-100% EtOAc in heptane, using a 120 g silica column, loading with DCM. The product containing fractions were combined, concentrated under reduced pressure and dried under vacuum overnight to give tert-butyl ((R)-1-(1-methyl-1H-pyrazol-4-yl)-2-((S)-3-methylpiperidin-1-yl)-2-oxoethyl)carbamate as a white solid (6.16 g, 93%). MS m/z=337.1 [M+H]⁺.

Step 2: To a solution of tert-butyl ((R)-1-(1-methyl-1H-pyrazol-4-yl)-2-((S)-3-methylpiperidin-1-yl)-2-oxoethyl)carbamate (2.46 g, 7.31 mmol) in THF (18.28 ml) was added BH3.DMS (2M in THF) (18.28 ml, 36.6 mmol, 5.0 equiv.) at 0° C. Then the mixture was warmed to 25° C. and stirred overnight. LC-MS indicated all starting material was consumed. The RXN mixture was quenched with MeOH until no more bubbling observed. The mixture was stirred for 30 min then concentrated. The residue was diluted with MeOH (10 mL) then pyridine (5.91 ml, 73.1 mmol) was added to the solution. The resulting solution was stirred at rt for 2 days. RXN mixture was concentrated and diluted with MeOH for reverse phase column chromatography purification (20-80% MeCN/Water with 0.1% NH₄OH modifier, 150 g ISCO gold C18 column) and lyophilization drying to give tert-butyl ((R)-1-(1-methyl-1H-pyrazol-4-yl)-2-((S)-3-methylpiperidin-1-yl)ethyl)carbamate as a colorless oil (1.83 g, 78% yield). MS m/z=323.3 [M+H]+.

Step 3: To a solution of tert-butyl ((R)-1-(1-methyl-1H-pyrazol-4-yl)-2-((S)-3-methylpiperidin-1-yl)ethyl)carbamate (1.64 g, 5.09 mmol) in MeOH (10 ml) was added HCl (6.36 ml, 25.4 mmol, 4 N in Dioxane) solution. The reaction was stirred at room temperature for 4 h. The reaction mixture was concentrated under reduced pressure and dried under vacuum for overnight to give (R)-1-(1-methyl-1H-pyrazol-4-yl)-2-((S)-3-methylpiperidin-1-yl)ethan-1-amine dihydrochloride as a light pale solid in quantitative yield. MS m/z=223.3 [M+H]+.

Example 10—Preparation of Intermediate 10: (3R,5R)-3-methoxy-5-methylpiperidine

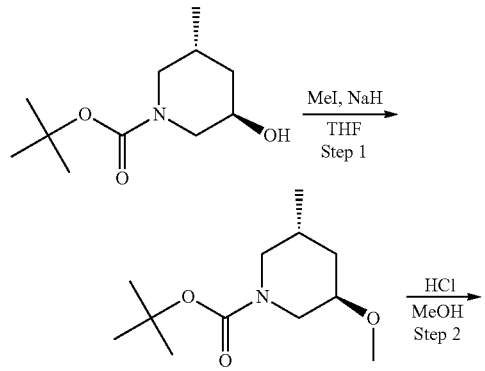

-continued

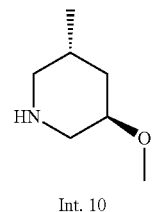

Int. 10

Step 1: To a solution of tert-butyl (3R,5R)-3-hydroxy-5-methylpiperidine-1-carboxylate (4500.0 mg, 1 Eq, 20.902 mmol) in THF (104 mL) was added NaH (2.090 g, 60% Wt, 2.5 Eq, 52 mmol) at 0° C. Then the reaction mixture was stirred at 0° C. for 0.5 h and MeI (7.42 g, 3.27 mL, 2.5 Eq, 52 mmol) was added dropwise. The mixture was stirred at 25° C. for another 1.5 h. LCMS showed one major peak with desired mass was detected. The mixture was quenched with saturated NH₄C₁ (100 mL) and extracted with EtOAc (100 mL*2). The combined organic phase was dried over anhydrous Na₂SO₄, filtered and concentrated to afford the residue. The residue was purified by flash silica gel chromatography(ISCO®; 80 g SepaFlash® Silica Flash Column, Eluent of 0-100% EtOAc/Heptane) and the eluent was concentrated to give desired product as a colorless oil. LCMS m/z [M−55]⁺=174.2.

Step 2: To a solution of tert-butyl (3R,5R)-3-methoxy-5-methylpiperidine-1-carboxylate (4.4 g, 1 Eq, 19 mmol) in MeOH (50 mL) was added HCl (4N in dioxane) (3.5 g, 24 mL, 4.000 molar, 5 Eq, 96 mmol) at 0° C. Then the reaction mixture was stirred at rt for 2 h and LC-MS indicated all SM was consumed. The mixture was concentrated under reduced pressure to give a colorless oil. The crude product was used next step without further purification. LCMS m/z [M+H]+=130.1.

Example 11—Preparation of Intermediate 11: 2-((tert-butoxycarbonyl)amino)-2-(3-fluoro-1-methyl-1H-pyrazol-4-yl)acetic acid

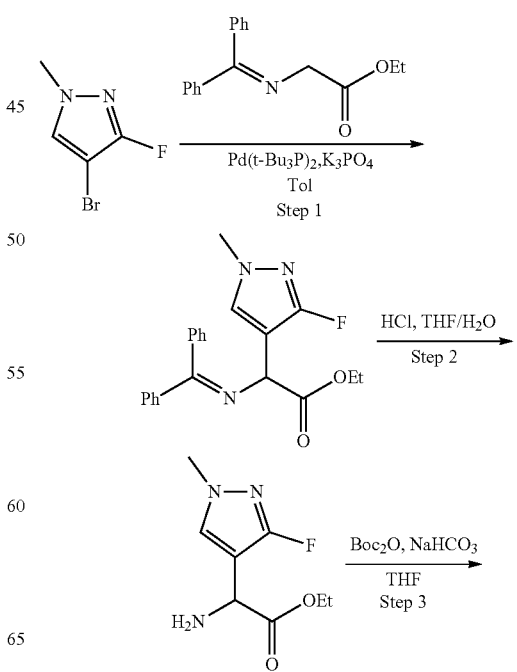

-continued

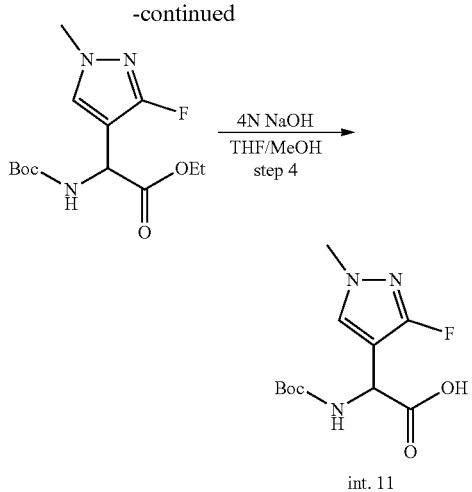

int. 11

Step 1: To a solution of ethyl 2-((diphenylmethylene)amino)acetate (1.25 g, 4.68 mmol) 4-bromo-3-fluoro-1-methyl-1H-pyrazole (0.92 g, 5.14 mmol) in Toluene (30 mL) was added $K_3PO_4$ (2.98 g, 14.03 mmol) and Pd(t-$Bu_3P)_2$ (0.24 g, 0.468 mmol) at 25° C. under $N_2$. Then the mixture was stirred at 100° C. for 16 h. LCMS showed desired mass was detected. The reaction mixture was poured into $H_2O$ (50 mL) and the aqueous layer was extracted with EA (50 mL*3). The combined organic phase was dried over $Na_2SO_4$, filtered and concentrated. The residue was purified by flash silica gel chromatography (ISCO®; 40 g Sepa-Flash® Silica Flash Column, Eluent of 0-100% Ethyl acetate/Petroleum ether gradient @ 100 mL/min) then concentrated to afford ethyl 2-((diphenylmethylene)amino)-2-(3-fluoro-1-methyl-1H-pyrazol-4-yl)acetate (250 mg, 60% purity) as a yellow oil. LCMS m/z [M+H]+=366.0.

Step 2: To a solution of ethyl 2-((diphenylmethylene)amino)-2-(3-fluoro-1-methyl-1H-pyrazol-4-yl)acetate (250 mg, 0.41 mmol, 60% purity) in dioxane (2 mL) was added 4M HCl/dioxane (2 mL). The resulting mixture was stirred at 25° C. for 4 h. LCMS showed desired mass was detected. The mixture was added $H_2O$ (4 mL) and then extracted with PE (4 mL*3), The aqueous phase (0.41 mmol, in $H_2O$ (4 mL)) was taken to the next step without further purification. The combined organic phase was discarded. LCMS m/z [M+H]+=202.1.

Step 3: To a mixture of ethyl 2-amino-2-(3-fluoro-1-methyl-1H-pyrazol-4-yl)acetate (0.41 mmol, in $H_2O$ (4 mL)) in THF (4 mL) was added $NaHCO_3$ (345 mg, 4.10 mmol) and $Boc_2O$ (179 mg, 0.82 mmol). The resulting mixture was stirred at 25° C. for 16 h. LCMS showed desired mass was detected. The mixture was extracted with EA (15 mL*3). The combined organic was dried over anhydrous $Na_2SO_4$, filtered, and concentrated to give ethyl 2-((tert-butoxycarbonyl)amino)-2-(3-fluoro-1-methyl-1H-pyrazol-4-yl)acetate (200 mg, crude) as yellow oil. LCMS m/z [M−55]*=246.2.

Step 4: A solution of ethyl 2-((tert-butoxycarbonyl)amino)-2-(3-fluoro-1-methyl-1H-pyrazol-4-yl)acetate (200 mg, Crude) in THF/MeOH/4M NaOH=2:1:1 (4 mL) was stirred at 40° C. for 1 h. LCMS showed desired mass was detected. The reaction mixture was concentrated to give the residue. The residue was added $H_2O$ (4 mL) and extracted with PE (4 mL*3), The aqueous phase was adjusted PH-5 with 1N HCl and extracted with EA (5 mL*3). The combined organic was dried over anhydrous $Na_2SO_4$, filtered, and concentrated to give 2-((tert-butoxycarbonyl)amino)-2-(3-fluoro-1-methyl-1H-pyrazol-4-yl)acetic acid (110 mg, crude) as yellow gum.

Example 12: Synthesis of (1R,4r)-4-((R)-1-(((R)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid (Compound 48) and (1R,4r)-4-((R)-1-(((S)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid (Compound 141)

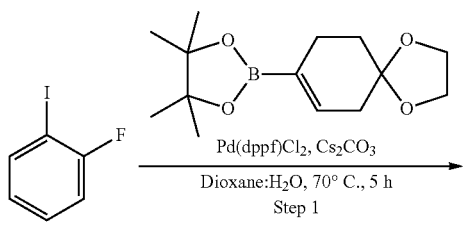

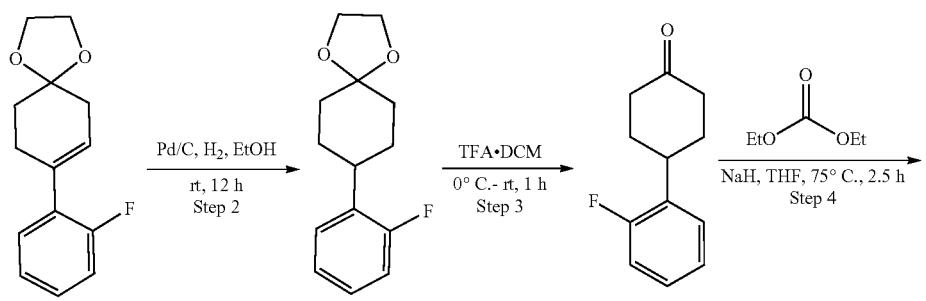

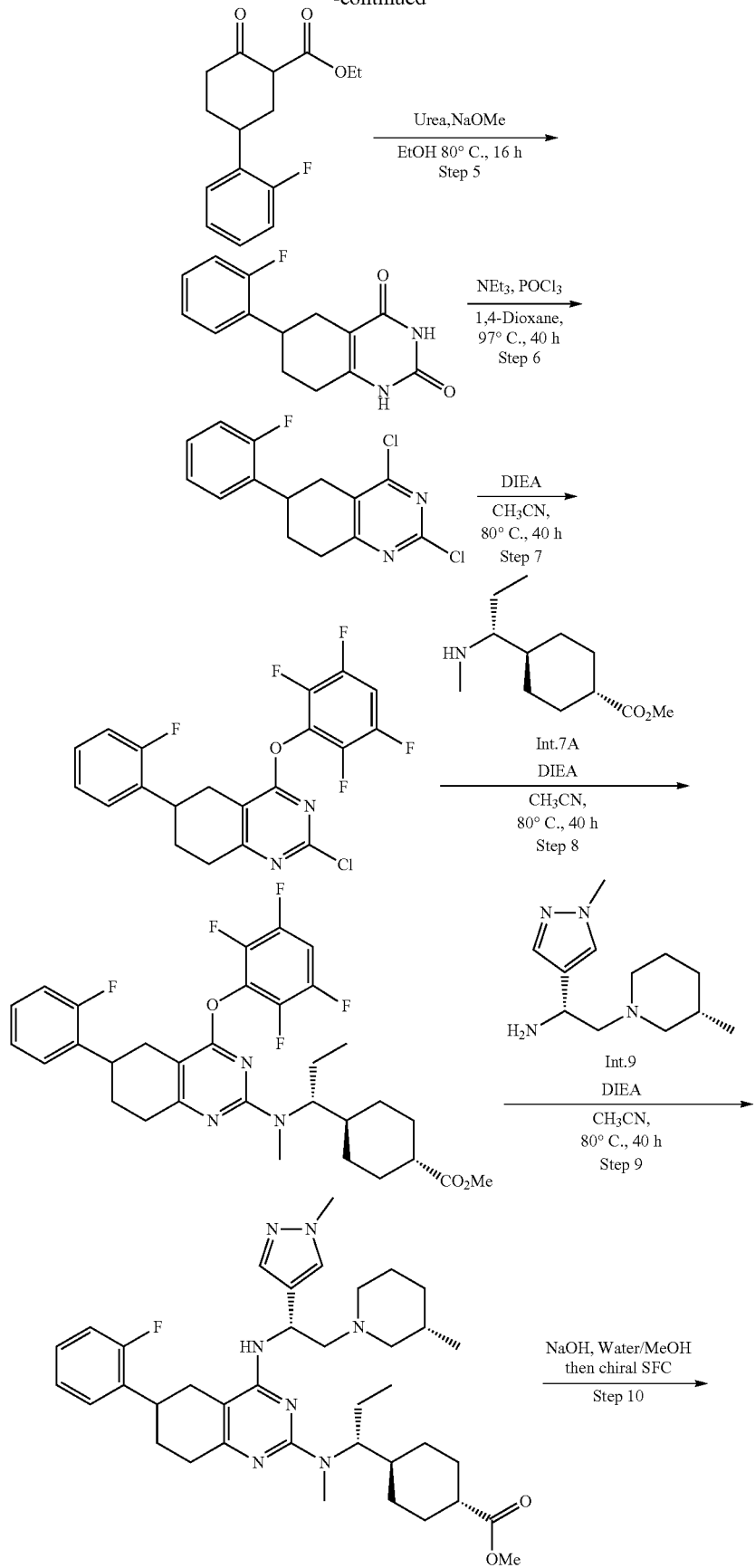

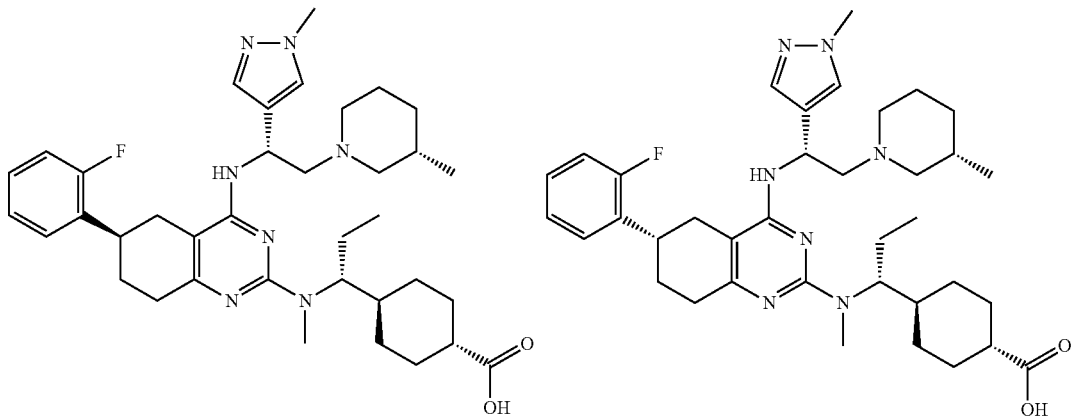

Step 1: To a flask with 4,4,5,5-tetramethyl-2-(1,4-dioxaspiro[4.5]dec-7-en-8-yl)-1,3,2-dioxaborolane (5 g, 18.79 mmol), 1-fluoro-2-iodobenzene (5 g, 22.54 mmol) and sodium carbonate (7.96 g, 75 mmol) were added dioxane (75 ml) and water (18.75 ml). The reaction mixture was degassed with nitrogen for 5 min, and then added $PdCl_2$ (dppf)·$CH_2Cl_2$ adduct (0.767 g, 0.939 mmol) and heated at 90° C. for overnight. The reaction was monitored with LCMS and cooled to room temperature. The reaction was diluted with EtOAc and filtered through celite, and washed with EtOAc. The filtrate was concentrated, and purified by chromotography (40 g, silica gel, 0-20% EtOAc in Heptane) to afford 8-(2-fluorophenyl)-1,4-dioxaspiro[4.5]dec-7-ene (4.26 g, 18.18 mmol, 97% yield). LCMS: m/z=235.2 [M+H]$^+$; $^1$H NMR (400 MHz, Chloroform-d) δ 7.26-7.17 (m, 1H), 7.11 (ddd, J=7.3, 5.1, 2.0 Hz, 1H), 7.05-6.88 (m, 2H), 5.83-5.67 (m, 1H), 3.96 (s, 4H), 2.57 (ddt, J=6.3, 3.9, 1.9 Hz, 2H), 2.40 (q, J=2.6 Hz, 2H), 1.84 (t, J=6.5 Hz, 2H).

Step 2: A solution of 8-(2-fluorophenyl)-1,4-dioxaspiro[4.5]dec-7-ene (4.26 g, 18.18 mmol) in MeOH (100 mL), was added Pd/C (10%, 1.355 g) and flushed with hydrogen three times. The resulting solution was stirred under hydrogen balloon for 16 h. The mixture was flushed with nitrogen and filtered through celite. The filtrate was concentrated to afford desired product 8-(2-fluorophenyl)-1,4-dioxaspiro[4.5]decane, which was taken to the next step as such. LCMS: m/z=237 [M+H]+; $^1$H NMR (400 MHz, Chloroform-d) δ 7.37-7.24 (m, 1H), 7.18 (tdd, J=7.4, 5.1, 1.8 Hz, 1H), 7.10 (td, J=7.6, 1.4 Hz, 1H), 7.06-6.95 (m, 1H), 4.01 (s, 4H), 3.03-2.86 (m, 1H), 1.96-1.65 (m, 9H).

Step 3: Crude 8-(2-fluorophenyl)-1,4-dioxaspiro[4.5]decane residue was dissolved in DCM (15 mL) and added TFA (28.0 mL, 364 mmol) at room temperature. The mixture was stirred at room temperature for 2 days. LCMS showed one single peak of desired product. The mixture was concentrated, diluted with EtOAc and washed with sodium bicarbonate saturated aqueous solution, water, brine, dried over sodium sulfate, and concentrated. The residue was purified by chromatography (silica gel, 120 g, 0-50% EtOAc/Heptane) to afford 4-(2-fluorophenyl)cyclohexan-1-one (3.6 g, 98% yield). $^1$H NMR (400 MHz, Chloroform-d) δ 7.61-7.22 (m, 2H), 7.10 (dt, J=26.2, 8.5 Hz, 2H), 3.61-3.28 (m, 1H), 2.82-2.44 (m, 4H), 2.44-2.17 (m, 2H), 2.17-1.87 (m, 2H).

Step 4: NaH (1.032 g, 25.8 mmol) was added to diethyl carbonate (23.45 mL, 194 mmol) at room temperature in portions. 4-(2-fluorophenyl)cyclohexan-1-one (3.1 g, 16.13 mmol) was then added in portions to the reaction mixture. When the reaction was heated to 60° C., the formed foam rising up. The reaction was cooled down and THF (20 mL) was used to rinse back. The mixture was heated to 75° C. for 2 h. The reaction was allowed to cool to room temperature and then neutralized by 2 M HCl aqueous solution. The resulting mixture was extracted with EtOAc (2×50 mL). The combined organic layers were dried over sodium sulfate, filtered and concentrated. The residue was purified by chromatography (80 g, silica gel, EtOAc/Heptane 0-30%) to afford ethyl 5-(2-fluorophenyl)-2-oxocyclohexane-1-carboxylate (2.6 g, 54.9% yield). LCMS: m/z=263 [M–H]+.

Step 5: To a flask with ethyl 5-(2-fluorophenyl)-2-oxocyclohexane-1-carboxylate (2.3 g, 8.70 mmol) and urea (1.045 g, 17.40 mmol) was added NaOMe (0.940 g, 17.40 mmol) and MeOH (Volume: 20 mL). The mixture was heated at 70° C. for 16 h. The reaction was cooled down to room temperature, and the precipitate was filtered and washed with $Et_2O$, and dried to afford 6-(2-fluorophenyl)-5,6,7,8-tetrahydroquinazoline-2,4-diol (2.1 g, 93% yield). LCMS: m/z=261.1 [M+H]+; $^1$H NMR (400 MHz, Methanol-d4) δ 8.57 (s, 1H), 7.34 (td, J=7.6, 1.9 Hz, 1H), 7.24 (tdd, J=7.3, 5.2, 1.8 Hz, 1H), 7.18-7.11 (m, 1H), 7.11-6.96 (m, 1H), 3.19 (tq, J=9.0, 4.6 Hz, 1H), 2.75 (dd, J=16.2, 5.3 Hz, 1H), 2.69-2.49 (m, 2H), 2.45-2.30 (m, 1H), 2.00 (dq, J=10.9, 5.4 Hz, 2H).

Step 6: To a solution of 6-(2-fluorophenyl)-5,6,7,8-tetrahydroquinazoline-2,4-diol (2.1 g, 8.07 mmol) and $Et_3N$ (2.68 mL, 19.36 mmol) in dioxane (8 mL) at 0° C. was slowly added $POCl_3$ (7.52 mL, 81 mmol). The reaction was heated at 97° C. for 40 h. The reaction mixture was concentrated and poured to ice-cold water and stirred for 30 min. The mixture was extracted with EtOAc (4×100 mL) until no product in aqueous layer. The organic layers were combined and concentrated. The reside was purified by chromatography (silica gel, 120 g, 0-30% EtOAc/Heptane) afforded 2,4-dichloro-6-(2-fluorophenyl)-5,6,7,8-tetrahydroquinazoline (0.4 g, 17% yield). LCMS: m/z=297 [M+H]+; $^1$H NMR (400 MHz, Methanol-d4) δ 7.46-7.25 (m, 2H), 7.25-7.04 (m, 2H), 3.85-3.68 (m, 1H), 3.47-3.36 (m, 1H), 3.20-2.94 (m, 2H), 2.83 (ddd, J=17.7, 11.3, 1.5 Hz, 1H), 2.25-2.05 (m, 2H).

Step 7: A solution of 2,4-dichloro-6-(2-fluorophenyl)-5,6,7,8-tetrahydroquinazoline (0.4 g, 1.346 mmol), 2,3,5,6-tetrafluorophenol (0.268 g, 1.615 mmol) and DIPEA (0.306 mL, 1.750 mmol) in CH₃CN (2 mL) was stirred at 80° C. for 40 h. The residue was purified by chromatography (120 g, silica gel, 0-7% then flat 7% EtOAc/Heptane) to afford 2-chloro-6-(2-fluorophenyl)-4-(2,3,5,6-tetrafluorophenoxy)-5,6,7,8-tetrahydroquinazoline (560 mg, 97% yield). LCMS: m/z=427.1 [M+H]⁺; ¹H NMR (400 MHz, Methanol-d4) δ 7.58-7.46 (m, 1H), 7.46-7.38 (m, 1H), 7.31 (tdd, J=7.0, 5.1, 1.6 Hz, 1H), 7.20 (t, J=7.3 Hz, 1H), 7.13 (dd, J=10.8, 8.2 Hz, 1H), 3.46 (ddd, J=11.4, 6.1, 2.5 Hz, 1H), 3.22 (dd, J=17.3, 4.9 Hz, 1H), 3.13-2.99 (m, 2H), 2.90 (dd, J=17.3, 11.2 Hz, 1H), 2.22 (tt, J=8.9, 4.0 Hz, 2H).

Step 8: To 2-chloro-6-(2-fluorophenyl)-4-(2,3,5,6-tetrafluorophenoxy)-5,6,7,8-tetrahydroquinazoline (280 mg, 0.656 mmol), methyl (1R,4r)-4-((R)-1-(methylamino)propyl)cyclohexane-1-carboxylate (263 mg, 0.919 mmol) in anhydrous acetonitrile (Volume: 0.4 mL) in a 5 ml microwave vial was added DIPEA (0.458 mL, 2.62 mmol). The resulting mixture was heated to 100° C. for 72 h. The reaction mixture was purified by chromatography (40 g, silica gel, 0-10% EtOAc/Heptane) to afford Methyl (1R,4r)-4-((1R)-1-((6-(2-fluorophenyl)-4-(2,3,5,6-tetrafluorophenoxy)-5,6,7,8-tetrahydroquinazolin-2-yl)(methyl)amino)propyl)cyclohexane-1-carboxylate (176 mg, 44% yield).

LCMS: m/z=604.3 [M+H]⁺; ¹H NMR (400 MHz, Methanol-d4) δ 7.36 (s, 1H), 7.30 (td, J=7.6, 1.8 Hz, 1H), 7.16 (tdd, J=7.3, 5.1, 1.8 Hz, 1H), 7.07 (td, J=7.6, 1.4 Hz, 1H), 7.03-6.93 (m, 1H), 3.74 (s, 1H), 3.54 (s, 3H), 2.95 (dd, J=16.2, 5.2 Hz, 1H), 2.76 (d, J=17.6 Hz, 4H), 2.62 (dd, J=16.2, 11.3 Hz, 1H), 2.06 (s, 5H), 1.90-1.67 (m, 3H), 1.55-1.12 (m, 6H), 0.45-0.68 (m, 5H).

Step 9: A solution of (R)-1-(1-methyl-1H-pyrazol-4-yl)-2-((S)-3-methylpiperidin-1-yl)ethan-1-amine (103 mg, 0.350 mmol), methyl (1R,4r)-4-((1R)-1-((6-(2-fluorophenyl)-4-(2,3,5,6-tetrafluorophenoxy)-5,6,7,8-tetrahydroquinazolin-2-yl)(methyl)amino)propyl)cyclohexane-1-carboxylate (176 mg, 0.292 mmol) and DIPEA (0.204 mL, 1.166 mmol) in isopropanol (0.25 mL) in chem-glass pressure vessel (20 ml) was stirred at 110° C. for 2 days. 100 mg (R)-1-(1-methyl-1H-pyrazol-4-yl)-2-((S)-3-methylpiperidin-1-yl)ethan-1-amine (100 mg, 0.34 mmol) and DIPEA (0.2 ml, 1.16 mmol) were added and heated at 105° C. for 2 days. The mixture was concentrated in vacuo and the residue was purified through chromatography (40 g, silica gel, 0-85% EtOAc/DCM) to give methyl (1R,4r)-4-((1R)-1-((6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylate (0.1 g, 52% yield). LCMS: m/z=660.4 [M+H]⁺.

Step 10: A solution of methyl (1R,4r)-4-((1R)-1-((6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylate (100 mg, 0.152 mmol) in MeOH (2 mL) and Water (0.5 mL) was added NaOH (4M aqueous solution, 0.379 mL, 1.515 mmol) and stirred at 50° C. for 30 min. The reaction mixture was purified by SFC chiral separation (Column 2.0×25.0 cm ChromegaChiral CC4 from ES Industries, Methanol/Acetonitrile (1:3) with 30 mM Ammonium Acetate, 65% Co-solvent at 70 g/min, 100 bar, 25° C.) to afford (1R,4r)-4-((R)-1-(((R)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid (21 mg, 20% yield) and (1R,4r)-4-((R)-1-(((S)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid (19 mg, 18% yield).

(1R,4r)-4-((R)-1-(((R)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid: LCMS m/z=646.5 [M+H]+; ¹H NMR (400 MHz, DMSO-d6) δ 7.53-7.37 (m, 2H), 7.37-7.25 (m, 2H), 7.19 (q, J=10.1, 8.6 Hz, 2H), 6.13 (d, J=7.5 Hz, 1H), 5.31 (s, 1H), 4.49 (s, 1H), 3.75 (s, 3H), 3.18 (s, 2H), 2.89-2.58 (m, 7H), 2.29 (dd, J=23.7, 10.7 Hz, 2H), 2.09 (s, 3H), 2.03-1.46 (m, 12H), 1.25 (t, J=41.8 Hz, 6H), 1.02-0.46 (m, 7H).

(1R,4r)-4-((R)-1-(((S)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid: LCMS m/z=646.5 [M+H]+; ¹H NMR (400 MHz, DMSO-d6) δ 7.54-7.40 (m, 2H), 7.40-7.23 (m, 2H), 7.19 (q, J=8.6, 7.7 Hz, 2H), 6.14 (s, 1H), 5.31 (s, 1H), 4.50 (s, 1H), 3.75 (s, 3H), 3.18 (s, 2H), 2.71 (q, J=24.6, 23.9 Hz, 7H), 2.31 (d, J=15.6 Hz, 2H), 2.09 (s, 3H), 1.91 (s, 6H), 1.79-1.44 (m, 6H), 1.25 (t, J=40.5 Hz, 6H), 0.98-0.63 (m, 7H).

Example 13: Synthesis of (1R,4r)-4-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid (Compound 40)

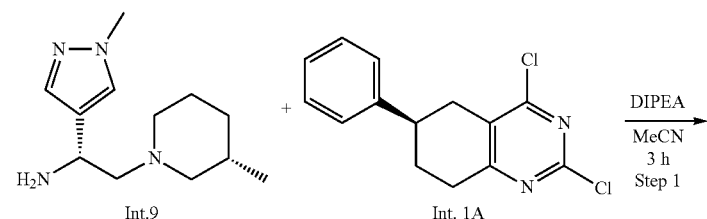

-continued

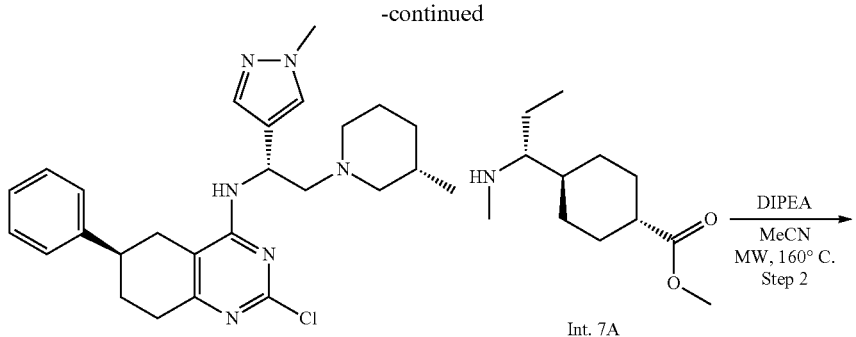

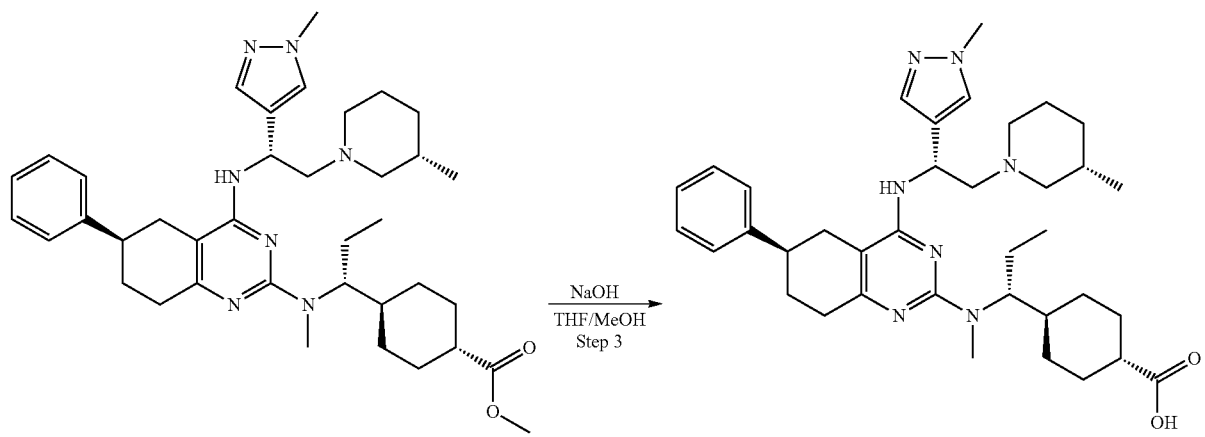

Step 1: A solution of (R)-2,4-dichloro-6-phenyl-5,6,7,8-tetrahydroquinazoline (1265 mg, 4.53 mmol), (R)-1-(1-methyl-1H-pyrazol-4-yl)-2-((S)-3-methylpiperidin-1-yl)ethan-1-amine dihydrochloride (1338 mg, 4.53 mmol) and DIPEA (2769 μl, 15.86 mmol) in MeCN (Volume: 22 mL) was stirred at 70° C. for 3 h. MeCN was removed under reduced pressure then the residue was extracted with EtOAc/water. The combined organic layer was washed with brine, dried over Na$_2$SO$_4$ and concentrated. The residue was purified through flash column chromatography (0-20% MeOH (0.1 N NH$_3$)/DCM) to give (R)-2-chloro-N—((R)-1-(1-methyl-1H-pyrazol-4-yl)-2-((S)-3-methylpiperidin-1-yl)ethyl)-6-phenyl-5,6,7,8-tetrahydroquinazolin-4-amine as a light pale solid (949 mg, 45%). MS: m/z=465.1 [M+H]$^+$.

Step 2: A solution of (R)-2-chloro-N—((R)-1-(1-methyl-1H-pyrazol-4-yl)-2-((S)-3-methylpiperidin-1-yl)ethyl)-6-phenyl-5,6,7,8-tetrahydroquinazolin-4-amine (920 mg, 1.98 mmol), methyl (1R,4r)-4-((R)-1-(methylamino)propyl)cyclohexane-1-carboxylate (844 mg, 3.96 mmol) and DIPEA (1.727 mL, 9.89 mmol) in MeCN (4 mL) was heated at 160° C. in a microwave reactor for 2 days. The reaction mixture was diluted with EtOAc, washed with brine, dried over Na$_2$SO$_4$ and concentrated. The residue was purified through flash column chromatography (0-20% MeOH(0.1 N NH$_3$)/DCM) to give off methyl (1R,4r)-4-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylate as a light pale solid (832 mg, 65%). MS: m/z=642.4 [M+H]$^+$.

Step 3: To a solution of methyl (1R,4r)-4-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylate (832 mg, 1.296 mmol) in THF (6 mL) and MeOH (3 mL) was added NaOH (4N aq solution) (1.620 mL, 6.48 mmol). The resulting suspension was stirred at 50° C. for 30 min then solvent was removed under reduced pressure then diluted with DMSO. The suspension was purified by reverse phase column. (150 g ISCO gold C-18 column, 20-70% MeCN/water, with 0.1% NH$_{40}$H as modifier). The pure fractions was combined and lyophilization drying gave (1R,4r)-4-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid sodium salt as a white solid (445 mg, 43%). MS: m/z=628.5 [M+H]$^+$; $^1$H NMR (400 MHz, Methanol-d4) δ 7.49 (s, 1H), 7.40 (s, 1H), 7.38-7.30 (m, 4H), 7.25-7.19 (m, 1H), 5.49 (s, 1H), 4.54 (s, 1H), 3.86 (s, 3H), 3.05-2.94 (m, 2H), 2.93-2.82 (m, 5H), 2.78-2.71 (m, 3H), 2.64 (dd, J=12.8, 5.3 Hz, 1H), 2.47-2.36 (m, 1H), 2.16-1.95 (m, 5H), 1.94-1.62 (m, 7H), 1.58-1.25 (m, 6H), 1.06-0.84 (m, 5H), 0.79 (t, J=7.2 Hz, 4H).

The following compounds were made using the above procedure or modifications to the above procedure using the corresponding intermediates.

| | | |
|---|---|---|
| 98 | 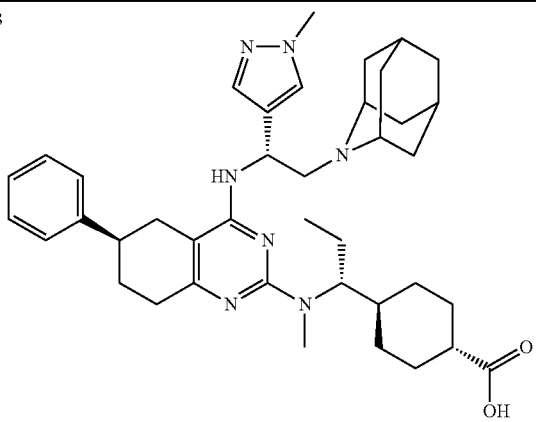 | LCMS m/z [M + H]⁺ = 666.6, ¹H NMR (400 MHz, MeOD) δ 7.40 (s, 1H), 7.30 (s, 1H), 7.28-7.17 (m, 5H), 7.16-6.99 (m, 1H), 5.17 (s, 1H), 3.75 (s, 3H), 2.96-2.53 (m, 9H), 2.37 (s, 1H), 2.13-1.10 (m, 29H), 0.90-0.58 (m, 3H). |
| 128 | 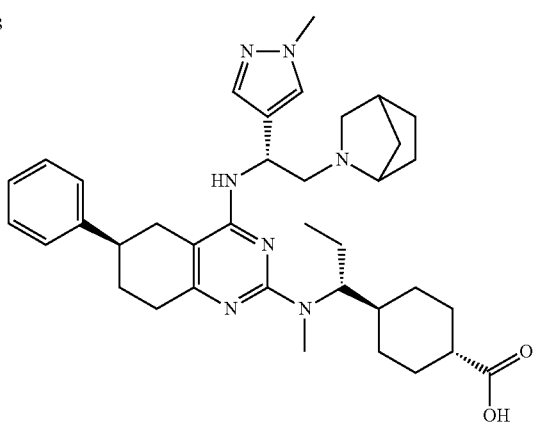 | LCMS m/z [M + H]⁺ = 626.4, ¹H NMR (400 MHz, Methanol-d4) δ 7.61-6.81 (m, 7H), 5.61 (d, J = 169.9 Hz, 1H), 4.37 (s, 1H), 3.73 (d, J = 8.9 Hz, 4H), 2.98-2.13 (m, 11H), 2.08-1.05 (m, 20H), 1.02-0.32 (m, 5H). |
| 136 | 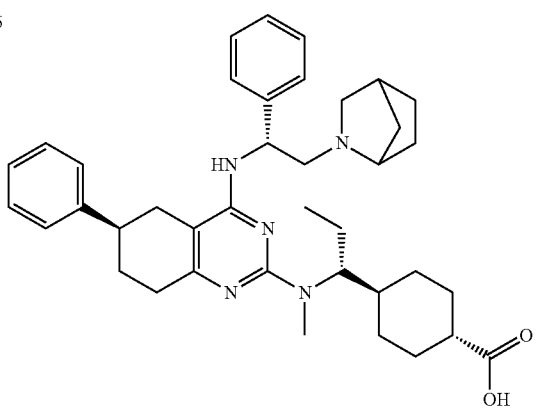 | LCMS m/z [M + H]⁺ = 622.3, ¹H NMR (400 MHz, MeOD) δ 7.19-6.93 (m, 10H), 4.96 (s, 1H), 4.11 (s, 1H), 2.74 (dd, J = 29.1, 13.1 Hz, 4H), 2.55 (s, 6H), 2.43-2.13 (m, 3H), 2.01-0.97 (m, 22H), 0.84 (d, J = 39.5 Hz, 2H). |
| 19 | 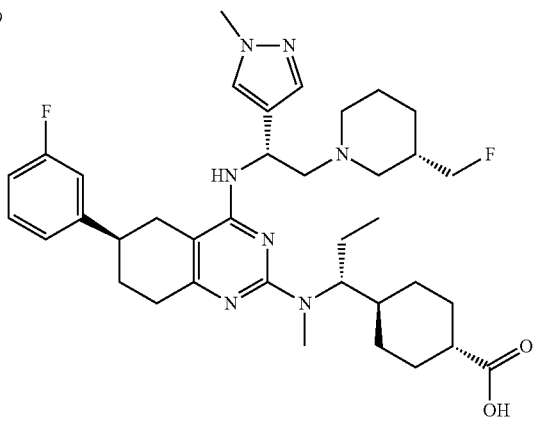 | LCMS m/z [M + H]⁺ = 664.3, ¹H NMR (400 MHz, Methanol-d4) δ 7.49 (s, 1H), 7.39 (s, 1H), 7.33 (td, J = 8.0, 6.1 Hz, 1H), 7.17 (dt, J = 7.8, 1.2 Hz, 1H), 7.10 (dt, J = 10.5, 2.1 Hz, 1H), 6.97-6.91 (m, 1H), 5.47 (s, 1H), 4.52 (s, 1H), 4.41-4.12 (m, 2H), 3.85 (s, 3H), 3.09 (t, J = 5.6 Hz, 2H), 3.03-2.87 (m, 4H), 2.78-2.70 (m, 3H), 2.65 (dd, J = 12.8, 5.5 Hz, 1H), 2.47-2.35 (m, 1H), 2.10 (td, J = 10.8, 2.7 Hz, 2H), 2.05-1.94 (m, 4H), 1.85-1.62 (m, 7H), 1.60-1.23 (m, 6H), 1.10 (dd, J = 11.2, 8.5 Hz, 1H), 0.94 (d, J = 12.7 Hz, 1H), 0.77 (t, J = 7.2 Hz, 3H), 0.65 (d, J = 13.3 Hz, 1H). |

| | | |
|---|---|---|
| 72 | 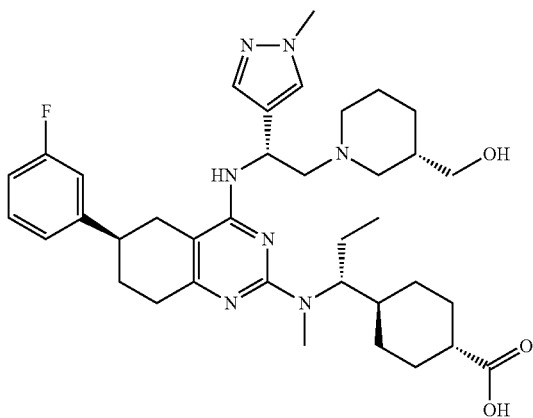 [SMILES: CC[C@H]([C@H]1CC[C@H](C(=O)O)CC1)N(C)c1nc2c(c(N[C@@H](CN3CCC[C@H](CO)C3)c3cnn(C)c3)n1)C[C@H](c1cccc(F)c1)CC2] | LCMS m/z [M + H]⁺ = 662.4, ¹H NMR (400 MHz, Methanol-d4) δ 7.37 (s, 1H), 7.32-7.19 (m, 2H), 7.07 (d, J = 7.8 Hz, 1H), 7.00 (dt, J = 10.5, 2.1 Hz, 1H), 6.83 (td, J = 8.3, 2.3 Hz, 1H), 5.34 (s, 1H), 4.40 (s, 1H), 3.74 (s, 3H), 3.32 (dd, J = 10.7, 5.7 Hz, 1H), 3.28-3.23 (m, 1H), 2.97-2.76 (m, 4H), 2.71 (s, 3H), 2.68-2.58 (m, 3H), 2.57-2.47 (m, 1H), 2.35-2.25 (m, 1H), 2.03-1.54 (m, 12H), 1.48-1.13 (m, 6H), 0.97-0.77 (m, 2H), 0.70-0.49 (m, 4H). |
| 75 | 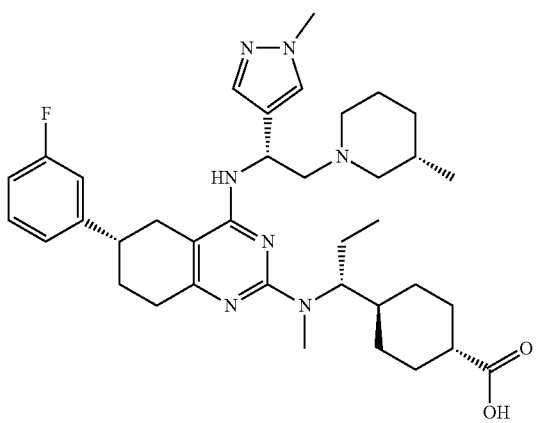 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@@H](c1cccc(F)c1)CC2] | LCMS m/z [M + H]⁺ = 646.3, ¹H NMR (400 MHz, Methanol-d4) δ 7.40 (s, 1H), 7.30 (s, 1H), 7.23 (td, J = 8.0, 6.1 Hz, 1H), 7.07 (dt, J = 7.8, 1.3 Hz, 1H), 7.00 (dt, J = 10.4, 2.1 Hz, 1H), 6.88-6.80 (m, 1H), 5.38 (s, 1H), 4.42 (s, 1H), 3.75 (s, 3H), 2.76 (d, J = 14.5 Hz, 7H), 2.69-2.50 (m, 4H), 2.35 (dd, J = 15.7, 10.8 Hz, 1H), 2.01 (d, J = 13.1 Hz, 1H), 1.96-1.83 (m, 4H), 1.82-1.50 (m, 7H), 1.49-1.14 (m, 6H), 0.89-0.73 (m, 5H), 0.72-0.64 (m, 3H), 0.59-0.49 (m, 1H) |
| 93 | 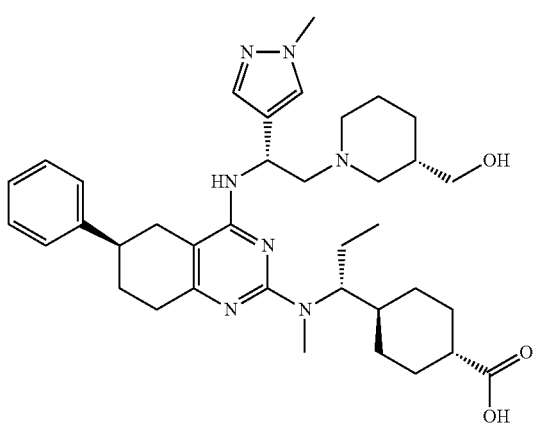 [SMILES: CC[C@H]([C@H]1CC[C@H](C(=O)O)CC1)N(C)c1nc2c(c(N[C@@H](CN3CCC[C@H](CO)C3)c3cnn(C)c3)n1)C[C@H](c1ccccc1)CC2] | LCMS m/z [M + H]⁺ = 644.4, ¹H NMR (400 MHz, Methanol-d4) δ 7.36 (d, J = 2.9 Hz, 1H), 7.30-7.18 (m, 5H), 7.12-7.06 (m, 1H), 5.32 (s, 1H), 4.40 (s, 1H), 3.74 (s, 3H), 3.31 (dd, J = 10.8, 5.7 Hz, 1H), 3.26-3.23 (m, 1H), 2.94-2.67 (m, 7H), 2.66-2.58 (m, 3H), 2.56-2.47 (m, 1H), 2.37-2.26 (m, 1H), 2.02-1.54 (m, 12H), 1.48-1.12 (m, 6H), 0.98-0.80 (m, 2H), 0.73-0.47 (m, 4H). |

| | | |
|---|---|---|
| 101 | 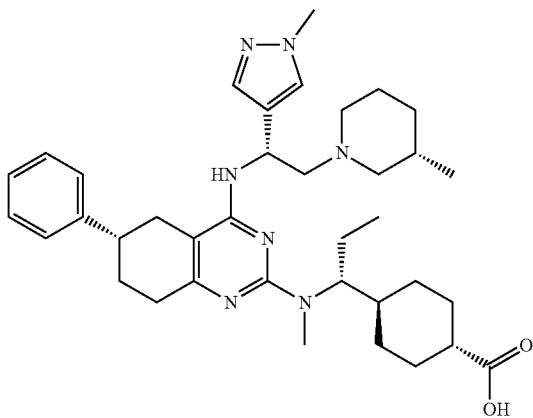 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@@H](c1ccccc1)CC2] | LCMS m/z [M + H]+ = 628.4, 1H NMR (400 MHz, Methanol-d4) δ 7.49 (s, 1H), 7.40 (s, 1H), 7.36-7.29 (m, 4H), 7.24-7.17 (m, 1H), 5.47 (s, 1H), 4.52 (s, 1H), 3.85 (s, 3H), 3.08-2.92 (m, 2H), 2.91-2.81 (m, 5H), 2.79-2.59 (m, 4H), 2.46 (dd, J = 15.8, 10.7 Hz, 1H), 2.14-2.07 (m, 1H), 2.05-1.93 (m, 4H), 1.92-1.61 (m, 7H), 1.58-1.24 (m, 6H), 1.04-0.83 (m, 5H), 0.79 (t, J = 7.2 Hz, 3H), 0.71-0.55 (m, 1H). |
| 103 | 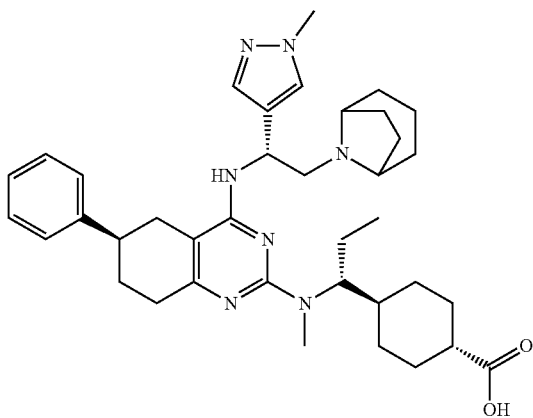 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@H](c1ccccc1)CC2] | LCMS m/z [M + H]+ = 640.4, 1H NMR (400 MHz, Methanol-d4) δ 7.38 (s, 1H), 7.29 (s, 1H), 7.26-7.19 (m, 4H), 7.10 (tt, J = 7.2, 1.9 Hz, 1H), 5.17 (s, 1H), 4.38 (s, 1H), 3.74 (s, 3H), 3.17 (s, 2H), 2.94-2.84 (m, 1H), 2.74 (d, J = 16.3 Hz, 5H), 2.63 (dt, J = 10.6, 5.4 Hz, 3H), 2.42-2.25 (m, 1H), 1.99 (d, J = 13.1 Hz, 1H), 1.88 (s, 5H), 1.80-1.46 (m, 8H), 1.44-1.15 (m, 8H), 0.82 (d, J = 13.2 Hz, 1H), 0.65 (t, J = 7.2 Hz, 3H), 0.54 (s, 1H). |
| 118 | 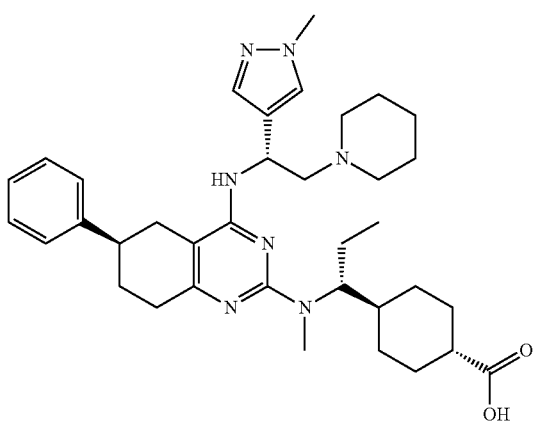 [SMILES: CC[C@H]([C@H]1CC[C@H](C(=O)O)CC1)N(C)c1nc2c(c(N[C@@H](CN3CCCCC3)c3cnn(C)c3)n1)C[C@H](c1ccccc1)CC2] | LCMS m/z [M + H]+ = 614.3, 1H NMR (400 MHz, Methanol-d4) δ 7.46 (s, 1H), 7.42-7.27 (m, 5H), 7.24-7.15 (m, 1H), 5.46 (s, 1H), 4.53 (s, 1H), 3.84 (s, 3H), 3.02-2.93 (m, 1H), 2.90-2.67 (m, 7H), 2.65-2.34 (m, 6H), 2.13-1.93 (m, 4H), 1.91-1.69 (m, 3H), 1.65-1.22 (m, 11H), 0.92 (d, J = 12.5 Hz, 1H), 0.83-0.57 (m, 4H). |

| | | |
|---|---|---|
| 83 | 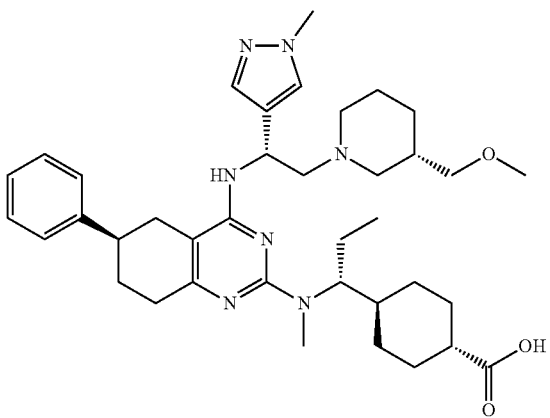 [SMILES: CC[C@H]([C@H]1CC[C@H](C(=O)O)CC1)N(C)c1nc2c(c(N[C@@H](CN3CCC[C@H](COC)C3)c3cnn(C)c3)n1)C[C@H](c1ccccc1)CC2] | LCMS m/z [M + H]⁺ = 658.9, ¹H NMR (400 MHz, Methanol-d4) δ 7.37 (s, 1H), 7.28 (s, 1H), 7.26-7.16 (m, 4H), 7.10 (t, J = 6.9 Hz, 1H), 5.33 (s, 1H), 4.42 (s, 2H), 3.74 (s, 3H), 3.18-3.01 (m, 5H), 2.95-2.47 (m, 11H), 2.32 (t, J = 13.5 Hz, 1H), 2.13-1.62 (m, 10H), 1.56 (d, J = 11.6 Hz, 2H), 1.49-1.10 (m, 6H), 0.92 (d, J = 10.9 Hz, 2H), 0.67 (t, J = 7.2 Hz, 3H). |
| 129 | 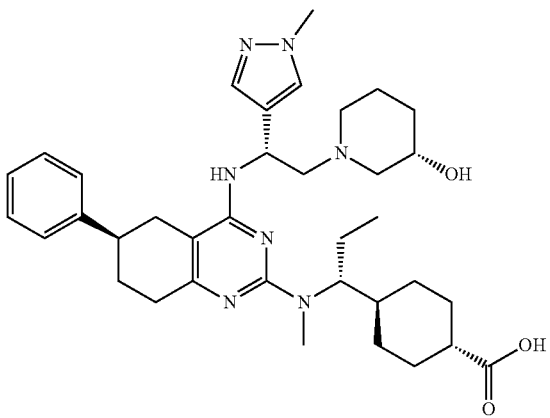 [SMILES: CC[C@H]([C@H]1CC[C@H](C(=O)O)CC1)N(C)c1nc2c(c(N[C@@H](CN3CCC[C@H](O)C3)c3cnn(C)c3)n1)C[C@H](c1ccccc1)CC2] | LCMS m/z [M + H]⁺ = 630.4, ¹H NMR (400 MHz, Methanol-d4) δ 7.52 (s, 1H), 7.46-7.28 (m, 5H), 7.28-7.17 (m, 1H), 5.43 (s, 1H), 3.87 (s, 3H), 3.63 (d, J = 10.0 Hz, 1H), 3.08-2.62 (m, 10H), 2.48 (d, J = 13.9 Hz, 1H), 2.20-1.14 (m, 17H), 0.96 (s, 1H), 0.80 (t, J = 7.3 Hz, 3H), 0.65 (s, 1H). Signal for 3H hidden under solvent peaks. |
| 134 | 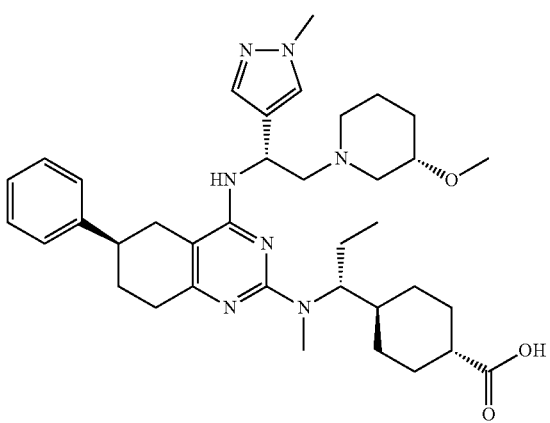 [SMILES: CC[C@H]([C@H]1CC[C@H](C(=O)O)CC1)N(C)c1nc2c(c(N[C@@H](CN3CCC[C@H](OC)C3)c3cnn(C)c3)n1)C[C@H](c1ccccc1)CC2] | LCMS m/z [M + H]⁺ = 644.5, ¹H NMR (400 MHz, Methanol-d4) δ 7.41 (s, 1H), 7.33-7.21 (m, 5H), 7.19-7.09 (m, 1H), 5.31 (s, 1H), 4.44 (d, J = 33.6 Hz, 1H), 3.76 (s, 3H), 3.16 (s, 3H), 2.90 (ddt, J = 8.9, 5.5, 3.2 Hz, 1H), 2.79 (s, 3H), 2.77-2.65 (m, 4H), 2.59 (dd, J = 12.9, 5.2 Hz, 2H), 2.36 (t, J = 13.5 Hz, 1H), 2.25-1.57 (m, 12H), 1.54-1.11 (m, 8H), 0.84 (d, J = 13.2 Hz, 1H), 0.69 (t, J = 7.2 Hz, 3H), 0.50 (d, J = 13.1 Hz, 1H). |

| | | |
|---|---|---|
| 145 | 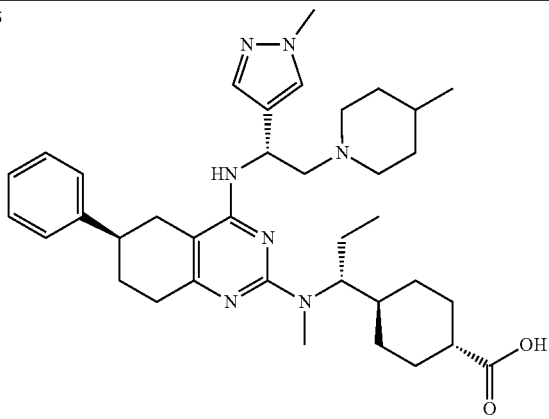 | LCMS m/z [M + H]⁺ = 628.3, ¹H NMR (400 MHz, Methanol-d4) δ 7.38 (s, 1H), 7.31-7.17 (m, 5H), 7.15-7.07 (m, 1H), 5.36 (s, 1H), 4.42 (s, 1H), 3.75 (s, 3H), 2.81 (t, J = 11.2 Hz, 4H), 2.74 (s, 3H), 2.65 (q, J = 6.8, 6.2 Hz, 3H), 2.54 (dd, J = 12.9, 4.8 Hz, 1H), 2.31 (t, J = 13.5 Hz, 1H), 2.17-1.59 (m, 9H), 1.52 (d, J = 12.9 Hz, 2H), 1.46-0.97 (m, 8H), 0.82 (d, J = 6.5 Hz, 4H), 0.66 (t, J = 7.1 Hz, 3H), 0.54 (d, J = 13.4 Hz, 1H). |
| 11 | 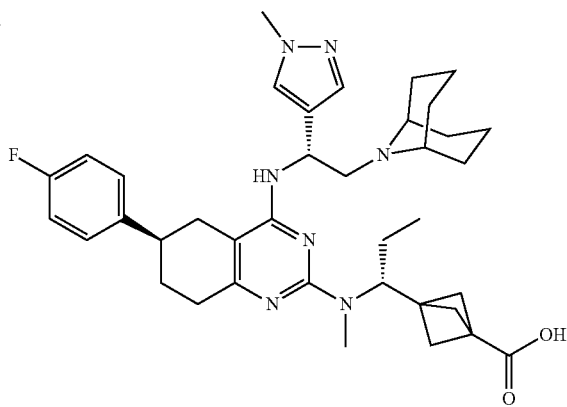 [SMILES: CC[C@@H](N(C)c1nc2c(c(N[C@@H](CN3C4CCCC3CCC4)c3cnn(C)c3)n1)C[C@H](c1ccc(F)cc1)CC2)C12CC(C(=O)O)(C1)C2] | LCMS m/z [M + H]⁺ = 656.4, ¹H NMR (400 MHz, Methanol-d4) δ 7.54 (s, 1H), 7.44 (s, 1H), 7.38-7.29 (m, 2H), 7.05 (t, J = 8.8 Hz, 2H), 5.41 (s, 1H), 4.73 (s, 1H), 3.84 (s, 3H), 2.92 (m, 6H), 2.83-2.68 (m, 3H), 2.47-2.37 (m, 1H), 2.15-1.42 (m, 24H), 0.81 (t, J = 7.4 Hz, 3H). |
| 14 | 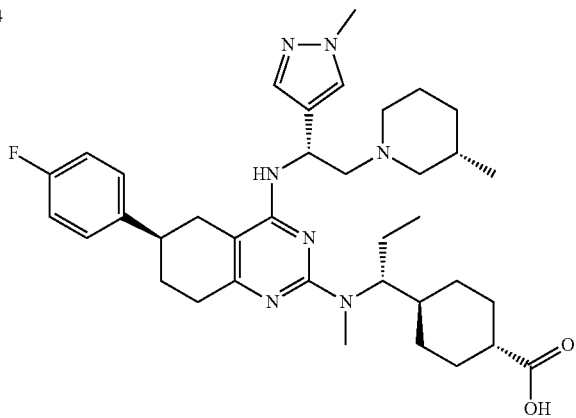 | LCMS m/z [M + H]⁺ = 646.4, ¹H NMR (400 MHz, Methanol-d4) δ 7.47 (s, 1H), 7.42-7.27 (m, 3H), 7.11-6.98 (m, 2H), 5.48 (s, 1H), 4.52 (s, 1H), 3.84 (s, 3H), 3.05-2.78 (m, 7H), 2.73 (dd, J = 10.4, 5.0 Hz, 3H), 2.63 (dd, J = 12.7, 5.1 Hz, 1H), 2.37 (t, J = 13.2 Hz, 1H), 2.12-1.20 (m, 18H), 1.03-0.81 (m, 5H), 0.76 (t, J = 7.2 Hz, 4H) |
| 77 | 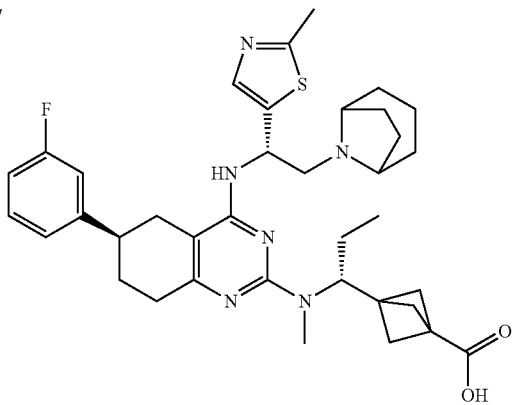 | LCMS m/z [M + H]⁺ = 659.0, ¹H NMR (400 MHz, Methanol-d4) δ 7.44 (s, 1H), 7.33 (td, J = 7.9, 5.9 Hz, 1H), 7.16 (d, J = 7.8 Hz, 1H), 7.09 (dt, J = 10.3, 2.2 Hz, 1H), 6.93 (td, J = 8.4, 2.5 Hz, 1H), 5.47 (s, 1H), 4.74 (s, 1H), 3.23 (d, J = 15.9 Hz, 2H), 3.01 (s, 1H), 2.85 (d, J = 15.7 Hz, 5H), 2.73 (q, J = 5.7, 5.1 Hz, 3H), 2.62 (s, 3H), 2.43 (dd, J = 15.4, 10.9 Hz, 1H), 2.11 (d, J = 13.2 Hz, 1H), 1.96 (s, 3H), 1.87-1.19 (m, 16H), 0.79 (t, J = 7.2 Hz, 3H). |

| 81 | 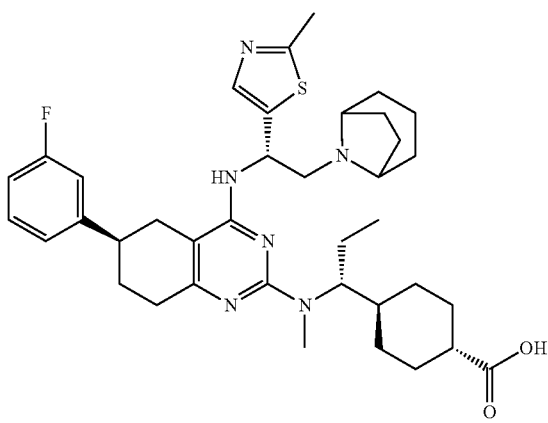 [SMILES: CC[C@H]([C@H]1CC[C@H](C(=O)O)CC1)N(C)c1nc2c(c(N[C@@H](CN3C4CCCC3CC4)c3cnc(C)s3)n1)C[C@H](c1cccc(F)c1)CC2] | LCMS m/z [M + H]+ = 675.3, 1H NMR (400 MHz, MeOD) δ 7.42 (s, 1H), 7.34 (td, J = 8.0, 6.0 Hz, 1H), 7.17 (d, J = 7.7 Hz, 1H), 7.11 (d, J = 10.5 Hz, 1H), 6.95 (td, J = 8.5, 2.6 Hz, 1H), 5.41 (s, 1H), 4.40 (s, 1H), 3.08-2.34 (m, 16H), 2.21-0.38 (m, 26H). |
|---|---|---|
| 53 | 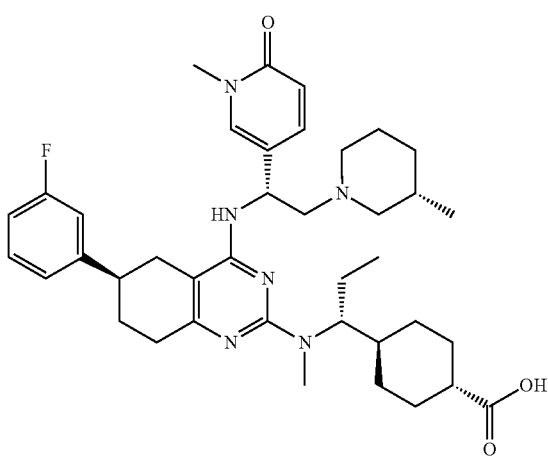 [SMILES: CC[C@H]([C@H]1CC[C@H](C(=O)O)CC1)N(C)c1nc2c(c(N[C@@H](CN3CCC[C@H](C)C3)c3ccc(=O)n(C)c3)n1)C[C@H](c1cccc(F)c1)CC2] | LCMS m/z [M + H]+ = 673.4, 1H NMR (400 MHz, MeOD) δ 7.48 (d, J = 9.9 Hz, 2H), 7.25 (td, J = 7.9, 5.9 Hz, 1H), 7.08 (d, J = 7.8 Hz, 1H), 7.02 (dt, J = 10.3, 2.2 Hz, 1H), 6.87 (td, J = 8.5, 2.6 Hz, 1H), 6.46 (d, J = 9.1 Hz, 1H), 5.13-4.88 (m, 1H), 4.48-4.12 (m, 1H), 3.45 (s, 3H), 3.01-2.60 (m, 11H), 2.59-2.29 (m, 2H), 2.18-0.99 (m, 18H), 1.02-0.51 (m, 9H), 0.34 (d, J = 13.5 Hz, 1H). |
| 88 | 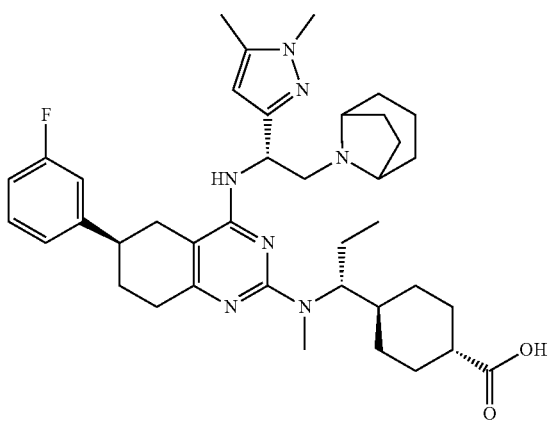 [SMILES: CC[C@H]([C@H]1CC[C@H](C(=O)O)CC1)N(C)c1nc2c(c(N[C@@H](CN3C4CCCC3CC4)c3cc(C)n(C)n3)n1)C[C@H](c1cccc(F)c1)CC2] | LCMS m/z [M + H]+ = 672.5, 1H NMR (400 MHz, MeOD) δ 7.24 (td, J = 7.9, 5.9 Hz, 1H), 7.08 (d, J = 7.8 Hz, 1H), 7.01 (dt, J = 10.6, 2.1 Hz, 1H), 6.85 (td, J = 8.5, 2.6 Hz, 1H), 5.87 (s, 1H), 5.38 (s, 1H), 4.45-4.18 (m, 1H), 3.78-3.42 (m, 5H), 3.16-3.05 (m, 1H), 3.01-2.86 (m, 1H), 2.85-2.54 (m, 6H), 2.49-2.28 (m, 1H), 2.24-1.09 (m, 26H), 0.98 (t, J = 12.4 Hz, 1H), 0.88-0.32 (m, 4H). |

| | | |
|---|---|---|
| 105 | 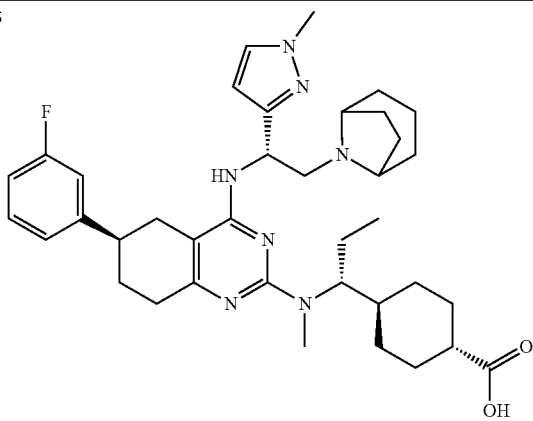 | LCMS m/z [M + H]⁺ = 658.6, ¹H NMR (400 MHz, MeOD) δ 7.48 (s, 1H), 7.25 (q, J = 7.4 Hz, 1H), 7.06 (dd, J = 25.3, 9.0 Hz, 2H), 6.94-6.80 (m, 1H), 6.06 (s, 1H), 5.43 (s, 1H), 4.45-4.15 (m, 1H), 3.77 (s, 3H), 3.67-3.41 (m, 1H), 3.01-2.87 (m, 1H), 2.85-2.61 (m, 6H), 2.44 (t, J = 13.5 Hz, 1H), 2.24-1.02 (m, 25H), 0.78 (d, J = 13.4 Hz, 1H), 0.66 (t, J = 7.3 Hz, 3H), 0.41 (d, J = 13.7 Hz, 1H). |
| 111 | 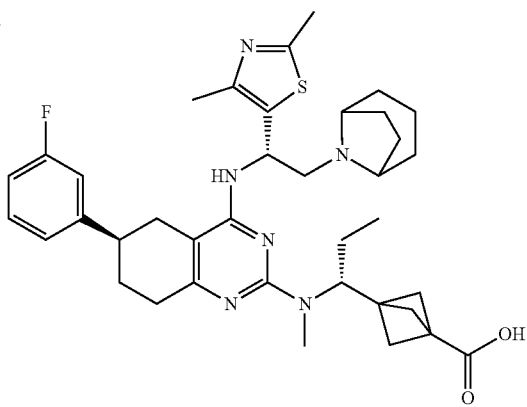 [SMILES: CC[C@@H](N(C)c1nc2c(c(N[C@@H](CN3C4CCCC3CC4)c3sc(C)nc3C)n1)C[C@H](c1cccc(F)c1)CC2)C12CC(C(=O)O)(C1)C2] | LCMS m/z [M + H]⁺ = 673.4, ¹H NMR (400 MHz, MeOD) δ 7.25 (td, J = 8.0, 6.1 Hz, 1H), 7.07 (d, J = 7.7 Hz, 1H), 7.01 (dt, J = 10.6, 2.1 Hz, 1H), 6.95-6.79 (m, 1H), 5.26 (s, 1H), 4.63 (s, 1H), 3.02-2.88 (m, 1H), 2.89-2.57 (m, 9H), 2.49 (s, 3H), 2.44-2.22 (m, 4H), 2.18-1.10 (m, 21H), 0.75 (q, J = 6.3 Hz, 3H). |
| 113 | 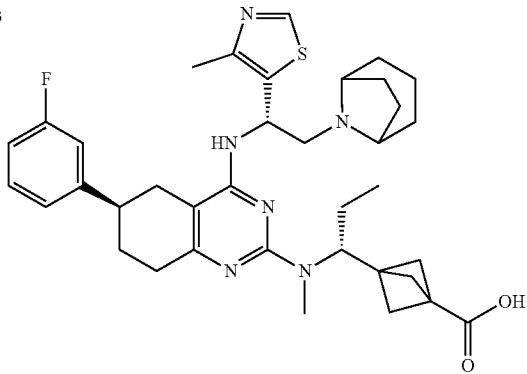 | LCMS m/z [M + H]⁺ = 659.5, ¹H NMR (400 MHz, MeOD) δ 8.68 (s, 1H), 7.26 (td, J = 7.9, 6.0 Hz, 1H), 7.07 (s, 1H), 7.02 (dt, J = 10.3, 2.0 Hz, 1H), 6.87 (td, J = 8.6, 2.6 Hz, 1H), 5.57-5.28 (m, 1H), 4.66-4.40 (m, 1H), 3.03-2.92 (m, 1H), 2.92-2.76 (m, 5H), 2.77-2.59 (m, 3H), 2.49-2.35 (m, 4H), 2.15-1.27 (m, 22H), 0.55-0.25 (m, 3H). |
| 148 | 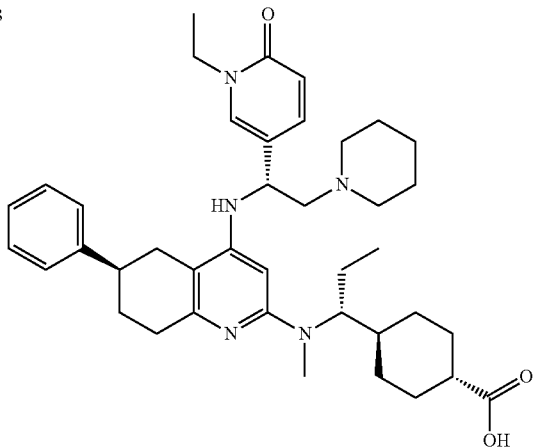 | LCMS m/z [M + H]⁺ = 655.4, ¹H NMR (400 MHz, MeOD) δ 7.59-7.38 (m, 2H), 7.32-7.17 (m, 4H), 7.19-7.01 (m, 1H), 6.42 (d, J = 9.3 Hz, 1H), 4.94-4.82 (m, 1H), 4.25 (t, J = 9.0 Hz, 1H), 3.90 (ddd, J = 45.2, 13.3, 6.8 Hz, 2H), 2.90 (ddt, J = 8.2, 5.4, 2.9 Hz, 1H), 2.78-2.53 (m, 7H), 2.40 (ddt, J = 35.1, 14.8, 7.7 Hz, 6H), 2.12-1.68 (m, 6H), 1.63-1.14 (m, 15H), 1.08-0.75 (m, 2H), 0.45-0.13 (m, 3H). |

| | | |
|---|---|---|
| 41 | 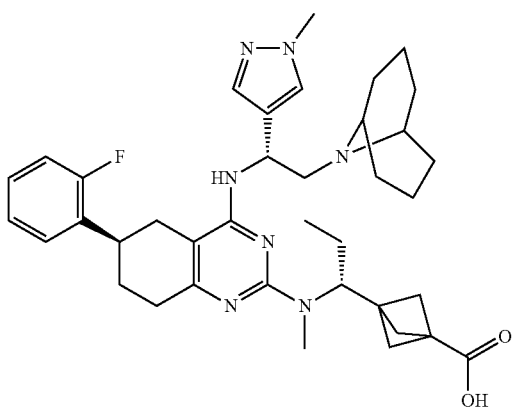 [SMILES: CC[C@@H](N(C)c1nc2c(c(N[C@@H](CN3C4CCCC3CCC4)c3cnn(C)c3)n1)C[C@H](c1ccccc1F)CC2)C12CC(C(=O)O)(C1)C2] | LCMS m/z [M + H]⁺ = 656.5, ¹H NMR (400 MHz, MeOD) δ 7.39 (s, 1H), 7.37-7.24 (m, 2H), 7.21-7.10 (m, 1H), 7.10-7.02 (m, 1H), 6.97 (dd, J = 10.8, 8.0 Hz, 1H), 5.10 (s, 1H), 4.65 (s, 2H), 3.73 (s, 3H), 3.13-2.95 (m, 1H), 2.96-2.50 (m, 9H), 2.31 (dd, J = 15.2, 11.0 Hz, 1H), 2.05-1.26 (m, 22H), 0.71 (t, J = 7.3 Hz, 3H). |
| 92 | 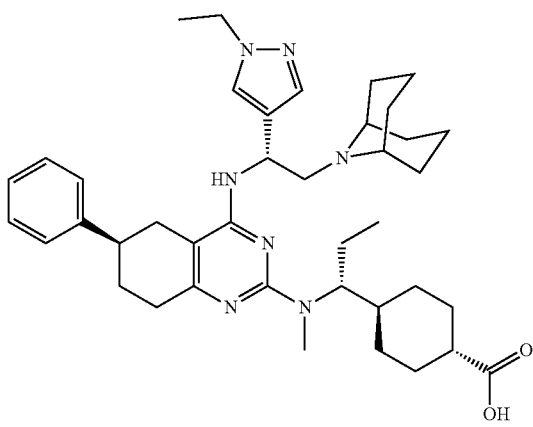 [SMILES: CC[C@H]([C@H]1CC[C@H](C(=O)O)CC1)N(C)c1nc2c(c(N[C@@H](CN3C4CCCC3CCC4)c3cnn(CC)c3)n1)C[C@H](c1ccccc1)CC2] | LCMS m/z [M + H]⁺ = 668.7, ¹H NMR (400 MHz, DMSO) δ 7.51 (s, 1H), 7.42-7.31 (m, 5H), 7.26-7.16 (m, 1H), 6.18-6.08 (m, 1H), 5.11-4.96 (m, 1H), 4.49-4.30 (m, 1H), 4.04 (q, J = 7.2 Hz, 2H), 2.96-2.80 (m, 3H), 2.80-2.58 (m, 7H), 2.39-2.23 (m, 1H), 2.01-1.58 (m, 13H), 1.56-1.45 (m, 2H), 1.45-1.06 (m, 14H), 0.89-0.78 (m, 1H), 0.65 (t, J = 7.3 Hz, 4H). |
| 138 | 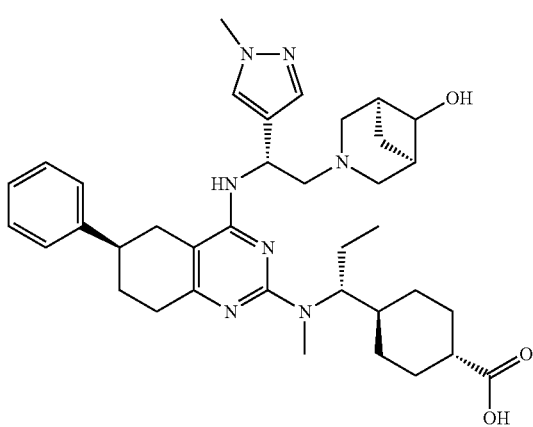 [SMILES: CC[C@H]([C@H]1CC[C@H](C(=O)O)CC1)N(C)c1nc2c(c(N[C@@H](CN3C[C@H]4C[C@@H](C3)C4O)c3cnn(C)c3)n1)C[C@H](c1ccccc1)CC2] | LCMS m/z [M + H]⁺ = 642.8, ¹H NMR (400 MHz, DMSO) δ 7.47 (s, 1H), 7.39-7.28 (m, 5H), 7.29-7.15 (m, 1H), 6.20 (d, J = 7.7 Hz, 1H), 5.40-5.26 (m, 1H), 4.61-4.42 (m, 1H), 3.88-3.71 (m, 4H), 3.07-2.94 (m, 2H), 2.93-2.82 (m, 2H), 2.80-2.70 (m, 5H), 2.67-2.55 (m, 3H), 2.37-2.19 (m, 3H), 2.05-1.56 (m, 8H), 1.42-0.97 (m, 8H), 0.92-0.79 (m, 1H), 0.74-0.57 (m, 4H). |

| | | |
|---|---|---|
| 169 | 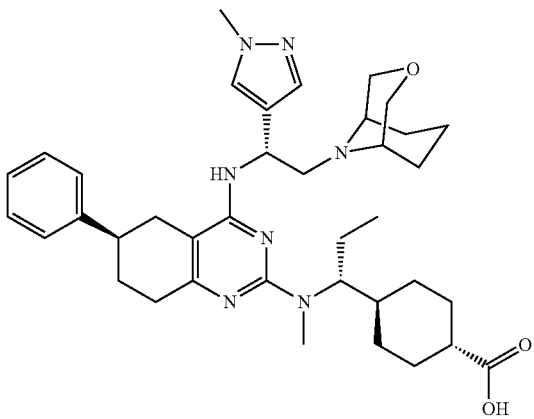 [SMILES: CC[C@H]([C@H]1CC[C@H](C(=O)O)CC1)N(C)c1nc2c(c(N[C@@H](CN3C4CCCC3COC4)c3cnn(C)c3)n1)C[C@H](c1ccccc1)CC2] | LCMS m/z [M + H]⁺ = 656.3, ¹H NMR (400 MHz, DMSO) δ 7.46 (s, 1H), 7.39-7.28 (m, 5H), 7.26-7.18 (m, 1H), 6.17-6.04 (m, 1H), 5.12-4.97 (m, 1H), 4.47-4.32 (m, 1H), 3.74 (s, 3H), 3.71-3.57 (m, 3H), 2.99-2.84 (m, 4H), 2.74-2.57 (m, 5H), 2.38-2.20 (m, 3H), 1.98-1.55 (m, 11H), 1.52-0.95 (m, 9H), 0.91-0.70 (m, 1H), 0.63 (t, J = 7.1 Hz, 3H). |
| 1 | 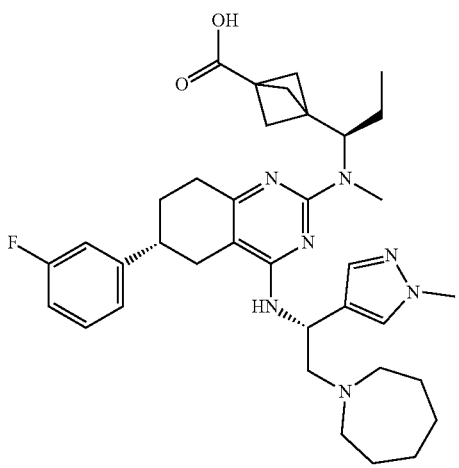 [SMILES: CC[C@@H](N(C)c1nc2c(c(N[C@@H](CN3CCCCCC3)c3cnn(C)c3)n1)C[C@H](c1cccc(F)c1)CC2)C12CC(C(=O)O)(C1)C2] | LCMS m/z [M + H]⁺ = 630.3, ¹H NMR (400 MHz, DMSO-d6) δ 7.50 (s, 1H), 7.41-7.29 (m, 2H), 7.20 (d, J = 7.8 Hz, 2H), 7.09-6.98 (m, 1H), 6.16 (d, J = 7.4 Hz, 1H), 5.26 (br s, 1H), 4.82 (br s, 1H), 3.75 (s, 3H), 2.97-2.91 (m, 1H), 2.86-2.82 (m, 1H), 2.80 (s, 3H), 2.75-2.70 (m, 1H), 2.68-2.63 (m, 4H), 2.59 (m, 1H), 2.53 (m, 1H), 2.31-2.23 (m, 1H), 1.95-1.86 (m, 2H), 1.81-1.67 (m, 6H), 1.48 (br s, 10H), 0.73 (t, J = 7.3 Hz, 3H). |
| 4 | 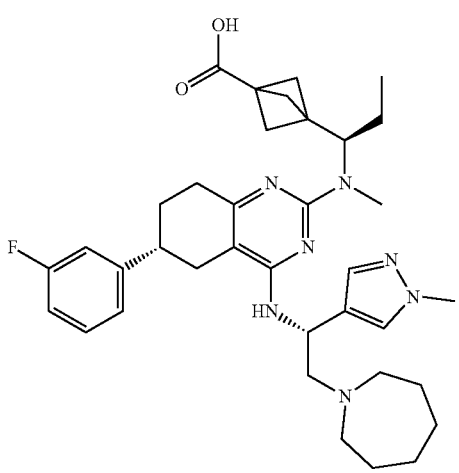 [SMILES: CC[C@@H](N(C)c1nc2c(c(N[C@@H](CN3CCCCCC3)c3cnn(C)c3)n1)C[C@H](c1cccc(F)c1)CC2)C12CC(C(=O)O)(C1)C2] | LCMS m/z [M + H]⁺ = 630.3, ¹H NMR (400 MHz, DMSO-d6) δ 7.59-7.44 (m, 1H), 7.42-7.27 (m, 2H), 7.23-7.14 (m, 2H), 7.08-7.01 (m, 1H), 6.18 (br s, 1H), 5.22 (br s, 1H), 4.76 (br s, 1H), 3.75 (s, 3H), 2.96-2.92 (m, 1H), 2.85-2.82 (m, 1H), 2.79 (s, 3H), 2.67-2.64 (m, 4H), 2.59 (m, 1H), 2.53 (m, 3H), 2.26 (br dd, J = 11.5, 14.9 Hz, 1H), 1.99-1.90 (br s, 2H), 1.84-1.77 (m, 6H), 1.48 (br s, 10H), 0.74-0.60 (m, 3H). |

| | | |
|---|---|---|
| 7 | 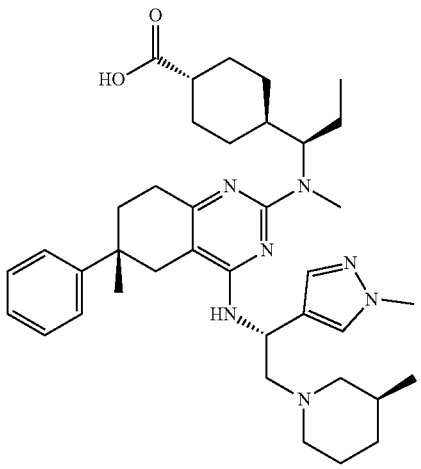 [SMILES: CC[C@H]([C@H]1CC[C@H](C(=O)O)CC1)N(C)c1nc2c(c(N[C@@H](CN3CCC[C@H](C)C3)c3cnn(C)c3)n1)C[C@](C)(c1ccccc1)CC2] | LCMS m/z [M + H]⁺ = 642.6, ¹H NMR (400 MHz, DMSO-d6) δ 7.51 (s, 1H), 7.44-7.37 (m, 2H), 7.37-7.27 (m, 3H), 7.22-7.13 (m, 1H), 6.28 (br d, J = 7.5 Hz, 1H), 5.58-5.24 (m, 1H), 4.52-4.38 (m, 1H), 3.79 (s, 3H), 2.89-2.70 (m, 4H), 2.69 (br s, 3H), 2.62-2.54 (m, 1H), 2.41-2.32 (m, 2H), 2.22-2.08 (m, 2H), 2.03-1.78 (m, 6H), 1.76-1.55 (m, 6H), 1.45-1.24 (m, 8H), 1.23-1.02 (m, 2H), 0.90-0.80 (m, 5H), 0.74-0.53 (m, 4H) |
| 8 | 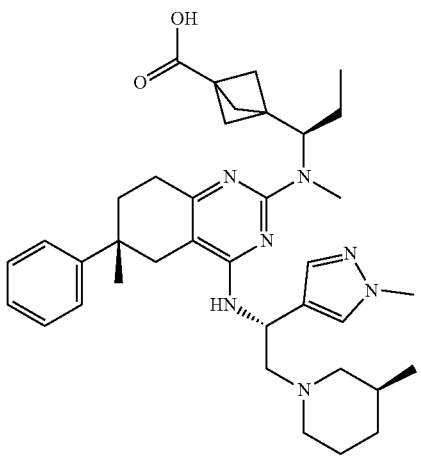 [SMILES: CC[C@@H](N(C)c1nc2c(c(N[C@@H](CN3CCC[C@H](C)C3)c3cnn(C)c3)n1)C[C@](C)(c1ccccc1)CC2)C12CC(C(=O)O)(C1)C2] | LCMS m/z [M + H]⁺ = 626.6, ¹H NMR (400 MHz, DMSO-d6) δ 7.55 (s, 1H), 7.41-7.33 (m, 3H), 7.29 (br t, J = 7.6 Hz, 2H), 7.21-7.12 (m, 1H), 6.32 (br d, J = 7.6 Hz, 1H), 5.61-5.29 (m, 1H), 4.77 (br s, 1H), 3.78 (s, 3H), 2.92-2.64 (m, 7H), 2.61-2.54 (m, 1H), 2.44-2.33 (m, 2H), 2.23-2.02 (m, 2H), 2.00-1.81 (m, 2H), 1.80-1.50 (m, 10H), 1.48-1.36 (m, 3H), 1.26 (s, 3H), 0.89-0.62 (m, 7H). |
| 12 | 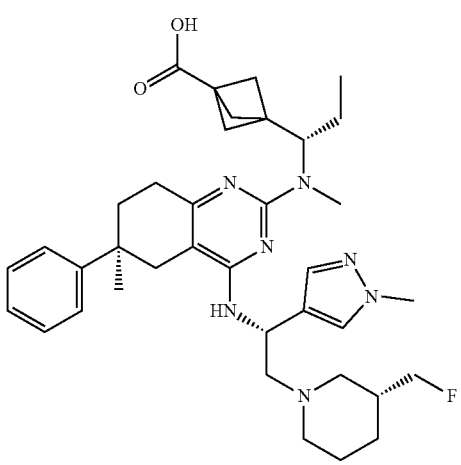 [SMILES: CC[C@H](N(C)c1nc2c(c(N[C@@H](CN3CCC[C@@H](CF)C3)c3cnn(C)c3)n1)C[C@@](C)(c1ccccc1)CC2)C12CC(C(=O)O)(C1)C2] | LCMS m/z [M + H]⁺ = 644.6, ¹H NMR (400 MHz, DMSO-d6) δ 7.56 (br s, 1H), 7.42-7.34 (m, 3H), 7.33-7.27 (m, 2H), 7.21-7.13 (m, 1H), 6.31 (br d, J = 7.3 Hz, 1H), 5.66-5.23 (m, 1H), 4.76 (br s, 1H), 4.46-4.35 (m, 1H), 4.34-4.22 (m, 1H), 4.21-4.12 (m, 1H), 3.78 (s, 3H), 2.93 (br d, J = 8.9 Hz, 1H), 2.84-2.66 (m, 6H), 2.60 (br dd, J = 7.1, 12.3 Hz, 2H), 2.45-2.31 (m, 2H), 2.27-2.17 (m, 1H), 2.16-2.03 (m, 2H), 2.00-1.83 (m, 3H), 1.81-1.64 (m, 5H), 1.59 (br d, J = 10.0 Hz, 2H), 1.52-1.37 (m, 3H), 1.33-1.21 (m, 3H), 1.09-0.96 (m, 1H), 0.72 (br t, J = 6.6 Hz, 3H). |

| | | |
|---|---|---|
| 13 | 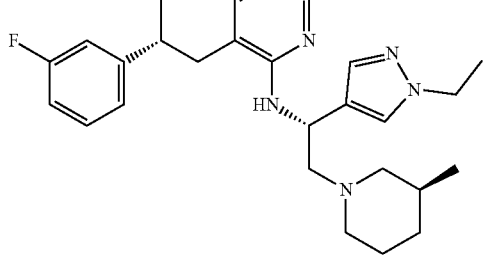 | LCMS m/z [M + H]⁺ = 644.6. $^1$H NMR (400 MHz, DMSO-d6) δ 12.50-12.06 (m, 1H), 7.76-7.57 (m, 1H), 7.47-7.33 (m, 2H), 7.31-7.17 (m, 2H), 7.13-7.00 (m, 1H), 5.03-4.68 (m, 1H), 4.07 (q, J = 7.3 Hz, 2H), 3.84-3.34 (m, 6H), 3.20-2.61 (m, 8H), 2.59-2.52 (m, 3H), 2.33-2.22 (m, 1H), 2.01-1.47 (m, 13H), 1.32 (t, J = 7.3 Hz, 3H), 0.93-0.65 m, 6H). |
| 16 | 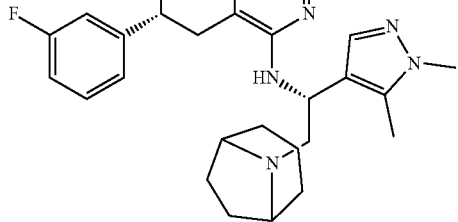 | LCMS m/z [M + H]⁺ = 672.6, $^1$H NMR (400 MHz, DMSO-d6) δ 7.40-7.32 (m, 1H), 7.28 (s, 1H), 7.18 (br d, J = 7.8 Hz, 2H), 7.07-6.98 (m, 1H), 6.11 (br d, J = 6.1 Hz, 1H), 5.31-4.97 (m, 1H), 4.51-4.42 (m, 1H), 3.65 (br s, 3H), 3.18 (br d, J = 3.1 Hz, 1H), 3.06 (br s, 1H), 2.95-2.89 (m, 2H), 2.72 (s, 3H), 2.61 (br dd, J = 3.3, 14.7 Hz, 5H), 2.34-2.22 (m, 2H), 2.19 (s, 3H), 1.99-1.87 (m, 4H), 1.85-1.75 (m, 4H), 1.72-1.53 (m, 3H), 1.51-1.44 (m, 4H), 1.40-1.20 (m, 8H), 1.16-1.10 (m, 1H), 0.69 (br t, J = 7.0 Hz, 3H). |
| 18 | 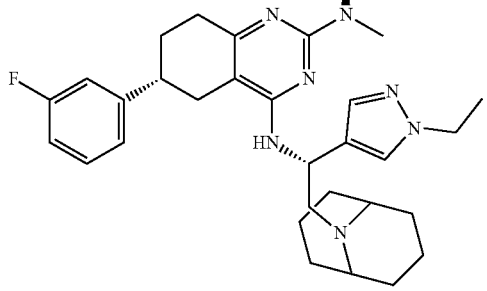 | LCMS m/z [M + H]⁺ = 686.7, $^1$H NMR (400 MHz, DMSO-d6) δ 7.50 (br s, 1H), 7.41-7.29 (m, 2H), 7.18 (br d, J = 8.2 Hz, 2H), 7.04 (br t, J = 8.1 Hz, 1H), 6.23-6.02 (m, 1H), 5.29-4.92 (m, 1H), 4.57-4.37 (m, 1H), 4.03 (q, J = 7.0 Hz, 2H), 3.01-2.81 (m, 4H), 2.80-2.55 (m, 8H), 2.36-2.26 (m, 1H), 2.07-1.73 (m, 12H), 1.73-1.48 (m, 4H), 1.44-1.21 (m, 11H), 1.15-1.03 (m, 1H), 0.83 (br d, J = 10.9 Hz, 1H), 0.74-0.48 (m, 4H). |

| | | |
|---|---|---|
| 21 | 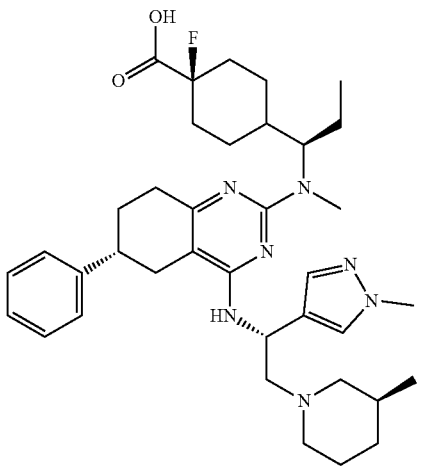 | LCMS m/z [M + H]⁺ = 646.6, ¹H NMR (400 MHz, DMSO-d6) δ 7.47 (s, 1H), 7.39-7.28 (m, 5H), 7.26-7.17 (m, 1H), 6.30-6.12 (m, 1H), 5.59-5.38 (m, 1H), 4.59 (br t, J = 9.2 Hz, 1H), 3.74 (s, 3H), 2.95-2.59 (m, 11H), 2.26-2.16 (m, 1H), 1.98-1.84 (m, 4H), 1.84-1.58 (m, 7H), 1.57-1.30 (m, 6H), 1.26-1.02 (m, 2H), 0.80 (br d, J = 6.1 Hz, 4H), 0.70 (br t, J = 6.0 Hz, 3H). |
| 25 | 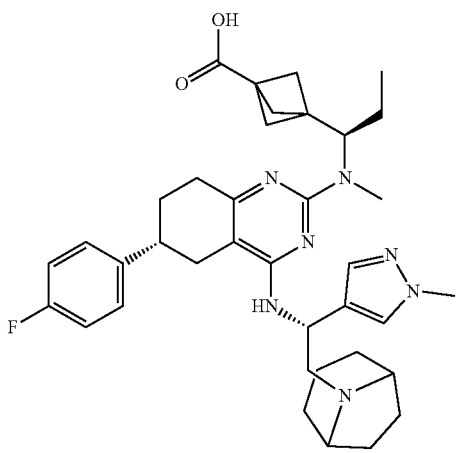 [SMILES: CC[C@@H](N(C)c1nc2c(c(N[C@@H](CN3C4CCCC3CC4)c3cnn(C)c3)n1)C[C@H](c1ccc(F)cc1)CC2)C12CC(C(=O)O)(C1)C2] | LCMS m/z [M + H]⁺ = 642.6, ¹H NMR (400 MHz, DMSO-d6) δ 7.52 (br s, 1H), 7.42-7.26 (m, 3H), 7.15 (t, J = 8.9 Hz, 2H), 6.31-6.07 (m, 1H), 5.34-5.00 (m, 1H), 4.90-4.68 (m, 1H), 3.74 (s, 3H), 3.18 (br s, 2H), 3.08 (br s, 1H), 2.94-2.87 (m, 1H), 2.79 (s, 3H), 2.64-2.55 (m, 4H), 2.31-2.21 (m, 1H), 1.93-1.63 (m, 10H), 1.58-1.39 (m, 7H), 1.35-1.29 (m, 1H), 1.23 (br s, 2H), 0.72 (br t, J = 7.3 Hz, 3H). |
| 27 | 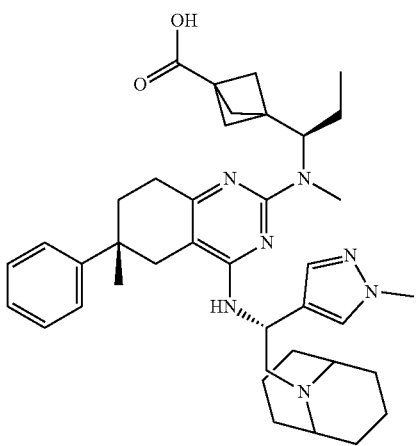 [SMILES: CC[C@@H](N(C)c1nc2c(c(N[C@@H](CN3C4CCCC3CCC4)c3cnn(C)c3)n1)C[C@](C)(c1ccccc1)CC2)C12CC(C(=O)O)(C1)C2] | LCMS m/z [M + H]⁺ = 652.6, ¹H NMR (400 MHz, DMSO-d6) δ 7.62-7.51 (m, 1H), 7.45-7.33 (m, 3H), 7.33-7.24 (m, 2H), 7.22-7.14 (m, 1H), 6.35-6.15 (m, 1H), 5.36-4.99 (m, 1H), 4.68 (br d, J = 7.8 Hz, 1H), 3.77 (s, 3H), 2.92 (br d, J = 6.5 Hz, 2H), 2.80-2.71 (m, 6H), 2.45-2.39 (m, 2H), 2.26-2.16 (m, 1H), 2.11-2.04 (m, 1H), 1.97-1.80 (m, 8H), 1.77-1.59 (m, 6H), 1.53 (br s, 2H), 1.48-1.37 (m, 6H), 1.26 (s, 3H), 0.76-0.64 (m, 3H). |

| | | |
|---|---|---|
| 28 | 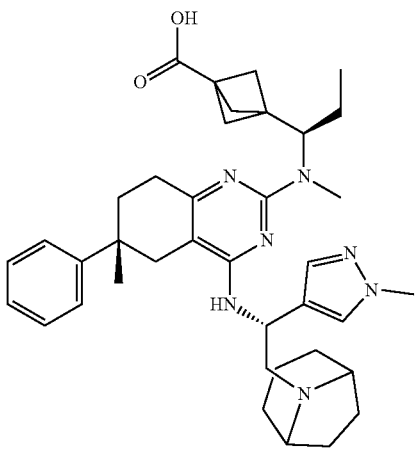 [SMILES: CC[C@@H](N(C)c1nc2c(c(N[C@@H](CN3C4CCCC3CC4)c3cnn(C)c3)n1)C[C@](C)(c1ccccc1)CC2)C12CC(C(=O)O)(C1)C2] | LCMS m/z [M + H]+ = 638.6, 1H NMR (400 MHz, DMSO-d6) δ 7.56 (br s, 1H), 7.45-7.35 (m, 3H), 7.31 (br t, J = 7.6 Hz, 2H), 7.23-7.13 (m, 1H), 6.38 (br s, 1H), 5.11 (br d, J = 3.9 Hz, 1H), 4.73 (br t, J = 6.7 Hz, 1H), 3.78 (s, 3H), 3.21 (br s, 2H), 3.12 (br s, 2H), 2.85-2.72 (m, 4H), 2.70-2.58 (m, 3H), 2.41 (br d, J = 16.0 Hz, 2H), 2.28-2.15 (m, 1H), 2.13-2.04 (m, 1H), 1.94-1.81 (m, 3H), 1.77-1.68 (m, 3H), 1.67-1.59 (m, 3H), 1.52 (br d, J = 8.4 Hz, 2H), 1.49-1.40 (m, 3H), 1.37 (br d, J = 6.7 Hz, 1H), 1.27 (s, 5H), 0.71 (br t, J = 6.6 Hz, 3H). |
| 29 | 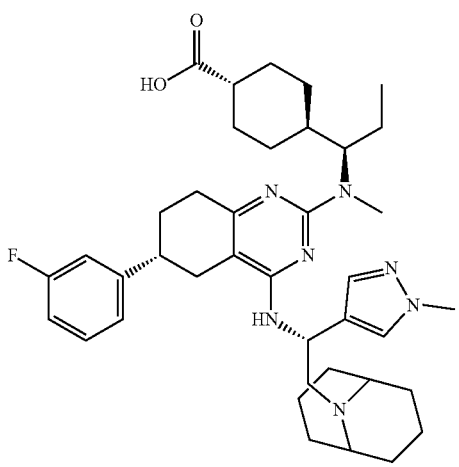 [SMILES: CC[C@H]([C@H]1CC[C@H](C(=O)O)CC1)N(C)c1nc2c(c(N[C@@H](CN3C4CCCC3CCC4)c3cnn(C)c3)n1)C[C@H](c1cccc(F)c1)CC2] | LCMS m/z [M + H]+ = 672.7, 1H NMR (400 MHz, DMSO-d6) δ 7.60-7.42 (m, 1H), 7.41-7.27 (m, 2H), 7.19 (br d, J = 7.8 Hz, 2H), 7.09-6.99 (m, 1H), 6.16 (br d, J = 6.4 Hz, 1H), 5.31-4.89 (m, 1H), 4.61-4.29 (m, 1H), 3.74 (s, 3H), 3.44 (br d, J = 7.1 Hz, 1H), 3.00-2.91 (m, 1H), 2.87 (br d, J = 6.6 Hz, 2H), 2.71 (s, 5H), 2.66-2.56 (m, 2H), 2.34-2.27 (m, 1H), 2.00-1.69 (m, 12H), 1.66-1.56 (m, 1H), 1.50 (br d, J = 5.4 Hz, 2H), 1.45-1.20 (m, 8H), 1.16-1.02 (m, 1H), 0.89-0.75 (m, 1H), 0.70-0.60 (m, 3H), 0.58-0.38 (m, 1H). |
| 31 | 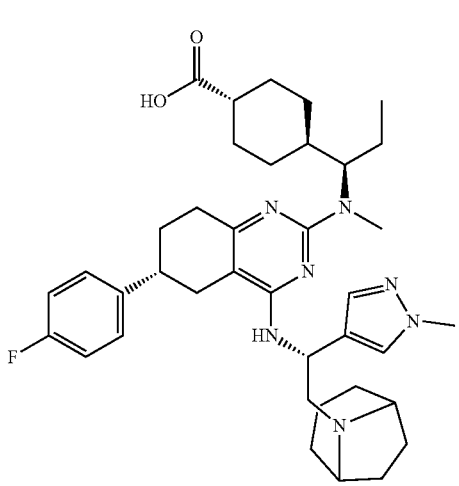 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@H](c1ccc(F)cc1)CC2] | LCMS m/z [M + H]+ = 658.6, 1H NMR (400 MHz, DMSO-d6) δ 7.57-7.43 (m, 1H), 7.42-7.30 (m, 3H), 7.15 (t, J = 8.9 Hz, 2H), 6.26-6.06 (m, 1H), 5.32-4.97 (m, 1H), 4.57-4.36 (m, 1H), 3.74 (s, 3H), 3.19-3.05 (m, 2H), 2.97-2.86 (m, 1H), 2.71 (s, 3H), 2.61-2.56 (m, 3H), 2.30-2.22 (m, 1H), 2.06-1.98 (m, 1H), 1.94-1.75 (m, 7H), 1.74-1.68 (m, 1H), 1.66-1.42 (m, 7H), 1.39-1.17 (m, 8H), 1.17-1.07 (m, 1H), 0.91-0.78 (m, 1H), 0.66 (br t, J = 7.2 Hz, 3H), 0.57-0.43 (m, 1H). |

| | | |
|---|---|---|
| 33 | 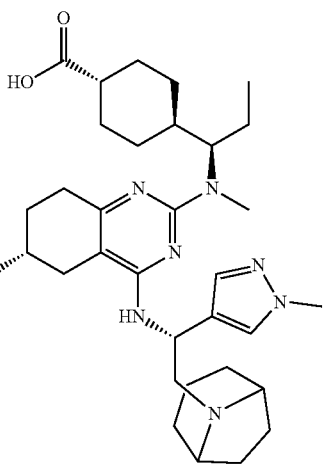 | LCMS m/z [M + H]⁺ = 658.6, ¹H NMR (400 MHz, DMSO-d6) δ 7.46 (s, 1H), 7.42-7.29 (m, 2H), 7.19 (br d, J = 8.1 Hz, 2H), 7.11-6.97 (m, 1H), 6.24 (br d, J = 6.6 Hz, 1H), 5.02 (br d, J = 6.4 Hz, 1H), 4.61-4.34 (m, 1H), 3.74 (s, 3H), 3.17-3.04 (m, 2H), 2.99-2.88 (m, 1H), 2.71 (s, 3H), 2.65-2.51 (m, 6H), 2.32-2.18 (m, 1H), 2.03-1.85 (m, 4H), 1.83-1.68 (m, 4H), 1.66-1.44 (m, 6H), 1.43-1.17 (m, 7H), 1.16-1.02 (m, 1H), 0.92-0.75 (m, 1H), 0.69-0.60 (m, 3H), 0.56-0.41 (m, 1H). |
| 34 | 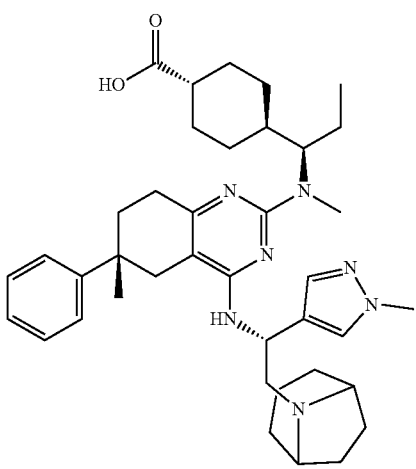 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@](C)(c1ccccc1)CC2] | LCMS m/z [M + H]⁺ = 654.6, ¹H NMR (400 MHz, DMSO-d6) δ 7.49 (s, 1H), 7.43-7.37 (m, 2H), 7.37-7.27 (m, 3H), 7.24-7.15 (m, 1H), 6.46-6.18 (m, 1H), 5.39-4.91 (m, 1H), 4.57-4.33 (m, 1H), 3.77 (s, 3H), 3.23-3.05 (m, 2H), 2.81 (br d, J = 16.0 Hz, 1H), 2.74-2.61 (m, 5H), 2.47-2.36 (m, 3H), 2.26-2.03 (m, 3H), 1.96-1.75 (m, 6H), 1.73-1.44 (m, 8H), 1.36-1.23 (m, 9H), 1.14-1.02 (m, 1H), 0.90-0.77 (m, 1H), 0.71-0.61 (m, 3H), 0.53-0.39 (m, 1H). |
| 35 | 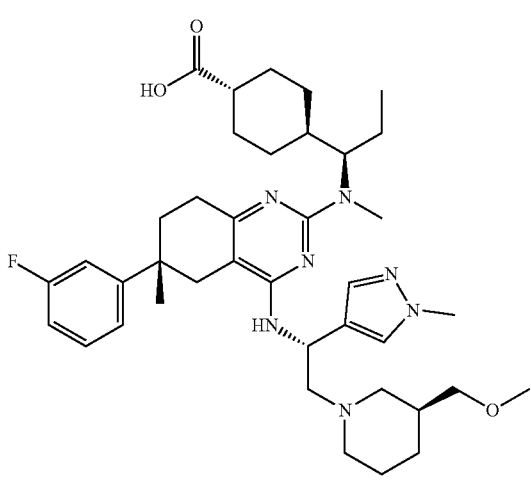 | LCMS m/z [M + H]⁺ = 676.6, ¹H NMR (400 MHz, DMSO-d6) δ 7.45 (s, 1H), 7.40-7.27 (m, 2H), 7.20 (br d, J = 7.8 Hz, 2H), 7.08-6.99 (m, 1H), 6.20-6.05 (m, 1H), 5.55-5.22 (m, 1H), 4.59-4.38 (m, 1H), 3.74 (s, 3H), 3.19-3.13 (m, 4H), 3.13-3.05 (m, 1H), 2.98-2.84 (m, 2H), 2.78-2.69 (m, 3H), 2.69-2.59 (m, 3H), 2.56 (br d, J = 4.4 Hz, 1H), 2.52 (d, J = 1.9 Hz, 2H), 2.32-2.22 (m, 1H), 2.05-1.95 (m, 2H), 1.95-1.78 (m, 5H), 1.74 (br dd, J = 9.0, 9.9 Hz, 2H), 1.66-1.48 (m, 3H), 1.47-1.20 (m, 5H), 1.19-1.05 (m, 1H), 0.99-0.81 (m, 2H), 0.68 (br t, J = 6.8 Hz, 3H), 0.62-0.49 (m, 1H). |

| | | |
|---|---|---|
| 36 | 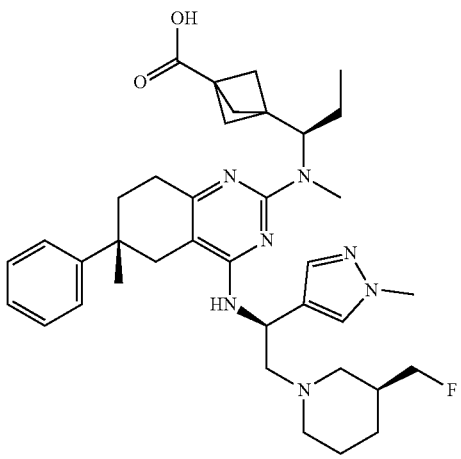 [SMILES: CC[C@@H](N(C)c1nc2c(c(N[C@H](CN3CCC[C@H](CF)C3)c3cnn(C)c3)n1)C[C@](C)(c1ccccc1)CC2)C12CC(C(=O)O)(C1)C2] | LCMS m/z [M + H]⁺ = 644.6, ¹H NMR (400 MHz, DMSO-d6) δ 7.58-7.50 (m, 1H), 7.34 (br d, J = 7.7 Hz, 3H), 7.31-7.24 (m, 2H), 7.22-7.11 (m, 1H), 6.43-6.23 (m, 1H), 5.44-5.18 (m, 1H), 4.82-4.64 (m, 1H), 4.47-4.13 (m, 2H), 3.77 (s, 3H), 3.17 (s, 1H), 2.85-2.66 (m, 6H), 2.43-2.28 (m, 3H), 2.25-1.97 (m, 5H), 1.92-1.72 (m, 7H), 1.61 (br d, J = 8.2 Hz, 2H), 1.53-1.37 (m, 3H), 1.35-1.22 (m, 3H), 1.12-1.01 (m, 1H), 0.62 (br d, J = 1.5 Hz, 3H). |
| 39 | 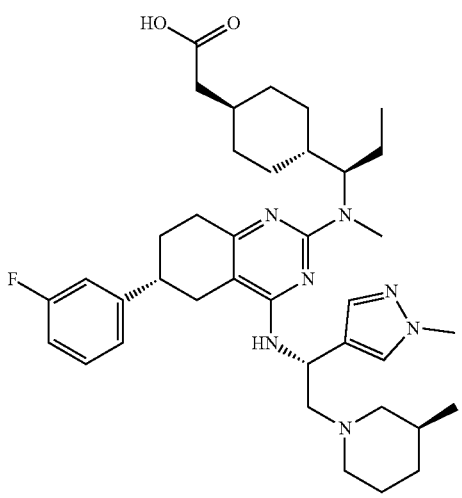 [SMILES: CC[C@H]([C@H]1CC[C@H](CC(=O)O)CC1)N(C)c1nc2c(c(N[C@@H](CN3CCC[C@H](C)C3)c3cnn(C)c3)n1)C[C@H](c1cccc(F)c1)CC2] | LCMS m/z [M + H]⁺ = 660.6, ¹H NMR (400 MHz, DMSO-d6) δ 7.54-7.44 (m, 1H), 7.40-7.33 (m, 1H), 7.30 (s, 1H), 7.19 (br d, J = 7.8 Hz, 2H), 7.08-6.99 (m, 1H), 6.22-6.05 (m, 1H), 5.55-5.25 (m, 1H), 4.59-4.44 (m, 1H), 3.75 (s, 3H), 2.99-2.88 (m, 1H), 2.81 (br d, J = 8.2 Hz, 1H), 2.72 (s, 3H), 2.66-2.58 (m, 3H), 2.57-2.54 (m, 3H), 2.29-2.19 (m, 1H), 2.04 (br d, J = 6.7 Hz, 2H), 1.97-1.84 (m, 3H), 1.82-1.70 (m, 2H), 1.68-1.57 (m, 4H), 1.56-1.46 (m, 3H), 1.43-1.21 (m, 4H), 0.90 (br t, J = 8.9 Hz, 2H), 0.85-0.74 (m, 5H), 0.68 (br t, J = 6.7 Hz, 4H). |
| 42 | 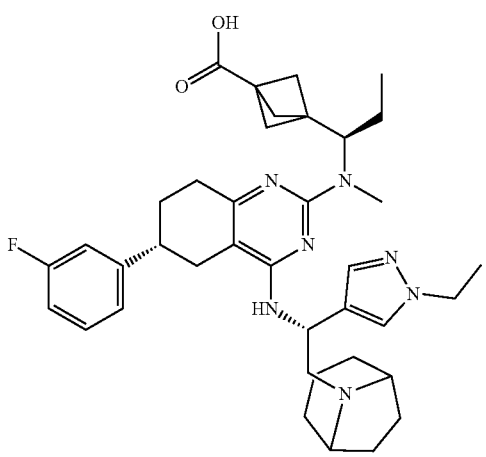 [SMILES: CC[C@@H](N(C)c1nc2c(c(N[C@@H](CN3C4CCCC3CC4)c3cnn(CC)c3)n1)C[C@H](c1cccc(F)c1)CC2)C12CC(C(=O)O)(C1)C2] | LCMS m/z [M + H]⁺ = 656.6, ¹H NMR (400 MHz, DMSO-d6) δ 7.56 (br s, 1H), 7.44-7.29 (m, 2H), 7.24-7.13 (m, 2H), 7.09-6.97 (m, 1H), 6.30-6.14 (m, 1H), 5.30-5.10 (m, 1H), 4.89-4.66 (m, 1H), 4.03 (q, J = 7.3 Hz, 2H), 3.19-3.08 (m, 3H), 2.96-2.91 (m, 1H), 2.79 (s, 3H), 2.64-2.59 (m, 3H), 2.36-2.21 (m, 2H), 1.94 (br s, 1H), 1.85-1.65 (m, 8H), 1.61-1.42 (m, 7H), 1.41-1.10 (m, 7H), 0.72 (br t, J = 7.2 Hz, 3H). |

| | | |
|---|---|---|
| 43 | 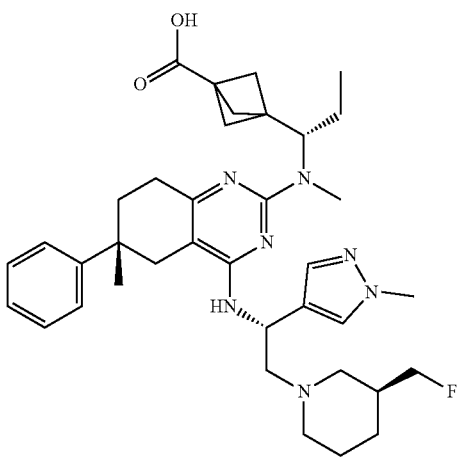 [SMILES: CC[C@H](N(C)c1nc2c(c(N[C@@H](CN3CCC[C@H](CF)C3)c3cnn(C)c3)n1)C[C@](C)(c1ccccc1)CC2)C12CC(C(=O)O)(C1)C2] | LCMS m/z [M + H]⁺ = 644.3, ¹H NMR (400 MHz, DMSO-d6) δ 7.66 (br d, J = 1.9 Hz, 1H), 7.49-7.27 (m, 5H), 7.21 (br t, J = 6.0 Hz, 1H), 6.07-5.34 (m, 1H), 4.75 (br s, 1H), 4.58-4.02 (m, 3H), 3.79 (s, 4H), 3.54 (br d, J = 9.4 Hz, 2H), 3.18-2.59 (m, 9H), 2.48-2.34 (m, 1H), 2.24-2.06 (m, 2H), 2.01-1.60 (m, 10H), 1.59-1.44 (m, 2H), 1.38-1.05 (m, 4H), 0.75 (br s, 3H). |
| 46 | 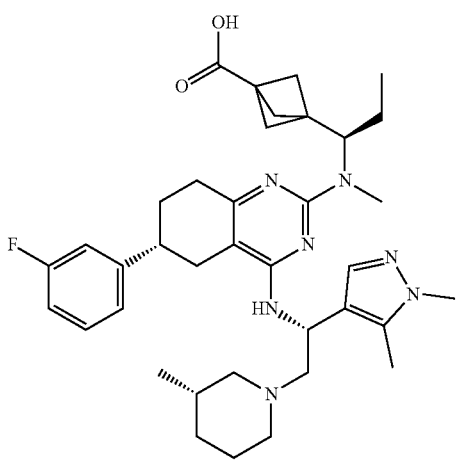 [SMILES: CC[C@@H](N(C)c1nc2c(c(N[C@@H](CN3CCC[C@H](C)C3)c3cnn(C)c3C)n1)C[C@H](c1cccc(F)c1)CC2)C12CC(C(=O)O)(C1)C2] | LCMS m/z [M + H]⁺ = 644.6, ¹H NMR (400 MHz, DMSO-d6) δ 7.43-7.27 (m, 2H), 7.19 (br d, J = 7.6 Hz, 2H), 7.08-7.01 (m, 1H), 6.57-6.03 (m, 1H), 5.87-5.18 (m, 1H), 4.99-4.70 (m, 1H), 3.66 (s, 3H), 2.98-2.77 (m, 6H), 2.65-2.57 (m, 4H), 2.27-2.12 (m, 4H), 2.02-1.72 (m, 10H), 1.70-1.35 (m, 6H), 0.96-0.64 (m, 7H). |
| 52 | 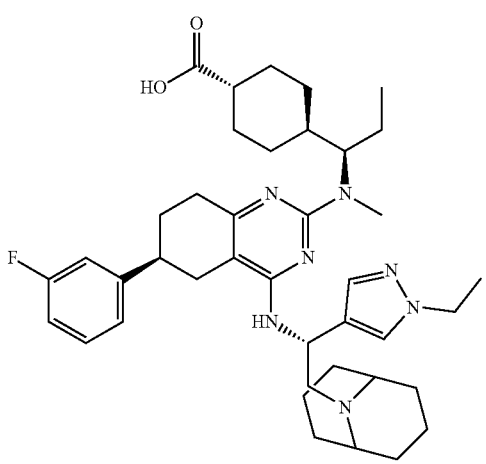 [SMILES: CC[C@H]([C@H]1CC[C@H](C(=O)O)CC1)N(C)c1nc2c(c(N[C@@H](CN3C4CCCC3CCC4)c3cnn(CC)c3)n1)C[C@@H](c1cccc(F)c1)CC2] | LCMS m/z [M + H]⁺ = 686.7, ¹H NMR (400 MHz, DMSO-d6) δ 7.62-7.50 (m, 1H), 7.41-7.32 (m, 2H), 7.23-7.15 (m, 2H), 7.08-7.00 (m, 1H), 6.20-6.04 (m, 1H), 5.28-4.96 (m, 1H), 4.58-4.36 (m, 1H), 4.03 (q, J = 7.2 Hz, 2H), 3.03-2.82 (m, 4H), 2.81-2.57 (m, 7H), 2.36-2.28 (m, 1H), 2.04-1.75 (m, 12H), 1.75-1.57 (m, 2H), 1.55-1.35 (m, 7H), 1.30 (br t, J = 7.3 Hz, 5H), 1.26-1.02 (m, 2H), 0.91-0.77 (m, 1H), 0.72-0.45 (m, 4H). |

| | | |
|---|---|---|
| 54 | 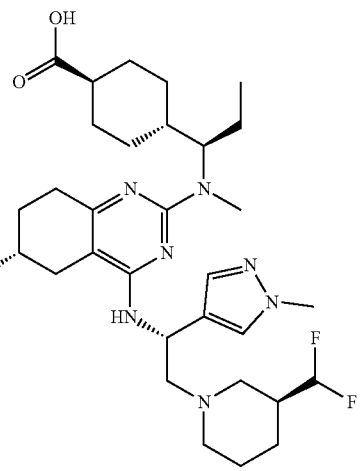 | LCMS m/z [M + H]⁺ = 682.6, ¹H NMR (400 MHz, DMSO-d6) δ 7.47 (s, 1H), 7.42-7.27 (m, 2H), 7.21 (br d, J = 7.9 Hz, 2H), 7.09-7.01 (m, 1H), 6.18 (br d, J = 7.3 Hz, 1H), 6.06-5.74 (m, 1H), 5.58-5.28 (m, 1H), 4.62-4.42 (m, 1H), 3.75 (s, 3H), 3.00-2.84 (m, 2H), 2.81-2.67 (m, 5H), 2.64-2.56 (m, 2H), 2.32-2.23 (m, 1H), 2.08-1.78 (m, 9H), 1.77-1.57 (m, 4H), 1.43-1.22 (m, 5H), 1.20-1.07 (m, 2H), 0.96-0.80 (m, 1H), 0.73-0.51 (m, 4H). |
| 62 | 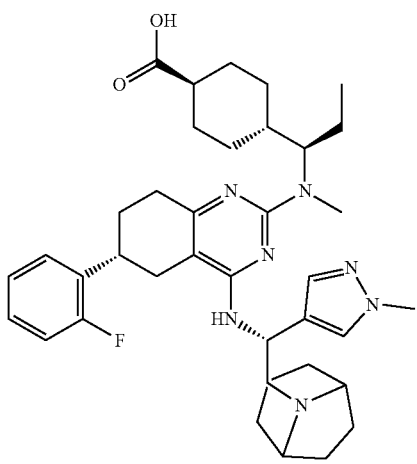 [SMILES: CC[C@H]([C@H]1CC[C@H](C(=O)O)CC1)N(C)c1nc2c(c(N[C@@H](CN3C4CCCC3CC4)c3cnn(C)c3)n1)C[C@H](c1ccccc1F)CC2] | LCMS m/z [M + H]⁺ = 658.6, ¹H NMR (400 MHz, DMSO-d6) δ 7.56-7.40 (m, 2H), 7.38-7.25 (m, 2H), 7.24-7.14 (m, 2H), 6.32-6.05 (m, 1H), 5.34-4.96 (m, 1H), 4.61-4.35 (m, 1H), 3.75 (s, 3H), 3.26-3.00 (m, 4H), 2.73 (s, 3H), 2.65-2.56 (m, 6H), 2.36-2.26 (m, 1H), 2.13-1.86 (m, 5H), 1.85-1.68 (m, 4H), 1.66-1.45 (m, 6H), 1.40-1.19 (m, 7H), 1.17-1.05 (m, 1H), 0.91-0.80 (m, 1H), 0.74-0.63(m, 3H), 0.61-0.38 (m, 1H). |
| 63 | 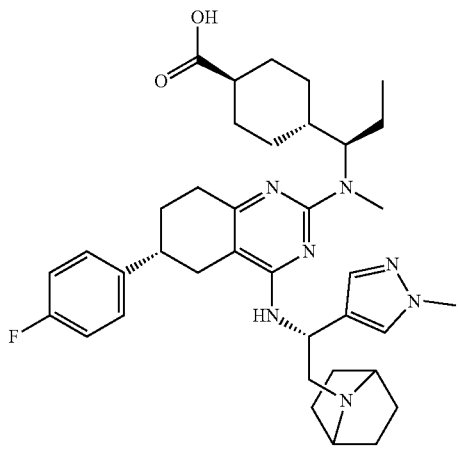 [SMILES: CC[C@H]([C@H]1CC[C@H](C(=O)O)CC1)N(C)c1nc2c(c(N[C@@H](CN3C4CCC3CC4)c3cnn(C)c3)n1)C[C@H](c1ccc(F)cc1)CC2] | LCMS m/z [M + H]⁺ = 644.4, ¹H NMR (400 MHz, DMSO-d6) δ 7.47-7.23 (m, 3H), 7.15 (br t, J = 8.7 Hz, 2H), 6.21 (br d, J = 7.3 Hz, 1H), 5.39-4.93 (m,1H), 4.67-4.34 (m, 1H), 3.74 (s, 3H), 3.24-3.13 (m, 3H), 2.98-2.86 (m, 2H), 2.81-2.64 (m, 5H), 2.63-2.57 (m, 2H), 2.34-2.18 (m, 2H), 2.05-1.97 (m, 1H), 1.94-1.80 (m, 4H), 1.75-1.67 (m, 1H), 1.58 (br d, J = 6.1 Hz, 4H), 1.40-1.26 (m, 3H), 1.19 (br d, J = 9.9 Hz, 4H), 1.14-1.07 (m, 1H), 0.95-0.77 (m, 2H), 0.67 (br t, J = 7.1 Hz, 3H), 0.57-0.42 (m, 1H). |

| 66 | 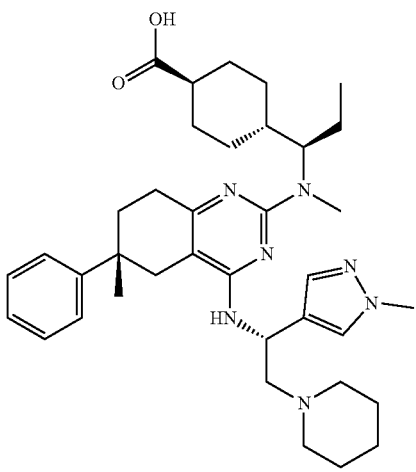 [SMILES: CC[C@H]([C@H]1CC[C@H](C(=O)O)CC1)N(C)c1nc2c(c(N[C@@H](CN3CCCCC3)c3cnn(C)c3)n1)C[C@](C)(c1ccccc1)CC2] | LCMS m/z [M + H]⁺ = 628.6, ¹H NMR (400 MHz, DMSO-d6) δ 7.48 (br s, 1H), 7.43-7.26 (m, 5H), 7.23-7.12 (m, 1H), 6.40-6.13 (m, 1H), 5.45-5.19 (m, 1H), 4.50-4.38 (m, 1H), 3.77 (s, 3H), 2.86-2.78 (m, 2H), 2.73-2.64 (m, 6H), 2.43 (br d, J = 1.7 Hz, 3H), 2.33 (br d, J = 3.5 Hz, 2H), 2.22-2.08 (m, 3H), 1.96-1.80 (m, 4H), 1.71-1.61 (m, 2H), 1.47 (br s, 4H), 1.40-1.23 (m, 9H), 0.89-0.74 (m, 2H), 0.70-0.58 (m, 3H). |
|---|---|---|
| 67 | 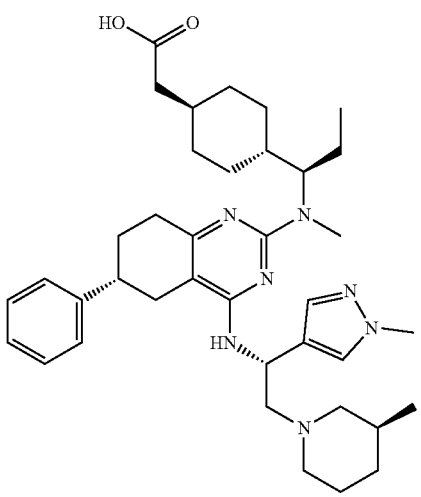 [SMILES: CC[C@H]([C@H]1CC[C@H](CC(=O)O)CC1)N(C)c1nc2c(c(N[C@@H](CN3CCC[C@H](C)C3)c3cnn(C)c3)n1)C[C@H](c1ccccc1)CC2] | LCMS m/z [M + H]⁺ = 642.6, ¹H NMR (400 MHz, DMSO-d6) δ 7.45 (s, 1H), 7.39-7.27 (m, 5H), 7.26-7.17 (m, 1H), 6.13 (br d, J = 7.2 Hz, 1H), 5.49-5.33 (m, 1H), 4.67-4.42 (m, 1H), 3.74 (s, 3H), 3.57 (s, 1H), 2.93-2.79 (m, 3H), 2.72 (br s, 3H), 2.67-2.62 (m, 2H), 2.35-2.24 (m, 2H), 2.10-2.01 (m, 3H), 1.94-1.85 (m, 3H), 1.82-1.71 (m, 2H), 1.67-1.58 (m, 3H), 1.51 (br d, J = 5.1 Hz, 3H), 1.38-1.32 (m, 3H), 1.24 (br s, 5H), 0.90 (br d, J = 9.4 Hz, 1H), 0.85 (br t, J = 6.8 Hz, 2H), 0.79 (br d, J = 6.5 Hz, 3H), 0.68 (br t, J = 6.8 Hz, 3H). |
| 68 | 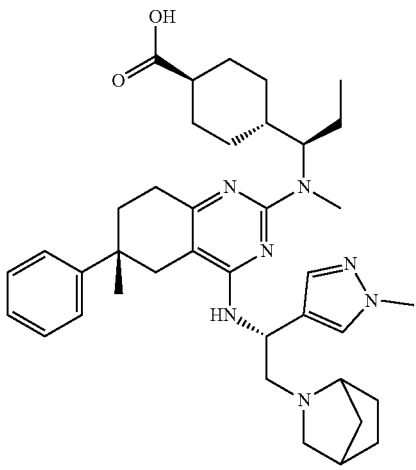 [SMILES: CC[C@H]([C@H]1CC[C@H](C(=O)O)CC1)N(C)c1nc2c(c(N[C@@H](CN3CC4CCC3C4)c3cnn(C)c3)n1)C[C@](C)(c1ccccc1)CC2] | LCMS m/z [M + H]⁺ = 640.6, ¹H NMR (400 MHz, DMSO-d6) δ 7.46 (s, 1H), 7.42-7.27 (m, 5H), 7.23-7.13 (m, 1H), 6.37-6.18 (m, 1H), 5.33-5.00 (m, 1H), 4.61-4.37 (m, 1H), 3.76 (s, 3H), 3.19 (br d, J = 9.7 Hz, 3H), 2.88-2.76 (m, 4H), 2.73-2.63 (m, 4H), 2.39-2.32 (m, 1H), 2.27 (br s, 1H), 2.23-2.03 (m, 4H), 1.91-1.75 (m, 4H), 1.71-1.46 (m, 6H), 1.39-1.23 (m, 8H), 1.19 (br d, J = 8.9 Hz, 2H), 1.12-1.02 (m, 1H), 0.90-0.78 (m, 1H), 0.71-0.59 (m, 3H). |

| | | |
|---|---|---|
| 69 | 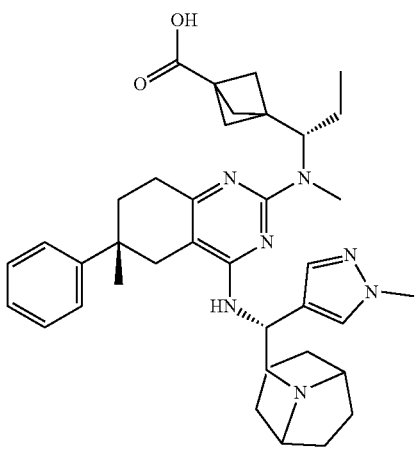 [SMILES: CC[C@H](N(C)c1nc2c(c(N[C@@H](CN3C4CCCC3CC4)c3cnn(C)c3)n1)C[C@](C)(c1ccccc1)CC2)C12CC(C(=O)O)(C1)C2] | LCMS m/z [M + H]⁺ = 638.5, ¹H NMR (400 MHz, DMSO-d6) δ 7.77-7.61 (m, 1H), 7.48-7.26 (m, 5H), 7.20 (br t, J = 7.3 Hz, 1H), 6.17-5.65 (m, 1H), 4.98-4.59 (m, 1H), 4.01-3.77 (m, 5H), 3.70-3.49 (m, 2H), 3.01-2.75 (m, 4H), 2.60 (br dd, J = 4.5, 10.0 Hz, 2H), 2.29-2.05 (m, 5H), 2.02-1.71 (m, 8H), 1.69-1.35 (m, 9H), 1.33-1.21 (m, 3H), 0.74 (br s, 3H). |
| 70 | 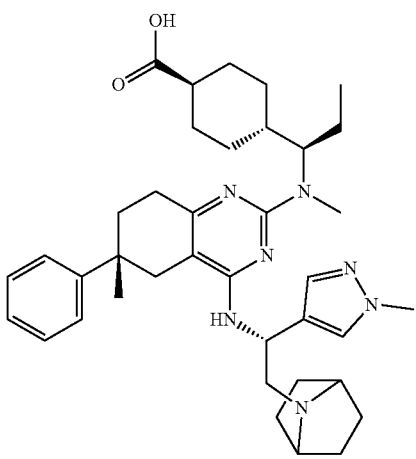 [SMILES: CC[C@H]([C@H]1CC[C@H](C(=O)O)CC1)N(C)c1nc2c(c(N[C@@H](CN3C4CCC3CC4)c3cnn(C)c3)n1)C[C@](C)(c1ccccc1)CC2] | LCMS m/z [M + H]⁺ = 640.6, ¹H NMR (400 MHz, DMSO-d6) δ 7.45 (s, 1H), 7.40 (br d, J = 7.6 Hz, 2H), 7.34-7.26 (m, 3H), 7.21-7.16 (m, 1H), 6.53-6.11 (m, 1H), 5.43-4.91 (m, 1H), 4.54-4.27 (m, 1H), 3.76 (s, 3H), 3.25-3.16 (m, 2H), 2.86-2.74 (m, 2H), 2.68-2.64 (m, 3H), 2.40-2.30 (m, 4H), 2.23-2.06 (m, 3H), 1.91-1.84 (m, 2H), 1.83-1.73 (m, 2H), 1.63 (br d, J = 2.3 Hz, 5H), 1.36-1.14 (m, 12H), 1.09-1.02 (m, 1H), 0.90-0.78 (m, 1H), 0.71-0.57 (m, 3H), 0.52-0.38 (m, 1H). |
| 78 | 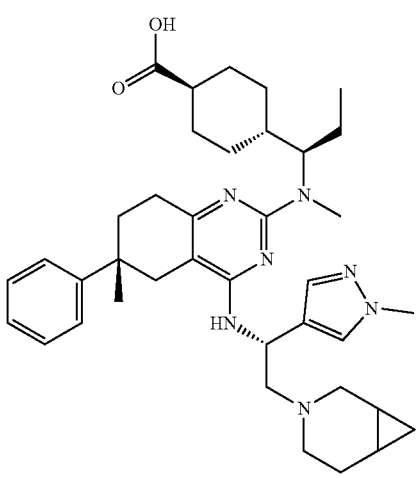 | LCMS m/z [M + H]⁺ = 626.6, ¹H NMR (400 MHz, DMSO-d6) δ 7.42 (br d, J = 2.8 Hz, 1H), 7.39-7.31 (m, 4H), 7.28 (s, 1H), 7.22 (dt, J = 2.8, 5.5 Hz, 1H), 6.13-5.98 (m, 1H), 5.16 (br d, J = 7.5 Hz, 1H), 4.61-4.38 (m, 1H), 3.74 (s, 3H), 2.94-2.84 (m, 1H), 2.72 (s, 3H), 2.62-2.53 (m, 4H), 2.46-2.39 (m, 2H), 2.32-2.18 (m, 2H), 2.09-1.76 (m, 8H), 1.76-1.45 (m, 4H), 1.41-1.18 (m, 4H), 1.17-1.05 (m, 1H), 0.95-0.79 (m, 3H), 0.68 (br t, J = 6.5 Hz, 3H), 0.58-0.37 (m, 2H), 0.19-0.08 (m, 1H). |

| | | |
|---|---|---|
| 79 | 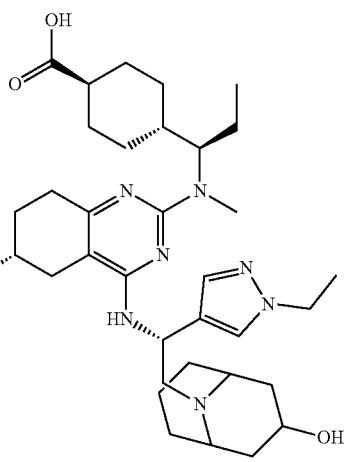 | LCMS m/z [M + H]⁺ = 702.6, ¹H NMR (400 MHz, DMSO-d6) δ 7.60-7.47 (m, 1H), 7.42-7.29 (m, 2H), 7.23-7.14 (m, 2H), 7.10-7.00 (m, 1H), 6.42-5.97 (m, 1H), 5.37-4.96 (m, 1H), 4.60-4.34 (m, 2H), 4.25-4.09 (m, 1H), 4.07-4.00 (m, 2H), 3.78 (br d, J = 2.1 Hz, 1H), 2.98-2.81 (m, 4H), 2.72 (s, 3H), 2.64-2.57 (m, 2H), 2.29-2.05 (m, 2H), 2.03-1.77 (m, 6H), 1.76-1.54 (m, 6H), 1.53-1.46 (m,1H), 1.44-1.23 (m, 9H), 1.22-0.98 (m, 4H), 0.93-0.78 (m, 1H), 0.71-0.70 (m, 1H), 0.73-0.63 (m, 2H), 0.62-0.51 (m, 1H). |
| 82 | 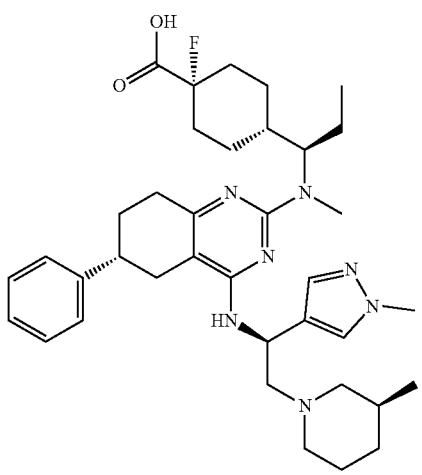 [SMILES: CC[C@H]([C@H]1CC[C@](F)(C(=O)O)CC1)N(C)c1nc2c(c(N[C@H](CN3CCC[C@H](C)C3)c3cnn(C)c3)n1)C[C@H](c1ccccc1)CC2] | LCMS m/z [M + H]⁺ = 646.6, ¹H NMR (400 MHz, DMSO-d6) δ 7.53 (br s, 1H), 7.38-7.28 (m, 5H), 7.21 (dt, J = 2.8, 5.9 Hz, 1H), 6.19-5.92 (m, 1H), 5.58-5.42 (m, 1H), 4.96-4.70 (m, 1H), 3.76-3.72 (m, 3H), 3.17 (s, 1H), 2.96-2.83 (m, 2H), 2.80-2.72 (m, 5H), 2.64-2.60 (m, 2H), 2.20-2.06 (m, 3H), 1.99-1.83 (m, 3H), 1.82-1.71 (m, 2H), 1.69-1.32 (m, 13H), 1.30-1.21 (m, 1H), 0.84-0.76 (m, 4H), 0.69 (br t, J = 7.2 Hz, 3H). |
| 89 | 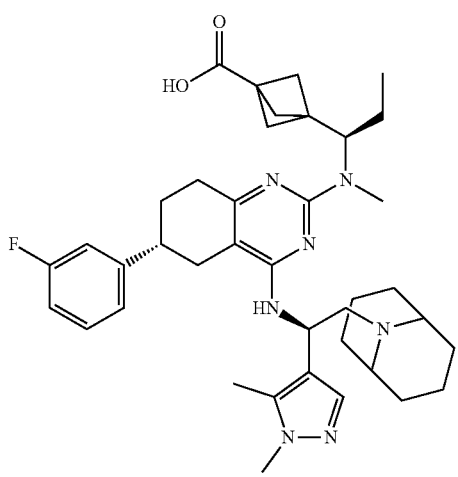 [SMILES: CC[C@@H](N(C)c1nc2c(c(N[C@@H](CN3C4CCCC3CCC4)c3cnn(C)c3C)n1)C[C@H](c1cccc(F)c1)CC2)C12CC(C(=O)O)(C1)C2] | LCMS m/z [M + H]⁺ = 670.6, ¹H NMR (400 MHz, DMSO-d6) δ 7.40-7.32 (m, 1H), 7.29 (s, 1H), 7.18 (br d, J = 7.9 Hz, 2H), 7.07-7.00 (m, 1H), 6.08-5.95 (m, 1H), 5.33-4.99 (m, 1H), 4.84-4.70 (m, 1H), 3.66 (s, 3H), 2.97-2.81 (m, 3H), 2.78 (s, 3H), 2.73 (br s, 2H), 2.65-2.57 (m, 2H), 2.28-2.21 (m, 1H), 2.18 (s, 3H), 2.01-1.60 (m, 16H), 1.50-1.32 (m, 8H), 0.78-0.66 (m, 3H). |

| | | |
|---|---|---|
| 91 | 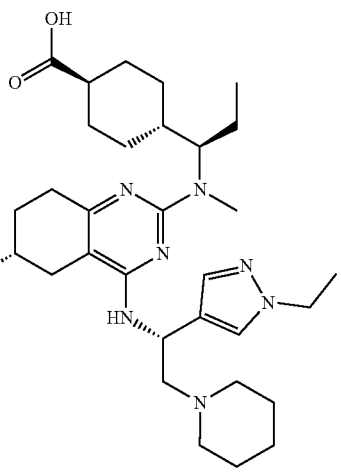 | LCMS m/z [M + H]+ = 646.7, 1H NMR (400 MHz, DMSO-d6) δ 8.25 (s, 1H), 7.49 (s, 1H), 7.41-7.30 (m, 2H), 7.20 (br d, J = 7.9 Hz, 2H), 7.08-7.00 (m, 1H), 6.21 (br d, J = 7.4 Hz, 1H), 5.52-5.25 (m, 1H), 4.60-4.42 (m, 1H), 4.06-3.99 (m, 2H), 2.98-2.8 (m, 2H), 2.72 (s, 3H), 2.70-2.62 (m, 2H), 2.61-2.55 (m, 2H), 2.39 (br s, 4H), 2.31-2.23 (m, 1H), 2.02-1.80 (m, 5H), 1.76-1.57 (m, 2H), 1.44 (br s, 4H), 1.35 (br d, J = 4.1 Hz, 3H), 1.32-1.27 (m, 4H), 1.26-1.08 (m, 2H), 1.07-0.80 (m, 2H), 0.74-0.50 (m, 4H). |
| 102 | 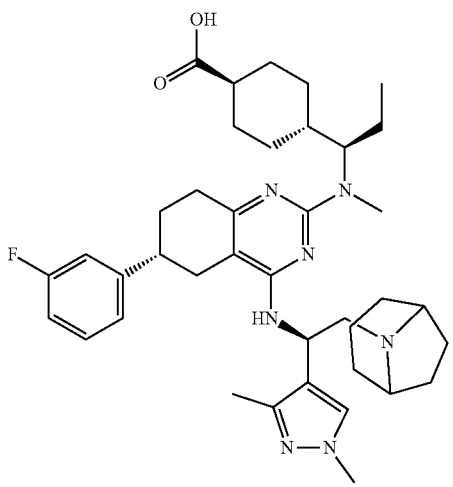 [SMILES: CC[C@H]([C@H]1CC[C@H](C(=O)O)CC1)N(C)c1nc2c(c(N[C@@H](CN3C4CCCC3CC4)c3cn(C)nc3C)n1)C[C@H](c1cccc(F)c1)CC2] | LCMS m/z [M + H]+ = 672.6, 1H NMR (400 MHz, DMSO-d6) δ 7.55-7.29 (m, 2H), 7.19 (br d, J = 7.9 Hz, 2H), 7.05 (br t, J = 8.1 Hz, 1H), 6.09 (br d, J = 6.0 Hz, 1H), 4.96 (br d, J = 6.2 Hz, 1H), 4.59-4.38 (m, 1H), 3.67 (s, 3H), 3.18-3.03 (m, 4H), 3.00-2.88 (m, 2H), 2.71 (s, 3H), 2.60 (br dd, J = 4.5, 16.2 Hz, 3H), 2.36-2.19 (m, 2H), 2.11 (s, 3H), 1.98-1.84 (m, 4H), 1.84-1.81 (m, 1H), 1.73-1.59 (m, 2H), 1.56-1.39 (m, 5H), 1.36-1.17 (m, 7H), 1.14-1.02 (m, 1H), 0.95-0.80 (m, 1H), 0.69 (br t, J = 6.7 Hz, 3H), 0.53-0.33 (m, 1H). |
| 104 | 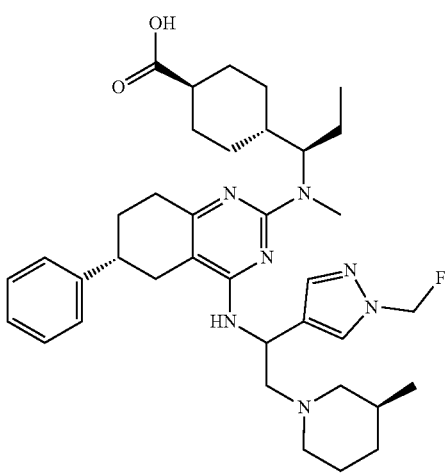 | LCMS m/z [M + H]+ = 676.7, 0.82 min; 1H NMR (400 MHz, DMSO-d6) δ 7.50 (s, 1H), 7.42-7.30 (m, 2H), 7.19 (br d, J = 7.9 Hz, 2H), 7.08-6.97 (m, 1H), 6.26 (br d, J = 7.8 Hz, 1H), 5.41-5.21 (m, 1H), 4.56-4.46 (m, 1H), 4.03 (q, J = 7.3 Hz, 2H), 3.49 (td, J = 5.0, 10.4 Hz, 2H), 3.01-2.87 (m, 3H), 2.75-2.70 (m, 3H), 2.62 (br dd, J = 4.8, 10.7 Hz, 2H), 2.38 (br d, J = 7.0 Hz, 1H), 2.30-2.22 (m, 2H), 2.01-1.78 (m, 6H), 1.71-1.49 (m, 4H), 1.43-1.18 (m, 14H), 1.12-1.02 (m, 1H), 0.91-0.81 (m, 1H), 0.74-0.53 (m, 4H). |

| | | |
|---|---|---|
| 107 | 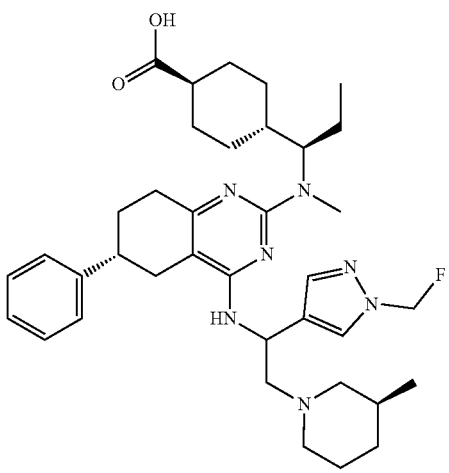 [SMILES: CC[C@H]([C@H]1CC[C@H](C(=O)O)CC1)N(C)c1nc2c(c(NC(CN3CCC[C@H](C)C3)c3cnn(CF)c3)n1)C[C@H](c1ccccc1)CC2] | LCMS m/z [M + H]⁺ = 646.6, ¹H NMR (400 MHz, DMSO-d6) δ 7.98 (br s, 1H), 7.76-7.67 (m, 1H), 7.37 (br d, J = 4.3 Hz, 5H), 7.29-7.23 (m, 1H), 6.21-6.13 (m, 1H), 6.08-5.99 (m, 1H), 4.58-4.26 (m, 1H), 3.78-3.65 (m, 2H), 3.63-3.58 (m, 1H), 2.90 (br s, 5H), 2.82-2.71 (m, 4H), 2.45-2.29 (m, 2H), 2.03-1.91 (m, 5H), 1.87-1.80 (m, 2H), 1.76 (br s, 5H), 1.52-1.38 (m, 3H), 1.36-1.22 (m, 3H), 1.20-1.11 (m, 1H), 1.09-0.94 (m, 3H), 0.87 (br d, J = 5.9 Hz, 3H), 0.70 (br s, 3H). |
| 135 | 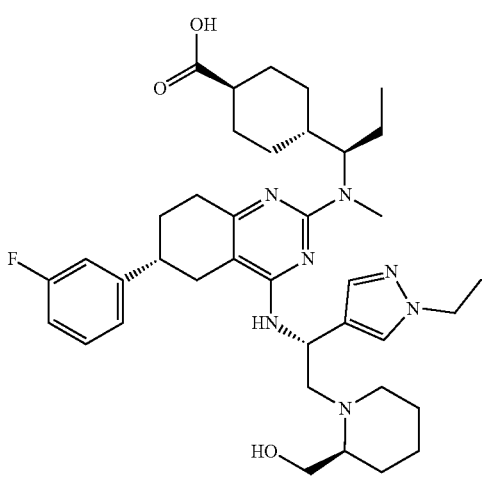 [SMILES: CC[C@H]([C@H]1CC[C@H](C(=O)O)CC1)N(C)c1nc2c(c(N[C@@H](CN3CCCC[C@H]3CO)c3cnn(CC)c3)n1)C[C@H](c1cccc(F)c1)CC2] | LCMS m/z [M + H]⁺ = 676.5, ¹H NMR (400 MHz, DMSO-d6) δ 7.74 (s, 1H), 7.49-7.45 (m, 1H), 7.40-7.29 (m, 2H), 7.23-7.18 (m, 2H), 7.09-7.00 (m, 1H), 6.29-6.13 (m, 1H), 5.34-5.28 (m, 1H), 4.07-4.01 (m, 2H), 3.26-3.22 (m, 3H), 2.74-2.70 (m, 2H), 2.03-1.97 (m, 4H), 1.90-1.82 (m, 3H), 1.59-1.48 (m, 4H), 1.37-1.34 (m, 2H), 1.32 (br d, J = 4.4 Hz, 3H), 1.29 (br d, J = 7.3 Hz, 5H), 1.23 (br s, 13H), 0.86-0.82 (m, 2H), 0.69-0.65 (m, 2H). |
| 140 | 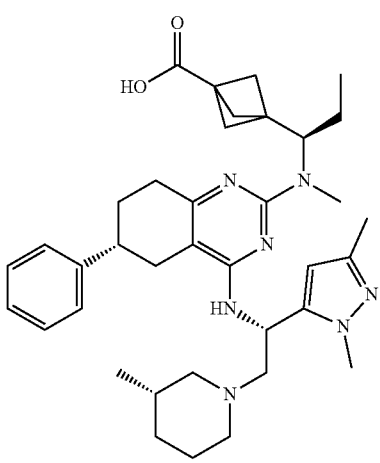 [SMILES: CC[C@@H](N(C)c1nc2c(c(N[C@@H](CN3CCC[C@H](C)C3)c3cc(C)nn3C)n1)C[C@H](c1ccccc1)CC2)C12CC(C(=O)O)(C1)C2] | LCMS m/z [M + H]⁺ = 626.6, ¹H NMR (400 MHz, DMSO-d6) δ 7.37-7.28 (m, 4H), 7.25-7.18 (m, 1H), 6.32 (br d, J = 7.5 Hz, 1H), 5.92 (s, 1H), 5.54-5.29 (m, 1H), 4.87-4.74 (m, 1H), 3.66 (s, 3H), 2.91-2.75 (m, 5H), 2.74-2.68 (m, 1H), 2.64-2.58 (m, 3H), 2.52-2.52 (m, 2H), 2.23 (br dd, J = 11.9, 15.1 Hz, 1H), 2.05 (s, 3H), 1.97-1.86 (m, 3H), 1.80 (br d, J = 8.4 Hz, 3H), 1.70 (br d, J = 6.7 Hz, 3H), 1.67-1.55 (m, 2H), 1.53-1.42 (m, 4H), 1.38-1.21 (m, 1H), 0.83-0.65 (m, 7H). |

| | | |
|---|---|---|
| 144 | 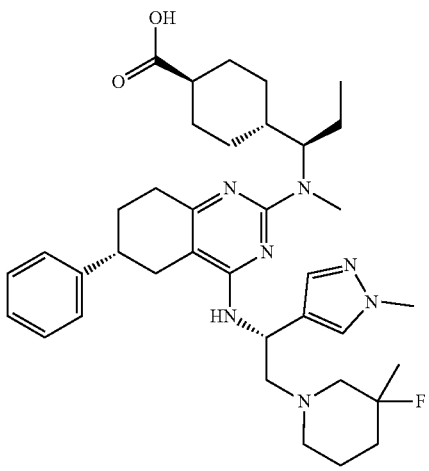 [SMILES: CC[C@H]([C@H]1CC[C@H](C(=O)O)CC1)N(C)c1nc2c(c(N[C@@H](CN3CCCC(C)(F)C3)c3cnn(C)c3)n1)C[C@H](c1ccccc1)CC2] | LCMS m/z [M + H]+ = 646.7, 1H NMR (400 MHz, DMSO-d6) δ 12.21-11.44 (m, 1H), 7.47 (br s, 1H), 7.34 (br d, J = 4.3 Hz, 5H), 7.27-7.17 (m, 1H), 5.38-5.17 (m, 1H), 4.46 (br s, 1H), 3.74 (s, 3H), 2.99-2.83 (m, 1H), 2.82-2.69 (m, 4H), 2.65-2.55 (m, 3H), 2.38-2.19 (m, 3H), 2.11-1.78 (m, 6H), 1.75-1.48 (m, 5H), 1.44-1.07 (m, 9H), 1.01-0.76 (m, 2H), 0.69 (br s, 3H), 0.60-0.46 (m, 1H). |
| 155 | 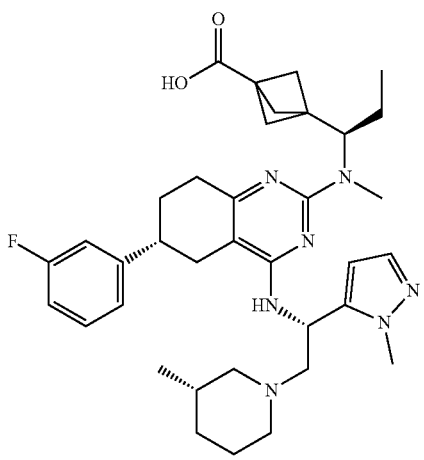 [SMILES: CC[C@@H](N(C)c1nc2c(c(N[C@@H](CN3CCC[C@H](C)C3)c3ccnn3C)n1)C[C@H](c1cccc(F)c1)CC2)C12CC(C(=O)O)(C1)C2] | LCMS m/z [M + H]+ = 630.3, 1H NMR (400 MHz, DMSO-d6) δ 12.68-11.64 (m, 1H), 7.37 (dt, J = 6.5, 7.9 Hz, 1H), 7.27 (d, J = 1.4 Hz, 1H), 7.23-7.17 (m, 2H), 7.08-7.00 (m, 1H), 6.37 (br d, J = 7.8 Hz, 1H), 6.17 (d, J = 1.8 Hz, 1H), 5.85-5.35 (m, 1H), 4.84 (br t, J = 6.9 Hz, 1H), 3.77 (s, 3H), 3.00-2.89 (m, 1H), 2.88-2.83 (m, 1H), 2.80 (s, 3H), 2.75-2.60 (m, 5H), 2.59-2.55 (m, 1H), 2.53 (br d, J = 2.0 Hz, 1H), 2.31-2.18 (m, 1H), 2.00-1.88 (m, 3H), 1.85-1.79 (m, 3H), 1.77-1.65 (m, 3H), 1.63-1.55 (m, 1H), 1.55-1.42 (m, 4H), 1.38-1.25 (m, 1H), 0.85-0.69 (m, 7H). |
| 161 | 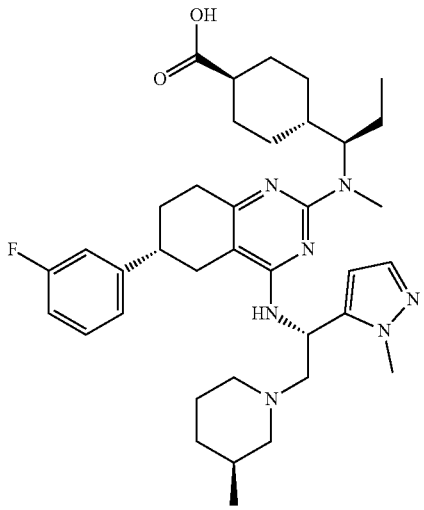 [SMILES: CC[C@H]([C@H]1CC[C@H](C(=O)O)CC1)N(C)c1nc2c(c(N[C@@H](CN3CCC[C@H](C)C3)c3ccnn3C)n1)C[C@H](c1cccc(F)c1)CC2] | LCMS m/z [M + H]+ = 646.6, 1H NMR (400 MHz, DMSO-d6) δ 7.42-7.31 (m, 1H), 7.25 (d, J = 1.5 Hz, 1H), 7.19 (br d, J = 7.8 Hz, 2H), 7.07-7.00 (m, 1H), 6.32 (br d, J = 7.5 Hz, 1H), 6.14 (s, 1H), 5.52-5.40 (m, 1H), 4.43 (br t, J = 9.2 Hz, 1H), 3.78 (s, 3H), 2.96-2.83 (m, 2H), 2.72 (s, 4H), 2.68-2.57 (m, 4H), 2.31-2.20 (m, 1H), 2.13-2.00 (m, 1H), 1.97-1.88 (m, 4H), 1.81 (br d, J = 9.5 Hz, 2H), 1.75-1.56 (m, 4H), 1.49 (br d, J = 2.9 Hz, 2H), 1.41-1.21 (m, 5H), 1.19-1.05 (m, 1H), 1.03-0.88 (m, 1H), 0.79 (br d, J = 6.4 Hz, 4H), 0.71 (br t, J = 6.9 Hz, 3H), 0.65 (br d, J = 3.9 Hz, 1H), 0.56-0.41 (m, 1H). |

| | | |
|---|---|---|
| 163 | 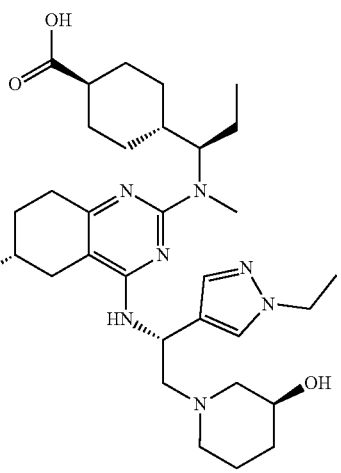 | LCMS m/z [M + H]⁺ = 662.5, ¹H NMR (400 MHz, DMSO-d6) δ 7.62-7.49 (m, 1H), 7.41-7.28 (m, 2H), 7.20 (br d, J = 8.6 Hz, 2H), 7.04 (br t, J = 8.9 Hz, 1H), 6.20 (br d, J = 7.5 Hz, 1H), 5.47-5.30 (m, 1H), 4.60-4.42 (m, 1H), 4.03 (q, J = 6.6 Hz, 2H), 2.99-2.86 (m, 2H), 2.84-2.63 (m, 8H), 2.63-2.57 (m, 3H), 2.34-2.17 (m, 2H), 2.04-1.69 (m, 10H), 1.58-1.52 (m, 1H), 1.41-1.17 (m, 9H), 1.10-0.85 (m, 4H), 0.56 (br t, J = 6.7 Hz, 2H). |
| 164 | 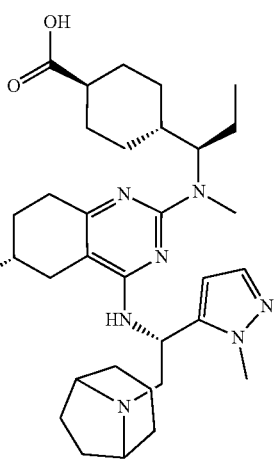 | LCMS m/z [M + H]⁺ = 658.6, ¹H NMR (400 MHz, DMSO-d6) δ 12.19-11.72 (m, 1H), 7.38 (q, J = 7.4 Hz, 1H), 7.27-7.15 (m, 3H), 7.05 (dt, J = 1.7, 8.2 Hz, 1H), 6.35 (br d, J = 6.0 Hz, 1H), 6.21-6.08 (m, 1H), 5.19 (br d, J = 6.0 Hz, 1H), 4.38 (br t, J = 8.5 Hz, 1H), 3.84 (s, 3H), 3.14 (br s, 1H), 3.05-2.85 (m, 2H), 2.77-2.69 (m, 3H), 2.69-2.60 (m, 4H), 2.33-2.22 (m, 1H), 2.14-1.62 (m, 10H), 1.60-0.92 (m, 15H), 0.71 (br t, J = 7.0 Hz, 2H), 0.47-0.31 (m, 1H). |
| 172 | 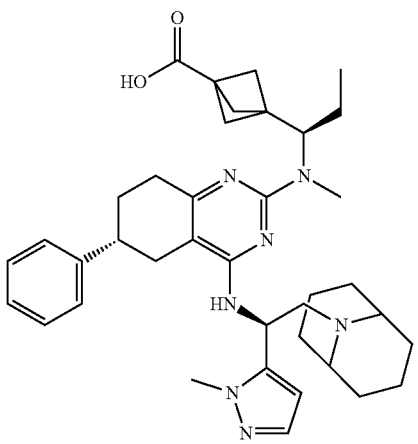 [SMILES: CC[C@@H](N(C)c1nc2c(c(N[C@@H](CN3C4CCCC3CCC4)c3ccnn3C)n1)C[C@H](c1ccccc1)CC2)C12CC(C(=O)O)(C1)C2] | LCMS m/z [M + H]⁺ = 638.6, ¹H NMR (400 MHz, DMSO-d6) δ 7.43-7.28 (m, 4H), 7.27-7.15 (m, 2H), 6.24 (br d, J = 7.6 Hz, 1H), 6.15 (s, 1H), 5.52-5.14 (m, 1H), 4.88-4.64 (m, 1H), 3.80 (s, 3H), 2.95 (br d, J = 6.2 Hz, 2H), 2.93-2.81 (m, 2H), 2.78 (s, 3H), 2.69 (br s, 3H), 2.63 (br d, J = 4.3 Hz, 1H), 2.56 (br s, 1H), 2.31-2.21 (m, 1H), 1.97-1.87 (m, 3H), 1.83 (br d, J = 13.1 Hz, 3H), 1.77 (br d, J = 6.4 Hz, 4H), 1.70 (br d, J = 7.7 Hz, 3H), 1.46 (br d, J = 6.4 Hz, 4H), 1.42-1.32 (m, 4H), 0.72 (br t, J = 6.4 Hz, 3H). |

| | | |
|---|---|---|
| 173 | 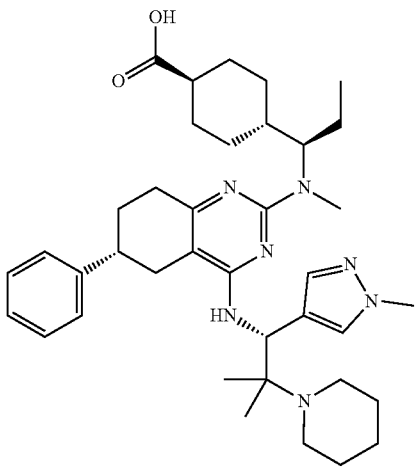 [SMILES: CC[C@H]([C@H]1CC[C@H](C(=O)O)CC1)N(C)c1nc2c(c(N[C@H](c3cnn(C)c3)C(C)(C)N3CCCCC3)n1)C[C@H](c1ccccc1)CC2] | LCMS m/z [M + H]⁺ = 642.7, ¹H NMR (400 MHz, DMSO-d6) δ 7.92-7.82 (m, 1H), 7.64-7.52 (m, 1H), 7.39 (br d, J = 7.5 Hz, 4H), 7.28 (br d, J = 8.1 Hz, 1H), 5.81-5.72 (m, 1H), 4.46-4.21 (m, 1H), 3.79 (s, 3H), 3.63-3.54 (m, 1H), 2.96-2.85 (m, 6H), 2.08 (s, 3H), 1.98-1.80 (m, 8H), 1.74-1.63 (m, 4H), 1.48-1.39 (m, 6H), 1.32-1.22 (m, 6H), 1.20-1.13 (m, 3H), 1.00-0.85 (m, 2H), 0.74-0.67 (m, 3H). |
| 6 | 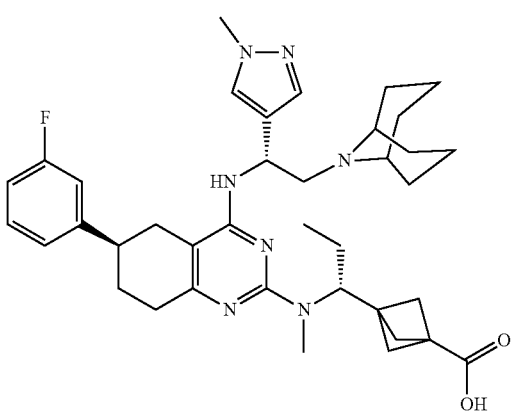 [SMILES: CC[C@@H](N(C)c1nc2c(c(N[C@@H](CN3C4CCCC3CCC4)c3cnn(C)c3)n1)C[C@H](c1cccc(F)c1)CC2)C12CC(C(=O)O)(C1)C2] | LCMS m/z [M + H]⁺ = 656.40, ¹H NMR (300 MHz, METHANOL-d₄) δ ppm 7.54 (s, 1 H), 7.44 (s, 1 H), 7.38-7.28 (m, 1 H), 7.21-7.07 (m, 2 H), 7.01-6.88 (m, 1 H), 5.53-5.27 (m, 1 H), 4.78-4.65 (m, 1 H), 3.84 (s, 3 H), 3.14-2.88 (m, 6 H), 2.86-2.75 (m, 4 H), 2.53-2.28 (m, 1 H), 2.23-1.98 (m, 9 H), 1.90-1.53 (m, 13 H), 1.31 (br d, J = 11.71 Hz, 1 H), 0.93-0.68 (m, 3 H). |
| 9 | 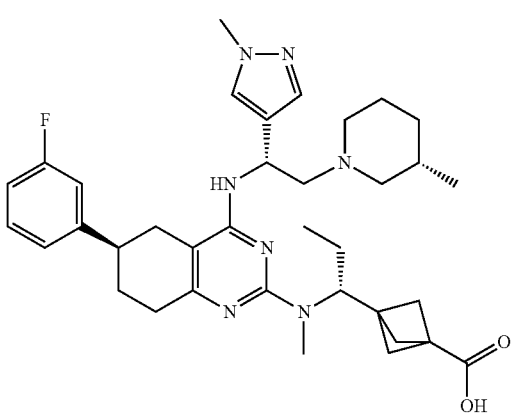 [SMILES: CC[C@@H](N(C)c1nc2c(c(N[C@@H](CN3CCC[C@H](C)C3)c3cnn(C)c3)n1)C[C@H](c1cccc(F)c1)CC2)C12CC(C(=O)O)(C1)C2] | LCMS m/z [M + H]⁺ = 630.45, ¹H NMR (400 MHz, METHANOL-d₄) δ ppm 7.53 (s, 1 H), 7.42 (s, 1 H), 7.38-7.29 (m, 1 H), 7.17 (br d, J = 7.82 Hz, 1 H), 7.11 (br d, J = 10.17 Hz, 1 H), 7.00-6.92 (m, 1 H), 5.63 (br d, J = 5.48 Hz, 2 H), 4.10 (q, J = 7.30 Hz, 2 H), 3.84 (s, 3 H), 3.09-2.87 (m, 6 H), 2.85-2.64 (m, 4 H), 2.43-2.39 (m, 2 H), 2.25-1.93 (m, 6 H), 1.89-1.55 (m, 8 H), 1.24 (t, J = 7.24 Hz, 3 H), 0.96-0.77 (m, 4 H) |

| 44 | 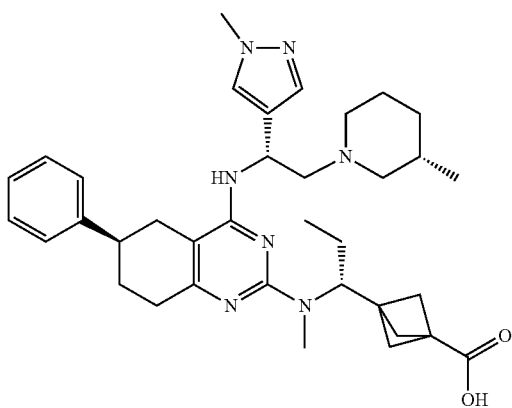 [SMILES: CC[C@@H](N(C)c1nc2c(c(N[C@@H](CN3CCC[C@H](C)C3)c3cnn(C)c3)n1)C[C@H](c1ccccc1)CC2)C12CC(C(=O)O)(C1)C2] | LCMS m/z [M + H]⁺ = 612.60, ¹H NMR (400 MHz, METHANOL-d₄) δ ppm 7.53 (s, 1 H), 7.41 (s, 1 H), 7.37-7.28 (m, 4 H), 7.24-7.20 (m, 1 H) 5.60 (br d, J = 4.30 Hz, 1 H), 4.85-4.76 (m, 1 H) 3.83 (s, 3 H), 2.96 (s, 6 H), 2.81 (br d, J = 8.22 Hz, 7 H), 2.44-2.40 (m, 2 H), 2.21-1.94 (m, 5 H) 1.92-1.56 (m, 11 H) 1.00-0.76 (m, 4 H) |
|---|---|---|
| 47 | 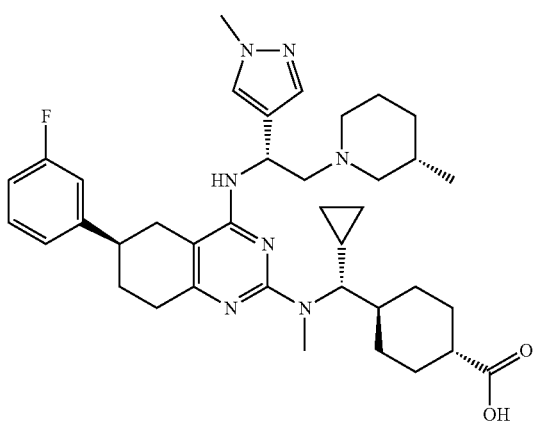 [SMILES: C[C@H]1CCCN(C[C@H](Nc2nc(N(C)[C@H](C3CC3)[C@H]3CC[C@H](C(=O)O)CC3)nc3c2C[C@H](c2cccc(F)c2)CC3)c2cnn(C)c2)C1] | LCMS m/z [M + H]⁺ = 658.40, ¹H NMR (400 MHz, METHANOL-d₄) δ ppm 7.46 (br s, 1 H), 7.40-7.29 (m, 2 H), 7.17 (br d, J = 7.43 Hz, 1 H), 7.11 (br d, J = 10.17 Hz, 1 H), 7.01-6.89 (m, 1 H), 5.46-5.30 (m, 1 H), 4.10 (q, J = 7.30 Hz, 1 H), 3.89-3.71 (m, 4 H), 3.10-2.90 (m, 5 H), 2.89-2.60 (m, 5 H), 2.48-2.34 (m, 1 H), 2.26-1.92 (m, 6 H), 1.89-1.62 (m, 6 H), 1.60-1.17 (m, 5 H), 1.12-0.56 (m, 8 H), 0.39 (br s, 2 H) |
| 97 | 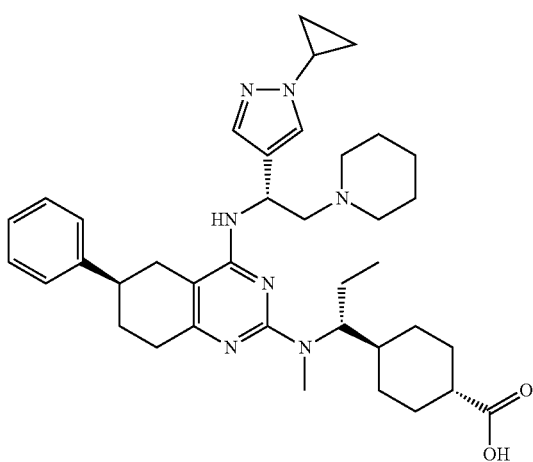 | LCMS m/z [M + H]⁺ = 644.45, ¹H NMR (400 MHz, METHANOL-d₄) δ 8.52 (br s, 1 H), 7.59 (br s, 1 H), 7.39 (br s, 1 H), 7.37-7.29 (m, 3 H), 7.26-7.18 (m, 1 H) 5.59-5.49 (m, 1 H) 4.57-4.46 (m, 1 H) 3.76-3.53 (m, 2 H) 3.09-2.35 (m, 14 H) 2.22-1.76 (m, 7 H) 1.71-1.24 (m, 12 H) 1.01 (br d, J = 5.70 Hz, 4 H), 0.78 (br t, J = 7.02 Hz, 3 H) |

| | | |
|---|---|---|
| 112 | 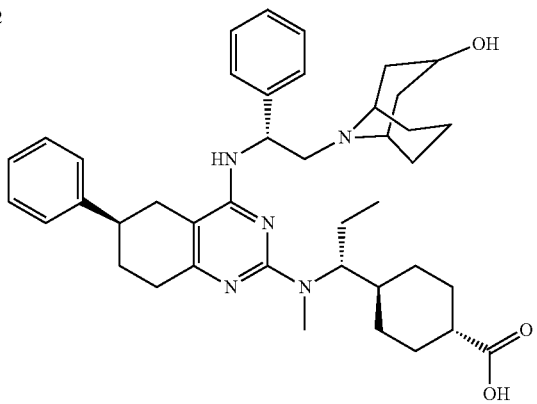 | LCMS m/z [M + H]⁺ = 665.90, ¹H NMR (400 MHz, METHANOL-d₄) δ ppm 8.53 (s, 1 H), 7.34-7.42 (m, 6 H), 7.23-7.33 (m, 4 H), 4.99 (br dd, J = 9.21, 4.82 Hz, 1 H), 4.27 (br t, J = 9.21 Hz, 1 H), 3.93-4.04 (m, 1 H), 3.13-3.23 (m, 1 H), 2.96-3.12 (m, 3 H), 2.70-2.91 (m, 7 H), 2.56-2.68 (m, 2 H), 2.14-2.39 (m, 5 H), 2.01-2.12 (m, 2 H), 1.69-2.00 (m, 6 H), 1.61 (br d, J = 12.28 Hz, 2 H), 1.26-1.50 (m, 7 H), 1.06-1.24 (m, 4 H). |
| 120 | 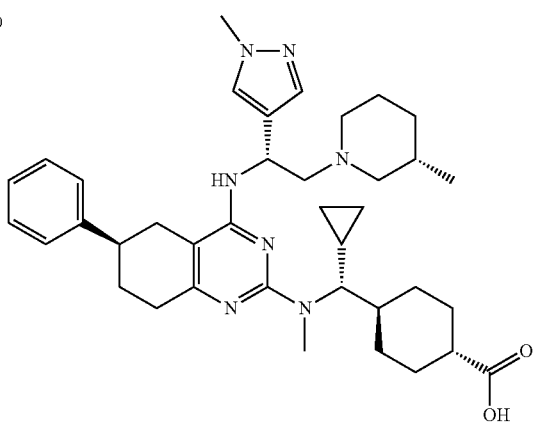 | LCMS m/z [M + H]⁺ = 640.65, ¹H NMR (400 MHz, METHANOL-d₄) δ ppm 7.42 (br s, 1 H), 7.28-7.37 (m, 5 H), 7.17-7.23 (m, 1 H), 5.34 (br d, J = 2.63 Hz, 1 H), 3.73-3.92 (m, 4 H), 2.91-3.06 (m, 4 H), 2.77-2.89 (m, 2 H), 2.66-2.76 (m, 3 H), 2.61-2.57 (m, 1 H), 2.41-2.37 (m, 1 H), 2.14-2.26 (m, 1 H), 1.91-2.13 (m, 5 H), 1.58-1.87 (m, 7 H), 1.52 (br d, J = 8.77 Hz, 2 H), 1.43 (br dd, J = 13.59, 2.63 Hz, 1 H), 1.32 (br d, J = 11.84 Hz, 2 H), 0.77-1.07 (m, 6 H), 0.71 (br s, 2 H), 0.33 (br d, J = 6.58 Hz, 2 H). |
| 133 | 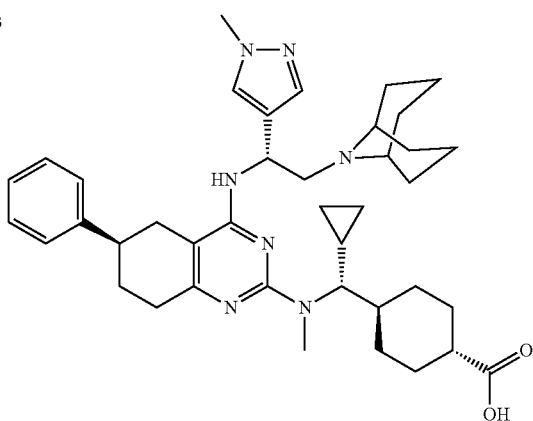 | LCMS m/z [M + H]⁺ = 676.70, ¹H NMR (400 MHz, METHANOL-d4) δ ppm 8.53 (s, 1H), 7.49 (br s, 1H), 7.37 (br s, 1H), 7.33 (br d, J = 3.1 Hz, 4H), 7.22 (dt, J = 2.9, 5.6 Hz, 1H), 5.19 (br s, 1H), 3.85 (s, 3H), 3.76-3.58 (m, 1H), 3.51-3.44 (m, 1H), 3.40 (br s, 1H), 3.16-2.90 (m, 5H), 2.90-2.63 (m, 4H), 2.61-2.34 (m, 2H), 2.20-2.12 (m, 3H), 2.10-1.88 (m, 8H), 1.86-1.71 (m, 2H), 1.62 (br s, 5H), 1.46-1.32 (m, 2H), 1.29 (br d, J = 4.4 Hz, 2H), 1.06-0.86 (m, 2H), 0.84-0.73 (m, 1H), 0.56 (br d, J = 13.6 Hz, 1H), 0.40 (br s, 2H). |
| 146 | 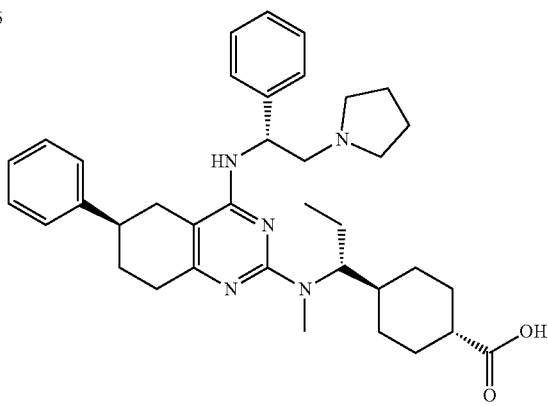 | LCMS m/z [M + H]⁺ = 596.2, ¹H NMR (300 MHz, METHANOL-d₄) δ ppm 7.26-7.41 (m, 9 H), 7.17-7.24 (m, 1 H), 5.34 (br d, J = 7.90 Hz, 1 H), 4.37 (br t, J = 9.55 Hz, 1 H), 2.67-3.09 (m, 10 H), 2.42-2.59 (m, 1 H), 1.72-2.11 (m, 8 H), 1.53-1.63 (m, 1 H), 1.21-1.48 (m, 10 H), 1.09-1.18 (m, 2 H), 0.80 (br t, J = 6.91 Hz, 3 H). |

| | | |
|---|---|---|
| 147 | 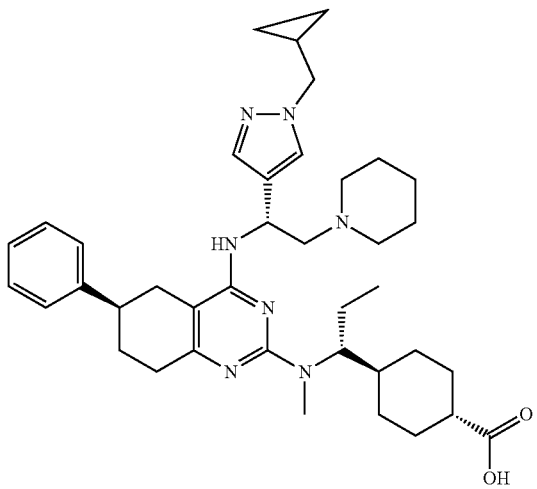 [SMILES: CC[C@H]([C@H]1CC[C@H](C(=O)O)CC1)N(C)c1nc2c(c(N[C@@H](CN3CCCCC3)c3cnn(CC4CC4)c3)n1)C[C@H](c1ccccc1)CC2] | LCMS m/z [M + H]⁺ = 654.30, ¹H NMR (400 MHz, METHANOL-d₄) δ ppm 7.61 (br s, 1 H) 7.41 (br s, 1 H) 7.29-7.38 (m, 4 H) 7.18-7.27 (m, 1 H) 5.58 (br d, J = 3.07 Hz, 1 H) 4.50-4.66 (m, 1 H) 3.96 (br d, J = 7.02 Hz, 2 H) 2.95-3.06 (m, 2 H) 2.90 (s, 3 H) 2.37-2.84 (m, 10 H) 1.75-2.18 (m, 8 H) 1.43-1.69 (m, 8 H) 1.20-1.35 (m, 4 H) 0.79 (br t, J = 7.23 Hz, 3 H) 0.51-0.63 (m, 2 H) 0.36 (q, J = 4.82 Hz, 2 H). |
| 150 | 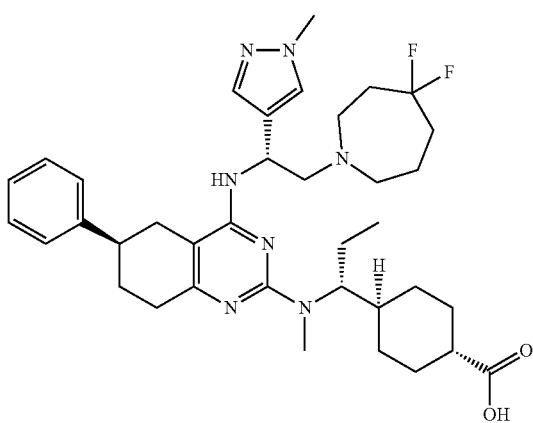 [SMILES: CC[C@H]([C@H]1CC[C@H](C(=O)O)CC1)N(C)c1nc2c(c(N[C@@H](CN3CCCC(F)(F)CC3)c3cnn(C)c3)n1)C[C@H](c1ccccc1)CC2] | LCMS m/z [M + H]⁺ = 664.6, ¹H NMR (400 MHz, METHANOL-d₄) δ ppm 7.49 (br s, 1 H), 7.39 (br s, 1 H), 7.27-7.36 (m, 4 H), 7.22 (br dd, J = 5.92, 2.41 Hz, 1 H), 5.33 (br d, J = 4.38 Hz, 1 H), 4.49 (br d, J = 11.40 Hz, 1 H), 2.63-3.04 (m, 13 H), 2.39-2.51 (m, 1 H), 1.94-2.16 (m, 9 H), 1.76-1.92 (m, 3 H), 1.63-1.73 (m, 2 H), 1.21-1.55 (m, 7 H), 0.87-1.01 (m, 1 H), 0.77 (br t, J = 7.02 Hz, 3 H), 0.66-0.62 (m, 1 H) |
| 154 | 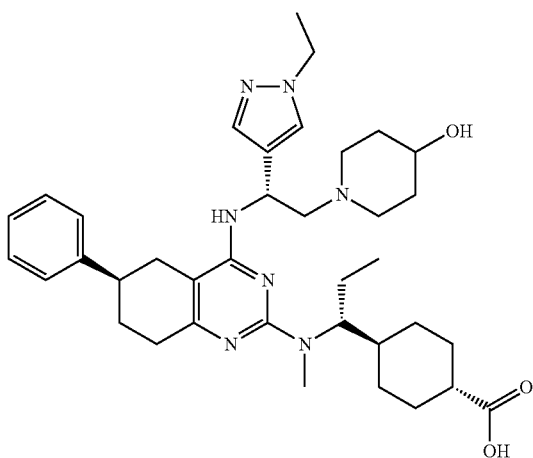 [SMILES: CC[C@H]([C@H]1CC[C@H](C(=O)O)CC1)N(C)c1nc2c(c(N[C@@H](CN3CCC(O)CC3)c3cnn(CC)c3)n1)C[C@H](c1ccccc1)CC2] | LCMS m/z [M + H]⁺ = 644.3, ¹H NMR (300 MHz, METHANOL-d₄) δ ppm 7.57 (s, 1 H), 7.42 (s, 1 H), 7.38-7.30 (m, 4 H), 7.24 (dt, J = 5.76, 2.71 Hz, 1 H), 5.54-5.50 (m, 1 H), 4.52 (br t, J = 9.21 Hz, 1 H), 4.13 (q, J = 7.24 Hz, 2 H), 3.69-3.56 (m, 1 H), 3.12-2.16 (m, 12 H), 2.57-2.23 (m, 3 H), 2.20-1.73 (m, 10 H), 1.65-1.24 (m, 11 H), 0.80 (br t, J = 7.24 Hz, 3 H). |

| | | |
|---|---|---|
| 156 | 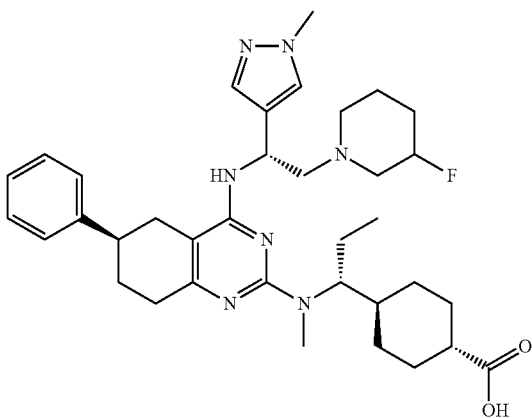 [SMILES: CC[C@H]([C@H]1CC[C@H](C(=O)O)CC1)N(C)c1nc2c(c(N[C@@H](CN3CCCC(F)C3)c3cnn(C)c3)n1)C[C@H](c1ccccc1)CC2] | LCMS m/z [M + H]⁺ = 632.70, ¹H NMR (400 MHz, METHANOL-d₄) δ ppm 8.54 (s, 1 H), 7.52 (br s, 1 H), 7.40 (br s, 1 H), 7.38-7.29 (m, 4 H), 7.28-7.20 (m, 1 H), 5.44 (br dd, J = 8.55, 4.60 Hz, 1 H), 4.61 (br s, 1 H), 4.50 (br s, 2 H), 2.97-3.08 (m, 1 H), 2.65-2.97 (m, 7 H), 2.41-2.60 (m, 4 H), 2.11-2.22 (m, 2 H), 1.96-2.10 (m, 3 H), 1.72-1.95 (m, 5 H), 1.63 (br d, J = 8.33 Hz, 2 H), 1.36-1.56 (m, 5 H), 1.20-1.35 (m, 3 H), 0.89-1.05 (m, 1 H), 0.81 (br t, J = 7.02 Hz, 3 H), 0.57 (br d, J = 13.59 Hz, 1 H). |
| 162 | 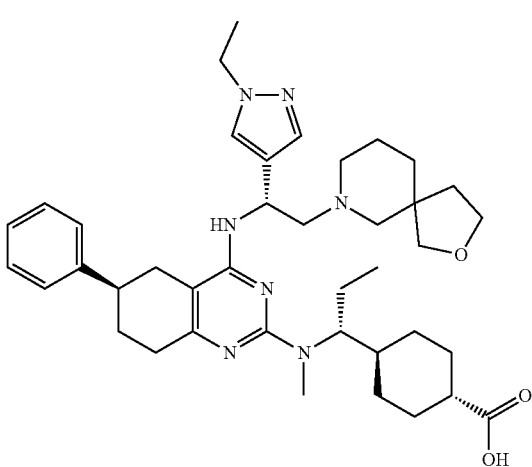 [SMILES: CC[C@H]([C@H]1CC[C@H](C(=O)O)CC1)N(C)c1nc2c(c(N[C@@H](CN3CCCC4(CCOC4)C3)c3cnn(CC)c3)n1)C[C@H](c1ccccc1)CC2] | LCMS m/z [M + H]⁺ = 683.90, ¹H NMR (400 MHz, METHANOL-d₄) δ ppm 7.56 (br s, 1 H), 7.42 (br s, 1 H), 7.38-7.29 (m, 4 H), 7.27-7.20 (m, 1 H), 5.46-5.33 (m, 1 H), 4.64-4.47 (m, 2 H), 4.21-4.07 (m, 2 H), 3.78-3.59 (m, 3 H), 3.53 (br d, J = 8.33 Hz, 1 H), 3.39 (br d, J = 9.21 Hz, 1 H), 3.07-2.96 (m, 2 H), 2.91 (s, 3 H), 2.87-2.77 (m, 3 H), 2.74-2.59 (m, 3 H), 2.54-2.26 (m, 5 H), 2.14 (br d, J = 10.96 Hz, 1 H), 2.09-1.68 (m, 7 H), 1.65-1.35 (m, 11 H), 0.80 (br t, J = 7.02 Hz, 3 H). |
| 167 | 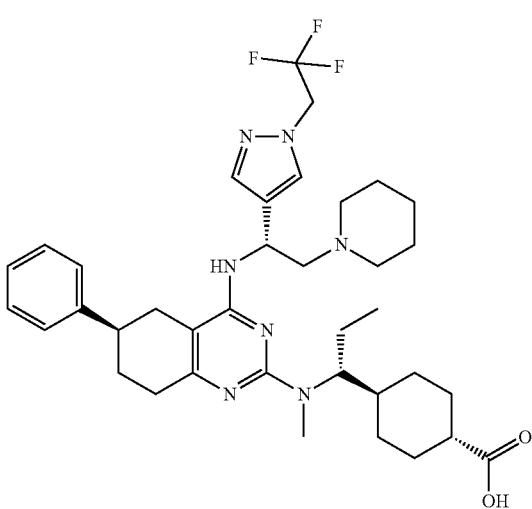 [SMILES: CC[C@H]([C@H]1CC[C@H](C(=O)O)CC1)N(C)c1nc2c(c(N[C@@H](CN3CCCCC3)c3cnn(CC(F)(F)F)c3)n1)C[C@H](c1ccccc1)CC2] | LCMS m/z [M + H]⁺ = 681.95, ¹H NMR (400 MHz, METHANOL-d₄) δ ppm 7.68 (br s, 1 H), 7.53 (br s, 1 H), 7.29-7.39 (m, 4 H), 7.17-7.27 (m, 1 H), 5.56 (br s, 1 H), 4.46-4.68 (m, 1 H), 2.92-3.07 (m, 3 H), 2.89 (s, 3 H), 2.67-2.83 (m, 4 H), 2.40-2.66 (m, 5 H), 2.08-2.18 (m, 1 H), 1.74-2.07 (m, 6 H), 1.25-1.67 (m, 12 H), 0.90 (br s, 1 H), 0.78 (br t, J = 7.02 Hz, 3 H), 0.66-0.59 (m, 1 H). |

| | | |
|---|---|---|
| 74 | 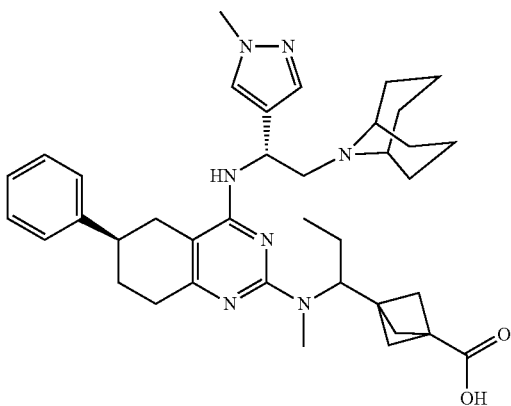 [SMILES: CCC(N(C)c1nc2c(c(N[C@@H](CN3C4CCCC3CCC4)c3cnn(C)c3)n1)C[C@H](c1ccccc1)CC2)C12CC(C(=O)O)(C1)C2] | LCMS m/z [M + H]⁺ = 638.85, ¹H NMR (400 MHz, METHANOL-d4) δ = 7.51 (s, 1H), 7.43 (s, 1H), 7.37-7.26 (m, 4H), 7.22-7.18 (m, 1H), 5.48-5.19 (m, 2H), 4.82-4.70 (m, 1H), 3.83 (s, 3H), 3.54-3.40 (m, 1H), 3.32-3.32 (m, 1H), 3.25-3.21 (m, 1H), 3.17-3.04 (m, 1H), 2.32-2.26 (m, 2H), 2.89 (s, 3H), 2.81 (br d, J = 6.3 Hz, 1H), 2.77-2.67 (m, 2H), 2.55-2.33 (m, 2H), 2.13-2.06 (m, 1H), 2.04-1.96 (m, 4H), 1.95-1.87 (m, 1H), 1.78 (br d, J = 8.2 Hz, 2H), 1.71 (br s, 2H), 1.66 (br s, 1H), 1.62-1.50 (m, 5H), 1.28 (br d, J = 3.9 Hz, 2H), 1.04 (br d, J = 6.7 Hz, 1H), 0.89 (br s, 1H), 0.80 (t, J = 7.4 Hz, 2H). |
| 149 | 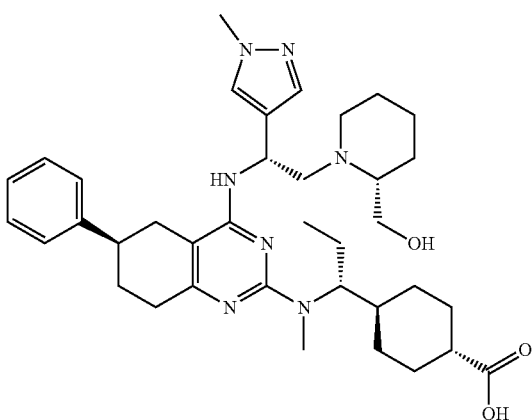 | LCMS m/z [M + H − 16]⁺ = 628.45, ¹H NMR (400 MHz, METHANOL-d4) δ ppm 7.50 (br s, 1 H), 7.41 (br s, 1 H), 7.37-7.27 (m, 4 H), 7.24-7.16 (m, 1 H), 5.50 (br d, J = 4.38 Hz, 1 H), 4.64-4.49 (m, 1 H), 2.96 (br d, J = 11.40 Hz, 3 H), 2.85 (br s, 3 H), 2.79-2.65 (m, 3 H), 2.56-2.38 (m, 3 H), 2.14-1.78 (m, 8 H), 1.70-1.24 (m, 14 H), 1.10 (br d, J = 6.58 Hz, 3 H), 1.01-0.90 (m, 1 H), 0.78 (br t, J = 7.02 Hz, 3 H). |
| 116 | 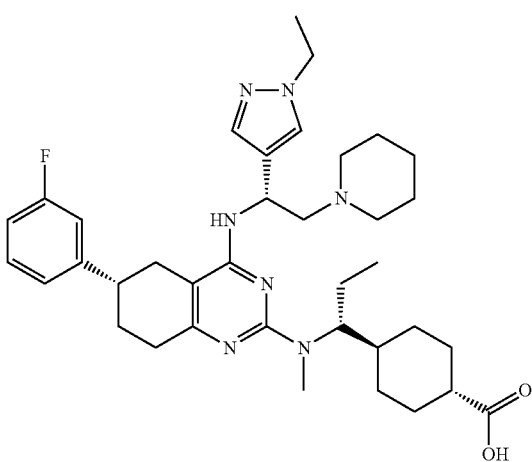 [SMILES: CC[C@H]([C@H]1CC[C@H](C(=O)O)CC1)N(C)c1nc2c(c(N[C@@H](CN3CCCCC3)c3cnn(CC)c3)n1)C[C@@H](c1cccc(F)c1)CC2] | LCMS m/z [M + H]⁺ = 646.6, ¹H NMR (400 MHz, DMSO-d6) δ 7.50 (s, 1H), 7.41-7.31 (m, 2H), 7.20 (br d, J = 7.9 Hz, 2H), 7.08-7.00 (m, 1H), 6.15 (br d, J = 7.3 Hz, 1H), 5.30 (br d, J = 6.1 Hz, 1H), 4.57-4.43 (m, 1H), 4.08-3.99 (m, 2H), 2.99-2.88 (m, 1H), 2.72 (s, 3H), 2.66-2.57 (m, 2H), 2.52-2.51 (m, 2H), 2.37 (br s, 4H), 2.29-2.21 (m, 1H), 2.09-1.78 (m, 6H), 1.75-1.53 (m, 2H), 1.43 (br s, 4H), 1.38-1.33 (m, 3H), 1.33-1.19 (m, 6H), 1.18-1.05 (m, 1H), 0.93-0.81 (m, 1H), 0.76-0.50 (m, 4H) |

| 125 | 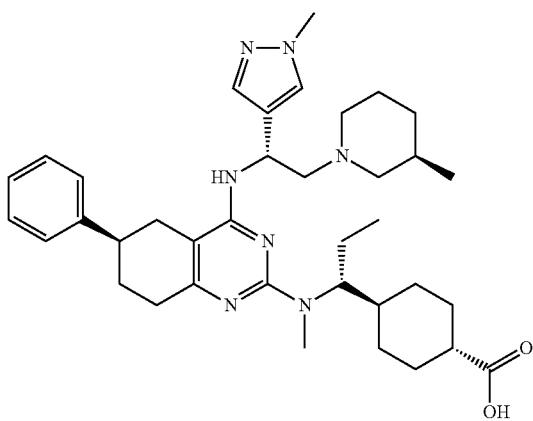 [SMILES: CC[C@H]([C@H]1CC[C@H](C(=O)O)CC1)N(C)c1nc2c(c(N[C@@H](CN3CCC[C@@H](C)C3)c3cnn(C)c3)n1)C[C@H](c1ccccc1)CC2] | LCMS m/z [M + H]+ = 628.3, 1H NMR (400 MHz, Methanol-d4) δ 7.36 (s, 1H), 7.31-7.17 (m, 5H), 7.13-7.05 (m, 1H), 5.34 (s, 1H), 4.43 (s, 1H), 3.74 (s, 3H), 2.91-2.67 (m, 7H), 2.66-2.58 (m, 3H), 2.50 (dd, J = 12.8, 5.2 Hz, 1H), 2.37-2.24 (m, 1H), 2.02-1.83 (m, 5H), 1.75 (t, J = 17.7 Hz, 2H), 1.51 (ddd, J = 40.3, 25.2, 13.3 Hz, 7H), 1.26 (dt, J = 38.3, 12.2 Hz, 4H), 0.91-0.72 (m, 5H), 0.71-0.51 (m, 4H). |
| 143 | 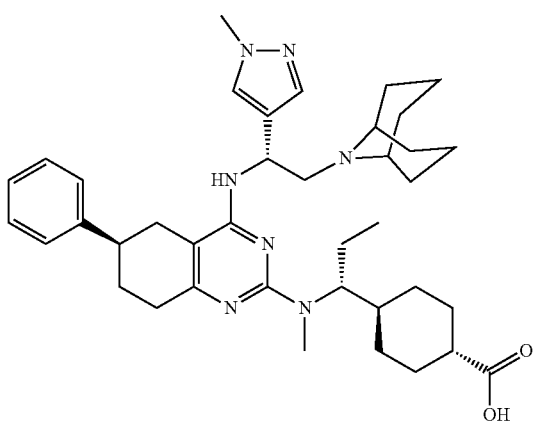 [SMILES: CC[C@H]([C@H]1CC[C@H](C(=O)O)CC1)N(C)c1nc2c(c(N[C@@H](CN3C4CCCC3CCC4)c3cnn(C)c3)n1)C[C@H](c1ccccc1)CC2] | LCMS m/z [M + H]+ = 654.7, 1H NMR (400 MHz, MeOD) δ 7.52 (s, 1H), 7.40 (s, 1H), 7.38-7.28 (m, 4H), 7.22 (dq, J = 5.6, 2.5 Hz, 1H), 5.28 (br s, 1H), 4.43 (br s, 1H), 3.85 (s, 3H), 3.23-3.07 (br m, 1H), 3.07-2.61 (m, 9H), 2.59-2.34 (m, 1H), 2.30-1.15 (m, 24H), 1.02-0.83 (m, 1H), 0.83-0.67 (m, 3H), 0.68-0.43 (m, 1H). |
| 175 | 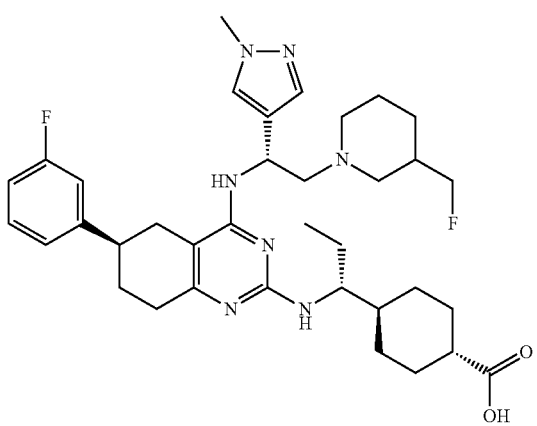 [SMILES: CC[C@@H](Nc1nc2c(c(N[C@@H](CN3CCCC(CF)C3)c3cnn(C)c3)n1)C[C@H](c1cccc(F)c1)CC2)[C@H]1CC[C@H](C(=O)O)CC1] | LCMS m/z [M + H]+ = 650.6, 1H NMR (400 MHz CD3OD) δ 7.42 (s, 1H), 7.30 (s, 1H), 7.27-7.18 (m, 1H), 7.10-6.95 (m, 1H), 6.91-6.80 (m, 1H), 5.52 (s, 1H), 4.25 (s, 1H), 4.21-4.03 (m, 2H), 3.74 (s, 3H), 2.98-2.51 (m, 9H), 2.36-2.22 (m, 1H), 2.10-1.74 (m, 10H), 1.65-1.52 (m, 4H), 1.51-1.11 (m, 6H), 1.07-0.86 (m, 3H), 0.83 (t, J = 7.2 Hz, 3H). |

Example 14: Synthesis of (1R,4r)-4-((R)-1-((6-phenyl-4-(((R)-1-phenyl-2-(pyrrolidin-1-yl)ethyl)amino)-5,6,7,8-tetrahydropyrido[4,3-d]pyrimidin-2-yl)amino)propyl)cyclohexane-1-carboxylic acid (Compound 131)

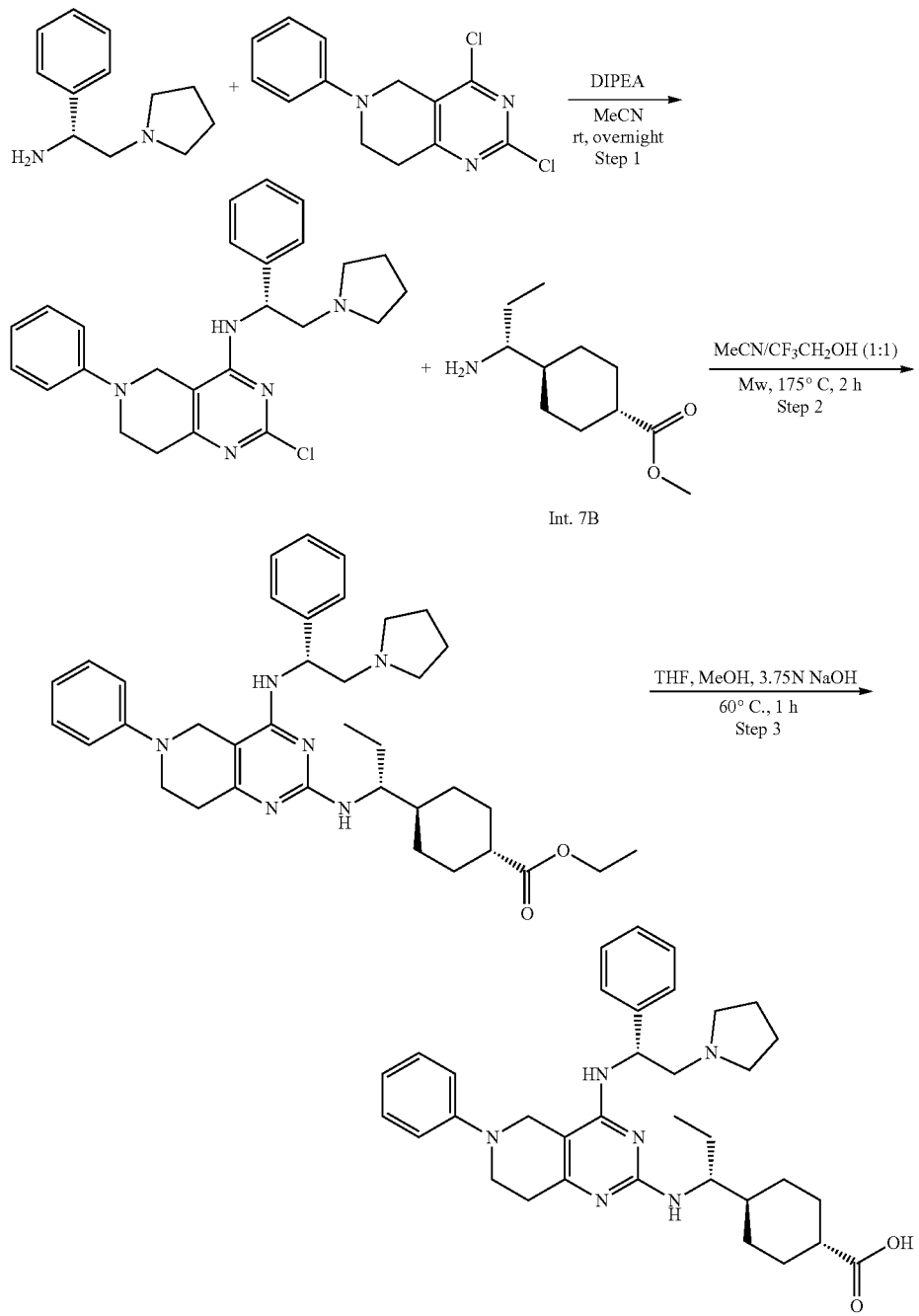

Step 1: (R)-1-phenyl-2-(pyrrolidin-1-yl)ethan-1-amine (230 mg, 0.874 mmol) and DIPEA (0.763 ml, 4.37 mmol) were combined with MeCN (3 ml) and then 2,4-dichloro-6-phenyl-5,6,7,8-tetrahydropyrido[4,3-d]pyrimidine (245 mg, 0.874 mmol) was added in one portion. The reaction was stirred at 70° C. overnight at which time LCMS indicated formation of desired product. It was concentrated under reduced pressure. The crude material was directly purified by ISCO combiflash chromatography (24 gram, 0-20% (0.1% ammonia in MeOH/DCM) to provide desired product (R)-2-chloro-6-phenyl-N-(1-phenyl-2-(pyrrolidin-1-yl)ethyl)-5,6,7,8-tetrahydropyrido[4,3-d]pyrimidin-4-amine (163 mg, 0.376 mmol, 43% yield). MS: m/z=434.1 [M+H]$^+$.

Step 2: To a microwave vial containing ethyl (1R,4r)-4-((R)-1-aminopropyl)cyclohexane-1-carboxylate (159 mg, 0.636 mmol) and ethyl (1R,4r)-4-((R)-1-aminopropyl)cyclohexane-1-carboxylate (138 mg, 0.318 mmol) were added MeCN (0.7 ml, Ratio: 1.000) and 2,2,2-trifluoroethanol (0.700 ml, Ratio: 1.000). The reaction was heated in a microwave reactor at 175° C. for 2 h at which time LCMS indicated formation of desired product. The reaction mixture was diluted with EtOAc, washed with saturated NaHCO$_3$, brine, dried over MgSO$_4$, and concentrated under reduced pressure to provide crude product. It was purified by ISCO combiflash chromatography (12 gram, 0-10% (0.1% ammonia in MeOH/DCM) to provide desired product ethyl (1R,4r)-4-((R)-1-((6-phenyl-4-(((R)-1-phenyl-2-(pyrrolidin-1-yl)ethyl)amino)-5,6,7,8-tetrahydropyrido[4,3-d]pyrimidin-2-yl)amino)propyl)cyclohexane-1-carboxylate (20 mg, 0.033 mmol, 10.3% yield). MS: m/z=611.3 [M+H]$^+$.

Step 3: To a vial containing ethyl (1R,4r)-4-((R)-1-((6-phenyl-4-(((R)-1-phenyl-2-(pyrrolidin-1-yl)ethyl)amino)-5,6,7,8-tetrahydropyrido[4,3-d]pyrimidin-2-yl)amino)propyl)cyclohexane-1-carboxylate (20 mg, 0.033 mmol) was added THF (1 mL, Ratio: 2), MeOH (0.500 mL, Ratio: 1.000) and then 3.75N NaOH (0.087 mL, 0.327 mmol). The mixture was agitated at 60° C. for 1 h at which point LCMS indicated formation of desired product. The reaction mixture was cooled to room temperature and concentrated under reduced pressure. The resulting residue was diluted with ACN, water and MeOH and purified via basic prep HPLC (25-50%-Acetonitrile/Water, 5 mM NH$_{40}$H, wavelength 393, low threshold). Desired fractions were combined and lyophilized to provide with desired product (1R,4r)-4-((R)-1-((6-phenyl-4-(((R)-1-phenyl-2-(pyrrolidin-1-yl)ethyl)amino)-5,6,7,8-tetrahydropyrido[4,3-d]pyrimidin-2-yl)amino)propyl)cyclohexane-1-carboxylic acid (9.3 mg, 0.014 mmol, 44.1% yield). MS: m/z=583.2 [M+H]+; $^1$H NMR (400 MHz, Methanol-d4) δ 7.31-7.00 (m, 10H), 6.76 (tt, J=7.2, 1.0 Hz, 1H), 5.33 (dd, J=10.7, 3.9 Hz, 1H), 4.13-3.88 (m, 2H), 3.66-3.52 (m, 1H), 3.50-3.33 (m, 2H), 3.10 (dd, J=12.7, 10.8 Hz, 1H), 2.63-2.51 (m, 6H), 1.89-1.80 (m, 1H), 1.77-1.67 (m, 6H), 1.56-1.47 (m, 2H), 1.39-1.32 (m, 1H), 1.27-1.10 (m, 4H), 0.84-0.72 (m, 4H), 0.65-0.49 (m, 1H).

Example 15: Syntheis of (1R,4r)-4-((R)-1-(((R)-4-(((R)-2-(4-fluoropiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid (Compound 142)

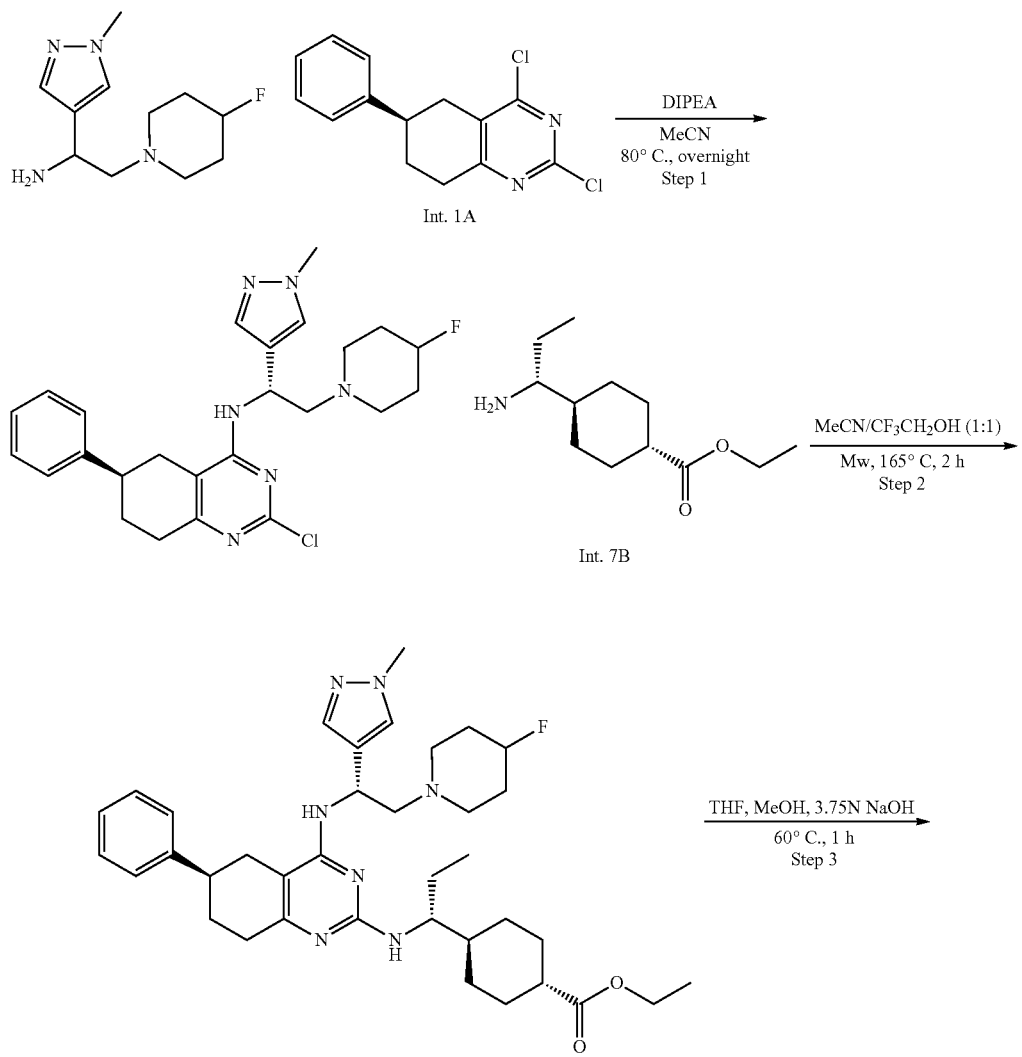

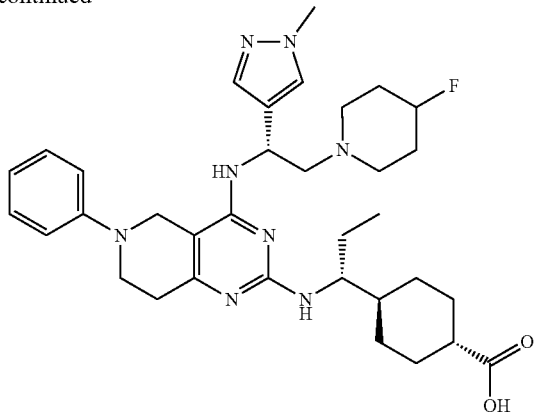

Step 1: A solution of (R)-2,4-dichloro-6-phenyl-5,6,7,8-tetrahydroquinazoline (740 mg, 2.65 mmol), 2-(4-fluoropiperidin-1-yl)-1-(1-methyl-1H-pyrazol-4-yl)ethan-1-amine bis-hydrochloride (720 mg, 3.18 mmol, prepared according to intermediate 8) and DIPEA (1.389 ml, 7.95 mmol) in MeCN (10 ml) was heated at 80° C. overnight at which time LCMS indicated formation of desired product. The reaction mixture was concentrated under reduced pressure, partitioned between EtOAc and water. The organic phase was washed with saturated NaHCO₃ solution, washed with brine and dried over MgSO₄. The solid was filtered off and the resulting solution was concentrated under reduced pressure. It was purified by ISCO combiflash chromatography (40 gram, 0-100% (10% MeOH in DCM/DCM) to provide desired product (6R)-2-chloro-N-(2-(4-fluoropiperidin-1-yl)-1-(1-methyl-1H-pyrazol-4-yl)ethyl)-6-phenyl-5,6,7,8-tetrahydroquinazolin-4-amine (480 mg, 1.023 mmol, 38.6% yield). MS: m/z=469.2 [M+H]+.

Step 2: To a microwave vial containing ethyl (1R,4r)-4-((R)-1-aminopropyl)cyclohexane-1-carboxylate (213 mg, 0.853 mmol) and (6R)-2-chloro-N-(2-(4-fluoropiperidin-1-yl)-1-(1-methyl-1H-pyrazol-4-yl)ethyl)-6-phenyl-5,6,7,8-tetrahydroquinazolin-4-amine (200 mg, 0.426 mmol) were added MeCN (1 ml, Ratio: 1.000) and 2,2,2-Trifluoroethanol (1 ml, Ratio: 1.000). The reaction was heated in a microwave reactor at 165° C. for 1.5 h at which time LCMS indicated formation of desired product. The reaction mixture was diluted with EtOAc, washed with saturated NaHCO₄, brine and dried over MgSO₄, and concentrated under reduced pressure. It was purified by ISCO combiflash chromatography (24 gram, 0-20% (0.1% ammonia in MeOH/DCM) to provide desired product ethyl (1R,4r)-4-((1R)-1-(((6R)-4-((2-(4-fluoropiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylate (109 mg, 0.169 mmol, 39.6% yield). MS: m/z=646.4 [M+H]+.

Step 3: To a vial containing ethyl (1R,4r)-4-((1R)-1-(((6R)-4-((2-(4-fluoropiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylate (109 mg, 0.169 mmol) was added THF (1 mL, Ratio: 2), MeOH (0.500 mL, Ratio: 1.000) and then 3.75N NaOH (0.450 mL, 1.688 mmol). The mixture was agitated at 60° C. for 1 h at which time LCMS indicated formation of desired product. The reaction mixture was cooled to room temperature and concentrated under reduced pressure. The resulting residue was diluted with ACN, water and MeOH and purified via basic prep HPLC (15-40%-Acetonitrile/Water, 5 mM NH₄₀H, wavelength 396, mass detector). Desired fractions were combined and lyophilized to provide with desired product (31 mg, 0.046 mmol, 27.2% yield). MS: m/z=618.3 [M+H]+; ¹H NMR (400 MHz, Methanol-d4) δ 7.42 (s, 1H), 7.30 (d, J=0.8 Hz, 1H), 7.27-7.20 (m, 4H), 7.17-7.09 (m, 1H), 5.49 (dd, J=9.7, 5.0 Hz, 1H), 4.63-4.44 (m, 1H), 3.74 (s, 3H), 2.97-2.78 (m, 2H), 2.70-2.42 (m, 7H), 2.38-2.27 (m, 2H), 2.08-1.52 (m, 13H), 1.45-1.22 (m, 4H), 1.02-0.86 (m, 2H), 0.83 (t, J=7.3 Hz, 3H).

The following compounds were made using the above procedure or modifications to the above procedure using the corresponding intermediates.

| 22 | 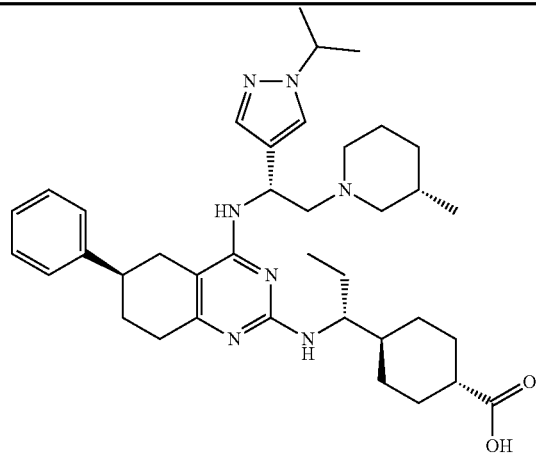 | LCMS m/z [M + H]⁺ = 642.4, ¹H NMR (400 MHz, Methanol-d4) δ 7.62 (s, 1H), 7.50-7.40 (m, 1H), 7.38-7.30 (m, 4H), 7.24 (ddt, J = 8.6, 5.4, 2.6 Hz, 1H), 5.70 (dd, J = 10.0, 4.7 Hz, 1H), 4.51-4.40 (m, 1H), 3.89 (s, 1H), 3.14-2.93 (m, 3H), 2.91-2.59 (m, 5H), 2.42 (dd, J = 15.8, 11.0 Hz, 1H), 2.19-1.91 (m, 6H), 1.84 (t, J = 10.4 Hz, 2H), 1.77-1.60 (m, 5H), 1.60-1.30 (m, 11H), 1.18-0.98 (m, 2H), 0.95 (t, J = 7.3 Hz, 4H), 0.88 (d, J = 6.4 Hz, 3H). |
|---|---|---|

| | | |
|---|---|---|
| 32 | 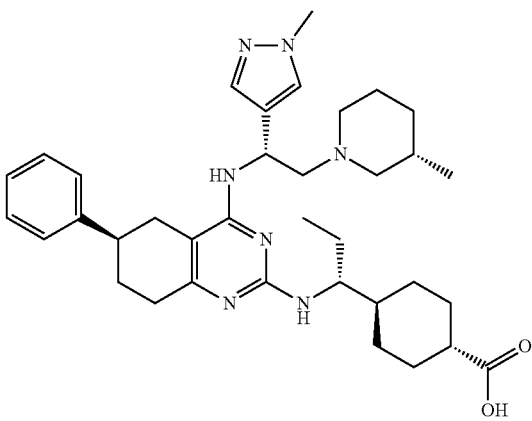 [SMILES: CC[C@@H](Nc1nc2c(c(N[C@@H](CN3CCC[C@H](C)C3)c3cnn(C)c3)n1)C[C@H](c1ccccc1)CC2)[C@H]1CC[C@H](C(=O)O)CC1] | LCMS m/z [M + H]⁺ = 614.4, ¹H NMR (400 MHz, Methanol-d4) δ 7.42 (s, 1H), 7.29 (d, J = 4.8 Hz, 1H), 7.26-7.16 (m, 4H), 7.12 (tt, J = 6.2, 2.8 Hz, 1H), 5.55 (dd, J = 10.2, 4.9 Hz, 1H), 3.73 (s, 4H), 2.99-2.42 (m, 8H), 2.29 (dd, J = 15.9, 11.2 Hz, 1H), 2.03-1.10 (m, 18H), 1.04-0.52 (m, 9H). |
| 38 | 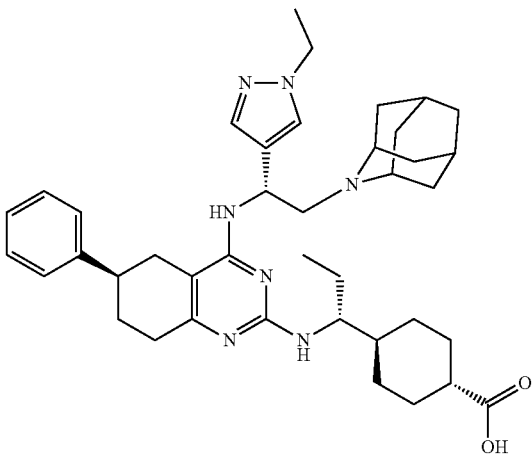 [SMILES: CC[C@@H](Nc1nc2c(c(N[C@@H](CN3C4CC5CC(C4)CC3C5)c3cnn(CC)c3)n1)C[C@H](c1ccccc1)CC2)[C@H]1CC[C@H](C(=O)O)CC1] | LCMS m/z [M + H]⁺ = 666.5, ¹H NMR (400 MHz, MeOD) δ 7.52 (s, 1H), 7.37 (s, 1H), 7.23 (q, J = 4.1 Hz, 4H), 7.11 (ddt, J = 8.4, 5.5, 2.6 Hz, 1H), 4.03 (q, J = 7.3 Hz, 2H), 3.71 (dt, J = 9.7, 4.9 Hz, 1H), 3.01-2.81 (m, 3H), 2.61 (dt, J = 15.8, 10.0 Hz, 3H), 2.35 (d, J = 13.4 Hz, 1H), 2.17-1.74 (m, 14H), 1.74-1.48 (m, 7H), 1.31 (t, J = 7.3 Hz, 8H), 0.82 (t, J = 7.3 Hz, 6H). |
| 45 | 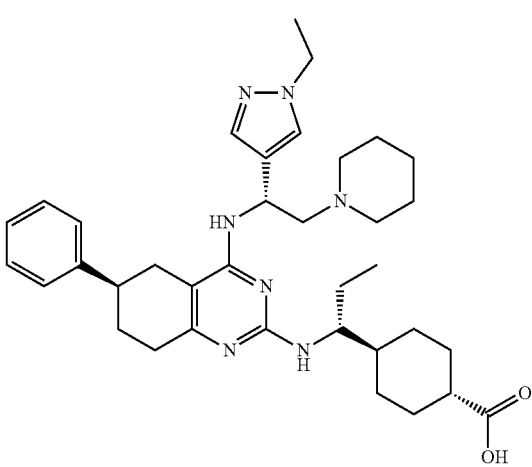 [SMILES: CC[C@@H](Nc1nc2c(c(N[C@@H](CN3CCCCC3)c3cnn(CC)c3)n1)C[C@H](c1ccccc1)CC2)[C@H]1CC[C@H](C(=O)O)CC1] | LCMS m/z [M + H]⁺ = 614.4, ¹H NMR (400 MHz, MeOD) δ 7.55 (s, 1H), 7.43 (s, 1H), 7.39-7.29 (m, 4H), 7.28-7.18 (m, 1H), 5.63 (dd, J = 9.8, 4.8 Hz, 1H), 4.14 (q, J = 7.3 Hz, 2H), 3.84 (s, 1H), 3.05-2.89 (m, 2H), 2.76 (dd, J = 15.8, 5.4 Hz, 2H), 2.70-2.55 (m, 4H), 2.54-2.36 (m, 3H), 2.15-1.91 (m, 5H), 1.82 (d, J = 12.9 Hz, 1H), 1.75-1.54 (m, 6H), 1.51-1.39 (m, 8H), 1.11-1.00 (m, 2H), 0.94 (t, J = 7.3 Hz, 3H). |

| | | |
|---|---|---|
| 58 | 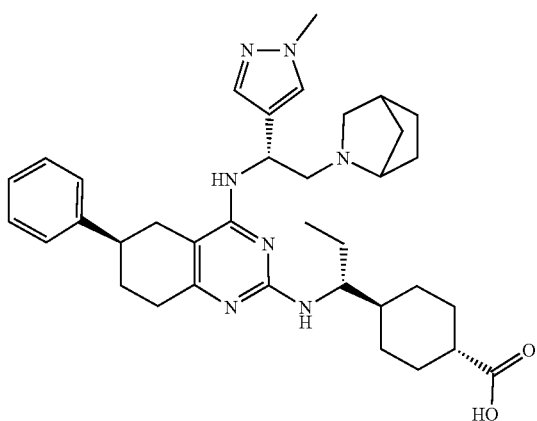 [SMILES: CC[C@@H](Nc1nc2c(c(N[C@@H](CN3CC4CCC3C4)c3cnn(C)c3)n1)C[C@H](c1ccccc1)CC2)[C@H]1CC[C@H](C(=O)O)CC1] | LCMS m/z [M + H]⁺ = 612.4, ¹H NMR (400 MHz, MeOD) δ 7.52 (d, J = 3.3 Hz, 1H), 7.42 (d, J = 4.1 Hz, 1H), 7.34 (d, J = 6.4 Hz, 3H), 7.21 (d, J = 7.1 Hz, 1H), 5.53 (s, 1H), 3.83 (d, J = 14.4 Hz, 4H), 3.55 (s, 1H), 2.96 (d, J = 10.8 Hz, 3H), 2.82-2.57 (m, 3H), 2.52-2.28 (m, 3H), 2.14-1.87 (m, 6H), 1.85-1.60 (m, 6H), 1.59-1.26 (m, 7H), 1.15-0.97 (m, 2H), 0.93 (t, J = 7.4 Hz, 3H). |
| 71 | 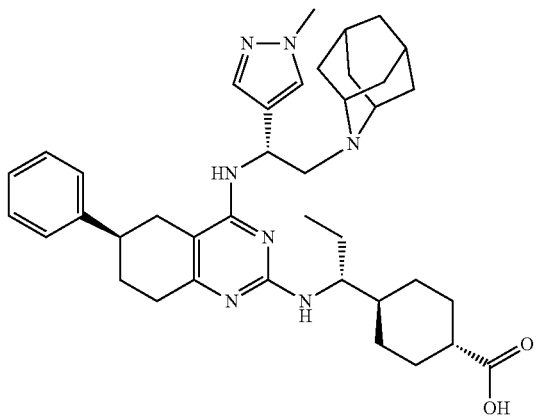 [SMILES: CC[C@@H](Nc1nc2c(c(N[C@@H](CN3C4CC5CC(C4)CC3C5)c3cnn(C)c3)n1)C[C@H](c1ccccc1)CC2)[C@H]1CC[C@H](C(=O)O)CC1] | LCMS m/z [M + H]⁺ = 652.4, ¹H NMR (400 MHz, Methanol-d4) δ 7.51 (dd, J = 40.1, 8.4 Hz, 2H), 7.38-7.02 (m, 5H), 5.42 (s, 1H), 3.91-3.73 (m, 4H), 3.19-2.85 (m, 4H), 2.82-2.58 (m, 3H), 2.45 (dd, J = 15.8, 10.6 Hz, 1H), 2.25-1.53 (m, 21H), 1.49-1.24 (m, 4H), 1.09 (dtd, J = 18.9, 13.8, 13.4, 9.9 Hz, 2H), 0.83 (t, J = 7.5 Hz, 3H) |
| 84 | 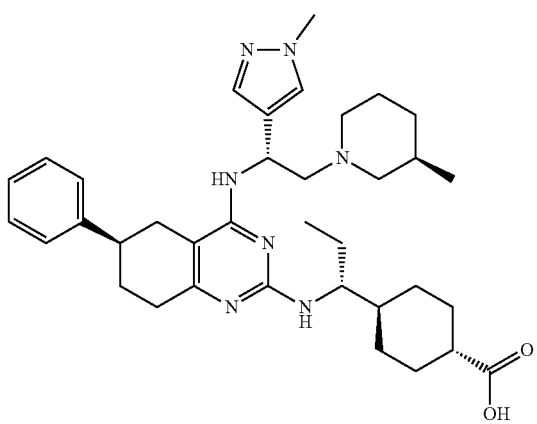 [SMILES: CC[C@@H](Nc1nc2c(c(N[C@@H](CN3CCC[C@@H](C)C3)c3cnn(C)c3)n1)C[C@H](c1ccccc1)CC2)[C@H]1CC[C@H](C(=O)O)CC1] | LCMS m/z [M + H]⁺ = 614.34, ¹H NMR (400 MHz, MeOD) δ 7.42 (s, 1H), 7.37-7.22 (m, 5H), 7.13 (qt, J = 5.3, 2.8 Hz, 1H), 5.55 (s, 1H), 3.74 (s, 4H), 2.99-2.50 (m, 8H), 2.43-2.24 (m, 1H), 2.14-1.16 (m, 20H), 0.89-0.74 (m, 7H). |

| | | |
|---|---|---|
| 86 | 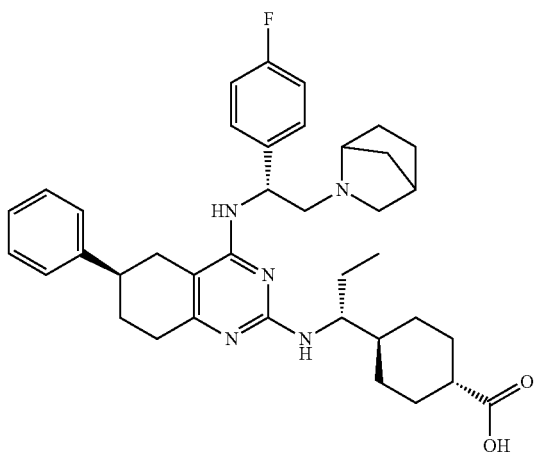 [SMILES: CC[C@@H](Nc1nc2c(c(N[C@@H](CN3CC4CCC3C4)c3ccc(F)cc3)n1)C[C@H](c1ccccc1)CC2)[C@H]1CC[C@H](C(=O)O)CC1] | LCMS m/z [M + H]⁺ = 626.3, ¹H NMR (400 MHz, Methanol-d4) δ 7.34-7.18 (m, 6H), 7.11 (tq, J = 6.4, 2.2 Hz, 1H), 7.02-6.90 (m, 2H), 5.24 (s, 1H), 3.59 (ddt, J = 9.1, 6.1, 2.9 Hz, 1H), 3.40 (s, 1H), 3.03-2.79 (m, 3H), 2.75-2.49 (m, 3H), 2.36 (q, J = 12.1, 10.9 Hz, 3H), 2.10-1.07 (m, 19H), 0.81 (t, J = 7.3 Hz, 5H). |
| 90 | 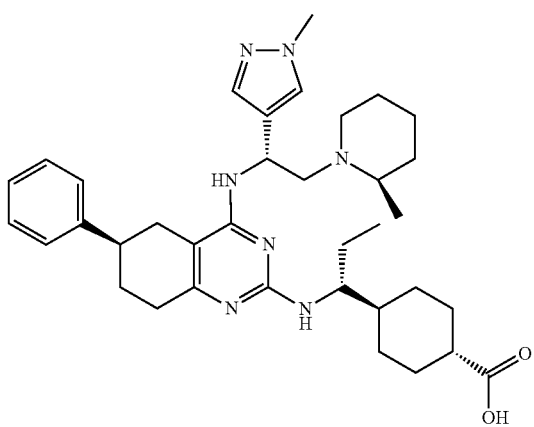 [SMILES: CC[C@@H](Nc1nc2c(c(N[C@@H](CN3CCCC[C@H]3C)c3cnn(C)c3)n1)C[C@H](c1ccccc1)CC2)[C@H]1CC[C@H](C(=O)O)CC1] | LCMS m/z [M + H]⁺ = 614.4, ¹H NMR (400 MHz, MeOD) δ 7.48 (s, 1H), 7.40 (d, J = 0.8 Hz, 1H), 7.38-7.30 (m, 4H), 7.27-7.17 (m, 1H), 5.63 (dd, J = 10.2, 4.1 Hz, 1H), 3.85 (s, 4H), 3.19 (dd, J = 13.6, 10.3 Hz, 1H), 3.10-2.93 (m, 2H), 2.80-2.29 (m, 7H), 2.12-1.87 (m, 5H), 1.80 (d, J = 12.9 Hz, 1H), 1.75-1.56 (m, 5H), 1.55-1.26 (m, 7H), 1.17-0.98 (m, 5H), 0.93 (t, J = 7.3 Hz, 3H). |
| 95 | 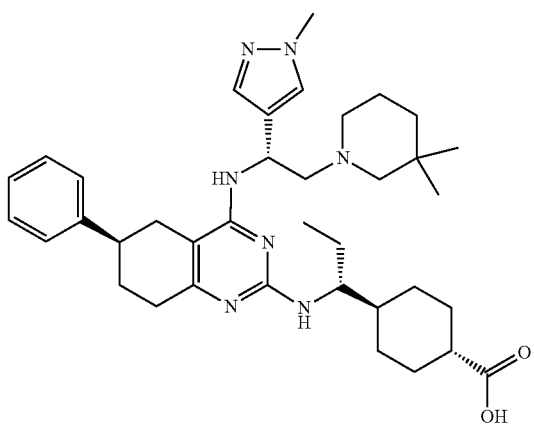 [SMILES: CC[C@@H](Nc1nc2c(c(N[C@@H](CN3CCCC(C)(C)C3)c3cnn(C)c3)n1)C[C@H](c1ccccc1)CC2)[C@H]1CC[C@H](C(=O)O)CC1] | LCMS m/z [M + H]⁺ = 628.4, ¹H NMR (400 MHz, Methanol-d4) δ 7.42 (s, 1H), 7.31 (s, 1H), 7.23 (d, J = 4.9 Hz, 4H), 7.18-7.07 (m, 1H), 5.42 (d, J = 8.2 Hz, 1H), 3.74 (s, 4H), 2.86 (tdd, J = 11.3, 5.2, 2.8 Hz, 1H), 2.77-2.51 (m, 4H), 2.45 (dd, J = 12.7, 5.5 Hz, 1H), 2.38-2.20 (m, 3H), 2.17-1.78 (m, 7H), 1.75-1.52 (m, 3H), 1.50-1.20 (m, 6H), 1.15-1.04 (m, 2H), 1.00-0.81 (m, 5H), 0.76 (d, J = 8.4 Hz, 6H). |

| | | |
|---|---|---|
| 96 | 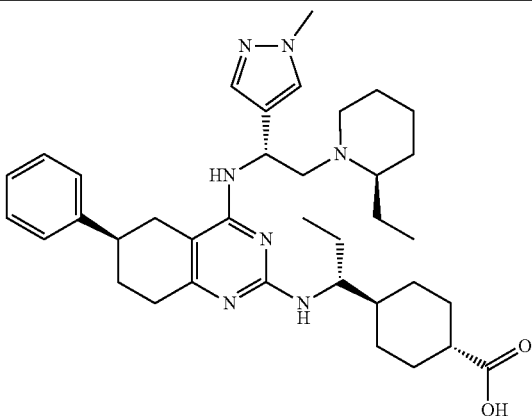 | LCMS m/z [M + H]⁺ = 628.4, ¹H NMR (400 MHz, MeOD) δ 7.55-7.24 (m, 6H), 6.98 (dt, J = 8.6, 4.2 Hz, 1H), 5.76 (s, 1H), 3.75 (d, J = 2.3 Hz, 4H), 3.06-2.84 (m, 2H), 2.63-2.16 (m, 2H), 2.16-0.48 (m, 34H). |
| 123 | 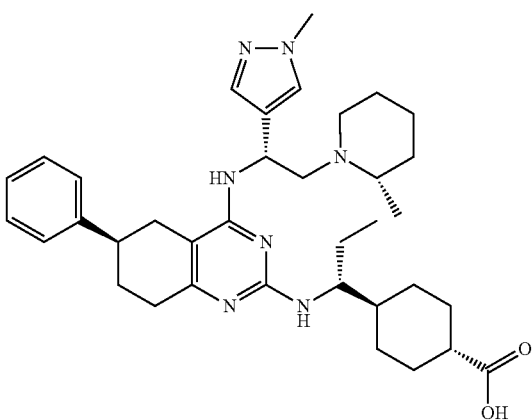 [SMILES: CC[C@@H](Nc1nc2c(c(N[C@@H](CN3CCCC[C@@H]3C)c3cnn(C)c3)n1)C[C@H](c1ccccc1)CC2)[C@H]1CC[C@H](C(=O)O)CC1] | LCMS m/z [M + H]⁺ = 614.3, ¹H NMR (400 MHz, MeOD) δ 7.50 (s, 1H), 7.43 (s, 1H), 7.39-7.30 (m, 4H), 7.21 (ddd, J = 8.5, 6.0, 2.2 Hz, 1H), 5.60 (dd, J = 7.6, 5.8 Hz, 1H), 3.85 (s, 4H), 3.11-2.81 (m, 4H), 2.77-2.33 (m, 6H), 2.17-1.88 (m, 5H), 1.81 (d, J = 12.9 Hz, 1H), 1.75-1.23 (m, 12H), 1.16-1.00 (m, 5H), 0.94 (t, J = 7.3 Hz, 3H). |
| 49 | 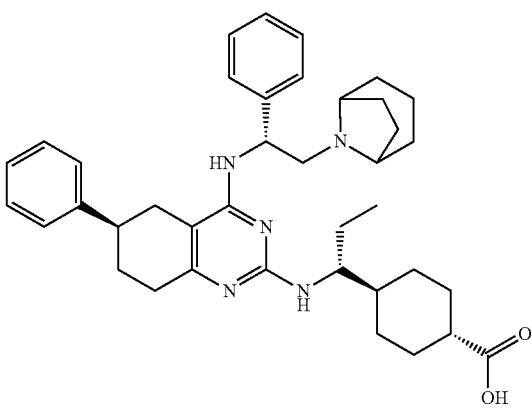 [SMILES: CC[C@@H](Nc1nc2c(c(N[C@@H](CN3C4CCCC3CC4)c3ccccc3)n1)C[C@H](c1ccccc1)CC2)[C@H]1CC[C@H](C(=O)O)CC1] | LCMS m/z [M + H]⁺ = 623.0, ¹H NMR (400 MHz, Methanol-d4) δ 7.39-7.27 (m, 8H), 7.27-7.19 (m, 2H), 5.13 (s, 1H), 4.65 (s, 1H), 3.59 (ddd, J = 10.0, 6.3, 3.8 Hz, 1H), 3.22-3.10 (m, 1H), 3.01 (tdd, J = 11.2, 5.3, 2.9 Hz, 1H), 2.81 (tq, J = 10.3, 5.1 Hz, 3H), 2.72-2.60 (m, 2H), 2.53 (dd, J = 15.5, 11.0 Hz, 1H), 2.15-2.06 (m, 1H), 2.06-1.88 (m, 4H), 1.83-1.51 (m, 9H), 1.47-1.14 (m, 8H), 0.90 (t, J = 7.3 Hz, 3H), 0.85-0.72 (m, 1H), 0.66-0.48 (m, 1H). |
| 56 | 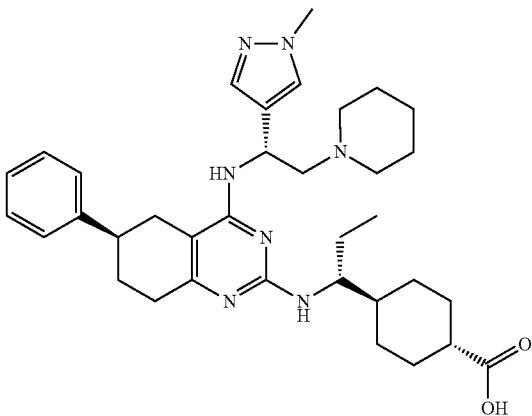 [SMILES: CC[C@@H](Nc1nc2c(c(N[C@@H](CN3CCCCC3)c3cnn(C)c3)n1)C[C@H](c1ccccc1)CC2)[C@H]1CC[C@H](C(=O)O)CC1] | LCMS m/z [M + H]⁺ = 600.3, ¹H NMR (400 MHz, DMSO-d6) δ 7.48 (s, 1H), 7.40-7.26 (m, 5H), 7.26-7.19 (m, 1H), 6.12 (d, J = 8.0 Hz, 1H), 5.81 (s, 1H), 5.40 (q, J = 7.6 Hz, 1H), 3.74 (s, 3H), 3.68-3.61 (m, 1H), 3.17 (s, 1H), 2.87 (tq, J = 9.0, 4.5 Hz, 1H), 2.70-2.52 (m, 3H), 2.48-2.32 (m, 5H), 2.22 (dd, J = 15.6, 11.3 Hz, 1H), 1.94-1.84 (m, 2H), 1.78 (d, J = 12.7 Hz, 2H), 1.72-1.58 (m, 3H), 1.56-1.39 (m, 5H), 1.38-1.21 (m, 4H), 1.20-1.00 (m, 2H), 0.98-0.72 (m, 5H). |

| | | |
|---|---|---|
| 60 | 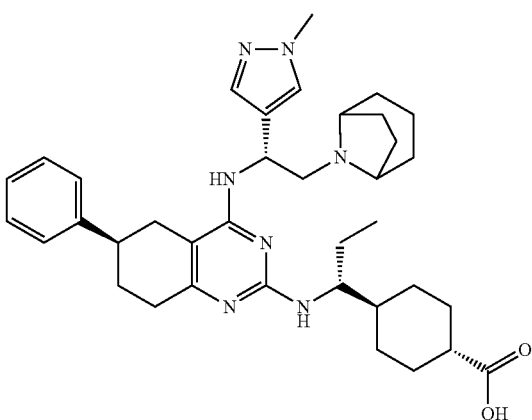 [SMILES: CC[C@@H](Nc1nc2c(c(N[C@@H](CN3C4CCCC3CC4)c3cnn(C)c3)n1)C[C@H](c1ccccc1)CC2)[C@H]1CC[C@H](C(=O)O)CC1] | LCMS m/z [M + H]⁺ = 626.4, ¹H NMR (400 MHz, Methanol-d4) δ 7.50 (s, 1H), 7.41 (s, 1H), 7.35-7.28 (m, 4H), 7.23-7.17 (m, 1H), 5.46-5.34 (m, 1H), 3.84-3.74 (m, 4H), 3.29-3.25 (m, 2H), 2.97 (tdd, J = 11.2, 5.2, 2.7 Hz, 1H), 2.85 (q, J = 8.0, 7.4 Hz, 2H), 2.76-2.56 (m, 3H), 2.41 (dd, J = 15.5, 11.0 Hz, 1H), 2.12-1.86 (m, 7H), 1.81-1.53 (m, 8H), 1.47-1.30 (m, 7H), 1.10-0.95 (m, 2H), 0.91 (t, J = 7.3 Hz, 3H). |
| 151 | 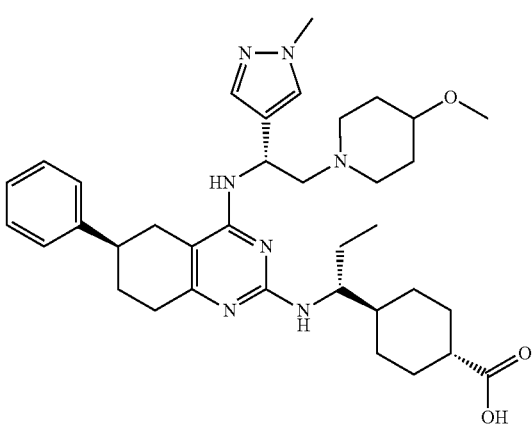 [SMILES: CC[C@@H](Nc1nc2c(c(N[C@@H](CN3CCC(OC)CC3)c3cnn(C)c3)n1)C[C@H](c1ccccc1)CC2)[C@H]1CC[C@H](C(=O)O)CC1] | LCMS m/z [M + H]⁺ = 630.3, ¹H NMR (400 MHz, Methanol-d4) δ 7.49 (s, 1H), 7.39 (s, 1H), 7.37-7.29 (m, 4H), 7.21 (tt, J = 6.4, 2.1 Hz, 1H), 5.57 (dd, J = 9.8, 4.9 Hz, 1H), 3.87-3.72 (m, 4H), 3.30 (s, 3H), 3.28-3.22 (m, 1H), 3.01-2.86 (m, 3H), 2.82-2.55 (m, 5H), 2.38 (dd, J = 14.8, 10.9 Hz, 2H), 2.24 (t, J = 10.6 Hz, 1H), 2.14-1.84 (m, 7H), 1.78 (d, J = 12.7 Hz, 1H), 1.71-1.61 (m, 2H), 1.58-1.24 (m, 6H), 1.10-0.95 (m, 2H), 0.92 (t, J = 7.3 Hz, 3H). |
| 61 | 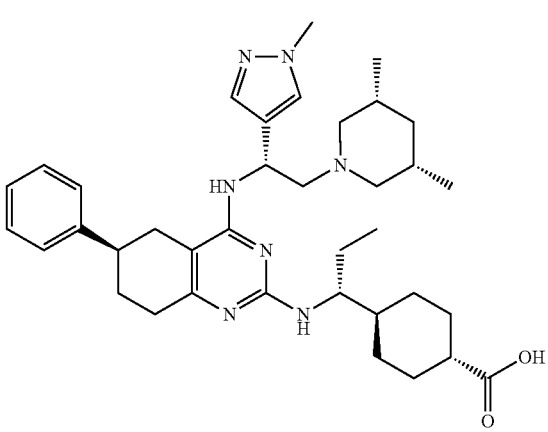 [SMILES: CC[C@@H](Nc1nc2c(c(N[C@@H](CN3C[C@H](C)C[C@H](C)C3)c3cnn(C)c3)n1)C[C@H](c1ccccc1)CC2)[C@H]1CC[C@H](C(=O)O)CC1] | LCMS m/z [M + H]⁺ = 628.4, ¹H NMR (400 MHz, Methanol-d4) δ 7.41 (s, 1H), 7.30 (d, J = 0.8 Hz, 1H), 7.28-7.17 (m, 4H), 7.11 (ddd, J = 8.6, 5.7, 2.7 Hz, 1H), 5.53 (dd, J = 9.8, 4.9 Hz, 1H), 3.73 (s, 4H), 2.96-2.74 (m, 4H), 2.71-2.45 (m, 4H), 2.29 (dd, J = 15.7, 11.1 Hz, 1H), 2.07-1.77 (m, 5H), 1.60 (ddd, J = 44.7, 33.6, 11.2 Hz, 8H), 1.44-1.14 (m, 4H), 1.02-0.87 (m, 2H), 0.84 (t, J = 7.3 Hz, 3H), 0.75 (d, J = 5.7 Hz, 6H), 0.53-0.34 (m, 1H). |

| | | |
|---|---|---|
| 121 | 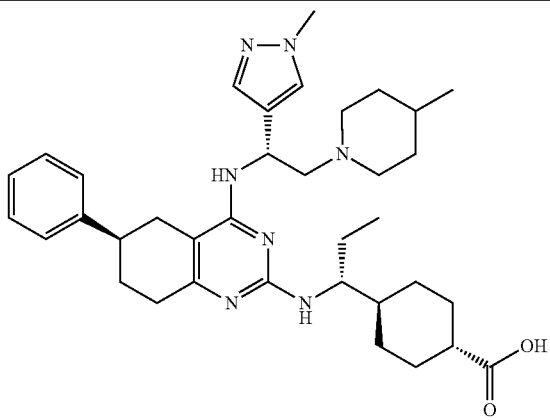 | LCMS m/z [M + H]⁺ = 614.3, ¹H NMR (400 MHz, Methanol-d4) δ 7.44 (s, 1H), 7.31 (s, 1H), 7.24 (q, J = 4.0, 2.9 Hz, 4H), 7.13 (td, J = 5.9, 2.8 Hz, 1H), 5.58 (s, 1H), 3.74 (s, 4H), 3.10-2.79 (m, 4H), 2.79-2.51 (m, 4H), 2.41-2.27 (m, 1H), 2.27-1.77 (m, 7H), 1.57 (d, J = 13.4 Hz, 5H), 1.50-0.90 (m, 9H), 0.83 (d, J = 6.5 Hz, 6H). |
| 85 | 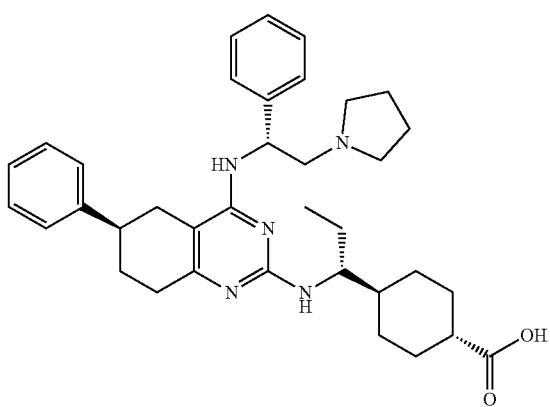 | LCMS m/z [M + H]⁺ = 582.8, ¹H NMR (400 MHz, DMSO) δ 7.43-7.30 (m, 6H), 7.25 (t, J = 7.4 Hz, 3H), 7.16 (t, J = 7.2 Hz, 1H), 6.43 (d, J = 7.2 Hz, 1H), 5.87 (s, 1H), 5.25 (s, 1H), 3.61 (s, 1H), 2.91 (ddd, J = 14.7, 11.3, 7.4 Hz, 2H), 2.67-2.38 (m, 9H), 2.31 (dd, J = 15.7, 11.4 Hz, 1H), 2.03-1.85 (m, 3H), 1.79 (d, J = 14.6 Hz, 2H), 1.67-1.42 (m, 6H), 1.37-1.01 (m, 4H), 0.81 (t, J = 7.2 Hz, 5H). |
| 115 | 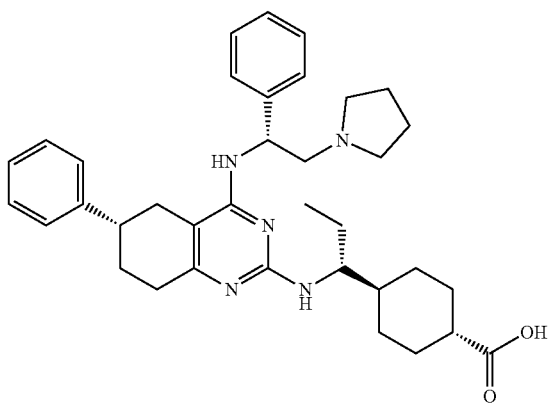 [SMILES: CC[C@@H](Nc1nc2c(c(N[C@@H](CN3CCCC3)c3ccccc3)n1)C[C@@H](c1ccccc1)CC2)[C@H]1CC[C@H](C(=O)O)CC1] | LCMS m/z [M + H]⁺ = 582.6, ¹H NMR (400 MHz, DMSO) δ 7.42-7.30 (m, 6H), 7.30-7.20 (m, 3H), 7.16 (t, J = 7.2 Hz, 1H), 6.37 (d, J = 7.3 Hz, 1H), 5.79 (s, 1H), 5.26 (s, 1H), 3.61 (d, J = 8.5 Hz, 1H), 2.96-2.81 (m, 2H), 2.67 (dd, J = 15.7, 5.3 Hz, 1H), 2.61-2.36 (m, 6H), 2.25 (dd, J = 15.6, 11.3 Hz, 1H), 1.92 (td, J = 9.9, 4.9 Hz, 3H), 1.78 (d, J = 13.8 Hz, 2H), 1.69-1.40 (m, 7H), 1.37-1.05 (m, 5H), 0.93-0.51 (m, 5H). |
| 119 | 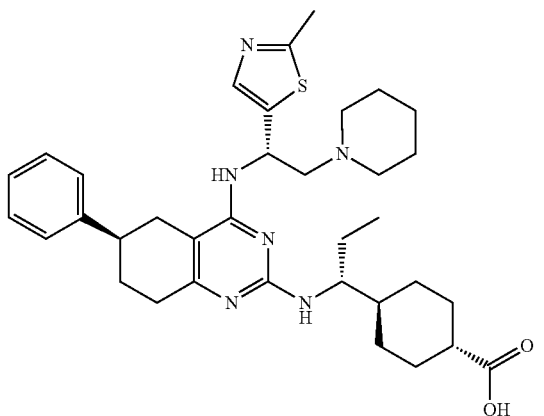 [SMILES: CC[C@@H](Nc1nc2c(c(N[C@@H](CN3CCCCC3)c3cnc(C)s3)n1)C[C@H](c1ccccc1)CC2)[C@H]1CC[C@H](C(=O)O)CC1] | LCMS m/z [M + H]⁺ = 617.4, ¹H NMR (400 MHz, DMSO) δ 7.37-7.21 (m, 5H), 7.18-7.09 (m, 1H), 6.43 (s, 1H), 5.85 (s, 1H), 5.52 (s, 1H), 3.51 (s, 1H), 2.81 (s, 1H), 2.63-2.35 (m, 8H), 2.32-2.11 (m, 4H), 1.85 (s, 3H), 1.72 (s, 2H), 1.55 (s, 2H), 1.39 (d, J = 5.5 Hz, 5H), 1.26 (d, J = 33.9 Hz, 5H), 1.05 (s, 2H), 0.73 (t, J = 7.2 Hz, 5H). |

| | | |
|---|---|---|
| 139 | 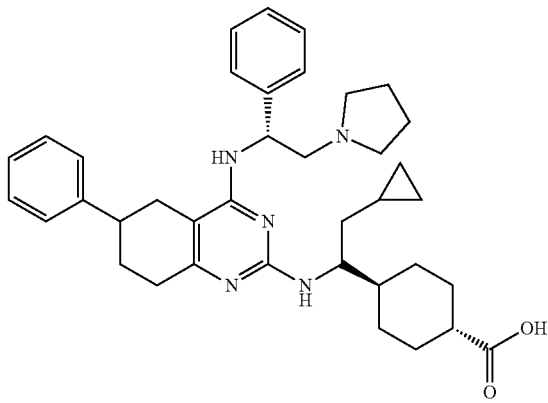 [SMILES: O=C(O)[C@H]1CC[C@H](C(CC2CC2)Nc2nc3c(c(N[C@@H](CN4CCCC4)c4ccccc4)n2)CC(c2ccccc2)CC3)CC1] | LCMS m/z [M + H]⁺ = 608.7, Rt = 0.94 min (Method: A: 5mM Ammonium Hydroxide in Water, B: 5mM Ammonium Hydroxide in ACN, pH 10.2, 50° C., 2-98% B. AcQuity UPLC BEH C18 1.7 μm 2.1 × 30 mm, 1 mL/min ) |
| 158 | 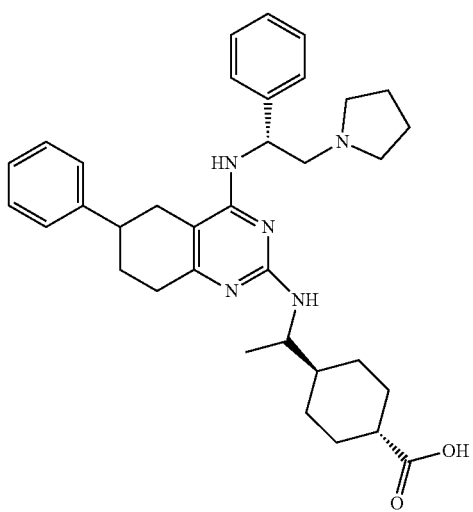 [SMILES: CC(Nc1nc2c(c(N[C@@H](CN3CCCC3)c3ccccc3)n1)CC(c1ccccc1)CC2)[C@H]1CC[C@H](C(=O)O)CC1] | LCMS m/z [M + H]⁺ = 568.4, $^1$H NMR (400 MHz, Methanol-d4) δ 7.42-7.16 (m, 10H), 5.55-5.33 (m, 1H), 3.82 (td, J = 9.3, 8.0, 5.7 Hz, 1H), 3.06-2.29 (m, 10H), 2.10-1.75 (m, 10H), 1.66-1.18 (m, 5H), 1.18-0.84 (m, 5H). |
| 24 | 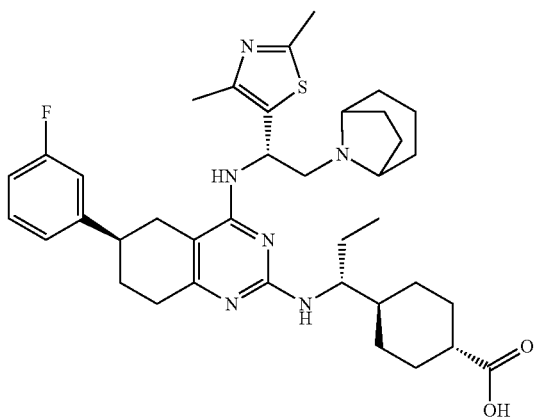 [SMILES: CC[C@@H](Nc1nc2c(c(N[C@@H](CN3C4CCCC3CC4)c3sc(C)nc3C)n1)C[C@H](c1cccc(F)c1)CC2)[C@H]1CC[C@H](C(=O)O)CC1] | LCMS m/z [M + H]⁺ = 675.6, $^1$H NMR (400 MHz, MeOD) δ 7.25 (td, J = 8.1, 6.1 Hz, 1H), 7.10-7.04 (m, 1H), 7.00 (dt, J = 10.3, 2.2 Hz, 1H), 6.86 (td, J = 8.6, 2.7 Hz, 1H), 5.65-5.24 (m, 1H), 3.86-3.58 (m, 1H), 2.95 (dddd, J = 11.3, 8.3, 5.2, 2.7 Hz, 1H), 2.77 (d, J = 7.0 Hz, 2H), 2.73-2.54 (m, 3H), 2.48 (s, 3H), 2.43-2.25 (m, 4H), 2.14-1.12 (m, 24H), 1.00 (qt, J = 12.7, 6.4 Hz, 2H), 0.64 (t, J = 7.3 Hz, 3H). |

| | | |
|---|---|---|
| 26 | 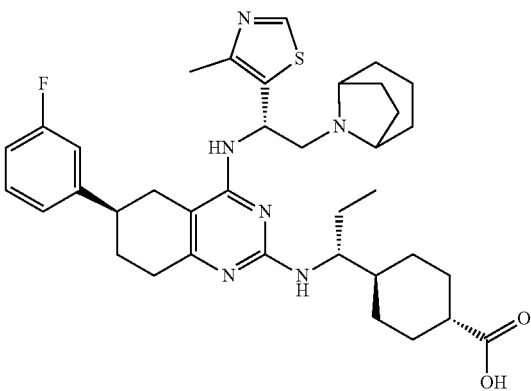 [SMILES: CC[C@@H](Nc1nc2c(c(N[C@@H](CN3C4CCCC3CC4)c3scnc3C)n1)C[C@H](c1cccc(F)c1)CC2)[C@H]1CC[C@H](C(=O)O)CC1] | LCMS m/z [M + H]⁺ = 661.4, ¹H NMR (400 MHz, MeOD) δ 8.81 (s, 1H), 7.35 (td, J = 8.0, 6.1 Hz, 1H), 7.17 (d, J = 7.9 Hz, 1H), 7.11 (dt, J = 10.3, 2.2 Hz, 1H), 7.02-6.91 (m, 1H), 5.45 (s, 1H), 3.83-3.58 (m, 1H), 3.23-3.14 (m, 1H), 3.11-2.98 (m, 1H), 2.95-2.61 (m, 5H), 2.56-2.38 (m, 4H), 2.24-1.81 (m, 7H), 1.81-1.50 (m, 8H), 1.50-1.17 (m, 8H), 0.93 (t, J = 7.3 Hz, 4H), 0.82-0.54 (m, 1H). |
| 73 | 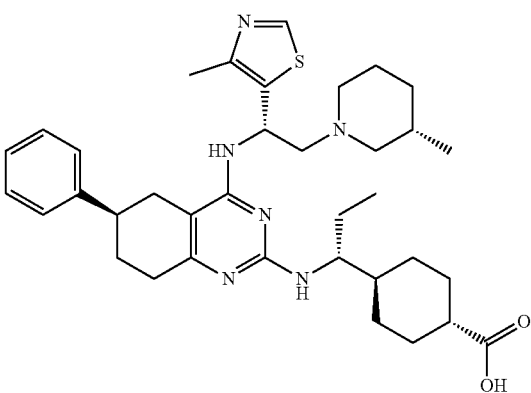 [SMILES: CC[C@@H](Nc1nc2c(c(N[C@@H](CN3CCC[C@H](C)C3)c3scnc3C)n1)C[C@H](c1ccccc1)CC2)[C@H]1CC[C@H](C(=O)O)CC1] | LCMS m/z [M + H]⁺ = 631.5, ¹H NMR (400 MHz, MeOD) δ 8.69 (s, 1H), 7.29-7.19 (m, 4H), 7.12 (dt, J = 5.8, 2.9 Hz, 1H), 5.45 (dd, J = 9.5, 5.3 Hz, 1H), 3.56 (ddd, J = 10.2, 6.6, 4.0 Hz, 1H), 2.99-2.26 (m, 12H), 2.08-1.09 (m, 18H), 1.00-0.69 (m, 8H), 0.70-0.49 (m, 1H). |
| 114 | 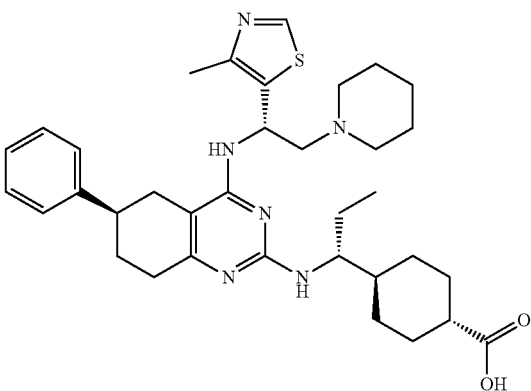 [SMILES: CC[C@@H](Nc1nc2c(c(N[C@@H](CN3CCCCC3)c3scnc3C)n1)C[C@H](c1ccccc1)CC2)[C@H]1CC[C@H](C(=O)O)CC1] | LCMS m/z [M + H]⁺ = 617.5, ¹H NMR (400 MHz, MeOD) δ 8.68 (s, 1H), 7.29-7.19 (m, 4H), 7.14 (dt, J = 6.1, 3.2 Hz, 1H), 5.69 (s, 1H), 3.70 (s, 1H), 2.90 (ddt, J = 8.3, 5.3, 2.5 Hz, 1H), 2.82 (dd, J = 12.9, 9.7 Hz, 1H), 2.75-2.28 (m, 12H), 1.96 (dtd, J = 31.6, 13.0, 7.8 Hz, 5H), 1.83-1.66 (m, 2H), 1.58-1.15 (m, 11H), 1.10-0.91 (m, 2H), 0.63 (t, J = 7.3 Hz, 3H). |
| 127 | 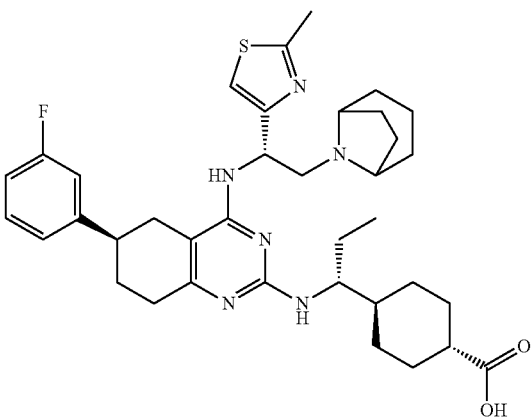 [SMILES: CC[C@@H](Nc1nc2c(c(N[C@@H](CN3C4CCCC3CC4)c3csc(C)n3)n1)C[C@H](c1cccc(F)c1)CC2)[C@H]1CC[C@H](C(=O)O)CC1] | LCMS m/z [M + H]⁺ = 661.4, ¹H NMR (400 MHz, MeOD) δ 7.35 (td, J = 8.0, 6.1 Hz, 1H), 7.26-7.15 (m, 2H), 7.11 (dt, J = 10.3, 2.2 Hz, 1H), 6.96 (td, J = 8.5, 2.6 Hz, 1H), 5.61 (s, 1H), 3.72 (ddd, J = 9.8, 6.0, 3.8 Hz, 1H), 3.61-3.38 (m, 2H), 3.25-2.98 (m, 3H), 2.92-2.58 (m, 6H), 2.57-2.40 (m, 1H), 2.24-1.90 (m, 7H), 1.90-1.22 (m, 15H), 1.19-0.97 (m, 2H), 0.75 (s, 3H). |

| | | |
|---|---|---|
| 159 | 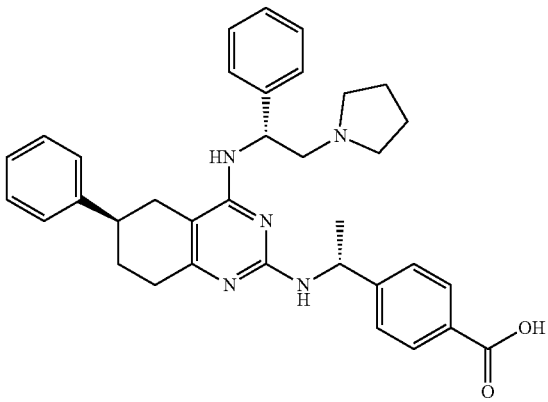 [SMILES: C[C@@H](Nc1nc2c(c(N[C@@H](CN3CCCC3)c3ccccc3)n1)C[C@H](c1ccccc1)CC2)c1ccc(C(=O)O)cc1] | LCMS m/z [M + H]⁺ = 562.6, ¹H NMR (400 MHz, DMSO) δ 7.77 (d, J = 8.1 Hz, 2H), 7.39-7.27 (m, 6H), 7.27-7.18 (m, 1H), 7.17-6.97 (m, 5H), 6.40 (d, J = 8.3 Hz, 1H), 5.29 (d, J = 7.1 Hz, 1H), 5.00 (t, J = 7.3 Hz, 1H), 2.96-2.76 (m, 3H), 2.66-2.53 (m, 3H), 2.49-2.40 (m, 3H), 2.29-2.07 (m, 1H), 2.00-1.74 (m, 2H), 1.72-1.56 (m, 4H), 1.38 (d, J = 7.0 Hz, 3H). |
| 160 | 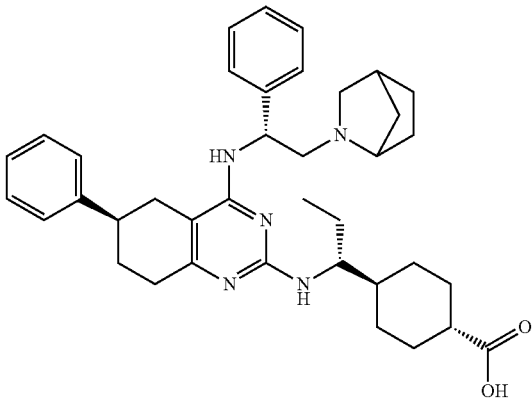 [SMILES: CC[C@@H](Nc1nc2c(c(N[C@@H](CN3CC4CCC3C4)c3ccccc3)n1)C[C@H](c1ccccc1)CC2)[C@H]1CC[C@H](C(=O)O)CC1] | LCMS m/z [M + H]⁺ = 607.8, ¹H NMR (400 MHz, MeOD) δ 7.34-7.16 (m, 8H), 7.12 (dtd, J = 4.7, 2.6, 1.3 Hz, 2H), 5.15 (dd, J = 10.0, 4.1 Hz, 1H), 3.56 (ddd, J = 9.7, 5.8, 4.0 Hz, 1H), 3.32 (s, 1H), 2.97-2.71 (m, 4H), 2.71-2.35 (m, 4H), 2.26 (dd, J = 19.3, 8.5 Hz, 2H), 2.11-0.87 (m, 20H), 0.50 (t, J = 7.2 Hz, 3H). |
| 168 | 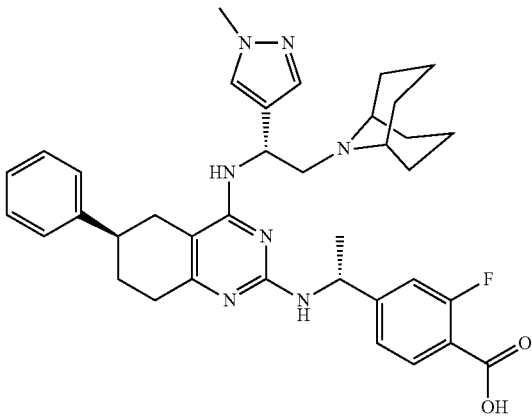 [SMILES: C[C@@H](Nc1nc2c(c(N[C@@H](CN3C4CCCC3CCC4)c3cnn(C)c3)n1)C[C@H](c1ccccc1)CC2)c1ccc(C(=O)O)c(F)c1] | LCMS m/z [M + H]⁺ = 638.4, ¹H NMR (400 MHz, MeOD) δ 7.60 (td, J = 7.8, 2.9 Hz, 1H), 7.37 (s, 1H), 7.34-7.24 (m, 4H), 7.24-7.14 (m, 1H), 7.14-6.92 (m, 3H), 5.47 (s, 1H), 5.14-4.93 (m, 1H), 3.75 (s, 3H), 3.6-3.1 (Signals for 5H overlap MeOD solvent peak), 3.04-2.83 (m, 1H), 2.82-2.53 (m, 3H), 2.39-2.27 (m, 1H), 2.26-1.86 (m, 8H), 1.87-1.54 (m, 5H), 1.49 (d, J = 6.9 Hz, 3H). |
| 59 | 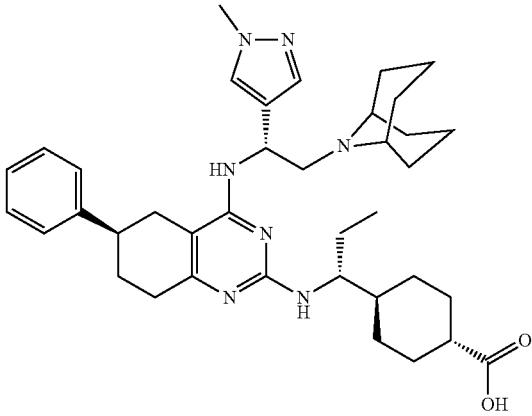 [SMILES: CC[C@@H](Nc1nc2c(c(N[C@@H](CN3C4CCCC3CCC4)c3cnn(C)c3)n1)C[C@H](c1ccccc1)CC2)[C@H]1CC[C@H](C(=O)O)CC1] | LCMS m/z [M + H]⁺ = 640.5, ¹H NMR (400 MHz, DMSO) δ 7.51 (s, 1H), 7.37-7.28 (m, 5H), 7.27-7.17 (m, 1H), 6.04 (s, 1H), 5.71 (s, 1H), 5.29-5.14 (m, 1H), 3.75 (s, 3H), 3.67-3.60 (m, 1H), 2.95-2.82 (m, 3H), 2.76-2.70 (m, 2H), 2.64-2.52 (m, 2H), 2.36-2.22 (m, 1H), 1.99-1.73 (m, 10H), 1.72-1.62 (m, 3H), 1.55-1.45 (m, 3H), 1.45-1.34 (m, 4H), 1.34-1.21 (m, 3H), 1.20-1.05 (m, 2H), 0.98-0.81 (m, 2H), 0.75 (t, J = 7.2 Hz, 3H). |

| | | |
|---|---|---|
| 65 | 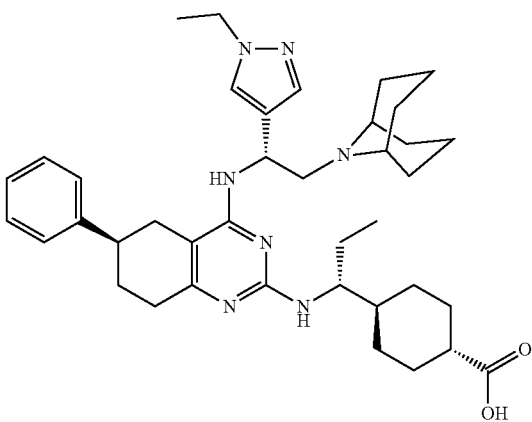 [SMILES: CC[C@@H](Nc1nc2c(c(N[C@@H](CN3C4CCCC3CCC4)c3cnn(CC)c3)n1)C[C@H](c1ccccc1)CC2)[C@H]1CC[C@H](C(=O)O)CC1] | LCMS m/z [M + H]⁺ = 654.7, ¹H NMR (400 MHz, DMSO) δ 7.54 (s, 1H), 7.42-7.30 (m, 5H), 7.27-7.15 (m, 1H), 6.03 (s, 1H), 5.70 (s, 1H), 5.16 (q, J = 7.2 Hz, 1H), 4.03 (q, J = 7.2 Hz, 2H), 3.63 (s, 1H), 2.91-2.79 (m, 3H), 2.73 (s, 2H), 2.68-2.55 (m, 2H), 2.36-2.18 (m, 1H), 2.00-1.74 (m, 10H), 1.68-1.60 (m, 3H), 1.56-1.47 (m, 3H), 1.44-1.37 (m, 4H), 1.35-1.24 (m, 6H), 1.17-1.06 (m, 2H), 0.96-0.74 (m, 5H). |
| 100 | 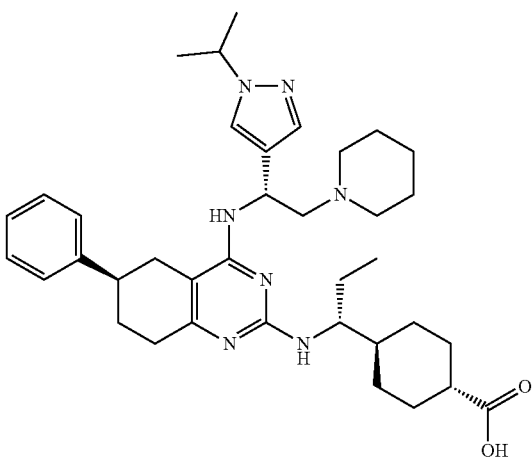 [SMILES: CC[C@@H](Nc1nc2c(c(N[C@@H](CN3CCCCC3)c3cnn(C(C)C)c3)n1)C[C@H](c1ccccc1)CC2)[C@H]1CC[C@H](C(=O)O)CC1] | LCMS m/z [M + H]+ = 628.6, ¹H NMR (400 MHz, DMSO) δ 7.53 (s, 1H), 7.41-7.29 (m, 5H), 7.27-7.16 (m, 1H), 6.12 (s, 1H), 5.78 (s, 1H), 5.49-5.39 (m, 1H), 4.49-4.29 (m, 1H), 3.78-3.63 (m, 1H), 2.95-2.85 (m, 1H), 2.75-2.66 (m, 2H), 2.61-2.52 (m, 3H), 2.45-2.37 (m, 3H), 2.29-2.19 (m, 1H), 2.02-1.78 (m, 5H), 1.74-1.64 (m, 2H), 1.56-1.39 (m, 5H), 1.37-1.28 (m, 10H), 1.25-1.11 (m, 3H), 1.04-0.91 (m, 2H), 0.81 (t, J = 7.2 Hz, 3H). |
| 108 | 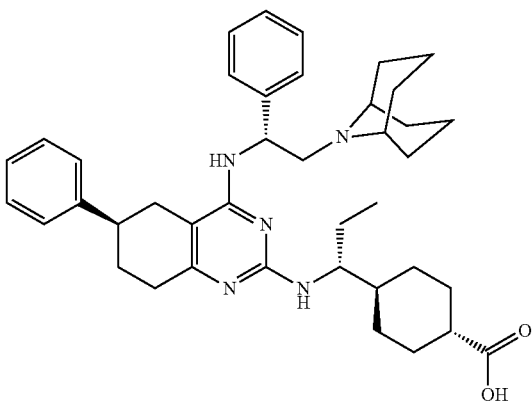 [SMILES: CC[C@@H](Nc1nc2c(c(N[C@@H](CN3C4CCCC3CCC4)c3ccccc3)n1)C[C@H](c1ccccc1)CC2)[C@H]1CC[C@H](C(=O)O)CC1] | LCMS m/z [M + H]⁺ = 636.7, ¹H NMR (400 MHz, DMSO) δ 7.42-7.30 (m, 6H), 7.29-7.21 (m, 3H), 7.19-7.08 (m, 1H), 6.32 (s, 1H), 5.69 (s, 1H), 5.09-4.84 (m, 1H), 3.08-2.86 (m, 2H), 2.82-2.52 (m, 5H), 2.45-2.28 (m, 2H), 2.01-1.58 (m, 12H), 1.55-1.31 (m, 10H), 1.30-0.83 (m, 5H), 0.78 (t, J = 7.3 Hz, 3H). |

| | | |
|---|---|---|
| 153 | 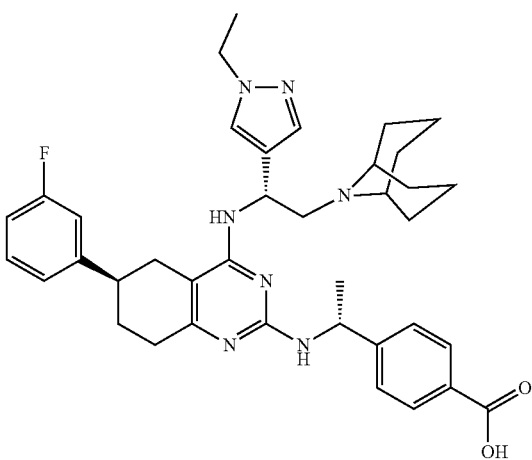 [SMILES: CCn1cc([C@H](CN2C3CCCC2CCC3)Nc2nc(N[C@H](C)c3ccc(C(=O)O)cc3)nc3c2C[C@H](c2cccc(F)c2)CC3)cn1] | LCMS m/z [M + H]⁺ = 652.3, ¹H NMR (400 MHz, MeOD) δ 7.94-7.84 (m, 2H), 7.36 (s, 1H), 7.29 (dd, J = 7.8, 3.8 Hz, 3H), 7.14-7.08 (m, 1H), 7.08-7.01 (m, 1H), 6.92 (ddd, J = 11.0, 8.4, 4.2 Hz, 2H), 5.48 (s, 2H), 5.29-5.23 (m, 1H), 5.07-5.01 (m, 1H), 4.03-3.92 (m, 2H), 3.21-2.82 (m, 5H), 2.76-2.56 (m, 3H), 2.36-2.25 (m, 1H), 2.14-1.85 (m, 9H), 1.68-1.54 (m, 5H), 1.47 (dd, J = 7.0, 1.2 Hz, 3H), 1.31 (td, J = 7.3, 1.0 Hz, 3H). |
| 171 | 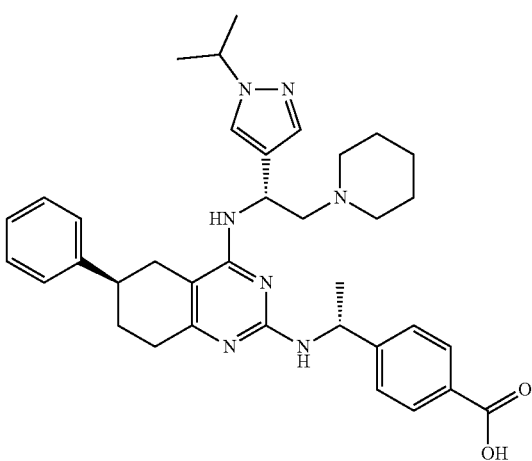 [SMILES: CC(C)n1cc([C@H](CN2CCCCC2)Nc2nc(N[C@H](C)c3ccc(C(=O)O)cc3)nc3c2C[C@H](c2ccccc2)CC3)cn1] | LCMS m/z [M + H]⁺ = 608.6, ¹H NMR (400 MHz, DMSO) δ 7.76 (d, J = 8.1 Hz, 2H), 7.38-7.12 (m, 9H), 6.62 (s, 1H), 6.12 (d, J = 8.4 Hz, 1H), 5.45-5.34 (m, 1H), 5.10-4.98 (m, 1H), 4.41-4.23 (m, 1H), 2.92-2.77 (m, 1H), 2.68-2.56 (m, 2H), 2.54 (s, 3H), 2.48-2.30 (m, 5H), 2.25-2.12 (m, 1H), 1.96-1.78 (m, 2H), 1.54-1.18 (m, 14H). |
| 2 | 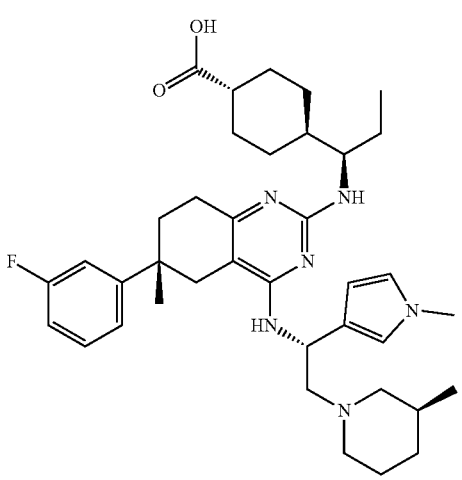 | LCMS m/z [M + H]⁺ = 646.3, ¹H NMR(400 MHz, DMSO-d6) δ 7.52 (s, 1H), 7.41-7.27 (m, 2H), 7.25-7.12 (m, 2H), 7.00 (dt, J = 2.1, 8.4 Hz, 1H), 6.46-6.22 (br s, 1H), 6.11 (br s, 1H), 5.45 (q, J = 7.4 Hz, 1H), 3.76 (s, 3H), 3.69-3.59 (m, 1H), 2.85 (br d, J = 9.4 Hz, 1H), 2.81-2.70 (m, 2H), 2.70-2.63 (m, 1H), 2.61-2.54 (m, 1H), 2.54-2.51 (m, 2H), 2.45-2.31 (m, 2H), 2.19-2.08 (m, 1H), 2.07-2.00 (m, 1H), 1.95 (m, 1H), 1.92-1.78 (m, 3H), 1.72-1.59 (m, 4H), 1.58-1.50 (m, 2H), 1.48-1.40 (m, 1H), 1.37-1.22 (m, 5H), 1.20-1.06 (m, 2H), 1.00-0.86 (m, 2H), 0.85-0.72 (m, 7H). |

| | | |
|---|---|---|
| 3 | 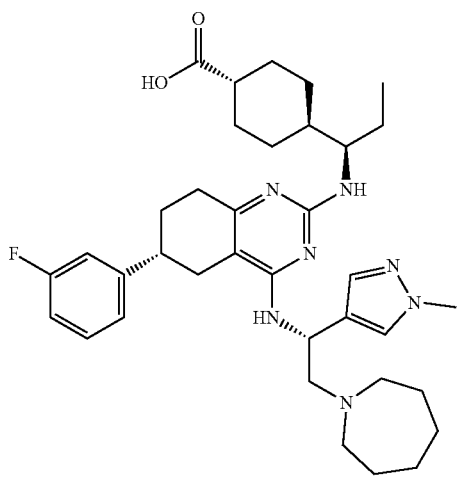 [SMILES: CC[C@@H](Nc1nc2c(c(N[C@@H](CN3CCCCCC3)c3cnn(C)c3)n1)C[C@H](c1cccc(F)c1)CC2)[C@H]1CC[C@H](C(=O)O)CC1] | LCMS m/z [M + H]⁺ = 632.5 , ¹H NMR(400 MHz, DMSO-d6) δ 7.46 (s, 1H), 7.40-7.33 (m, 1H), 7.33-7.31 (m, 1H), 7.19 (d, J = 7.8 Hz, 1H), 7.14 (br d, J = 10.5 Hz, 1H), 7.01 (dt, J = 1.9, 8.6 Hz, 1H), 5.81 (br d, J = 7.6 Hz, 1H), 5.36-5.27 (m, 2H), 3.76 (s, 3H), 3.75-3.68 (m, 1H), 3.03-2.93 (m, 2H), 2.92-2.76 (m, 3H), 2.69 (br t, J = 5.1 Hz, 4H), 2.66-2.58 (m, 2H), 2.33 (br dd, J = 11.2, 15.2 Hz, 1H), 2.09-1.98 (m, 2H), 1.89 (br dd, J = 6.2, 11.8 Hz, 3H), 1.74 (br t, J = 12.8 Hz, 2H), 1.52 (br s, 8H), 1.46-1.33 (m, 2H), 1.33-1.18 (m, 2H), 1.08-0.95 (m, 2H), 0.86 (t, J = 7.3 Hz, 3H). |
| 5 | 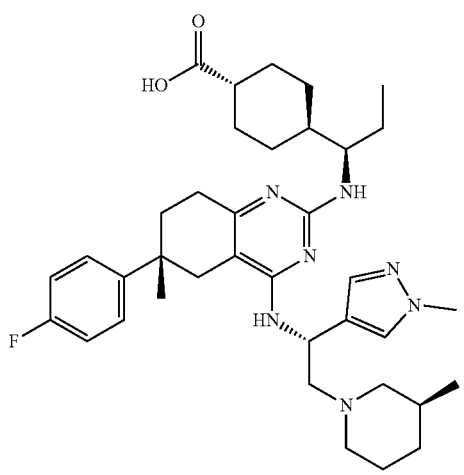 | LCMS m/z [M + H]⁺ = 646.6, ¹H NMR(400 MHz, DMSO-d6) δ 7.53 (s, 1H), 7.38 (m, 2H), 7.34 (s, 1H), 7.11 (t, J = 8.8 Hz, 2H), 6.37 (br s, 1H), 6.20 (br s, 1H), 5.44 (q, J = 7.1 Hz, 1H), 3.77 (s, 3H), 3.65 (br s, 1H), 2.85 (br d, J = 10.3 Hz, 1H), 2.81-2.61 (m, 3H), 2.57 (br dd, J = 7.5, 12.2 Hz, 2H), 2.44-2.30 (m, 2H), 2.19-1.88 (m, 4H), 1.87-1.77 (m, 3H), 1.74-1.50 (m, 6H), 1.49-1.28 (m, 4H), 1.25 (s, 3H), 1.21-1.06 (m, 2H), 1.02-0.87 (m, 2H), 0.81 (br d, J = 6.4 Hz, 6H) |
| 10 | 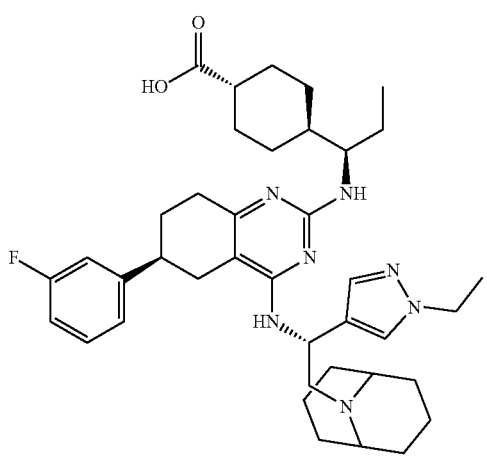 [SMILES: CC[C@@H](Nc1nc2c(c(N[C@@H](CN3C4CCCC3CCC4)c3cnn(CC)c3)n1)C[C@@H](c1cccc(F)c1)CC2)[C@H]1CC[C@H](C(=O)O)CC1] | LCMS m/z [M + H]⁺ = 672.7, ¹H NMR(400 MHz, DMSO-d6) δ 7.55 (br s, 1H), 7.40-7.33 (m, 2H), 7.20-7.15 (m, 2H), 7.07-7.00 (m, 1H), 6.22-6.02 (m, 1H), 5.20-5.13 (m, 1H), 4.03 (q, J = 7.2 Hz, 2H), 3.00-2.90 (m, 2H), 2.90-2.83 (m, 2H), 2.72 (br s, 2H), 2.63-2.54 (m, 3H), 2.43 (br d, J = 1.6 Hz, 1H), 2.28 (br dd, J = 11.2, 15.0 Hz, 1H), 2.04-1.89 (m, 4H), 1.84 (br dd, J = 6.3, 11.7 Hz, 8H), 1.65 (br d, J = 0.9 Hz, 2H), 1.54-1.45 (m, 3H), 1.43-1.33 (m, 5H), 1.30 (t, J = 7.3 Hz, 4H), 1.24-1.13 (m, 2H), 0.98-0.87 (m, 2H), 0.80 (t, J = 7.2 Hz, 3H). |

| | | |
|---|---|---|
| 15 | 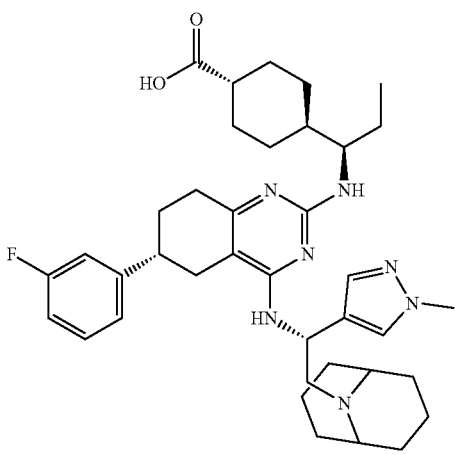 [SMILES: CC[C@@H](Nc1nc2c(c(N[C@@H](CN3C4CCCC3CCC4)c3cnn(C)c3)n1)C[C@H](c1cccc(F)c1)CC2)[C@H]1CC[C@H](C(=O)O)CC1] | LCMS m/z [M + H]⁺ = 658.4, ¹H NMR(400 MHz, DMSO-d6) δ 7.49 (s, 1H), 7.42-7.34 (m, 1H), 7.31 (s, 1H), 7.19 (br d, J = 7.8 Hz, 2H), 7.08-7.00 (m, 1H), 6.27-5.88 (m, 2H), 5.14 (q, J = 7.0 Hz, 1H), 3.74 (s, 3H), 3.62 (br dd, J = 1.3, 3.6 Hz, 2H), 3.00-2.80 (m, 4H), 2.73 (br s, 2H), 2.66-2.54 (m, 2H), 2.34-2.21 (m, 1H), 2.10-1.76 (m, 11H), 1.65 (br d, J = 8.8 Hz, 2H), 1.57-1.46 (m, 3H), 1.45-1.35 (m, 4H), 1.34-1.25 (m, 2H), 1.24-1.09 (m, 2H), 0.92 (br dd, J = 1.6, 7.1 Hz, 2H), 0.80 (br t, J = 7.2 Hz, 3H) |
| 17 | 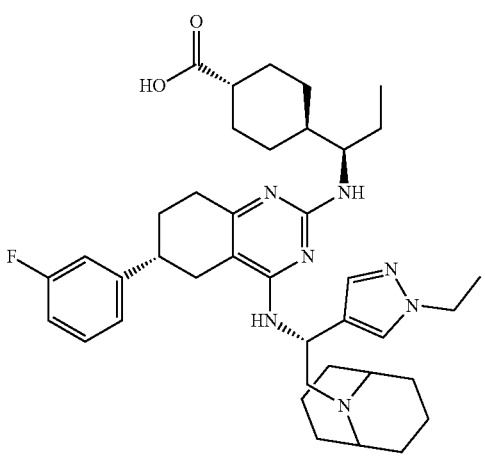 [SMILES: CC[C@@H](Nc1nc2c(c(N[C@@H](CN3C4CCCC3CCC4)c3cnn(CC)c3)n1)C[C@H](c1cccc(F)c1)CC2)[C@H]1CC[C@H](C(=O)O)CC1] | LCMS m/z [M + H]⁺ = 672.7, ¹H NMR(400 MHz, DMSO-d6) δ 7.54 (br s, 1H), 7.40-7.31 (m, 2H), 7.19 (d, J = 7.7 Hz, 2H), 7.08-7.00 (m, 1H), 6.22-6.00 (m, 1H), 5.98-5.77 (m, 1H), 5.16 (q, J = 7.2 Hz, 1H), 4.03 (q, J = 7.3 Hz, 2H), 2.99-2.90 (m, 2H), 2.72 (br s, 3H), 2.63(br d, J = 5.3 Hz, 2H), 2.59 (br d, J = 4.9 Hz, 2H), 2.26 (br dd, J = 12.0, 14.7 Hz, 1H), 1.99-1.89 (m, 4H), 1.89-1.77 (m, 8H), 1.70-1.60 (m, 2H), 1.54-1.35 (m, 8H), 1.30 (t, J = 7.3 Hz, 5H), 1.22-1.12 (m, 2H), 0.98-0.87 (m, 2H), 0.79 (t, J = 7.3 Hz, 3H). |
| 20 | 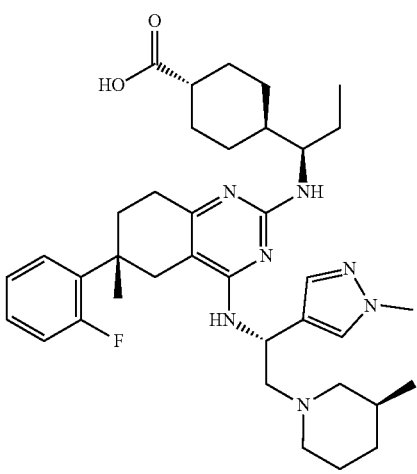 [SMILES: CC[C@@H](Nc1nc2c(c(N[C@@H](CN3CCC[C@H](C)C3)c3cnn(C)c3)n1)C[C@](C)(c1ccccc1F)CC2)[C@H]1CC[C@H](C(=O)O)CC1] | LCMS m/z [M + H]⁺ = 646.3, ¹H NMR(400 MHz, DMSO-d6) § 7.55 (s, 1H), 7.35 (s, 1H), 7.30-7.23 (m, 1H), 7.19-7.04 (m, 3H), 6.40-6.25 (m, 1H), 6.08-5.85 (m, 1H), 5.44 (q, J = 7.6 Hz, 1H), 3.78 (s, 3H), 3.69-3.61 (m, 1H), 2.85 (br d, J = 15.8 Hz, 2H), 2.78 (br d, J = 10.5 Hz, 1H), 2.71-2.65 (m, 1H), 2.61-2.56 (m, 1H), 2.53 (d, J = 1.9 Hz, 1H), 2.45-2.37 (m, 2H), 2.36-2.31 (m, 1H), 2.30-2.21 (m, 1H), 2.10-1.98 (m, 2H), 1.97-1.90 (m, 1H), 1.89-1.78 (m, 3H), 1.72-1.60 (m, 4H), 1.59-1.51 (m, 2H), 1.46 (dt, J = 4.0, 6.9 Hz, 1H), 1.36 (s, 3H), 1.34-1.26 (m, 1H), 1.25-1.07 (m, 2H), 1.00-0.88 (m, 2H), 0.86-0.72 (m, 7H). |

| | | |
|---|---|---|
| 30 | 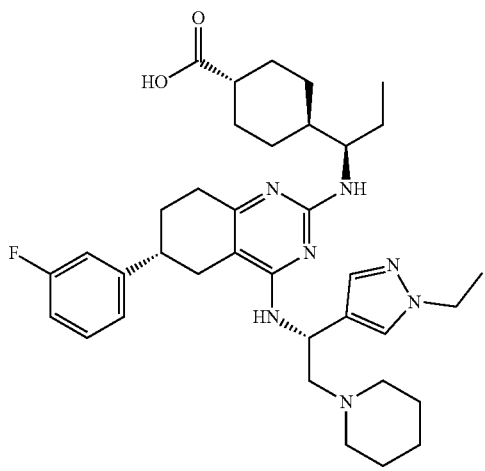 [SMILES: CC[C@@H](Nc1nc2c(c(N[C@@H](CN3CCCCC3)c3cnn(CC)c3)n1)C[C@H](c1cccc(F)c1)CC2)[C@H]1CC[C@H](C(=O)O)CC1] | LCMS m/z [M + H]⁺ = 632.6, ¹H NMR(400 MHz, DMSO-d6) δ 7.54-7.49 (m, 1H), 7.40-7.33 (m, 1H), 7.31 (s, 1H), 7.20 (d, J = 7.6 Hz, 2H), 7.07-7.00 (m, 1H), 6.19-6.10 (m, 1H), 5.93-5.75 (m, 1H), 5.47-5.38 (m, 1H), 4.07-3.99 (m, 2H), 3.71-3.64 (m, 1H), 2.96-2.90 (m, 1H), 2.70-2.64 (m, 2H), 2.39 (br s, 4H), 2.30-2.17 (m, 2H), 2.00-1.80 (m, 6H), 1.72-1.63 (m, 2H), 1.42 (br d, J = 4.4 Hz, 6H), 1.37-1.28 (m, 8H), 1.22-1.14 (m, 2H), 1.00-0.91 (m, 2H), 0.83-0.78 (m, 3H). |
| 117 | 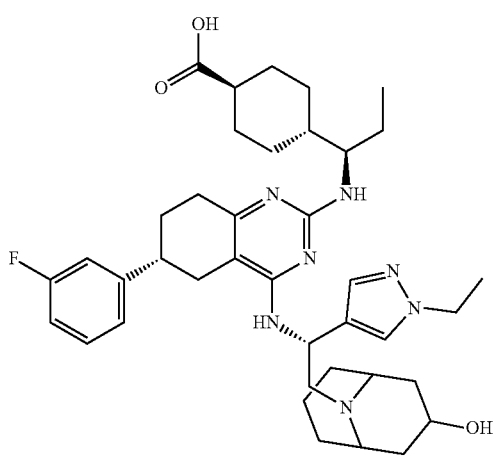 [SMILES: CC[C@@H](Nc1nc2c(c(N[C@@H](CN3C4CCCC3CC(O)C4)c3cnn(CC)c3)n1)C[C@H](c1cccc(F)c1)CC2)[C@H]1CC[C@H](C(=O)O)CC1] | LCMS m/z [M + H]⁺ = 688.6, ¹H NMR(400 MHz, DMSO-d6) δ 7.53 (br d, J = 7.5 Hz, 1H), 7.42-7.30 (m, 2H), 7.19 (br d, J = 9.3 Hz, 2H), 7.09-7.00 (m, 1H), 6.27-6.08 (m, 1H), 5.29-5.16 (m, 1H), 4.43-4.26 (m, 1H), 4.09-3.99 (m, 2H), 3.80-3.73 (m, 1H), 3.69-3.64 (m, 1H), 2.94 (br s, 2H), 2.83-2.77 (m, 2H), 2.61 (br d, J = 4.2 Hz, 4H), 2.30-2.15 (m, 3H), 2.15-2.01 (m, 4H), 1.95-1.83 (m, 4H), 1.79-1.65 (m, 4H), 1.56-1.44 (m, 2H), 1.34-1.28 (m, 5H), 1.23-1.11 (m, 4H), 1.09-0.94 (m, 4H), 0.83-0.75 (m, 3H). |
| 130 | 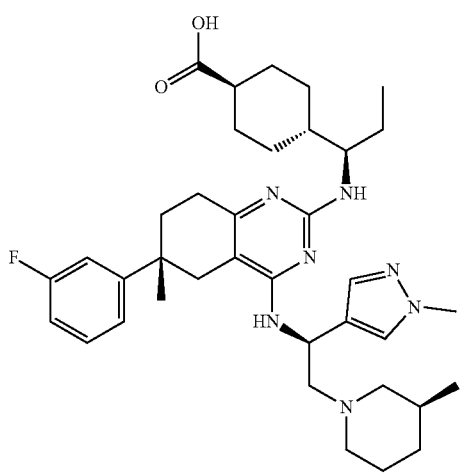 [SMILES: CC[C@@H](Nc1nc2c(c(N[C@H](CN3CCC[C@H](C)C3)c3cnn(C)c3)n1)C[C@](C)(c1cccc(F)c1)CC2)[C@H]1CC[C@H](C(=O)O)CC1] | LCMS m/z [M + H]⁺ = 646.3, ¹H NMR(400 MHz, DMSO-d6) δ 7.63-7.48 (m, 1H), 7.43-7.25 (m, 2H), 7.23-7.09 (m, 2H), 7.00 (dt, J = 2.3, 8.4 Hz, 1H), 6.53-6.21 (m, 1H), 6.12-5.86 (m, 1H), 5.52-5.38 (m, 1H), 3.76 (s, 3H), 3.69-3.61 (m, 1H), 2.90-2.70 (m, 4H), 2.59-2.55 (m, 1H), 2.54-2.52 (m, 2H), 2.40-2.30 (m, 2H), 2.13-1.95 (m, 4H), 1.91-1.80 (m, 3H), 1.72 (br d, J = 11.9 Hz, 2H), 1.67-1.58 (m, 2H), 1.55 (br d, J = 3.1 Hz, 1H), 1.50-1.40 (m, 2H), 1.39-1.25 (m, 4H), 1.24-1.13 (m, 2H), 1.08-0.91 (m, 2H), 0.89-0.70 (m, 7H). |

| | | |
|---|---|---|
| 37 | 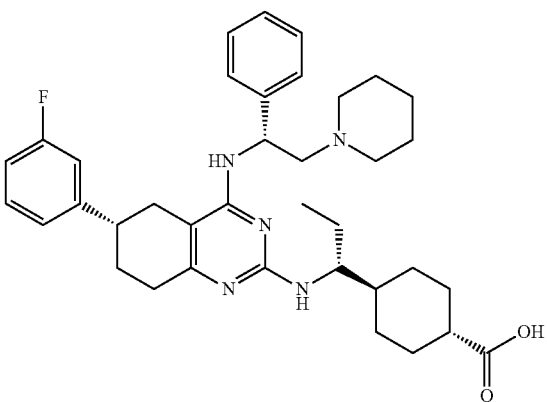 [SMILES: CC[C@@H](Nc1nc2c(c(N[C@@H](CN3CCCCC3)c3ccccc3)n1)C[C@@H](c1cccc(F)c1)CC2)[C@H]1CC[C@H](C(=O)O)CC1] | LCMS m/z [M + H]⁺ = 614.2, ¹H NMR (400 MHz, DMSO-d₆) δ ppm 8.53 (s, 1H), 7.41-7.34 (m, 6H) 7.29-7.14 (m, 2H) 7.02-6.97 (m, 1H) 5.38 (br d, J = 2.63 Hz, 1H) 3.70 (brs, 1H), 3.07-2.99 (m, 2H), 2.88-2.50 (m, 9H) 2.16-1.98 (m, 4H), 1.84-1.25 (m, 14H) 0.93 (t, J = 6.8 Hz, 3H), 0.84-0.81 (m, 1H) 0.58-0.56 (m, 1H). |
| 50 | 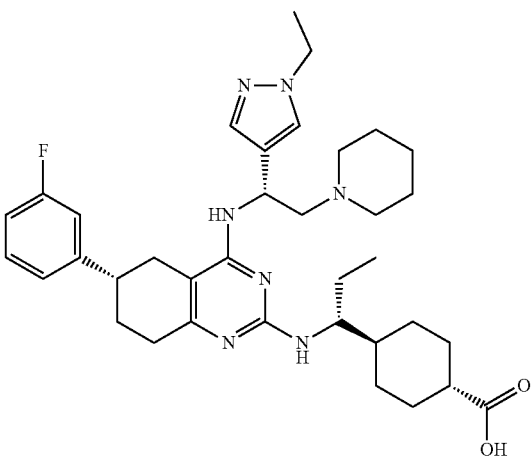 [SMILES: CC[C@@H](Nc1nc2c(c(N[C@@H](CN3CCCCC3)c3cnn(CC)c3)n1)C[C@@H](c1cccc(F)c1)CC2)[C@H]1CC[C@H](C(=O)O)CC1] | LCMS m/z [M + H]⁺ = 632.70, ¹H NMR (400 MHz, DMSO-d6 ) δ ppm 7.53 (br s, 1H), 7.40-7.33 (m, 1H), 7.32 (s, 1H), 7.19 (d, J = 7.7 Hz, 2H), 7.08-7.00 (m, 1H), 6.26-6.08 (m, 1H), 5.99-5.72 (m, 1H), 5.47-5.37 (m, 1H), 4.07-3.97 (m, 2H), 3.73-3.63 (m, 2H), 2.97-2.86 (m, 2H), 2.68-2.63 (m, 1H), 2.60-2.55 (m, 2H), 2.45-2.42 (m, 2H), 2.38 (br s, 4H), 2.27-2.19 (m, 1H), 2.07-1.98 (m, 1H), 1.96-1.88 (m, 2H), 1.87-1.81 (m, 2H), 1.74-1.63 (m, 2H), 1.42 (br d, J = 4.6 Hz, 4H), 1.37-1.28 (m, 7H), 1.26-1.15 (m, 2H), 1.01-0.88 (m, 2H), 0.85-0.78 (m, 3H). |
| 51 | 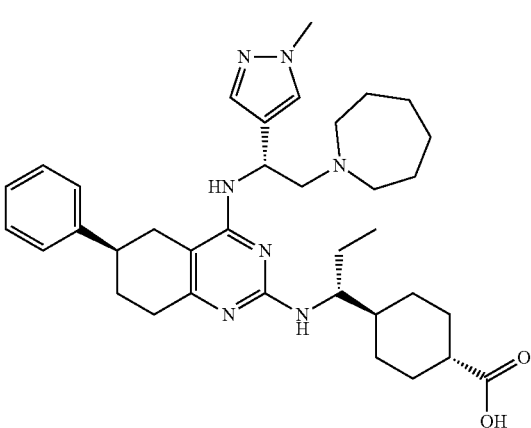 [SMILES: CC[C@@H](Nc1nc2c(c(N[C@@H](CN3CCCCCC3)c3cnn(C)c3)n1)C[C@H](c1ccccc1)CC2)[C@H]1CC[C@H](C(=O)O)CC1] | LCMS m/z [M + H]⁺ = 614.40, ¹H NMR (400 MHz, METHANOL-d4) δ ppm 7.53 (s, 1H), 7.42 (s, 1H), 7.35-7.32 (m, 4H), 7.24-7.21 (m, 1H), 5.06 (br s, 1H), 3.85 (s, 3H), 3.02-2.98 (m, 3H), 2.83-2.73 (m, 6H), 2.48-2.42 (m, 1H), 2.23-1.98 (m, 7H), 2.14-1.93 (m, 5H), 1.82-1.31 (m, 10H), 1.09-0.92 (m, 5H) |

| | | |
|---|---|---|
| 64 | 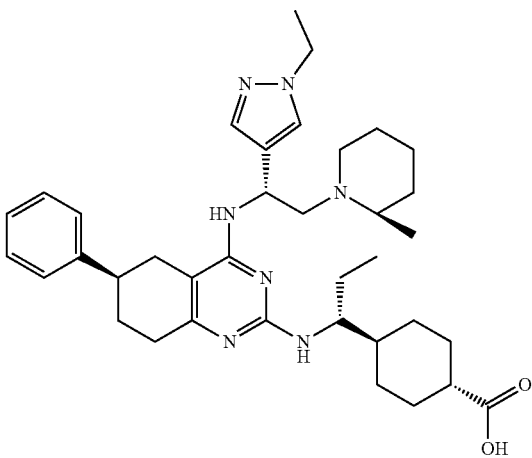 [SMILES: CC[C@@H](Nc1nc2c(c(N[C@@H](CN3CCCC[C@H]3C)c3cnn(CC)c3)n1)C[C@H](c1ccccc1)CC2)[C@H]1CC[C@H](C(=O)O)CC1] | LCMS m/z [M + H]⁺ = 628.00, ¹H NMR (400 MHz, METHANOL-d₄) δ ppm 7.60 (s, 1H), 7.44 (s, 1H), 7.29-7.39 (m, 4H), 7.19-7.27 (m, 1H), 5.71-5.82 (m, 1H), 4.14 (q, J = 7.45 Hz, 2H), 3.86 (br s, 1H), 3.38 (br s, 1H), 3.14 (br s, 1H), 3.01 (br s, 2H), 2.53-2.90 (m, 5H), 2.35-2.51 (m, 2H), 1.88-2.19 (m, 5H), 1.59-1.86 (m, 6H), 1.46-1.58 (m, 3H), 1.32-1.45 (m, 6H), 1.17 (br d, J = 6.14 Hz, 2H), 1.00-1.10 (m, 2H), 0.95 (br t, J = 7.23 Hz, 4H). |
| 109 | 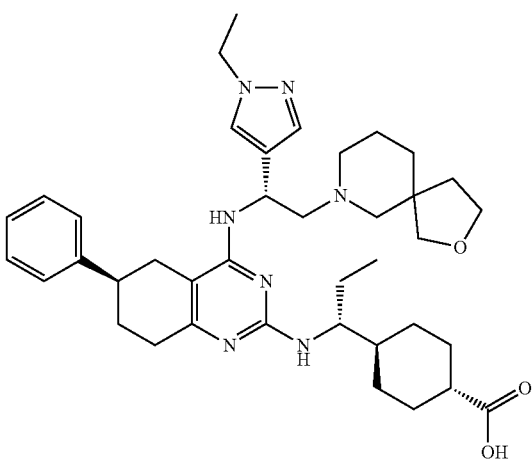 | LCMS m/z [M + H]⁺ = 669.80, ¹H NMR (400 MHz, METHANOL-d₄) δ ppm 7.55 (s, 1H), 7.43 (s, 1H), 7.28-7.37 (m, 4H), 7.24-7.20 (m, 1H), 5.54-5.49 (m, 1H), 4.13 (q, J = 7.31 Hz, 2H), 3.82 (br s, 1H), 3.59-3.77 (m, 2H), 3.52 (br d, J = 8.77 Hz, 2H), 3.33-3.43 (m, 1H), 2.92-3.04 (m, 1H), 2.56-2.86 (m, 5H), 2.31-2.51 (m, 3H), 2.21 (s, 2H), 1.87-2.13 (m, 6H), 1.26-1.85 (m, 14H), 1.01-1.11 (m, 2H), 0.94 (t, J = 7.45 Hz, 3H). |
| 122 | 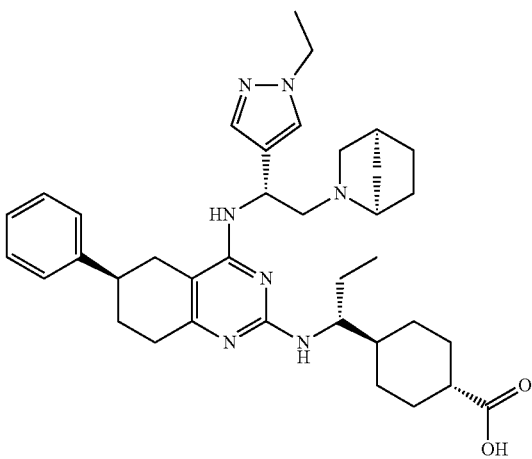 [SMILES: CC[C@@H](Nc1nc2c(c(N[C@@H](CN3C[C@H]4CC[C@@H]3C4)c3cnn(CC)c3)n1)C[C@H](c1ccccc1)CC2)[C@H]1CC[C@H](C(=O)O)CC1] | LCMS m/z [M + H]⁺ = 625.90, ¹H NMR (400 MHz, METHANOL-d₄) δ ppm 7.63 (br s, 1 H), 7.45-7.55 (m, 1H), 7.29-7.39 (m, 4 H), 7.23 (br d, J = 5.70 Hz, 1H), 5.68-5.90 (m, 2H), 4.57-4.77 (m, 1H), 4.15 (q, J = 7.02 Hz, 2H), 3.86 (br s, 2H), 3.45-3.63 (m, 2H), 3.06-3.26 (m, 2H), 2.98 (br s, 2 H), 2.54-2.88 (m, 5H), 2.33-2.51 (m, 1 H), 1.59-2.20 (m, 11H), 1.21-1.57 (m, 8 H), 1.04 (br d, J = 4.38 Hz, 1H), 0.95 (br t, J = 7.23 Hz, 2H). |

| | | |
|---|---|---|
| 126 | 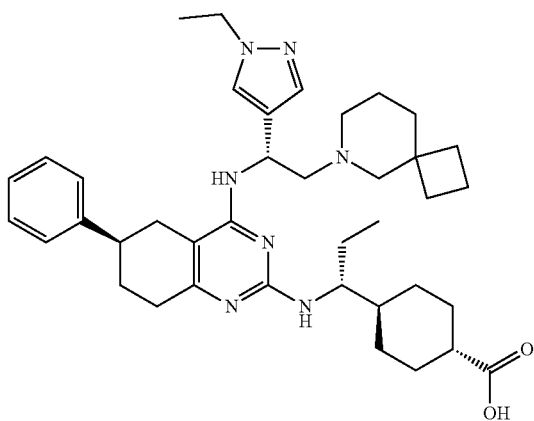 [SMILES: CC[C@@H](Nc1nc2c(c(N[C@@H](CN3CCCC4(CCC4)C3)c3cnn(CC)c3)n1)C[C@H](c1ccccc1)CC2)[C@H]1CC[C@H](C(=O)O)CC1] | LCMS m/z [M + H]⁺ = 653.75, ¹H NMR (300 MHz, METHANOL-d₄) δ ppm 7.60 (d, J = 7.24 Hz, 1H) 7.44 (d, J = 6.58 Hz, 1H) 7.27-7.38 (m, 4H) 7.19-7.26 (m, 1H) 5.58 (br s, 1H) 4.12 (qd, J = 7.24, 1.97 Hz, 1H) 3.89 (br s, 1H) 2.86-3.10 (m, 2H) 2.60-2.84 (m, 5H) 2.29-2.58 (m, 5H) 1.61-2.21 (m, 14H) 1.31-1.58 (m, 11H) 0.77-1.23 (m, 5 H) |
| 137 | 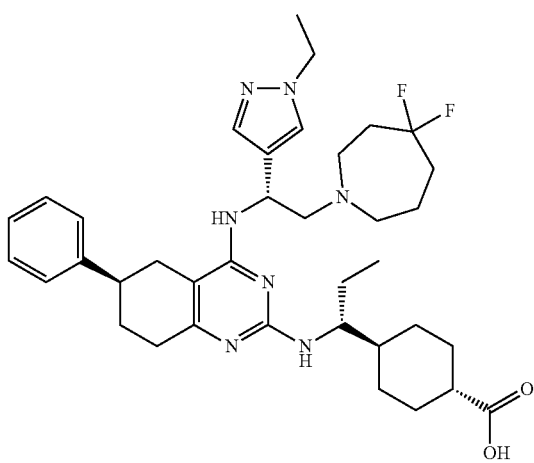 [SMILES: CC[C@@H](Nc1nc2c(c(N[C@@H](CN3CCCC(F)(F)CC3)c3cnn(CC)c3)n1)C[C@H](c1ccccc1)CC2)[C@H]1CC[C@H](C(=O)O)CC1] | LCMS m/z [M + H]⁺ = 664.35, ¹H NMR (400 MHz, METHANOL-d₄) δ ppm 8.53 (s, 1H), 7.58 (s, 1H), 7.42 (s, 1H), 7.35-7.31 (m, 4 H), 7.16-7.26 (m, 1H), 5.54 (br s, 1H), 4.12 (q, J = 7.16 Hz, 2H), 3.88 (br d, J = 2.19 Hz, 1H), 2.94-3.06 (m, 2H), 2.55-2.93 (m, 9 H), 2.38-2.52 (m, 1H), 1.88-2.20 (m, 9H), 1.60-1.86 (m, 5H), 1.26-1.57 (m, 6H), 0.87-1.14 (m, 5H) |
| 165 | 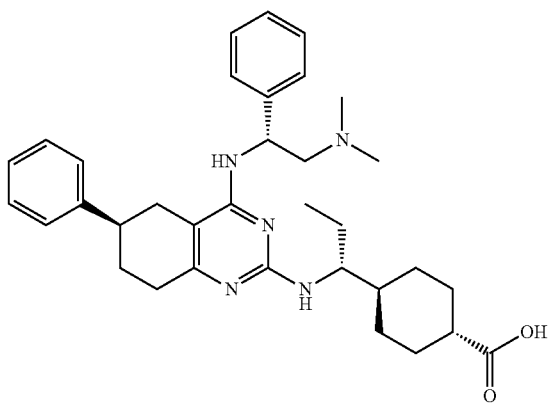 [SMILES: CC[C@@H](Nc1nc2c(c(N[C@@H](CN(C)C)c3ccccc3)n1)C[C@H](c1ccccc1)CC2)[C@H]1CC[C@H](C(=O)O)CC1] | LCMS m/z [M + H]⁺ = 556.30, ¹H NMR (400 MHz, METHANOL-d₄) δ ppm 8.51 (br s, 1 H), 7.37-7.35 (m, 7H), 7.28-7.25 (m, 2H), 5.46-5.38 (m, 1H), 3.78-3.76 (m, 1H), 3.12-2.62 (m, 8H), 2.52-2.50 (m, 2H), 2.38-2.32 (m, 5H), 2.14-1.98 (m, 3H), 1.89-1.26 (m, 9H), 0.96-0.92 (m, 3H). |

| | | |
|---|---|---|
| 166 | 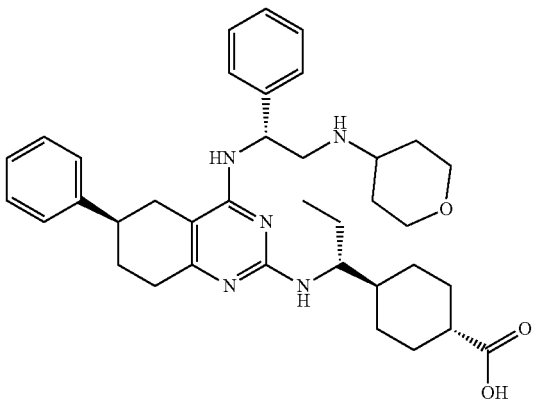 [SMILES: CC[C@@H](Nc1nc2c(c(N[C@@H](CNC3CCOCC3)c3ccccc3)n1)C[C@H](c1ccccc1)CC2)[C@H]1CC[C@H](C(=O)O)CC1] | LCMS m/z [M + H]⁺ = 612.30, ¹H NMR (400 MHz, METHANOL-d4) δ ppm 8.51 (s, 1H), 7.44-7.29 (m, 9H), 7.27 (br d, J = 6.58 Hz, 1H), 5.36 (br d, J = 3.95 Hz, 1H), 3.94 (br d, J = 12.28 Hz, 2H), 3.77 (br s, 1H), 3.45-3.36 (m, 2H), 3.25-3.12 (m, 1H), 3.10-2.96 (m, 2H), 2.93-2.63 (m, 4H), 2.61-2.48 (m, 1H), 2.24-1.95 (m, 4H), 1.92-1.66 (m, 4H), 1.64-1.17 (m, 9H), 0.95 (br t, J = 7.23 Hz, 3H), 0.84 (br s, 1H), 0.55 (br d, J = 11.84 Hz, 1H) |
| 94 | 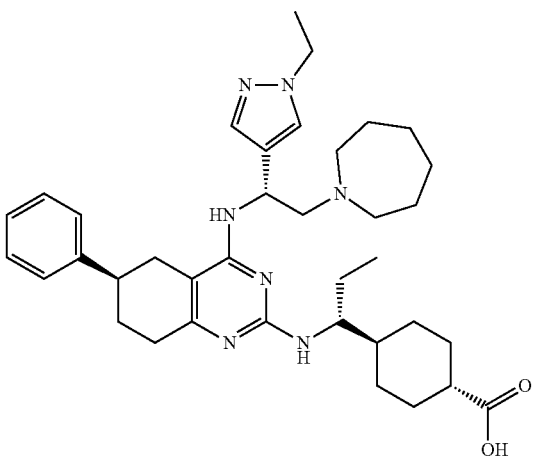 [SMILES: CC[C@@H](Nc1nc2c(c(N[C@@H](CN3CCCCCC3)c3cnn(CC)c3)n1)C[C@H](c1ccccc1)CC2)[C@H]1CC[C@H](C(=O)O)CC1] | LCMS m/z [M + H]⁺ = 627.90, ¹H NMR (METHANOL-d4) δ 7.61 (s, 1H), 7.45 (s, 1H), 7.30-7.39 (m, 4H), 7.24-7.22 (m, 1H), 5.65 (brs, 1H), 4.14 (q, J = 7.3 Hz, 2H), 3.11-3.15 (m, 3H), 3.00-2.71 (m, 8H), 2.49-2.42 (m, 2H), 2.12-1.95 (m, 6H), 1.83-1.63 (m, 8H), 1.55-1.49 (m, 2H), 1.47-1.42 (m, 2H), 1.40-1.31 (m, 3H), 1.11-1.02 (m, 3H), 0.97-0.91 (m, 3H). |
| 132 | 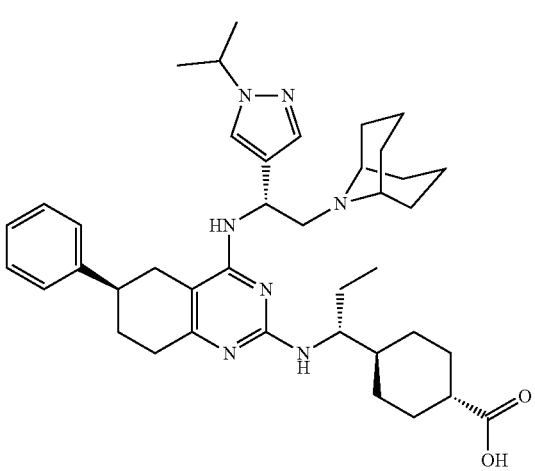 | LCMS m/z [M + H]⁺ = 668.5, ¹H NMR (400 MHz, DMSO) δ 7.50 (s, 1H), 7.26 (d, J = 4.6 Hz, 5H), 7.15 (tt, J = 5.5, 3.1 Hz, 1H), 6.02 (s, 1H), 5.87 (s, 1H), 5.11 (q, J = 7.3 Hz, 1H), 4.32 (p, J = 6.6 Hz, 1H), 3.58 (s, 1H), 2.81 (t, J = 6.8 Hz, 3H), 2.65 (s, 2H), 2.53 (td, J = 13.4, 5.7 Hz, 2H), 2.20 (dd, J = 15.4, 11.1 Hz, 1H), 2.00-1.70 (m, 11H), 1.71-1.55 (m, 2H), 1.42 (q, J = 7.6 Hz, 3H), 1.37-1.23 (m, 13H), 1.22-1.05 (m, 2H), 0.95-0.79 (m, 2H), 0.73 (t, J = 7.2 Hz, 3H). |

| | | |
|---|---|---|
| 176 | 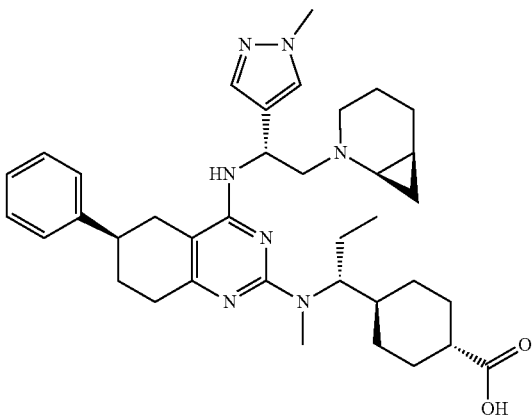 [SMILES: CC[C@H]([C@H]1CC[C@H](C(=O)O)CC1)N(C)c1nc2c(c(N[C@@H](CN3CCC[C@H]4C[C@H]43)c3cnn(C)c3)n1)C[C@H](c1ccccc1)CC2] | LCMS m/z [M + H]⁺ = 626.5, ¹H NMR (400 MHz, DMSO-d6) δ = 7.58-7.43 (m, 1H), 7.38-7.26 (m, 5H), 7.25-7.18 (m, 1H), 6.20-6.08 (m, 1H), 5.70-5.47 (m, 1H), 4.54-4.41 (m, 1H), 3.75 (s, 3H), 2.92-2.80 (m, 2H), 2.74-2.69 (m, 3H), 2.65-2.55 (m, 2H), 2.47-2.43 (m, 1H), 2.30-2.18 (m, 2H), 2.17-2.09 (m, 1H), 2.07 (s, 1H), 2.03-1.77 (m, 5H), 1.73-1.59 (m, 3H), 1.50-1.33 (m, 3H), 1.32-1.21 (m, 5H), 1.20-1.05 (m, 2H), 1.01-0.91 (m, 1H), 0.90-0.72 (m, 2H), 0.71-0.60 (m, 3H), 0.37-0.10 (m, 2H). |
| 177 | 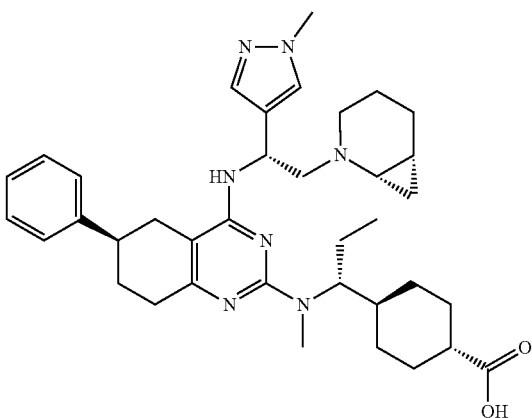 [SMILES: CC[C@H]([C@H]1CC[C@H](C(=O)O)CC1)N(C)c1nc2c(c(N[C@@H](CN3CCC[C@@H]4C[C@@H]43)c3cnn(C)c3)n1)C[C@H](c1ccccc1)CC2] | LCMS m/z [M + H]⁺ = 626.5, ¹H NMR (400 MHz, DMSO-d6) δ = 7.56-7.41 (m, 1H), 7.39-7.27 (m, 5H), 7.25-7.17 (m, 1H), 6.18-6.04 (m, 1H), 5.63-5.37 (m, 1H), 4.56-4.42 (m, 1H), 3.75 (s, 3H), 2.97-2.85 (m, 2H), 2.74-2.68 (m, 3H), 2.65-2.54 (m, 2H), 2.46-2.40 (m, 1H), 2.31-2.22 (m, 1H), 2.21-2.09 (m, 2H), 2.04-1.89 (m, 2H), 1.87-1.76 (m, 3H), 1.67 (br s, 3H), 1.45-1.21 (m, 8H), 1.19-1.02 (m, 2H), 0.99-0.92 (m, 1H), 0.88-0.79 (m, 1H), 0.71-0.63 (m, 3H), 0.63-0.51 (m, 1H), 0.30-0.11 (m, 2H). |
| 178 | 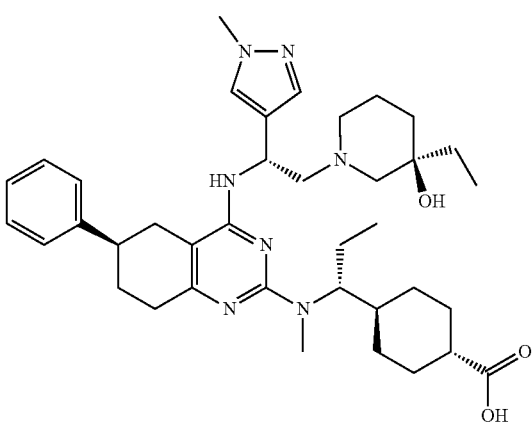 [SMILES: CC[C@H]([C@H]1CC[C@H](C(=O)O)CC1)N(C)c1nc2c(c(N[C@@H](CN3CCC[C@](O)(CC)C3)c3cnn(C)c3)n1)C[C@H](c1ccccc1)CC2] | LCMS m/z [M + H]⁺ = 658.4, ¹H NMR (400 MHz, DMSO-d6) δ = 7.58-7.40 (m, 1H), 7.39-7.25 (m, 5H), 7.25-7.18 (m, 1H), 6.17-5.98 (m, 1H), 5.51-5.12 (m, 1H), 4.60-4.36 (m, 1H), 3.74 (s, 3H), 2.91-2.82 (m, 1H), 2.78-2.68 (m, 3H), 2.68-2.57 (m, 3H), 2.57-2.51 (m, 3H), 2.45-2.32 (m, 2H), 2.31-2.13 (m, 2H), 2.11-1.99 (m, 1H), 1.97-1.79 (m, 3H), 1.79-1.58 (m, 4H), 1.56-1.46 (m, 1H), 1.45-0.97 (m, 10H), 0.92-0.77 (m, 1H), 0.76-0.60 (m, 6H), 0.59-0.44 (m, 1H). |

| | | |
|---|---|---|
| 179 | 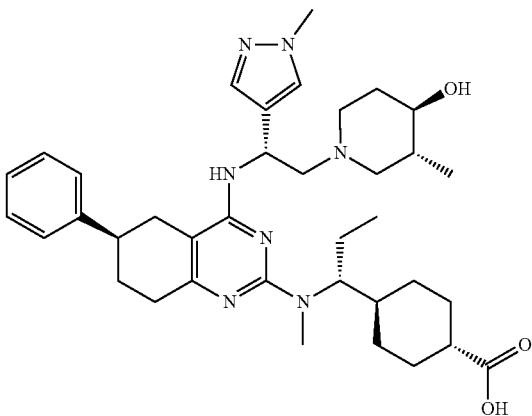 [SMILES: CC[C@H]([C@H]1CC[C@H](C(=O)O)CC1)N(C)c1nc2c(c(N[C@@H](CN3CC[C@@H](O)[C@H](C)C3)c3cnn(C)c3)n1)C[C@H](c1ccccc1)CC2] | LCMS m/z [M + H]⁺ = 644.5, ¹H NMR (600 MHz, DMSO) δ 11.86 (d, J = 248.6 Hz, 1H), 11.27 (s, 1H), 10.04 (s, 1H), 8.26 (s, 1H), 7.60 (s, 1H), 7.40 (s, 1H), 7.39-7.31 (m, 4H), 7.26 (ddd, J = 8.7, 5.1, 3.5 Hz, 1H), 5.70 (s, 1H), 4.40 (s, 2H), 3.78 (s, 4H), 3.50 (s, 2H), 3.35 (d, J = 14.5 Hz, 2H), 3.27 (d, J = 11.9 Hz, 1H), 3.18 (d, J = 12.3 Hz, 1H), 3.05 (d, J = 23.9 Hz, 1H), 2.97-2.65 (m, 6H), 2.43-2.23 (m, 1H), 2.16-1.80 (m, 5H), 1.72 (d, J = 13.5 Hz, 3H), 1.60 (p, J = 15.8 Hz, 1H), 1.43 (d, J = 11.9 Hz, 2H), 1.37-1.22 (m, 2H), 1.16 (q, J = 12.5 Hz, 1H), 1.03-0.78 (m, 5H), 0.72 (d, J = 23.2 Hz, 3H), 0.46 (d, J = 14.0 Hz, 1H) |
| 180 | 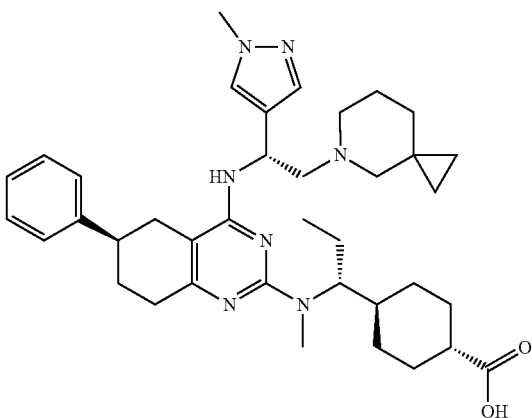 | LCMS m/z [M + H]⁺ = 640.5, ¹H NMR (400 MHz CD₃OD) δ 7.27 (s, 1H), 7.17 (s, 1H), 7.14-7.05 (m, 4H), 7.04-6.93 (m, 1H), 5.04 (s, 1H), 4.23 (s, 1H), 3.59 (s, 3H), 2.84-2.71 (m, 1H), 2.69-2.14 (m, 12H), 2.15-1.95 (m, 2H), 1.94-1.58 (m, 7H), 1.56-1.31 (m, 5H), 1.29-0.97 (m, 7H), 0.94-0.61 (m, 3H), 0.308 (t, J = 7.2 Hz, 3H). |
| 181 | 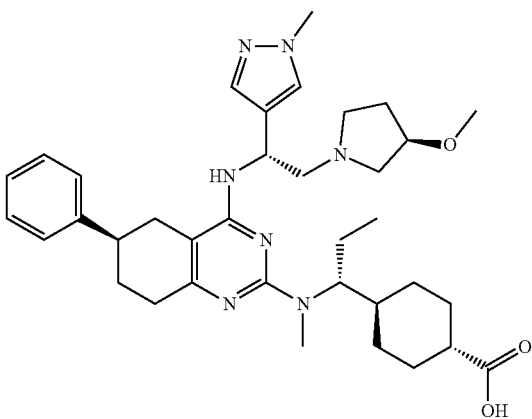 [SMILES: CC[C@H]([C@H]1CC[C@H](C(=O)O)CC1)N(C)c1nc2c(c(N[C@@H](CN3CC[C@@H](OC)C3)c3cnn(C)c3)n1)C[C@H](c1ccccc1)CC2] | LCMS m/z [M + H]⁺ = 630.5, ¹H NMR (400 MHz, DMSO-d6) δ = 7.54-7.42 (m, 1H), 7.38-7.27 (m, 5H), 7.25-7.18 (m, 1H), 6.23-6.12 (m, 1H), 5.50-5.19 (m, 1H), 4.60-4.44 (m, 1H), 3.81 (br s, 1H), 3.74 (s, 3H), 3.12 (s, 3H), 2.95-2.85 (m, 1H), 2.84-2.74 (m, 2H), 2.72 (s, 2H), 2.70-2.65 (m, 1H), 2.65-2.56 (m, 3H), 2.54 (br s, 2H), 2.47-2.40 (m, 2H), 2.31-2.20 (m, 1H), 2.01-1.80 (m, 6H), 1.77-1.54 (m, 3H), 1.42-1.06 (m, 5H), 0.95-0.80 (m, 1H), 0.73-0.63 (m, 3H), 0.63-0.49 (m, 1H). |

| 182 | 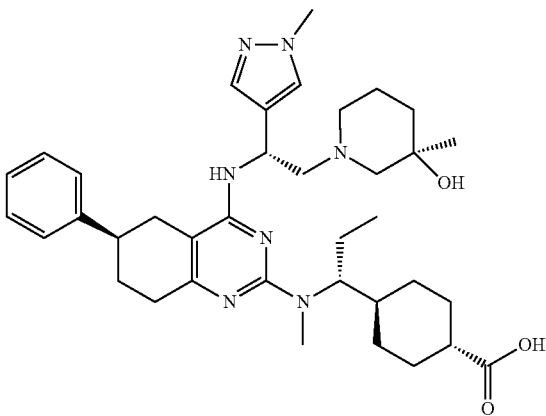 [SMILES: CC[C@H]([C@H]1CC[C@H](C(=O)O)CC1)N(C)c1nc2c(c(N[C@@H](CN3CCC[C@@](C)(O)C3)c3cnn(C)c3)n1)C[C@H](c1ccccc1)CC2] | LCMS m/z [M + H]⁺ = 644.4, ¹H NMR (400 MHz, DMSO) δ 7.46 (s, 1H), 7.38-7.29 (m, 5H), 7.22 (ddt, J = 8.6, 5.2, 3.2 Hz, 1H), 6.13 (d, J = 7.3 Hz, 1H), 5.23 (d, J = 7.4 Hz, 1H), 4.47 (t, J = 10.3 Hz, 1H), 3.74 (s, 3H), 2.87 (tt, J = 10.5, 4.6 Hz, 1H), 2.72 (s, 3H), 2.61 (dtd, J = 31.0, 13.8, 6.1 Hz, 5H), 2.39 (s, 1H), 2.23 (dq, J = 22.6, 12.5 Hz, 4H), 2.01 (d, J = 11.4 Hz, 1H), 1.90 (s, 3H), 1.81 (d, J = 11.4 Hz, 1H), 1.72 (d, J = 12.3 Hz, 1H), 1.64 (s, 1H), 1.54 (s, 1H), 1.31 (t, J = 19.9 Hz, 7H), 1.13 (t, J = 12.8 Hz, 1H), 1.03 (s, 3H), 0.87 (d, J = 13.4 Hz, 1H), 0.69 (t, J = 7.2 Hz, 3H), 0.55 (t, J = 12.7 Hz, 1H). |
|---|---|---|
| 183 | 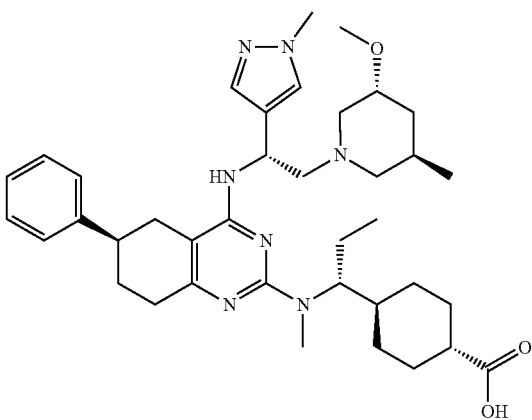 [SMILES: CC[C@H]([C@H]1CC[C@H](C(=O)O)CC1)N(C)c1nc2c(c(N[C@@H](CN3C[C@H](C)C[C@@H](OC)C3)c3cnn(C)c3)n1)C[C@H](c1ccccc1)CC2] | LCMS m/z [M + H]⁺ = 658.3, ¹H NMR (400 MHz, DMSO-d6) δ = 7.56-7.41 (m, 1H), 7.39-7.27 (m, 5H), 7.26-7.19 (m, 1H), 6.25-6.08 (m, 1H), 5.55-5.11 (m, 1H), 4.62-4.39 (m, 1H), 3.74 (s, 3H), 3.08 (s, 3H), 2.94-2.83 (m, 1H), 2.83-2.69 (m, 4H), 2.68-2.51 (m, 7H), 2.35-2.12 (m, 2H), 1.98-1.75 (m, 7H), 1.74-1.51 (m, 3H), 1.40-1.01 (m, 6H), 0.89-0.74 (m, 4H), 0.68 (br t, J = 6.8 Hz, 3H), 0.58-0.40 (m, 1H) |
| 184 | 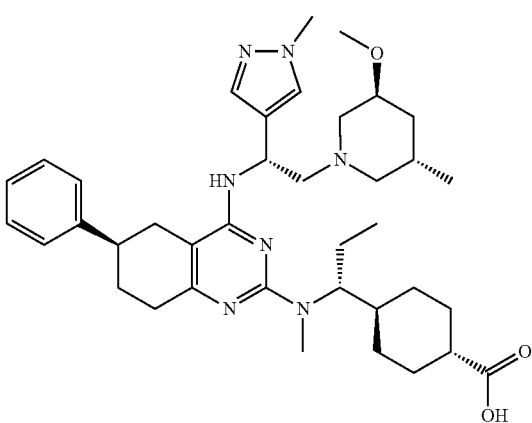 [SMILES: CC[C@H]([C@H]1CC[C@H](C(=O)O)CC1)N(C)c1nc2c(c(N[C@@H](CN3C[C@@H](C)C[C@H](OC)C3)c3cnn(C)c3)n1)C[C@H](c1ccccc1)CC2] | LCMS m/z [M + H]⁺ = 658.5, ¹H NMR (400 MHz, DMSO-d6) δ = 11.91 (br s, 1H), 7.56-7.44 (m, 1H), 7.42-7.29 (m, 5H), 7.26-7.19 (m, 1H), 6.24-6.11 (m, 1H), 5.53-5.12 (m, 1H), 4.64-4.38 (m, 1H), 3.74 (s, 3H), 3.07 (s, 3H), 2.93-2.82 (m, 1H), 2.79-2.57 (m, 8H), 2.57-2.51 (m, 2H), 2.49-2.45 (m, 1H), 2.34-2.14 (m, 2H), 2.03-1.77 (m, 7H), 1.77-1.56 (m, 3H), 1.46-1.20 (m, 4H), 1.19-1.04 (m, 2H), 0.93-0.82 (m, 1H), 0.78 (br d, J = 6.0 Hz, 3H), 0.68 (br s, 1H), 0.59-0.41 (m, 1H) |

| | | |
|---|---|---|
| 185 | 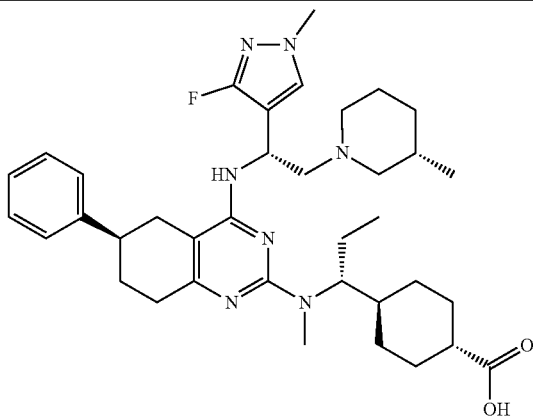 | LCMS m/z [M + H]⁺ = 646.4, ¹H NMR (400 MHz, DMSO-d6) δ = 11.88 (br s, 1H), 7.50-7.38 (m, 1H), 7.37-7.29 (m, 4H), 7.26-7.18 (m, 1H), 6.20 (br s, 1H), 5.49-5.21 (m, 1H), 4.57-4.45 (m, 1H), 3.63 (s, 3H), 2.94-2.84 (m, 1H), 2.83-2.77 (m, 1H), 2.72 (s, 3H), 2.71-2.67 (m, 1H), 2.66-2.62 (m, 1H), 2.61-2.58 (m, 1H), 2.57-2.52 (m, 2H), 2.47-2.43 (m, 1H), 2.30-2.21 (m, 1H), 2.10-1.99 (m, 1H), 1.94-1.79 (m, 5H), 1.76-1.68 (m, 1H), 1.67-1.56 (m, 3H), 1.55-1.46 (m, 2H), 1.41-1.22 (m, 5H), 1.21-1.08 (m, 1H), 1.02-0.92 (m, 1H), 0.83-0.75 (m, 4H), 0.74-0.64 (m, 3H), 0.60-0.44 (m, 1H) |
| 186 | 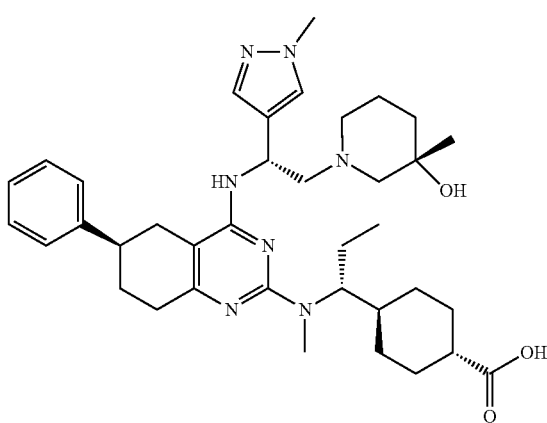 [SMILES: CC[C@H]([C@H]1CC[C@H](C(=O)O)CC1)N(C)c1nc2c(c(N[C@@H](CN3CCC[C@](C)(O)C3)c3cnn(C)c3)n1)C[C@H](c1ccccc1)CC2] | LCMS m/z [M + H]⁺ = 644.4, ¹H NMR (400 MHz, DMSO) δ 8.18 (s, 1H), 7.46 (s, 1H), 7.37-7.28 (m, 5H), 7.22 (ddd, J = 8.6, 5.3, 3.3 Hz, 1H), 6.20 (d, J = 7.0 Hz, 1H), 5.23-5.17 (m, 1H), 4.45 (t, J = 10.2 Hz, 1H), 3.74 (s, 3H), 2.37-2.29 (m, 1H), 2.26 (d, J = 13.0 Hz, 2H), 2.13 (d, J = 10.6 Hz, 1H), 2.05-1.85 (m, 4H), 1.80 (d, J = 11.6 Hz, 1H), 1.55 (s, 1H), 1.40-1.20 (m, 7H), 1.13 (t, J = 12.4 Hz, 1H), 1.03 (d, J = 8.8 Hz, 3H), 0.88 (q, J = 12.5 Hz, 1H), 0.68 (t, J = 7.1 Hz, 3H), 0.51 (q, J = 12.5 Hz, 1H), 2.88 (s, 1H), 2.72 (s, 3H), 2.70-2.52 (m, 5H), 2.41 (s, 1H), 1.71 (d, J = 12.9 Hz, 1H), 1.65 (s, 1H). |

Example 16: Synthesis of (1R,4r)-4-((R)-1-((6-cyclohexyl-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid (Compound 152)

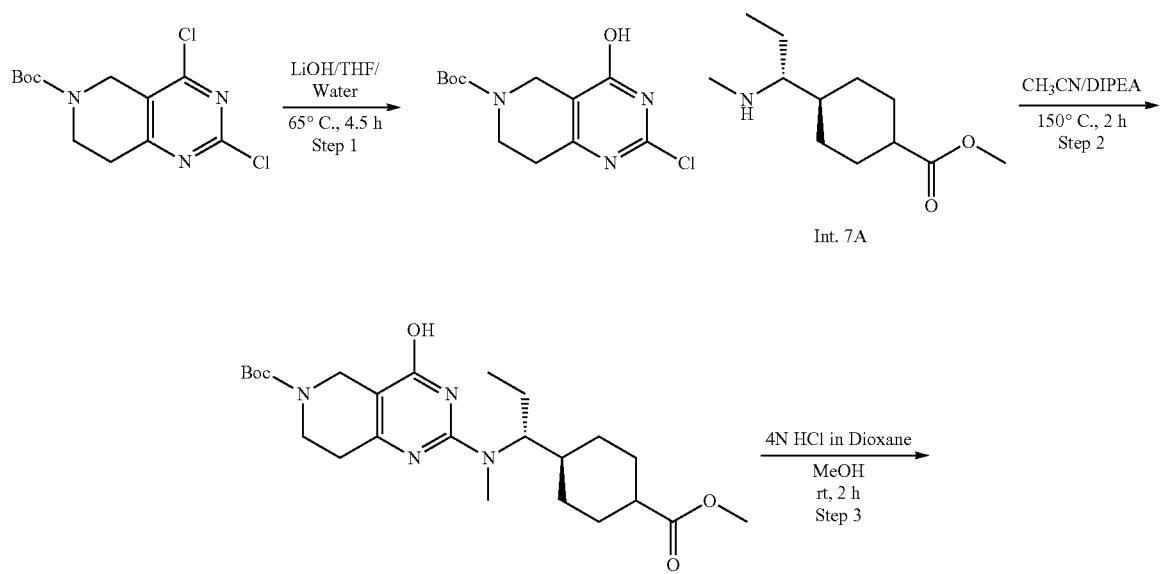

-continued
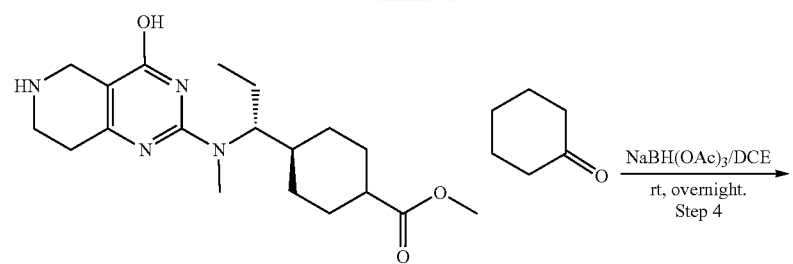
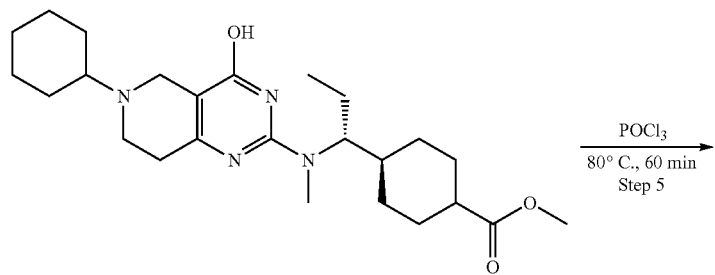
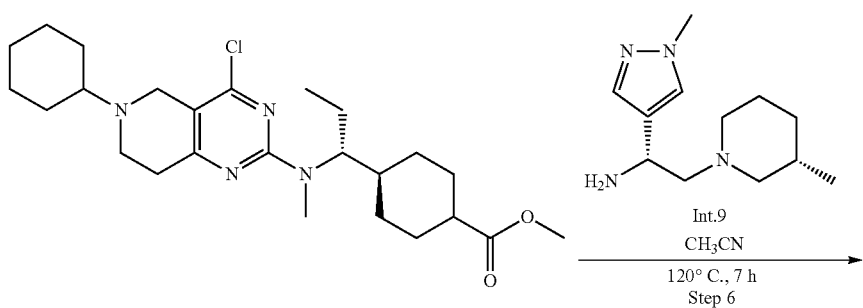
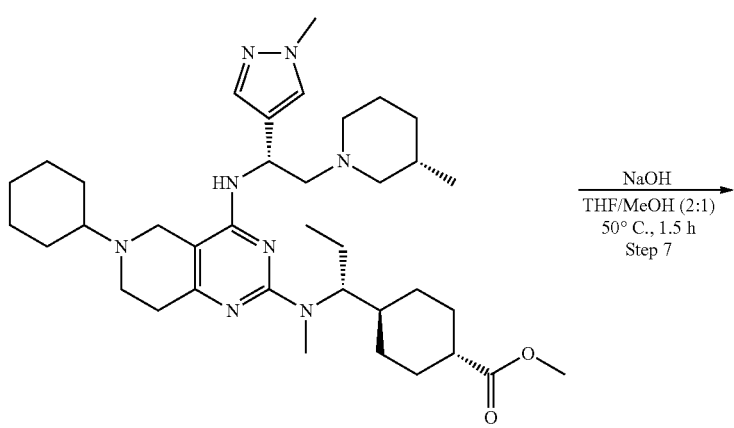
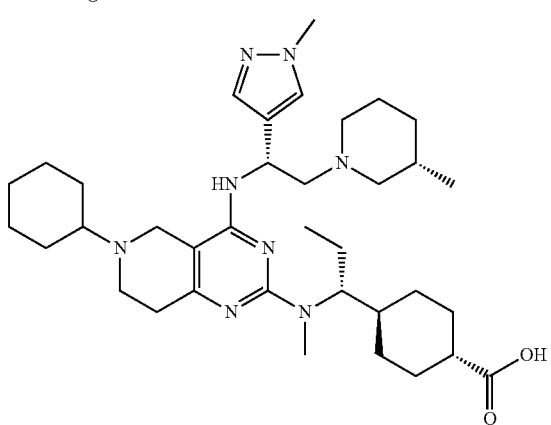

Step 1: A solution of tert-butyl 2,4-dichloro-7,8-dihydropyrido[4,3-d]pyrimidine-6(5H)-carboxylate (3 g, 9.86 mmol), LiOH (0.828 g, 19.73 mmol) in THF (24 mL, Ratio: 2) and Water (12 mL, Ratio: 1.000) was stirred at 65° C. for 4.5 h at which time LCMS indicated formation of desired product. HCl (2N) solution was added to neutralize the reaction. The reaction mixture was diluted with EtOAc, washed with water, brine and dried over $Na_2SO_4$, and concentrated under reduced pressure to provide crude product. It was purified by ISCO combiflash chromatography (80 gram, 0-100% EtOAc/DCM) to provide desired product tert-butyl 2-chloro-4-hydroxy-7,8-dihydropyrido[4,3-d]pyrimidine-6(5H)-carboxylate (1.15 g, 4.02 mmol, 40.8% yield). MS: m/z=286.0 $[M+H]^+$.

Step 2: A microwave vial containing tert-butyl 2-chloro-4-hydroxy-7,8-dihydropyrido[4,3-d]pyrimidine-6(5H)-carboxylate (600 mg, 2.100 mmol), methyl (1R,4r)-4-((R)-1-(methylamino)propyl)cyclohexane-1-carboxylate hydrochloride (661 mg, 2.310 mmol) in anhydrous $CH_3CN$ (3.5 mL) and DIPEA (1.467 mL, 8.40 mmol) was irradiated to 150° C. for 3.5 h at which time LCMS indicated formation of desired product. The crude was filtered to remove precipitates and concentrated. It was purified by ISCO combiflash chromatography (40 gram, 0-10% MeOH/DCM) to provide desired product tert-butyl 4-hydroxy-2-(((R)-1-((1r,4R)-4-(methoxycarbonyl)cyclohexyl)propyl)(methyl)amino)-7,8-dihydropyrido[4,3-d]pyrimidine-6(5H)-carboxylate (405 mg, 0.876 mmol, 41.7% yield). MS: m/z=463.3 $[M+H]^+$.

Step 3: To a solution of tert-butyl 4-hydroxy-2-(((R)-1-((1r,4R)-4-(methoxycarbonyl)cyclohexyl)propyl)(methyl)amino)-7,8-dihydropyrido[4,3-d]pyrimidine-6(5H)-carboxylate (400 mg, 0.865 mmol) in MeOH (1.667 ml) was added 4N HCl in Dioxane (2.162 ml, 8.65 mmol) and stirred at room temperature for 1.5 h at which time LCMS indicated formation of desired product. The reaction mixture was concentrated under reduced pressure and azeotroped twice with DCM. The resulting residue was dried under vacuum for several hours to provide desired product methyl (1R,4r)-4-((R)-1-((4-hydroxy-5,6,7,8-tetrahydropyrido[4,3-d]pyrimidin-2-yl)(methyl)amino)propyl)cyclohexane-1-carboxylate (351 mg, 0.880 mmol, 100% yield). MS: m/z=363.2 $[M+H]^+$.

Step 4: In a vial was added cyclohexanone (0.016 μl, 0.153 mmol) and methyl (1R,4r)-4-((R)-1-((4-hydroxy-5,6,7,8-tetrahydropyrido[4,3-d]pyrimidin-2-yl)(methyl)amino)propyl)cyclohexane-1-carboxylate (60.9 mg, 0.168 mmol) followed by DCE (1.5 mL) under $N_2$. It was stirred for 15 min and then sodium triacetoxyborohydride (64.8 mg, 0.306 mmol) was added and continued to stir overnight at which time LCMS showed incomplete reaction. Additional 2 eq of cyclohexanone was added and stirred for 15 min. Then 2 eq of sodium triacetoxyborohydride was added and stirred for additional 1 h at which point LCMS indicated formation of desired product. It was directly purified by ISCO combiflash chromatography (24 gram, 0-30% MeOH/DCM) to provide desired product methyl (1R,4r)-4-((R)-1-((6-cyclohexyl-4-hydroxy-5,6,7,8-tetrahydropyrido[4,3-d]pyrimidin-2-yl)(methyl)amino)propyl)cyclohexane-1-carboxylate (57.5 mg, 0.129 mmol, 85% yield). MS: m/z=445.3 [M+H]+.

Step 5: To a solution of (1R,4r)-4-((R)-1-((6-cyclohexyl-4-hydroxy-5,6,7,8-tetrahydropyrido[4,3-d]pyrimidin-2-yl)(methyl)amino)propyl)cyclohexane-1-carboxylate (57.5 mg, 0.129 mmol) in anhydrous ACN (0.3 mL) in a microwave vial was added $POCl_3$ (0.036 mL, 0.388 mmol) dropwise at rt. The reaction mixture was heated to 80° C. for 60 min at which time LCMS indicated formation of desired product. It was diluted with EtOAc and quenched by careful addition of saturated $NaHCO_3$ aq solution. Two phases were separated and the aqueous was extracted twice with EtOAc, dried over $Na_2SO_4$, concentrated. It was further dried under high vac to provide desired product methyl (1R,4r)-4-((R)-1-((4-chloro-6-cyclohexyl-5,6,7,8-tetrahydropyrido[4,3-d]pyrimidin-2-yl)(methyl)amino)propyl)cyclohexane-1-carboxylate (60 mg, 0.130 mmol, 100% yield). MS: m/z=463.2 $[M+H]^+$.

Step 6: To a microwave vial containing methyl (1R,4r)-4-((R)-1-((4-chloro-6-cyclohexyl-5,6,7,8-tetrahydropyrido[4,3-d]pyrimidin-2-yl)(methyl)amino)propyl)cyclohexane-1-carboxylate (60 mg, 0.130 mmol), (R)-1-(1-methyl-1H-pyrazol-4-yl)-2-((S)-3-methylpiperidin-1-yl)ethan-1-amine (38.3 mg, 0.130 mmol) in $CH_3CN$ (0.5 mL) was added HCl in dioxane (0.032 mL, 0.130 mmol) and irradiated at 120° C. in MW for 7 h followed by further heating at 130° C. for 1 h at which time LCMS indicated ~35% formation of desired product. The reaction mixture was concentrated in vacuo. It was further dried under high vac to provide desired crude product methyl (1R,4r)-4-((R)-1-((6-cyclohexyl-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylate (84 mg, 0.052 mmol, 40% yield). MS: m/z=649.4 [M+H]+.

Step 7: To a vial containing methyl (1R,4r)-4-((R)-1-((6-cyclohexyl-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylate (84 mg, 0.052 mmol) was added THF (0.4 ml, Ratio: 2) and MeOH (0.200 ml, Ratio: 1.000) and then 4M NaOH (0.065 ml, 0.259 mmol). The mixture was agitated at 50° C. for 1.5 h at which time LCMS indicated formation of desired product. The reaction mixture was cooled to room temperature and concentrated under reduced pressure. The resulting residue was diluted with MeOH and purified via basic prep HPLC (25-50%-Acetonitrile/Water, 5 mM $NH_4OH$, wavelength 396, mass detector). Desired fractions were combined and lyophilized to provide with desired product (1R,4r)-4-((R)-1-((6-cyclohexyl-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid (10 mg, 0.014 mmol, 27.9% yield). LCMS: m/z=635.5 [M+H]+; $^1$H NMR (400 MHz, Methanol-d4) δ 7.45 (s, 1H), 7.36 (s, 1H), 5.46 (s, 1H), 4.47 (s, 1H), 3.82 (s, 3H), 3.54-3.37 (m, 2H), 2.92-2.74 (m, 8H), 2.68-2.62 (m, 2H), 2.53-2.45 (m, 1H), 2.04-1.91 (m, 5H), 1.88-1.59 (m, 11H), 1.51-1.20 (m, 11H), 0.92-0.67 (m, 9H).

Example 17: Synthesis of (1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid (Compound 23)
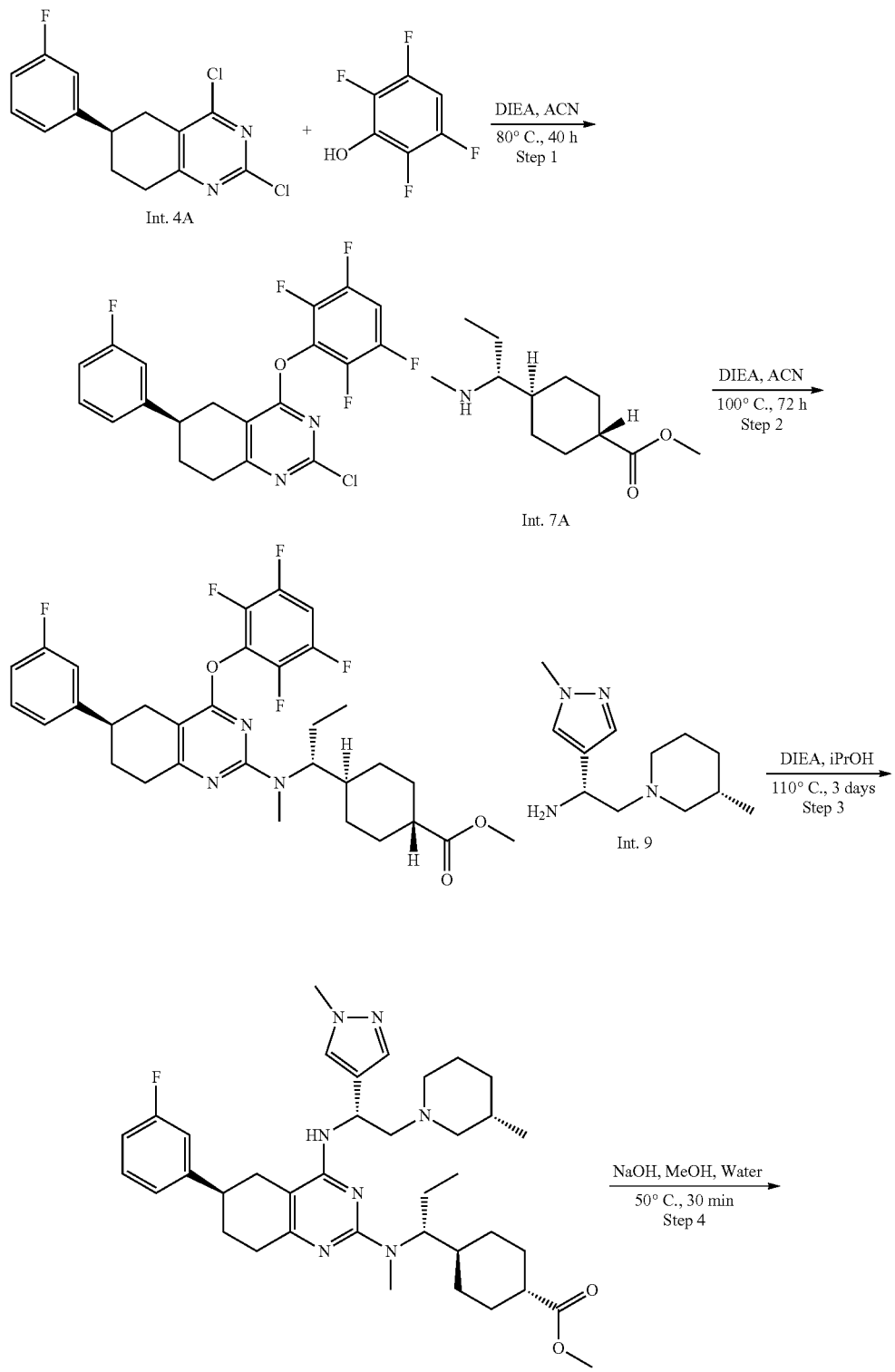

-continued

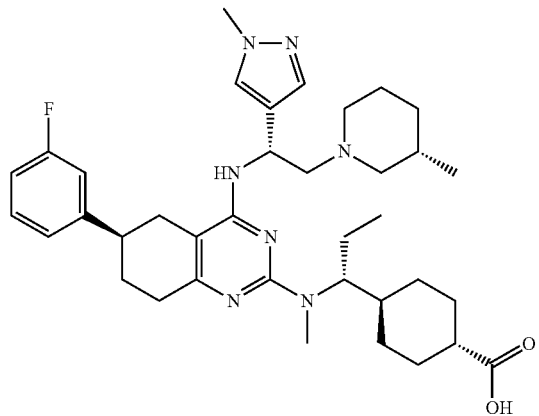

Step 1: A solution of (R)-2,4-dichloro-6-(3-fluorophenyl)-5,6,7,8-tetrahydroquinazoline (10 g, 33.7 mmol), 2,3,5,6-tetrafluorophenol (6.71 g, 40.4 mmol) and DIPEA (7.64 mL, 43.7 mmol) in $CH_3CN$ (Volume: 50 mL) was stirred at 80° C. for 40 h. The mixture was concentrated and added EtOAc (200 ml), and washed with $NaHCO_3$sat. aqueous solution, water and brine, dried over $Na_2SO_4$, and concentrated. LCMS showed some product in the aqueous layer, 6N HCl aq. solution was used to neutralize to pH=4, and extract with EtOAc (200 mL). The organic layer was dried over $Na_2SO_4$ and concentrated. The residue was purified by chromatography (2×330 g, silica gel, 0-5% with flat 5% EtOAc/Heptane) to afford desired product. $^1$H NMR (400 MHz, DMSO-d6) δ 8.01 (tt, J=10.9, 7.3 Hz, 1H), 7.40 (td, J=8.0, 6.0 Hz, 1H), 7.33-7.18 (m, 2H), 7.08 (td, J=9.1, 8.7, 2.6 Hz, 1H), 3.24-2.91 (m, 4H), 2.85 (dd, J=16.6, 11.1 Hz, 1H), 2.10 (td, J=8.0, 7.3, 3.4 Hz, 2H).

Step 2: (R)-2-chloro-6-(3-fluorophenyl)-4-(2,3,5,6-tetrafluorophenoxy)-5,6,7,8-tetrahydroquinazoline (8.6 g, 20.15 mmol), methyl (1R,4r)-4-((R)-1-(methylamino)propyl)cyclohexane-1-carboxylate (8.08 g, 28.2 mmol) in anhydrous acetonitrile (Volume: 12 mL) was added DIPEA (14.08 mL, 81 mmol) in a 100 mL pressure reactor. The resulting mixture was heated to 100° C. for 72 h. The reaction mixture was diluted with EtOAc (250 ml) and washed with $NaHCO_3$sat. aqu. solution, water and brine, then dried over $Na_2SO_4$ and concentrated. The residue was purified by flash chromatography (330 g, silica gel, 0-10% EtOAc/Heptane; product eluting at ~9% EtOAc/Heptane); $^1$H NMR (400 MHz, DMSO-d6) δ 8.06-7.91 (m, 1H), 7.38 (td, J=7.8, 6.0 Hz, 1H), 7.23 (dd, J=10.1, 2.8 Hz, 2H), 7.06 (td, J=8.8, 2.2 Hz, 1H), 3.69 (s, 1H), 3.58 (s, 3H), 3.08 (dt, J=10.7, 6.0 Hz, 1H), 2.95 (dd, J=16.1, 5.0 Hz, 1H), 2.89-2.71 (m, 4H), 2.65 (dd, J=15.8, 11.5 Hz, 1H), 2.04 (tt, J=10.8, 5.2 Hz, 2H), 1.80 (dd, J=34.3, 12.7 Hz, 2H), 1.55-1.10 (m, 5H), 0.92-0.77 (m, 2H), 0.59-0.43 (m, 3H).

Step 3: A solution of (R)-1-(1-methyl-1H-pyrazol-4-yl)-2-((S)-3-methylpiperidin-1-yl)ethan-1-amine bis-hydrochloride (1.174 g, 3.98 mmol), methyl (1R,4r)-4-((R)-1-(((R)-6-(3-fluorophenyl)-4-(2,3,5,6-tetrafluorophenoxy)-5,6,7,8-tetrahydroquinazolin-2-yl)(methyl)amino)propyl)cyclohexane-1-carboxylate (2 g, 3.31 mmol) in iPrOH (Volume: 3 mL) and DIPEA (2.315 mL, 13.25 mmol) was stirred at 110° C. for 3 days. The mixture was added EtOAc (100 ml) and washed with $NaHCO_3$sat. solution and brine, dried over $Na_2SO_4$, and concentrated. The residue was purified through flash column chromatography (0-25% EtOAc/Heptane to elute SM out, 40-85% EtOAc/DCM to elute product out, 120 silica column, 1 injection) to give desired product methyl (1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylate as a light pale solid (1.25 g). LCMS: m/z=660.4 [M+H]$^+$.

Step 4: A solution of methyl (1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylate (1.05 g, 1.591 mmol) in MeOH (Volume: 12 mL, Ratio: 2.000) and Water (Volume: 6 mL, Ratio: 1.000) was added NaOH,(4M, 3.98 mL, 15.91 mmol) and stirred at 50° C. for 30 min and the mixture was half concentrated and directly load to be purified by reverse phase column. (120 g ISCO gold C-18 column, 10-60% MeCN/water, with 0.1% $NH_4OH$ as modifier to afford 0.77 g of (1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl) cyclohexane-1-carboxylic acid. LCMS: m/z=646.7 [M+H]+; $^1$H NMR (400 MHz, Methanol-d4) δ 7.39 (s, 1H), 7.35-7.17 (m, 2H), 7.12-6.96 (m, 2H), 6.84 (td, J=8.6, 2.7 Hz, 1H), 5.41 (d, J=9.5 Hz, 1H), 4.39 (s, 1H), 3.73 (s, 3H), 3.01-2.82 (m, 3H), 2.77 (s, 4H), 2.66 (dq, J=15.9, 10.7, 8.1 Hz, 4H), 2.42-2.19 (m, 1H), 2.10-1.50 (m, 12H), 1.50-1.05 (m, 6H), 0.94-0.73 (m, 5H), 0.67 (t, J=7.2 Hz, 3H), 0.50 (d, J=12.7 Hz, 1H).

The following compounds were made using the above procedure or modifications to the above procedure using the corresponding intermediates.

| | | |
|---|---|---|
| 87 | 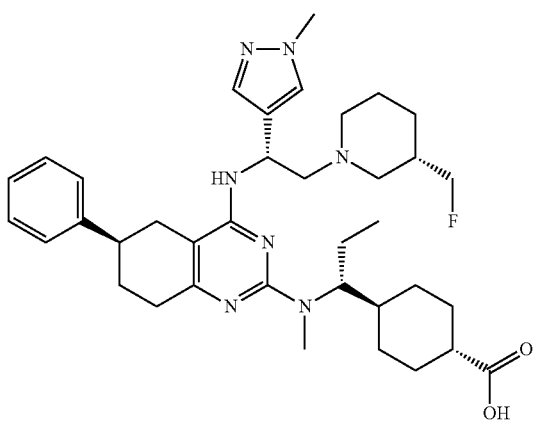 [SMILES: CC[C@H]([C@H]1CC[C@H](C(=O)O)CC1)N(C)c1nc2c(c(N[C@@H](CN3CCC[C@H](CF)C3)c3cnn(C)c3)n1)C[C@H](c1ccccc1)CC2] | LCMS m/z [M + H]⁺ = 646.4, ¹H NMR (400 MHz, MeOD) δ 7.41 (s, 1H), 7.36-7.19 (m, 5H), 7.13 (ddd, J = 8.5, 5.5, 2.5 Hz, 1H), 5.51-5.23 (m, 1H), 4.55-4.32 (m, 1H), 4.30-4.00 (m, 2H), 3.75 (s, 3H), 2.97-2.61 (m, 10H), 2.56 (dd, J = 12.9, 5.3 Hz, 1H), 2.48-2.24 (m, 1H), 2.12-1.65 (m, 10H), 1.65-1.52 (m, 2H), 1.52-1.10 (m, 6H), 1.10-0.77 (m, 2H), 0.69 (t, J = 7.3 Hz, 3H), 0.53 (d, J = 12.7 Hz, 1H). |
| 57 | 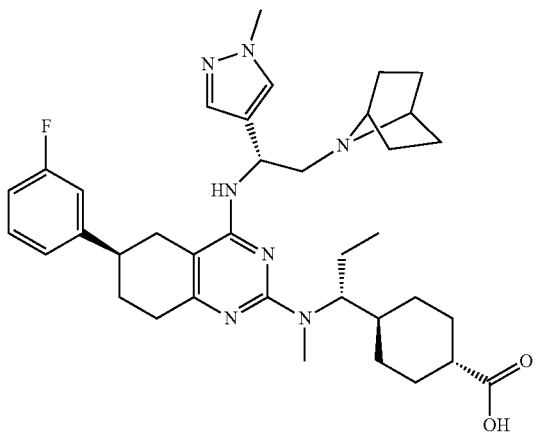 [SMILES: CC[C@H]([C@H]1CC[C@H](C(=O)O)CC1)N(C)c1nc2c(c(N[C@@H](CN3C4CCC3CC4)c3cnn(C)c3)n1)C[C@H](c1cccc(F)c1)CC2] | LCMS m/z [M + H]⁺ = 644.3, ¹H NMR (400 MHz, DMSO) δ 7.54-7.18 (m, 3H), 7.13 (d, J = 8.6 Hz, 2H), 6.97 (t, J = 8.6 Hz, 1H), 6.34-5.86 (m, 1H), 5.40-4.87 (m, 1H), 4.63-4.26 (m, 1H), 3.68 (s, 3H), 2.97-2.80 (m, 2H), 2.76-2.49 (m, 8H), 2.31-2.05 (m, 2H), 2.00-1.39 (m, 11H), 1.16 (dd, J = 39.4, 22.6 Hz, 9H), 0.77 (d, J = 12.0 Hz, 1H), 0.60 (t, J = 7.3 Hz, 4H). |

Example 18: Synthesis of (1R,4r)-4-((R)-1-((6-(3-fluorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid (Compound 55)

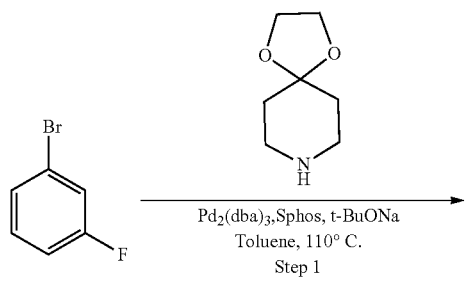

-continued
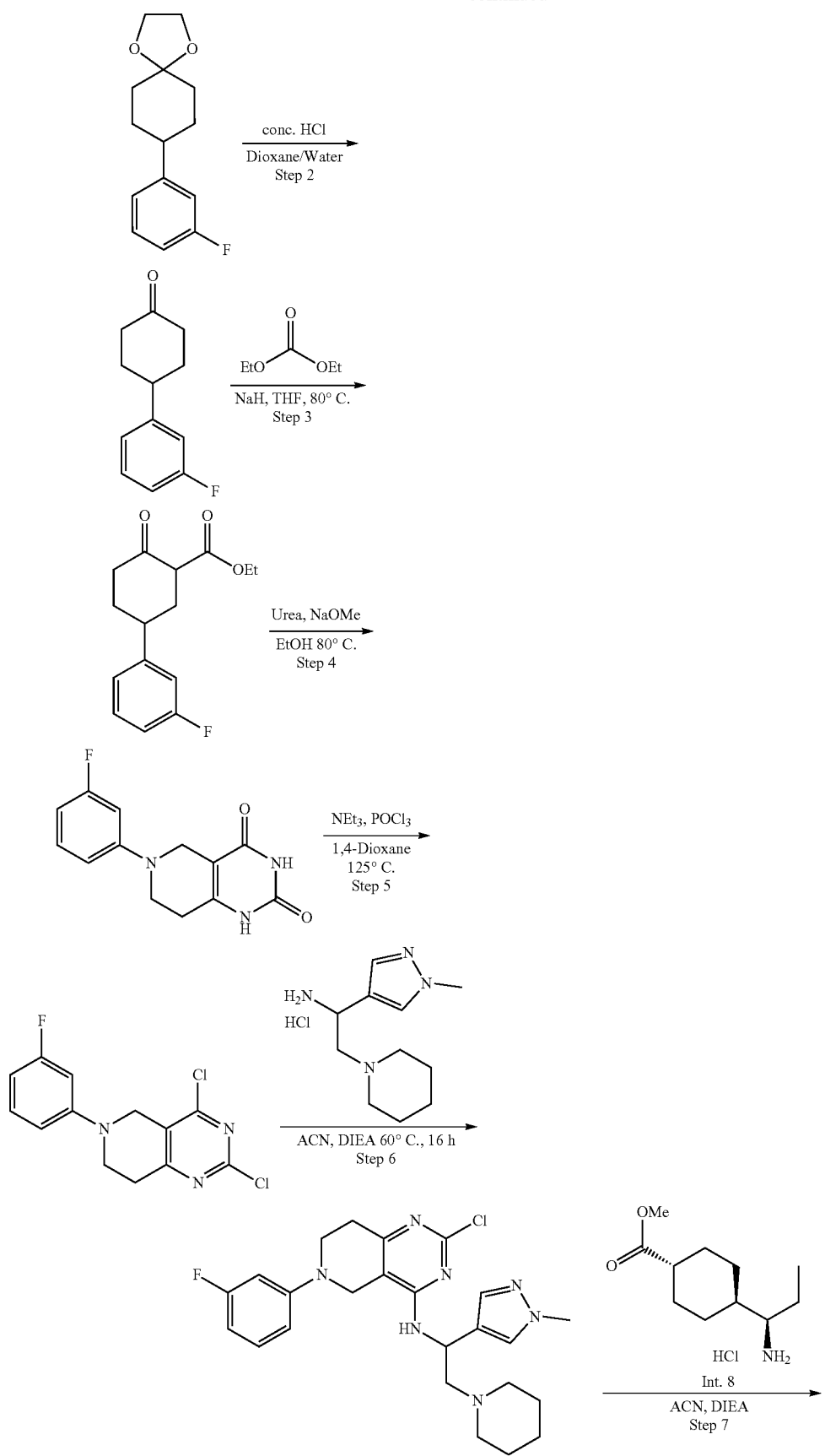

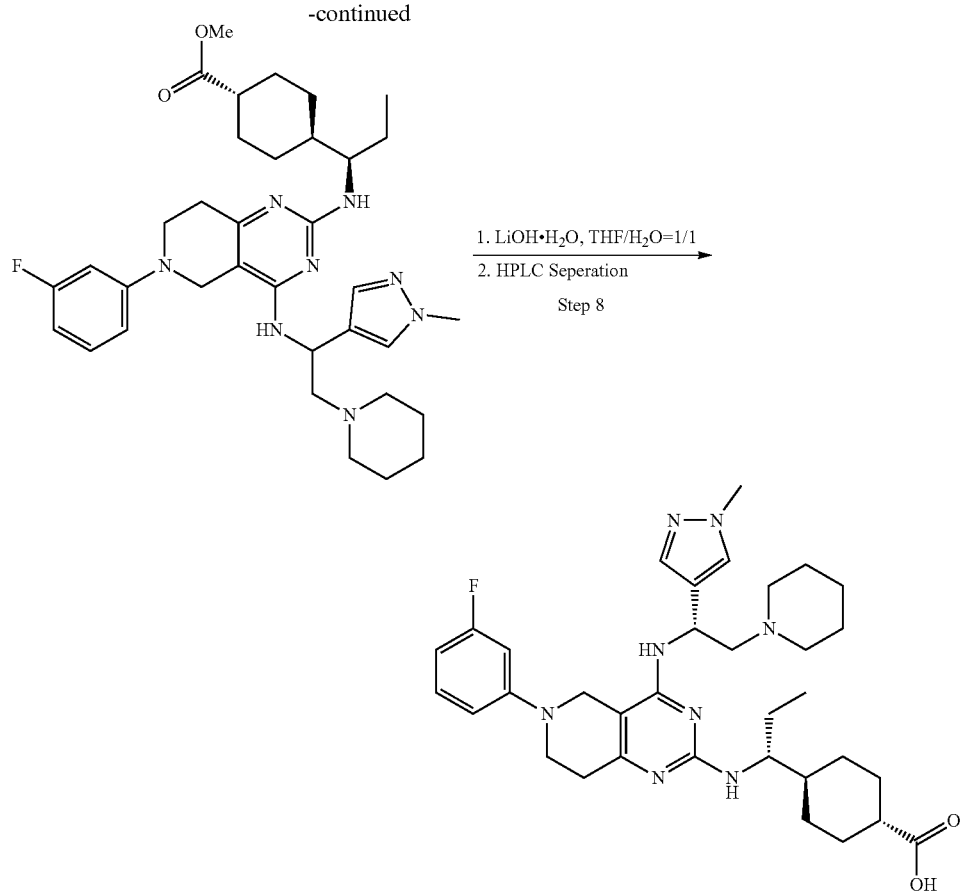

Step 1: To a solution of 1-bromo-3-fluorobenzene (30 g, 209.52 mmol) and 1,4-dioxa-8-azaspiro[4.5]decane (73.33 g, 419.04 mmol) in toluene (500 mL) was added t-BuONa (40.27 g, 139.68 mmol), Sphos (8.60 g, 20.95 mmol) and Pd$_2$(dba)$_3$ (9.59 g, 10.48 mmol) at 25° C. under N$_2$. Then the mixture was stirred at 110° C. for 16 h before degassed three times by N$_2$. LCMS showed desired mass was detected. The reaction mixture was poured into H$_2$O (1000 mL) and acidified by 3N HCl to adjust pH=1, then extracted with EtOAc (800 mL×2). The aqueous phase was adjust pH=7-8 by addition of NaHCO$_3$. Extracted with EtOAc (800 mL×3), the combined organic phase was dried over anhydrous Na$_2$SO$_4$, filtered and concentrated to afford 8-(3-fluorophenyl)-1,4-dioxa-8-azaspiro[4.5]decane (42 g, 91.28% purity) as a yellow oil. LCMS: RT=0.651 min, m/z=238.1 [M+H]$^+$.

Step 2: To a solution of 8-(3-fluorophenyl)-1,4-dioxa-8-azaspiro[4.5]decane (42 g, 177.01 mmol) in Dioxane/H$_2$O (450 mL, V/V=2/1) was added conc. HCl (150 mL) at 25° C. Then the mixture was stirred at 60° C. for 24 h. TLC (Petroleum ether/Ethylacetate=5/1) showed most of starting material (Rf=0.5) was consumed and one major spot (Rf=0.4) was detected. The reaction mixture was poured into H$_2$O (1000 mL) and basified by 6N NaOH solution to adjust pH=7-8. The mixture was extracted with EtOAc (1000 mL×3). The combined organic phase was dried over anhydrous Na$_2$SO$_4$, filtered and concentrated. The residue was purified by combiflash on silica gel column chromatography (From PE to 50% EA) and concentrated to afford 1-(3-fluorophenyl)piperidin-4-one (20 g, 95% purity) as a colorless oil. LCMS: RT=0.723 min, m/z=194.0 [M+H]$^+$.

Step 3: To a solution of Diethyl carbonate (36.68 g, 310.53 mmol) in THF (60 mL) was added NaH (2.98 g, 60%, 74.53 mmol) portionwise. Then the mixture was heated to 80° C. and a solution of 1-(3-fluorophenyl)piperidin-4-one (12 g, 62.11 mmol) in THF (60 mL) was added to the mixture dropwise. The reaction mixture was stirred at 80° C. for 2 h. TLC (Petroleum ether/Ethylacetate=5/1) showed starting material (Rf=0.4) was consumed completely and one major spot (Rf=0.8) was detected. The reaction mixture was quenched with saturated NH$_4$C$_1$ solution (300 mL) and extracted with EtOAc (200 mL×3). The combined organic phase was dried over anhydrous Na$_2$SO$_4$, filtered and concentrated. The residue was purified by combiflash on silica gel column chromatography (From PE to 50% EA) and concentrated to afford ethyl 1-(3-fluorophenyl)-4-oxopiperidine-3-carboxylate (8.0 g, 80% purity) as a colorless oil. LCMS: RT=0.927 min, m/z=266.0 [M+H]+.

Step 4: To a solution of ethyl 1-(3-fluorophenyl)-4-oxopiperidine-3-carboxylate (4 g, 15.08 mmol) in EtOH (100 mL) was added urea (1.81 g, 30.16 mmol) and NaOMe (1.63 g, 30.16 mmol) at 25° C. Then the mixture was stirred at 80° C. for 16 h. LCMS showed one major peak with desired mass was detected. The precipitated was filtered and dried under reduced pressure to afford 6-(3-fluorophenyl)-5,6,7,8-tetrahydropyrido[4,3-d]pyrimidine-2,4(1H,3H)-dione (1.2 g, 87% purity) as a yellow solid. LCMS: RT=0.683 min, m/z=262.0 [M+H]+.

Step 5: To a solution of 6-(3-fluorophenyl)-5,6,7,8-tetrahydropyrido[4,3-d]pyrimidine-2,4(1H,3H)-dione (1.2 g, 4.59 mmol) in dioxane (10 mL) was added POCl$_3$ (7 mL) at 25° C. Then the reaction mixture was heated to 125° C. and stirred for 16 h. LCMS showed one major peak with desired mass was detected. The reaction mixture was concentrated under reduced pressured to remove POCl₃. Then the residue was diluted with EA (50 mL) and washed with saturated NaHCO₃ solution (50 mL×2). The combined organic phase was dried over anhydrous Na₂SO₄, filtered and concentrated. The residue was purified by silica gel column chromatography (Petroleum ether/Ethylacetate=10/1—Petroleum ether/Ethylacetate=2/1) and concentrated to afford 2,4-dichloro-6-(3-fluorophenyl)-5,6,7,8-tetrahydropyrido[4,3-d]pyrimidine (400 mg, 87% purity) as a yellow solid. LCMS: RT=0.910 min, m/z=297.9 [M+H]+.

Step 6: To a solution of 2,4-dichloro-6-(3-fluorophenyl)-5,6,7,8-tetrahydropyrido[4,3-d]pyrimidine (150 mg, 0.503 mmol) and 1-(1-methyl-1H-pyrazol-4-yl)-2-(piperidin-1-yl)ethan-1-amine bis-hydrochloride (212 mg, 0.603 mmol) in MeCN (2 mL) was added DPIEA (325 mg, 2.52 mmol). Then the mixture was stirred at 80° C. for 4 h. LCMS showed one major peak with desired mass was detected. The reaction mixture was diluted with H₂O (5 mL) and extracted with ethylacetate (3 mL×3). The combined organic phase was dried over anhydrous Na₂SO₄, filtered and concentrated. The residue was purified by silica gel column chromatography (From petroleum ether to ethylacetate) and concentrated to afford 2-chloro-6-(3-fluorophenyl)-N-(1-(1-methyl-1H-pyrazol-4-yl)-2-(piperidin-1-yl)ethyl)-5,6,7,8-tetrahydropyrido[4,3-d]pyrimidin-4-amine (100 mg, 96% purity) as a yellow solid. LCMS: RT=0.731 min, m/z=470.1 [M+H]+.

Step 7: To a solution of 2-chloro-6-(3-fluorophenyl)-N-(1-(1-methyl-1H-pyrazol-4-yl)-2-(piperidin-1-yl)ethyl)-5,6,7,8-tetrahydropyrido[4,3-d]pyrimidin-4-amine (100 mg, 0.425 mmol) in ACN (0.5 mL) was added DPIEA (82 mg, 0.638 mmol) and methyl (1R,4r)-4-((R)-1-aminopropyl)cyclohexane-1-carboxylate hydrochloride (100 mg, 0.212 mmol) at 25° C. Then the mixture was stirred at 160° C. for 10 h under microwave. LCMS showed starting materail was consumed completely and one major peak with desired mass was detected. The reaction mixture was diluted with H₂O (5 mL) and extracted with EtOAc (3 mL×3). The combined organic phase was dried over anhydrous Na₂SO₄, filtered and concentrated. The residue was purified by prep-TLC (EA) and to afford methyl (1R,4r)-4-((1R)-1-((6-(3-fluorophenyl)-4-((1-(1-methyl-1H-pyrazol-4-yl)-2-(piperidin-1-yl)ethyl)amino)-5,6,7,8-tetrahydropyrido[4,3-d]pyrimidin-2-yl)amino)propyl)cyclohexane-1-carboxylate (120 mg, 82% purity) as a yellow oil. LCMS: RT=0.724 min, m/z=633.3 [M+H]+.

Step 8: To a solution of methyl (1R,4r)-4-((1R)-1-((6-(3-fluorophenyl)-4-((1-(1-methyl-1H-pyrazol-4-yl)-2-(piperidin-1-yl)ethyl)amino)-5,6,7,8-tetrahydropyrido[4,3-d]pyrimidin-2-yl)amino)propyl)cyclohexane-1-carboxylate (100 mg, 0.158 mmol) in THF/H₂O (1 mL, V/V=1/1) was added LiOH·H₂O (33 mg, 0.790 mmol) at 25° C. Then the mixture was stirred at 25° C. for 4 h. LCMS showed starting material was consumed completely and desired mass was detected. Saturated citric acid solution was added to the reaction mixture to adjust pH=7. The mixture was concentrated to remove THF. The aqueous phase was purified by prep-HPLC (Column: Phenomenex Gemini-NX C18 75*30 mm*3 um, Condition: water(10 mM NH₄HCO₃)-ACN, Begin B: 24, End B: 44, Gradient Time(min):8, 100% B Hold Time(min): 2, FlowRate(mL/min):30) to afford 19.8 mg of (1R,4r)-4-((R)-1-((6-(3-fluorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid as a yellow solid. LCMS: RT=0.820 min, m/z=619.7 [M+H]+; ¹H NMR (400 MHz, DMSO-d6) δ 7.50 (s, 1H), 7.36 (s, 1H), 7.26-7.17 (m, 1H), 6.88-6.78 (m, 2H), 6.49 (dt, J=2.1, 8.3 Hz, 1H), 6.12 (br d, J=7.8 Hz, 1H), 5.51-5.38 (m, 2H), 3.97 (s, 1H), 3.78 (s, 2H), 3.74-3.65 (m, 1H), 3.56-3.46 (m, 2H), 2.78-2.62 (m, 4H), 2.62-2.56 (N, 2H), 2.47 (br d, J=5.6 Hz, 4H), 2.09-1.96 (m, 2H), 1.88 (br d, J5=11.3 Hz, 2H), 1.79-1.66 (m, 2H), 1.59-1.15 (3, 12H), 1.04-0.91 (m, 2H), 0.85 (br t, J=7.3 Hz, 3H).

The following compounds were made using the above procedure or modifications to the above procedure using the corresponding intermediates.

| 80 | 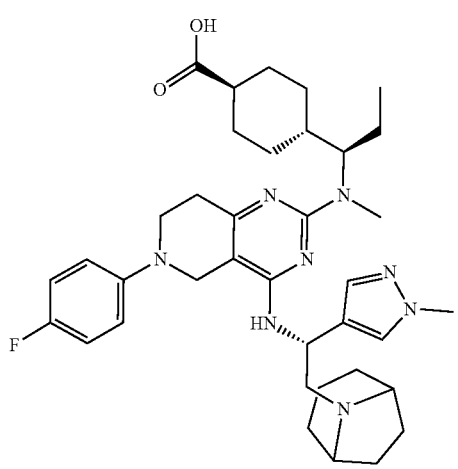 | LCMS m/z [M + H]⁺ = 659.6, ¹H NMR(400 MHz, DMSO-d6) δ ppm 12.60-11.13 (m, 1H), 7.53 (s, 1H), 7.38 (s, 1H), 7.17-7.01 (m, 4H), 6.46 (br d, J = 6.8 Hz, 1H), 5.14 (q, J = 6.2 Hz, 1H), 4.63-4.36 (m, 1H), 3.98-3.84 (m, 2H), 3.77 (s, 3H), 3.44 (br t, J = 5.0 Hz, 2H), 3.12 (br s, 1H), 2.73 (s, 3H), 2.69-2.59 (m, 5H), 2.04-1.94 (m, 1H), 1.92-1.78 (m, 4H), 1.75-1.44 (m, 8H), 1.39-1.25 (m, 6H), 1.18-1.04 (m, 1H), 0.93-0.78 (m, 1H), 0.67 (br t, J = 7.1 Hz, 3H), 0.62-0.40 (m, 1H). |

| | | |
|---|---|---|
| 124 | 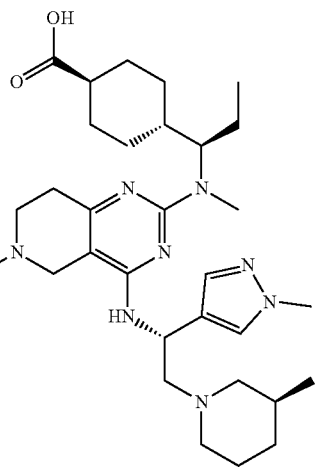 | LCMS m/z [M + H]⁺ = 647.6, ¹H NMR(400 MHz, DMSO-d6) δ ppm 7.70-7.44 (m, 1H), 7.44-7.31 (m, 1H), 7.29-7.16 (m, 1H), 6.90 (br d, J = 9.3 Hz, 2H), 6.58-6.40 (m, 2H), 5.51-5.35 (m, 1H), 4.62-4.44 (m, 1H), 3.92 (br s, 1H), 3.85-3.68 (m, 2H), 3.58-3.49 (m, 1H), 3.50-3.38 (m, 3H), 2.95-2.83 (m, 2H), 2.81-2.72 (m, 3H), 2.60 (br dd, J = 6.3, 8.0 Hz, 4H), 2.05-1.79 (m, 5H), 1.78-1.48 (m, 7H), 1.47-1.08 (m, 7H), 0.97-0.75 (m, 5H), 0.73-0.62 (m, 3H). |
| 157 | 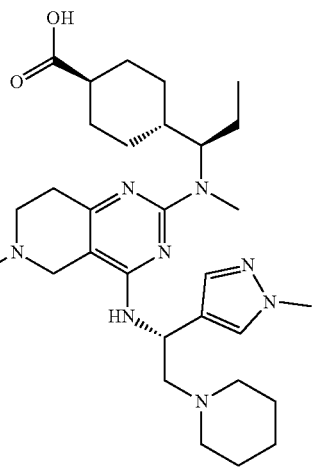 | LCMS m/z [M + H]⁺ = 633.7, ¹H NMR(400 MHz, DMSO-d6) δ ppm 7.53 (s, 1H), 7.36 (s, 1H), 7.23 (q, J = 7.8 Hz, 1H), 6.90 (br d, J = 9.8 Hz, 2H), 6.57-6.45 (m, 2H), 5.38 (br d, J = 6.7 Hz, 1H), 4.52-4.40 (m, 1H), 3.92 (br d, J = 6.0 Hz, 2H), 3.77 (s, 4H), 3.53 (br t, J = 5.3 Hz, 2H), 2.77-2.67 (m, 5H), 2.61 (br s, 2H), 2.02-1.93 (m, 1H), 1.92-1.77 (m, 3H), 1.76-1.57 (m, 3H), 1.47 (br d, J = 3.9 Hz, 4H), 1.36 (br d, J = 3.5 Hz, 4H), 1.22-1.06 (m, 2H), 0.94-0.79 (m, 2H), 0.74-0.47 (m, 5H). |
| 76 | 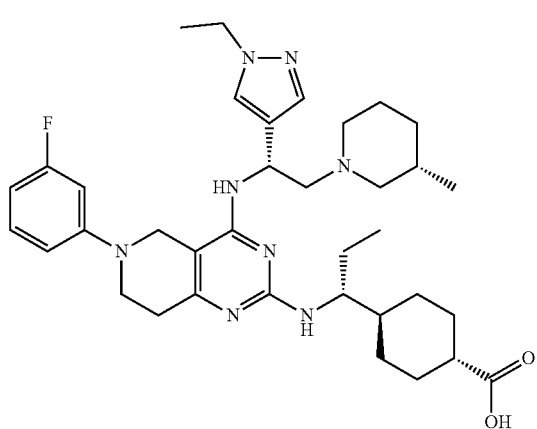 [SMILES: CC[C@@H](Nc1nc2c(c(N[C@@H](CN3CCC[C@H](C)C3)c3cnn(CC)c3)n1)CN(c1cccc(F)c1)CC2)[C@H]1CC[C@H](C(=O)O)CC1] | LCMS m/z [M + H]⁺ = 647.60, ¹H NMR (400 MHz, METHANOL-d₄) δ ppm 7.59 (s, 1H) 7.46 (s, 1H) 7.15-7.28 (m, 1H) 6.76-6.93 (m, 2H) 6.51 (td, J = 8.31, 2.15 Hz, 1H) 5.74 (br dd, J = 9.78, 4.70 Hz, 1H) 4.03-4.21 (m, 3H) 3.87-3.99 (m, 1H) 3.82 (br s, 1H) 3.43-3.67 (m, 3H) 2.87-3.16 (m, 4H) 2.66-2.83 (m, 3H) 1.84-2.13 (m, 6H) 1.52-1.83 (m, 6H) 1.22-1.49 (m, 7H) 0.96-1.11 (m, 2H) 0.82-0.95 (m, 5H). |

| | | |
|---|---|---|
| 99 | 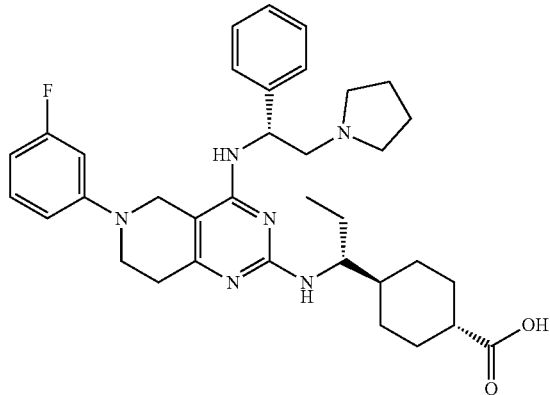 [SMILES: CC[C@@H](Nc1nc2c(c(N[C@@H](CN3CCCC3)c3ccccc3)n1)CN(c1cccc(F)c1)CC2)[C@H]1CC[C@H](C(=O)O)CC1] | LCMS m/z [M + H]⁺ = 600.80, ¹H NMR (300 MHz, METHANOL-d₄) δ ppm 8.51 (s, 1H) 7.13-7.50 (m, 7H) 6.76-6.97 (m, 2H) 6.54 (td, J = 8.23, 1.97 Hz, 1H) 5.73 (br d, J = 10.53 Hz, 1H) 3.95-4.33 (m, 2H) 3.43-3.85 (m, 5H) 3.17 (br d, J = 4.61 Hz, 4H) 2.77 (br s, 3H) 1.13-2.10 (m, 13H) 0.92 (br t, J = 7.24 Hz, 4H) 0.69 (br d, J = 11.19 Hz, 1H). |
| 106 | 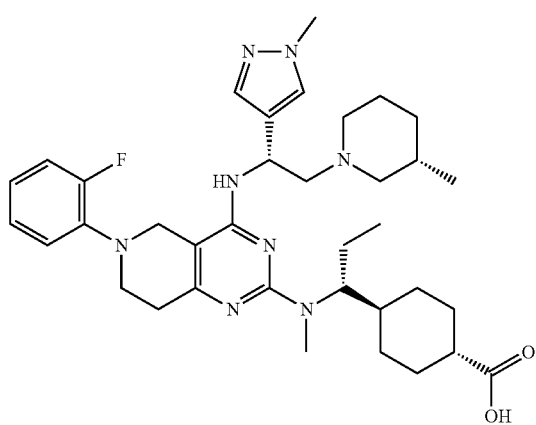 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(c1ccccc1F)CC2] | LCMS m/z [M + H]⁺ = 647.70, ¹H NMR (400 MHz, METHANOL-d4) δ = 7.53 (s, 1H), 7.43 (br s, 1H), 7.23-7.16 (m, 1H), 7.13-7.04 (m, 2H), 7.03-6.96 (m, 1H), 5.60 (br s, 1H), 4.51 (br s, 1H), 4.04-3.93 (m, 3H), 3.86 (s, 3H), 3.49-3.39 (m, 2H), 3.14-3.06 (m, 3H), 2.99-2.96 (m, 1H), 2.87-2.84 (m, 5H), 2.00-1.74 (m, 8H), 1.60-1.25 (m, 7H), 0.98-0.89 (m, 5H), 0.79 (t, J = 7 Hz, 3H), 0.62-0.59 (m, 1H). |
| 110 | 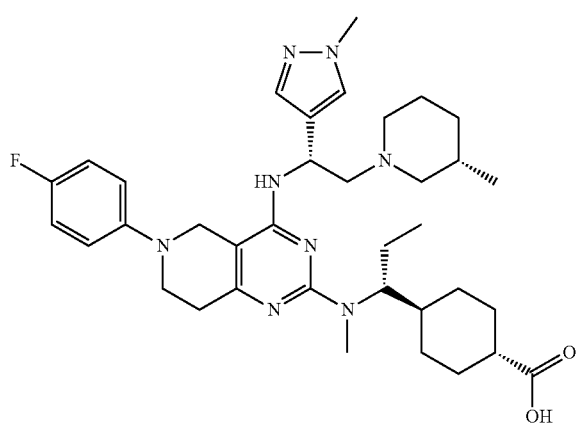 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(c1ccc(F)cc1)CC2] | LCMS m/z [M + H]⁺ = 647.5, ¹H NMR (400 MHz, METHANOL-d₄) δ ppm 7.51 (br s, 1 H), 7.41 (br s, 1H), 7.07-7.16 (m, 2H), 6.94-7.05 (m, 2H), 5.57 (br d, J = 3.07 Hz, 1H), 4.51 (br s, 1H), 3.88-4.04 (m, 2H), 3.84 (s, 3H), 3.39-3.53 (m, 2H), 2.89-3.07 (m, 3H), 2.72-2.88 (m, 5H), 1.61-2.12 (m, 10H), 1.20-1.60 (m, 8H), 0.87 (br d, J = 6.14 Hz, 5H), 0.76 (br t, J = 7.02 Hz, 3H). |

-continued

| | | |
|---|---|---|
| 174 | 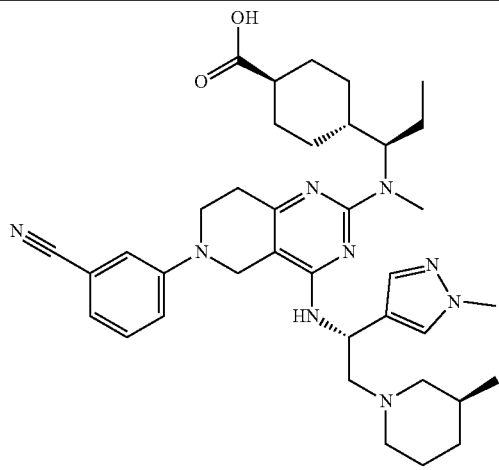 | LCMS m/z [M + H]⁺ = 654.6, ¹H NMR(400 MHz, DMSO-d6) δ 7.57 (s, 1H), 7.47-7.38 (m, 4H), 7.18-7.13 (m, 1H), 6.48 (br d, J = 7.9 Hz, 1H), 5.45 (br d, J = 7.3 Hz, 1H), 4.56-4.44 (m, 1H), 3.96 (br s, 2H), 3.79 (s, 3H), 3.66-3.49 (m, 3H), 2.95-2.88 (m, 1H), 2.82-2.72 (m, 4H), 2.66-2.62 (m, 2H), 2.02-1.77 (m, 5H), 1.75-1.50 (m, 7H), 1.45-1.19 (m, 6H), 1.16-1.09 (m, 1H), 0.90-0.78 (m, 5H), 0.72-0.66 (m, 3H). |
| 170 | 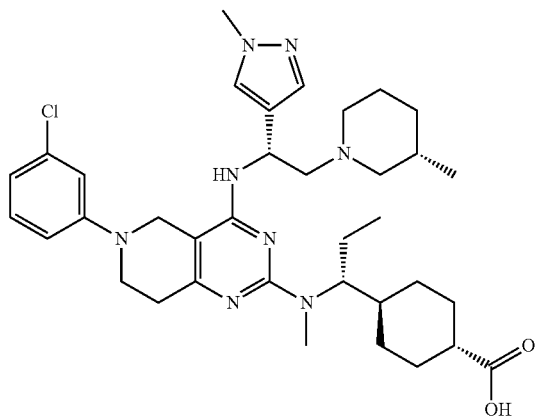 [SMILES: CC[C@H]([C@H]1CC[C@H](C(=O)O)CC1)N(C)c1nc2c(c(N[C@@H](CN3CCC[C@H](C)C3)c3cnn(C)c3)n1)CN(c1cccc(Cl)c1)CC2] | LCMS m/z [M + H]⁺ = 663.55, ¹H NMR (400 MHz, METHANOL-d4) δ = 7.51 (s, 1H), 7.41(s, 1H), 7.13-7.09 (m, 2H), 7.02-6.97 (m, 2H), 5.57 (br s, 1H), 4.53 (br s, 1H), 4.00-3.93 (m, 2H), 3.84 (s, 3H), 3.47-3.60 (m, 3H), 3.10-2.89 (m, 3H), 2.81-2.54 (m, 6H), 2.10-1.70 (m, 9H), 1.60-1.15 (m, 7H), 1.05-0.86 (m, 5H), 0.77-0.74 (m, 3H). |

Example 19—Biological Assay—Cellular cGMP Production

The 174 compounds described were tested for their functional activity in a cellular cGMP production assay using human NPR1 expressing CHO—$K_1$ cells (DiscoverX (Cat. #93-0804C2) and monkey NPR1 expressing CHO—$K_1$ cells (generated in-house using pcDNA3.1(−)Neo-CynoNPR1). For the functional characterization of the compounds, the production of cyclic guanosine 3',5'-cyclic monophosphate (cGMP) upon binding to and stimulation of NPR1 expressed on the cell surface of CHO—$K_1$ cells was monitored. Cellular cGMP is a major second messenger that mediates cell activities and is synthesized by activated NPR1 triggered by binding of the natural ligand ANP. Therefore, a commercial assay kit was used (CisBio HTRF Assay Kit (Cat. #62GM2PEB)). The assay was performed according to manufacturer's instructions with minor deviations. In brief, human NPR1 cells were adjusted to $2 \times 10^4$ cells/mL and monkey NPR1 cells adjusted to $2.5 \times 10^4$ cells/mL, and 20 μL/well were seeded in 384-well microtiter plates and incubated overnight. All compound stocks were diluted in PBS+0.1% BSA at 2-fold the final assay concentration. After addition of 10 μL/well of assay buffer (PBS+0.1% BSA+1 mM IBMX) and 10 μL/well of the compounds in different concentrations (12-point dose-response with 3-fold dilutions from a top concentration of 30 μM), the plate was incubated for 30 min at 37° C. to allow for cGMP production. In parallel, a standard curve using a calibrator (contained in the kit) was generated. The cells were lysed and a mix of cGMP-d2 and anti-cGMP-cryptate was added and incubated for 1 h at room temperature. The readout was performed using an Envision plate reader (PerkinElmer) with an excitation wavelength of 317 nm and an emission wavelength of 665 nm. cGMP concentration (Delta F [° %]) was calculated according to the following formulae:

$$\text{Ratio} = [(A_{665\ nm}/B_{620nm}) \ast 10^4]$$

$$\text{Mean Ratio} = (\Sigma \text{ratios}/2)$$

$$CV = [(Std\ \text{deviation/Mean ratio}) \ast 100]$$

$$\text{Delta } F = [((\text{Calibrator or sample Ratio} - \text{Ratio}_{neg})/\text{Ratio}_{neg}) \ast 100]$$

Ratio$_{neg}$: negative control

An ANP (Phoenix Pharmaceuticals (Cat. #005-06)) dose-response curve was used as a control for each assay run, and Amax (the maximum cGMP production achieved) for each compound was expressed as a percentage of the maximum cGMP produced with ANP.

TABLE 1

In vitro functional data

| Compound # | Human NPR1 AC50 (μM) | Human NPR1 Amax (% of ANP) | Monkey NPR1 AC50 (μM) | Monkey NPR1 Amax (% of ANP) |
|---|---|---|---|---|
| 1 | 0.014 | 93.788 | 0.010 | 97.462 |
| 2 | 0.042 | 96.935 | 0.044 | 103.371 |
| 3 | 0.066 | 105.403 | 0.045 | 107.571 |
| 4 | 0.072 | 99.041 | 0.070 | 101.838 |
| 5 | 0.072 | 85.741 | 0.068 | 104.503 |
| 6 | 0.077 | 98.462 | 0.058 | 98.535 |
| 7 | 0.080 | 97.105 | 0.050 | 102.341 |
| 8 | 0.087 | 92.409 | 0.077 | 101.778 |
| 9 | 0.088 | 95.056 | 0.045 | 95.667 |
| 10 | 0.091 | 96.065 | 0.073 | 97.058 |
| 11 | 0.094 | 103.738 | 0.070 | 113.853 |
| 12 | 0.094 | 96.068 | 0.073 | 95.099 |
| 13 | 0.094 | 99.405 | 0.064 | 100.145 |
| 14 | 0.097 | 94.761 | 0.062 | 88.286 |
| 15 | 0.102 | 106.001 | 0.092 | 109.175 |
| 16 | 0.103 | 100.021 | 0.047 | 98.785 |
| 17 | 0.105 | 97.959 | 0.068 | 99.682 |
| 18 | 0.107 | 97.609 | 0.071 | 100.607 |
| 19 | 0.108 | 100.504 | 0.082 | 98.174 |
| 20 | 0.109 | 95.253 | 0.060 | 92.710 |
| 21 | 0.111 | 96.122 | 0.093 | 101.974 |
| 22 | 0.114 | 102.676 | 0.074 | 103.742 |
| 23 | 0.115 | 120.018 | 0.072 | 132.182 |
| 24 | 0.125 | 112.884 | 0.102 | 128.837 |
| 25 | 0.126 | 102.816 | 0.108 | 106.072 |
| 26 | 0.131 | 115.149 | 0.091 | 102.667 |
| 27 | 0.137 | 92.458 | 0.137 | 102.654 |
| 28 | 0.139 | 103.247 | 0.134 | 105.314 |
| 29 | 0.140 | 102.911 | 0.137 | 128.079 |
| 30 | 0.140 | 99.863 | 0.077 | 99.091 |
| 31 | 0.144 | 92.978 | 0.089 | 100.914 |
| 32 | 0.144 | 99.842 | 0.084 | 92.720 |
| 33 | 0.145 | 99.163 | 0.104 | 106.934 |
| 34 | 0.146 | 95.375 | 0.091 | 100.553 |
| 35 | 0.148 | 92.607 | 0.127 | 104.934 |
| 36 | 0.150 | 101.036 | 0.133 | 101.251 |
| 37 | 0.150 | 105.989 | 0.158 | 107.224 |
| 38 | 0.161 | 101.675 | 0.083 | 101.007 |
| 39 | 0.162 | 100.189 | 0.102 | 97.588 |
| 40 | 0.166 | 102.476 | 0.127 | 105.150 |
| 41 | 0.168 | 96.843 | 0.144 | 92.494 |
| 42 | 0.169 | 92.080 | 0.146 | 101.138 |
| 43 | 0.170 | 101.178 | 0.158 | 104.036 |
| 44 | 0.173 | 99.256 | 0.102 | 107.199 |
| 45 | 0.175 | 98.472 | 0.125 | 99.911 |
| 46 | 0.179 | 93.728 | 0.146 | 101.294 |
| 47 | 0.180 | 101.280 | 0.097 | 96.550 |
| 48 | 0.183 | 106.036 | 0.101 | 101.062 |
| 49 | 0.185 | 104.186 | 0.138 | 106.033 |
| 50 | 0.187 | 93.357 | 0.135 | 107.881 |
| 51 | 0.187 | 106.105 | 0.110 | 104.734 |
| 52 | 0.188 | 97.880 | 0.167 | 106.496 |
| 53 | 0.190 | 101.185 | 0.101 | 101.261 |
| 54 | 0.194 | 95.979 | 0.174 | 103.704 |
| 55 | 0.194 | 92.712 | 0.142 | 93.391 |
| 56 | 0.198 | 102.955 | 0.196 | 108.953 |
| 57 | 0.199 | 101.340 | 0.082 | 103.000 |
| 58 | 0.201 | 99.715 | 0.149 | 95.422 |
| 59 | 0.205 | 99.614 | 0.153 | 104.401 |
| 60 | 0.205 | 93.233 | 0.099 | 106.189 |
| 61 | 0.207 | 104.236 | 0.122 | 102.127 |
| 62 | 0.207 | 94.244 | 0.133 | 103.497 |
| 63 | 0.210 | 100.629 | 0.196 | 99.684 |
| 64 | 0.213 | 93.045 | 0.175 | 92.911 |
| 65 | 0.217 | 106.664 | 0.128 | 99.329 |
| 66 | 0.219 | 96.868 | 0.123 | 98.088 |
| 67 | 0.229 | 95.228 | 0.155 | 98.233 |
| 68 | 0.234 | 96.721 | 0.095 | 101.066 |
| 69 | 0.234 | 98.634 | 0.220 | 100.449 |
| 70 | 0.234 | 97.399 | 0.230 | 100.673 |
| 71 | 0.237 | 91.827 | 0.078 | 121.791 |
| 72 | 0.242 | 99.718 | 0.137 | 104.824 |
| 73 | 0.245 | 94.290 | 0.172 | 99.527 |
| 74 | 0.246 | 102.182 | 0.167 | 117.270 |
| 75 | 0.247 | 93.803 | 0.162 | 102.588 |
| 76 | 0.247 | 100.752 | 0.147 | 100.861 |
| 77 | 0.249 | 95.666 | 0.134 | 96.715 |
| 78 | 0.254 | 99.406 | 0.212 | 102.158 |
| 79 | 0.257 | 101.351 | 0.327 | 104.610 |
| 80 | 0.267 | 94.876 | 0.137 | 102.546 |
| 81 | 0.271 | 101.636 | 0.175 | 100.863 |
| 82 | 0.272 | 96.493 | 0.278 | 106.556 |
| 83 | 0.282 | 98.117 | 0.173 | 98.205 |
| 84 | 0.284 | 100.223 | 0.191 | 102.883 |
| 85 | 0.285 | 102.461 | 0.238 | 95.638 |
| 86 | 0.286 | 101.050 | 0.192 | 92.318 |
| 87 | 0.292 | 93.715 | 0.235 | 100.104 |
| 88 | 0.303 | 98.817 | 0.255 | 94.699 |
| 89 | 0.309 | 98.816 | 0.268 | 103.084 |
| 90 | 0.313 | 103.308 | 0.224 | 106.347 |
| 91 | 0.315 | 98.135 | 0.184 | 102.129 |
| 92 | 0.317 | 99.678 | 0.249 | 99.824 |
| 93 | 0.318 | 92.058 | 0.261 | 91.105 |
| 94 | 0.326 | 101.620 | 0.226 | 105.567 |
| 95 | 0.334 | 97.121 | 0.173 | 94.323 |
| 96 | 0.336 | 103.654 | 0.106 | 101.912 |
| 97 | 0.338 | 107.286 | 0.192 | 96.148 |
| 98 | 0.346 | 100.756 | 0.179 | 105.533 |
| 99 | 0.351 | 102.315 | 0.256 | 94.886 |
| 100 | 0.354 | 92.848 | 0.161 | 105.588 |
| 101 | 0.377 | 93.777 | 0.335 | 101.874 |
| 102 | 0.382 | 96.769 | 0.279 | 107.819 |
| 103 | 0.393 | 101.239 | 0.350 | 106.030 |
| 104 | 0.396 | 106.357 | 0.290 | 109.908 |
| 105 | 0.396 | 99.945 | 0.272 | 97.086 |
| 106 | 0.399 | 100.198 | 0.254 | 104.076 |
| 107 | 0.404 | 97.223 | 0.224 | 100.163 |
| 108 | 0.410 | 93.072 | 0.248 | 99.706 |
| 109 | 0.412 | 91.101 | 0.190 | 115.338 |
| 110 | 0.419 | 99.979 | 0.238 | 103.438 |
| 111 | 0.424 | 106.085 | 0.271 | 103.264 |
| 112 | 0.427 | 90.394 | 0.394 | 97.009 |
| 113 | 0.438 | 98.462 | 0.460 | 99.894 |
| 114 | 0.449 | 108.428 | 0.296 | 113.348 |
| 115 | 0.474 | 111.049 | 0.387 | 106.285 |
| 116 | 0.477 | 95.817 | 0.471 | 104.029 |
| 117 | 0.524 | 100.635 | 0.500 | 109.499 |
| 118 | 0.540 | 94.446 | 0.400 | 99.466 |
| 119 | 0.542 | 89.681 | 0.378 | 90.965 |
| 120 | 0.553 | 96.905 | 0.427 | 102.755 |
| 121 | 0.570 | 100.330 | 0.382 | 102.117 |
| 122 | 0.574 | 102.209 | 0.411 | 99.605 |
| 123 | 0.592 | 103.006 | 0.377 | 102.761 |
| 124 | 0.617 | 106.069 | 0.406 | 101.428 |
| 125 | 0.619 | 106.130 | 0.410 | 114.072 |
| 126 | 0.620 | 98.906 | 0.452 | 102.477 |
| 127 | 0.623 | 102.596 | 0.355 | 102.089 |
| 128 | 0.629 | 105.430 | 0.416 | 95.117 |
| 129 | 0.646 | 93.751 | 0.362 | 91.227 |
| 130 | 0.671 | 88.663 | 0.205 | 114.798 |
| 131 | 0.693 | 101.666 | 0.582 | 109.531 |
| 132 | 0.757 | 97.440 | 0.620 | 103.231 |
| 133 | 0.765 | 95.978 | 0.647 | 99.809 |
| 134 | 0.792 | 101.936 | 0.684 | 96.371 |
| 135 | 0.805 | 94.757 | 0.604 | 99.242 |
| 136 | 0.812 | 103.913 | 0.516 | 96.754 |
| 137 | 0.840 | 95.603 | 0.379 | 99.351 |
| 138 | 0.852 | 105.993 | 0.734 | 101.929 |
| 139 | 0.876 | 105.089 | 0.696 | 111.911 |
| 140 | 0.885 | 89.152 | 0.499 | 96.883 |
| 141 | 0.888 | 102.728 | 0.731 | 105.798 |
| 142 | 0.901 | 107.815 | 0.313 | 95.614 |
| 143 | 0.920 | 104.085 | 0.694 | 100.784 |
| 144 | 0.985 | 114.314 | 0.873 | 152.392 |
| 145 | 1.049 | 97.636 | 0.900 | 103.150 |
| 146 | 1.069 | 104.657 | 0.702 | 96.864 |
| 147 | 1.077 | 97.612 | 0.671 | 101.537 |
| 148 | 1.084 | 93.518 | 0.834 | 102.851 |

TABLE 1-continued

In vitro functional data

| Compound # | Human NPR1 AC50 (μM) | Human NPR1 Amax (% of ANP) | Monkey NPR1 AC50 (μM) | Monkey NPR1 Amax (% of ANP) |
|---|---|---|---|---|
| 149 | 1.142 | 130.209 | 1.021 | 164.167 |
| 150 | 1.156 | 130.487 | 1.036 | 156.200 |
| 151 | 1.183 | 88.350 | 1.333 | 96.950 |
| 152 | 1.185 | 104.537 | 0.600 | 106.260 |
| 153 | 1.195 | 93.868 | 0.753 | 98.372 |
| 154 | 1.237 | 105.125 | 0.802 | 97.456 |
| 155 | 1.288 | 97.313 | 0.648 | 95.840 |
| 156 | 1.299 | 93.013 | 1.165 | 105.900 |
| 157 | 1.428 | 99.549 | 0.999 | 105.667 |
| 158 | 1.431 | 109.837 | 1.268 | 165.777 |
| 159 | 1.578 | 92.446 | 0.503 | 98.468 |
| 160 | 1.623 | 94.868 | 1.431 | 102.098 |
| 161 | 1.681 | 108.479 | 0.989 | 97.242 |
| 162 | 1.696 | 83.721 | 1.311 | 89.971 |
| 163 | 1.713 | 103.903 | 1.273 | 102.145 |
| 164 | 1.776 | 94.088 | 0.946 | 92.193 |
| 165 | 1.814 | 90.595 | 1.078 | 87.861 |
| 166 | 1.997 | 101.913 | 1.982 | 96.913 |
| 167 | 2.086 | 112.087 | 1.431 | 98.847 |
| 168 | 2.233 | 96.777 | 1.542 | 93.654 |
| 169 | 2.665 | 67.375 | 1.921 | 96.574 |
| 170 | 2.737 | 97.591 | 0.790 | 124.109 |
| 171 | 2.773 | 96.419 | 2.322 | 83.963 |
| 172 | 3.680 | 94.632 | 2.579 | 111.107 |
| 173 | 4.200 | 102.335 | 2.578 | 102.204 |
| 174 | 0.014 | 93.788 | 0.010 | 97.462 |
| 175 | 0.089 | 109.91 | ND | ND |
| 176 | 0.359 | 107.70 | ND | ND |
| 177 | 0.488 | 107.75 | ND | ND |
| 178 | 0.362 | 112.78 | ND | ND |
| 179 | 2.710 | 97.72 | ND | ND |
| 180 | 0.465 | 86.52 | ND | ND |
| 181 | 1.810 | 101.57 | ND | ND |
| 182 | 0.250 | 110.06 | ND | ND |
| 183 | 0.380 | 98.57 | ND | ND |
| 184 | 0.940 | 103.67 | ND | ND |
| 185 | 0.201 | 98.01 | ND | ND |
| 186 | 0.406 | 110.66 | ND | ND |

*ND = not determined

Equivalents

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of Formula (I):

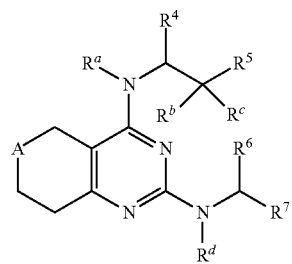

or a pharmaceutically acceptable salt thereof wherein:
A is $NR^1$ or $CR^2R^3$;
$R^1$ and $R^2$ are each, independently H, $(C_3-C_6)$cycloalkyl, or $(C_6-C_{10})$aryl, wherein the $(C_6-C_{10})$aryl is optionally substituted with 1, 2, 3, 4, or 5 substituents independently selected from halo, —CN, —OH, —$CO_2H$, $(C_1-C_6)$alkyl and $(C_3-C_6)$cycloalkyl;
$R^3$ is H or $(C_1-C_6)$alkyl;
$R^4$ is $(C_6-C_{10})$aryl or a 5- or 6-membered heteroaryl comprising 1, 2, 3, or 4 heteroatoms selected from N, O, and S, wherein the $(C_6-C_{10})$aryl or the 5- or 6-membered heteroaryl are each optionally substituted with 1, 2, 3, 4, or 5 substituents independently selected from halo, —CN, —OH, —$CO_2H$, oxo, $(C_1-C_6)$alkyl, $(C_1-C_6)$haloalkyl, $(C_3-C_6)$cycloalkyl, $(C_3-C_6)$cycloalkyl-$(C_1-C_6)$alkyl, and $(C_1-C_6)$alkyl$(C_3-C_6)$cycloalkyl;
$R^5$ is $NR^8R^9$;
$R^6$ is selected from H, $(C_1-C_6)$alkyl, $(C_3-C_6)$cycloalkyl, and $(C_3-C_6)$cycloalkyl-$(C_1-C_6)$alkyl;
$R^7$ is $(C_3-C_6)$cycloalkyl or $(C_6-C_{10})$aryl, wherein the $(C_3-C_6)$cycloalkyl and $(C_6-C_{10})$aryl are each optionally substituted with 1, 2, 3, 4, or 5 substituents independently selected from halo, —CN, —OH, —$CO_2H$, and $HO_2C$—$(C_1-C_6)$alkyl;
$R^8$ and $R^9$ are each, independently H, $(C_1-C_6)$alkyl or a 3- to 6-membered heterocycle comprising 1 to 3 heteroatoms selected from N, O, and S; or
$R^8$ and $R^9$ together with the N to which they are bound form a 3- to 10-membered heterocycle optionally comprising 1 or 2 additional heteroatoms selected from N, O, and S, wherein the 3- to 10-membered heterocycle is optionally substituted with 1, 2, 3, 4, or 5 substituents independently selected from halo, —CN, —OH, —$CO_2H$, $(C_1-C_6)$alkyl, $(C_1-C_6)$haloalkyl, $(C_3-C_6)$cycloalkyl-$(C_1-C_6)$alkyl, $(C_3-C_6)$cycloalkyl, $(C_1-C_6)$alkyl-O—$(C_1-C_6)$alkyl, $(C_1-C_6)$hydroxyalkyl, $(C_1-C_6)$alkoxy, and a 3- to 7-membered heterocycle comprising 1 to 2 heteroatoms selected from N, O, and S; and
$R^a$, $R^b$, $R^c$, and $R^d$ are each, independently H or $(C_1-C_6)$alkyl.

2. The compound according to claim 1 or a pharmaceutically acceptable salt thereof, wherein A is $NR^1$ and $R^1$ is phenyl which is optionally substituted with 1 or 2 substituents independently selected from halo and —CN.

3. The compound according to claim 1 or a pharmaceutically acceptable salt thereof, wherein A is $NR^1$ and $R^1$ is selected from

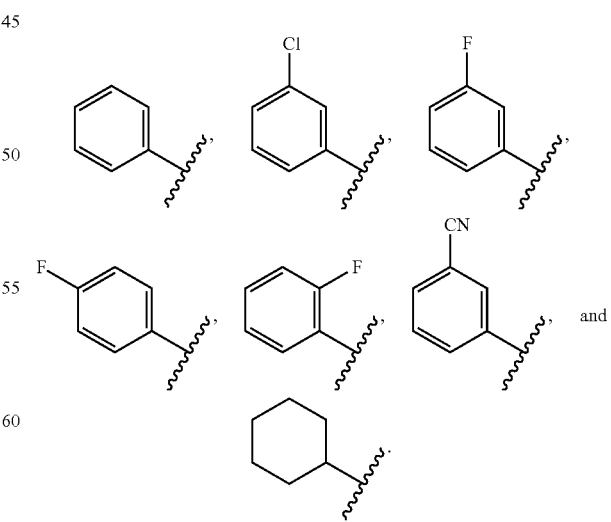

4. The compound according to claim 1 or a pharmaceutically acceptable salt thereof, wherein A is $CR^2R^3$ and $R^2$ is phenyl which is optionally substituted with 1 or 2 substituents independently selected from halo.

5. The compound according to claim 1 or a pharmaceutically acceptable salt thereof, wherein A is CR²R³ and R² is selected from

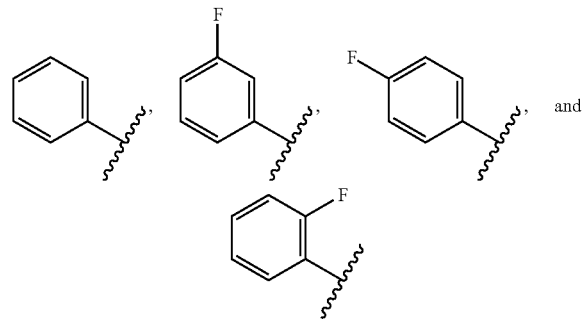

and R³ is selected from H.

6. The compound according to claim 1 or a pharmaceutically acceptable salt thereof, wherein R⁴ is a 5- or 6-membered heteroaryl comprising 1 to 2 heteroatoms selected from N and S, which is optionally substituted with 1, 2, or 3 substituents independently selected from halo, oxo, ($C_1$-$C_6$)alkyl, ($C_1$-$C_6$)haloalkyl, ($C_3$-$C_6$)cycloalkyl, and ($C_3$-$C_6$)cycloalkyl-($C_1$-$C_6$)alkyl.

7. The compound according to claim 1 or a pharmaceutically acceptable salt thereof, wherein R⁴ is a 5-membered heteroaryl comprising 1 to 2 heteroatoms selected from N and S, which is optionally substituted with 1, 2, or 3 substituents independently selected from halo, oxo, ($C_1$-$C_6$)alkyl, ($C_1$-$C_6$)fluoroalkyl, ($C_3$-$C_6$)cycloalkyl, and ($C_3$-$C_6$)cycloalkyl-($C_1$-$C_6$)alkyl.

8. The compound according to claim 1 or a pharmaceutically acceptable salt thereof, wherein R⁴ is a 5-membered heteroaryl comprising 1 to 2 heteroatoms selected from N, which is optionally substituted with 1, 2, or 3 substituents independently selected from halo, ($C_1$-$C_6$)alkyl, ($C_1$-$C_6$)fluoroalkyl, ($C_3$-$C_6$)cycloalkyl, and ($C_3$-$C_6$)cycloalkyl-($C_1$-$C_6$)alkyl.

9. The compound according to claim 1 or a pharmaceutically acceptable salt thereof, wherein R⁴ is phenyl, which is optionally substituted with 1, 2, or 3 substituents independently selected from halo.

10. The compound according to claim 1 or a pharmaceutically acceptable salt thereof, wherein R⁴ is selected from

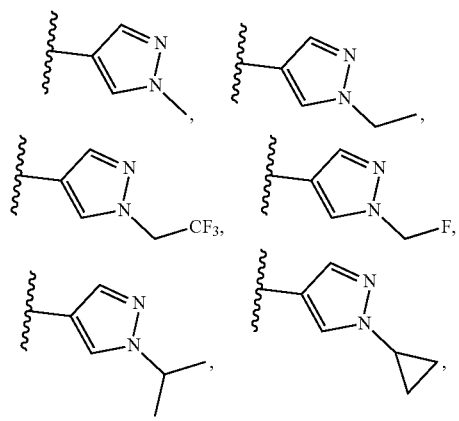

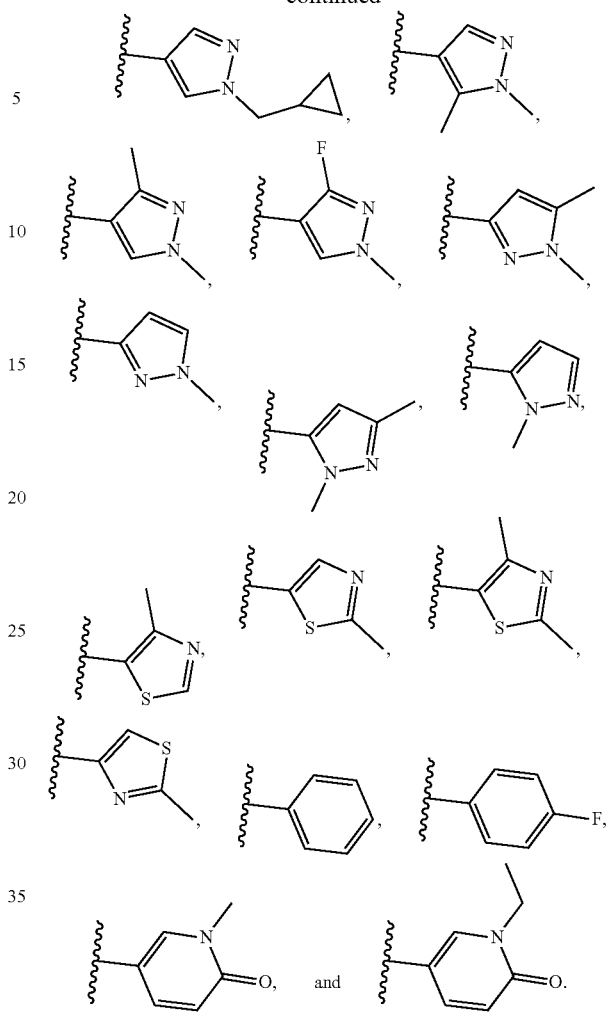

11. The compound according to claim 1 or a pharmaceutically acceptable salt thereof, wherein R⁵ is NR⁸R⁹ and R⁸ and R⁹ together with the N to which they are bound form a 5- to 10-membered heterocycle optionally comprising 1 to 2 additional O heteroatoms, wherein the 5- to 10-membered heterocycle is optionally substituted with 1, 2, or 3 substituents independently selected from halo, —OH, ($C_1$-$C_6$)alkyl, ($C_1$-$C_6$)haloalkyl, ($C_3$-$C_6$)cycloalkyl, ($C_1$-$C_6$)alkyl-O—($C_1$-$C_6$)alkyl, ($C_1$-$C_6$)hydroxyalkyl, ($C_1$-$C_6$)alkoxy, and a 3- to 7-membered heterocycle comprising a heteroatom selected from N and O.

12. The compound according to claim 11 or a pharmaceutically acceptable salt thereof, wherein the 5- to 10-membered heterocycle is optionally substituted with 1, 2, or 3 substituents independently selected from fluoro, —OH, ($C_1$-$C_6$)alkyl, ($C_1$-$C_6$)fluoroalkyl, $CH_{3O}$—($C_1$-$C_6$)alkyl, ($C_1$-$C_6$)hydroxyalkyl, and a 5-membered heterocycle comprising a heteroatom selected from O.

13. The compound according to claim 11 or a pharmaceutically acceptable salt thereof, wherein the 5- to 10-membered heterocycle is optionally substituted with 1, 2, or 3 substituents independently selected from fluoro, —OH, —CH₃, —CH₂F, CF₂H, —CH₂CH₃, —CH₂OH, —OCH₃, and —CH₂OCH₃.

14. The compound according to claim 1 or a pharmaceutically acceptable salt thereof, wherein R⁵ is NR⁸R⁹ and R⁸ and $R^9$ together with the N to which they are bound form a 5- to 10-membered heterocycle, wherein the 5- to 10-membered heterocycle is optionally substituted with 1, 2, or 3 substituents independently selected from halo, —OH, ($C_1$-$C_6$)alkyl, ($C_1$-$C_6$)haloalkyl, ($C_3$-$C_6$)cycloalkyl, ($C_1$-$C_6$)alkyl-O—($C_1$-$C_6$)alkyl, ($C_1$-$C_6$)hydroxyalkyl, and ($C_1$-$C_6$)alkoxy.

15. The compound according to claim 1 or a pharmaceutically acceptable salt thereof, wherein $R^5$ is selected from

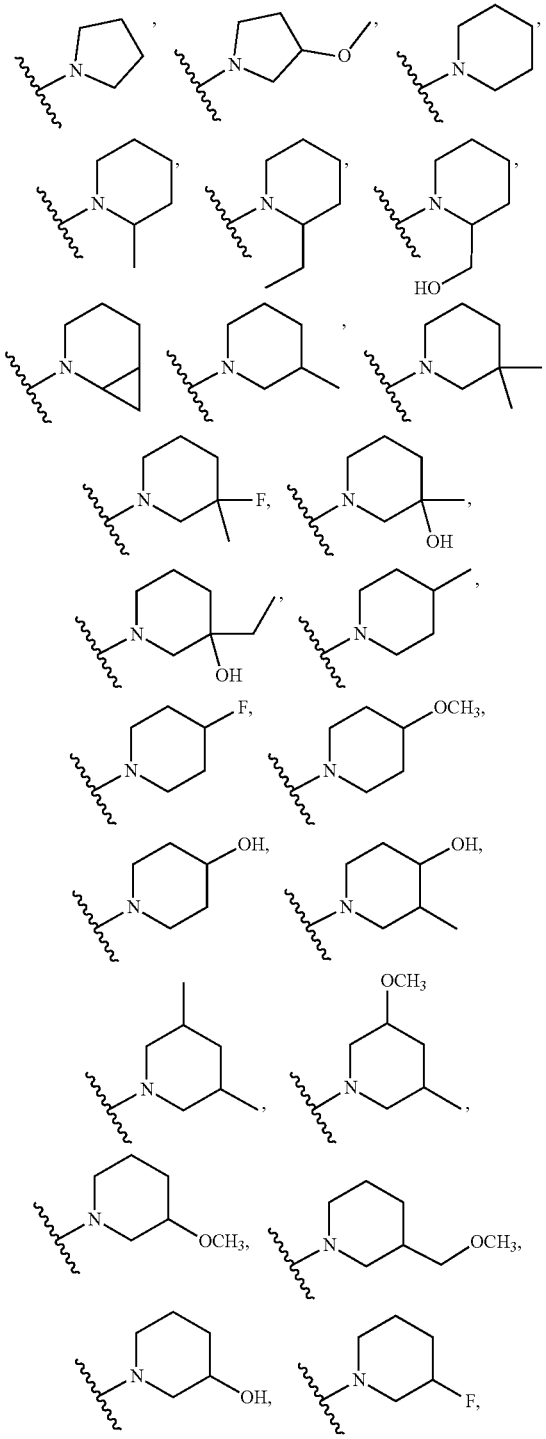

-continued

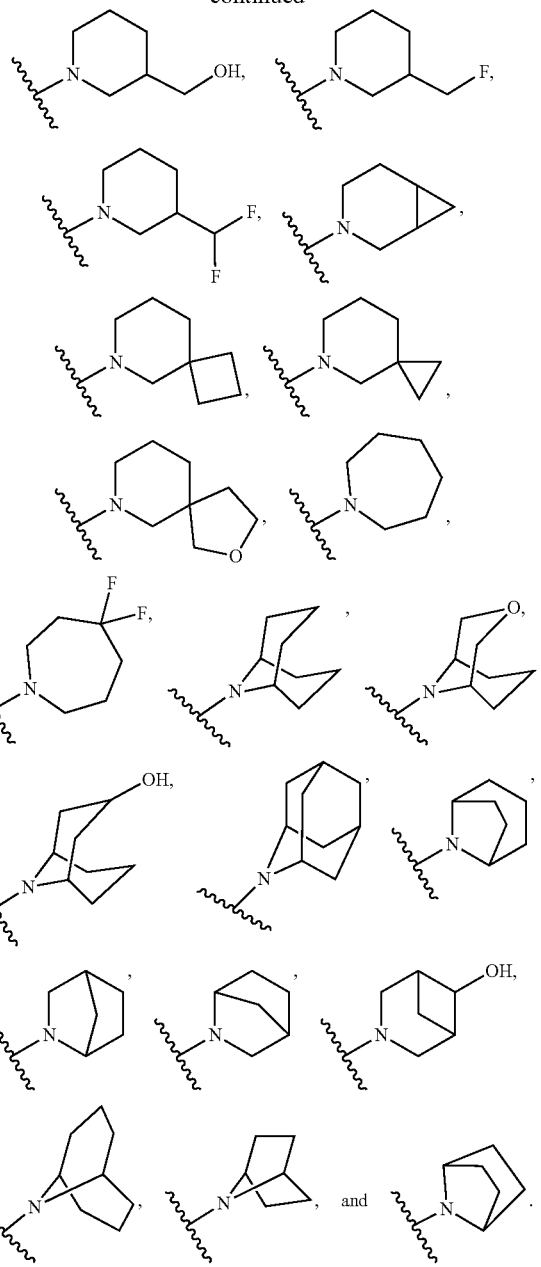

16. The compound according to claim 1 or a pharmaceutically acceptable salt thereof, wherein $R^6$ is selected from selected from ($C_1$-$C_4$)alkyl, ($C_3$-$C_5$)cycloalkyl, and ($C_3$-$C_5$)cycloalkyl-($C_1$-$C_4$)alkyl.

17. The compound according to claim 1 or a pharmaceutically acceptable salt thereof, wherein $R^6$ is A selected from —$CH_3$, and —$CH_2CH_3$.

18. The compound according to claim 1 or a pharmaceutically acceptable salt thereof, wherein $R^7$ is selected from ($C_5$-$C_6$)cycloalkyl or ($C_6$-$C_{10}$)aryl, wherein the ($C_5$-$C_6$)cycloalkyl and ($C_6$-$C_{10}$)aryl are each optionally substituted with 1 or 2 substituents independently selected from fluoro, —$CO_2H$, and —$CH_2CO_2H$.

19. The compound according to claim 1 or a pharmaceutically acceptable salt thereof, wherein $R^7$ is selected from

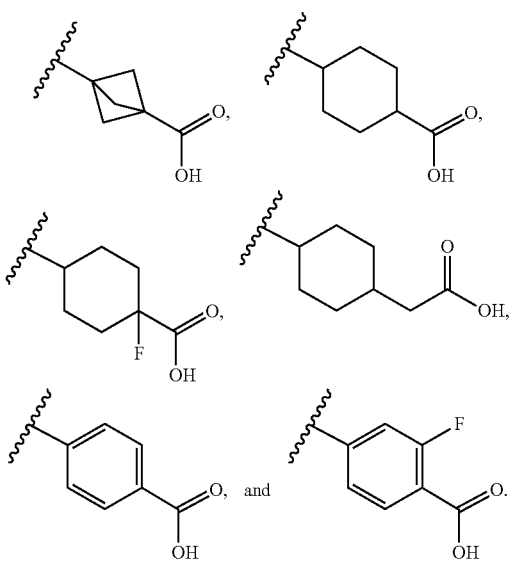

20. The compound according to claim 1 or a pharmaceutically acceptable salt thereof, wherein $R^a$, $R^b$, $R^c$, and $R^d$ are each, independently H or —$CH_3$.

21. The compound according to claim 1 or a pharmaceutically acceptable salt thereof, wherein
A is $CR^2R^3$;
$R^2$ is phenyl which is optionally substituted with 1 or 2 substituents independently selected from halo;
$R^3$ is H;
$R^4$ is a 5-membered heteroaryl comprising 1 to 2 heteroatoms selected from N and S, which is optionally substituted with 1, 2, or 3 substituents independently selected from halo, oxo, $(C_1$-$C_6)$alkyl, $(C_1$-$C_6)$fluoroalkyl, $(C_3$-$C_6)$cycloalkyl, and $(C_3$-$C_6)$cycloalkyl-$(C_1$-$C_6)$alkyl;
$R^5$ is $NR^8R^9$ and $R^8$ and $R^9$ together with the N to which they are bound form a 5- to 10-membered heterocycle optionally comprising 1 to 2 additional O heteroatoms, wherein the 5- to 10-membered heterocycle is optionally substituted with 1, 2, or 3 substituents independently selected from halo, —OH, $(C_1$-$C_6)$alkyl, $(C_1$-$C_6)$haloalkyl, $(C_3$-$C_6)$cycloalkyl, $(C_1$-$C_6)$alkyl-O—$(C_1$-$C_6)$alkyl, $(C_1$-$C_6)$hydroxyalkyl, $(C_1$-$C_6)$alkoxy, and a 3- to 7-membered heterocycle comprising a heteroatom selected from N and O;
$R^6$ is selected from selected from $(C_1$-$C_4)$alkyl;
$R^7$ is selected from $(C_5$-$C_6)$cycloalkyl or $(C_6$-$C_{10})$aryl, wherein the $(C_5$-$C_6)$cycloalkyl and $(C_6$-$C_{10})$aryl are each optionally substituted with 1 or 2 substituents independently selected from fluoro, —$CO_2H$, and —$CH_2CO_2H$; and
$R^a$, $R^b$, $R^c$, and $R^d$ are each, independently H or —$CH_3$.

22. The compound according to claim 1 or a pharmaceutically acceptable salt thereof, wherein
A is $CR^2R^3$;
$R^2$ is phenyl which is optionally substituted with 1 or 2 substituents independently selected from halo;
$R^3$ is H;
$R^4$ is a 5-membered heteroaryl comprising 1 to 2 heteroatoms selected from N, which is optionally substituted with 1, 2, or 3 substituents independently selected from halo, $(C_1$-$C_6)$alkyl, $(C_1$-$C_6)$fluoroalkyl, $(C_3$-$C_6)$cycloalkyl, and $(C_3$-$C_6)$cycloalkyl-$(C_1$-$C_6)$alkyl;

$R^5$ is $NR^8R^9$ and $R^8$ and $R^9$ together with the N to which they are bound form a 5- to 10-membered heterocycle, wherein the 5- to 10-membered heterocycle is optionally substituted with 1, 2, or 3 substituents independently selected from fluoro, —OH, $(C_1$-$C_6)$alkyl, $(C_1$-$C_6)$fluoroalkyl, $CH_{3O}$—$(C_1$-$C_6)$alkyl, $(C_1$-$C_6)$hydroxyalkyl, and a 5-membered heterocycle comprising a heteroatom selected from 0;
$R^6$ is selected from selected from $(C_1$-$C_4)$alkyl;
$R^7$ is selected from $(C_5$-$C_6)$cycloalkyl or $(C_6$-$C_{10})$aryl, wherein the $(C_5$-$C_6)$cycloalkyl and $(C_6$-$C_{10})$aryl are each optionally substituted with 1 or 2 substituents independently selected from fluoro, —$CO_2H$, and —$CH_2CO_2H$; and
$R^a$, $R^b$, $R^c$, and $R^d$ are each, independently H or —$CH_3$.

23. The compound according to claim 1 or a pharmaceutically acceptable salt thereof, wherein the compound is selected from
- 3-((R)-1-(((R)-4-(((R)-2-(azepan-1-yl)-1-(1-methyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid;
- (1R,4r)-4-((R)-1-(((R)-6-(3-fluorophenyl)-6-methyl-4-(((R)-1-(1-methyl-1H-pyrazol-4-yl)-2-((S)-3-methylpiperidin-1-yl)ethyl)amino)-5,6,7,8-tetrahydroquinazolin-2-yl)amino)propyl)cyclohexane-1-carboxylic acid;
- (1R,4r)-4-((R)-1-(((R)-4-(((R)-2-(azepan-1-yl)-1-(1-methyl-1H-pyrazol-4-yl)ethyl)amino)-6-(3-fluorophenyl)-5,6,7,8-tetrahydroquinazolin-2-yl)amino)propyl)cyclohexane-1-carboxylic acid;
- 3-((R)-1-(((R)-4-(((S)-2-(azepan-1-yl)-1-(1-methyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid;
- (1R,4r)-4-((R)-1-(((R)-6-(4-fluorophenyl)-6-methyl-4-(((R)-1-(1-methyl-1H-pyrazol-4-yl)-2-((S)-3-methylpiperidin-1-yl)ethyl)amino)-5,6,7,8-tetrahydroquinazolin-2-yl)amino)propyl)cyclohexane-1-carboxylic acid;
- 3-((R)-1-(((R)-4-(((R)-2-((1S,5S)-9-azabicyclo[3.3.1]nonan-9-yl)-1-(1-methyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid;
- (1R,4r)-4-((R)-1-(methyl((R)-6-methyl-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid;
- 3-((R)-1-(methyl((R)-6-methyl-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)bicyclo[1.1.1]pentane-1-carboxylic acid;
- 3-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)bicyclo[1.1.1]pentane-1-carboxylic acid;
- (1R,4r)-4-((R)-1-(((S)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)amino)propyl)cyclohexane-1-carboxylic acid;
- 3-((R)-1-(((R)-4-(((R)-2-((1S,5S)-9-azabicyclo[3.3.1]nonan-9-yl)-1-(1-methyl-1H-pyrazol-4-yl)ethyl)

amino)-6-(4-fluorophenyl)-5,6,7,8-tetrahydroquinazolin-2-yl)(methyl)amino)propyl)bicyclo[1.1.1]pentane-1-carboxylic acid;

3-((R)-1-(((R)-4-(((R)-2-((S)-3-(fluoromethyl)piperidin-1-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid;

3-((R)-1-(((R)-4-(((R)-1-(1-ethyl-1H-pyrazol-4-yl)-2-((S)-3-methylpiperidin-1-yl)ethyl)amino)-6-(3-fluorophenyl)-5,6,7,8-tetrahydroquinazolin-2-yl)(methyl)amino)propyl)bicyclo[1.1.1]pentane-1-carboxylic acid;

(1R,4r)-4-((R)-1-(((R)-6-(4-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid;

(1R,4r)-4-((R)-1-(((R)-4-(((R)-2-((1S,5S)-9-azabicyclo[3.3.1]nonan-9-yl)-1-(1-methyl-1H-pyrazol-4-yl)ethyl)amino)-6-(3-fluorophenyl)-5,6,7,8-tetrahydroquinazolin-2-yl)amino)propyl)cyclohexane-1-carboxylic acid;

(1R,4r)-4-((1R)-1-(((6R)-4-(((1R)-2-(8-azabicyclo[3.2.1]octan-8-yl)-1-(1,5-dimethyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((R)-1-(((R)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)amino)propyl)cyclohexane-1-carboxylic acid;

(1R,4r)-4-((R)-1-(((R)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((R)-1-(((R)-4-(((R)-2-((S)-3-(fluoromethyl)piperidin-1-yl)-1-(1-methyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((R)-1-(((R)-6-(2-fluorophenyl)-6-methyl-4-(((R)-1-(1-methyl-1H-pyrazol-4-yl)-2-((S)-3-methylpiperidin-1-yl)ethyl)amino)-5,6,7,8-tetrahydroquinazolin-2-yl)amino)propyl)cyclohexane-1-carboxylic acid;

(1S,4r)-1-fluoro-4-((S)-1-(methyl((S)-4-(((S)-1-(1-methyl-1H-pyrazol-4-yl)-2-((R)-3-methylpiperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-(((R)-4-(((R)-1-(1-isopropyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid;

(1R,4r)-4-((1R)-1-(((6R)-4-(((1S)-2-(8-azabicyclo[3.2.1]octan-8-yl)-1-(2,4-dimethylthiazol-5-yl)ethyl)amino)-6-(3-fluorophenyl)-5,6,7,8-tetrahydroquinazolin-2-yl)amino)propyl)cyclohexane-1-carboxylic acid;

3-((1R)-1-(((6R)-4-(((1R)-2-(8-azabicyclo[3.2.1]octan-8-yl)-1-(1-methyl-1H-pyrazol-4-yl)ethyl)amino)-6-(4-fluorophenyl)-5,6,7,8-tetrahydroquinazolin-2-yl)(methyl)amino)propyl)bicyclo[1.1.1]pentane-1-carboxylic acid;

(1R,4r)-4-((1R)-1-(((6R)-4-(((1S)-2-(8-azabicyclo[3.2.1]octan-8-yl)-1-(4-methylthiazol-5-yl)ethyl)amino)-6-(3-fluorophenyl)-5,6,7,8-tetrahydroquinazolin-2-yl)amino)propyl)cyclohexane-1-carboxylic acid;

3-((R)-1-(((R)-4-(((R)-2-((1S,5S)-9-azabicyclo[3.3.1]nonan-9-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid;

3-((1R)-1-(((6R)-4-(((1R)-2-(8-azabicyclo[3.2.1]octan-8-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid;

(1R,4r)-4-((R)-1-(((R)-4-(((R)-2-((1S,5S)-9-azabicyclo[3.3.1]nonan-9-yl)-1-(1-methyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((R)-1-(((R)-4-(((R)-1-(1-ethyl-1H-pyrazol-4-yl)-2-(piperidin-1-yl)ethyl)amino)-6-(3-fluorophenyl)-5,6,7,8-tetrahydroquinazolin-2-yl)amino)propyl)cyclohexane-1-carboxylic acid;

(1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-(4-fluorophenyl)-5,6,7,8-tetrahydroquinazolin-2-yl)(methyl)amino)propyl)cyclohexane-1-carboxylic acid;

(1R,4r)-4-((R)-1-(((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid;

(1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((1R)-1-(((6R)-4-(((1R)-2-(8-azabicyclo[3.2.1]octan-8-yl)-1-(1-methyl-1H-pyrazol-4-yl)ethyl)amino)-6-methyl-6-phenyl-5,6,7,8-tetrahydroquinazolin-2-yl)(methyl)amino)propyl)cyclohexane-1-carboxylic acid;

(1R,4r)-4-((R)-1-(((R)-6-(3-fluorophenyl)-4-(((R)-2-((S)-3-(methoxymethyl)piperidin-1-yl)-1-(1-methyl-1H-pyrazol-4-yl)ethyl)amino)-5,6,7,8-tetrahydroquinazolin-2-yl)(methyl)amino)propyl)cyclohexane-1-carboxylic acid;

3-((S)-1-(((S)-4-(((R)-2-((R)-3-(fluoromethyl)piperidin-1-yl)-1-(1-methyl-1H-pyrazol-4-yl)ethyl)amino)-6-methyl-6-phenyl-5,6,7,8-tetrahydroquinazolin-2-yl)(methyl)amino)propyl)bicyclo[1.1.1]pentane-1-carboxylic acid;

(1R,4r)-4-((R)-1-(((S)-6-(3-fluorophenyl)-4-(((R)-1-phenyl-2-(piperidin-1-yl)ethyl)amino)-5,6,7,8-tetrahydroquinazolin-2-yl)amino)propyl)cyclohexane-1-carboxylic acid;

(1R,4r)-4-((R)-1-(((R)-4-(((R)-2-((1R,3R,5R,7R)-2-azaadamantan-2-yl)-1-(1-ethyl-1H-pyrazol-4-yl)ethyl)amino)-6-phenyl-5,6,7,8-tetrahydroquinazolin-2-yl)amino)propyl)cyclohexane-1-carboxylic acid;

2-((1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexyl)acetic acid;

(1R,4r)-4-((R)-1-(methyl((R)-4-(((R)-1-(1-methyl-1H-pyrazol-4-yl)-2-((S)-3-methylpiperidin-1-yl)ethyl)

amino)-6-phenyl-5,6,7,8-tetrahydroquinazolin-2-yl) amino)propyl)cyclohexane-1-carboxylic acid;

3-((R)-1-(((R)-4-(((R)-2-(9-azabicyclo[3.3.1]nonan-9-yl)-1-(1-methyl-1H-pyrazol-4-yl)ethyl)amino)-6-(2-fluorophenyl)-5,6,7,8-tetrahydroquinazolin-2-yl) (methyl)amino)propyl)bicyclo[1.1.1]pentane-1-carboxylic acid;

3-((1R)-1-(((6R)-4-(((1R)-2-(8-azabicyclo[3.2.1]octan-8-yl)-1-(1-ethyl-1H-pyrazol-4-yl)ethyl)amino)-6-(3-fluorophenyl)-5,6,7,8-tetrahydroquinazolin-2-yl) (methyl)amino)propyl)bicyclo[1.1.1]pentane-1-carboxylic acid;

3-((S)-1-(((R)-4-(((R)-2-((S)-3-(fluoromethyl)piperidin-1-yl)-1-(1-methyl-1H-pyrazol-4-yl)ethyl)amino)-6-methyl-6-phenyl-5,6,7,8-tetrahydroquinazolin-2-yl) (methyl)amino)propyl)bicyclo[1.1.1]pentane-1-carboxylic acid;

3-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl) bicyclo[1.1.1]pentane-1-carboxylic acid;

(1R,4r)-4-((R)-1-(((R)-4-(((R)-1-(1-ethyl-1H-pyrazol-4-yl)-2-(piperidin-1-yl)ethyl)amino)-6-phenyl-5,6,7,8-tetrahydroquinazolin-2-yl)amino)propyl)cyclohexane-1-carboxylic acid;

3-((R)-1-(((R)-4-(((R)-1-(1,5-dimethyl-1H-pyrazol-4-yl)-2-((S)-3-methylpiperidin-1-yl)ethyl)amino)-6-(3-fluorophenyl)-5,6,7,8-tetrahydroquinazolin-2-yl)(methyl) amino)propyl)bicyclo[1.1.1]pentane-1-carboxylic acid;

(1R,4r)-4-((R)-cyclopropyl(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)methyl)cyclohexane-1-carboxylic acid;

(1R,4r)-4-((R)-1-(((R)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl) (methyl)amino)propyl)cyclohexane-1-carboxylic acid;

(1R,4r)-4-((1R)-1-(((6R)-4-(((1R)-2-(8-azabicyclo[3.2.1] octan-8-yl)-1-phenylethyl)amino)-6-phenyl-5,6,7,8-tetrahydroquinazolin-2-yl)amino)propyl)cyclohexane-1-carboxylic acid;

(1R,4r)-4-((R)-1-(((S)-4-(((R)-1-(1-ethyl-1H-pyrazol-4-yl)-2-(piperidin-1-yl)ethyl)amino)-6-(3-fluorophenyl)-5,6,7,8-tetrahydroquinazolin-2-yl)amino)propyl)cyclohexane-1-carboxylic acid;

(1R,4r)-4-((R)-1-(((R)-4-(((R)-2-(azepan-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid;

(1R,4r)-4-((R)-1-(((S)-4-(((R)-2-((1S,5S)-9-azabicyclo [3.3.1]nonan-9-yl)-1-(1-ethyl-1H-pyrazol-4-yl)ethyl) amino)-6-(3-fluorophenyl)-5,6,7,8-tetrahydroquinazolin-2-yl)(methyl)amino)propyl)cyclohexane-1-carboxylic acid;

(1R,4r)-4-((R)-1-(((R)-6-(3-fluorophenyl)-4-(((R)-1-(1-methyl-6-oxo-1,6-dihydropyridin-3-yl)-2-((S)-3-methylpiperidin-1-yl)ethyl)amino)-5,6,7,8-tetrahydroquinazolin-2-yl)(methyl)amino)propyl)cyclohexane-1-carboxylic acid;

(1R,4r)-4-((R)-1-(((R)-4-(((R)-2-((S)-3-(difluoromethyl) piperidin-1-yl)-1-(1-methyl-1H-pyrazol-4-yl)ethyl) amino)-6-(3-fluorophenyl)-5,6,7,8-tetrahydroquinazolin-2-yl)(methyl)amino)propyl)cyclohexane-1-carboxylic acid;

(1R,4r)-4-((R)-1-((6-(3-fluorophenyl)-4-(((R)-1-(1-methyl-1H-pyrazol-4-yl)-2-(piperidin-1-yl)ethyl) amino)-5,6,7,8-tetrahydropyrido[4,3-d]pyrimidin-2-yl) amino)propyl)cyclohexane-1-carboxylic acid;

(1R,4r)-4-((R)-1-(((R)-4-(((R)-1-(1-methyl-1H-pyrazol-4-yl)-2-(piperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-(((R)-4-(((R)-2-(7-azabicyclo[2.2.1] heptan-7-yl)-1-(1-methyl-1H-pyrazol-4-yl)ethyl) amino)-6-(3-fluorophenyl)-5,6,7,8-tetrahydroquinazolin-2-yl)(methyl)amino)propyl)cyclohexane-1-carboxylic acid;

(1R,4r)-4-((1R)-1-(((6R)-4-(((1R)-2-(2-azabicyclo[2.2.1] heptan-2-yl)-1-(1-methyl-1H-pyrazol-4-yl)ethyl) amino)-6-phenyl-5,6,7,8-tetrahydroquinazolin-2-yl) amino)propyl)cyclohexane-1-carboxylic acid;

(1R,4r)-4-((R)-1-(((R)-4-(((R)-2-((1S,5S)-9-azabicyclo [3.3.1]nonan-9-yl)-1-(1-methyl-1H-pyrazol-4-yl)ethyl) amino)-6-phenyl-5,6,7,8-tetrahydroquinazolin-2-yl) amino)propyl)cyclohexane-1-carboxylic acid;

(1R,4r)-4-((1R)-1-(((6R)-4-(((1R)-2-(8-azabicyclo[3.2.1] octan-8-yl)-1-(1-methyl-1H-pyrazol-4-yl)ethyl) amino)-6-phenyl-5,6,7,8-tetrahydroquinazolin-2-yl) amino)propyl)cyclohexane-1-carboxylic acid;

(1R,4r)-4-((R)-1-(((R)-4-(((R)-2-((3S,5R)-3,5-dimethylpiperidin-1-yl)-1-(1-methyl-1H-pyrazol-4-yl)ethyl) amino)-6-phenyl-5,6,7,8-tetrahydroquinazolin-2-yl) amino)propyl)cyclohexane-1-carboxylic acid;

(1R,4r)-4-((1R)-1-(((6R)-4-(((1R)-2-(8-azabicyclo[3.2.1] octan-8-yl)-1-(1-methyl-1H-pyrazol-4-yl)ethyl) amino)-6-(2-fluorophenyl)-5,6,7,8-tetrahydroquinazolin-2-yl)(methyl)amino)propyl)cyclohexane-1-carboxylic acid;

(1R,4r)-4-((R)-1-(((R)-4-(((R)-2-(7-azabicyclo[2.2.1] heptan-7-yl)-1-(1-methyl-1H-pyrazol-4-yl)ethyl) amino)-6-(4-fluorophenyl)-5,6,7,8-tetrahydroquinazolin-2-yl)(methyl)amino)propyl)cyclohexane-1-carboxylic acid;

(1R,4r)-4-((R)-1-(((R)-4-(((R)-1-(1-ethyl-1H-pyrazol-4-yl)-2-((R)-2-methylpiperidin-1-yl)ethyl)amino)-6-phenyl-5,6,7,8-tetrahydroquinazolin-2-yl)amino)propyl) cyclohexane-1-carboxylic acid;

(1R,4r)-4-((R)-1-(((R)-4-(((R)-2-((1S,5S)-9-azabicyclo [3.3.1]nonan-9-yl)-1-(1-ethyl-1H-pyrazol-4-yl)ethyl) amino)-6-phenyl-5,6,7,8-tetrahydroquinazolin-2-yl) amino)propyl)cyclohexane-1-carboxylic acid;

(1R,4r)-4-((R)-1-(methyl((R)-6-methyl-4-(((R)-1-(1-methyl-1H-pyrazol-4-yl)-2-(piperidin-1-yl)ethyl) amino)-6-phenyl-5,6,7,8-tetrahydroquinazolin-2-yl) amino)propyl)cyclohexane-1-carboxylic acid;

2-((1R,4r)-4-((R)-1-(methyl((R)-4-(((R)-1-(1-methyl-1H-pyrazol-4-yl)-2-((S)-3-methylpiperidin-1-yl)ethyl) amino)-6-phenyl-5,6,7,8-tetrahydroquinazolin-2-yl) amino)propyl)cyclohexyl)acetic acid;

(1R,4r)-4-((1R)-1-(((6R)-4-(((1R)-2-(2-azabicyclo[2.2.1] heptan-2-yl)-1-(1-methyl-1H-pyrazol-4-yl)ethyl) amino)-6-methyl-6-phenyl-5,6,7,8-tetrahydroquinazolin-2-yl)(methyl)amino)propyl)cyclohexane-1-carboxylic acid;

3-((1S)-1-(((6R)-4-(((1R)-2-(8-azabicyclo[3.2.1]octan-8-yl)-1-(1-methyl-1H-pyrazol-4-yl)ethyl)amino)-6-methyl-6-phenyl-5,6,7,8-tetrahydroquinazolin-2-yl) (methyl)amino)propyl)bicyclo[1.1.1]pentane-1-carboxylic acid;

(1R,4r)-4-((R)-1-(((R)-4-(((R)-2-(7-azabicyclo[2.2.1] heptan-7-yl)-1-(1-methyl-1H-pyrazol-4-yl)ethyl)

amino)-6-methyl-6-phenyl-5,6,7,8-tetrahydroquinazo-
lin-2-yl)(methyl)amino)propyl)cyclohexane-1-
carboxylic acid;

(1R,4r)-4-((R)-1-(((R)-4-(((R)-2-((5R,7R)-2-azaadaman-
tan-2-yl)-1-(1-methyl-1H-pyrazol-4-yl)ethyl)amino)-
6-phenyl-5,6,7,8-tetrahydroquinazolin-2-yl)amino)
propyl)cyclohexane-1-carboxylic acid;

(1R,4r)-4-((R)-1-(((R)-6-(3-fluorophenyl)-4-(((R)-2-((S)-
3-(hydroxymethyl)piperidin-1-yl)-1-(1-methyl-1H-
pyrazol-4-yl)ethyl)amino)-5,6,7,8-tetrahydroquinazo-
lin-2-yl)(methyl)amino)propyl)cyclohexane-1-
carboxylic acid;

(1R,4r)-4-((R)-1-(((R)-4-(((S)-2-((S)-3-methylpiperidin-
1-yl)-1-(4-methylthiazol-5-yl)ethyl)amino)-6-phenyl-
5,6,7,8-tetrahydroquinazolin-2-yl)amino)propyl)cyclo-
hexane-1-carboxylic acid;

3-(1-(((R)-4-(((R)-2-((1S,5S)-9-azabicyclo [3.3.1]nonan-
9-yl)-1-(1-methyl-1H-pyrazol-4-yl)ethyl)amino)-6-
phenyl-5,6,7,8-tetrahydroquinazolin-2-yl)(methyl)
amino)-113-propyl)bicyclo[1.1.1]pentane-1-
carboxylic acid;

(1R,4r)-4-((R)-1-(((S)-6-(3-fluorophenyl)-4-(((R)-1-(1-
methyl-1H-pyrazol-4-yl)-2-((S)-3-methylpiperidin-1-
yl)ethyl)amino)-5,6,7,8-tetrahydroquinazolin-2-yl)
(methyl)amino)propyl)cyclohexane-1-carboxylic acid;

(1R,4r)-4-((R)-1-((4-(((R)-1-(1-ethyl-1H-pyrazol-4-yl)-
2-((S)-3-methylpiperidin-1-yl)ethyl)amino)-6-(3-fluo-
rophenyl)-5,6,7,8-tetrahydropyrido[4,3-d]pyrimidin-2-
yl)amino)propyl)cyclohexane-1-carboxylic acid;

3-((1R)-1-(((6R)-4-(((1S)-2-(8-azabicyclo[3.2.1]octan-8-
yl)-1-(2-methylthiazol-5-yl)ethyl)amino)-6-(3-fluoro-
phenyl)-5,6,7,8-tetrahydroquinazolin-2-yl)(methyl)
amino)propyl)bicyclo[1.1.1]pentane-1-carboxylic
acid;

(1R,4r)-4-((1R)-1-(((6R)-4-(((1R)-2-(3-azabicyclo[4.1.0]
heptan-3-yl)-1-(1-methyl-1H-pyrazol-4-yl)ethyl)
amino)-6-phenyl-5,6,7,8-tetrahydroquinazolin-2-yl)
(methyl)amino)propyl)cyclohexane-1-carboxylic acid;

(1R,4r)-4-((1R)-1-(((6R)-4-(((1R)-1-(1-ethyl-1H-pyra-
zol-4-yl)-2-((1R,5S)-3-hydroxy-9-azabicyclo[3.3.1]
nonan-9-yl)ethyl)amino)-6-(3-fluorophenyl)-5,6,7,8-
tetrahydroquinazolin-2-yl)(methyl)amino)propyl)
cyclohexane-1-carboxylic acid;

(1R,4r)-4-((1R)-1-((4-(((1R)-2-(8-azabicyclo[3.2.1]oc-
tan-8-yl)-1-(1-methyl-1H-pyrazol-4-yl)ethyl)amino)-
6-(4-fluorophenyl)-5,6,7,8-tetrahydropyrido[4,3-d]py-
rimidin-2-yl)(methyl)amino)propyl)cyclohexane-1-
carboxylic acid;

(1R,4r)-4-((1R)-1-(((6R)-4-(((1S)-2-(8-azabicyclo[3.2.1]
octan-8-yl)-1-(2-methylthiazol-5-yl)ethyl)amino)-6-
(3-fluorophenyl)-5,6,7,8-tetrahydroquinazolin-2-yl)
(methyl)amino)propyl)cyclohexane-1-carboxylic acid;

(1S,4s)-1-fluoro-4-((R)-1-(methyl((R)-4-(((S)-1-(1-
methyl-1H-pyrazol-4-yl)-2-((S)-3-methylpiperidin-1-
yl)ethyl)amino)-6-phenyl-5,6,7,8-tetrahydroquinazo-
lin-2-yl)amino)propyl)cyclohexane-1-carboxylic acid;

(1R,4r)-4-((R)-1-(((R)-4-(((R)-2-((S)-3-(methoxymethyl)
piperidin-1-yl)-1-(1-methyl-1H-pyrazol-4-yl)ethyl)
amino)-6-phenyl-5,6,7,8-tetrahydroquinazolin-2-yl)
(methyl)amino)propyl)cyclohexane-1-carboxylic acid;

(1R,4r)-4-((R)-1-(((R)-4-(((R)-1-(1-methyl-1H-pyrazol-
4-yl)-2-((R)-3-methylpiperidin-1-yl)ethyl)amino)-6-
phenyl-5,6,7,8-tetrahydroquinazolin-2-yl)amino)pro-
pyl)cyclohexane-1-carboxylic acid;

(1R,4r)-4-((R)-1-(((R)-6-phenyl-4-(((R)-1-phenyl-2-(pyr-
rolidin-1-yl)ethyl)amino)-5,6,7,8-tetrahydroquinazo-
lin-2-yl)amino)propyl)cyclohexane-1-carboxylic acid;

(1R,4r)-4-((1R)-1-(((6R)-4-(((1R)-2-(2-azabicyclo[2.2.1]
heptan-2-yl)-1-(4-fluorophenyl)ethyl)amino)-6-phe-
nyl-5,6,7,8-tetrahydroquinazolin-2-yl)amino)propyl)
cyclohexane-1-carboxylic acid;

(1R,4r)-4-((R)-1-(((R)-4-(((R)-2-((S)-3-(fluoromethyl)pi-
peridin-1-yl)-1-(1-methyl-1H-pyrazol-4-yl)ethyl)
amino)-6-phenyl-5,6,7,8-tetrahydroquinazolin-2-yl)
(methyl)amino)propyl)cyclohexane-1-carboxylic acid;

(1R,4r)-4-((1R)-1-(((6R)-4-(((1S)-2-(8-azabicyclo[3.2.1]
octan-8-yl)-1-(1,5-dimethyl-1H-pyrazol-3-yl)ethyl)
amino)-6-(3-fluorophenyl)-5,6,7,8-tetrahydroquinazo-
lin-2-yl)(methyl)amino)propyl)cyclohexane-1-
carboxylic acid;

3-((R)-1-(((R)-4-(((R)-2-((1S,5S)-9-azabicyclo[3.3.1]
nonan-9-yl)-1-(1,5-dimethyl-1H-pyrazol-4-yl)ethyl)
amino)-6-(3-fluorophenyl)-5,6,7,8-tetrahydroquinazo-
lin-2-yl)(methyl)amino)propyl)bicyclo[1.1.1]pentane-
1-carboxylic acid;

(1R,4r)-4-((R)-1-(((R)-4-(((R)-1-(1-methyl-1H-pyrazol-
4-yl)-2-((R)-2-methylpiperidin-1-yl)ethyl)amino)-6-
phenyl-5,6,7,8-tetrahydroquinazolin-2-yl)amino)pro-
pyl)cyclohexane-1-carboxylic acid;

(1R,4r)-4-((R)-1-(((R)-4-(((R)-1-(1-ethyl-1H-pyrazol-4-
yl)-2-(piperidin-1-yl)ethyl)amino)-6-(3-fluorophenyl)-
5,6,7,8-tetrahydroquinazolin-2-yl)(methyl)amino)pro-
pyl)cyclohexane-1-carboxylic acid;

(1R,4r)-4-((R)-1-(((R)-4-(((R)-2-((1S,5S)-9-azabicyclo
[3.3.1]nonan-9-yl)-1-(1-ethyl-1H-pyrazol-4-yl)ethyl)
amino)-6-phenyl-5,6,7,8-tetrahydroquinazolin-2-yl)
(methyl)amino)propyl)cyclohexane-1-carboxylic acid;

(1R,4r)-4-((R)-1-(((R)-4-(((R)-2-((S)-3-(hydroxymethyl)
piperidin-1-yl)-1-(1-methyl-1H-pyrazol-4-yl)ethyl)
amino)-6-phenyl-5,6,7,8-tetrahydroquinazolin-2-yl)
(methyl)amino)propyl)cyclohexane-1-carboxylic acid;

(1R,4r)-4-((R)-1-(((R)-4-(((R)-2-(azepan-1-yl)-1-(1-
ethyl-1H-pyrazol-4-yl)ethyl)amino)-6-phenyl-5,6,7,8-
tetrahydroquinazolin-2-yl)amino)propyl)cyclohexane-
1-carboxylic acid;

(1R,4r)-4-((R)-1-(((R)-4-(((R)-2-(3,3-dimethylpiperidin-
1-yl)-1-(1-methyl-1H-pyrazol-4-yl)ethyl)amino)-6-
phenyl-5,6,7,8-tetrahydroquinazolin-2-yl)amino)pro-
pyl)cyclohexane-1-carboxylic acid;

(1R,4r)-4-((R)-1-(((R)-4-(((R)-2-ethylpiperidin-1-
yl)-1-(1-methyl-1H-pyrazol-4-yl)ethyl)amino)-6-phe-
nyl-5,6,7,8-tetrahydroquinazolin-2-yl)amino)propyl)
cyclohexane-1-carboxylic acid;

(1R,4r)-4-((R)-1-(((R)-4-(((R)-1-(1-cyclopropyl-1H-
pyrazol-4-yl)-2-(piperidin-1-yl)ethyl)amino)-6-phe-
nyl-5,6,7,8-tetrahydroquinazolin-2-yl)(methyl)amino)
propyl)cyclohexane-1-carboxylic acid;

(1R,4r)-4-((R)-1-(((R)-4-(((R)-2-((1R,3R,5R,7R)-2-aza-
adamantan-2-yl)-1-(1-methyl-1H-pyrazol-4-yl)ethyl)
amino)-6-phenyl-5,6,7,8-tetrahydroquinazolin-2-yl)
(methyl)amino)propyl)cyclohexane-1-carboxylic acid;

(1R,4r)-4-((R)-1-((6-(3-fluorophenyl)-4-(((R)-1-phenyl-
2-(pyrrolidin-1-yl)ethyl)amino)-5,6,7,8-tetrahydro-
pyrido[4,3-d]pyrimidin-2-yl)amino)propyl)cyclo-
hexane-1-carboxylic acid;

(1R,4r)-4-((R)-1-(((R)-4-(((R)-1-(1-isopropyl-1H-pyra-
zol-4-yl)-2-(piperidin-1-yl)ethyl)amino)-6-phenyl-5,6,
7,8-tetrahydroquinazolin-2-yl)amino)propyl)cyclo-
hexane-1-carboxylic acid;

(1R,4r)-4-((R)-1-(methyl((S)-4-(((R)-1-(1-methyl-1H-
pyrazol-4-yl)-2-((S)-3-methylpiperidin-1-yl)ethyl)
amino)-6-phenyl-5,6,7,8-tetrahydroquinazolin-2-yl)
amino)propyl)cyclohexane-1-carboxylic acid;

(1R,4r)-4-(((1R)-1-(((6R)-4-(((1R)-2-(8-azabicyclo[3.2.1]octan-8-yl)-1-(1,3-dimethyl-1H-pyrazol-4-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-(((1R)-1-(((6R)-4-(((1R)-2-(8-azabicyclo[3.2.1]octan-8-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-1-(1-ethyl-1H-pyrazol-4-yl)-2-((R)-2-(hydroxymethyl)piperidin-1-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-(((1R)-1-(((6R)-4-(((1S)-2-(8-azabicyclo[3.2.1]octan-8-yl)-1-(1-methyl-1H-pyrazol-3-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((R)-1-((6-(2-fluorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid;

(1R,4r)-4-(((1R)-1-(((6R)-4-((1-(1-(fluoromethyl)-1H-pyrazol-4-yl)-2-((S)-3-methylpiperidin-1-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((1S,5S)-9-azabicyclo[3.3.1]nonan-9-yl)-1-phenylethyl)amino)-6-phenyl-5,6,7,8-tetrahydroquinazolin-2-yl)amino)propyl)cyclohexane-1-carboxylic acid;

(1R,4r)-4-(((1R)-1-(((6R)-4-(((1R)-1-(1-ethyl-1H-pyrazol-4-yl)-2-(2-oxa-7-azaspiro[4.5]decan-7-yl)ethyl)amino)-6-phenyl-5,6,7,8-tetrahydroquinazolin-2-yl)amino)propyl)cyclohexane-1-carboxylic acid;

(1R,4r)-4-((R)-1-((6-(4-fluorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid;

3-((1R)-1-(((6R)-4-(((1S)-2-(8-azabicyclo[3.2.1]octan-8-yl)-1-(2,4-dimethylthiazol-5-yl)ethyl)amino)-6-(3-fluorophenyl)-5,6,7,8-tetrahydroquinazolin-2-yl)(methyl)amino)propyl)bicyclo[1.1.1]pentane-1-carboxylic acid;

(1R,4r)-4-(((1R)-1-(((6R)-4-(((1R)-2-((1R,5S)-3-hydroxy-9-azabicyclo[3.3.1]nonan-9-yl)-1-phenylethyl)amino)-6-phenyl-5,6,7,8-tetrahydroquinazolin-2-yl)(methyl)amino)propyl)cyclohexane-1-carboxylic acid;

3-((1R)-1-(((6R)-4-(((1S)-2-(8-azabicyclo[3.2.1]octan-8-yl)-1-(4-methylthiazol-5-yl)ethyl)amino)-6-(3-fluorophenyl)-5,6,7,8-tetrahydroquinazolin-2-yl)(methyl)amino)propyl)bicyclo[1.1.1]pentane-1-carboxylic acid;

(1R,4r)-4-((R)-1-(((R)-4-(((S)-1-(4-methylthiazol-5-yl)-2-(piperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-(((S)-6-phenyl-4-(((R)-1-phenyl-2-(pyrrolidin-1-yl)ethyl)amino)-5,6,7,8-tetrahydroquinazolin-2-yl)amino)propyl)cyclohexane-1-carboxylic acid;

(1R,4r)-4-((R)-1-(((S)-4-(((R)-1-(1-ethyl-1H-pyrazol-4-yl)-2-(piperidin-1-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-(((1R)-1-(((6R)-4-(((1R)-1-(1-ethyl-1H-pyrazol-4-yl)-2-((1R,5S)-3-hydroxy-9-azabicyclo[3.3.1]nonan-9-yl)ethyl)amino)-6-(3-fluorophenyl)-5,6,7,8-tetrahydroquinazolin-2-yl)amino)propyl)cyclohexane-1-carboxylic acid;

(1R,4r)-4-((R)-1-(methyl((R)-4-(((R)-1-(1-methyl-1H-pyrazol-4-yl)-2-(piperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-(((R)-4-(((S)-1-(2-methylthiazol-5-yl)-2-(piperidin-1-yl)ethyl)amino)-6-phenyl-5,6,7,8-tetrahydroquinazolin-2-yl)amino)propyl)cyclohexane-1-carboxylic acid;

(1R,4r)-4-((R)-cyclopropyl(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)methyl)cyclohexane-1-carboxylic acid;

(1R,4r)-4-((R)-1-(((R)-4-(((R)-1-(1-methyl-1H-pyrazol-4-yl)-2-(4-methylpiperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-(((R)-4-(((R)-2-((1R,4S)-2-azabicyclo[2.2.1]heptan-2-yl)-1-(1-ethyl-1H-pyrazol-4-yl)ethyl)amino)-6-phenyl-5,6,7,8-tetrahydroquinazolin-2-yl)amino)propyl)cyclohexane-1-carboxylic acid;

(1R,4r)-4-((R)-1-(((R)-4-(((R)-1-(1-methyl-1H-pyrazol-4-yl)-2-((S)-2-methylpiperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-((6-(3-fluorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid;

(1R,4r)-4-((R)-1-(methyl((R)-4-(((R)-1-(1-methyl-1H-pyrazol-4-yl)-2-((R)-3-methylpiperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-(((R)-4-(((R)-1-(1-ethyl-1H-pyrazol-4-yl)-2-(6-azaspiro[3.5]nonan-6-yl)ethyl)amino)-6-phenyl-5,6,7,8-tetrahydroquinazolin-2-yl)amino)propyl)cyclohexane-1-carboxylic aci;

(1R,4r)-4-(((1R)-1-(((6R)-4-(((1S)-2-(8-azabicyclo[3.2.1]octan-8-yl)-1-(2-methylthiazol-4-yl)ethyl)amino)-6-(3-fluorophenyl)-5,6,7,8-tetrahydroquinazolin-2-yl)amino)propyl)cyclohexane-1-carboxylic acid;

(1R,4r)-4-(((1R)-1-(((6R)-4-(((1R)-2-(2-azabicyclo[2.2.1]heptan-2-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((S)-3-hydroxypiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1S,4r)-4-(((S)-1-(((S)-6-(3-fluorophenyl)-6-methyl-4-(((R)-1-(1-methyl-1H-pyrazol-4-yl)-2-((R)-3-methylpiperidin-1-yl)ethyl)amino)-5,6,7,8-tetrahydroquinazolin-2-yl)amino)propyl)cyclohexane-1-carboxylic acid;

(1R,4r)-4-((R)-1-((6-phenyl-4-(((R)-1-phenyl-2-(pyrrolidin-1-yl)ethyl)amino)-5,6,7,8-tetrahydropyrido[4,3-d]pyrimidin-2-yl)amino)propyl)cyclohexane-1-carboxylic acid;

(1R,4r)-4-((R)-1-(((R)-4-(((R)-2-((1S,5S)-9-azabicyclo[3.3.1]nonan-9-yl)-1-(1-isopropyl-1H-pyrazol-4-yl)ethyl)amino)-6-phenyl-5,6,7,8-tetrahydroquinazolin-2-yl)amino)propyl)cyclohexane-1-carboxylic acid;

(1R,4r)-4-((R)-(((R)-4-(((R)-2-((1S,5S)-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)(methyl)amino)(cyclopropyl)methyl)cyclohexane-1-carboxylic acid;

(1R,4r)-4-((R)-1-(((R)-4-(((R)-2-((S)-3-methoxypiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-1-(1-ethyl-1H-pyrazol-4-yl)-2-((S)-2-(hydroxymethyl)piperidin-1-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((1R)-1-(((6R)-4-(((1R)-2-(2-azabicyclo[2.2.1]heptan-2-yl)-1-phenylethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-(4,4-difluoroazepan-1-yl)-1-(1-ethyl-1H-pyrazol-4-yl)ethyl)amino)-6-phenyl-5,6,7,8-tetrahydroquinazolin-2-yl)amino)propyl)cyclohexane-1-carboxylic acid;

(1R,4r)-4-((1R)-1-(((6R)-4-(((1R,5S)-6-hydroxy-3-azabicyclo[3.1.1]heptan-3-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((1R)-2-cyclopropyl-1-(((6-phenyl-4-(((R)-1-phenyl-2-(pyrrolidin-1-yl)ethyl)amino)-5,6,7,8-tetrahydroquinazolin-2-yl)amino)ethyl)cyclohexane-1-carboxylic acid;

3-(1-(((R)-4-(((S)-1-(1,3-dimethyl-1H-pyrazol-5-yl)-2-((S)-3-methylpiperidin-1-yl)ethyl)amino)-6-phenyl-5,6,7,8-tetrahydroquinazolin-2-yl)(methyl)amino)-113-propyl)bicyclo[1.1.1]pentane-1-carboxylic acid;

(1R,4r)-4-((R)-1-(((S)-6-(2-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexane-1-carboxylic acid;

(1R,4r)-4-((R)-1-(((R)-4-(((R)-2-(4-fluoropiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid;

(1R,4r)-4-((R)-1-(((R)-4-(((R)-2-((1S,5S)-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((1R)-1-(((6R)-4-(((1R)-2-(3-fluoro-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(methyl((R)-4-(((R)-1-(1-methyl-1H-pyrazol-4-yl)-2-(4-methylpiperidin-1-yl)ethyl)amino)-6-phenyl-5,6,7,8-tetrahydroquinazolin-2-yl)amino)propyl)cyclohexane-1-carboxylic acid;

(1R,4r)-4-((R)-1-(methyl((R)-6-phenyl-4-(((R)-1-phenyl-2-(pyrrolidin-1-yl)ethyl)amino)-5,6,7,8-tetrahydroquinazolin-2-yl)amino)propyl)cyclohexane-1-carboxylic acid;

(1R,4r)-4-((R)-1-(((R)-4-(((R)-1-(1-(cyclopropylmethyl)-1H-pyrazol-4-yl)-2-(piperidin-1-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(1-ethyl-6-oxo-1,6-dihydropyridin-3-yl)-2-(piperidin-1-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((R)-2-(hydroxymethyl)piperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-(4,4-difluoroazepan-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-(4-methoxypiperidin-1-yl)-1-(1-methyl-1H-pyrazol-4-yl)ethyl)amino)-6-phenyl-5,6,7,8-tetrahydroquinazolin-2-yl)amino)propyl)cyclohexane-1-carboxylic acid;

(1R,4r)-4-((R)-1-((6-cyclohexyl-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid;

4-((R)-1-(((R)-4-(((R)-2-((1S,5S)-9-azabicyclo[3.3.1]nonan-9-yl)-1-(1-ethyl-1H-pyrazol-4-yl)ethyl)amino)-6-(3-fluorophenyl)-5,6,7,8-tetrahydroquinazolin-2-yl)amino)ethyl)benzoic acid;

(1R,4r)-4-((R)-1-(((R)-4-(((R)-1-(1-ethyl-1H-pyrazol-4-yl)-2-(4-hydroxypiperidin-1-yl)ethyl)amino)-6-phenyl-5,6,7,8-tetrahydroquinazolin-2-yl)(methyl)amino)propyl)cyclohexane-1-carboxylic acid;

3-((R)-1-(((R)-6-(3-fluorophenyl)-4-(((S)-1-(1-methyl-1H-pyrazol-5-yl)-2-((S)-3-methylpiperidin-1-yl)ethyl)amino)-5,6,7,8-tetrahydroquinazolin-2-yl)(methyl)amino)propyl)bicyclo[1.1.1]pentane-1-carboxylic acid;

(1R,4r)-4-((1R)-1-(((6R)-4-(((1R)-2-(3-fluoropiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-((6-(3-fluorophenyl)-4-(((R)-1-(1-methyl-1H-pyrazol-4-yl)-2-(piperidin-1-yl)ethyl)amino)-5,6,7,8-tetrahydropyrido[4,3-d]pyrimidin-2-yl)(methyl)amino)propyl)cyclohexane-1-carboxylic acid;

(1S,4r)-4-((1S)-1-((6-phenyl-4-(((R)-1-phenyl-2-(pyrrolidin-1-yl)ethyl)amino)-5,6,7,8-tetrahydroquinazolin-2-yl)amino)ethyl)cyclohexane-1-carboxylic acid;

4-((R)-1-(((R)-6-phenyl-4-(((R)-1-phenyl-2-(pyrrolidin-1-yl)ethyl)amino)-5,6,7,8-tetrahydroquinazolin-2-yl)amino)ethyl)benzoic acid;

(1R,4r)-4-((1R)-1-(((6R)-4-(((1R)-2-(2-azabicyclo[2.2.1]heptan-2-yl)-1-phenylethyl)amino)-6-phenyl-5,6,7,8-tetrahydroquinazolin-2-yl)amino)propyl)cyclohexane-1-carboxylic acid;

(1R,4r)-4-((R)-1-(((R)-6-(3-fluorophenyl)-4-(((S)-1-(1-methyl-1H-pyrazol-5-yl)-2-((S)-3-methylpiperidin-1-yl)ethyl)amino)-5,6,7,8-tetrahydroquinazolin-2-yl)(methyl)amino)propyl)cyclohexane-1-carboxylic acid;

(1R,4r)-4-((1R)-1-(((6R)-4-(((1R)-1-(1-ethyl-1H-pyrazol-4-yl)-2-(2-oxa-7-azaspiro[4.5]decan-7-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-1-(1-ethyl-1H-pyrazol-4-yl)-2-((S)-3-hydroxypiperidin-1-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((1R)-1-(((6R)-4-(((1S)-2-(8-azabicyclo[3.2.1]octan-8-yl)-1-(1-methyl-1H-pyrazol-5-yl)ethyl)amino)-6-(3-fluorophenyl)-5,6,7,8-tetrahydroquinazolin-2-yl)(methyl)amino)propyl)cyclohexane-1-carboxylic acid;

(1R,4r)-4-((R)-1-(((R)-4-(((R)-2-(dimethylamino)-1-phenylethyl)amino)-6-phenyl-5,6,7,8-tetrahydroquinazolin-2-yl)amino)propyl)cyclohexane-1-carboxylic acid;

(1R,4r)-4-((R)-1-(((R)-6-phenyl-4-(((R)-1-phenyl-2-((tetrahydro-2H-pyran-4-yl)amino)ethyl)amino)-5,6,7,8-tetrahydroquinazolin-2-yl)amino)propyl)cyclohexane-1-carboxylic acid;

(1R,4r)-4-((R)-1-(methyl((R)-6-phenyl-4-(((R)-2-(piperidin-1-yl)-1-(1-(2,2,2-trifluoroethyl)-1H-pyrazol-4-yl)ethyl)amino)-5,6,7,8-tetrahydroquinazolin-2-yl)amino)propyl)cyclohexane-1-carboxylic acid;

4-((R)-1-(((R)-4-(((R)-2-((1S,5S)-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)amino)ethyl)-2-fluorobenzoic acid;

(1R,4r)-4-((R)-1-(((R)-4-(((R)-2-((1R,5S)-3-oxa-9-azabicyclo[3.3.1]nonan-9-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-((6-(3-chlorophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid;

4-((R)-1-(((R)-4-(((R)-1-(1-isopropyl-1H-pyrazol-4-yl)-2-(piperidin-1-yl)ethyl)amino)-6-phenyl-5,6,7,8-tetrahydroquinazolin-2-yl)amino)ethyl)benzoic acid;

3-((R)-1-(((R)-4-(((S)-2-((1R,5R)-9-azabicyclo[3.3.1]nonan-9-yl)-1-(1-methyl-1H-pyrazol-5-yl)ethyl)amino)-6-phenyl-5,6,7,8-tetrahydroquinazolin-2-yl)(methyl)amino)propyl)bicyclo[1.1.1]pentane-1-carboxylic acid;

(1R,4r)-4-((R)-1-(methyl((R)-4-(((R)-2-methyl-1-(1-methyl-1H-pyrazol-4-yl)-2-(piperidin-1-yl)propyl)amino)-6-phenyl-5,6,7,8-tetrahydroquinazolin-2-yl)amino)propyl)cyclohexane-1-carboxylic acid;

(1R,4r)-4-((R)-1-((6-(3-cyanophenyl)-4-(((R)-1-(1-methyl-1H-pyrazol-4-yl)-2-((S)-3-methylpiperidin-1-yl)ethyl)amino)-5,6,7,8-tetrahydropyrido[4,3-d]pyrimidin-2-yl)(methyl)amino)propyl)cyclohexane-1-carboxylic acid;

(1R,4r)-4-((1R)-1-(((6R)-4-(((1R)-2-(3-(fluoromethyl)piperidin-1-yl)-1-(1-methyl-1H-pyrazol-4-yl)ethyl)amino)-6-(3-fluorophenyl)-5,6,7,8-tetrahydroquinazolin-2-yl)amino)propyl)cyclohexane-1-carboxylic acid;

(1R,4r)-4-((R)-1-(((R)-4-(((R)-2-((1R,6S)-2-azabicyclo[4.1.0]heptan-2-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((1S,6R)-2-azabicyclo[4.1.0]heptan-2-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((R)-3-ethyl-3-hydroxypiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((3R,4R)-4-hydroxy-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(methyl((R)-4-(((R)-1-(1-methyl-1H-pyrazol-4-yl)-2-(5-azaspiro[2.5]octan-5-yl)ethyl)amino)-6-phenyl-5,6,7,8-tetrahydroquinazolin-2-yl)amino)propyl)cyclohexane-1-carboxylic acid (1R,4r)-4-((R)-1-(((R)-4-(((R)-2-((R)-3-methoxypyrrolidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((R)-3-hydroxy-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((3R,5R)-3-methoxy-5-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((R)-2-((3S,5S)-3-methoxy-5-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

(1R,4r)-4-((R)-1-(((R)-4-(((S)-1-(3-fluoro-1-methyl-1H-pyrazol-4-yl)-2-((S)-3-methylpiperidin-1-yl)ethyl)amino)-6-phenyl-5,6,7,8-tetrahydroquinazolin-2-yl)(methyl)amino)propyl)cyclohexane-1-carboxylic acid; and (1R,4r)-4-((R)-1-(((R)-4-(((R)-2-((S)-3-hydroxy-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid.

24. The compound according to claim 1 or a pharmaceutically acceptable salt thereof, wherein the compound is selected from

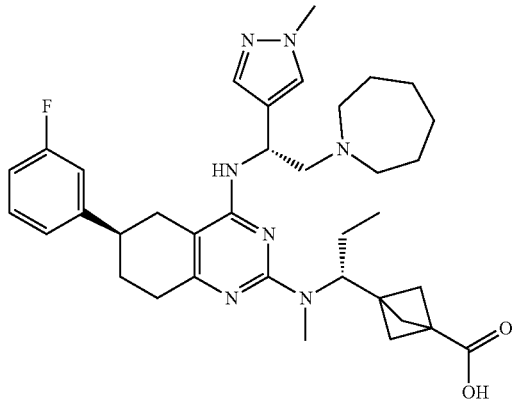 [SMILES: CC[C@@H](N(C)c1nc2c(c(N[C@@H](CN3CCCCCC3)c3cnn(C)c3)n1)C[C@H](c1cccc(F)c1)CC2)C12CC(C(=O)O)(C1)C2]

3-((R)-1-(((R)-4-(((R)-2-(azepan-1-yl)-1-(1-methyl-1H-pyrazol-4-yl)ethyl)amino)-6-(3-fluorophenyl)-5,6,7,8-tetrahydroquinazolin-2-yl)(methyl)amino)propyl)bicyclo[1.1.1]pentane-1-carboxylic acid;

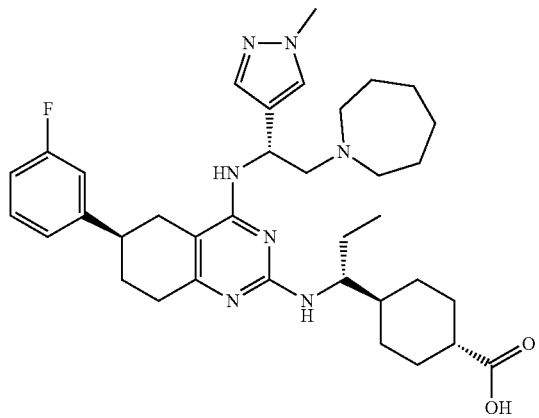

345

(1R,4r)-4-((R)-1-(((R)-4-(((R)-2-(azepan-1-yl)-1-(1-methyl-1H-pyrazol-4-yl)ethyl)amino)-6-(3-fluorophenyl)-5,6,7,8-tetrahydroquinazolin-2-yl)amino)propyl)cyclohexane-1-carboxylic acid;

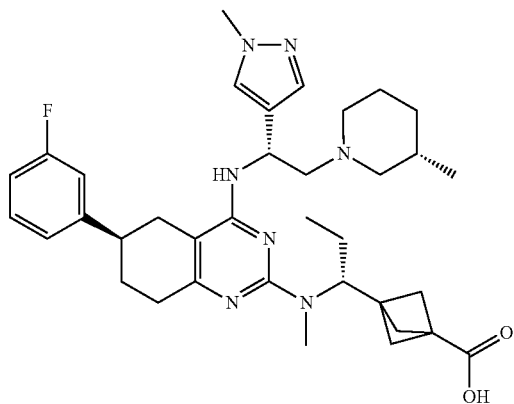 [SMILES: CC[C@@H](N(C)c1nc2c(c(N[C@@H](CN3CCC[C@H](C)C3)c3cnn(C)c3)n1)C[C@H](c1cccc(F)c1)CC2)C12CC(C(=O)O)(C1)C2]

3-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)bicyclo[1.1.1]pentane-1-carboxylic acid;

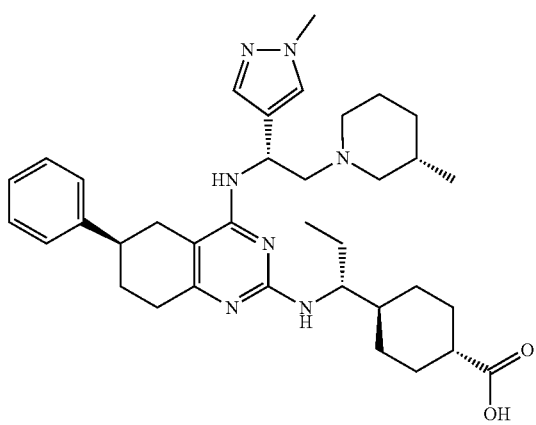 [SMILES: CC[C@@H](Nc1nc2c(c(N[C@@H](CN3CCC[C@H](C)C3)c3cnn(C)c3)n1)C[C@H](c1ccccc1)CC2)[C@H]1CC[C@H](C(=O)O)CC1]

(1R,4r)-4-((R)-1-(((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylic acid;

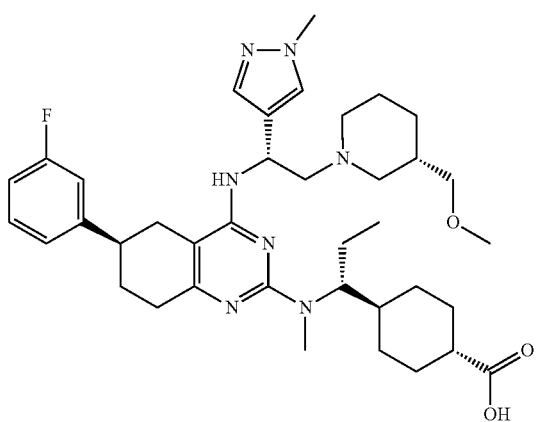 [SMILES: CC[C@H]([C@H]1CC[C@H](C(=O)O)CC1)N(C)c1nc2c(c(N[C@@H](CN3CCC[C@H](COC)C3)c3cnn(C)c3)n1)C[C@H](c1cccc(F)c1)CC2]

346

(1R,4r)-4-((R)-1-(((R)-6-(3-fluorophenyl)-4-(((R)-2-((S)-3-(methoxymethyl)piperidin-1-yl)-1-(1-methyl-1H-pyrazol-4-yl)ethyl)amino)-5,6,7,8-tetrahydroquinazolin-2-yl)(methyl)amino)propyl)cyclohexane-1-carboxylic acid;

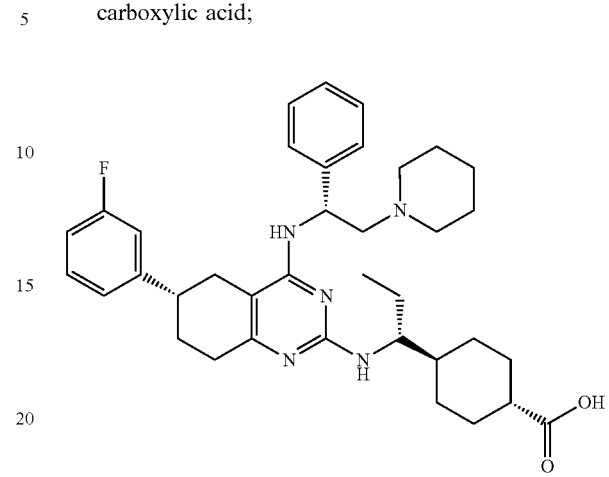

(1R,4r)-4-((R)-1-(((S)-6-(3-fluorophenyl)-4-(((R)-1-phenyl-2-(piperidin-1-yl)ethyl)amino)-5,6,7,8-tetrahydroquinazolin-2-yl)amino)propyl)cyclohexane-1-carboxylic acid;

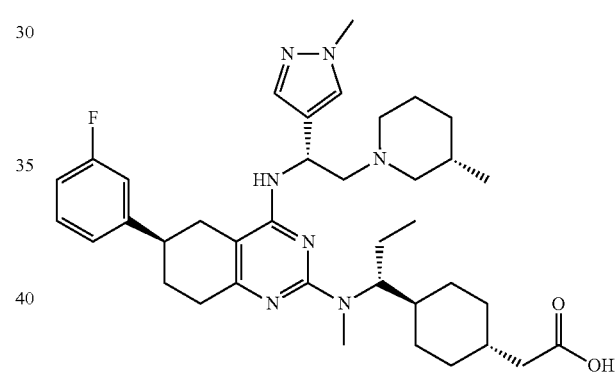

2-((1R,4r)-4-((R)-1-(((R)-6-(3-fluorophenyl)-4-(((R)-1-(1-methyl-1H-pyrazol-4-yl)-2-((S)-3-methylpiperidin-1-yl)ethyl)amino)-5,6,7,8-tetrahydroquinazolin-2-yl)(methyl)amino)propyl)cyclohexyl)acetic acid;

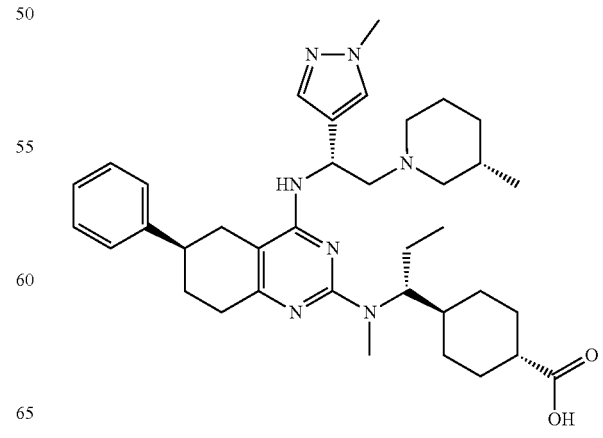

347

(1R,4r)-4-((R)-1-(methyl((R)-4-(((R)-1-(1-methyl-1H-pyrazol-4-yl)-2-((S)-3-methylpiperidin-1-yl)ethyl)amino)-6-phenyl-5,6,7,8-tetrahydroquinazolin-2-yl)amino)propyl)cyclohexane-1-carboxylicacid;

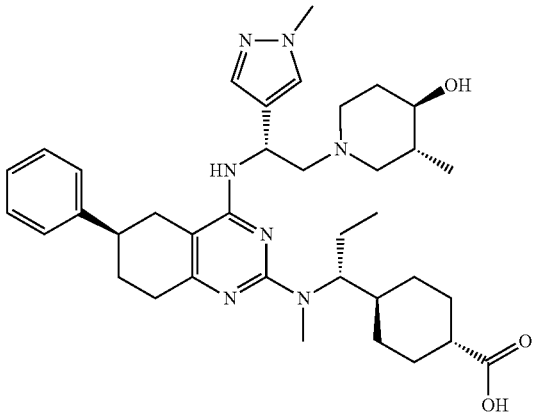 [SMILES: CC[C@H]([C@H]1CC[C@H](C(=O)O)CC1)N(C)c1nc2c(c(N[C@@H](CN3CC[C@@H](O)[C@H](C)C3)c3cnn(C)c3)n1)C[C@H](c1ccccc1)CC2]

(1R,4r)-4-((R)-1-(((R)-4-(((R)-2-((3R,4R)-4-hydroxy-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

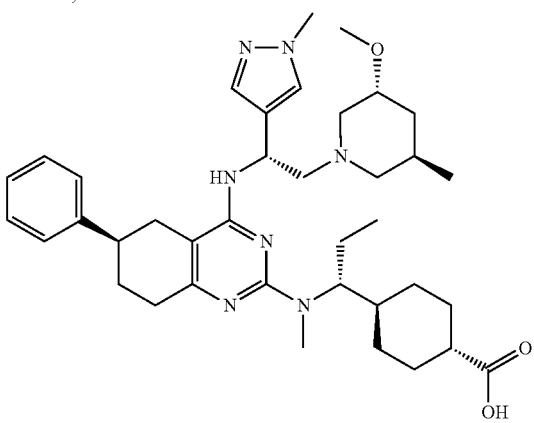

(1R,4r)-4-((R)-1-(((R)-4-(((R)-2-((3R,5R)-3-methoxy-5-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid;

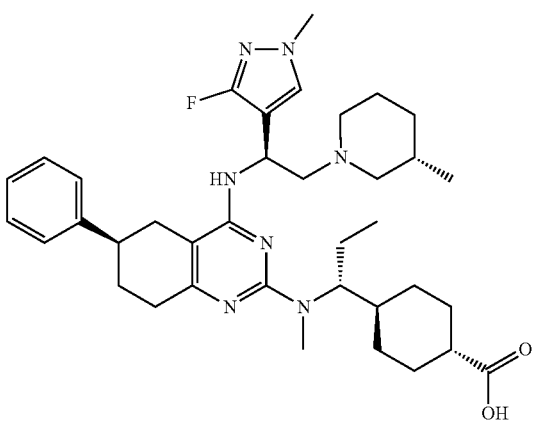 [SMILES: CC[C@H]([C@H]1CC[C@H](C(=O)O)CC1)N(C)c1nc2c(c(N[C@H](CN3CCC[C@H](C)C3)c3cn(C)nc3F)n1)C[C@H](c1ccccc1)CC2]

348

(1R,4r)-4-((R)-1-(((R)-4-(((S)-1-(3-fluoro-1-methyl-1H-pyrazol-4-yl)-2-((S)-3-methylpiperidin-1-yl)ethyl)amino)-6-phenyl-5,6,7,8-tetrahydroquinazolin-2-yl)(methyl)amino)propyl)cyclohexane-1-carboxylic acid; and

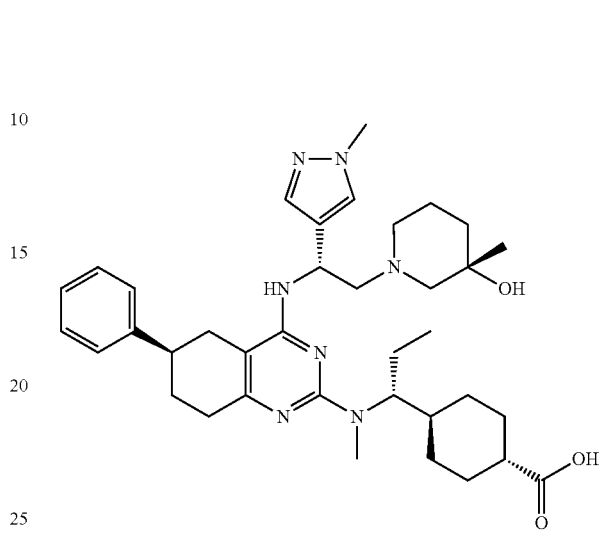

(1R,4r)-4-((R)-1-(((R)-4-(((R)-2-((S)-3-hydroxy-3-methylpiperidin-1-yl)-1-(1-methyl-1H-pyrazol-4-yl)ethyl)amino)-6-phenyl-5,6,7,8-tetrahydroquinazolin-2-yl)(methyl)amino)propyl)cyclohexane-1-carboxylic acid.

25. The compound according to claim 1 or a pharmaceutically acceptable salt thereof, wherein the pharmaceutically acceptable salt is the sodium salt.

26. A pharmaceutical composition comprising a compound according to claim 1 or a pharmaceutically acceptable salt thereof and one or more pharmaceutically acceptable carriers.

27. The pharmaceutical composition according to claim 26, further comprising at least one additional pharmaceutically active agent.

28. A method for treating or preventing a cardiovascular disease or disorder comprising administering to a patient in need thereof a therapeutically effective amount of a compound according to claim 1 or a pharmaceutically acceptable salt thereof.

29. The method according to claim 28, wherein the cardiovascular disease or disorder is selected from hypertension, peripheral vascular disease, heart failure, coronary artery disease (CAD), ischemic heart disease (IHD), mitral stenosis and regurgitation, angina, hypertrophic cardiomyopathy, diabetic cardiomyopathy, supraventricular and ventricular arrhythmias, cardiac dysrhythmia, atrial fibrillation (AF), new onset of atrial fibrillation, recurrent atrial fibrillation, cardiac fibrosis, atrial flutter, detrimental vascular remodeling, plaque stabilization, and myocardial infarction (MI).

30. The method according to claim 29, wherein the heart failure is selected from a heart failure with reduced ejection fraction (HFrEF), heart failure with preserved ejection fraction (HFpEF), heart failure after acute myocardial infarction, or acute decompensated heart failure.

* * * * *